(12) United States Patent
Cox et al.

(10) Patent No.: US 7,227,020 B2
(45) Date of Patent: *Jun. 5, 2007

(54) AZAINDOLES

(75) Inventors: Paul Joseph Cox, Flemington, NJ (US); Tahir Nadeem Majid, Hoboken, NJ (US); Shelley Amendola, Bedminster, NJ (US); Stephanie Daniele Deprets, Paris (FR); Christoper David Edlin, Hitchin (GB); Justine Yeun Quai Lai, Epping (GB); Andrew David Morley, Macclesfield (GB)

(73) Assignee: Aventis Pharma Limited, West Malling (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/827,978

(22) Filed: Apr. 20, 2004

(65) Prior Publication Data

US 2004/0198737 A1    Oct. 7, 2004

Related U.S. Application Data

(60) Division of application No. 10/178,667, filed on Jun. 24, 2002, now Pat. No. 6,770,643, which is a continuation of application No. PCT/GB00/04933, filed on Dec. 27, 2000.

(60) Provisional application No. 60/215,818, filed on Jul. 5, 2000.

(30) Foreign Application Priority Data

Dec. 24, 1999    (GB)    ................... 9930698.7

(51) Int. Cl.
*C07D 471/04*    (2006.01)
*A61K 31/437*    (2006.01)

(52) U.S. Cl. ................... 544/127; 546/113; 514/234.5; 514/300

(58) Field of Classification Search ............... 546/113; 544/127; 514/234.5, 300
See application file for complete search history.

(56) References Cited

U.S. PATENT DOCUMENTS

| | | | |
|---|---|---|---|
| 5,338,849 | A | 8/1994 | Festal et al. |
| 5,521,213 | A | 5/1996 | Prasit |
| 5,681,959 | A | 10/1997 | Bishop |
| 5,714,495 | A * | 2/1998 | Viaud et al. ................. 514/300 |
| 6,025,366 | A | 2/2000 | Walsh |
| 6,169,091 | B1 | 1/2001 | Cockerill |
| 6,207,699 | B1 | 3/2001 | Cockerill |
| 6,232,320 | B1 | 5/2001 | Stewart |
| 6,348,487 | B1 | 2/2002 | Connor |
| 6,384,235 | B2 | 5/2002 | Henkelmann |
| 6,387,900 | B1 | 5/2002 | Pevarello |
| 6,407,259 | B1 | 6/2002 | Harris |
| 6,897,207 | B2 * | 5/2005 | Cox et al. ................... 514/183 |

FOREIGN PATENT DOCUMENTS

| | | |
|---|---|---|
| EP | 0405602 | 1/1991 |
| EP | 0509974 | 10/1992 |
| EP | 509974 A1 * | 10/1992 |
| EP | 0557171 | 7/1995 |
| EP | 0737685 | 10/1996 |
| EP | 0716855 | 8/1998 |
| EP | 1088950 | 3/2001 |
| GB | 966264 | 8/1964 |
| GB | 2298199 | 8/1996 |
| JP | 06-247966 | 9/1994 |
| WO | WO98/10513 | 4/1995 |
| WO | WO96/06840 | 3/1996 |
| WO | WO98/06703 | 2/1998 |

(Continued)

OTHER PUBLICATIONS

Mahabaleshwar et al., PubMed Abstract (J. Biol. Chem. 278(8):6209-21) Feb. 2003.*

(Continued)

*Primary Examiner*—Deepak Rao
(74) *Attorney, Agent, or Firm*—James W. Bolcsak

(57) ABSTRACT

Chemical compositions containing physiologically active compounds of general formula (I):

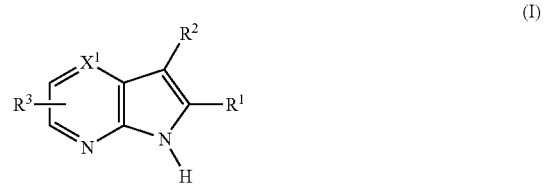

wherein $R^1$ is aryl or heteroaryl; $R^2$ represents hydrogen, acyl, cyano, halo, lower alkenyl or lower alkyl optionally substituted by a substituent selected from cyano, heteroaryl, heterocycloalkyl, $-Z^1R^8$, $-C(=O)-NY^3Y^4$, $-CO_2R^8$, $-NY^3Y^4$, $-N(R^6)-C(=O)-R^7$, $-N(R^6)-C(=O)-NY^3Y^4$, $-N(R^6)-C(=O)-OR^7$, $-N(R^6)-SO_2-R^7$, $-N(R^6)-SO_2-NY^3Y^4$ and one or more halogen atoms; $R^3$ represents hydrogen, aryl, cyano, halo, heteroaryl, lower alkyl, $-C(=O)-OR^5$ or $-C(=O)-NY^3Y$; and $X^1$ represents N, CH, C-halo, C-CN, C-$R^7$, C-$NY^3Y^4$, C-OH, C-$Z^2R^7$, C-$C(=O)-OR^5$, C-$C(=O)-NY^3Y^4$, C-$N(R^8)-C(=O)-R^7$, C-$SO_2-NY^3Y^4$, C-$N(R^8)-SO_2-R^7$, C-alkenyl, C-alkynyl or C-$NO_2$; and their prodrugs, and pharmaceutically acceptable salts and solvates of such compounds and their prodrugs, as well as to novel compounds within the scope of formula (I).

Such compounds and compositions have valuable pharmaceutical properties, in particular the ability to inhibit protein kinases.

9 Claims, No Drawings

FOREIGN PATENT DOCUMENTS

| WO | WO98/22457 | 5/1998 |
|---|---|---|
| WO | WO98/47899 | 10/1998 |
| WO | WO99/20624 | 4/1999 |
| WO | WO 9920624 A1 * | 4/1999 |
| WO | WO01/30774 | 10/1999 |
| WO | WO99/51231 | 10/1999 |
| WO | WO99/51232 | 10/1999 |
| WO | WO99/51234 | 10/1999 |
| WO | WO99/51595 | 10/1999 |
| WO | WO99/58518 | 11/1999 |
| WO | WO00/17202 | 3/2000 |
| WO | WO00/40547 | 7/2000 |
| WO | WO00/75117 | 12/2000 |
| WO | WO01/02369 | 1/2001 |
| WO | WO01/30774 | 5/2001 |
| WO | WO01/47922 | 7/2001 |
| WO | WO01/53268 | 7/2001 |
| WO | WO01/60816 | 8/2001 |
| WO | WO01/62262 | 8/2001 |
| WO | WO01/30774 | 10/2001 |
| WO | WO01/72720 | 10/2001 |
| WO | WO01/96336 | 12/2001 |
| WO | WO02/10137 | 2/2002 |
| WO | WO01/30774 | 3/2002 |
| WO | WO02/22601 | 3/2002 |
| WO | WO02/22602 | 3/2002 |
| WO | WO02/22603 | 3/2002 |
| WO | WO02/22604 | 3/2002 |
| WO | WO02/22605 | 3/2002 |
| WO | WO02/22606 | 3/2002 |
| WO | WO02/22607 | 3/2002 |
| WO | WO03/000688 | 1/2003 |

OTHER PUBLICATIONS

Casanova et al., PubMed Abstract (Rev Neurol. 28(9):909-15), May 1999.*

Herbert et al., CAPLUS Abstract 71:49810, 1969.*

Herbert et al., CAPLUS Abstract 72:105131, 1970.*

Hands et al., CAPLUS Abstract 125:167834, 1996.*

Marot et al., Pharmacophoric Search and 3D-QSAR Comparative Molecular Field Analysis Studies on Agonists of Melatonin Sheep Receptors, J. Med. Chem., vol. 41, No. 23, pp. 4453-4465, 1998.*

Cheng et al., CAPLUS Abstract 130:325138, 1999.*

Liu et al., Syntheses, Structures, and Electroluminescence of New Blue/Green Luminescent Chelate Compounds, J. Am. Chem. Soc., vol. 122, No. 15, pp. 3671-3678, Mar. 2000.*

West, Solid Solutions, Solid state chemistry and it's applications, Wiley, New York, pp. 358 and 365, 1988.*

Vippagunta et al., Crystalline solids, Advanced Drug Delivery Reviews, 48 (2001), pp. 3-26, 2001.*

U.S. Appl. No. 09/847,982, filed May 2, 2001, Li.

Busev et al., Extraction-Photometric Determination of Molybdenum by Means of 6,7-Dihydroxy-2,4-Diphenylbenzopyrilium Chloride, Zhurn. Anblit. Khimii, vol. 16, pp. 571-577, 1961.*

Chumakov, Yu I. et al., 3-Formyl-7-Azaindoles, Byulletan Izobretnii i Tovamykh Znakor, V. 10, p. 22, 1964, Su 162534.*

Clark, B. A. J. et al., Mass Spectrometry of Pyrrolo[2,3-b]pyrazines and Pyrazino[2,3-b]indole, Org. Mass Spectrom, vol. 12(7), pp. 421-423, 1977.*

Clark, Bernard A. J. et al., Preparation of pyrrolo[2,3-b]pyrazines and pyrazino[2,3-b]indole, Chemistry and Industry (London), 1976, pp. 215-216.*

Clark, B. A. J. et al., Formation of Certain Substituted 5H-Pyrrolo[2,3-b]pyrazines by Thermal Cyclisation of Pyrazinylthydrazones and a Route to 5H-Pyrazino[2,3-b]indole; a Synthesis of 5H-Pyrrolo[2,3-b] pyrazine and Some of its Properties, Journal of Chemical Society, Perkin Transactions 1, vol. 1(13), pp. 1361-1363, 1976.*

Davis, Michael L. et al., Reactions of beta-(Lithiomethyl)azines with Nitriles as a Route to Pyrrolo-pyridines, -quinolines, -pyrazines, -quinoxalines and -pyrimidines, Tetrahedron, vol. 48, No. 5, pp. 939-952, 1992.*

Hands, David et al., A Convenient Method for the Preparation of 5-, 6- and 7-Azaindotes and Their Derivatives, Synthesis, Jul. 1996, pp. 877-882.*

Hardy, C. R. et al., Ring Opening or Rearrangement vs. N-Oxidation in the Action of Peracids upon Pyrrolo[2,3-b]pyridines, Pyrrolo[2,3-b]pyrazines, & Triazolo[1,5-a]- & Triazolo[4,3-a]-pyrazine. Some Chemical & Spectroscopic Properties of the Triazolopyrazines & Their N-Oxides, J.G.S., Perkin Trans.1, 506-511, 1980.*

Henry, James R. et al., 6-amino-2(4-flurophnyl)-4-methoxy-3-(4-pyridyl)-1H-pyrrolo[2,3-b]pyrdine (RWY 66354): A Potent and Selective p38 Kinase Inhibitor, J. Med. Chem., vol. 41, No. 22, 4196-4198, 1998.*

Herbert, R. et al., 1H-Pyrrolo[2,3-b]pyridines. Part II. Fragmentation of Some 1H-Pyrrolo[2,3-b]pyridines induced by Electron Impact, Journal of the Chemical Society Sect. B. Physical Organic, 1970, vol. 3, pp. 459-463.*

Herbert, R. et al., Syntheses and Properties of 1H-Pyrrolo[2,3-b]pyridines, J. Chem. Soc., 1969, pp. 1505-1514.*

Kruse, C. G. et al., Furo- and Thieno[2,3-b]pyrazines, Part 2. Chemical Properties of 2-Substituted Derivatives, Recueil des Travaux Chimiques des Pays-Bas, Journal of the Royal Netherlands Chemical Society, vol. 97(6), pp. 151-155, 1978.

Marot, Christophe et al., Pharmacophoric Search and 3D-QSAR Comparative Molecular Field Analysis Studies on Agonists of Melatonin Sheep Receptors, J. Med. Chem., vol. 41, No. 23, pp. 4453-4465, 1998.

Martin, par Christian et al., Reactions Selectives de L'O. Chlorobenzonitrils: SNAr, Tetrahedron Letters, vol. 30, No. 8, pp. 935-936, 1989.

Park, Sang Sun et al., A Facile Synthesis of 2,3-Disubstituted Pyrrolo[2,3-b]pyridines via Palladium-Catalyzed Heteroannulation with Internal Alkynes, Tetrahedron Letters, NL, Elsevier Science Publishers, vol. 39, No. 7, pp. 627-630, 1998.

Protiva, Miroslav et al., Antihistaminove latky XXVI. Nekolik novyoh heterocyklickych derivatu ethylendiaminu, Chem. Italy, vol. 46, pp. 551-554, 1952.

Rustsov, M.V. et al., Preparation of Vinylpyridines, Byulleten Izobretnil I Tovamykh Znakor, V. 10, p. 22, 1964, SU 162535.

Vierfond, par Jean-Michel et al., Cyclisation par Amination Intramoleculaire Dane la Serie de la Pyrazine, Tetrahedron Letters, vol. 22, No. 13, pp. 1219-1222, 1981.

* cited by examiner

AZAINDOLES

This application is a divisional application of U.S. application Ser. No. 10/178,667, filed Jun. 24, 2004, now U.S. Pat. No. 6,770,643 which is a continuation of International Application No. PCT/GB00/04933, filed Dec. 27, 2000 which claims the priority from earlier filed applications GB 9930698.7, filed Dec. 24, 1999 and U.S. Provisional Application No. 60/215,818, filed Jul. 5, 2000. The content of the above-identified applications is incorporated herein in its entirety.

This invention is directed to substituted azaindoles, their preparation, pharmaceutical compositions containing these compounds, and their pharmaceutical use in the treatment of disease states capable of being modulated by the inhibition of the protein kinases.

Protein kinases participate in the signalling events which control the activation, growth and differentiation of cells in response to extracellular mediators and to changes in the environment. In general, these kinases fall into several groups; those which preferentially phosphorylate serine and/or threonine residues and those which preferentially phosphorylate tyrosine residues [S. K. Hanks and T. Hunter, FASEB. J., 1995, 9, pages 576–596]. The serine/threonine kinases include for example, protein kinase C isoforms [A. C. Newton, J. Biol. Chem., 1995, 270, pages 28495–28498] and a group of cyclin-dependent kinases such as cdc2 [J. Pines, Trends in Biochemical Sciences, 1995, 18, pages 195–197]. The tyrosine kinases include membrane-spanning growth factor receptors such as the epidermal growth factor receptor [S. Iwashita and M. Kobayashi, Cellular Signalling, 1992, 4, pages 123–132], and cytosolic non-receptor kinases such as p56tck, p59fYn, ZAP-70 and csk kinases [C. Chan et. al., Ann. Rev. Immunol., 1994, 12, pages 555–592].

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or underproduction of cytokines or growth factors also participating in the transduction of signals upstream or downstream of the kinase. In all of these instances, selective inhibition of the action of the kinase might be expected to have a beneficial effect.

Syk is a 72-kDa cytoplasmic protein tyrosine kinase that is expressed in a variety of hematopoietic cells and is an essential element in several cascades that couple antigen receptors to cellular responses. Thus, Syk plays a pivotal role in signalling of the high affinity IgE receptor, FcεFR1, in mast cells and in receptor antigen signalling in T and B lymphocytes. The signal transduction pathways present in mast, T and B cells have common features. The ligand binding domain of the receptor lacks intrinsic tyrosine kinase activity. However, they interact with transducing subunits that contain immunoreceptor tyrosine based activation motifs (ITAMS) [M. Reth, Nature, 1989, 338, pages 383–384]. These motifs are present in both the β and γ subunits of the FcεR1, in the ξ-subunit the of T cell receptor (TCR) and in the IgGα and IgG β subunits of the B cell receptor (BCR). [N. S. van Oers and A. Weiss, Seminars in Immunology, 1995, 7, pages 227–236] Upon binding of antigen and multimerization, the ITAM residues are phosphorylated by protein tyrosine kinases of the Src family. Syk belongs to a unique class of tyrosine kinases that have two tandem Src homology 2 (SH2) domains and a C terminal catalytic domain. These SH2 domains bind with high affinity to ITAMs and this SR2-mediated association of Syk with an activated receptor stimulates Syk kinase activity and localises Syk to the plasma membrane.

In Syk deficient mice, mast cell degranulation is inhibited, suggesting that this is an important target for the development of mast cell stabilising agents [P. S. Costello, Oncogene, 1996, 13, pages 2595–2605]. Similar studies have demonstrated a critical role for Syk in BCR and TCR signalling [A. M. Cheng, Nature, 1995, 378, pages 303–306, (1995) and D. H. Chu et al., Immunological Reviews, 1998, 165, pages 167–180]. Syk also appears to be involved in eosinophil survival in response to IL-5 and GM-CSF [S. Yousefi et al., J. Exp. Med., 1996, 183, pages 1407–1414]. Despite the key role of Syk in mast cell, BCR and T cell signalling, little is known about the mechanism by which Syk transmits downstream effectors. Two adaptor proteins, BLNK (B cell Linker protein, SLP-65) and SLP-76 have been shown to be substrates of Syk in B cells and mast cells respectively and have been postulated to interface Syk with downstream effectors [M. Ishiai et al., Immunity, 1999, 10, pages 117–125 and L. R. Hendricks-Taylor et al., J. Biol. Chem, 1997, 272, pages 1363–1367]. In addition Syk appears to play an important role in the CD40 signalling pathway, which plays an important role in B cell proliferation [M. Faris et al., J. Exp. Med., 1994, 179, pages 1923–1931].

Syk is further involved in the activation of platelets stimulated via the low-affinity IgG receptor (Fc gamma-RIIA) or stimulated by collagen [F. Yanaga et al., Biochem. J., 1995, 311, (Pt. 2) pages 471–478].

Focal adhesion kinase (FAK) is a non-receptor tyrosine kinase involved in integrin-mediated signal transduction pathways. FAK colocalizes with integrins in focal contact sites and FAK activation and its tyrosine phosphorylation have been shown in many cell types to be dependent on integrins binding to their extracellular ligands. Results from several studies support the hypothesis that FAK inhibitors could be useful in cancer treatment. For example, FAK-deficient cells migrate poorly in response to chemotactic signals and overexpression of C-terminal domain of FAK blocks cell spreading as well as chemotactic migration (Sieg et al, J. Cell Science, 1999, 112, 2677–2691; Richardson A. and Parsons T., Cell, 1997, 97, 221–231); in addition, tumor cells treated with FAK antisense oligonucleotides lost their attachment and underwent apoptosis (Xu et al, Cell Growth Differ. 1996, 4, 413–418). FAK has been reported to be overexpressed in prostate, breast, thyroid, colon and lung cancers. The level of expression of FAK is directly correlated with tumors demonstrating the most aggressive phenotype.

Angiogenesis or the formation of new blood vessels by sprouting from the preexisting vasculature is of central importance for embryonic development and organogenesis. Abnormal enhanced neovascularization is observed in rheumatoid arthritis, diabetic retinopathy and during tumor development (Folkman, Nat. Med., 1995, 1, 27–31. ). Angiogenesis is a complex multistage process which includes activation, migration, proliferation and survival of endothelial cells. Extensive studies in the field of tumor angiogenesis in the past two decades have identified a number of therapeutic targets including kinases, proteases and integrins resulting in the discovery of many new anti-angiogenic agents, including KDR inhibitors some of which are currently under clinical evaluation (Jekunen, et al Cancer Treatment Rev. 1997, 23, 263–286. ). Angiogenesis inhibitors may be used in frontline, adjuvant and even preventive settings for the emergence or regrowth of malignancies.

Several proteins involved in chromosome segregation and spindle assembly have been identified in yeast and *drosophila*. Disruption of these proteins results in chromosome missegregation and monopolar or disrupted spindles. Among these kinases are the Ip11 and aurora kinases from *S.cerevisiae* and *drosophila* respectively, which are required for centrosome separation and chromosome segregation. One human homologue of yeast Ip11 was recently cloned and characterized by different laboratories. This kinase termed Aurora2, STK15 or BTAK belongs to the serine/threonine kinase family. Bischoff et al showed that Aurora2 is oncogenic and is amplified in human colorectal cancers (EMBO J, 1998, 17, 3052–3065). It has also been exemplified in cancers involving epithelial tumors such as breast cancer.

We have now found a novel group of substituted azaindoles, which have valuable pharmaceutical properties, in particular, the ability to inhibit protein kinases, more particularly, the ability to selectively inhibit Syk kinase.

Thus, in one aspect, the present invention is directed to pharmaceutical compositions comprising compounds of general formula (I):

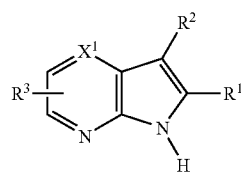

(I)

wherein:

$R^1$ represents aryl or heteroaryl each optionally substituted by one or more groups selected from acyl, alkylenedioxy, alkenyl, alkenyloxy, alkynyl, aryl, cyano, halo, hydroxy, heteroaryl, heterocycloalkyl, nitro, $R^4$, —C(=O)—$NY^1Y^2$, —C(=O)—$OR^5$, —$NY^1Y^2$, —N($R^6$)—C(=O)—$R^7$, —N($R^6$)—C(=O)—$NY^3Y^4$, —N($R^6$)—C(=O)—$OR^7$, —N($R^6$)—$SO_2$—$R^7$, —N($R^6$)—$SO_2$—$NY^3Y^4$, —$SO_2$—$NY^1Y^2$ and -$Z^2R^4$;

$R^2$ represents hydrogen, acyl, cyano, halo, lower alkenyl or lower alkyl optionally substituted by a substituent selected from cyano, heteroaryl, heterocycloalkyl, -$Z^1R^8$, —C(=O)—$NY^3Y^4$, —$CO_2R^8$, —$NY^3Y^4$, —N($R^6$)—C(=O)—$R^7$, —N($R^6$)—C(=O)—$NY^3Y^4$, —N($R^6$)—C(=O)—$OR^7$, —N($R^6$)—$SO_2$—$R^7$, —N($R^6$)—$SO_2$—$NY^3Y^4$ and one or more halogen atoms;

$R^3$ represents hydrogen, aryl, cyano, halo, heteroaryl, lower alkyl, —C(=O)—$OR^5$ or —C(=O)—$NY^3Y$;

$R^4$ represents alkyl, cycloalkyl or cycloalkylalkyl each optionally substituted by a substituent selected from aryl, cycloalkyl, cyano, halo, heteroaryl, heterocycloalkyl, —CHO (or a 5-, 6- or 7-membered cyclic acetal derivative thereof), —C(=O)—$NY^1Y^2$, —C(=O)—$OR^5$, —$NY^1Y^2$, —N($R^6$)—C(=O)—$R^7$, —N($R^6$)—C(=O)—$NY^3Y^4$, —N($R^6$)—$SO_2$—$R^7$, —N($R^6$)—$SO_2$—$NY^3Y^4$, —$OR^7$ and one or more groups selected from hydroxy and carboxy;

$R^5$ represents hydrogen, alkyl, alkenyl, aryl, arylalkyl, heteroaryl or heteroarylalkyl;

$R^6$ represents hydrogen or lower alkyl;

$R^7$ represents alkyl, aryl, arylalkyl, cycloalkyl, cycloalkylalkyl, heteroaryl, heteroarylalkyl, heterocycloalkyl or heterocycloalkylalkyl;

$R^8$ represents hydrogen or lower alkyl;

$X^1$ represents N, CH, C-halo, C—CN, C—$R^7$, C—$NY^3Y^4$, C—OH, C-$Z^2R^7$, C—C(=O)—$OR^5$, C—C(=O)—$NY^3Y^4$, C—N($R^8$)—C(=O)—$R^7$, C—$SO_2$—$NY^3Y^4$, C—N($R^8$)—$SO_2$—$R^7$, C-alkenyl, C-alkynyl or C—$NO_2$;

$Y^1$ and $Y^2$ are independently hydrogen, alkenyl, aryl, cycloalkyl, heteroaryl or alkyl optionally substituted by one or more groups selected from aryl, halo, heteroaryl, hydroxy, —C(=O)—$NY^3Y^4$, —C(=O)—$OR^5$, —$NY^3Y^4$, —N($R^6$)—C(=O)—$R^7$, —N($R^6$)—C(=O)—$NY^3Y^4$, —N($R^6$)—$SO_2$—$R^7$, —N($R^6$)—$SO_2$—$NY^3Y^4$ and —$OR^7$; or the group —$NY^1Y^2$ may form a cyclic amine;

$Y^3$ and $Y^4$ are independently hydrogen, alkenyl, alkyl, aryl, arylalkyl, cycloalkyl, heteroaryl or heteroarylalkyl; or the group —$NY^3Y^4$ may form a cyclic amine;

$Z^1$ represents O or S;

$Z^2$ represents O or $S(O)_n$;

n is zero or an integer 1 or 2;

and their corresponding N-oxides, and their prodrugs, and their acid bioisosteres; and pharmaceutically acceptable salts and solvates (e.g. hydrates) of such compounds and their N-oxides and their prodrugs, and their acid bioisosteres; together with one or more pharmaceutically acceptable carriers or excipients.

In another aspect, the invention concerns the compounds of formula (I) as defined above, but excluding the compounds 2-phenyl-1H-pyrrolo[2,3-b]pyridine, 2-(4-bromophenyl)-3-methyl-1H-pyrrolo[2,3-b]pyridine, 4-(3-methyl-1H-pyrrolo[2,3-b]pyridin-2-yl)-benzoic acid methyl ester, 2-(4-chloro-phenyl)-1H-pyrrolo[2,3-b]pyridine, 2-(4-methoxy-phenyl)-1H-pyrrolo[2,3-b]pyridine, 5-methyl-2-phenyl-1H-pyrrolo[2,3-b]pyridine, 4-methyl-2-phenyl-1H-pyrrolo[2,3-b]pyridine, 2-pyridin-3-yl-1H-pyrrolo[2,3-b]pyridine, 4-(3-methyl-1H-pyrrolo[2,3-b]pyridin-2-yl)-benzoic acid, 2-(4-methoxy-phenyl)-3-methyl-1H-pyrrolo[2,3-b]pyridine, 2-(4-methyl-phenyl)-3-methyl-1H-pyrrolo[2,3-b]pyridine, 4-(3-methyl-1H-pyrrolo[2,3-b]pyridin-2-yl)-benzoic acid isopropyl ester, 2-phenyl-3-methyl-1H-pyrrolo[2,3-b]pyridine, 5-bromo-2-phenyl-3-methyl-1H-pyrrolo[2,3-b]pyridine, 6-chloro-2-phenyl-1H-pyrrolo[2,3-b]pyridine, 6-chloro-4-methyl-2-phenyl-1H-pyrrolo[2,3-b]pyridine, 4-methyl-2-phenyl-1H-pyrrolo[2,3-b]pyridin-3-yl-carboxaldehyde, 2-phenyl-1H-pyrrolo[2,3-b]pyridin-3-yl-acetonitrile, 2-phenyl-3-prop-1-enyl-1H-pyrrolo[2,3-b]pyridine, 4-methyl-2-phenyl-1H-pyrrolo[2,3-b]pyridin-3-yl-carboxaldehyde, dimethyl-(2-phenyl-1H-pyrrolo[2,3-b]pyridin-3-ylmethyl)-amine, 2,2'-diphenyl-1H, 1'H-[3,3']bi[pyrrolo[2,3-b]pyridinyl], 2-(2-phenyl-1H-pyrrolo[2,3-b]pyridin-3-yl)-acetamide, 3-allyl-2-phenyl-1H-pyrrolo[2,3-b]pyridine, (2-phenyl-1H-pyrrolo[2,3-b]pyridin-3-yl)-acetonitrile, 2-phenyl-1H-pyrrolo[2,3-b]pyridine-3-carbaldehyde, 3-morpholin-4-ylmethyl-2-phenyl-1H-pyrrolo[2,3-b]pyridine, N-[2-(2-phenyl-1H-pyrrolo[2,3-b]pyridin-3-yl)-ethyl]-acetamide, 6-phenyl-5H-pyrrolo[2,3-b]pyrazine, 6-(4-methoxy-phenyl)-5H-pyrrolo[2,3-b]pyrazine, 6-(4-chloro-phenyl)-5H-pyrrolo[2,3-b]pyrazine, 6-(2-chloro-phenyl)-5H-pyrrolo[2,3-b]pyrazine, 3-methyl-6-phenyl-5H-pyrrolo[2,3-b]pyrazine, 2-methyl-6-phenyl-5H-pyrrolo[2,3-b]pyrazine and 7-methyl-6-phenyl-5H-pyrrolo[2,3-b]pyrazine.

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, p283 "Bioisosterism In Drug Design"; Yun, Hwahak Sekye, 1993, 33, pages 576–579 "Application Of Bioisosterism To New Drug Design"; Zhao, Huaxue Tongbao, 1995, pages 34–38 "Bioisosteric Replacement And Development Of Lead Compounds In Drug Design"; Graham, Theochem, 1995, 343, pages 105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydroxy-1-methylpyrazolyl.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably 2 to about 6 carbon atoms (e.g. 2 to 4 carbon atoms) in the chain. "Branched," as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain, which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" is an alkenyl-O— group wherein alkenyl is as defined above. Exemplary alkenyloxy groups include allyloxy.

"Alkoxy" means an alkyl-O— group in which the alkyl group is as described herein. Exemplary alkoxy groups include difluoromethoxy, methoxy, trifluoromethoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched chain having about 1 to about 15 carbon atoms in the chain, optionally substituted by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be a straight or branched chain having 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl. Exemplary alkyl groups substituted by one or more halogen atoms include trifluoromethyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-SO$_2$— group in which the alkyl group is as previously described. Preferred alkylsulfonyl groups are those in which the alkyl group is $C_{1-4}$alkyl.

"Alkylsulfonylcarbamoyl" means an alkyl-SO$_2$—NH—C(=O)— group in which the alkyl group is as previously described. Preferred alkylsulfonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which group may be a straight or branched chain having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Except where otherwise defined, aryl groups may be substituted with one or more aryl group substituents, which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy (or an acid bioisostere), cyano, halo, heteroaroyl, heteroaryl, heteroarylalkyloxy, heteroaroylamino, heteroaryloxy, hydroxy, nitro, trifluoromethyl, —NY$^3$Y$^4$, —CONY$^3$Y$^4$, —SO$_2$NY$^3$Y$^4$, —NY$^3$—C(=O)alkyl, —NY$^3$SO$_2$alkyl or alkyl optionally substituted with aryl, heteroaryl, hydroxy, or —NY$^3$Y$^4$.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl group is as previously described. Exemplary arylalkyloxy groups include benzyloxy and 1- or 2-naphthalenemethoxy.

"Arylalkyloxycarbonyl" means an arylalkyl-O—CO— group in which the arylalkyl group is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include phenoxy and naphthoxy, each optionally substituted.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylsulfonylcarbamoyl" means an aryl-$SO_2$—NH—C (=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are selected from carbon, oxygen, sulfur, and nitrogen. Examples of azaheteroaryl groups include benzimidazolyl, imidazolyl, indazolinyl, indolyl, isoquinolinyl, pyridyl, pyrimidinyl, pyrrolyl, quinolinyl, quinazolinyl and tetrahydroindolizinyl.

"Cyclic amine" means a 3 to 8 membered monocyclic cycloalkyl ring system wherein one of the ring carbon atoms is replaced by nitrogen and which (i) may also contain a further heteroatom-containing group selected from O, S, $SO_2$, or $NY^7$ (where $Y^7$ is hydrogen, alkyl, aryl, arylalkyl, —C(=O)—$R^7$, —C(=O)—$OR^7$ or —$SO_2R^7$); and (ii) may be fused to additional aryl (e.g. phenyl), heteroaryl (e.g. pyridyl), heterocycloalkyl or cycloalkyl rings to form a bicyclic or tricyclic ring system. Exemplary cyclic amines include pyrrolidine, piperidine, morpholine, piperazine, indoline, pyrindoline, tetrahydroquinoline and the like groups.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl and cycloheptenyl.

"Cycloalkyl" means a saturated monocyclic or bicyclic ring system of about 3 to about 10 carbon atoms, optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkyl" means a cycloalkyl-alkyl- group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Halo" or "halogen" means fluoro, chloro, bromo, or iodo. Preferred are fluoro and chloro.

"Heteroaroyl" means a heteroaryl-C(=O)— group in which the heteroaryl group is as described herein. Exemplary heteroaryl groups include pyridylcarbonyl.

"Heteroaroylamino" means a heteroaroyl-NH— group in which the heteroaryl moiety is as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulfur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above except where otherwise defined); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups, optionally substituted by one or more "aryl group substituents" as defined above, except where otherwise defined). Optional substituents include one or more "aryl group substituents" as defined above, except where otherwise defined.

"Heteroarylalkyl" means a heteroaryl-alkyl- group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroaryloxy" means an heteroaryl-O— group in which the heteroaryl group is as previously described. Exemplary heteroaryloxy groups include optionally substituted pyridyloxy.

"Heteroarylsulfonylcarbamoyl" means a heteroaryl-$SO_2$—NH—C(=O)— group in which the heteroaryl group is as previously described.

"Heterocycloalkyl" means: (i) a cycloalkyl group of about 3 to 7 ring members which contains one or more heteroatoms or heteroatom-containing groups selected from O, S and $NY^7$ and mat be optionally substituted by oxo; (ii) a partially saturated multicyclic heterocarbocyclic moiety in which an aryl (or heteroaryl) ring, each optionally substituted by one or more "aryl group substituents," and a heterocycloalkyl group are fused together to form a cyclic structure. (Examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule.

Alternatively, an ester of a compound of formula (I) containing a carboxy group may be convertible by hydrolysis in vivo to the parent molecule.

Suitable esters of compounds of formula (I) containing a hydroxy group are, for example acetates, citrates, lactates, tartrates, malonates, oxalates, salicylates, propionates, succinates, fumarates, maleates, methylene-bis-O-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of formula (I) containing a carboxy group are, for example, those described by F. J. Leinweber, Drug Metab. Res., 1987, 18, page 379.

Suitable esters of compounds of formula (I) containing both a carboxy group and a hydroxy group within the moiety -$L^1$-Y include lactones formed by loss of water between said carboxy and hydroxy groups. Examples of such lactones include caprolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent optionally substituted heteroaryl, especially optionally substituted azaheteroaryl. Exemplary optionally substituted azaheteroaryls include indolyl, furanyl, pyridyl, pyrrolyl, pyrazolyl, quinolinyl, isoquinolinyl, imidazolyl, indazolyl, indolizinyl, tetrahydroindolizinyl and indazolinyl. Optional substituents include one or more groups selected from alkylenedioxy, alkenyl, alkenyloxy, aryl, carboxy (or an acid bioisostere), cyano, halo, hydroxy, heteroaryl, heterocycloalkyl, $R^4$, $C(=O)$—$R^4$, —$C(=O)$—$NY^1Y^2$, —$NY^1Y^2$ and —$OR^4$. $R^1$ more preferably represents optionally substituted indolyl, optionally substituted indolizinyl or optionally substituted pyrrolyl and is more especially optionally substituted indol-3-yl, indolizin-1-yl or optionally substituted pyrrol-3-yl.

$R^1$ may also particularly represent optionally substituted aryl, especially optionally substituted phenyl. Optional substituents include one or more groups selected from alkylenedioxy, halo, $R^4$, —$NY^1Y^2$ and —$OR^4$. $R^1$ still more preferably represents 4-substituted phenyl, more especially 4-tertiarybutylphenyl, $R^2$ may particularly represent hydrogen.

$R^2$ may also particularly represent halo.

$R^2$ may also particularly represent lower alkyl optionally substituted by carboxy, cyano, halo, hydroxy, tetrazolyl, or —$CONY^3Y^4$.

$R^2$ may also particularly represent lower alkenyl.

$R^3$ may particularly represent hydrogen.

$R^3$ may also particularly represent optionally substituted aryl, especially optionally substituted phenyl.

$R^3$ may also particularly represent lower alkyl (e.g. methyl).

$X^1$ may particularly represent N.

$X^1$ may also particularly represent CH.

$X^1$ may also particularly represent C-lower alkoxy, especially C—$OCH_3$.

$X^1$ may also particularly represent C-aryl, especially C-phenyl.

$X^1$ may also particularly represent C-halo, especially C—Cl.

$X^1$ may also particularly represent C—CN.

It is to be understood that this invention covers all appropriate combinations of the particular and preferred groupings referred to herein.

A particular preferred group of compounds of the invention are compounds of formula (Ia):

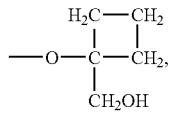

in which R² R³ and X¹ are as hereinbefore defined; R⁹ is hydrogen, R⁴, alkenyl or heterocycloalkyl; R¹⁰ is alkenyloxy, carboxy (or an acid bioisostere), cyano, halo, hydroxy, heteroaryl, R⁴, —C(=O)—R⁴, —C(=O)—NY¹Y², —OR⁴, —N(R⁶)—C(=O)—R⁷, —N(R⁶)—SO₂—R⁷ or —NY¹Y²; and p is zero, or an integer 1 or 2; and their prodrugs and pharmaceutically acceptable salts, and solvates (e.g. hydrates) of compounds of formula (Ia) and their prodrugs.

Compounds of formula (Ia) in which R² represents hydrogen are preferred.

Compounds of formula (Ia) in which R³ is hydrogen, optionally substituted aryl (e.g. phenyl) or lower alkyl (e.g. methyl), especially hydrogen, are preferred.

Compounds of formula (Ia) in which X¹ is CH, C-lower alkoxy (e.g. C—OCH₃), C-aryl, (e.g. C-phenyl), C-halo (e.g. C—Cl), C—CN or N are preferred.

Compounds of formula (Ia) in which R⁹ represents:
(i) hydrogen;
(ii) C₁₋₄alkyl [e.g. —CH₃];
(iii) C₁₋₄alkyl substituted by hydroxy [e.g. —CH₂OH, —CH₂CH₂OH or —CH₂CH₂CH₂OH];
(iv) C₁₋₄alkyl substituted by —N(R⁶)C(=O)—R⁷ [e.g. —CH₂CH₂CH₂NHC(=O)CH₃];
(v) C₁₋₄alkyl substituted by —C(=O)—NY¹Y²

[e.g. 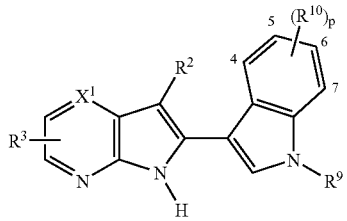];

or
(vi) cycloalkylalkyl substituted by hydroxy

[e.g. 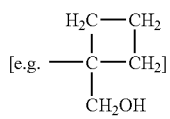]

are preferred. Compounds of formula (Ia) in which R⁹ represents hydrogen or —CH₃ are especially preferred.

Compounds of formula (Ia) in which R¹⁰ represents:
(i) hydroxy;
(ii) —OR⁴ in which R⁴ is alkyl [e.g. —OCH₃];
(iii) —OR⁴ in which R⁴ is alkyl or cycloalkylalkyl substituted by one or more hydroxy groups [e.g. —OCH₂CH₂OH, —OCH₂CH₂CH₂OH, —OCH(CH₃)CH₂OH, —OCH₂CH(OH)CH₃,

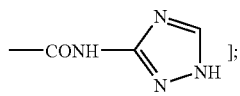

—OCH(OH)CH₂OH, or —OCH₂CH(OH)CH₂OH];
(iv) —OR⁴ in which R⁴ is alkyl substituted by one or more alkoxy groups [e.g. —OCH(CH₃)CH₂OCH₃];
(v) —OR⁴ in which R⁴ is alkyl or cycloalkyl substituted by one or more carboxy groups [e.g. —OCH₂CO₂H, —OCH(CH₃)CO₂H or

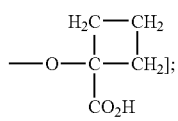];

(vi) —OR⁴ in which R⁴ is cycloalkyl substituted by —C(=O)—NY¹Y² [e.g.

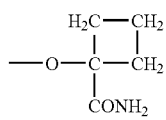

or

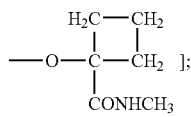];

(vii) —N(R⁶)—C(=O)—R⁷ [e.g. —NHC(=O)CH₃];
(viii) —CONY¹Y² [e.g. —CONH₂, —CONHCH₃, —CONHCH(CH₂OH)₂, —CONHCH₂CH₂OH, —CONHC(CH₃)₂CH₂OH, —CONHCH₂CH₂OCH₃, —CONHCH₂CH₂CO₂H, —CONHCH₂CH₂CONH₂ or

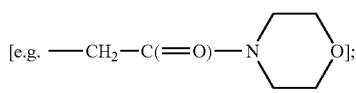];

(ix) carboxy
(x) alkyl substituted by carboxy [e.g. —CH₂CH₂CO₂H];
(xi) heteroaryl [e.g.

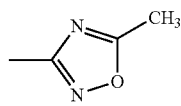

or pyridyl];
(xii) —C(=O)—R⁴ in which R⁴ is alkyl [e.g. —C(=O)—CH₃]; or are preferred. Compounds of formula (Ia) in which R¹⁰ represents

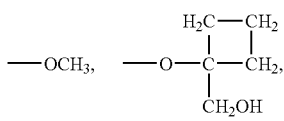, 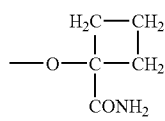, 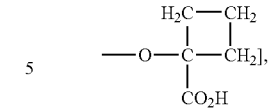 or

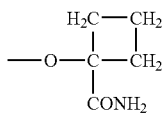

are especially preferred.

When p is 1, $R^{10}$ is preferably attached to position 5 of the indolyl ring.

When p is 2, the $R^{10}$ groups are preferably attached to positions 5 and 6 of the indolyl ring.

A preferred group of compounds of the invention are compounds of formula (Ia) in which: $R^2$ is hydrogen; $R^3$ is hydrogen, optionally substituted aryl (e.g. phenyl) or lower alkyl (e.g. methyl), especially hydrogen; $X^1$ is CH, C-lower alkoxy [especially C—$OCH_3$], C-aryl [especially C-phenyl], C-halo [especially C—Cl] or C—CN; $R^9$ is (i) hydrogen, (ii) $C_{1-4}$alkyl [e.g. —$CH_3$], (iii) $C_{1-4}$alkyl substituted by hydroxy [e.g. —$CH_2OH$, —$CH_2CH_2OH$ or —$CH_2CH_2CH_2OH$], (iv) $C_{1-4}$alkyl substituted by —N($R^6$)C(=O)—$R^7$ [e.g. —$CH_2CH_2CH_2NHC(=O)CH_3$], (v) $C_{1-4}$alkyl substituted by —C(=O)—$NY^1Y^2$ [e.g.

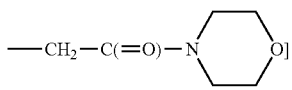

or (vi) cycloalkylalkyl substituted by hydroxy [e.g.

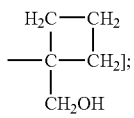

$R^{10}$ is (i) hydroxy, (ii) —$OR^4$ in which $R^4$ is alkyl [e.g. —$OCH_3$], (iii) —$OR^4$ in which $R^4$ is alkyl or cycloalkylalkyl substituted by one or more hydroxy groups [e.g. —$OCH_2CH_2OH$, —$OCH_2CH_2CH_2OH$, —$OCH_2CH(OH)CH_2OH$, —$OCH_2CH(OH)CH_3$, —$OCH(CH_3)CH_2OH$ or

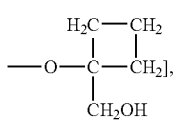

(iv) —$OR^4$ in which $R^4$ is alkyl substituted by one or more alkoxy groups [e.g. —$OCH(CH_3)CH_2OCH_3$], (v) —$OR^4$ in which $R^4$ is alkyl or cycloalkyl substituted by one or more carboxy groups [e.g. —$OCH_2CO_2H$, —$OCH(CH_3)CO_2H$ or

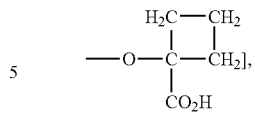

(vi) —$OR^4$ in which $R^4$ is cycloalkyl substituted by —C(=O)—$NY^1Y^2$

[e.g. 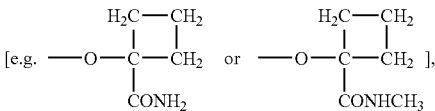 or 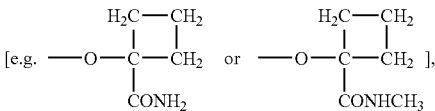], (vii) —N($R^6$)—C(=O)—$R^7$ [e.g. —NHC(=O)$CH_3$]; (viii) —$CONY^1Y^2$ [e.g. —$CONH_2$, —$CONHCH_3$, —CONHCH($CH_2OH)_2$, —$CONHCH_2CH_2OH$, —CONHC($CH_3)_2$$CH_2OH$, —$CONHCH_2CH_2OCH_3$, —$CONHCH_2CH_2CO_2H$, —$CONHCH_2CH_2CONH_2$ or

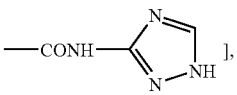

(ix) carboxy, (x) alkyl substituted by carboxy [e.g. —$CH_2CH_2CO_2H$], (xi) heteroaryl [e.g.

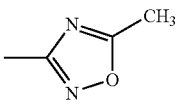

or pyridyl], (xii) —C(=O)—$R^4$ in which $R^4$ is alkyl [e.g. —C(=O)—$CH_3$] or (xii) tetrazolyl or N-methyltetrazolyl; the $R^{10}$ group is attached to position 5 of the indolyl ring when p is 1 and the $R^{10}$ groups are attached to position 5 and 6 of the indolyl ring when p is 2; and the corresponding N-oxides, and their prodrugs; and pharmaceutically acceptable salts and solvates (e.g. hydrates) of such compounds and their N-oxides and prodrugs.

A further preferred group of compounds of the invention are compounds of formula (Ia) in which: $R^2$ is hydrogen; $R^3$ is hydrogen or lower alkyl (e.g. methyl), especially hydrogen; $X^1$ is N; $R^9$ is (i) hydrogen, (ii) $C_{1-4}$alkyl [e.g. —$CH_3$], (iii) $C_{1-4}$alkyl substituted by hydroxy [e.g. —$CH_2OH$, —$CH_2CH_2OH$ or —$CH_2CH_2CH_2OH$], (iv) $C_{1-4}$alkyl substituted by —N($R^6$)C(=O)—$R^7$ [e.g. —$CH_2CH_2CH_2NHC(=O)CH_3$], (v) $C_{1-4}$alkyl substituted by —C(=O)—$NY^1Y^2$ [e.g.

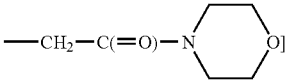

or (vi) cycloalkylalkyl substituted by hydroxy [e.g.

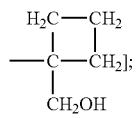

$R^{10}$ is (i) hydroxy, (ii) —$OR^4$ in which $R^4$ is alkyl [e.g. —$OCH_3$], (iii) —$OR^4$ in which $R^4$ alkyl or cycloalkylalkyl substituted by one or more hydroxy groups [e.g. —$OCH_2CH_2OH$, —$OCH_2CH_2CH_2OH$, —$OCH_2CH(OH)CH_2OH$, —$OCH_2CH(OH)CH_3$, —$OCH(CH_3)CH_2OH$ or

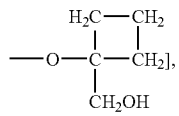

(iv) —$OR^4$ in which $R^4$ is alkyl substituted by one or more alkoxy groups [e.g. —$OCH(CH_3)CH_2OCH_3$], (v) —$OR^4$ in which $R^4$ is alkyl or cycloalkyl substituted by one or more carboxy groups [e.g. —$OCH_2CO_2H$, —$OCH(CH_3)CO_2H$ or

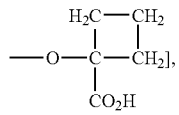

(vi) —$OR^4$ in which $R^4$ is cycloalkyl substituted by —$C(=O)$—$NY^1Y^2$

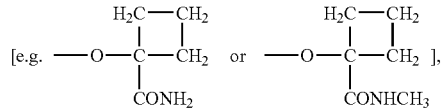

(vii) —$N(R^6)$—$C(=O)$—$R^7$ [e.g. —$NHC(=O)CH_3$]; (viii) —$CONY^1Y^2$ [e.g. —$CONH_2$, —$CONHCH_3$, —$CONHCH(CH_2OH)_2$, —$CONHCH_2CH_2OH$, —$CONHC(CH_3)_2CH_2OH$, —$CONHCH_2CH_2OCH_3$, —$CONHCH_2CH_2CO_2H$, —$CONHCH_2CH_2CONH_2$ or

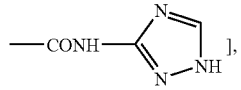

(ix) carboxy, (x) alkyl substituted by carboxy [e.g. —$CH_2CH_2CO_2H$], (xi) heteroaryl [e.g.

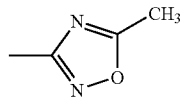

or pyridyl], (xii) —$C(=O)$—$R^4$ in which $R^4$ is alkyl [e.g. —$C(=O)$—$CH_3$] or (xii) tetrazolyl or N-methyltetrazolyl; the $R^{10}$ group is attached to position 5 of the indolyl ring when p is 1 and the $R^{10}$ groups are attached to position 5 and 6 of the indolyl ring when p is 2; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ib):

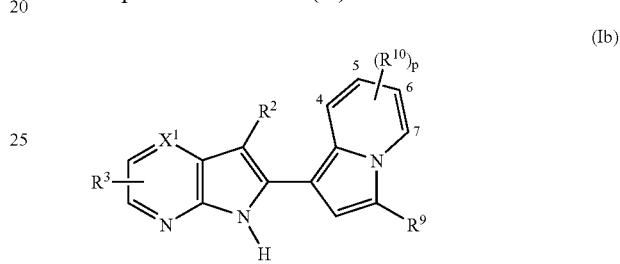

(Ib)

in which $R^2$, $R^3$, $R^9$, $R^{10}$, $X^1$ and p are as hereinbefore defined, and their prodrugs and pharmaceutically acceptable salts, and solvates (e.g. hydrates) of compounds of formula (Ib) and their prodrugs.

Compounds of formula (Ib) in which $R^2$ represents hydrogen are preferred.

Compounds of formula (Ib) in which $R^3$ is hydrogen, optionally substituted aryl (e.g. phenyl) or lower alkyl (e.g. methyl), especially hydrogen, are preferred.

Compounds of formula (Ib) in which $X^1$ is CH, C-lower alkoxy (e.g. C—$OCH_3$), C-aryl, (e.g. C-phenyl), C-halo (e.g. C—Cl), C—CN or N are preferred.

Compounds of formula (Ib) in which $R^9$ represents hydrogen are preferred.

Compounds of formula (Ib) in which $R^9$ represents $C_{1-4}$alkyl [e.g. —$CH_3$] are also preferred.

Compounds of formula (Ib) in which p is zero are preferred.

A preferred group of compounds of the invention are compounds of formula (Ib) in which: $R^2$ is hydrogen; $R^3$ is hydrogen, optionally substituted aryl (e.g. phenyl) or lower alkyl (e.g. methyl), especially hydrogen; $X^1$ is CH, C-lower alkoxy [especially C—$OCH_3$], C-aryl [especially C-phenyl], C-halo [especially C—Cl] or C—CN; $R^9$ is hydrogen or $C_{1-4}$alkyl [e.g. —$CH_3$]; p is zero; and the corresponding N-oxides, and their prodrugs; and pharmaceutically acceptable salts and solvates (e.g. hydrates) of such compounds and their N-oxides and prodrugs.

A further preferred group of compounds of the invention are compounds of formula (Ib) in which: $R^2$ is hydrogen; $R^3$ is hydrogen or lower alkyl (e.g. methyl), especially hydrogen; $X^1$ is N; $R^9$ is hydrogen or $C_{1-4}$alkyl [e.g. —$CH_3$]; p is zero; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ic):

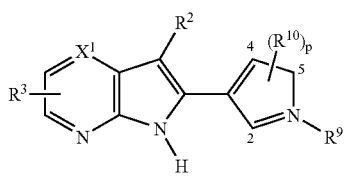

in which $R^2$, $R^3$, $R^9$, $R^{10}$, $X^1$ and p are as hereinbefore defined, and their prodrugs and pharmaceutically acceptable salts, and solvates (e.g. hydrates) of compounds of formula (Ic) and their prodrugs.

Compounds of formula (Ic) in which $R^2$ represents hydrogen are preferred.

Compounds of formula (Ic) in which $R^3$ is hydrogen, optionally substituted aryl (e.g. phenyl) or lower alkyl (e.g. methyl), especially hydrogen, are preferred.

Compounds of formula (Ic) in which $X^1$ is CH, C-lower alkoxy (e.g. C—OCH$_3$), C-aryl, (e.g. C-phenyl), C-halo (e.g. C—Cl), C—CN or N are preferred.

Compounds of formula (Ic) in which $R^9$ represents $C_{1-4}$alkyl [e.g. —CH$_3$] are also preferred.

Compounds of formula (Ic) in which p is 1 are preferred.

Compounds of formula (Ic) in which $R^{10}$ represents aryl [e.g. phenyl] are preferred.

$R^{10}$ is preferably attached at position 4 of the pyrrole ring.

A preferred group of compounds of the invention are compounds of formula (Ic) in which: $R^2$ is hydrogen; $R^3$ is hydrogen, optionally substituted aryl (e.g. phenyl) or lower alkyl (e.g. methyl), especially hydrogen; $X^1$ is CH, C-lower alkoxy [especially C—OCH$_3$], C-aryl [especially C-phenyl], C-halo [especially C—Cl] or C—CN; $R^9$ is $C_{1-4}$alkyl [e.g. —CH$_3$]; p is 1; $R^{10}$ is aryl [e.g. phenyl] and $R^{10}$ is attached at position 4 of the pyrrole ring; and the corresponding N-oxides, and their prodrugs; and pharmaceutically acceptable salts and solvates (e.g. hydrates) of such compounds and their N-oxides and prodrugs. $R^3$ is hydrogen, optionally substituted aryl (e.g. phenyl) or lower alkyl (e.g. methyl), especially hydrogen; $X^1$ is CH, C-lower alkoxy [especially C—OCH$_3$], C-aryl [especially C-phenyl], C-halo [especially C—Cl] or C—CN;

A further preferred group of compounds of the invention are compounds of formula (Ic) in which: $R^2$ is hydrogen; $R^3$ is hydrogen; $X^1$ is N; $R^9$ is $C_{1-4}$alkyl [e.g. —CH$_3$]; p is 1; $R^{10}$ is aryl [e.g. phenyl] and $R^{10}$ is attached at position 4 of the pyrrole ring; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Id):

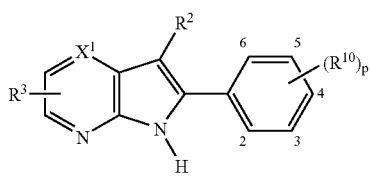

in which $R^2$, $R^3$, $R^{10}$, $X^1$ and p are as hereinbefore defined, and their prodrugs and pharmaceutically acceptable salts, and solvates (e.g. hydrates) of compounds of formula (Id) and their prodrugs.

Compounds of formula (Id) in which $R^2$ represents hydrogen, lower alkyl (e.g. methyl), lower alkyl substituted by —CONY$^3$Y$^4$ (e.g. —CH$_2$CH$_2$CONH$_2$ or —CH$_2$CH$_2$CONHCH$_3$), lower alkyl substituted by carboxy (e.g. —CH$_2$CH$_2$CO$_2$H), lower alkyl substituted by tetrazolyl (e.g.

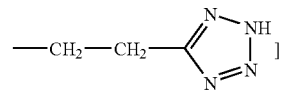

or lower alkyl substituted by hydroxy [e.g. —CH$_2$CH$_2$CH$_2$OH] are preferred.

Compounds of formula (Id) in which $R^3$ is hydrogen, optionally substituted aryl (e.g. phenyl) or lower alkyl (e.g. methyl), especially hydrogen, are preferred.

Compounds of formula (Id) in which $X^1$ is CH, C-lower alkoxy (e.g. C—OCH$_3$), C-aryl, (e.g. C-phenyl), C-halo (e.g. C—Cl), C—CN or N are preferred.

Compounds of formula (Id) in which p is 1 are preferred.

Compounds of formula (Id) in which $R^{10}$ represents alkyl [e.g. tertiarybutyl] are preferred.

$R^{10}$ is preferably attached at position 4.

A preferred group of compounds of the invention are compounds of formula (Id) in which: $R^2$ is hydrogen, lower alkyl (e.g. methyl), lower alkyl substituted by —CONY$^3$Y$^4$ (e.g. —CH$_2$CH$_2$CONH$_2$ or —CH$_2$CH$_2$CONHCH$_3$), lower alkyl substituted by carboxy (e.g. —CH$_2$CH$_2$CO$_2$H), lower alkyl substituted by tetrazolyl (e.g.

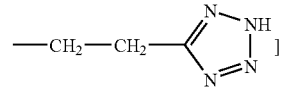

or lower alkyl substituted by hydroxy [e.g. —CH$_2$CH$_2$CH$_2$OH]; $R^3$ is hydrogen, optionally substituted aryl (e.g. phenyl) or lower alkyl (e.g. methyl), especially hydrogen; $X^1$ is CH, C-lower alkoxy [especially C—OCH$_3$], C-aryl [especially C-phenyl], C-halo [especially C—Cl] or C—CN; p is 1; $R^{10}$ is alkyl [e.g. tertiary-butyl] and $R^{10}$ is attached at position 4; and the corresponding N-oxides, and their prodrugs; and pharmaceutically acceptable salts and solvates (e.g. hydrates) of such compounds and their N-oxides and prodrugs.

A further preferred group of compounds of the invention are compounds of formula (Id) in which: $R^2$ is hydrogen, lower alkyl (e.g. methyl), lower alkyl substituted by —CONY$^3$Y$^4$ (e.g. —CH$_2$CH$_2$CONH$_2$ or —CH$_2$CH$_2$CONHCH$_3$), lower alkyl substituted by carboxy (e.g. —CH$_2$CH$_2$CO$_2$H), lower alkyl substituted by tetrazolyl (e.g.

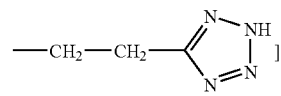

or lower alkyl substituted by hydroxy [e.g. —CH$_2$CH$_2$CH$_2$OH]; R$^3$ is hydrogen; X$^1$ is N; p is 1; R$^{10}$ is alkyl [e.g. tertiary-butyl] and R$^{10}$ is attached at position 4; and the corresponding N-oxides, and their prodrugs; and pharmaceutically acceptable salts and solvates (e.g. hydrates) of such compounds and their N-oxides and prodrugs.

Particular compounds of the invention of formula (Ia) are selected from the compounds formed by joining the carbon atom (C*) of one of the azaindoles fragments (A1 to A28) shown in Table 1 to the carbon atom (*C) in the five membered ring of one of the fragments (B1 to B19) shown in Table 2, and joining the carbon atom (C*) of the phenyl ring in one of the fragments (B1 to B19) shown in Table 2 to the oxygen atom (*O) of one of the fragments (C1 to C19) depicted in Table 3.

Particular compounds of the invention of formula (Ia) are also selected from the compounds formed by joining the carbon atom (C*) of one of the azaindoles fragments (A1 to A28) shown in Table 1 to the carbon atom (*C) in the five membered ring of one of the fragments (B1 to B19) shown in Table 2, and joining the carbon atom (C*) of the phenyl ring in one of the fragments (B1 to B19) shown in Table 2 to the carbon atom (*C) of one of the fragments (C20 to C44) depicted in Table 3.

Particular compounds of the invention of formula (Ia) are also selected from the compounds formed by joining the carbon atom (C*) of one of the azaindoles fragments (A1 to A28) shown in Table 1 to the carbon atom (*C) in the five membered ring of one of the fragments (B1 to B19) shown in Table 2, and joining the carbon atom (C*) of the phenyl ring in one of the fragments (B1 to B19) shown in Table 2 to the nitrogen atom (*N) of the fragment (C45) or a hydrogen atom (*H, fragment (C46)) depicted in Table 3.

Particular compounds of the invention of formula (Ib) are selected from the compounds formed by joining the carbon atom (C*) of one of the azaindoles fragments (A1 to A28) shown in Table 1 to the carbon atom (*C) in the five membered ring of one of the indolizine fragments (B20 or B21) shown in Table 2, and joining the carbon atom (C*) in the six membered ring of one of the indolizine fragments (B20 or B21) shown in Table 2 to (i) the oxygen atom (*O) of one of the fragments (C1 to C19), (ii) the carbon atom (*C) of one of the fragments (C20 to C42), (iii) the nitrogen atom (*N) of the fragment (C45) or (iv) a hydrogen atom (*H, fragment (C46)) depicted in Table 3.

Particular compounds of the invention of formula (Ib) are also selected from the compounds formed by joining the carbon atom (C*) of one of the azaindoles fragments (A1 to A28) shown in Table 1 to the carbon atom (*C) in the indolizine fragments (B22) shown in Table 2.

Particular compounds of the invention of formula (Ic) are selected from the compounds formed by joining the carbon atom (C*) of one of the azaindoles fragments (A1 to A28) shown in Table 1 to the carbon atom (*C) in one of the pyrrole fragments (B23 to B32) shown in Table 2.

Particular compounds of the invention of formula (Id) are selected from the compounds formed by joining the carbon atom (C*) of one of the azaindoles fragments (A29 to A41) shown in Table 1 to the carbon atom (*C) in one of the fragments (B33 to B44) shown in Table 2.

TABLE 1

| | |
|---|---|
| A1 | 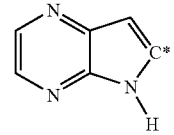 |
| A2 | 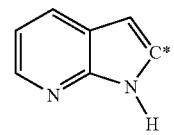 |
| A3 | 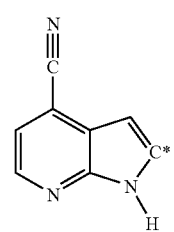 |
| A4 | 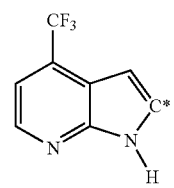 |
| A5 |  |
| A6 | 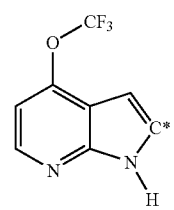 |
| A7 | 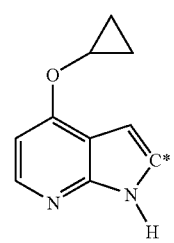 |

TABLE 1-continued
| A8 | 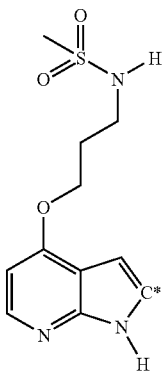 |
| A9 |  |
| A10 | 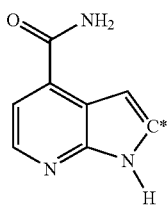 |
| A11 | 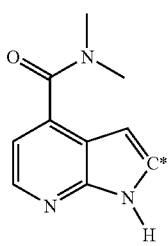 |
| A12 | 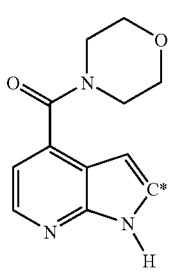 |
| A13 | 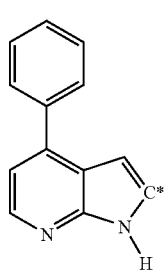 |
TABLE 1-continued
| A14 | 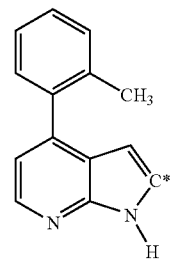 |
| A15 | 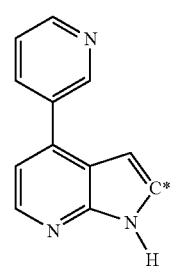 |
| A16 | 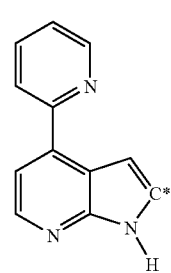 |
| A17 | 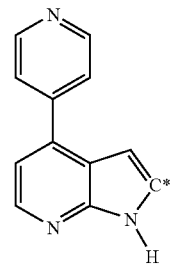 |
| A18 | 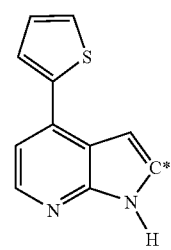 |
| A19 | 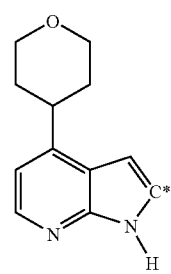 |

TABLE 1-continued
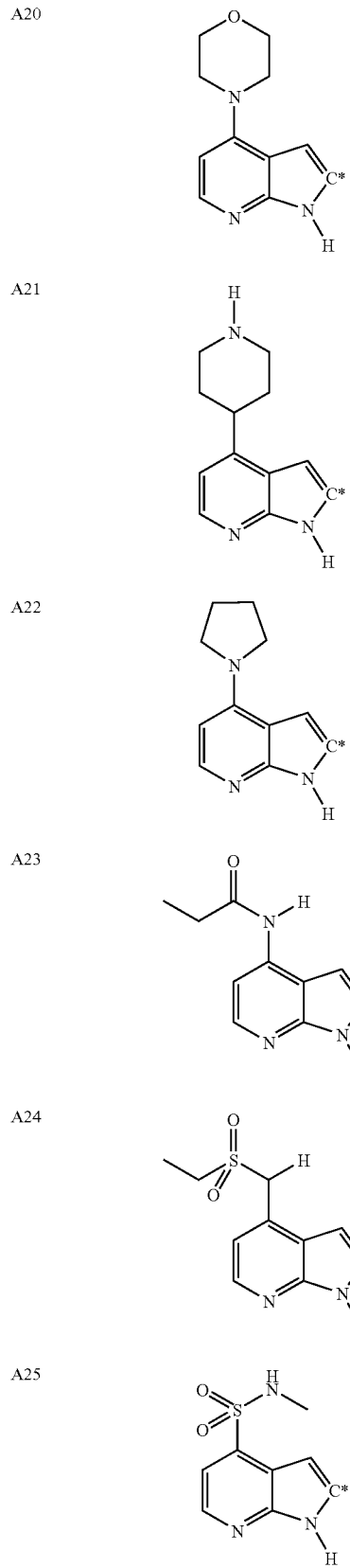
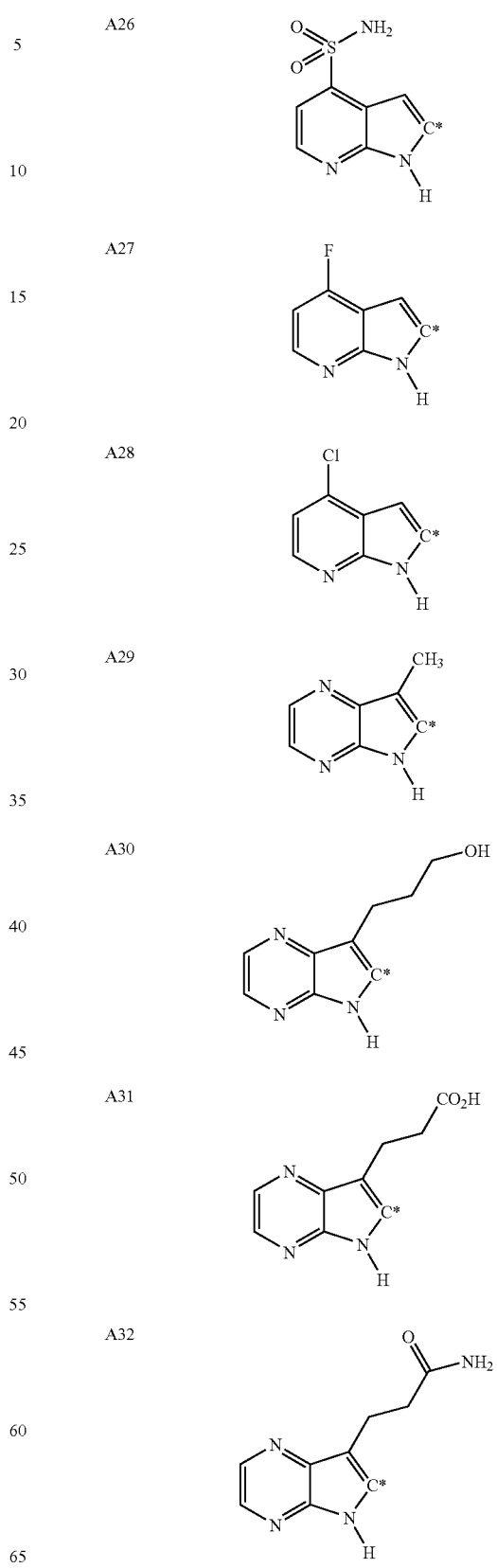

TABLE 1-continued
A33 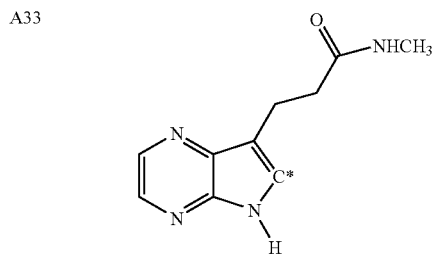
A34 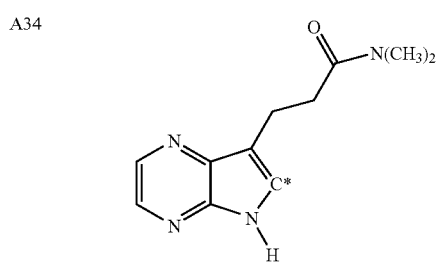
A35 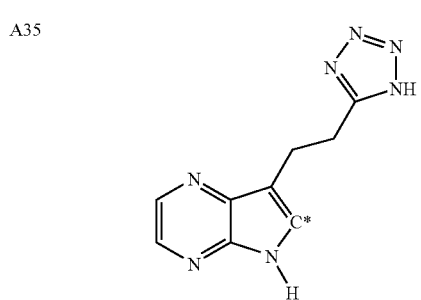
A36 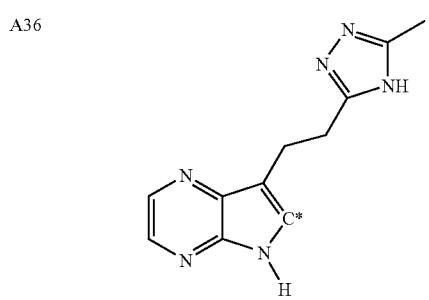
A37 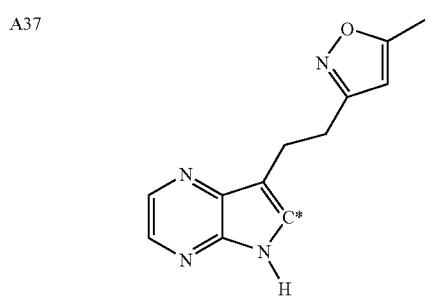
TABLE 1-continued
A38 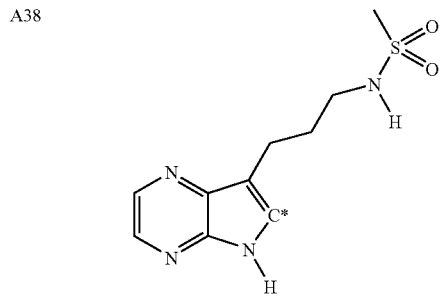
A39 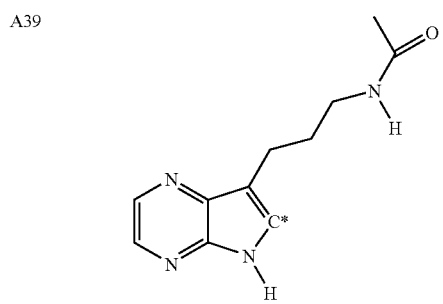
A40 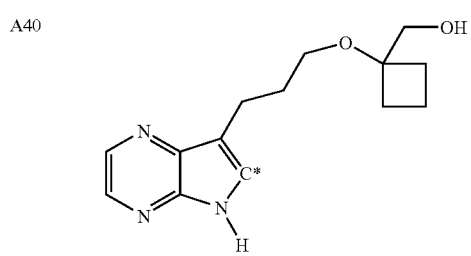
A41 
TABLE 2
B1 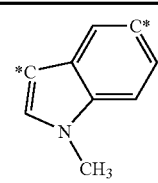
B2 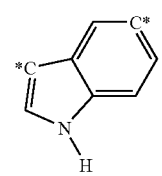

TABLE 2-continued

| | |
|---|---|
| B3 | indole, N-CH₂CH₃ |
| B4 | indole, N-CH₂OH |
| B5 | indole, N-CH₂CH₂OH |
| B6 | indole, N-CH₂CH₂CH₂OH |
| B7 | indole, N-CH₂CH₂CH₂NHCOCH₃ |
| B8 | indole, N-CH₂-C(=O)-morpholine |
| B9 | indole, N-CH₂-C(=O)NH₂ |
| B10 | indole, N-CH₂-C(=O)-N(CH₂CH₂OH)₂ |
| B11 | indole, N-CH₂-C(=O)-NH-CH₂CH₂OH |
| B12 | indole, N-(1-carboxycyclobutyl) |
| B13 | indole, N-(1-hydroxymethylcyclobutyl) |
| B14 | indole, N-CH₂CH(OH)CH₃ |
| B15 | 2-chloro-1-methyl-indole |

TABLE 2-continued
| | | |
|---|---|---|
| B16 | 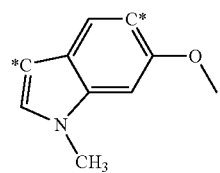 | |
| B17 | 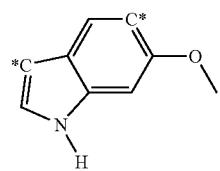 | |
| B18 | 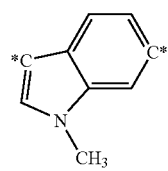 | |
| B19 | 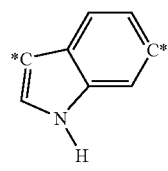 | |
| B20 | 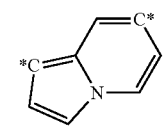 | |
| B21 | 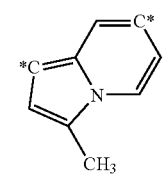 | |
| B22 | 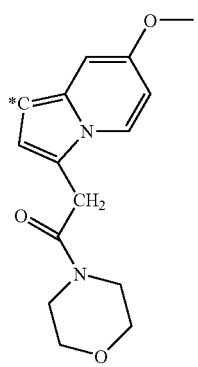 | |
| B23 | 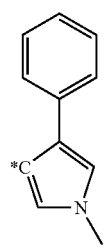 | |
| B24 | 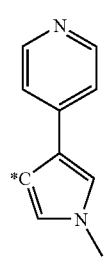 | |
| B25 | 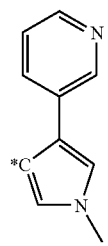 | |
| B26 | 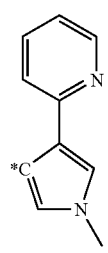 | |
| B27 | 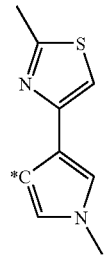 | |
| B28 | 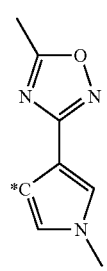 | |

TABLE 2-continued
| | |
|---|---|
| B29 | 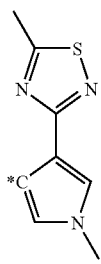 |
| B30 | 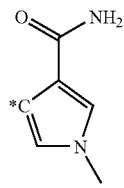 |
| B31 | 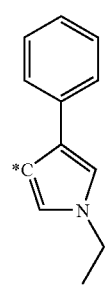 |
| B32 | 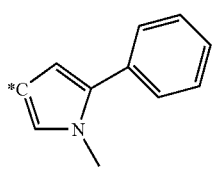 |
| B33 | 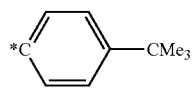 |
| B34 | 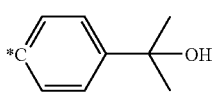 |
| B35 | 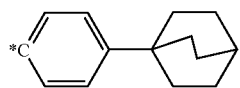 |
| B36 | 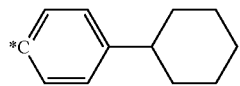 |
| B37 | 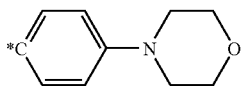 |
| B38 | 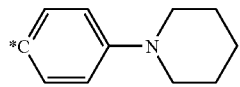 |
| B38 | 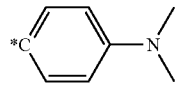 |
TABLE 2-continued
| | |
|---|---|
| B40 | 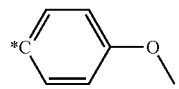 |
| B41 | 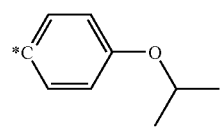 |
| B42 | 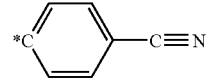 |
| B43 | 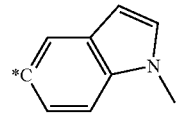 |
| B44 | 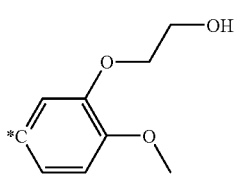 |
TABLE 3
| | |
|---|---|
| C1 | *O—CH$_3$ |
| C2 | 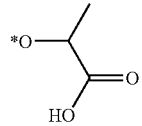 |
| C3 | 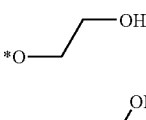 |
| C4 | 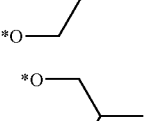 |
| C5 | 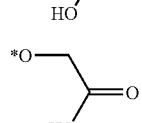 |
| C6 | 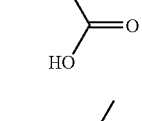 |
| C7 | 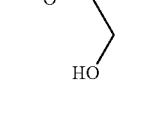 |

TABLE 3-continued

| | | |
|---|---|---|
| C8 | *OCH₂C(=O)NH-CH₂CH₂-OH | |
| C9 | *O-CH₂-CH(OH)-CH₂OH | |
| C10 | *O—H | |
| C11 | *O-(1-carboxycyclobutyl) | |
| C12 | *O-(1-hydroxymethylcyclobutyl) | |
| C13 | *O-(1-methoxymethylcyclobutyl) | |
| C14 | *O-(1-(N-(2-hydroxyethyl)carbamoyl)cyclobutyl) | |
| C15 | *O-(1-carbamoylcyclobutyl) | |
| C16 | *O-(1-(N-methylcarbamoyl)cyclobutyl) | |
| C17 | *O-CH(CH₃)-CH₂-OCH₃ | |
| C18 | *O-CH₂CH₂-NH-C(=O)CH₃ | |
| C19 | *O-CH₂-C(CH₃)(CH₂OH)₂ (showing one OH) | |
| C20 | *C(=O)-CH₃ | |
| C21 | *CH₂—CH₂—CO₂H | |
| C22 | *CH₂—CH₂—CONH₂ | |
| C23 | *C(=O)—NH—CH₃ | |
| C24 | *C(=O)—NH—CH₂—CH₂—CONH₂ | |
| C25 | *C(=O)—NH—CH₂—CH₂—OCH₃ | |
| C26 | *C(=O)—NH—CH₂—CH₂—CON(H)CH₃ | |
| C27 | *C(=O)—NH—CH₂CH₂-(3-thienyl) | |
| C28 | *C(=O)—OH | |
| C29 | *C(=O)—NH₂ | |
| C30 | *C(=O)—NH—C(CH₃)(CH₂OH)₂ | |
| C31 | *C(=O)—NH—C(CH₃)₂—CH₂OH | |
| C32 | *C(=O)—NH—CH(CH₂OH)₂ (with OH) | |
| C33 | *C(=O)—NH—CH(CH₂OH)₂ | |
| C34 | *C(=O)—NH—CH₂—CH₂—OH | |

TABLE 3-continued

| | | |
|---|---|---|
| C35 | 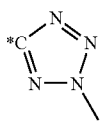 | |
| C36 | 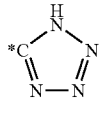 | |
| C37 | 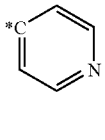 | |
| C38 | 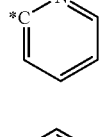 | |
| C39 |  | |
| C40 | 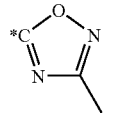 | |
| C41 | *CH$_2$—NH—SO$_2$—CH$_3$ | |
| C42 | 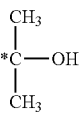 | |
| C43 | 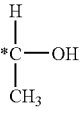 | |
| C44 | *CH$_2$—NH—CO—NHCH$_2$CH$_3$ | |
| C45 | 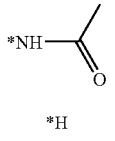 | |
| C46 | *H | |

Particularly preferred examples of fragments "A", "B", and "C" are illustrated below:

A1-B1-C1;   A1-B1-C2;   A1-B1-C3;   A1-B1-C4;   A1-B1-C5;   A1-B1-C6;
A1-B1-C7;   A1-B1-C8;   A1-B1-C9;   A1-B1-C10;  A1-B1-C11;  A1-B1-C12;
A1-B1-C13;  A1-B1-C14;  A1-B1-C15;  A1-B1-C16;  A1-B1-C17;  A1-B1-C18;
A1-B1-C19;  A1-B1-C20;  A1-B1-C21;  A1-B1-C22;  A1-B1-C23;  A1-B1-C24;
A1-B1-C25;  A1-B1-C26;  A1-B1-C27;  A1-B1-C28;  A1-B1-C29;  A1-B1-C30;
A1-B1-C31;  A1-B1-C32;  A1-B1-C33;  A1-B1-C34;  A1-B1-C35;  A1-B1-C36;
A1-B1-C37;  A1-B1-C38;  A1-B1-C39;  A1-B1-C40;  A1-B1-C41;  A1-B1-C42;
A1-B1-C43;  A1-B1-C44;  A1-B1-C45;  A1-B1-C46;  A2-B1-C1;   A2-B1-C2;
A2-B1-C3;   A2-B1-C4;   A2-B1-C5;   A2-B1-C6;   A2-B1-C7;   A2-B1-C8;
A2-B1-C9;   A2-B1-C10;  A2-B1-C11;  A2-B1-C12;  A2-B1-C13;  A2-B1-C14;
A2-B1-C15;  A2-B1-C16;  A2-B1-C17;  A2-B1-C18;  A2-B1-C19;  A2-B1-C20;
A2-B1-C21;  A2-B1-C22;  A2-B1-C23;  A2-B1-C24;  A2-B1-C25;  A2-B1-C26;
A2-B1-C27;  A2-B1-C28;  A2-B1-C29;  A2-B1-C30;  A2-B1-C31;  A2-B1-C32;
A2-B1-C33;  A2-B1-C34;  A2-B1-C35;  A2-B1-C36;  A2-B1-C37;  A2-B1-C38;
A2-B1-C39;  A2-B1-C40;  A2-B1-C41;  A2-B1-C42;  A2-B1-C43;  A2-B1-C44;
A2-B1-C45;  A2-B1-C46;  A3-B1-C1;   A3-B1-C2;   A3-B1-C3;   A3-B1-C4;
A3-B1-C5;   A3-B1-C6;   A3-B1-C7;   A3-B1-C8;   A3-B1-C9;   A3-B1-C10;
A3-B1-C11;  A3-B1-C12;  A3-B1-C13;  A3-B1-C14;  A3-B1-C15;  A3-B1-C16;
A3-B1-C17;  A3-B1-C18;  A3-B1-C19;  A3-B1-C20;  A3-B1-C21;  A3-B1-C22;
A3-B1-C23;  A3-B1-C24;  A3-B1-C25;  A3-B1-C26;  A3-B1-C27;  A3-B1-C28;
A3-B1-C29;  A3-B1-C30;  A3-B1-C31;  A3-B1-C32;  A3-B1-C33;  A3-B1-C34;
A3-B1-C35;  A3-B1-C36;  A3-B1-C37;  A3-B1-C38;  A3-B1-C39;  A3-B1-C40;
A3-B1-C41;  A3-B1-C42;  A3-B1-C43;  A3-B1-C44;  A3-B1-C45;  A3-B1-C46;
A4-B1-C1;   A4-B1-C2;   A4-B1-C3;   A4-B1-C4;   A4-B1-C5;   A4-B1-C6;
A4-B1-C7;   A4-B1-C8;   A4-B1-C9;   A4-B1-C10;  A4-B1-C11;  A4-B1-C12;
A4-B1-C13;  A4-B1-C14;  A4-B1-C15;  A4-B1-C16;  A4-B1-C17;  A4-B1-C18;
A4-B1-C19;  A4-B1-C20;  A4-B1-C21;  A4-B1-C22;  A4-B1-C23;  A4-B1-C24;
A4-B1-C25;  A4-B1-C26;  A4-B1-C27;  A4-B1-C28;  A4-B1-C29;  A4-B1-C30;
A4-B1-C31;  A4-B1-C32;  A4-B1-C33;  A4-B1-C34;  A4-B1-C35;  A4-B1-C36;
A4-B1-C37;  A4-B1-C38;  A4-B1-C39;  A4-B1-C40;  A4-B1-C41;  A4-B1-C42;
A4-B1-C43;  A4-B1-C44;  A4-B1-C45;  A4-B1-C46;  A5-B1-C1;   A5-B1-C2;
A5-B1-C3;   A5-B1-C4;   A5-B1-C5;   A5-B1-C6;   A5-B1-C7;   A5-B1-C8;
A5-B1-C9;   A5-B1-C10;  A5-B1-C11;  A5-B1-C12;  A5-B1-C13;  A5-B1-C14;
A5-B1-C15;  A5-B1-C16;  A5-B1-C17;  A5-B1-C18;  A5-B1-C19;  A5-B1-C20;
A5-B1-C21;  A5-B1-C22;  A5-B1-C23;  A5-B1-C24;  A5-B1-C25;  A5-B1-C26;
A5-B1-C27;  A5-B1-C28;  A5-B1-C29;  A5-B1-C30;  A5-B1-C31;  A5-B1-C32;
A5-B1-C33;  A5-B1-C34;  A5-B1-C35;  A5-B1-C36;  A5-B1-C37;  A5-B1-C38;
A5-B1-C39;  A5-B1-C40;  A5-B1-C41;  A5-B1-C42;  A5-B1-C43;  A5-B1-C44;
A5-B1-C45;  A5-B1-C46;  A6-B1-C1;   A6-B1-C2;   A6-B1-C3;   A6-B1-C4;
A6-B1-C5;   A6-B1-C6;   A6-B1-C7;   A6-B1-C8;   A6-B1-C9;   A6-B1-C10;

-continued

| | | | | | |
|---|---|---|---|---|---|
| A6-B1-C11; | A6-B1-C12; | A6-B1-C13; | A6-B1-C14; | A6-B1-C15; | A6-B1-C16; |
| A6-B1-C17; | A6-B1-C18; | A6-B1-C19; | A6-B1-C20; | A6-B1-C21; | A6-B1-C22; |
| A6-B1-C23; | A6-B1-C24; | A6-B1-C25; | A6-B1-C26; | A6-B1-C27; | A6-B1-C28; |
| A6-B1-C29; | A6-B1-C30; | A6-B1-C31; | A6-B1-C32; | A6-B1-C33; | A6-B1-C34; |
| A6-B1-C35; | A6-B1-C36; | A6-B1-C37; | A6-B1-C38; | A6-B1-C39; | A6-B1-C40; |
| A6-B1-C41; | A6-B1-C42; | A6-B1-C43; | A6-B1-C44; | A6-B1-C45; | A6-B1-C46; |
| A7-B1-C1; | A7-B1-C2; | A7-B1-C3; | A7-B1-C4; | A7-B1-C5; | A7-B1-C6; |
| A7-B1-C7; | A7-B1-C8; | A7-B1-C9; | A7-B1-C10; | A7-B1-C11; | A7-B1-C12; |
| A7-B1-C13; | A7-B1-C14; | A7-B1-C15; | A7-B1-C16; | A7-B1-C17; | A7-B1-C18; |
| A7-B1-C19; | A7-B1-C20; | A7-B1-C21; | A7-B1-C22; | A7-B1-C23; | A7-B1-C24; |
| A7-B1-C25; | A7-B1-C26; | A7-B1-C27; | A7-B1-C28; | A7-B1-C29; | A7-B1-C30; |
| A7-B1-C31; | A7-B1-C32; | A7-B1-C33; | A7-B1-C34; | A7-B1-C35; | A7-B1-C36; |
| A7-B1-C37; | A7-B1-C38; | A7-B1-C39; | A7-B1-C40; | A7-B1-C41; | A7-B1-C42; |
| A7-B1-C43; | A7-B1-C44; | A7-B1-C45; | A7-B1-C46; | A8-B1-C1; | A8-B1-C2; |
| A8-B1-C3; | A8-B1-C4; | A8-B1-C5; | A8-B1-C6; | A8-B1-C7; | A8-B1-C8; |
| A8-B1-C9; | A8-B1-C10; | A8-B1-C11; | A8-B1-C12; | A8-B1-C13; | A8-B1-C14; |
| A8-B1-C15; | A8-B1-C16; | A8-B1-C17; | A8-B1-C18; | A8-B1-C19; | A8-B1-C20; |
| A8-B1-C21; | A8-B1-C22; | A8-B1-C23; | A8-B1-C24; | A8-B1-C25; | A8-B1-C26; |
| A8-B1-C27; | A8-B1-C28; | A8-B1-C29; | A8-B1-C30; | A8-B1-C31; | A8-B1-C32; |
| A8-B1-C33; | A8-B1-C34; | A8-B1-C35; | A8-B1-C36; | A8-B1-C37; | A8-B1-C38; |
| A8-B1-C39; | A8-B1-C40; | A8-B1-C41; | A8-B1-C42; | A8-B1-C43; | A8-B1-C44; |
| A8-B1-C45; | A8-B1-C46; | A9-B1-C1; | A9-B1-C2; | A9-B1-C3; | A9-B1-C4; |
| A9-B1-C5; | A9-B1-C6; | A9-B1-C7; | A9-B1-C8; | A9-B1-C9; | A9-B1-C10; |
| A9-B1-C11; | A9-B1-C12; | A9-B1-C13; | A9-B1-C14; | A9-B1-C15; | A9-B1-C16; |
| A9-B1-C17; | A9-B1-C18; | A9-B1-C19; | A9-B1-C20; | A9-B1-C21; | A9-B1-C22; |
| A9-B1-C23; | A9-B1-C24; | A9-B1-C25; | A9-B1-C26; | A9-B1-C27; | A9-B1-C28; |
| A9-B1-C29; | A9-B1-C30; | A9-B1-C31; | A9-B1-C32; | A9-B1-C33; | A9-B1-C34; |
| A9-B1-C35; | A9-B1-C36; | A9-B1-C37; | A9-B1-C38; | A9-B1-C39; | A9-B1-C40; |
| A9-B1-C41; | A9-B1-C42; | A9-B1-C43; | A9-B1-C44; | A9-B1-C45; | A9-B1-C46; |
| A10-B1-C1; | A10-B1-C2; | A10-B1-C3; | A10-B1-C4; | A10-B1-C5; | A10-B1-C6; |
| A10-B1-C7; | A10-B1-C8; | A10-B1-C9; | A10-B1-C10; | A10-B1-C11; | A10-B1-C12; |
| A10-B1-C13; | A10-B1-C14; | A10-B1-C15; | A10-B1-C16; | A10-B1-C17; | A10-B1-C18; |
| A10-B1-C19; | A10-B1-C20; | A10-B1-C21; | A10-B1-C22; | A10-B1-C23; | A10-B1-C24; |
| A10-B1-C25; | A10-B1-C26; | A10-B1-C27; | A10-B1-C28; | A10-B1-C29; | A10-B1-C30; |
| A10-B1-C31; | A10-B1-C32; | A10-B1-C33; | A10-B1-C34; | A10-B1-C35; | A10-B1-C36; |
| A10-B1-C37; | A10-B1-C38; | A10-B1-C39; | A10-B1-C40; | A10-B1-C41; | A10-B1-C42; |
| A10-B1-C43; | A10-B1-C44; | A10-B1-C45; | A10-B1-C46; | A11-B1-C1; | A11-B1-C2; |
| A11-B1-C3; | A11-B1-C4; | A11-B1-C5; | A11-B1-C6; | A11-B1-C7; | A11-B1-C8; |
| A11-B1-C9; | A11-B1-C10; | A11-B1-C11; | A11-B1-C12; | A11-B1-C13; | A11-B1-C14; |
| A11-B1-C15; | A11-B1-C16; | A11-B1-C17; | A11-B1-C18; | A11-B1-C19; | A11-B1-C20; |
| A11-B1-C21; | A11-B1-C22; | A11-B1-C23; | A11-B1-C24; | A11-B1-C25; | A11-B1-C26; |
| A11-B1-C27; | A11-B1-C28; | A11-B1-C29; | A11-B1-C30; | A11-B1-C31; | A11-B1-C32; |
| A11-B1-C33; | A11-B1-C34; | A11-B1-C35; | A11-B1-C36; | A11-B1-C37; | A11-B1-C38; |
| A11-B1-C39; | A11-B1-C40; | A11-B1-C41; | A11-B1-C42; | A11-B1-C43; | A11-B1-C44; |
| A11-B1-C45; | A11-B1-C46; | A12-B1-C1; | A12-B1-C2; | A12-B1-C3; | A12-B1-C4; |
| A12-B1-C5; | A12-B1-C6; | A12-B1-C7; | A12-B1-C8; | A12-B1-C9; | A12-B1-C10; |
| A12-B1-C11; | A12-B1-C12; | A12-B1-C13; | A12-B1-C14; | A12-B1-C15; | A12-B1-C16; |
| A12-B1-C17; | A12-B1-C18; | A12-B1-C19; | A12-B1-C20; | A12-B1-C21; | A12-B1-C22; |
| A12-B1-C23; | A12-B1-C24; | A12-B1-C25; | A12-B1-C26; | A12-B1-C27; | A12-B1-C28; |
| A12-B1-C29; | A12-B1-C30; | A12-B1-C31; | A12-B1-C32; | A12-B1-C33; | A12-B1-C34; |
| A12-B1-C35; | A12-B1-C36; | A12-B1-C37; | A12-B1-C38; | A12-B1-C39; | A12-B1-C40; |
| A12-B1-C41; | A12-B1-C42; | A12-B1-C43; | A12-B1-C44; | A12-B1-C45; | A12-B1-C46; |
| A13-B1-C1; | A13-B1-C2; | A13-B1-C3; | A13-B1-C4; | A13-B1-C5; | A13-B1-C6; |
| A13-B1-C7; | A13-B1-C8; | A13-B1-C9; | A13-B1-C10; | A13-B1-C11; | A13-B1-C12; |
| A13-B1-C13; | A13-B1-C14; | A13-B1-C15; | A13-B1-C16; | A13-B1-C17; | A13-B1-C18; |
| A13-B1-C19; | A13-B1-C20; | A13-B1-C21; | A13-B1-C22; | A13-B1-C23; | A13-B1-C24; |
| A13-B1-C25; | A13-B1-C26; | A13-B1-C27; | A13-B1-C28; | A13-B1-C29; | A13-B1-C30; |
| A13-B1-C31; | A13-B1-C32; | A13-B1-C33; | A13-B1-C34; | A13-B1-C35; | A13-B1-C36; |
| A13-B1-C37; | A13-B1-C38; | A13-B1-C39; | A13-B1-C40; | A13-B1-C41; | A13-B1-C42; |
| A13-B1-C43; | A13-B1-C44; | A13-B1-C45; | A13-B1-C46; | A14-B1-C1; | A14-B1-C2; |
| A14-B1-C3; | A14-B1-C4; | A14-B1-C5; | A14-B1-C6; | A14-B1-C7; | A14-B1-C8; |
| A14-B1-C9; | A14-B1-C10; | A14-B1-C11; | A14-B1-C12; | A14-B1-C13; | A14-B1-C14; |
| A14-B1-C15; | A14-B1-C16; | A14-B1-C17; | A14-B1-C18; | A14-B1-C19; | A14-B1-C20; |
| A14-B1-C21; | A14-B1-C22; | A14-B1-C23; | A14-B1-C24; | A14-B1-C25; | A14-B1-C26; |
| A14-B1-C27; | A14-B1-C28; | A14-B1-C29; | A14-B1-C30; | A14-B1-C31; | A14-B1-C32; |
| A14-B1-C33; | A14-B1-C34; | A14-B1-C35; | A14-B1-C36; | A14-B1-C37; | A14-B1-C38; |
| A14-B1-C39; | A14-B1-C40; | A14-B1-C41; | A14-B1-C42; | A14-B1-C43; | A14-B1-C44; |
| A14-B1-C45; | A14-B1-C46; | A15-B1-C1; | A15-B1-C2; | A15-B1-C3; | A15-B1-C4; |
| A15-B1-C5; | A15-B1-C6; | A15-B1-C7; | A15-B1-C8; | A15-B1-C9; | A15-B1-C10; |
| A15-B1-C11; | A15-B1-C12; | A15-B1-C13; | A15-B1-C14; | A15-B1-C15; | A15-B1-C16; |
| A15-B1-C17; | A15-B1-C18; | A15-B1-C19; | A15-B1-C20; | A15-B1-C21; | A15-B1-C22; |
| A15-B1-C23; | A15-B1-C24; | A15-B1-C25; | A15-B1-C26; | A15-B1-C27; | A15-B1-C28; |
| A15-B1-C29; | A15-B1-C30; | A15-B1-C31; | A15-B1-C32; | A15-B1-C33; | A15-B1-C34; |
| A15-B1-C35; | A15-B1-C36; | A15-B1-C37; | A15-B1-C38; | A15-B1-C39; | A15-B1-C40; |
| A15-B1-C41; | A15-B1-C42; | A15-B1-C43; | A15-B1-C44; | A15-B1-C45; | A15-B1-C46; |
| A16-B1-C1; | A16-B1-C2; | A16-B1-C3; | A16-B1-C4; | A16-B1-C5; | A16-B1-C6; |
| A16-B1-C7; | A16-B1-C8; | A16-B1-C9; | A16-B1-C10; | A16-B1-C11; | A16-B1-C12; |
| A16-B1-C13; | A16-B1-C14; | A16-B1-C15; | A16-B1-C16; | A16-B1-C17; | A16-B1-C18; |
| A16-B1-C19; | A16-B1-C20; | A16-B1-C21; | A16-B1-C22; | A16-B1-C23; | A16-B1-C24; |

-continued

A16-B1-C25; A16-B1-C26; A16-B1-C27; A16-B1-C28; A16-B1-C29; A16-B1-C30;
A16-B1-C31; A16-B1-C32; A16-B1-C33; A16-B1-C34; A16-B1-C35; A16-B1-C36;
A16-B1-C37; A16-B1-C38; A16-B1-C39; A16-B1-C40; A16-B1-C41; A16-B1-C42;
A16-B1-C43; A16-B1-C44; A16-B1-C45; A16-B1-C46; A17-B1-C1; A17-B1-C2;
A17-B1-C3; A17-B1-C4; A17-B1-C5; A17-B1-C6; A17-B1-C7; A17-B1-C8;
A17-B1-C9; A17-B1-C10; A17-B1-C11; A17-B1-C12; A17-B1-C13; A17-B1-C14;
A17-B1-C15; A17-B1-C16; A17-B1-C17; A17-B1-C18; A17-B1-C19; A17-B1-C20;
A17-B1-C21; A17-B1-C22; A17-B1-C23; A17-B1-C24; A17-B1-C25; A17-B1-C26;
A17-B1-C27; A17-B1-C28; A17-B1-C29; A17-B1-C30; A17-B1-C31; A17-B1-C32;
A17-B1-C33; A17-B1-C34; A17-B1-C35; A17-B1-C36; A17-B1-C37; A17-B1-C38;
A17-B1-C39; A17-B1-C40; A17-B1-C41; A17-B1-C42; A17-B1-C43; A17-B1-C44;
A17-B1-C45; A17-B1-C46; A18-B1-C1; A18-B1-C2; A18-B1-C3; A18-B1-C4;
A18-B1-C5; A18-B1-C6; A18-B1-C7; A18-B1-C8; A18-B1-C9; A18-B1-C10;
A18-B1-C11; A18-B1-C12; A18-B1-C13; A18-B1-C14; A18-B1-C15; A18-B1-C16;
A18-B1-C17; A18-B1-C18; A18-B1-C19; A18-B1-C20; A18-B1-C21; A18-B1-C22;
A18-B1-C23; A18-B1-C24; A18-B1-C25; A18-B1-C26; A18-B1-C27; A18-B1-C28;
A18-B1-C29; A18-B1-C30; A18-B1-C31; A18-B1-C32; A18-B1-C33; A18-B1-C34;
A18-B1-C35; A18-B1-C36; A18-B1-C37; A18-B1-C38; A18-B1-C39; A18-B1-C40;
A18-B1-C41; A18-B1-C42; A18-B1-C43; A18-B1-C44; A18-B1-C45; A18-B1-C46;
A19-B1-C1; A19-B1-C2; A19-B1-C3; A19-B1-C4; A19-B1-C5; A19-B1-C6;
A19-B1-C7; A19-B1-C8; A19-B1-C9; A19-B1-C10; A19-B1-C11; A19-B1-C12;
A19-B1-C13; A19-B1-C14; A19-B1-C15; A19-B1-C16; A19-B1-C17; A19-B1-C18;
A19-B1-C19; A19-B1-C20; A19-B1-C21; A19-B1-C22; A19-B1-C23; A19-B1-C24;
A19-B1-C25; A19-B1-C26; A19-B1-C27; A19-B1-C28; A19-B1-C29; A19-B1-C30;
A19-B1-C31; A19-B1-C32; A19-B1-C33; A19-B1-C34; A19-B1-C35; A19-B1-C36;
A19-B1-C37; A19-B1-C38; A19-B1-C39; A19-B1-C40; A19-B1-C41; A19-B1-C42;
A19-B1-C43; A19-B1-C44; A19-B1-C45; A19-B1-C46; A20-B1-C1; A20-B1-C2;
A20-B1-C3; A20-B1-C4; A20-B1-C5; A20-B1-C6; A20-B1-C7; A20-B1-C8;
A20-B1-C9; A20-B1-C10; A20-B1-C11; A20-B1-C12; A20-B1-C13; A20-B1-C14;
A20-B1-C15; A20-B1-C16; A20-B1-C17; A20-B1-C18; A20-B1-C19; A20-B1-C20;
A20-B1-C21; A20-B1-C22; A20-B1-C23; A20-B1-C24; A20-B1-C25; A20-B1-C26;
A20-B1-C27; A20-B1-C28; A20-B1-C29; A20-B1-C30; A20-B1-C31; A20-B1-C32;
A20-B1-C33; A20-B1-C34; A20-B1-C35; A20-B1-C36; A20-B1-C37; A20-B1-C38;
A20-B1-C39; A20-B1-C40; A20-B1-C41; A20-B1-C42; A20-B1-C43; A20-B1-C44;
A20-B1-C45; A20-B1-C46; A21-B1-C1; A21-B1-C2; A21-B1-C3; A21-B1-C4;
A21-B1-C5; A21-B1-C6; A21-B1-C7; A21-B1-C8; A21-B1-C9; A21-B1-C10;
A21-B1-C11; A21-B1-C12; A21-B1-C13; A21-B1-C14; A21-B1-C15; A21-B1-C16;
A21-B1-C17; A21-B1-C18; A21-B1-C19; A21-B1-C20; A21-B1-C21; A21-B1-C22;
A21-B1-C23; A21-B1-C24; A21-B1-C25; A21-B1-C26; A21-B1-C27; A21-B1-C28;
A21-B1-C29; A21-B1-C30; A21-B1-C31; A21-B1-C32; A21-B1-C33; A21-B1-C34;
A21-B1-C35; A21-B1-C36; A21-B1-C37; A21-B1-C38; A21-B1-C39; A21-B1-C40;
A21-B1-C41; A21-B1-C42; A21-B1-C43; A21-B1-C44; A21-B1-C45; A21-B1-C46;
A22-B1-C1; A22-B1-C2; A22-B1-C3; A22-B1-C4; A22-B1-C5; A22-B1-C6;
A22-B1-C7; A22-B1-C8; A22-B1-C9; A22-B1-C10; A22-B1-C11; A22-B1-C12;
A22-B1-C13; A22-B1-C14; A22-B1-C15; A22-B1-C16; A22-B1-C17; A22-B1-C18;
A22-B1-C19; A22-B1-C20; A22-B1-C21; A22-B1-C22; A22-B1-C23; A22-B1-C24;
A22-B1-C25; A22-B1-C26; A22-B1-C27; A22-B1-C28; A22-B1-C29; A22-B1-C30;
A22-B1-C31; A22-B1-C32; A22-B1-C33; A22-B1-C34; A22-B1-C35; A22-B1-C36;
A22-B1-C37; A22-B1-C38; A22-B1-C39; A22-B1-C40; A22-B1-C41; A22-B1-C42;
A22-B1-C43; A22-B1-C44; A22-B1-C45; A22-B1-C46; A23-B1-C1; A23-B1-C2;
A23-B1-C3; A23-B1-C4; A23-B1-C5; A23-B1-C6; A23-B1-C7; A23-B1-C8;
A23-B1-C9; A23-B1-C10; A23-B1-C11; A23-B1-C12; A23-B1-C13; A23-B1-C14;
A23-B1-C15; A23-B1-C16; A23-B1-C17; A23-B1-C18; A23-B1-C19; A23-B1-C20;
A23-B1-C21; A23-B1-C22; A23-B1-C23; A23-B1-C24; A23-B1-C25; A23-B1-C26;
A23-B1-C27; A23-B1-C28; A23-B1-C29; A23-B1-C30; A23-B1-C31; A23-B1-C32;
A23-B1-C33; A23-B1-C34; A23-B1-C35; A23-B1-C36; A23-B1-C37; A23-B1-C38;
A23-B1-C39; A23-B1-C40; A23-B1-C41; A23-B1-C42; A23-B1-C43; A23-B1-C44;
A23-B1-C45; A23-B1-C46; A24-B1-C1; A24-B1-C2; A24-B1-C3; A24-B1-C4;
A24-B1-C5; A24-B1-C6; A24-B1-C7; A24-B1-C8; A24-B1-C9; A24-B1-C10;
A24-B1-C11; A24-B1-C12; A24-B1-C13; A24-B1-C14; A24-B1-C15; A24-B1-C16;
A24-B1-C17; A24-B1-C18; A24-B1-C19; A24-B1-C20; A24-B1-C21; A24-B1-C22;
A24-B1-C23; A24-B1-C24; A24-B1-C25; A24-B1-C26; A24-B1-C27; A24-B1-C28;
A24-B1-C29; A24-B1-C30; A24-B1-C31; A24-B1-C32; A24-B1-C33; A24-B1-C34;
A24-B1-C35; A24-B1-C36; A24-B1-C37; A24-B1-C38; A24-B1-C39; A24-B1-C40;
A24-B1-C41; A24-B1-C42; A24-B1-C43; A24-B1-C44; A24-B1-C45; A24-B1-C46;
A25-B1-C1; A25-B1-C2; A25-B1-C3; A25-B1-C4; A25-B1-C5; A25-B1-C6;
A25-B1-C7; A25-B1-C8; A25-B1-C9; A25-B1-C10; A25-B1-C11; A25-B1-C12;
A25-B1-C13; A25-B1-C14; A25-B1-C15; A25-B1-C16; A25-B1-C17; A25-B1-C18;
A25-B1-C19; A25-B1-C20; A25-B1-C21; A25-B1-C22; A25-B1-C23; A25-B1-C24;
A25-B1-C25; A25-B1-C26; A25-B1-C27; A25-B1-C28; A25-B1-C29; A25-B1-C30;
A25-B1-C31; A25-B1-C32; A25-B1-C33; A25-B1-C34; A25-B1-C35; A25-B1-C36;
A25-B1-C37; A25-B1-C38; A25-B1-C39; A25-B1-C40; A25-B1-C41; A25-B1-C42;
A25-B1-C43; A25-B1-C44; A25-B1-C45; A25-B1-C46; A26-B1-C1; A26-B1-C2;
A26-B1-C3; A26-B1-C4; A26-B1-C5; A26-B1-C6; A26-B1-C7; A26-B1-C8;
A26-B1-C9; A26-B1-C10; A26-B1-C11; A26-B1-C12; A26-B1-C13; A26-B1-C14;
A26-B1-C15; A26-B1-C16; A26-B1-C17; A26-B1-C18; A26-B1-C19; A26-B1-C20;
A26-B1-C21; A26-B1-C22; A26-B1-C23; A26-B1-C24; A26-B1-C25; A26-B1-C26;
A26-B1-C27; A26-B1-C28; A26-B1-C29; A26-B1-C30; A26-B1-C31; A26-B1-C32;
A26-B1-C33; A26-B1-C34; A26-B1-C35; A26-B1-C36; A26-B1-C37; A26-B1-C38;

-continued

| | | | | | |
|---|---|---|---|---|---|
| A26-B1-C39; | A26-B1-C40; | A26-B1-C41; | A26-B1-C42; | A26-B1-C43; | A26-B1-C44; |
| A26-B1-C45; | A26-B1-C46; | A27-B1-C1; | A27-B1-C2; | A27-B1-C3; | A27-B1-C4; |
| A27-B1-C5; | A27-B1-C6; | A27-B1-C7; | A27-B1-C8; | A27-B1-C9; | A27-B1-C10; |
| A27-B1-C11; | A27-B1-C12; | A27-B1-C13; | A27-B1-C14; | A27-B1-C15; | A27-B1-C16; |
| A27-B1-C17; | A27-B1-C18; | A27-B1-C19; | A27-B1-C20; | A27-B1-C21; | A27-B1-C22; |
| A27-B1-C23; | A27-B1-C24; | A27-B1-C25; | A27-B1-C26; | A27-B1-C27; | A27-B1-C28; |
| A27-B1-C29; | A27-B1-C30; | A27-B1-C31; | A27-B1-C32; | A27-B1-C33; | A27-B1-C34; |
| A27-B1-C35; | A27-B1-C36; | A27-B1-C37; | A27-B1-C38; | A27-B1-C39; | A27-B1-C40; |
| A27-B1-C41; | A27-B1-C42; | A27-B1-C43; | A27-B1-C44; | A27-B1-C45; | A27-B1-C46; |
| A28-B1-C1; | A28-B1-C2; | A28-B1-C3; | A28-B1-C4; | A28-B1-C5; | A28-B1-C6; |
| A28-B1-C7; | A28-B1-C8; | A28-B1-C9; | A28-B1-C10; | A28-B1-C11; | A28-B1-C12; |
| A28-B1-C13; | A28-B1-C14; | A28-B1-C15; | A28-B1-C16; | A28-B1-C17; | A28-B1-C18; |
| A28-B1-C19; | A28-B1-C20; | A28-B1-C21; | A28-B1-C22; | A28-B1-C23; | A28-B1-C24; |
| A28-B1-C25; | A28-B1-C26; | A28-B1-C27; | A28-B1-C28; | A28-B1-C29; | A28-B1-C30; |
| A28-B1-C31; | A28-B1-C32; | A28-B1-C33; | A28-B1-C34; | A28-B1-C35; | A28-B1-C36; |
| A28-B1-C37; | A28-B1-C38; | A28-B1-C39; | A28-B1-C40; | A28-B1-C41; | A28-B1-C42; |
| A28-B1-C43; | A28-B1-C44; | A28-B1-C45; | A28-B1-C46; | A1-B2-C1; | A1-B2-C2; |
| A1-B2-C3; | A1-B2-C4; | A1-B2-C5; | A1-B2-C6; | A1-B2-C7; | A1-B2-C8; |
| A1-B2-C9; | A1-B2-C10; | A1-B2-C11; | A1-B2-C12; | A1-B2-C13; | A1-B2-C14; |
| A1-B2-C15; | A1-B2-C16; | A1-B2-C17; | A1-B2-C18; | A1-B2-C19; | A1-B2-C20; |
| A1-B2-C21; | A1-B2-C22; | A1-B2-C23; | A1-B2-C24; | A1-B2-C25; | A1-B2-C26; |
| A1-B2-C27; | A1-B2-C28; | A1-B2-C29; | A1-B2-C30; | A1-B2-C31; | A1-B2-C32; |
| A1-B2-C33; | A1-B2-C34; | A1-B2-C35; | A1-B2-C36; | A1-B2-C37; | A1-B2-C38; |
| A1-B2-C39; | A1-B2-C40; | A1-B2-C41; | A1-B2-C42; | A1-B2-C43; | A1-B2-C44; |
| A1-B2-C45; | A1-B2-C46; | A2-B2-C1; | A2-B2-C2; | A2-B2-C3; | A2-B2-C4; |
| A2-B2-C5; | A2-B2-C6; | A2-B2-C7; | A2-B2-C8; | A2-B2-C9; | A2-B2-C10; |
| A2-B2-C11; | A2-B2-C12; | A2-B2-C13; | A2-B2-C14; | A2-B2-C15; | A2-B2-C16; |
| A2-B2-C17; | A2-B2-C18; | A2-B2-C19; | A2-B2-C20; | A2-B2-C21; | A2-B2-C22; |
| A2-B2-C23; | A2-B2-C24; | A2-B2-C25; | A2-B2-C26; | A2-B2-C27; | A2-B2-C28; |
| A2-B2-C29; | A2-B2-C30; | A2-B2-C31; | A2-B2-C32; | A2-B2-C33; | A2-B2-C34; |
| A2-B2-C35; | A2-B2-C36; | A2-B2-C37; | A2-B2-C38; | A2-B2-C39; | A2-B2-C40; |
| A2-B2-C41; | A2-B2-C42; | A2-B2-C43; | A2-B2-C44; | A2-B2-C45; | A2-B2-C46; |
| A3-B2-C1; | A3-B2-C2; | A3-B2-C3; | A3-B2-C4; | A3-B2-C5; | A3-B2-C6; |
| A3-B2-C7; | A3-B2-C8; | A3-B2-C9; | A3-B2-C10; | A3-B2-C11; | A3-B2-C12; |
| A3-B2-C13; | A3-B2-C14; | A3-B2-C15; | A3-B2-C16; | A3-B2-C17; | A3-B2-C18; |
| A3-B2-C19; | A3-B2-C20; | A3-B2-C21; | A3-B2-C22; | A3-B2-C23; | A3-B2-C24; |
| A3-B2-C25; | A3-B2-C26; | A3-B2-C27; | A3-B2-C28; | A3-B2-C29; | A3-B2-C30; |
| A3-B2-C31; | A3-B2-C32; | A3-B2-C33; | A3-B2-C34; | A3-B2-C35; | A3-B2-C36; |
| A3-B2-C37; | A3-B2-C38; | A3-B2-C39; | A3-B2-C40; | A3-B2-C41; | A3-B2-C42; |
| A3-B2-C43; | A3-B2-C44; | A3-B2-C45; | A3-B2-C46; | A4-B2-C1; | A4-B2-C2; |
| A4-B2-C3; | A4-B2-C4; | A4-B2-C5; | A4-B2-C6; | A4-B2-C7; | A4-B2-C8; |
| A4-B2-C9; | A4-B2-C10; | A4-B2-C11; | A4-B2-C12; | A4-B2-C13; | A4-B2-C14; |
| A4-B2-C15; | A4-B2-C16; | A4-B2-C17; | A4-B2-C18; | A4-B2-C19; | A4-B2-C20; |
| A4-B2-C21; | A4-B2-C22; | A4-B2-C23; | A4-B2-C24; | A4-B2-C25; | A4-B2-C26; |
| A4-B2-C27; | A4-B2-C28; | A4-B2-C29; | A4-B2-C30; | A4-B2-C31; | A4-B2-C32; |
| A4-B2-C33; | A4-B2-C34; | A4-B2-C35; | A4-B2-C36; | A4-B2-C37; | A4-B2-C38; |
| A4-B2-C39; | A4-B2-C40; | A4-B2-C41; | A4-B2-C42; | A4-B2-C43; | A4-B2-C44; |
| A4-B2-C45; | A4-B2-C46; | A5-B2-C1; | A5-B2-C2; | A5-B2-C3; | A5-B2-C4; |
| A5-B2-C5; | A5-B2-C6; | A5-B2-C7; | A5-B2-C8; | A5-B2-C9; | A5-B2-C10; |
| A5-B2-C11; | A5-B2-C12; | A5-B2-C13; | A5-B2-C14; | A5-B2-C15; | A5-B2-C16; |
| A5-B2-C17; | A5-B2-C18; | A5-B2-C19; | A5-B2-C20; | A5-B2-C21; | A5-B2-C22; |
| A5-B2-C23; | A5-B2-C24; | A5-B2-C25; | A5-B2-C26; | A5-B2-C27; | A5-B2-C28; |
| A5-B2-C29; | A5-B2-C30; | A5-B2-C31; | A5-B2-C32; | A5-B2-C33; | A5-B2-C34; |
| A5-B2-C35; | A5-B2-C36; | A5-B2-C37; | A5-B2-C38; | A5-B2-C39; | A5-B2-C40; |
| A5-B2-C41; | A5-B2-C42; | A5-B2-C43; | A5-B2-C44; | A5-B2-C45; | A5-B2-C46; |
| A6-B2-C1; | A6-B2-C2; | A6-B2-C3; | A6-B2-C4; | A6-B2-C5; | A6-B2-C6; |
| A6-B2-C7; | A6-B2-C8; | A6-B2-C9; | A6-B2-C10; | A6-B2-C11; | A6-B2-C12; |
| A6-B2-C13; | A6-B2-C14; | A6-B2-C15; | A6-B2-C16; | A6-B2-C17; | A6-B2-C18; |
| A6-B2-C19; | A6-B2-C20; | A6-B2-C21; | A6-B2-C22; | A6-B2-C23; | A6-B2-C24; |
| A6-B2-C25; | A6-B2-C26; | A6-B2-C27; | A6-B2-C28; | A6-B2-C29; | A6-B2-C30; |
| A6-B2-C31; | A6-B2-C32; | A6-B2-C33; | A6-B2-C34; | A6-B2-C35; | A6-B2-C36; |
| A6-B2-C37; | A6-B2-C38; | A6-B2-C39; | A6-B2-C40; | A6-B2-C41; | A6-B2-C42; |
| A6-B2-C43; | A6-B2-C44; | A6-B2-C45; | A6-B2-C46; | A7-B2-C1; | A7-B2-C2; |
| A7-B2-C3; | A7-B2-C4; | A7-B2-C5; | A7-B2-C6; | A7-B2-C7; | A7-B2-C8; |
| A7-B2-C9; | A7-B2-C10; | A7-B2-C11; | A7-B2-C12; | A7-B2-C13; | A7-B2-C14; |
| A7-B2-C15; | A7-B2-C16; | A7-B2-C17; | A7-B2-C18; | A7-B2-C19; | A7-B2-C20; |
| A7-B2-C21; | A7-B2-C22; | A7-B2-C23; | A7-B2-C24; | A7-B2-C25; | A7-B2-C26; |
| A7-B2-C27; | A7-B2-C28; | A7-B2-C29; | A7-B2-C30; | A7-B2-C31; | A7-B2-C32; |
| A7-B2-C33; | A7-B2-C34; | A7-B2-C35; | A7-B2-C36; | A7-B2-C37; | A7-B2-C38; |
| A7-B2-C39; | A7-B2-C40; | A7-B2-C41; | A7-B2-C42; | A7-B2-C43; | A7-B2-C44; |
| A7-B2-C45; | A7-B2-C46; | A8-B2-C1; | A8-B2-C2; | A8-B2-C3; | A8-B2-C4; |
| A8-B2-C5; | A8-B2-C6; | A8-B2-C7; | A8-B2-C8; | A8-B2-C9; | A8-B2-C10; |
| A8-B2-C11; | A8-B2-C12; | A8-B2-C13; | A8-B2-C14; | A8-B2-C15; | A8-B2-C16; |
| A8-B2-C17; | A8-B2-C18; | A8-B2-C19; | A8-B2-C20; | A8-B2-C21; | A8-B2-C22; |
| A8-B2-C23; | A8-B2-C24; | A8-B2-C25; | A8-B2-C26; | A8-B2-C27; | A8-B2-C28; |
| A8-B2-C29; | A8-B2-C30; | A8-B2-C31; | A8-B2-C32; | A8-B2-C33; | A8-B2-C34; |
| A8-B2-C35; | A8-B2-C36; | A8-B2-C37; | A8-B2-C38; | A8-B2-C39; | A8-B2-C40; |
| A8-B2-C41; | A8-B2-C42; | A8-B2-C43; | A8-B2-C44; | A8-B2-C45; | A8-B2-C46; |
| A9-B2-C1; | A9-B2-C2; | A9-B2-C3; | A9-B2-C4; | A9-B2-C5; | A9-B2-C6; |

-continued

| | | | | | |
|---|---|---|---|---|---|
| A9-B2-C7; | A9-B2-C8; | A9-B2-C9; | A9-B2-C10; | A9-B2-C11; | A9-B2-C12; |
| A9-B2-C13; | A9-B2-C14; | A9-B2-C15; | A9-B2-C16; | A9-B2-C17; | A9-B2-C18; |
| A9-B2-C19; | A9-B2-C20; | A9-B2-C21; | A9-B2-C22; | A9-B2-C23; | A9-B2-C24; |
| A9-B2-C25; | A9-B2-C26; | A9-B2-C27; | A9-B2-C28; | A9-B2-C29; | A9-B2-C30; |
| A9-B2-C31; | A9-B2-C32; | A9-B2-C33; | A9-B2-C34; | A9-B2-C35; | A9-B2-C36; |
| A9-B2-C37; | A9-B2-C38; | A9-B2-C39; | A9-B2-C40; | A9-B2-C41; | A9-B2-C42; |
| A9-B2-C43; | A9-B2-C44; | A9-B2-C45; | A9-B2-C46; | A10-B2-C1; | A10-B2-C2; |
| A10-B2-C3; | A10-B2-C4; | A10-B2-C5; | A10-B2-C6; | A10-B2-C7; | A10-B2-C8; |
| A10-B2-C9; | A10-B2-C10; | A10-B2-C11; | A10-B2-C12; | A10-B2-C13; | A10-B2-C14; |
| A10-B2-C15; | A10-B2-C16; | A10-B2-C17; | A10-B2-C18; | A10-B2-C19; | A10-B2-C20; |
| A10-B2-C21; | A10-B2-C22; | A10-B2-C23; | A10-B2-C24; | A10-B2-C25; | A10-B2-C26; |
| A10-B2-C27; | A10-B2-C28; | A10-B2-C29; | A10-B2-C30; | A10-B2-C31; | A10-B2-C32; |
| A10-B2-C33; | A10-B2-C34; | A10-B2-C35; | A10-B2-C36; | A10-B2-C37; | A10-B2-C38; |
| A10-B2-C39; | A10-B2-C40; | A10-B2-C41; | A10-B2-C42; | A10-B2-C43; | A10-B2-C44; |
| A10-B2-C45; | A10-B2-C46; | A11-B2-C1; | A11-B2-C2; | A11-B2-C3; | A11-B2-C4; |
| A11-B2-C5; | A11-B2-C6; | A11-B2-C7; | A11-B2-C8; | A11-B2-C9; | A11-B2-C10; |
| A11-B2-C11; | A11-B2-C12; | A11-B2-C13; | A11-B2-C14; | A11-B2-C15; | A11-B2-C16; |
| A11-B2-C17; | A11-B2-C18; | A11-B2-C19; | A11-B2-C20; | A11-B2-C21; | A11-B2-C22; |
| A11-B2-C23; | A11-B2-C24; | A11-B2-C25; | A11-B2-C26; | A11-B2-C27; | A11-B2-C28; |
| A11-B2-C29; | A11-B2-C30; | A11-B2-C31; | A11-B2-C32; | A11-B2-C33; | A11-B2-C34; |
| A11-B2-C35; | A11-B2-C36; | A11-B2-C37; | A11-B2-C38; | A11-B2-C39; | A11-B2-C40; |
| A11-B2-C41; | A11-B2-C42; | A11-B2-C43; | A11-B2-C44; | A11-B2-C45; | A11-B2-C46; |
| A12-B2-C1; | A12-B2-C2; | A12-B2-C3; | A12-B2-C4; | A12-B2-C5; | A12-B2-C6; |
| A12-B2-C7; | A12-B2-C8; | A12-B2-C9; | A12-B2-C10; | A12-B2-C11; | A12-B2-C12; |
| A12-B2-C13; | A12-B2-C14; | A12-B2-C15; | A12-B2-C16; | A12-B2-C17; | A12-B2-C18; |
| A12-B2-C19; | A12-B2-C20; | A12-B2-C21; | A12-B2-C22; | A12-B2-C23; | A12-B2-C24; |
| A12-B2-C25; | A12-B2-C26; | A12-B2-C27; | A12-B2-C28; | A12-B2-C29; | A12-B2-C30; |
| A12-B2-C31; | A12-B2-C32; | A12-B2-C33; | A12-B2-C34; | A12-B2-C35; | A12-B2-C36; |
| A12-B2-C37; | A12-B2-C38; | A12-B2-C39; | A12-B2-C40; | A12-B2-C41; | A12-B2-C42; |
| A12-B2-C43; | A12-B2-C44; | A12-B2-C45; | A12-B2-C46; | A13-B2-C1; | A13-B2-C2; |
| A13-B2-C3; | A13-B2-C4; | A13-B2-C5; | A13-B2-C6; | A13-B2-C7; | A13-B2-C8; |
| A13-B2-C9; | A13-B2-C10; | A13-B2-C11; | A13-B2-C12; | A13-B2-C13; | A13-B2-C14; |
| A13-B2-C15; | A13-B2-C16; | A13-B2-C17; | A13-B2-C18; | A13-B2-C19; | A13-B2-C20; |
| A13-B2-C21; | A13-B2-C22; | A13-B2-C23; | A13-B2-C24; | A13-B2-C25; | A13-B2-C26; |
| A13-B2-C27; | A13-B2-C28; | A13-B2-C29; | A13-B2-C30; | A13-B2-C31; | A13-B2-C32; |
| A13-B2-C33; | A13-B2-C34; | A13-B2-C35; | A13-B2-C36; | A13-B2-C37; | A13-B2-C38; |
| A13-B2-C39; | A13-B2-C40; | A13-B2-C41; | A13-B2-C42; | A13-B2-C43; | A13-B2-C44; |
| A13-B2-C45; | A13-B2-C46; | A14-B2-C1; | A14-B2-C2; | A14-B2-C3; | A14-B2-C4; |
| A14-B2-C5; | A14-B2-C6; | A14-B2-C7; | A14-B2-C8; | A14-B2-C9; | A14-B2-C10; |
| A14-B2-C11; | A14-B2-C12; | A14-B2-C13; | A14-B2-C14; | A14-B2-C15; | A14-B2-C16; |
| A14-B2-C17; | A14-B2-C18; | A14-B2-C19; | A14-B2-C20; | A14-B2-C21; | A14-B2-C22; |
| A14-B2-C23; | A14-B2-C24; | A14-B2-C25; | A14-B2-C26; | A14-B2-C27; | A14-B2-C28; |
| A14-B2-C29; | A14-B2-C30; | A14-B2-C31; | A14-B2-C32; | A14-B2-C33; | A14-B2-C34; |
| A14-B2-C35; | A14-B2-C36; | A14-B2-C37; | A14-B2-C38; | A14-B2-C39; | A14-B2-C40; |
| A14-B2-C41; | A14-B2-C42; | A14-B2-C43; | A14-B2-C44; | A14-B2-C45; | A14-B2-C46; |
| A15-B2-C1; | A15-B2-C2; | A15-B2-C3; | A15-B2-C4; | A15-B2-C5; | A15-B2-C6; |
| A15-B2-C7; | A15-B2-C8; | A15-B2-C9; | A15-B2-C10; | A15-B2-C11; | A15-B2-C12; |
| A15-B2-C13; | A15-B2-C14; | A15-B2-C15; | A15-B2-C16; | A15-B2-C17; | A15-B2-C18; |
| A15-B2-C19; | A15-B2-C20; | A15-B2-C21; | A15-B2-C22; | A15-B2-C23; | A15-B2-C24; |
| A15-B2-C25; | A15-B2-C26; | A15-B2-C27; | A15-B2-C28; | A15-B2-C29; | A15-B2-C30; |
| A15-B2-C31; | A15-B2-C32; | A15-B2-C33; | A15-B2-C34; | A15-B2-C35; | A15-B2-C36; |
| A15-B2-C37; | A15-B2-C38; | A15-B2-C39; | A15-B2-C40; | A15-B2-C41; | A15-B2-C42; |
| A15-B2-C43; | A15-B2-C44; | A15-B2-C45; | A15-B2-C46; | A16-B2-C1; | A16-B2-C2; |
| A16-B2-C3; | A16-B2-C4; | A16-B2-C5; | A16-B2-C6; | A16-B2-C7; | A16-B2-C8; |
| A16-B2-C9; | A16-B2-C10; | A16-B2-C11; | A16-B2-C12; | A16-B2-C13; | A16-B2-C14; |
| A16-B2-C15; | A16-B2-C16; | A16-B2-C17; | A16-B2-C18; | A16-B2-C19; | A16-B2-C20; |
| A16-B2-C21; | A16-B2-C22; | A16-B2-C23; | A16-B2-C24; | A16-B2-C25; | A16-B2-C26; |
| A16-B2-C27; | A16-B2-C28; | A16-B2-C29; | A16-B2-C30; | A16-B2-C31; | A16-B2-C32; |
| A16-B2-C33; | A16-B2-C34; | A16-B2-C35; | A16-B2-C36; | A16-B2-C37; | A16-B2-C38; |
| A16-B2-C39; | A16-B2-C40; | A16-B2-C41; | A16-B2-C42; | A16-B2-C43; | A16-B2-C44; |
| A16-B2-C45; | A16-B2-C46; | A17-B2-C1; | A17-B2-C2; | A17-B2-C3; | A17-B2-C4; |
| A17-B2-C5; | A17-B2-C6; | A17-B2-C7; | A17-B2-C8; | A17-B2-C9; | A17-B2-C10; |
| A17-B2-C11; | A17-B2-C12; | A17-B2-C13; | A17-B2-C14; | A17-B2-C15; | A17-B2-C16; |
| A17-B2-C17; | A17-B2-C18; | A17-B2-C19; | A17-B2-C20; | A17-B2-C21; | A17-B2-C22; |
| A17-B2-C23; | A17-B2-C24; | A17-B2-C25; | A17-B2-C26; | A17-B2-C27; | A17-B2-C28; |
| A17-B2-C29; | A17-B2-C30; | A17-B2-C31; | A17-B2-C32; | A17-B2-C33; | A17-B2-C34; |
| A17-B2-C35; | A17-B2-C36; | A17-B2-C37; | A17-B2-C38; | A17-B2-C39; | A17-B2-C40; |
| A17-B2-C41; | A17-B2-C42; | A17-B2-C43; | A17-B2-C44; | A17-B2-C45; | A17-B2-C46; |
| A18-B2-C1; | A18-B2-C2; | A18-B2-C3; | A18-B2-C4; | A18-B2-C5; | A18-B2-C6; |
| A18-B2-C7; | A18-B2-C8; | A18-B2-C9; | A18-B2-C10; | A18-B2-C11; | A18-B2-C12; |
| A18-B2-C13; | A18-B2-C14; | A18-B2-C15; | A18-B2-C16; | A18-B2-C17; | A18-B2-C18; |
| A18-B2-C19; | A18-B2-C20; | A18-B2-C21; | A18-B2-C22; | A18-B2-C23; | A18-B2-C24; |
| A18-B2-C25; | A18-B2-C26; | A18-B2-C27; | A18-B2-C28; | A18-B2-C29; | A18-B2-C30; |
| A18-B2-C31; | A18-B2-C32; | A18-B2-C33; | A18-B2-C34; | A18-B2-C35; | A18-B2-C36; |
| A18-B2-C37; | A18-B2-C38; | A18-B2-C39; | A18-B2-C40; | A18-B2-C41; | A18-B2-C42; |
| A18-B2-C43; | A18-B2-C44; | A18-B2-C45; | A18-B2-C46; | A19-B2-C1; | A19-B2-C2; |
| A19-B2-C3; | A19-B2-C4; | A19-B2-C5; | A19-B2-C6; | A19-B2-C7; | A19-B2-C8; |
| A19-B2-C9; | A19-B2-C10; | A19-B2-C11; | A19-B2-C12; | A19-B2-C13; | A19-B2-C14; |
| A19-B2-C15; | A19-B2-C16; | A19-B2-C17; | A19-B2-C18; | A19-B2-C19; | A19-B2-C20; |

-continued

| | | | | | |
|---|---|---|---|---|---|
| A19-B2-C21; | A19-B2-C22; | A19-B2-C23; | A19-B2-C24; | A19-B2-C25; | A19-B2-C26; |
| A19-B2-C27; | A19-B2-C28; | A19-B2-C29; | A19-B2-C30; | A19-B2-C31; | A19-B2-C32; |
| A19-B2-C33; | A19-B2-C34; | A19-B2-C35; | A19-B2-C36; | A19-B2-C37; | A19-B2-C38; |
| A19-B2-C39; | A19-B2-C40; | A19-B2-C41; | A19-B2-C42; | A19-B2-C43; | A19-B2-C44; |
| A19-B2-C45; | A19-B2-C46; | A20-B2-C1; | A20-B2-C2; | A20-B2-C3; | A20-B2-C4; |
| A20-B2-C5; | A20-B2-C6; | A20-B2-C7; | A20-B2-C8; | A20-B2-C9; | A20-B2-C10; |
| A20-B2-C11; | A20-B2-C12; | A20-B2-C13; | A20-B2-C14; | A20-B2-C15; | A20-B2-C16; |
| A20-B2-C17; | A20-B2-C18; | A20-B2-C19; | A20-B2-C20; | A20-B2-C21; | A20-B2-C22; |
| A20-B2-C23; | A20-B2-C24; | A20-B2-C25; | A20-B2-C26; | A20-B2-C27; | A20-B2-C28; |
| A20-B2-C29; | A20-B2-C30; | A20-B2-C31; | A20-B2-C32; | A20-B2-C33; | A20-B2-C34; |
| A20-B2-C35; | A20-B2-C36; | A20-B2-C37; | A20-B2-C38; | A20-B2-C39; | A20-B2-C40; |
| A20-B2-C41; | A20-B2-C42; | A20-B2-C43; | A20-B2-C44; | A20-B2-C45; | A20-B2-C46; |
| A21-B2-C1; | A21-B2-C2; | A21-B2-C3; | A21-B2-C4; | A21-B2-C5; | A21-B2-C6; |
| A21-B2-C7; | A21-B2-C8; | A21-B2-C9; | A21-B2-C10; | A21-B2-C11; | A21-B2-C12; |
| A21-B2-C13; | A21-B2-C14; | A21-B2-C15; | A21-B2-C16; | A21-B2-C17; | A21-B2-C18; |
| A21-B2-C19; | A21-B2-C20; | A21-B2-C21; | A21-B2-C22; | A21-B2-C23; | A21-B2-C24; |
| A21-B2-C25; | A21-B2-C26; | A21-B2-C27; | A21-B2-C28; | A21-B2-C29; | A21-B2-C30; |
| A21-B2-C31; | A21-B2-C32; | A21-B2-C33; | A21-B2-C34; | A21-B2-C35; | A21-B2-C36; |
| A21-B2-C37; | A21-B2-C38; | A21-B2-C39; | A21-B2-C40; | A21-B2-C41; | A21-B2-C42; |
| A21-B2-C43; | A21-B2-C44; | A21-B2-C45; | A21-B2-C46; | A22-B2-C1; | A22-B2-C2; |
| A22-B2-C3; | A22-B2-C4; | A22-B2-C5; | A22-B2-C6; | A22-B2-C7; | A22-B2-C8; |
| A22-B2-C9; | A22-B2-C10; | A22-B2-C11; | A22-B2-C12; | A22-B2-C13; | A22-B2-C14; |
| A22-B2-C15; | A22-B2-C16; | A22-B2-C17; | A22-B2-C18; | A22-B2-C19; | A22-B2-C20; |
| A22-B2-C21; | A22-B2-C22; | A22-B2-C23; | A22-B2-C24; | A22-B2-C25; | A22-B2-C26; |
| A22-B2-C27; | A22-B2-C28; | A22-B2-C29; | A22-B2-C30; | A22-B2-C31; | A22-B2-C32; |
| A22-B2-C33; | A22-B2-C34; | A22-B2-C35; | A22-B2-C36; | A22-B2-C37; | A22-B2-C38; |
| A22-B2-C39; | A22-B2-C40; | A22-B2-C41; | A22-B2-C42; | A22-B2-C43; | A22-B2-C44; |
| A22-B2-C45; | A22-B2-C46; | A23-B2-C1; | A23-B2-C2; | A23-B2-C3; | A23-B2-C4; |
| A23-B2-C5; | A23-B2-C6; | A23-B2-C7; | A23-B2-C8; | A23-B2-C9; | A23-B2-C10; |
| A23-B2-C11; | A23-B2-C12; | A23-B2-C13; | A23-B2-C14; | A23-B2-C15; | A23-B2-C16; |
| A23-B2-C17; | A23-B2-C18; | A23-B2-C19; | A23-B2-C20; | A23-B2-C21; | A23-B2-C22; |
| A23-B2-C23; | A23-B2-C24; | A23-B2-C25; | A23-B2-C26; | A23-B2-C27; | A23-B2-C28; |
| A23-B2-C29; | A23-B2-C30; | A23-B2-C31; | A23-B2-C32; | A23-B2-C33; | A23-B2-C34; |
| A23-B2-C35; | A23-B2-C36; | A23-B2-C37; | A23-B2-C38; | A23-B2-C39; | A23-B2-C40; |
| A23-B2-C41; | A23-B2-C42; | A23-B2-C43; | A23-B2-C44; | A23-B2-C45; | A23-B2-C46; |
| A24-B2-C1; | A24-B2-C2; | A24-B2-C3; | A24-B2-C4; | A24-B2-C5; | A24-B2-C6; |
| A24-B2-C7; | A24-B2-C8; | A24-B2-C9; | A24-B2-C10; | A24-B2-C11; | A24-B2-C12; |
| A24-B2-C13; | A24-B2-C14; | A24-B2-C15; | A24-B2-C16; | A24-B2-C17; | A24-B2-C18; |
| A24-B2-C19; | A24-B2-C20; | A24-B2-C21; | A24-B2-C22; | A24-B2-C23; | A24-B2-C24; |
| A24-B2-C25; | A24-B2-C26; | A24-B2-C27; | A24-B2-C28; | A24-B2-C29; | A24-B2-C30; |
| A24-B2-C31; | A24-B2-C32; | A24-B2-C33; | A24-B2-C34; | A24-B2-C35; | A24-B2-C36; |
| A24-B2-C37; | A24-B2-C38; | A24-B2-C39; | A24-B2-C40; | A24-B2-C41; | A24-B2-C42; |
| A24-B2-C43; | A24-B2-C44; | A24-B2-C45; | A24-B2-C46; | A25-B2-C1; | A25-B2-C2; |
| A25-B2-C3; | A25-B2-C4; | A25-B2-C5; | A25-B2-C6; | A25-B2-C7; | A25-B2-C8; |
| A25-B2-C9; | A25-B2-C10; | A25-B2-C11; | A25-B2-C12; | A25-B2-C13; | A25-B2-C14; |
| A25-B2-C15; | A25-B2-C16; | A25-B2-C17; | A25-B2-C18; | A25-B2-C19; | A25-B2-C20; |
| A25-B2-C21; | A25-B2-C22; | A25-B2-C23; | A25-B2-C24; | A25-B2-C25; | A25-B2-C26; |
| A25-B2-C27; | A25-B2-C28; | A25-B2-C29; | A25-B2-C30; | A25-B2-C31; | A25-B2-C32; |
| A25-B2-C33; | A25-B2-C34; | A25-B2-C35; | A25-B2-C36; | A25-B2-C37; | A25-B2-C38; |
| A25-B2-C39; | A25-B2-C40; | A25-B2-C41; | A25-B2-C42; | A25-B2-C43; | A25-B2-C44; |
| A25-B2-C45; | A25-B2-C46; | A26-B2-C1; | A26-B2-C2; | A26-B2-C3; | A26-B2-C4; |
| A26-B2-C5; | A26-B2-C6; | A26-B2-C7; | A26-B2-C8; | A26-B2-C9; | A26-B2-C10; |
| A26-B2-C11; | A26-B2-C12; | A26-B2-C13; | A26-B2-C14; | A26-B2-C15; | A26-B2-C16; |
| A26-B2-C17; | A26-B2-C18; | A26-B2-C19; | A26-B2-C20; | A26-B2-C21; | A26-B2-C22; |
| A26-B2-C23; | A26-B2-C24; | A26-B2-C25; | A26-B2-C26; | A26-B2-C27; | A26-B2-C28; |
| A26-B2-C29; | A26-B2-C30; | A26-B2-C31; | A26-B2-C32; | A26-B2-C33; | A26-B2-C34; |
| A26-B2-C35; | A26-B2-C36; | A26-B2-C37; | A26-B2-C38; | A26-B2-C39; | A26-B2-C40; |
| A26-B2-C41; | A26-B2-C42; | A26-B2-C43; | A26-B2-C44; | A26-B2-C45; | A26-B2-C46; |
| A27-B2-C1; | A27-B2-C2; | A27-B2-C3; | A27-B2-C4; | A27-B2-C5; | A27-B2-C6; |
| A27-B2-C7; | A27-B2-C8; | A27-B2-C9; | A27-B2-C10; | A27-B2-C11; | A27-B2-C12; |
| A27-B2-C13; | A27-B2-C14; | A27-B2-C15; | A27-B2-C16; | A27-B2-C17; | A27-B2-C18; |
| A27-B2-C19; | A27-B2-C20; | A27-B2-C21; | A27-B2-C22; | A27-B2-C23; | A27-B2-C24; |
| A27-B2-C25; | A27-B2-C26; | A27-B2-C27; | A27-B2-C28; | A27-B2-C29; | A27-B2-C30; |
| A27-B2-C31; | A27-B2-C32; | A27-B2-C33; | A27-B2-C34; | A27-B2-C35; | A27-B2-C36; |
| A27-B2-C37; | A27-B2-C38; | A27-B2-C39; | A27-B2-C40; | A27-B2-C41; | A27-B2-C42; |
| A27-B2-C43; | A27-B2-C44; | A27-B2-C45; | A27-B2-C46; | A28-B2-C1; | A28-B2-C2; |
| A28-B2-C3; | A28-B2-C4; | A28-B2-C5; | A28-B2-C6; | A28-B2-C7; | A28-B2-C8; |
| A28-B2-C9; | A28-B2-C10; | A28-B2-C11; | A28-B2-C12; | A28-B2-C13; | A28-B2-C14; |
| A28-B2-C15; | A28-B2-C16; | A28-B2-C17; | A28-B2-C18; | A28-B2-C19; | A28-B2-C20; |
| A28-B2-C21; | A28-B2-C22; | A28-B2-C23; | A28-B2-C24; | A28-B2-C25; | A28-B2-C26; |
| A28-B2-C27; | A28-B2-C28; | A28-B2-C29; | A28-B2-C30; | A28-B2-C31; | A28-B2-C32; |
| A28-B2-C33; | A28-B2-C34; | A28-B2-C35; | A28-B2-C36; | A28-B2-C37; | A28-B2-C38; |
| A28-B2-C39; | A28-B2-C40; | A28-B2-C41; | A28-B2-C42; | A28-B2-C43; | A28-B2-C44; |
| A28-B2-C45; | A28-B2-C46; | A1-B3-C1; | A1-B3-C2; | A1-B3-C3; | A1-B3-C4; |
| A1-B3-C5; | A1-B3-C6; | A1-B3-C7; | A1-B3-C8; | A1-B3-C9; | A1-B3-C10; |
| A1-B3-C11; | A1-B3-C12; | A1-B3-C13; | A1-B3-C14; | A1-B3-C15; | A1-B3-C16; |
| A1-B3-C17; | A1-B3-C18; | A1-B3-C19; | A1-B3-C20; | A1-B3-C21; | A1-B3-C22; |
| A1-B3-C23; | A1-B3-C24; | A1-B3-C25; | A1-B3-C26; | A1-B3-C27; | A1-B3-C28; |
| A1-B3-C29; | A1-B3-C30; | A1-B3-C31; | A1-B3-C32; | A1-B3-C33; | A1-B3-C34; |

-continued

| | | | | | |
|---|---|---|---|---|---|
| A1-B3-C35; | A1-B3-C36; | A1-B3-C37; | A1-B3-C38; | A1-B3-C39; | A1-B3-C40; |
| A1-B3-C41; | A1-B3-C42; | A1-B3-C43; | A1-B3-C44; | A1-B3-C45; | A1-B3-C46; |
| A2-B3-C1; | A2-B3-C2; | A2-B3-C3; | A2-B3-C4; | A2-B3-C5; | A2-B3-C6; |
| A2-B3-C7; | A2-B3-C8; | A2-B3-C9; | A2-B3-C10; | A2-B3-C11; | A2-B3-C12; |
| A2-B3-C13; | A2-B3-C14; | A2-B3-C15; | A2-B3-C16; | A2-B3-C17; | A2-B3-C18; |
| A2-B3-C19; | A2-B3-C20; | A2-B3-C21; | A2-B3-C22; | A2-B3-C23; | A2-B3-C24; |
| A2-B3-C25; | A2-B3-C26; | A2-B3-C27; | A2-B3-C28; | A2-B3-C29; | A2-B3-C30; |
| A2-B3-C31; | A2-B3-C32; | A2-B3-C33; | A2-B3-C34; | A2-B3-C35; | A2-B3-C36; |
| A2-B3-C37; | A2-B3-C38; | A2-B3-C39; | A2-B3-C40; | A2-B3-C41; | A2-B3-C42; |
| A2-B3-C43; | A2-B3-C44; | A2-B3-C45; | A2-B3-C46; | A3-B3-C1; | A3-B3-C2; |
| A3-B3-C3; | A3-B3-C4; | A3-B3-C5; | A3-B3-C6; | A3-B3-C7; | A3-B3-C8; |
| A3-B3-C9; | A3-B3-C10; | A3-B3-C11; | A3-B3-C12; | A3-B3-C13; | A3-B3-C14; |
| A3-B3-C15; | A3-B3-C16; | A3-B3-C17; | A3-B3-C18; | A3-B3-C19; | A3-B3-C20; |
| A3-B3-C21; | A3-B3-C22; | A3-B3-C23; | A3-B3-C24; | A3-B3-C25; | A3-B3-C26; |
| A3-B3-C27; | A3-B3-C28; | A3-B3-C29; | A3-B3-C30; | A3-B3-C31; | A3-B3-C32; |
| A3-B3-C33; | A3-B3-C34; | A3-B3-C35; | A3-B3-C36; | A3-B3-C37; | A3-B3-C38; |
| A3-B3-C39; | A3-B3-C40; | A3-B3-C41; | A3-B3-C42; | A3-B3-C43; | A3-B3-C44; |
| A3-B3-C45; | A3-B3-C46; | A4-B3-C1; | A4-B3-C2; | A4-B3-C3; | A4-B3-C4; |
| A4-B3-C5; | A4-B3-C6; | A4-B3-C7; | A4-B3-C8; | A4-B3-C9; | A4-B3-C10; |
| A4-B3-C11; | A4-B3-C12; | A4-B3-C13; | A4-B3-C14; | A4-B3-C15; | A4-B3-C16; |
| A4-B3-C17; | A4-B3-C18; | A4-B3-C19; | A4-B3-C20; | A4-B3-C21; | A4-B3-C22; |
| A4-B3-C23; | A4-B3-C24; | A4-B3-C25; | A4-B3-C26; | A4-B3-C27; | A4-B3-C28; |
| A4-B3-C29; | A4-B3-C30; | A4-B3-C31; | A4-B3-C32; | A4-B3-C33; | A4-B3-C34; |
| A4-B3-C35; | A4-B3-C36; | A4-B3-C37; | A4-B3-C38; | A4-B3-C39; | A4-B3-C40; |
| A4-B3-C41; | A4-B3-C42; | A4-B3-C43; | A4-B3-C44; | A4-B3-C45; | A4-B3-C46; |
| A5-B3-C1; | A5-B3-C2; | A5-B3-C3; | A5-B3-C4; | A5-B3-C5; | A5-B3-C6; |
| A5-B3-C7; | A5-B3-C8; | A5-B3-C9; | A5-B3-C10; | A5-B3-C11; | A5-B3-C12; |
| A5-B3-C13; | A5-B3-C14; | A5-B3-C15; | A5-B3-C16; | A5-B3-C17; | A5-B3-C18; |
| A5-B3-C19; | A5-B3-C20; | A5-B3-C21; | A5-B3-C22; | A5-B3-C23; | A5-B3-C24; |
| A5-B3-C25; | A5-B3-C26; | A5-B3-C27; | A5-B3-C28; | A5-B3-C29; | A5-B3-C30; |
| A5-B3-C31; | A5-B3-C32; | A5-B3-C33; | A5-B3-C34; | A5-B3-C35; | A5-B3-C36; |
| A5-B3-C37; | A5-B3-C38; | A5-B3-C39; | A5-B3-C40; | A5-B3-C41; | A5-B3-C42; |
| A5-B3-C43; | A5-B3-C44; | A5-B3-C45; | A5-B3-C46; | A6-B3-C1; | A6-B3-C2; |
| A6-B3-C3; | A6-B3-C4; | A6-B3-C5; | A6-B3-C6; | A6-B3-C7; | A6-B3-C8; |
| A6-B3-C9; | A6-B3-C10; | A6-B3-C11; | A6-B3-C12; | A6-B3-C13; | A6-B3-C14; |
| A6-B3-C15; | A6-B3-C16; | A6-B3-C17; | A6-B3-C18; | A6-B3-C19; | A6-B3-C20; |
| A6-B3-C21; | A6-B3-C22; | A6-B3-C23; | A6-B3-C24; | A6-B3-C25; | A6-B3-C26; |
| A6-B3-C27; | A6-B3-C28; | A6-B3-C29; | A6-B3-C30; | A6-B3-C31; | A6-B3-C32; |
| A6-B3-C33; | A6-B3-C34; | A6-B3-C35; | A6-B3-C36; | A6-B3-C37; | A6-B3-C38; |
| A6-B3-C39; | A6-B3-C40; | A6-B3-C41; | A6-B3-C42; | A6-B3-C43; | A6-B3-C44; |
| A6-B3-C45; | A6-B3-C46; | A7-B3-C1; | A7-B3-C2; | A7-B3-C3; | A7-B3-C4; |
| A7-B3-C5; | A7-B3-C6; | A7-B3-C7; | A7-B3-C8; | A7-B3-C9; | A7-B3-C10; |
| A7-B3-C11; | A7-B3-C12; | A7-B3-C13; | A7-B3-C14; | A7-B3-C15; | A7-B3-C16; |
| A7-B3-C17; | A7-B3-C18; | A7-B3-C19; | A7-B3-C20; | A7-B3-C21; | A7-B3-C22; |
| A7-B3-C23; | A7-B3-C24; | A7-B3-C25; | A7-B3-C26; | A7-B3-C27; | A7-B3-C28; |
| A7-B3-C29; | A7-B3-C30; | A7-B3-C31; | A7-B3-C32; | A7-B3-C33; | A7-B3-C34; |
| A7-B3-C35; | A7-B3-C36; | A7-B3-C37; | A7-B3-C38; | A7-B3-C39; | A7-B3-C40; |
| A7-B3-C41; | A7-B3-C42; | A7-B3-C43; | A7-B3-C44; | A7-B3-C45; | A7-B3-C46; |
| A8-B3-C1; | A8-B3-C2; | A8-B3-C3; | A8-B3-C4; | A8-B3-C5; | A8-B3-C6; |
| A8-B3-C7; | A8-B3-C8; | A8-B3-C9; | A8-B3-C10; | A8-B3-C11; | A8-B3-C12; |
| A8-B3-C13; | A8-B3-C14; | A8-B3-C15; | A8-B3-C16; | A8-B3-C17; | A8-B3-C18; |
| A8-B3-C19; | A8-B3-C20; | A8-B3-C21; | A8-B3-C22; | A8-B3-C23; | A8-B3-C24; |
| A8-B3-C25; | A8-B3-C26; | A8-B3-C27; | A8-B3-C28; | A8-B3-C29; | A8-B3-C30; |
| A8-B3-C31; | A8-B3-C32; | A8-B3-C33; | A8-B3-C34; | A8-B3-C35; | A8-B3-C36; |
| A8-B3-C37; | A8-B3-C38; | A8-B3-C39; | A8-B3-C40; | A8-B3-C41; | A8-B3-C42; |
| A8-B3-C43; | A8-B3-C44; | A8-B3-C45; | A8-B3-C46; | A9-B3-C1; | A9-B3-C2; |
| A9-B3-C3; | A9-B3-C4; | A9-B3-C5; | A9-B3-C6; | A9-B3-C7; | A9-B3-C8; |
| A9-B3-C9; | A9-B3-C10; | A9-B3-C11; | A9-B3-C12; | A9-B3-C13; | A9-B3-C14; |
| A9-B3-C15; | A9-B3-C16; | A9-B3-C17; | A9-B3-C18; | A9-B3-C19; | A9-B3-C20; |
| A9-B3-C21; | A9-B3-C22; | A9-B3-C23; | A9-B3-C24; | A9-B3-C25; | A9-B3-C26; |
| A9-B3-C27; | A9-B3-C28; | A9-B3-C29; | A9-B3-C30; | A9-B3-C31; | A9-B3-C32; |
| A9-B3-C33; | A9-B3-C34; | A9-B3-C35; | A9-B3-C36; | A9-B3-C37; | A9-B3-C38; |
| A9-B3-C39; | A9-B3-C40; | A9-B3-C41; | A9-B3-C42; | A9-B3-C43; | A9-B3-C44; |
| A9-B3-C45; | A9-B3-C46; | A10-B3-C1; | A10-B3-C2; | A10-B3-C3; | A10-B3-C4; |
| A10-B3-C5; | A10-B3-C6; | A10-B3-C7; | A10-B3-C8; | A10-B3-C9; | A10-B3-C10; |
| A10-B3-C11; | A10-B3-C12; | A10-B3-C13; | A10-B3-C14; | A10-B3-C15; | A10-B3-C16; |
| A10-B3-C17; | A10-B3-C18; | A10-B3-C19; | A10-B3-C20; | A10-B3-C21; | A10-B3-C22; |
| A10-B3-C23; | A10-B3-C24; | A10-B3-C25; | A10-B3-C26; | A10-B3-C27; | A10-B3-C28; |
| A10-B3-C29; | A10-B3-C30; | A10-B3-C31; | A10-B3-C32; | A10-B3-C33; | A10-B3-C34; |
| A10-B3-C35; | A10-B3-C36; | A10-B3-C37; | A10-B3-C38; | A10-B3-C39; | A10-B3-C40; |
| A10-B3-C41; | A10-B3-C42; | A10-B3-C43; | A10-B3-C44; | A10-B3-C45; | A10-B3-C46; |
| A11-B3-C1; | A11-B3-C2; | A11-B3-C3; | A11-B3-C4; | A11-B3-C5; | A11-B3-C6; |
| A11-B3-C7; | A11-B3-C8; | A11-B3-C9; | A11-B3-C10; | A11-B3-C11; | A11-B3-C12; |
| A11-B3-C13; | A11-B3-C14; | A11-B3-C15; | A11-B3-C16; | A11-B3-C17; | A11-B3-C18; |
| A11-B3-C19; | A11-B3-C20; | A11-B3-C21; | A11-B3-C22; | A11-B3-C23; | A11-B3-C24; |
| A11-B3-C25; | A11-B3-C26; | A11-B3-C27; | A11-B3-C28; | A11-B3-C29; | A11-B3-C30; |
| A11-B3-C31; | A11-B3-C32; | A11-B3-C33; | A11-B3-C34; | A11-B3-C35; | A11-B3-C36; |
| A11-B3-C37; | A11-B3-C38; | A11-B3-C39; | A11-B3-C40; | A11-B3-C41; | A11-B3-C42; |
| A11-B3-C43; | A11-B3-C44; | A11-B3-C45; | A11-B3-C46; | A12-B3-C1; | A12-B3-C2; |

-continued

| | | | | | |
|---|---|---|---|---|---|
| A12-B3-C3; | A12-B3-C4; | A12-B3-C5; | A12-B3-C6; | A12-B3-C7; | A12-B3-C8; |
| A12-B3-C9; | A12-B3-C10; | A12-B3-C11; | A12-B3-C12; | A12-B3-C13; | A12-B3-C14; |
| A12-B3-C15; | A12-B3-C16; | A12-B3-C17; | A12-B3-C18; | A12-B3-C19; | A12-B3-C20; |
| A12-B3-C21; | A12-B3-C22; | A12-B3-C23; | A12-B3-C24; | A12-B3-C25; | A12-B3-C26; |
| A12-B3-C27; | A12-B3-C28; | A12-B3-C29; | A12-B3-C30; | A12-B3-C31; | A12-B3-C32; |
| A12-B3-C33; | A12-B3-C34; | A12-B3-C35; | A12-B3-C36; | A12-B3-C37; | A12-B3-C38; |
| A12-B3-C39; | A12-B3-C40; | A12-B3-C41; | A12-B3-C42; | A12-B3-C43; | A12-B3-C44; |
| A12-B3-C45; | A12-B3-C46; | A13-B3-C1; | A13-B3-C2; | A13-B3-C3; | A13-B3-C4; |
| A13-B3-C5; | A13-B3-C6; | A13-B3-C7; | A13-B3-C8; | A13-B3-C9; | A13-B3-C10; |
| A13-B3-C11; | A13-B3-C12; | A13-B3-C13; | A13-B3-C14; | A13-B3-C15; | A13-B3-C16; |
| A13-B3-C17; | A13-B3-C18; | A13-B3-C19; | A13-B3-C20; | A13-B3-C21; | A13-B3-C22; |
| A13-B3-C23; | A13-B3-C24; | A13-B3-C25; | A13-B3-C26; | A13-B3-C27; | A13-B3-C28; |
| A13-B3-C29; | A13-B3-C30; | A13-B3-C31; | A13-B3-C32; | A13-B3-C33; | A13-B3-C34; |
| A13-B3-C35; | A13-B3-C36; | A13-B3-C37; | A13-B3-C38; | A13-B3-C39; | A13-B3-C40; |
| A13-B3-C41; | A13-B3-C42; | A13-B3-C43; | A13-B3-C44; | A13-B3-C45; | A13-B3-C46; |
| A14-B3-C1; | A14-B3-C2; | A14-B3-C3; | A14-B3-C4; | A14-B3-C5; | A14-B3-C6; |
| A14-B3-C7; | A14-B3-C8; | A14-B3-C9; | A14-B3-C10; | A14-B3-C11; | A14-B3-C12; |
| A14-B3-C13; | A14-B3-C14; | A14-B3-C15; | A14-B3-C16; | A14-B3-C17; | A14-B3-C18; |
| A14-B3-C19; | A14-B3-C20; | A14-B3-C21; | A14-B3-C22; | A14-B3-C23; | A14-B3-C24; |
| A14-B3-C25; | A14-B3-C26; | A14-B3-C27; | A14-B3-C28; | A14-B3-C29; | A14-B3-C30; |
| A14-B3-C31; | A14-B3-C32; | A14-B3-C33; | A14-B3-C34; | A14-B3-C35; | A14-B3-C36; |
| A14-B3-C37; | A14-B3-C38; | A14-B3-C39; | A14-B3-C40; | A14-B3-C41; | A14-B3-C42; |
| A14-B3-C43; | A14-B3-C44; | A14-B3-C45; | A14-B3-C46; | A15-B3-C1; | A15-B3-C2; |
| A15-B3-C3; | A15-B3-C4; | A15-B3-C5; | A15-B3-C6; | A15-B3-C7; | A15-B3-C8; |
| A15-B3-C9; | A15-B3-C10; | A15-B3-C11; | A15-B3-C12; | A15-B3-C13; | A15-B3-C14; |
| A15-B3-C15; | A15-B3-C16; | A15-B3-C17; | A15-B3-C18; | A15-B3-C19; | A15-B3-C20; |
| A15-B3-C21; | A15-B3-C22; | A15-B3-C23; | A15-B3-C24; | A15-B3-C25; | A15-B3-C26; |
| A15-B3-C27; | A15-B3-C28; | A15-B3-C29; | A15-B3-C30; | A15-B3-C31; | A15-B3-C32; |
| A15-B3-C33; | A15-B3-C34; | A15-B3-C35; | A15-B3-C36; | A15-B3-C37; | A15-B3-C38; |
| A15-B3-C39; | A15-B3-C40; | A15-B3-C41; | A15-B3-C42; | A15-B3-C43; | A15-B3-C44; |
| A15-B3-C45; | A15-B3-C46; | A16-B3-C1; | A16-B3-C2; | A16-B3-C3; | A16-B3-C4; |
| A16-B3-C5; | A16-B3-C6; | A16-B3-C7; | A16-B3-C8; | A16-B3-C9; | A16-B3-C10; |
| A16-B3-C11; | A16-B3-C12; | A16-B3-C13; | A16-B3-C14; | A16-B3-C15; | A16-B3-C16; |
| A16-B3-C17; | A16-B3-C18; | A16-B3-C19; | A16-B3-C20; | A16-B3-C21; | A16-B3-C22; |
| A16-B3-C23; | A16-B3-C24; | A16-B3-C25; | A16-B3-C26; | A16-B3-C27; | A16-B3-C28; |
| A16-B3-C29; | A16-B3-C30; | A16-B3-C31; | A16-B3-C32; | A16-B3-C33; | A16-B3-C34; |
| A16-B3-C35; | A16-B3-C36; | A16-B3-C37; | A16-B3-C38; | A16-B3-C39; | A16-B3-C40; |
| A16-B3-C41; | A16-B3-C42; | A16-B3-C43; | A16-B3-C44; | A16-B3-C45; | A16-B3-C46; |
| A17-B3-C1; | A17-B3-C2; | A17-B3-C3; | A17-B3-C4; | A17-B3-C5; | A17-B3-C6; |
| A17-B3-C7; | A17-B3-C8; | A17-B3-C9; | A17-B3-C10; | A17-B3-C11; | A17-B3-C12; |
| A17-B3-C13; | A17-B3-C14; | A17-B3-C15; | A17-B3-C16; | A17-B3-C17; | A17-B3-C18; |
| A17-B3-C19; | A17-B3-C20; | A17-B3-C21; | A17-B3-C22; | A17-B3-C23; | A17-B3-C24; |
| A17-B3-C25; | A17-B3-C26; | A17-B3-C27; | A17-B3-C28; | A17-B3-C29; | A17-B3-C30; |
| A17-B3-C31; | A17-B3-C32; | A17-B3-C33; | A17-B3-C34; | A17-B3-C35; | A17-B3-C36; |
| A17-B3-C37; | A17-B3-C38; | A17-B3-C39; | A17-B3-C40; | A17-B3-C41; | A17-B3-C42; |
| A17-B3-C43; | A17-B3-C44; | A17-B3-C45; | A17-B3-C46; | A18-B3-C1; | A18-B3-C2; |
| A18-B3-C3; | A18-B3-C4; | A18-B3-C5; | A18-B3-C6; | A18-B3-C7; | A18-B3-C8; |
| A18-B3-C9; | A18-B3-C10; | A18-B3-C11; | A18-B3-C12; | A18-B3-C13; | A18-B3-C14; |
| A18-B3-C15; | A18-B3-C16; | A18-B3-C17; | A18-B3-C18; | A18-B3-C19; | A18-B3-C20; |
| A18-B3-C21; | A18-B3-C22; | A18-B3-C23; | A18-B3-C24; | A18-B3-C25; | A18-B3-C26; |
| A18-B3-C27; | A18-B3-C28; | A18-B3-C29; | A18-B3-C30; | A18-B3-C31; | A18-B3-C32; |
| A18-B3-C33; | A18-B3-C34; | A18-B3-C35; | A18-B3-C36; | A18-B3-C37; | A18-B3-C38; |
| A18-B3-C39; | A18-B3-C40; | A18-B3-C41; | A18-B3-C42; | A18-B3-C43; | A18-B3-C44; |
| A18-B3-C45; | A18-B3-C46; | A19-B3-C1; | A19-B3-C2; | A19-B3-C3; | A19-B3-C4; |
| A19-B3-C5; | A19-B3-C6; | A19-B3-C7; | A19-B3-C8; | A19-B3-C9; | A19-B3-C10; |
| A19-B3-C11; | A19-B3-C12; | A19-B3-C13; | A19-B3-C14; | A19-B3-C15; | A19-B3-C16; |
| A19-B3-C17; | A19-B3-C18; | A19-B3-C19; | A19-B3-C20; | A19-B3-C21; | A19-B3-C22; |
| A19-B3-C23; | A19-B3-C24; | A19-B3-C25; | A19-B3-C26; | A19-B3-C27; | A19-B3-C28; |
| A19-B3-C29; | A19-B3-C30; | A19-B3-C31; | A19-B3-C32; | A19-B3-C33; | A19-B3-C34; |
| A19-B3-C35; | A19-B3-C36; | A19-B3-C37; | A19-B3-C38; | A19-B3-C39; | A19-B3-C40; |
| A19-B3-C41; | A19-B3-C42; | A19-B3-C43; | A19-B3-C44; | A19-B3-C45; | A19-B3-C46; |
| A20-B3-C1; | A20-B3-C2; | A20-B3-C3; | A20-B3-C4; | A20-B3-C5; | A20-B3-C6; |
| A20-B3-C7; | A20-B3-C8; | A20-B3-C9; | A20-B3-C10; | A20-B3-C11; | A20-B3-C12; |
| A20-B3-C13; | A20-B3-C14; | A20-B3-C15; | A20-B3-C16; | A20-B3-C17; | A20-B3-C18; |
| A20-B3-C19; | A20-B3-C20; | A20-B3-C21; | A20-B3-C22; | A20-B3-C23; | A20-B3-C24; |
| A20-B3-C25; | A20-B3-C26; | A20-B3-C27; | A20-B3-C28; | A20-B3-C29; | A20-B3-C30; |
| A20-B3-C31; | A20-B3-C32; | A20-B3-C33; | A20-B3-C34; | A20-B3-C35; | A20-B3-C36; |
| A20-B3-C37; | A20-B3-C38; | A20-B3-C39; | A20-B3-C40; | A20-B3-C41; | A20-B3-C42; |
| A20-B3-C43; | A20-B3-C44; | A20-B3-C45; | A20-B3-C46; | A21-B3-C1; | A21-B3-C2; |
| A21-B3-C3; | A21-B3-C4; | A21-B3-C5; | A21-B3-C6; | A21-B3-C7; | A21-B3-C8; |
| A21-B3-C9; | A21-B3-C10; | A21-B3-C11; | A21-B3-C12; | A21-B3-C13; | A21-B3-C14; |
| A21-B3-C15; | A21-B3-C16; | A21-B3-C17; | A21-B3-C18; | A21-B3-C19; | A21-B3-C20; |
| A21-B3-C21; | A21-B3-C22; | A21-B3-C23; | A21-B3-C24; | A21-B3-C25; | A21-B3-C26; |
| A21-B3-C27; | A21-B3-C28; | A21-B3-C29; | A21-B3-C30; | A21-B3-C31; | A21-B3-C32; |
| A21-B3-C33; | A21-B3-C34; | A21-B3-C35; | A21-B3-C36; | A21-B3-C37; | A21-B3-C38; |
| A21-B3-C39; | A21-B3-C40; | A21-B3-C41; | A21-B3-C42; | A21-B3-C43; | A21-B3-C44; |
| A21-B3-C45; | A21-B3-C46; | A22-B3-C1; | A22-B3-C2; | A22-B3-C3; | A22-B3-C4; |
| A22-B3-C5; | A22-B3-C6; | A22-B3-C7; | A22-B3-C8; | A22-B3-C9; | A22-B3-C10; |
| A22-B3-C11; | A22-B3-C12; | A22-B3-C13; | A22-B3-C14; | A22-B3-C15; | A22-B3-C16; |

-continued

| | | | | | |
|---|---|---|---|---|---|
| A22-B3-C17; | A22-B3-C18; | A22-B3-C19; | A22-B3-C20; | A22-B3-C21; | A22-B3-C22; |
| A22-B3-C23; | A22-B3-C24; | A22-B3-C25; | A22-B3-C26; | A22-B3-C27; | A22-B3-C28; |
| A22-B3-C29; | A22-B3-C30; | A22-B3-C31; | A22-B3-C32; | A22-B3-C33; | A22-B3-C34; |
| A22-B3-C35; | A22-B3-C36; | A22-B3-C37; | A22-B3-C38; | A22-B3-C39; | A22-B3-C40; |
| A22-B3-C41; | A22-B3-C42; | A22-B3-C43; | A22-B3-C44; | A22-B3-C45; | A22-B3-C46; |
| A23-B3-C1; | A23-B3-C2; | A23-B3-C3; | A23-B3-C4; | A23-B3-C5; | A23-B3-C6; |
| A23-B3-C7; | A23-B3-C8; | A23-B3-C9; | A23-B3-C10; | A23-B3-C11; | A23-B3-C12; |
| A23-B3-C13; | A23-B3-C14; | A23-B3-C15; | A23-B3-C16; | A23-B3-C17; | A23-B3-C18; |
| A23-B3-C19; | A23-B3-C20; | A23-B3-C21; | A23-B3-C22; | A23-B3-C23; | A23-B3-C24; |
| A23-B3-C25; | A23-B3-C26; | A23-B3-C27; | A23-B3-C28; | A23-B3-C29; | A23-B3-C30; |
| A23-B3-C31; | A23-B3-C32; | A23-B3-C33; | A23-B3-C34; | A23-B3-C35; | A23-B3-C36; |
| A23-B3-C37; | A23-B3-C38; | A23-B3-C39; | A23-B3-C40; | A23-B3-C41; | A23-B3-C42; |
| A23-B3-C43; | A23-B3-C44; | A23-B3-C45; | A23-B3-C46; | A24-B3-C1; | A24-B3-C2; |
| A24-B3-C3; | A24-B3-C4; | A24-B3-C5; | A24-B3-C6; | A24-B3-C7; | A24-B3-C8; |
| A24-B3-C9; | A24-B3-C10; | A24-B3-C11; | A24-B3-C12; | A24-B3-C13; | A24-B3-C14; |
| A24-B3-C15; | A24-B3-C16; | A24-B3-C17; | A24-B3-C18; | A24-B3-C19; | A24-B3-C20; |
| A24-B3-C21; | A24-B3-C22; | A24-B3-C23; | A24-B3-C24; | A24-B3-C25; | A24-B3-C26; |
| A24-B3-C27; | A24-B3-C28; | A24-B3-C29; | A24-B3-C30; | A24-B3-C31; | A24-B3-C32; |
| A24-B3-C33; | A24-B3-C34; | A24-B3-C35; | A24-B3-C36; | A24-B3-C37; | A24-B3-C38; |
| A24-B3-C39; | A24-B3-C40; | A24-B3-C41; | A24-B3-C42; | A24-B3-C43; | A24-B3-C44; |
| A24-B3-C45; | A24-B3-C46; | A25-B3-C1; | A25-B3-C2; | A25-B3-C3; | A25-B3-C4; |
| A25-B3-C5; | A25-B3-C6; | A25-B3-C7; | A25-B3-C8; | A25-B3-C9; | A25-B3-C10; |
| A25-B3-C11; | A25-B3-C12; | A25-B3-C13; | A25-B3-C14; | A25-B3-C15; | A25-B3-C16; |
| A25-B3-C17; | A25-B3-C18; | A25-B3-C19; | A25-B3-C20; | A25-B3-C21; | A25-B3-C22; |
| A25-B3-C23; | A25-B3-C24; | A25-B3-C25; | A25-B3-C26; | A25-B3-C27; | A25-B3-C28; |
| A25-B3-C29; | A25-B3-C30; | A25-B3-C31; | A25-B3-C32; | A25-B3-C33; | A25-B3-C34; |
| A25-B3-C35; | A25-B3-C36; | A25-B3-C37; | A25-B3-C38; | A25-B3-C39; | A25-B3-C40; |
| A25-B3-C41; | A25-B3-C42; | A25-B3-C43; | A25-B3-C44; | A25-B3-C45; | A25-B3-C46; |
| A26-B3-C1; | A26-B3-C2; | A26-B3-C3; | A26-B3-C4; | A26-B3-C5; | A26-B3-C6; |
| A26-B3-C7; | A26-B3-C8; | A26-B3-C9; | A26-B3-C10; | A26-B3-C11; | A26-B3-C12; |
| A26-B3-C13; | A26-B3-C14; | A26-B3-C15; | A26-B3-C16; | A26-B3-C17; | A26-B3-C18; |
| A26-B3-C19; | A26-B3-C20; | A26-B3-C21; | A26-B3-C22; | A26-B3-C23; | A26-B3-C24; |
| A26-B3-C25; | A26-B3-C26; | A26-B3-C27; | A26-B3-C28; | A26-B3-C29; | A26-B3-C30; |
| A26-B3-C31; | A26-B3-C32; | A26-B3-C33; | A26-B3-C34; | A26-B3-C35; | A26-B3-C36; |
| A26-B3-C37; | A26-B3-C38; | A26-B3-C39; | A26-B3-C40; | A26-B3-C41; | A26-B3-C42; |
| A26-B3-C43; | A26-B3-C44; | A26-B3-C45; | A26-B3-C46; | A27-B3-C1; | A27-B3-C2; |
| A27-B3-C3; | A27-B3-C4; | A27-B3-C5; | A27-B3-C6; | A27-B3-C7; | A27-B3-C8; |
| A27-B3-C9; | A27-B3-C10; | A27-B3-C11; | A27-B3-C12; | A27-B3-C13; | A27-B3-C14; |
| A27-B3-C15; | A27-B3-C16; | A27-B3-C17; | A27-B3-C18; | A27-B3-C19; | A27-B3-C20; |
| A27-B3-C21; | A27-B3-C22; | A27-B3-C23; | A27-B3-C24; | A27-B3-C25; | A27-B3-C26; |
| A27-B3-C27; | A27-B3-C28; | A27-B3-C29; | A27-B3-C30; | A27-B3-C31; | A27-B3-C32; |
| A27-B3-C33; | A27-B3-C34; | A27-B3-C35; | A27-B3-C36; | A27-B3-C37; | A27-B3-C38; |
| A27-B3-C39; | A27-B3-C40; | A27-B3-C41; | A27-B3-C42; | A27-B3-C43; | A27-B3-C44; |
| A27-B3-C45; | A27-B3-C46; | A28-B3-C1; | A28-B3-C2; | A28-B3-C3; | A28-B3-C4; |
| A28-B3-C5; | A28-B3-C6; | A28-B3-C7; | A28-B3-C8; | A28-B3-C9; | A28-B3-C10; |
| A28-B3-C11; | A28-B3-C12; | A28-B3-C13; | A28-B3-C14; | A28-B3-C15; | A28-B3-C16; |
| A28-B3-C17; | A28-B3-C18; | A28-B3-C19; | A28-B3-C20; | A28-B3-C21; | A28-B3-C22; |
| A28-B3-C23; | A28-B3-C24; | A28-B3-C25; | A28-B3-C26; | A28-B3-C27; | A28-B3-C28; |
| A28-B3-C29; | A28-B3-C30; | A28-B3-C31; | A28-B3-C32; | A28-B3-C33; | A28-B3-C34; |
| A28-B3-C35; | A28-B3-C36; | A28-B3-C37; | A28-B3-C38; | A28-B3-C39; | A28-B3-C40; |
| A28-B3-C41; | A28-B3-C42; | A28-B3-C43; | A28-B3-C44; | A28-B3-C45; | A28-B3-C46; |
| A1-B4-C1; | A1-B4-C2; | A1-B4-C3; | A1-B4-C4; | A1-B4-C5; | A1-B4-C6; |
| A1-B4-C7; | A1-B4-C8; | A1-B4-C9; | A1-B4-C10; | A1-B4-C11; | A1-B4-C12; |
| A1-B4-C13; | A1-B4-C14; | A1-B4-C15; | A1-B4-C16; | A1-B4-C17; | A1-B4-C18; |
| A1-B4-C19; | A1-B4-C20; | A1-B4-C21; | A1-B4-C22; | A1-B4-C23; | A1-B4-C24; |
| A1-B4-C25; | A1-B4-C26; | A1-B4-C27; | A1-B4-C28; | A1-B4-C29; | A1-B4-C30; |
| A1-B4-C31; | A1-B4-C32; | A1-B4-C33; | A1-B4-C34; | A1-B4-C35; | A1-B4-C36; |
| A1-B4-C37; | A1-B4-C38; | A1-B4-C39; | A1-B4-C40; | A1-B4-C41; | A1-B4-C42; |
| A1-B4-C43; | A1-B4-C44; | A1-B4-C45; | A1-B4-C46; | A2-B4-C1; | A2-B4-C2; |
| A2-B4-C3; | A2-B4-C4; | A2-B4-C5; | A2-B4-C6; | A2-B4-C7; | A2-B4-C8; |
| A2-B4-C9; | A2-B4-C10; | A2-B4-C11; | A2-B4-C12; | A2-B4-C13; | A2-B4-C14; |
| A2-B4-C15; | A2-B4-C16; | A2-B4-C17; | A2-B4-C18; | A2-B4-C19; | A2-B4-C20; |
| A2-B4-C21; | A2-B4-C22; | A2-B4-C23; | A2-B4-C24; | A2-B4-C25; | A2-B4-C26; |
| A2-B4-C27; | A2-B4-C28; | A2-B4-C29; | A2-B4-C30; | A2-B4-C31; | A2-B4-C32; |
| A2-B4-C33; | A2-B4-C34; | A2-B4-C35; | A2-B4-C36; | A2-B4-C37; | A2-B4-C38; |
| A2-B4-C39; | A2-B4-C40; | A2-B4-C41; | A2-B4-C42; | A2-B4-C43; | A2-B4-C44; |
| A2-B4-C45; | A2-B4-C46; | A3-B4-C1; | A3-B4-C2; | A3-B4-C3; | A3-B4-C4; |
| A3-B4-C5; | A3-B4-C6; | A3-B4-C7; | A3-B4-C8; | A3-B4-C9; | A3-B4-C10; |
| A3-B4-C11; | A3-B4-C12; | A3-B4-C13; | A3-B4-C14; | A3-B4-C15; | A3-B4-C16; |
| A3-B4-C17; | A3-B4-C18; | A3-B4-C19; | A3-B4-C20; | A3-B4-C21; | A3-B4-C22; |
| A3-B4-C23; | A3-B4-C24; | A3-B4-C25; | A3-B4-C26; | A3-B4-C27; | A3-B4-C28; |
| A3-B4-C29; | A3-B4-C30; | A3-B4-C31; | A3-B4-C32; | A3-B4-C33; | A3-B4-C34; |
| A3-B4-C35; | A3-B4-C36; | A3-B4-C37; | A3-B4-C38; | A3-B4-C39; | A3-B4-C40; |
| A3-B4-C41; | A3-B4-C42; | A3-B4-C43; | A3-B4-C44; | A3-B4-C45; | A3-B4-C46; |
| A4-B4-C1; | A4-B4-C2; | A4-B4-C3; | A4-B4-C4; | A4-B4-C5; | A4-B4-C6; |
| A4-B4-C7; | A4-B4-C8; | A4-B4-C9; | A4-B4-C10; | A4-B4-C11; | A4-B4-C12; |
| A4-B4-C13; | A4-B4-C14; | A4-B4-C15; | A4-B4-C16; | A4-B4-C17; | A4-B4-C18; |
| A4-B4-C19; | A4-B4-C20; | A4-B4-C21; | A4-B4-C22; | A4-B4-C23; | A4-B4-C24; |
| A4-B4-C25; | A4-B4-C26; | A4-B4-C27; | A4-B4-C28; | A4-B4-C29; | A4-B4-C30; |

-continued

| | | | | | |
|---|---|---|---|---|---|
| A4-B4-C31; | A4-B4-C32; | A4-B4-C33; | A4-B4-C34; | A4-B4-C35; | A4-B4-C36; |
| A4-B4-C37; | A4-B4-C38; | A4-B4-C39; | A4-B4-C40; | A4-B4-C41; | A4-B4-C42; |
| A4-B4-C43; | A4-B4-C44; | A4-B4-C45; | A4-B4-C46; | A5-B4-C1; | A5-B4-C2; |
| A5-B4-C3; | A5-B4-C4; | A5-B4-C5; | A5-B4-C6; | A5-B4-C7; | A5-B4-C8; |
| A5-B4-C9; | A5-B4-C10; | A5-B4-C11; | A5-B4-C12; | A5-B4-C13; | A5-B4-C14; |
| A5-B4-C15; | A5-B4-C16; | A5-B4-C17; | A5-B4-C18; | A5-B4-C19; | A5-B4-C20; |
| A5-B4-C21; | A5-B4-C22; | A5-B4-C23; | A5-B4-C24; | A5-B4-C25; | A5-B4-C26; |
| A5-B4-C27; | A5-B4-C28; | A5-B4-C29; | A5-B4-C30; | A5-B4-C31; | A5-B4-C32; |
| A5-B4-C33; | A5-B4-C34; | A5-B4-C35; | A5-B4-C36; | A5-B4-C37; | A5-B4-C38; |
| A5-B4-C39; | A5-B4-C40; | A5-B4-C41; | A5-B4-C42; | A5-B4-C43; | A5-B4-C44; |
| A5-B4-C45; | A5-B4-C46; | A6-B4-C1; | A6-B4-C2; | A6-B4-C3; | A6-B4-C4; |
| A6-B4-C5; | A6-B4-C6; | A6-B4-C7; | A6-B4-C8; | A6-B4-C9; | A6-B4-C10; |
| A6-B4-C11; | A6-B4-C12; | A6-B4-C13; | A6-B4-C14; | A6-B4-C15; | A6-B4-C16; |
| A6-B4-C17; | A6-B4-C18; | A6-B4-C19; | A6-B4-C20; | A6-B4-C21; | A6-B4-C22; |
| A6-B4-C23; | A6-B4-C24; | A6-B4-C25; | A6-B4-C26; | A6-B4-C27; | A6-B4-C28; |
| A6-B4-C29; | A6-B4-C30; | A6-B4-C31; | A6-B4-C32; | A6-B4-C33; | A6-B4-C34; |
| A6-B4-C35; | A6-B4-C36; | A6-B4-C37; | A6-B4-C38; | A6-B4-C39; | A6-B4-C40; |
| A6-B4-C41; | A6-B4-C42; | A6-B4-C43; | A6-B4-C44; | A6-B4-C45; | A6-B4-C46; |
| A7-B4-C1; | A7-B4-C2; | A7-B4-C3; | A7-B4-C4; | A7-B4-C5; | A7-B4-C6; |
| A7-B4-C7; | A7-B4-C8; | A7-B4-C9; | A7-B4-C10; | A7-B4-C11; | A7-B4-C12; |
| A7-B4-C13; | A7-B4-C14; | A7-B4-C15; | A7-B4-C16; | A7-B4-C17; | A7-B4-C18; |
| A7-B4-C19; | A7-B4-C20; | A7-B4-C21; | A7-B4-C22; | A7-B4-C23; | A7-B4-C24; |
| A7-B4-C25; | A7-B4-C26; | A7-B4-C27; | A7-B4-C28; | A7-B4-C29; | A7-B4-C30; |
| A7-B4-C31; | A7-B4-C32; | A7-B4-C33; | A7-B4-C34; | A7-B4-C35; | A7-B4-C36; |
| A7-B4-C37; | A7-B4-C38; | A7-B4-C39; | A7-B4-C40; | A7-B4-C41; | A7-B4-C42; |
| A7-B4-C43; | A7-B4-C44; | A7-B4-C45; | A7-B4-C46; | A8-B4-C1; | A8-B4-C2; |
| A8-B4-C3; | A8-B4-C4; | A8-B4-C5; | A8-B4-C6; | A8-B4-C7; | A8-B4-C8; |
| A8-B4-C9; | A8-B4-C10; | A8-B4-C11; | A8-B4-C12; | A8-B4-C13; | A8-B4-C14; |
| A8-B4-C15; | A8-B4-C16; | A8-B4-C17; | A8-B4-C18; | A8-B4-C19; | A8-B4-C20; |
| A8-B4-C21; | A8-B4-C22; | A8-B4-C23; | A8-B4-C24; | A8-B4-C25; | A8-B4-C26; |
| A8-B4-C27; | A8-B4-C28; | A8-B4-C29; | A8-B4-C30; | A8-B4-C31; | A8-B4-C32; |
| A8-B4-C33; | A8-B4-C34; | A8-B4-C35; | A8-B4-C36; | A8-B4-C37; | A8-B4-C38; |
| A8-B4-C39; | A8-B4-C40; | A8-B4-C41; | A8-B4-C42; | A8-B4-C43; | A8-B4-C44; |
| A8-B4-C45; | A8-B4-C46; | A9-B4-C1; | A9-B4-C2; | A9-B4-C3; | A9-B4-C4; |
| A9-B4-C5; | A9-B4-C6; | A9-B4-C7; | A9-B4-C8; | A9-B4-C9; | A9-B4-C10; |
| A9-B4-C11; | A9-B4-C12; | A9-B4-C13; | A9-B4-C14; | A9-B4-C15; | A9-B4-C16; |
| A9-B4-C17; | A9-B4-C18; | A9-B4-C19; | A9-B4-C20; | A9-B4-C21; | A9-B4-C22; |
| A9-B4-C23; | A9-B4-C24; | A9-B4-C25; | A9-B4-C26; | A9-B4-C27; | A9-B4-C28; |
| A9-B4-C29; | A9-B4-C30; | A9-B4-C31; | A9-B4-C32; | A9-B4-C33; | A9-B4-C34; |
| A9-B4-C35; | A9-B4-C36; | A9-B4-C37; | A9-B4-C38; | A9-B4-C39; | A9-B4-C40; |
| A9-B4-C41; | A9-B4-C42; | A9-B4-C43; | A9-B4-C44; | A9-B4-C45; | A9-B4-C46; |
| A10-B4-C1; | A10-B4-C2; | A10-B4-C3; | A10-B4-C4; | A10-B4-C5; | A10-B4-C6; |
| A10-B4-C7; | A10-B4-C8; | A10-B4-C9; | A10-B4-C10; | A10-B4-C11; | A10-B4-C12; |
| A10-B4-C13; | A10-B4-C14; | A10-B4-C15; | A10-B4-C16; | A10-B4-C17; | A10-B4-C18; |
| A10-B4-C19; | A10-B4-C20; | A10-B4-C21; | A10-B4-C22; | A10-B4-C23; | A10-B4-C24; |
| A10-B4-C25; | A10-B4-C26; | A10-B4-C27; | A10-B4-C28; | A10-B4-C29; | A10-B4-C30; |
| A10-B4-C31; | A10-B4-C32; | A10-B4-C33; | A10-B4-C34; | A10-B4-C35; | A10-B4-C36; |
| A10-B4-C37; | A10-B4-C38; | A10-B4-C39; | A10-B4-C40; | A10-B4-C41; | A10-B4-C42; |
| A10-B4-C43; | A10-B4-C44; | A10-B4-C45; | A10-B4-C46; | A11-B4-C1; | A11-B4-C2; |
| A11-B4-C3; | A11-B4-C4; | A11-B4-C5; | A11-B4-C6; | A11-B4-C7; | A11-B4-C8; |
| A11-B4-C9; | A11-B4-C10; | A11-B4-C11; | A11-B4-C12; | A11-B4-C13; | A11-B4-C14; |
| A11-B4-C15; | A11-B4-C16; | A11-B4-C17; | A11-B4-C18; | A11-B4-C19; | A11-B4-C20; |
| A11-B4-C21; | A11-B4-C22; | A11-B4-C23; | A11-B4-C24; | A11-B4-C25; | A11-B4-C26; |
| A11-B4-C27; | A11-B4-C28; | A11-B4-C29; | A11-B4-C30; | A11-B4-C31; | A11-B4-C32; |
| A11-B4-C33; | A11-B4-C34; | A11-B4-C35; | A11-B4-C36; | A11-B4-C37; | A11-B4-C38; |
| A11-B4-C39; | A11-B4-C40; | A11-B4-C41; | A11-B4-C42; | A11-B4-C43; | A11-B4-C44; |
| A11-B4-C45; | A11-B4-C46; | A12-B4-C1; | A12-B4-C2; | A12-B4-C3; | A12-B4-C4; |
| A12-B4-C5; | A12-B4-C6; | A12-B4-C7; | A12-B4-C8; | A12-B4-C9; | A12-B4-C10; |
| A12-B4-C11; | A12-B4-C12; | A12-B4-C13; | A12-B4-C14; | A12-B4-C15; | A12-B4-C16; |
| A12-B4-C17; | A12-B4-C18; | A12-B4-C19; | A12-B4-C20; | A12-B4-C21; | A12-B4-C22; |
| A12-B4-C23; | A12-B4-C24; | A12-B4-C25; | A12-B4-C26; | A12-B4-C27; | A12-B4-C28; |
| A12-B4-C29; | A12-B4-C30; | A12-B4-C31; | A12-B4-C32; | A12-B4-C33; | A12-B4-C34; |
| A12-B4-C35; | A12-B4-C36; | A12-B4-C37; | A12-B4-C38; | A12-B4-C39; | A12-B4-C40; |
| A12-B4-C41; | A12-B4-C42; | A12-B4-C43; | A12-B4-C44; | A12-B4-C45; | A12-B4-C46; |
| A13-B4-C1; | A13-B4-C2; | A13-B4-C3; | A13-B4-C4; | A13-B4-C5; | A13-B4-C6; |
| A13-B4-C7; | A13-B4-C8; | A13-B4-C9; | A13-B4-C10; | A13-B4-C11; | A13-B4-C12; |
| A13-B4-C13; | A13-B4-C14; | A13-B4-C15; | A13-B4-C16; | A13-B4-C17; | A13-B4-C18; |
| A13-B4-C19; | A13-B4-C20; | A13-B4-C21; | A13-B4-C22; | A13-B4-C23; | A13-B4-C24; |
| A13-B4-C25; | A13-B4-C26; | A13-B4-C27; | A13-B4-C28; | A13-B4-C29; | A13-B4-C30; |
| A13-B4-C31; | A13-B4-C32; | A13-B4-C33; | A13-B4-C34; | A13-B4-C35; | A13-B4-C36; |
| A13-B4-C37; | A13-B4-C38; | A13-B4-C39; | A13-B4-C40; | A13-B4-C41; | A13-B4-C42; |
| A13-B4-C43; | A13-B4-C44; | A13-B4-C45; | A13-B4-C46; | A14-B4-C1; | A14-B4-C2; |
| A14-B4-C3; | A14-B4-C4; | A14-B4-C5; | A14-B4-C6; | A14-B4-C7; | A14-B4-C8; |
| A14-B4-C9; | A14-B4-C10; | A14-B4-C11; | A14-B4-C12; | A14-B4-C13; | A14-B4-C14; |
| A14-B4-C15; | A14-B4-C16; | A14-B4-C17; | A14-B4-C18; | A14-B4-C19; | A14-B4-C20; |
| A14-B4-C21; | A14-B4-C22; | A14-B4-C23; | A14-B4-C24; | A14-B4-C25; | A14-B4-C26; |
| A14-B4-C27; | A14-B4-C28; | A14-B4-C29; | A14-B4-C30; | A14-B4-C31; | A14-B4-C32; |
| A14-B4-C33; | A14-B4-C34; | A14-B4-C35; | A14-B4-C36; | A14-B4-C37; | A14-B4-C38; |
| A14-B4-C39; | A14-B4-C40; | A14-B4-C41; | A14-B4-C42; | A14-B4-C43; | A14-B4-C44; |

| | | | | |
|---|---|---|---|---|
| A14-B4-C45; | A14-B4-C46; | A15-B4-C1; | A15-B4-C2; | A15-B4-C3; | A15-B4-C4; |
| A15-B4-C5; | A15-B4-C6; | A15-B4-C7; | A15-B4-C8; | A15-B4-C9; | A15-B4-C10; |
| A15-B4-C11; | A15-B4-C12; | A15-B4-C13; | A15-B4-C14; | A15-B4-C15; | A15-B4-C16; |
| A15-B4-C17; | A15-B4-C18; | A15-B4-C19; | A15-B4-C20; | A15-B4-C21; | A15-B4-C22; |
| A15-B4-C23; | A15-B4-C24; | A15-B4-C25; | A15-B4-C26; | A15-B4-C27; | A15-B4-C28; |
| A15-B4-C29; | A15-B4-C30; | A15-B4-C31; | A15-B4-C32; | A15-B4-C33; | A15-B4-C34; |
| A15-B4-C35; | A15-B4-C36; | A15-B4-C37; | A15-B4-C38; | A15-B4-C39; | A15-B4-C40; |
| A15-B4-C41; | A15-B4-C42; | A15-B4-C43; | A15-B4-C44; | A15-B4-C45; | A15-B4-C46; |
| A16-B4-C1; | A16-B4-C2; | A16-B4-C3; | A16-B4-C4; | A16-B4-C5; | A16-B4-C6; |
| A16-B4-C7; | A16-B4-C8; | A16-B4-C9; | A16-B4-C10; | A16-B4-C11; | A16-B4-C12; |
| A16-B4-C13; | A16-B4-C14; | A16-B4-C15; | A16-B4-C16; | A16-B4-C17; | A16-B4-C18; |
| A16-B4-C19; | A16-B4-C20; | A16-B4-C21; | A16-B4-C22; | A16-B4-C23; | A16-B4-C24; |
| A16-B4-C25; | A16-B4-C26; | A16-B4-C27; | A16-B4-C28; | A16-B4-C29; | A16-B4-C30; |
| A16-B4-C31; | A16-B4-C32; | A16-B4-C33; | A16-B4-C34; | A16-B4-C35; | A16-B4-C36; |
| A16-B4-C37; | A16-B4-C38; | A16-B4-C39; | A16-B4-C40; | A16-B4-C41; | A16-B4-C42; |
| A16-B4-C43; | A16-B4-C44; | A16-B4-C45; | A16-B4-C46; | A17-B4-C1; | A17-B4-C2; |
| A17-B4-C3; | A17-B4-C4; | A17-B4-C5; | A17-B4-C6; | A17-B4-C7; | A17-B4-C8; |
| A17-B4-C9; | A17-B4-C10; | A17-B4-C11; | A17-B4-C12; | A17-B4-C13; | A17-B4-C14; |
| A17-B4-C15; | A17-B4-C16; | A17-B4-C17; | A17-B4-C18; | A17-B4-C19; | A17-B4-C20; |
| A17-B4-C21; | A17-B4-C22; | A17-B4-C23; | A17-B4-C24; | A17-B4-C25; | A17-B4-C26; |
| A17-B4-C27; | A17-B4-C28; | A17-B4-C29; | A17-B4-C30; | A17-B4-C31; | A17-B4-C32; |
| A17-B4-C33; | A17-B4-C34; | A17-B4-C35; | A17-B4-C36; | A17-B4-C37; | A17-B4-C38; |
| A17-B4-C39; | A17-B4-C40; | A17-B4-C41; | A17-B4-C42; | A17-B4-C43; | A17-B4-C44; |
| A17-B4-C45; | A17-B4-C46; | A18-B4-C1; | A18-B4-C2; | A18-B4-C3; | A18-B4-C4; |
| A18-B4-C5; | A18-B4-C6; | A18-B4-C7; | A18-B4-C8; | A18-B4-C9; | A18-B4-C10; |
| A18-B4-C11; | A18-B4-C12; | A18-B4-C13; | A18-B4-C14; | A18-B4-C15; | A18-B4-C16; |
| A18-B4-C17; | A18-B4-C18; | A18-B4-C19; | A18-B4-C20; | A18-B4-C21; | A18-B4-C22; |
| A18-B4-C23; | A18-B4-C24; | A18-B4-C25; | A18-B4-C26; | A18-B4-C27; | A18-B4-C28; |
| A18-B4-C29; | A18-B4-C30; | A18-B4-C31; | A18-B4-C32; | A18-B4-C33; | A18-B4-C34; |
| A18-B4-C35; | A18-B4-C36; | A18-B4-C37; | A18-B4-C38; | A18-B4-C39; | A18-B4-C40; |
| A18-B4-C41; | A18-B4-C42; | A18-B4-C43; | A18-B4-C44; | A18-B4-C45; | A18-B4-C46; |
| A19-B4-C1; | A19-B4-C2; | A19-B4-C3; | A19-B4-C4; | A19-B4-C5; | A19-B4-C6; |
| A19-B4-C7; | A19-B4-C8; | A19-B4-C9; | A19-B4-C10; | A19-B4-C11; | A19-B4-C12; |
| A19-B4-C13; | A19-B4-C14; | A19-B4-C15; | A19-B4-C16; | A19-B4-C17; | A19-B4-C18; |
| A19-B4-C19; | A19-B4-C20; | A19-B4-C21; | A19-B4-C22; | A19-B4-C23; | A19-B4-C24; |
| A19-B4-C25; | A19-B4-C26; | A19-B4-C27; | A19-B4-C28; | A19-B4-C29; | A19-B4-C30; |
| A19-B4-C31; | A19-B4-C32; | A19-B4-C33; | A19-B4-C34; | A19-B4-C35; | A19-B4-C36; |
| A19-B4-C37; | A19-B4-C38; | A19-B4-C39; | A19-B4-C40; | A19-B4-C41; | A19-B4-C42; |
| A19-B4-C43; | A19-B4-C44; | A19-B4-C45; | A19-B4-C46; | A20-B4-C1; | A20-B4-C2; |
| A20-B4-C3; | A20-B4-C4; | A20-B4-C5; | A20-B4-C6; | A20-B4-C7; | A20-B4-C8; |
| A20-B4-C9; | A20-B4-C10; | A20-B4-C11; | A20-B4-C12; | A20-B4-C13; | A20-B4-C14; |
| A20-B4-C15; | A20-B4-C16; | A20-B4-C17; | A20-B4-C18; | A20-B4-C19; | A20-B4-C20; |
| A20-B4-C21; | A20-B4-C22; | A20-B4-C23; | A20-B4-C24; | A20-B4-C25; | A20-B4-C26; |
| A20-B4-C27; | A20-B4-C28; | A20-B4-C29; | A20-B4-C30; | A20-B4-C31; | A20-B4-C32; |
| A20-B4-C33; | A20-B4-C34; | A20-B4-C35; | A20-B4-C36; | A20-B4-C37; | A20-B4-C38; |
| A20-B4-C39; | A20-B4-C40; | A20-B4-C41; | A20-B4-C42; | A20-B4-C43; | A20-B4-C44; |
| A20-B4-C45; | A20-B4-C46; | A21-B4-C1; | A21-B4-C2; | A21-B4-C3; | A21-B4-C4; |
| A21-B4-C5; | A21-B4-C6; | A21-B4-C7; | A21-B4-C8; | A21-B4-C9; | A21-B4-C10; |
| A21-B4-C11; | A21-B4-C12; | A21-B4-C13; | A21-B4-C14; | A21-B4-C15; | A21-B4-C16; |
| A21-B4-C17; | A21-B4-C18; | A21-B4-C19; | A21-B4-C20; | A21-B4-C21; | A21-B4-C22; |
| A21-B4-C23; | A21-B4-C24; | A21-B4-C25; | A21-B4-C26; | A21-B4-C27; | A21-B4-C28; |
| A21-B4-C29; | A21-B4-C30; | A21-B4-C31; | A21-B4-C32; | A21-B4-C33; | A21-B4-C34; |
| A21-B4-C35; | A21-B4-C36; | A21-B4-C37; | A21-B4-C38; | A21-B4-C39; | A21-B4-C40; |
| A21-B4-C41; | A21-B4-C42; | A21-B4-C43; | A21-B4-C44; | A21-B4-C45; | A21-B4-C46; |
| A22-B4-C1; | A22-B4-C2; | A22-B4-C3; | A22-B4-C4; | A22-B4-C5; | A22-B4-C6; |
| A22-B4-C7; | A22-B4-C8; | A22-B4-C9; | A22-B4-C10; | A22-B4-C11; | A22-B4-C12; |
| A22-B4-C13; | A22-B4-C14; | A22-B4-C15; | A22-B4-C16; | A22-B4-C17; | A22-B4-C18; |
| A22-B4-C19; | A22-B4-C20; | A22-B4-C21; | A22-B4-C22; | A22-B4-C23; | A22-B4-C24; |
| A22-B4-C25; | A22-B4-C26; | A22-B4-C27; | A22-B4-C28; | A22-B4-C29; | A22-B4-C30; |
| A22-B4-C31; | A22-B4-C32; | A22-B4-C33; | A22-B4-C34; | A22-B4-C35; | A22-B4-C36; |
| A22-B4-C37; | A22-B4-C38; | A22-B4-C39; | A22-B4-C40; | A22-B4-C41; | A22-B4-C42; |
| A22-B4-C43; | A22-B4-C44; | A22-B4-C45; | A22-B4-C46; | A23-B4-C1; | A23-B4-C2; |
| A23-B4-C3; | A23-B4-C4; | A23-B4-C5; | A23-B4-C6; | A23-B4-C7; | A23-B4-C8; |
| A23-B4-C9; | A23-B4-C10; | A23-B4-C11; | A23-B4-C12; | A23-B4-C13; | A23-B4-C14; |
| A23-B4-C15; | A23-B4-C16; | A23-B4-C17; | A23-B4-C18; | A23-B4-C19; | A23-B4-C20; |
| A23-B4-C21; | A23-B4-C22; | A23-B4-C23; | A23-B4-C24; | A23-B4-C25; | A23-B4-C26; |
| A23-B4-C27; | A23-B4-C28; | A23-B4-C29; | A23-B4-C30; | A23-B4-C31; | A23-B4-C32; |
| A23-B4-C33; | A23-B4-C34; | A23-B4-C35; | A23-B4-C36; | A23-B4-C37; | A23-B4-C38; |
| A23-B4-C39; | A23-B4-C40; | A23-B4-C41; | A23-B4-C42; | A23-B4-C43; | A23-B4-C44; |
| A23-B4-C45; | A23-B4-C46; | A24-B4-C1; | A24-B4-C2; | A24-B4-C3; | A24-B4-C4; |
| A24-B4-C5; | A24-B4-C6; | A24-B4-C7; | A24-B4-C8; | A24-B4-C9; | A24-B4-C10; |
| A24-B4-C11; | A24-B4-C12; | A24-B4-C13; | A24-B4-C14; | A24-B4-C15; | A24-B4-C16; |
| A24-B4-C17; | A24-B4-C18; | A24-B4-C19; | A24-B4-C20; | A24-B4-C21; | A24-B4-C22; |
| A24-B4-C23; | A24-B4-C24; | A24-B4-C25; | A24-B4-C26; | A24-B4-C27; | A24-B4-C28; |
| A24-B4-C29; | A24-B4-C30; | A24-B4-C31; | A24-B4-C32; | A24-B4-C33; | A24-B4-C34; |
| A24-B4-C35; | A24-B4-C36; | A24-B4-C37; | A24-B4-C38; | A24-B4-C39; | A24-B4-C40; |
| A24-B4-C41; | A24-B4-C42; | A24-B4-C43; | A24-B4-C44; | A24-B4-C45; | A24-B4-C46; |
| A25-B4-C1; | A25-B4-C2; | A25-B4-C3; | A25-B4-C4; | A25-B4-C5; | A25-B4-C6; |
| A25-B4-C7; | A25-B4-C8; | A25-B4-C9; | A25-B4-C10; | A25-B4-C11; | A25-B4-C12; |

| | | | | | |
|---|---|---|---|---|---|
| A25-B4-C13; | A25-B4-C14; | A25-B4-C15; | A25-B4-C16; | A25-B4-C17; | A25-B4-C18; |
| A25-B4-C19; | A25-B4-C20; | A25-B4-C21; | A25-B4-C22; | A25-B4-C23; | A25-B4-C24; |
| A25-B4-C25; | A25-B4-C26; | A25-B4-C27; | A25-B4-C28; | A25-B4-C29; | A25-B4-C30; |
| A25-B4-C31; | A25-B4-C32; | A25-B4-C33; | A25-B4-C34; | A25-B4-C35; | A25-B4-C36; |
| A25-B4-C37; | A25-B4-C38; | A25-B4-C39; | A25-B4-C40; | A25-B4-C41; | A25-B4-C42; |
| A25-B4-C43; | A25-B4-C44; | A25-B4-C45; | A25-B4-C46; | A26-B4-C1; | A26-B4-C2; |
| A26-B4-C3; | A26-B4-C4; | A26-B4-C5; | A26-B4-C6; | A26-B4-C7; | A26-B4-C8; |
| A26-B4-C9; | A26-B4-C10; | A26-B4-C11; | A26-B4-C12; | A26-B4-C13; | A26-B4-C14; |
| A26-B4-C15; | A26-B4-C16; | A26-B4-C17; | A26-B4-C18; | A26-B4-C19; | A26-B4-C20; |
| A26-B4-C21; | A26-B4-C22; | A26-B4-C23; | A26-B4-C24; | A26-B4-C25; | A26-B4-C26; |
| A26-B4-C27; | A26-B4-C28; | A26-B4-C29; | A26-B4-C30; | A26-B4-C31; | A26-B4-C32; |
| A26-B4-C33; | A26-B4-C34; | A26-B4-C35; | A26-B4-C36; | A26-B4-C37; | A26-B4-C38; |
| A26-B4-C39; | A26-B4-C40; | A26-B4-C41; | A26-B4-C42; | A26-B4-C43; | A26-B4-C44; |
| A26-B4-C45; | A26-B4-C46; | A27-B4-C1; | A27-B4-C2; | A27-B4-C3; | A27-B4-C4; |
| A27-B4-C5; | A27-B4-C6; | A27-B4-C7; | A27-B4-C8; | A27-B4-C9; | A27-B4-C10; |
| A27-B4-C11; | A27-B4-C12; | A27-B4-C13; | A27-B4-C14; | A27-B4-C15; | A27-B4-C16; |
| A27-B4-C17; | A27-B4-C18; | A27-B4-C19; | A27-B4-C20; | A27-B4-C21; | A27-B4-C22; |
| A27-B4-C23; | A27-B4-C24; | A27-B4-C25; | A27-B4-C26; | A27-B4-C27; | A27-B4-C28; |
| A27-B4-C29; | A27-B4-C30; | A27-B4-C31; | A27-B4-C32; | A27-B4-C33; | A27-B4-C34; |
| A27-B4-C35; | A27-B4-C36; | A27-B4-C37; | A27-B4-C38; | A27-B4-C39; | A27-B4-C40; |
| A27-B4-C41; | A27-B4-C42; | A27-B4-C43; | A27-B4-C44; | A27-B4-C45; | A27-B4-C46; |
| A28-B4-C1; | A28-B4-C2; | A28-B4-C3; | A28-B4-C4; | A28-B4-C5; | A28-B4-C6; |
| A28-B4-C7; | A28-B4-C8; | A28-B4-C9; | A28-B4-C10; | A28-B4-C11; | A28-B4-C12; |
| A28-B4-C13; | A28-B4-C14; | A28-B4-C15; | A28-B4-C16; | A28-B4-C17; | A28-B4-C18; |
| A28-B4-C19; | A28-B4-C20; | A28-B4-C21; | A28-B4-C22; | A28-B4-C23; | A28-B4-C24; |
| A28-B4-C25; | A28-B4-C26; | A28-B4-C27; | A28-B4-C28; | A28-B4-C29; | A28-B4-C30; |
| A28-B4-C31; | A28-B4-C32; | A28-B4-C33; | A28-B4-C34; | A28-B4-C35; | A28-B4-C36; |
| A28-B4-C37; | A28-B4-C38; | A28-B4-C39; | A28-B4-C40; | A28-B4-C41; | A28-B4-C42; |
| A28-B4-C43; | A28-B4-C44; | A28-B4-C45; | A28-B4-C46; | A1-B5-C1; | A1-B5-C2; |
| A1-B5-C3; | A1-B5-C4; | A1-B5-C5; | A1-B5-C6; | A1-B5-C7; | A1-B5-C8; |
| A1-B5-C9; | A1-B5-C10; | A1-B5-C11; | A1-B5-C12; | A1-B5-C13; | A1-B5-C14; |
| A1-B5-C15; | A1-B5-C16; | A1-B5-C17; | A1-B5-C18; | A1-B5-C19; | A1-B5-C20; |
| A1-B5-C21; | A1-B5-C22; | A1-B5-C23; | A1-B5-C24; | A1-B5-C25; | A1-B5-C26; |
| A1-B5-C27; | A1-B5-C28; | A1-B5-C29; | A1-B5-C30; | A1-B5-C31; | A1-B5-C32; |
| A1-B5-C33; | A1-B5-C34; | A1-B5-C35; | A1-B5-C36; | A1-B5-C37; | A1-B5-C38; |
| A1-B5-C39; | A1-B5-C40; | A1-B5-C41; | A1-B5-C42; | A1-B5-C43; | A1-B5-C44; |
| A1-B5-C45; | A1-B5-C46; | A2-B5-C1; | A2-B5-C2; | A2-B5-C3; | A2-B5-C4; |
| A2-B5-C5; | A2-B5-C6; | A2-B5-C7; | A2-B5-C8; | A2-B5-C9; | A2-B5-C10; |
| A2-B5-C11; | A2-B5-C12; | A2-B5-C13; | A2-B5-C14; | A2-B5-C15; | A2-B5-C16; |
| A2-B5-C17; | A2-B5-C18; | A2-B5-C19; | A2-B5-C20; | A2-B5-C21; | A2-B5-C22; |
| A2-B5-C23; | A2-B5-C24; | A2-B5-C25; | A2-B5-C26; | A2-B5-C27; | A2-B5-C28; |
| A2-B5-C29; | A2-B5-C30; | A2-B5-C31; | A2-B5-C32; | A2-B5-C33; | A2-B5-C34; |
| A2-B5-C35; | A2-B5-C36; | A2-B5-C37; | A2-B5-C38; | A2-B5-C39; | A2-B5-C40; |
| A2-B5-C41; | A2-B5-C42; | A2-B5-C43; | A2-B5-C44; | A2-B5-C45; | A2-B5-C46; |
| A3-B5-C1; | A3-B5-C2; | A3-B5-C3; | A3-B5-C4; | A3-B5-C5; | A3-B5-C6; |
| A3-B5-C7; | A3-B5-C8; | A3-B5-C9; | A3-B5-C10; | A3-B5-C11; | A3-B5-C12; |
| A3-B5-C13; | A3-B5-C14; | A3-B5-C15; | A3-B5-C16; | A3-B5-C17; | A3-B5-C18; |
| A3-B5-C19; | A3-B5-C20; | A3-B5-C21; | A3-B5-C22; | A3-B5-C23; | A3-B5-C24; |
| A3-B5-C25; | A3-B5-C26; | A3-B5-C27; | A3-B5-C28; | A3-B5-C29; | A3-B5-C30; |
| A3-B5-C31; | A3-B5-C32; | A3-B5-C33; | A3-B5-C34; | A3-B5-C35; | A3-B5-C36; |
| A3-B5-C37; | A3-B5-C38; | A3-B5-C39; | A3-B5-C40; | A3-B5-C41; | A3-B5-C42; |
| A3-B5-C43; | A3-B5-C44; | A3-B5-C45; | A3-B5-C46; | A4-B5-C1; | A4-B5-C2; |
| A4-B5-C3; | A4-B5-C4; | A4-B5-C5; | A4-B5-C6; | A4-B5-C7; | A4-B5-C8; |
| A4-B5-C9; | A4-B5-C10; | A4-B5-C11; | A4-B5-C12; | A4-B5-C13; | A4-B5-C14; |
| A4-B5-C15; | A4-B5-C16; | A4-B5-C17; | A4-B5-C18; | A4-B5-C19; | A4-B5-C20; |
| A4-B5-C21; | A4-B5-C22; | A4-B5-C23; | A4-B5-C24; | A4-B5-C25; | A4-B5-C26; |
| A4-B5-C27; | A4-B5-C28; | A4-B5-C29; | A4-B5-C30; | A4-B5-C31; | A4-B5-C32; |
| A4-B5-C33; | A4-B5-C34; | A4-B5-C35; | A4-B5-C36; | A4-B5-C37; | A4-B5-C38; |
| A4-B5-C39; | A4-B5-C40; | A4-B5-C41; | A4-B5-C42; | A4-B5-C43; | A4-B5-C44; |
| A4-B5-C45; | A4-B5-C46; | A5-B5-C1; | A5-B5-C2; | A5-B5-C3; | A5-B5-C4; |
| A5-B5-C5; | A5-B5-C6; | A5-B5-C7; | A5-B5-C8; | A5-B5-C9; | A5-B5-C10; |
| A5-B5-C11; | A5-B5-C12; | A5-B5-C13; | A5-B5-C14; | A5-B5-C15; | A5-B5-C16; |
| A5-B5-C17; | A5-B5-C18; | A5-B5-C19; | A5-B5-C20; | A5-B5-C21; | A5-B5-C22; |
| A5-B5-C23; | A5-B5-C24; | A5-B5-C25; | A5-B5-C26; | A5-B5-C27; | A5-B5-C28; |
| A5-B5-C29; | A5-B5-C30; | A5-B5-C31; | A5-B5-C32; | A5-B5-C33; | A5-B5-C34; |
| A5-B5-C35; | A5-B5-C36; | A5-B5-C37; | A5-B5-C38; | A5-B5-C39; | A5-B5-C40; |
| A5-B5-C41; | A5-B5-C42; | A5-B5-C43; | A5-B5-C44; | A5-B5-C45; | A5-B5-C46; |
| A6-B5-C1; | A6-B5-C2; | A6-B5-C3; | A6-B5-C4; | A6-B5-C5; | A6-B5-C6; |
| A6-B5-C7; | A6-B5-C8; | A6-B5-C9; | A6-B5-C10; | A6-B5-C11; | A6-B5-C12; |
| A6-B5-C13; | A6-B5-C14; | A6-B5-C15; | A6-B5-C16; | A6-B5-C17; | A6-B5-C18; |
| A6-B5-C19; | A6-B5-C20; | A6-B5-C21; | A6-B5-C22; | A6-B5-C23; | A6-B5-C24; |
| A6-B5-C25; | A6-B5-C26; | A6-B5-C27; | A6-B5-C28; | A6-B5-C29; | A6-B5-C30; |
| A6-B5-C31; | A6-B5-C32; | A6-B5-C33; | A6-B5-C34; | A6-B5-C35; | A6-B5-C36; |
| A6-B5-C37; | A6-B5-C38; | A6-B5-C39; | A6-B5-C40; | A6-B5-C41; | A6-B5-C42; |
| A6-B5-C43; | A6-B5-C44; | A6-B5-C45; | A6-B5-C46; | A7-B5-C1; | A7-B5-C2; |
| A7-B5-C3; | A7-B5-C4; | A7-B5-C5; | A7-B5-C6; | A7-B5-C7; | A7-B5-C8; |
| A7-B5-C9; | A7-B5-C10; | A7-B5-C11; | A7-B5-C12; | A7-B5-C13; | A7-B5-C14; |
| A7-B5-C15; | A7-B5-C16; | A7-B5-C17; | A7-B5-C18; | A7-B5-C19; | A7-B5-C20; |
| A7-B5-C21; | A7-B5-C22; | A7-B5-C23; | A7-B5-C24; | A7-B5-C25; | A7-B5-C26; |

-continued

| | | | | | |
|---|---|---|---|---|---|
| A7-B5-C27; | A7-B5-C28; | A7-B5-C29; | A7-B5-C30; | A7-B5-C31; | A7-B5-C32; |
| A7-B5-C33; | A7-B5-C34; | A7-B5-C35; | A7-B5-C36; | A7-B5-C37; | A7-B5-C38; |
| A7-B5-C39; | A7-B5-C40; | A7-B5-C41; | A7-B5-C42; | A7-B5-C43; | A7-B5-C44; |
| A7-B5-C45; | A7-B5-C46; | A8-B5-C1; | A8-B5-C2; | A8-B5-C3; | A8-B5-C4; |
| A8-B5-C5; | A8-B5-C6; | A8-B5-C7; | A8-B5-C8; | A8-B5-C9; | A8-B5-C10; |
| A8-B5-C11; | A8-B5-C12; | A8-B5-C13; | A8-B5-C14; | A8-B5-C15; | A8-B5-C16; |
| A8-B5-C17; | A8-B5-C18; | A8-B5-C19; | A8-B5-C20; | A8-B5-C21; | A8-B5-C22; |
| A8-B5-C23; | A8-B5-C24; | A8-B5-C25; | A8-B5-C26; | A8-B5-C27; | A8-B5-C28; |
| A8-B5-C29; | A8-B5-C30; | A8-B5-C31; | A8-B5-C32; | A8-B5-C33; | A8-B5-C34; |
| A8-B5-C35; | A8-B5-C36; | A8-B5-C37; | A8-B5-C38; | A8-B5-C39; | A8-B5-C40; |
| A8-B5-C41; | A8-B5-C42; | A8-B5-C43; | A8-B5-C44; | A8-B5-C45; | A8-B5-C46; |
| A9-B5-C1; | A9-B5-C2; | A9-B5-C3; | A9-B5-C4; | A9-B5-C5; | A9-B5-C6; |
| A9-B5-C7; | A9-B5-C8; | A9-B5-C9; | A9-B5-C10; | A9-B5-C11; | A9-B5-C12; |
| A9-B5-C13; | A9-B5-C14; | A9-B5-C15; | A9-B5-C16; | A9-B5-C17; | A9-B5-C18; |
| A9-B5-C19; | A9-B5-C20; | A9-B5-C21; | A9-B5-C22; | A9-B5-C23; | A9-B5-C24; |
| A9-B5-C25; | A9-B5-C26; | A9-B5-C27; | A9-B5-C28; | A9-B5-C29; | A9-B5-C30; |
| A9-B5-C31; | A9-B5-C32; | A9-B5-C33; | A9-B5-C34; | A9-B5-C35; | A9-B5-C36; |
| A9-B5-C37; | A9-B5-C38; | A9-B5-C39; | A9-B5-C40; | A9-B5-C41; | A9-B5-C42; |
| A9-B5-C43; | A9-B5-C44; | A9-B5-C45; | A9-B5-C46; | A10-B5-C1; | A10-B5-C2; |
| A10-B5-C3; | A10-B5-C4; | A10-B5-C5; | A10-B5-C6; | A10-B5-C7; | A10-B5-C8; |
| A10-B5-C9; | A10-B5-C10; | A10-B5-C11; | A10-B5-C12; | A10-B5-C13; | A10-B5-C14; |
| A10-B5-C15; | A10-B5-C16; | A10-B5-C17; | A10-B5-C18; | A10-B5-C19; | A10-B5-C20; |
| A10-B5-C21; | A10-B5-C22; | A10-B5-C23; | A10-B5-C24; | A10-B5-C25; | A10-B5-C26; |
| A10-B5-C27; | A10-B5-C28; | A10-B5-C29; | A10-B5-C30; | A10-B5-C31; | A10-B5-C32; |
| A10-B5-C33; | A10-B5-C34; | A10-B5-C35; | A10-B5-C36; | A10-B5-C37; | A10-B5-C38; |
| A10-B5-C39; | A10-B5-C40; | A10-B5-C41; | A10-B5-C42; | A10-B5-C43; | A10-B5-C44; |
| A10-B5-C45; | A10-B5-C46; | A11-B5-C1; | A11-B5-C2; | A11-B5-C3; | A11-B5-C4; |
| A11-B5-C5; | A11-B5-C6; | A11-B5-C7; | A11-B5-C8; | A11-B5-C9; | A11-B5-C10; |
| A11-B5-C11; | A11-B5-C12; | A11-B5-C13; | A11-B5-C14; | A11-B5-C15; | A11-B5-C16; |
| A11-B5-C17; | A11-B5-C18; | A11-B5-C19; | A11-B5-C20; | A11-B5-C21; | A11-B5-C22; |
| A11-B5-C23; | A11-B5-C24; | A11-B5-C25; | A11-B5-C26; | A11-B5-C27; | A11-B5-C28; |
| A11-B5-C29; | A11-B5-C30; | A11-B5-C31; | A11-B5-C32; | A11-B5-C33; | A11-B5-C34; |
| A11-B5-C35; | A11-B5-C36; | A11-B5-C37; | A11-B5-C38; | A11-B5-C39; | A11-B5-C40; |
| A11-B5-C41; | A11-B5-C42; | A11-B5-C43; | A11-B5-C44; | A11-B5-C45; | A11-B5-C46; |
| A12-B5-C1; | A12-B5-C2; | A12-B5-C3; | A12-B5-C4; | A12-B5-C5; | A12-B5-C6; |
| A12-B5-C7; | A12-B5-C8; | A12-B5-C9; | A12-B5-C10; | A12-B5-C11; | A12-B5-C12; |
| A12-B5-C13; | A12-B5-C14; | A12-B5-C15; | A12-B5-C16; | A12-B5-C17; | A12-B5-C18; |
| A12-B5-C19; | A12-B5-C20; | A12-B5-C21; | A12-B5-C22; | A12-B5-C23; | A12-B5-C24; |
| A12-B5-C25; | A12-B5-C26; | A12-B5-C27; | A12-B5-C28; | A12-B5-C29; | A12-B5-C30; |
| A12-B5-C31; | A12-B5-C32; | A12-B5-C33; | A12-B5-C34; | A12-B5-C35; | A12-B5-C36; |
| A12-B5-C37; | A12-B5-C38; | A12-B5-C39; | A12-B5-C40; | A12-B5-C41; | A12-B5-C42; |
| A12-B5-C43; | A12-B5-C44; | A12-B5-C45; | A12-B5-C46; | A13-B5-C1; | A13-B5-C2; |
| A13-B5-C3; | A13-B5-C4; | A13-B5-C5; | A13-B5-C6; | A13-B5-C7; | A13-B5-C8; |
| A13-B5-C9; | A13-B5-C10; | A13-B5-C11; | A13-B5-C12; | A13-B5-C13; | A13-B5-C14; |
| A13-B5-C15; | A13-B5-C16; | A13-B5-C17; | A13-B5-C18; | A13-B5-C19; | A13-B5-C20; |
| A13-B5-C21; | A13-B5-C22; | A13-B5-C23; | A13-B5-C24; | A13-B5-C25; | A13-B5-C26; |
| A13-B5-C27; | A13-B5-C28; | A13-B5-C29; | A13-B5-C30; | A13-B5-C31; | A13-B5-C32; |
| A13-B5-C33; | A13-B5-C34; | A13-B5-C35; | A13-B5-C36; | A13-B5-C37; | A13-B5-C38; |
| A13-B5-C39; | A13-B5-C40; | A13-B5-C41; | A13-B5-C42; | A13-B5-C43; | A13-B5-C44; |
| A13-B5-C45; | A13-B5-C46; | A14-B5-C1; | A14-B5-C2; | A14-B5-C3; | A14-B5-C4; |
| A14-B5-C5; | A14-B5-C6; | A14-B5-C7; | A14-B5-C8; | A14-B5-C9; | A14-B5-C10; |
| A14-B5-C11; | A14-B5-C12; | A14-B5-C13; | A14-B5-C14; | A14-B5-C15; | A14-B5-C16; |
| A14-B5-C17; | A14-B5-C18; | A14-B5-C19; | A14-B5-C20; | A14-B5-C21; | A14-B5-C22; |
| A14-B5-C23; | A14-B5-C24; | A14-B5-C25; | A14-B5-C26; | A14-B5-C27; | A14-B5-C28; |
| A14-B5-C29; | A14-B5-C30; | A14-B5-C31; | A14-B5-C32; | A14-B5-C33; | A14-B5-C34; |
| A14-B5-C35; | A14-B5-C36; | A14-B5-C37; | A14-B5-C38; | A14-B5-C39; | A14-B5-C40; |
| A14-B5-C41; | A14-B5-C42; | A14-B5-C43; | A14-B5-C44; | A14-B5-C45; | A14-B5-C46; |
| A15-B5-C1; | A15-B5-C2; | A15-B5-C3; | A15-B5-C4; | A15-B5-C5; | A15-B5-C6; |
| A15-B5-C7; | A15-B5-C8; | A15-B5-C9; | A15-B5-C10; | A15-B5-C11; | A15-B5-C12; |
| A15-B5-C13; | A15-B5-C14; | A15-B5-C15; | A15-B5-C16; | A15-B5-C17; | A15-B5-C18; |
| A15-B5-C19; | A15-B5-C20; | A15-B5-C21; | A15-B5-C22; | A15-B5-C23; | A15-B5-C24; |
| A15-B5-C25; | A15-B5-C26; | A15-B5-C27; | A15-B5-C28; | A15-B5-C29; | A15-B5-C30; |
| A15-B5-C31; | A15-B5-C32; | A15-B5-C33; | A15-B5-C34; | A15-B5-C35; | A15-B5-C36; |
| A15-B5-C37; | A15-B5-C38; | A15-B5-C39; | A15-B5-C40; | A15-B5-C41; | A15-B5-C42; |
| A15-B5-C43; | A15-B5-C44; | A15-B5-C45; | A15-B5-C46; | A16-B5-C1; | A16-B5-C2; |
| A16-B5-C3; | A16-B5-C4; | A16-B5-C5; | A16-B5-C6; | A16-B5-C7; | A16-B5-C8; |
| A16-B5-C9; | A16-B5-C10; | A16-B5-C11; | A16-B5-C12; | A16-B5-C13; | A16-B5-C14; |
| A16-B5-C15; | A16-B5-C16; | A16-B5-C17; | A16-B5-C18; | A16-B5-C19; | A16-B5-C20; |
| A16-B5-C21; | A16-B5-C22; | A16-B5-C23; | A16-B5-C24; | A16-B5-C25; | A16-B5-C26; |
| A16-B5-C27; | A16-B5-C28; | A16-B5-C29; | A16-B5-C30; | A16-B5-C31; | A16-B5-C32; |
| A16-B5-C33; | A16-B5-C34; | A16-B5-C35; | A16-B5-C36; | A16-B5-C37; | A16-B5-C38; |
| A16-B5-C39; | A16-B5-C40; | A16-B5-C41; | A16-B5-C42; | A16-B5-C43; | A16-B5-C44; |
| A16-B5-C45; | A16-B5-C46; | A17-B5-C1; | A17-B5-C2; | A17-B5-C3; | A17-B5-C4; |
| A17-B5-C5; | A17-B5-C6; | A17-B5-C7; | A17-B5-C8; | A17-B5-C9; | A17-B5-C10; |
| A17-B5-C11; | A17-B5-C12; | A17-B5-C13; | A17-B5-C14; | A17-B5-C15; | A17-B5-C16; |
| A17-B5-C17; | A17-B5-C18; | A17-B5-C19; | A17-B5-C20; | A17-B5-C21; | A17-B5-C22; |
| A17-B5-C23; | A17-B5-C24; | A17-B5-C25; | A17-B5-C26; | A17-B5-C27; | A17-B5-C28; |
| A17-B5-C29; | A17-B5-C30; | A17-B5-C31; | A17-B5-C32; | A17-B5-C33; | A17-B5-C34; |
| A17-B5-C35; | A17-B5-C36; | A17-B5-C37; | A17-B5-C38; | A17-B5-C39; | A17-B5-C40; |

|            |            |            |            |            |            |
|------------|------------|------------|------------|------------|------------|
| A17-B5-C41; | A17-B5-C42; | A17-B5-C43; | A17-B5-C44; | A17-B5-C45; | A17-B5-C46; |
| A18-B5-C1;  | A18-B5-C2;  | A18-B5-C3;  | A18-B5-C4;  | A18-B5-C5;  | A18-B5-C6;  |
| A18-B5-C7;  | A18-B5-C8;  | A18-B5-C9;  | A18-B5-C10; | A18-B5-C11; | A18-B5-C12; |
| A18-B5-C13; | A18-B5-C14; | A18-B5-C15; | A18-B5-C16; | A18-B5-C17; | A18-B5-C18; |
| A18-B5-C19; | A18-B5-C20; | A18-B5-C21; | A18-B5-C22; | A18-B5-C23; | A18-B5-C24; |
| A18-B5-C25; | A18-B5-C26; | A18-B5-C27; | A18-B5-C28; | A18-B5-C29; | A18-B5-C30; |
| A18-B5-C31; | A18-B5-C32; | A18-B5-C33; | A18-B5-C34; | A18-B5-C35; | A18-B5-C36; |
| A18-B5-C37; | A18-B5-C38; | A18-B5-C39; | A18-B5-C40; | A18-B5-C41; | A18-B5-C42; |
| A18-B5-C43; | A18-B5-C44; | A18-B5-C45; | A18-B5-C46; | A19-B5-C1;  | A19-B5-C2;  |
| A19-B5-C3;  | A19-B5-C4;  | A19-B5-C5;  | A19-B5-C6;  | A19-B5-C7;  | A19-B5-C8;  |
| A19-B5-C9;  | A19-B5-C10; | A19-B5-C11; | A19-B5-C12; | A19-B5-C13; | A19-B5-C14; |
| A19-B5-C15; | A19-B5-C16; | A19-B5-C17; | A19-B5-C18; | A19-B5-C19; | A19-B5-C20; |
| A19-B5-C21; | A19-B5-C22; | A19-B5-C23; | A19-B5-C24; | A19-B5-C25; | A19-B5-C26; |
| A19-B5-C27; | A19-B5-C28; | A19-B5-C29; | A19-B5-C30; | A19-B5-C31; | A19-B5-C32; |
| A19-B5-C33; | A19-B5-C34; | A19-B5-C35; | A19-B5-C36; | A19-B5-C37; | A19-B5-C38; |
| A19-B5-C39; | A19-B5-C40; | A19-B5-C41; | A19-B5-C42; | A19-B5-C43; | A19-B5-C44; |
| A19-B5-C45; | A19-B5-C46; | A20-B5-C1;  | A20-B5-C2;  | A20-B5-C3;  | A20-B5-C4;  |
| A20-B5-C5;  | A20-B5-C6;  | A20-B5-C7;  | A20-B5-C8;  | A20-B5-C9;  | A20-B5-C10; |
| A20-B5-C11; | A20-B5-C12; | A20-B5-C13; | A20-B5-C14; | A20-B5-C15; | A20-B5-C16; |
| A20-B5-C17; | A20-B5-C18; | A20-B5-C19; | A20-B5-C20; | A20-B5-C21; | A20-B5-C22; |
| A20-B5-C23; | A20-B5-C24; | A20-B5-C25; | A20-B5-C26; | A20-B5-C27; | A20-B5-C28; |
| A20-B5-C29; | A20-B5-C30; | A20-B5-C31; | A20-B5-C32; | A20-B5-C33; | A20-B5-C34; |
| A20-B5-C35; | A20-B5-C36; | A20-B5-C37; | A20-B5-C38; | A20-B5-C39; | A20-B5-C40; |
| A20-B5-C41; | A20-B5-C42; | A20-B5-C43; | A20-B5-C44; | A20-B5-C45; | A20-B5-C46; |
| A21-B5-C1;  | A21-B5-C2;  | A21-B5-C3;  | A21-B5-C4;  | A21-B5-C5;  | A21-B5-C6;  |
| A21-B5-C7;  | A21-B5-C8;  | A21-B5-C9;  | A21-B5-C10; | A21-B5-C11; | A21-B5-C12; |
| A21-B5-C13; | A21-B5-C14; | A21-B5-C15; | A21-B5-C16; | A21-B5-C17; | A21-B5-C18; |
| A21-B5-C19; | A21-B5-C20; | A21-B5-C21; | A21-B5-C22; | A21-B5-C23; | A21-B5-C24; |
| A21-B5-C25; | A21-B5-C26; | A21-B5-C27; | A21-B5-C28; | A21-B5-C29; | A21-B5-C30; |
| A21-B5-C31; | A21-B5-C32; | A21-B5-C33; | A21-B5-C34; | A21-B5-C35; | A21-B5-C36; |
| A21-B5-C37; | A21-B5-C38; | A21-B5-C39; | A21-B5-C40; | A21-B5-C41; | A21-B5-C42; |
| A21-B5-C43; | A21-B5-C44; | A21-B5-C45; | A21-B5-C46; | A22-B5-C1;  | A22-B5-C2;  |
| A22-B5-C3;  | A22-B5-C4;  | A22-B5-C5;  | A22-B5-C6;  | A22-B5-C7;  | A22-B5-C8;  |
| A22-B5-C9;  | A22-B5-C10; | A22-B5-C11; | A22-B5-C12; | A22-B5-C13; | A22-B5-C14; |
| A22-B5-C15; | A22-B5-C16; | A22-B5-C17; | A22-B5-C18; | A22-B5-C19; | A22-B5-C20; |
| A22-B5-C21; | A22-B5-C22; | A22-B5-C23; | A22-B5-C24; | A22-B5-C25; | A22-B5-C26; |
| A22-B5-C27; | A22-B5-C28; | A22-B5-C29; | A22-B5-C30; | A22-B5-C31; | A22-B5-C32; |
| A22-B5-C33; | A22-B5-C34; | A22-B5-C35; | A22-B5-C36; | A22-B5-C37; | A22-B5-C38; |
| A22-B5-C39; | A22-B5-C40; | A22-B5-C41; | A22-B5-C42; | A22-B5-C43; | A22-B5-C44; |
| A22-B5-C45; | A22-B5-C46; | A23-B5-C1;  | A23-B5-C2;  | A23-B5-C3;  | A23-B5-C4;  |
| A23-B5-C5;  | A23-B5-C6;  | A23-B5-C7;  | A23-B5-C8;  | A23-B5-C9;  | A23-B5-C10; |
| A23-B5-C11; | A23-B5-C12; | A23-B5-C13; | A23-B5-C14; | A23-B5-C15; | A23-B5-C16; |
| A23-B5-C17; | A23-B5-C18; | A23-B5-C19; | A23-B5-C20; | A23-B5-C21; | A23-B5-C22; |
| A23-B5-C23; | A23-B5-C24; | A23-B5-C25; | A23-B5-C26; | A23-B5-C27; | A23-B5-C28; |
| A23-B5-C29; | A23-B5-C30; | A23-B5-C31; | A23-B5-C32; | A23-B5-C33; | A23-B5-C34; |
| A23-B5-C35; | A23-B5-C36; | A23-B5-C37; | A23-B5-C38; | A23-B5-C39; | A23-B5-C40; |
| A23-B5-C41; | A23-B5-C42; | A23-B5-C43; | A23-B5-C44; | A23-B5-C45; | A23-B5-C46; |
| A24-B5-C1;  | A24-B5-C2;  | A24-B5-C3;  | A24-B5-C4;  | A24-B5-C5;  | A24-B5-C6;  |
| A24-B5-C7;  | A24-B5-C8;  | A24-B5-C9;  | A24-B5-C10; | A24-B5-C11; | A24-B5-C12; |
| A24-B5-C13; | A24-B5-C14; | A24-B5-C15; | A24-B5-C16; | A24-B5-C17; | A24-B5-C18; |
| A24-B5-C19; | A24-B5-C20; | A24-B5-C21; | A24-B5-C22; | A24-B5-C23; | A24-B5-C24; |
| A24-B5-C25; | A24-B5-C26; | A24-B5-C27; | A24-B5-C28; | A24-B5-C29; | A24-B5-C30; |
| A24-B5-C31; | A24-B5-C32; | A24-B5-C33; | A24-B5-C34; | A24-B5-C35; | A24-B5-C36; |
| A24-B5-C37; | A24-B5-C38; | A24-B5-C39; | A24-B5-C40; | A24-B5-C41; | A24-B5-C42; |
| A24-B5-C43; | A24-B5-C44; | A24-B5-C45; | A24-B5-C46; | A25-B5-C1;  | A25-B5-C2;  |
| A25-B5-C3;  | A25-B5-C4;  | A25-B5-C5;  | A25-B5-C6;  | A25-B5-C7;  | A25-B5-C8;  |
| A25-B5-C9;  | A25-B5-C10; | A25-B5-C11; | A25-B5-C12; | A25-B5-C13; | A25-B5-C14; |
| A25-B5-C15; | A25-B5-C16; | A25-B5-C17; | A25-B5-C18; | A25-B5-C19; | A25-B5-C20; |
| A25-B5-C21; | A25-B5-C22; | A25-B5-C23; | A25-B5-C24; | A25-B5-C25; | A25-B5-C26; |
| A25-B5-C27; | A25-B5-C28; | A25-B5-C29; | A25-B5-C30; | A25-B5-C31; | A25-B5-C32; |
| A25-B5-C33; | A25-B5-C34; | A25-B5-C35; | A25-B5-C36; | A25-B5-C37; | A25-B5-C38; |
| A25-B5-C39; | A25-B5-C40; | A25-B5-C41; | A25-B5-C42; | A25-B5-C43; | A25-B5-C44; |
| A25-B5-C45; | A25-B5-C46; | A26-B5-C1;  | A26-B5-C2;  | A26-B5-C3;  | A26-B5-C4;  |
| A26-B5-C5;  | A26-B5-C6;  | A26-B5-C7;  | A26-B5-C8;  | A26-B5-C9;  | A26-B5-C10; |
| A26-B5-C11; | A26-B5-C12; | A26-B5-C13; | A26-B5-C14; | A26-B5-C15; | A26-B5-C16; |
| A26-B5-C17; | A26-B5-C18; | A26-B5-C19; | A26-B5-C20; | A26-B5-C21; | A26-B5-C22; |
| A26-B5-C23; | A26-B5-C24; | A26-B5-C25; | A26-B5-C26; | A26-B5-C27; | A26-B5-C28; |
| A26-B5-C29; | A26-B5-C30; | A26-B5-C31; | A26-B5-C32; | A26-B5-C33; | A26-B5-C34; |
| A26-B5-C35; | A26-B5-C36; | A26-B5-C37; | A26-B5-C38; | A26-B5-C39; | A26-B5-C40; |
| A26-B5-C41; | A26-B5-C42; | A26-B5-C43; | A26-B5-C44; | A26-B5-C45; | A26-B5-C46; |
| A27-B5-C1;  | A27-B5-C2;  | A27-B5-C3;  | A27-B5-C4;  | A27-B5-C5;  | A27-B5-C6;  |
| A27-B5-C7;  | A27-B5-C8;  | A27-B5-C9;  | A27-B5-C10; | A27-B5-C11; | A27-B5-C12; |
| A27-B5-C13; | A27-B5-C14; | A27-B5-C15; | A27-B5-C16; | A27-B5-C17; | A27-B5-C18; |
| A27-B5-C19; | A27-B5-C20; | A27-B5-C21; | A27-B5-C22; | A27-B5-C23; | A27-B5-C24; |
| A27-B5-C25; | A27-B5-C26; | A27-B5-C27; | A27-B5-C28; | A27-B5-C29; | A27-B5-C30; |
| A27-B5-C31; | A27-B5-C32; | A27-B5-C33; | A27-B5-C34; | A27-B5-C35; | A27-B5-C36; |
| A27-B5-C37; | A27-B5-C38; | A27-B5-C39; | A27-B5-C40; | A27-B5-C41; | A27-B5-C42; |
| A27-B5-C43; | A27-B5-C44; | A27-B5-C45; | A27-B5-C46; | A28-B5-C1;  | A28-B5-C2;  |
| A28-B5-C3;  | A28-B5-C4;  | A28-B5-C5;  | A28-B5-C6;  | A28-B5-C7;  | A28-B5-C8;  |

|  |  |  |  |  |  |
|---|---|---|---|---|---|
| A28-B5-C9; | A28-B5-C10; | A28-B5-C11; | A28-B5-C12; | A28-B5-C13; | A28-B5-C14; |
| A28-B5-C15; | A28-B5-C16; | A28-B5-C17; | A28-B5-C18; | A28-B5-C19; | A28-B5-C20; |
| A28-B5-C21; | A28-B5-C22; | A28-B5-C23; | A28-B5-C24; | A28-B5-C25; | A28-B5-C26; |
| A28-B5-C27; | A28-B5-C28; | A28-B5-C29; | A28-B5-C30; | A28-B5-C31; | A28-B5-C32; |
| A28-B5-C33; | A28-B5-C34; | A28-B5-C35; | A28-B5-C36; | A28-B5-C37; | A28-B5-C38; |
| A28-B5-C39; | A28-B5-C40; | A28-B5-C41; | A28-B5-C42; | A28-B5-C43; | A28-B5-C44; |
| A28-B5-C45; | A28-B5-C46; | A1-B6-C1; | A1-B6-C2; | A1-B6-C3; | A1-B6-C4; |
| A1-B6-C5; | A1-B6-C6; | A1-B6-C7; | A1-B6-C8; | A1-B6-C9; | A1-B6-C10; |
| A1-B6-C11; | A1-B6-C12; | A1-B6-C13; | A1-B6-C14; | A1-B6-C15; | A1-B6-C16; |
| A1-B6-C17; | A1-B6-C18; | A1-B6-C19; | A1-B6-C20; | A1-B6-C21; | A1-B6-C22; |
| A1-B6-C23; | A1-B6-C24; | A1-B6-C25; | A1-B6-C26; | A1-B6-C27; | A1-B6-C28; |
| A1-B6-C29; | A1-B6-C30; | A1-B6-C31; | A1-B6-C32; | A1-B6-C33; | A1-B6-C34; |
| A1-B6-C35; | A1-B6-C36; | A1-B6-C37; | A1-B6-C38; | A1-B6-C39; | A1-B6-C40; |
| A1-B6-C41; | A1-B6-C42; | A1-B6-C43; | A1-B6-C44; | A1-B6-C45; | A1-B6-C46; |
| A2-B6-C1; | A2-B6-C2; | A2-B6-C3; | A2-B6-C4; | A2-B6-C5; | A2-B6-C6; |
| A2-B6-C7; | A2-B6-C8; | A2-B6-C9; | A2-B6-C10; | A2-B6-C11; | A2-B6-C12; |
| A2-B6-C13; | A2-B6-C14; | A2-B6-C15; | A2-B6-C16; | A2-B6-C17; | A2-B6-C18; |
| A2-B6-C19; | A2-B6-C20; | A2-B6-C21; | A2-B6-C22; | A2-B6-C23; | A2-B6-C24; |
| A2-B6-C25; | A2-B6-C26; | A2-B6-C27; | A2-B6-C28; | A2-B6-C29; | A2-B6-C30; |
| A2-B6-C31; | A2-B6-C32; | A2-B6-C33; | A2-B6-C34; | A2-B6-C35; | A2-B6-C36; |
| A2-B6-C37; | A2-B6-C38; | A2-B6-C39; | A2-B6-C40; | A2-B6-C41; | A2-B6-C42; |
| A2-B6-C43; | A2-B6-C44; | A2-B6-C45; | A2-B6-C46; | A3-B6-C1; | A3-B6-C2; |
| A3-B6-C3; | A3-B6-C4; | A3-B6-C5; | A3-B6-C6; | A3-B6-C7; | A3-B6-C8; |
| A3-B6-C9; | A3-B6-C10; | A3-B6-C11; | A3-B6-C12; | A3-B6-C13; | A3-B6-C14; |
| A3-B6-C15; | A3-B6-C16; | A3-B6-C17; | A3-B6-C18; | A3-B6-C19; | A3-B6-C20; |
| A3-B6-C21; | A3-B6-C22; | A3-B6-C23; | A3-B6-C24; | A3-B6-C25; | A3-B6-C26; |
| A3-B6-C27; | A3-B6-C28; | A3-B6-C29; | A3-B6-C30; | A3-B6-C31; | A3-B6-C32; |
| A3-B6-C33; | A3-B6-C34; | A3-B6-C35; | A3-B6-C36; | A3-B6-C37; | A3-B6-C38; |
| A3-B6-C39; | A3-B6-C40; | A3-B6-C41; | A3-B6-C42; | A3-B6-C43; | A3-B6-C44; |
| A3-B6-C45; | A3-B6-C46; | A4-B6-C1; | A4-B6-C2; | A4-B6-C3; | A4-B6-C4; |
| A4-B6-C5; | A4-B6-C6; | A4-B6-C7; | A4-B6-C8; | A4-B6-C9; | A4-B6-C10; |
| A4-B6-C11; | A4-B6-C12; | A4-B6-C13; | A4-B6-C14; | A4-B6-C15; | A4-B6-C16; |
| A4-B6-C17; | A4-B6-C18; | A4-B6-C19; | A4-B6-C20; | A4-B6-C21; | A4-B6-C22; |
| A4-B6-C23; | A4-B6-C24; | A4-B6-C25; | A4-B6-C26; | A4-B6-C27; | A4-B6-C28; |
| A4-B6-C29; | A4-B6-C30; | A4-B6-C31; | A4-B6-C32; | A4-B6-C33; | A4-B6-C34; |
| A4-B6-C35; | A4-B6-C36; | A4-B6-C37; | A4-B6-C38; | A4-B6-C39; | A4-B6-C40; |
| A4-B6-C41; | A4-B6-C42; | A4-B6-C43; | A4-B6-C44; | A4-B6-C45; | A4-B6-C46; |
| A5-B6-C1; | A5-B6-C2; | A5-B6-C3; | A5-B6-C4; | A5-B6-C5; | A5-B6-C6; |
| A5-B6-C7; | A5-B6-C8; | A5-B6-C9; | A5-B6-C10; | A5-B6-C11; | A5-B6-C12; |
| A5-B6-C13; | A5-B6-C14; | A5-B6-C15; | A5-B6-C16; | A5-B6-C17; | A5-B6-C18; |
| A5-B6-C19; | A5-B6-C20; | A5-B6-C21; | A5-B6-C22; | A5-B6-C23; | A5-B6-C24; |
| A5-B6-C25; | A5-B6-C26; | A5-B6-C27; | A5-B6-C28; | A5-B6-C29; | A5-B6-C30; |
| A5-B6-C31; | A5-B6-C32; | A5-B6-C33; | A5-B6-C34; | A5-B6-C35; | A5-B6-C36; |
| A5-B6-C37; | A5-B6-C38; | A5-B6-C39; | A5-B6-C40; | A5-B6-C41; | A5-B6-C42; |
| A5-B6-C43; | A5-B6-C44; | A5-B6-C45; | A5-B6-C46; | A6-B6-C1; | A6-B6-C2; |
| A6-B6-C3; | A6-B6-C4; | A6-B6-C5; | A6-B6-C6; | A6-B6-C7; | A6-B6-C8; |
| A6-B6-C9; | A6-B6-C10; | A6-B6-C11; | A6-B6-C12; | A6-B6-C13; | A6-B6-C14; |
| A6-B6-C15; | A6-B6-C16; | A6-B6-C17; | A6-B6-C18; | A6-B6-C19; | A6-B6-C20; |
| A6-B6-C21; | A6-B6-C22; | A6-B6-C23; | A6-B6-C24; | A6-B6-C25; | A6-B6-C26; |
| A6-B6-C27; | A6-B6-C28; | A6-B6-C29; | A6-B6-C30; | A6-B6-C31; | A6-B6-C32; |
| A6-B6-C33; | A6-B6-C34; | A6-B6-C35; | A6-B6-C36; | A6-B6-C37; | A6-B6-C38; |
| A6-B6-C39; | A6-B6-C40; | A6-B6-C41; | A6-B6-C42; | A6-B6-C43; | A6-B6-C44; |
| A6-B6-C45; | A6-B6-C46; | A7-B6-C1; | A7-B6-C2; | A7-B6-C3; | A7-B6-C4; |
| A7-B6-C5; | A7-B6-C6; | A7-B6-C7; | A7-B6-C8; | A7-B6-C9; | A7-B6-C10; |
| A7-B6-C11; | A7-B6-C12; | A7-B6-C13; | A7-B6-C14; | A7-B6-C15; | A7-B6-C16; |
| A7-B6-C17; | A7-B6-C18; | A7-B6-C19; | A7-B6-C20; | A7-B6-C21; | A7-B6-C22; |
| A7-B6-C23; | A7-B6-C24; | A7-B6-C25; | A7-B6-C26; | A7-B6-C27; | A7-B6-C28; |
| A7-B6-C29; | A7-B6-C30; | A7-B6-C31; | A7-B6-C32; | A7-B6-C33; | A7-B6-C34; |
| A7-B6-C35; | A7-B6-C36; | A7-B6-C37; | A7-B6-C38; | A7-B6-C39; | A7-B6-C40; |
| A7-B6-C41; | A7-B6-C42; | A7-B6-C43; | A7-B6-C44; | A7-B6-C45; | A7-B6-C46; |
| A8-B6-C1; | A8-B6-C2; | A8-B6-C3; | A8-B6-C4; | A8-B6-C5; | A8-B6-C6; |
| A8-B6-C7; | A8-B6-C8; | A8-B6-C9; | A8-B6-C10; | A8-B6-C11; | A8-B6-C12; |
| A8-B6-C13; | A8-B6-C14; | A8-B6-C15; | A8-B6-C16; | A8-B6-C17; | A8-B6-C18; |
| A8-B6-C19; | A8-B6-C20; | A8-B6-C21; | A8-B6-C22; | A8-B6-C23; | A8-B6-C24; |
| A8-B6-C25; | A8-B6-C26; | A8-B6-C27; | A8-B6-C28; | A8-B6-C29; | A8-B6-C30; |
| A8-B6-C31; | A8-B6-C32; | A8-B6-C33; | A8-B6-C34; | A8-B6-C35; | A8-B6-C36; |
| A8-B6-C37; | A8-B6-C38; | A8-B6-C39; | A8-B6-C40; | A8-B6-C41; | A8-B6-C42; |
| A8-B6-C43; | A8-B6-C44; | A8-B6-C45; | A8-B6-C46; | A9-B6-C1; | A9-B6-C2; |
| A9-B6-C3; | A9-B6-C4; | A9-B6-C5; | A9-B6-C6; | A9-B6-C7; | A9-B6-C8; |
| A9-B6-C9; | A9-B6-C10; | A9-B6-C11; | A9-B6-C12; | A9-B6-C13; | A9-B6-C14; |
| A9-B6-C15; | A9-B6-C16; | A9-B6-C17; | A9-B6-C18; | A9-B6-C19; | A9-B6-C20; |
| A9-B6-C21; | A9-B6-C22; | A9-B6-C23; | A9-B6-C24; | A9-B6-C25; | A9-B6-C26; |
| A9-B6-C27; | A9-B6-C28; | A9-B6-C29; | A9-B6-C30; | A9-B6-C31; | A9-B6-C32; |
| A9-B6-C33; | A9-B6-C34; | A9-B6-C35; | A9-B6-C36; | A9-B6-C37; | A9-B6-C38; |
| A9-B6-C39; | A9-B6-C40; | A9-B6-C41; | A9-B6-C42; | A9-B6-C43; | A9-B6-C44; |
| A9-B6-C45; | A9-B6-C46; | A10-B6-C1; | A10-B6-C2; | A10-B6-C3; | A10-B6-C4; |
| A10-B6-C5; | A10-B6-C6; | A10-B6-C7; | A10-B6-C8; | A10-B6-C9; | A10-B6-C10; |
| A10-B6-C11; | A10-B6-C12; | A10-B6-C13; | A10-B6-C14; | A10-B6-C15; | A10-B6-C16; |
| A10-B6-C17; | A10-B6-C18; | A10-B6-C19; | A10-B6-C20; | A10-B6-C21; | A10-B6-C22; |

-continued

| | | | | | |
|---|---|---|---|---|---|
| A10-B6-C23; | A10-B6-C24; | A10-B6-C25; | A10-B6-C26; | A10-B6-C27; | A10-B6-C28; |
| A10-B6-C29; | A10-B6-C30; | A10-B6-C31; | A10-B6-C32; | A10-B6-C33; | A10-B6-C34; |
| A10-B6-C35; | A10-B6-C36; | A10-B6-C37; | A10-B6-C38; | A10-B6-C39; | A10-B6-C40; |
| A10-B6-C41; | A10-B6-C42; | A10-B6-C43; | A10-B6-C44; | A10-B6-C45; | A10-B6-C46; |
| A11-B6-C1; | A11-B6-C2; | A11-B6-C3; | A11-B6-C4; | A11-B6-C5; | A11-B6-C6; |
| A11-B6-C7; | A11-B6-C8; | A11-B6-C9; | A11-B6-C10; | A11-B6-C11; | A11-B6-C12; |
| A11-B6-C13; | A11-B6-C14; | A11-B6-C15; | A11-B6-C16; | A11-B6-C17; | A11-B6-C18; |
| A11-B6-C19; | A11-B6-C20; | A11-B6-C21; | A11-B6-C22; | A11-B6-C23; | A11-B6-C24; |
| A11-B6-C25; | A11-B6-C26; | A11-B6-C27; | A11-B6-C28; | A11-B6-C29; | A11-B6-C30; |
| A11-B6-C31; | A11-B6-C32; | A11-B6-C33; | A11-B6-C34; | A11-B6-C35; | A11-B6-C36; |
| A11-B6-C37; | A11-B6-C38; | A11-B6-C39; | A11-B6-C40; | A11-B6-C41; | A11-B6-C42; |
| A11-B6-C43; | A11-B6-C44; | A11-B6-C45; | A11-B6-C46; | A12-B6-C1; | A12-B6-C2; |
| A12-B6-C3; | A12-B6-C4; | A12-B6-C5; | A12-B6-C6; | A12-B6-C7; | A12-B6-C8; |
| A12-B6-C9; | A12-B6-C10; | A12-B6-C11; | A12-B6-C12; | A12-B6-C13; | A12-B6-C14; |
| A12-B6-C15; | A12-B6-C16; | A12-B6-C17; | A12-B6-C18; | A12-B6-C19; | A12-B6-C20; |
| A12-B6-C21; | A12-B6-C22; | A12-B6-C23; | A12-B6-C24; | A12-B6-C25; | A12-B6-C26; |
| A12-B6-C27; | A12-B6-C28; | A12-B6-C29; | A12-B6-C30; | A12-B6-C31; | A12-B6-C32; |
| A12-B6-C33; | A12-B6-C34; | A12-B6-C35; | A12-B6-C36; | A12-B6-C37; | A12-B6-C38; |
| A12-B6-C39; | A12-B6-C40; | A12-B6-C41; | A12-B6-C42; | A12-B6-C43; | A12-B6-C44; |
| A12-B6-C45; | A12-B6-C46; | A13-B6-C1; | A13-B6-C2; | A13-B6-C3; | A13-B6-C4; |
| A13-B6-C5; | A13-B6-C6; | A13-B6-C7; | A13-B6-C8; | A13-B6-C9; | A13-B6-C10; |
| A13-B6-C11; | A13-B6-C12; | A13-B6-C13; | A13-B6-C14; | A13-B6-C15; | A13-B6-C16; |
| A13-B6-C17; | A13-B6-C18; | A13-B6-C19; | A13-B6-C20; | A13-B6-C21; | A13-B6-C22; |
| A13-B6-C23; | A13-B6-C24; | A13-B6-C25; | A13-B6-C26; | A13-B6-C27; | A13-B6-C28; |
| A13-B6-C29; | A13-B6-C30; | A13-B6-C31; | A13-B6-C32; | A13-B6-C33; | A13-B6-C34; |
| A13-B6-C35; | A13-B6-C36; | A13-B6-C37; | A13-B6-C38; | A13-B6-C39; | A13-B6-C40; |
| A13-B6-C41; | A13-B6-C42; | A13-B6-C43; | A13-B6-C44; | A13-B6-C45; | A13-B6-C46; |
| A14-B6-C1; | A14-B6-C2; | A14-B6-C3; | A14-B6-C4; | A14-B6-C5; | A14-B6-C6; |
| A14-B6-C7; | A14-B6-C8; | A14-B6-C9; | A14-B6-C10; | A14-B6-C11; | A14-B6-C12; |
| A14-B6-C13; | A14-B6-C14; | A14-B6-C15; | A14-B6-C16; | A14-B6-C17; | A14-B6-C18; |
| A14-B6-C19; | A14-B6-C20; | A14-B6-C21; | A14-B6-C22; | A14-B6-C23; | A14-B6-C24; |
| A14-B6-C25; | A14-B6-C26; | A14-B6-C27; | A14-B6-C28; | A14-B6-C29; | A14-B6-C30; |
| A14-B6-C31; | A14-B6-C32; | A14-B6-C33; | A14-B6-C34; | A14-B6-C35; | A14-B6-C36; |
| A14-B6-C37; | A14-B6-C38; | A14-B6-C39; | A14-B6-C40; | A14-B6-C41; | A14-B6-C42; |
| A14-B6-C43; | A14-B6-C44; | A14-B6-C45; | A14-B6-C46; | A15-B6-C1; | A15-B6-C2; |
| A15-B6-C3; | A15-B6-C4; | A15-B6-C5; | A15-B6-C6; | A15-B6-C7; | A15-B6-C8; |
| A15-B6-C9; | A15-B6-C10; | A15-B6-C11; | A15-B6-C12; | A15-B6-C13; | A15-B6-C14; |
| A15-B6-C15; | A15-B6-C16; | A15-B6-C17; | A15-B6-C18; | A15-B6-C19; | A15-B6-C20; |
| A15-B6-C21; | A15-B6-C22; | A15-B6-C23; | A15-B6-C24; | A15-B6-C25; | A15-B6-C26; |
| A15-B6-C27; | A15-B6-C28; | A15-B6-C29; | A15-B6-C30; | A15-B6-C31; | A15-B6-C32; |
| A15-B6-C33; | A15-B6-C34; | A15-B6-C35; | A15-B6-C36; | A15-B6-C37; | A15-B6-C38; |
| A15-B6-C39; | A15-B6-C40; | A15-B6-C41; | A15-B6-C42; | A15-B6-C43; | A15-B6-C44; |
| A15-B6-C45; | A15-B6-C46; | A16-B6-C1; | A16-B6-C2; | A16-B6-C3; | A16-B6-C4; |
| A16-B6-C5; | A16-B6-C6; | A16-B6-C7; | A16-B6-C8; | A16-B6-C9; | A16-B6-C10; |
| A16-B6-C11; | A16-B6-C12; | A16-B6-C13; | A16-B6-C14; | A16-B6-C15; | A16-B6-C16; |
| A16-B6-C17; | A16-B6-C18; | A16-B6-C19; | A16-B6-C20; | A16-B6-C21; | A16-B6-C22; |
| A16-B6-C23; | A16-B6-C24; | A16-B6-C25; | A16-B6-C26; | A16-B6-C27; | A16-B6-C28; |
| A16-B6-C29; | A16-B6-C30; | A16-B6-C31; | A16-B6-C32; | A16-B6-C33; | A16-B6-C34; |
| A16-B6-C35; | A16-B6-C36; | A16-B6-C37; | A16-B6-C38; | A16-B6-C39; | A16-B6-C40; |
| A16-B6-C41; | A16-B6-C42; | A16-B6-C43; | A16-B6-C44; | A16-B6-C45; | A16-B6-C46; |
| A17-B6-C1; | A17-B6-C2; | A17-B6-C3; | A17-B6-C4; | A17-B6-C5; | A17-B6-C6; |
| A17-B6-C7; | A17-B6-C8; | A17-B6-C9; | A17-B6-C10; | A17-B6-C11; | A17-B6-C12; |
| A17-B6-C13; | A17-B6-C14; | A17-B6-C15; | A17-B6-C16; | A17-B6-C17; | A17-B6-C18; |
| A17-B6-C19; | A17-B6-C20; | A17-B6-C21; | A17-B6-C22; | A17-B6-C23; | A17-B6-C24; |
| A17-B6-C25; | A17-B6-C26; | A17-B6-C27; | A17-B6-C28; | A17-B6-C29; | A17-B6-C30; |
| A17-B6-C31; | A17-B6-C32; | A17-B6-C33; | A17-B6-C34; | A17-B6-C35; | A17-B6-C36; |
| A17-B6-C37; | A17-B6-C38; | A17-B6-C39; | A17-B6-C40; | A17-B6-C41; | A17-B6-C42; |
| A17-B6-C43; | A17-B6-C44; | A17-B6-C45; | A17-B6-C46; | A18-B6-C1; | A18-B6-C2; |
| A18-B6-C3; | A18-B6-C4; | A18-B6-C5; | A18-B6-C6; | A18-B6-C7; | A18-B6-C8; |
| A18-B6-C9; | A18-B6-C10; | A18-B6-C11; | A18-B6-C12; | A18-B6-C13; | A18-B6-C14; |
| A18-B6-C15; | A18-B6-C16; | A18-B6-C17; | A18-B6-C18; | A18-B6-C19; | A18-B6-C20; |
| A18-B6-C21; | A18-B6-C22; | A18-B6-C23; | A18-B6-C24; | A18-B6-C25; | A18-B6-C26; |
| A18-B6-C27; | A18-B6-C28; | A18-B6-C29; | A18-B6-C30; | A18-B6-C31; | A18-B6-C32; |
| A18-B6-C33; | A18-B6-C34; | A18-B6-C35; | A18-B6-C36; | A18-B6-C37; | A18-B6-C38; |
| A18-B6-C39; | A18-B6-C40; | A18-B6-C41; | A18-B6-C42; | A18-B6-C43; | A18-B6-C44; |
| A18-B6-C45; | A18-B6-C46; | A19-B6-C1; | A19-B6-C2; | A19-B6-C3; | A19-B6-C4; |
| A19-B6-C5; | A19-B6-C6; | A19-B6-C7; | A19-B6-C8; | A19-B6-C9; | A19-B6-C10; |
| A19-B6-C11; | A19-B6-C12; | A19-B6-C13; | A19-B6-C14; | A19-B6-C15; | A19-B6-C16; |
| A19-B6-C17; | A19-B6-C18; | A19-B6-C19; | A19-B6-C20; | A19-B6-C21; | A19-B6-C22; |
| A19-B6-C23; | A19-B6-C24; | A19-B6-C25; | A19-B6-C26; | A19-B6-C27; | A19-B6-C28; |
| A19-B6-C29; | A19-B6-C30; | A19-B6-C31; | A19-B6-C32; | A19-B6-C33; | A19-B6-C34; |
| A19-B6-C35; | A19-B6-C36; | A19-B6-C37; | A19-B6-C38; | A19-B6-C39; | A19-B6-C40; |
| A19-B6-C41; | A19-B6-C42; | A19-B6-C43; | A19-B6-C44; | A19-B6-C45; | A19-B6-C46; |
| A20-B6-C1; | A20-B6-C2; | A20-B6-C3; | A20-B6-C4; | A20-B6-C5; | A20-B6-C6; |
| A20-B6-C7; | A20-B6-C8; | A20-B6-C9; | A20-B6-C10; | A20-B6-C11; | A20-B6-C12; |
| A20-B6-C13; | A20-B6-C14; | A20-B6-C15; | A20-B6-C16; | A20-B6-C17; | A20-B6-C18; |
| A20-B6-C19; | A20-B6-C20; | A20-B6-C21; | A20-B6-C22; | A20-B6-C23; | A20-B6-C24; |
| A20-B6-C25; | A20-B6-C26; | A20-B6-C27; | A20-B6-C28; | A20-B6-C29; | A20-B6-C30; |
| A20-B6-C31; | A20-B6-C32; | A20-B6-C33; | A20-B6-C34; | A20-B6-C35; | A20-B6-C36; |

-continued

A20-B6-C37; A20-B6-C38; A20-B6-C39; A20-B6-C40; A20-B6-C41; A20-B6-C42;
A20-B6-C43; A20-B6-C44; A20-B6-C45; A20-B6-C46; A21-B6-C1; A21-B6-C2;
A21-B6-C3; A21-B6-C4; A21-B6-C5; A21-B6-C6; A21-B6-C7; A21-B6-C8;
A21-B6-C9; A21-B6-C10; A21-B6-C11; A21-B6-C12; A21-B6-C13; A21-B6-C14;
A21-B6-C15; A21-B6-C16; A21-B6-C17; A21-B6-C18; A21-B6-C19; A21-B6-C20;
A21-B6-C21; A21-B6-C22; A21-B6-C23; A21-B6-C24; A21-B6-C25; A21-B6-C26;
A21-B6-C27; A21-B6-C28; A21-B6-C29; A21-B6-C30; A21-B6-C31; A21-B6-C32;
A21-B6-C33; A21-B6-C34; A21-B6-C35; A21-B6-C36; A21-B6-C37; A21-B6-C38;
A21-B6-C39; A21-B6-C40; A21-B6-C41; A21-B6-C42; A21-B6-C43; A21-B6-C44;
A21-B6-C45; A21-B6-C46; A22-B6-C1; A22-B6-C2; A22-B6-C3; A22-B6-C4;
A22-B6-C5; A22-B6-C6; A22-B6-C7; A22-B6-C8; A22-B6-C9; A22-B6-C10;
A22-B6-C11; A22-B6-C12; A22-B6-C13; A22-B6-C14; A22-B6-C15; A22-B6-C16;
A22-B6-C17; A22-B6-C18; A22-B6-C19; A22-B6-C20; A22-B6-C21; A22-B6-C22;
A22-B6-C23; A22-B6-C24; A22-B6-C25; A22-B6-C26; A22-B6-C27; A22-B6-C28;
A22-B6-C29; A22-B6-C30; A22-B6-C31; A22-B6-C32; A22-B6-C33; A22-B6-C34;
A22-B6-C35; A22-B6-C36; A22-B6-C37; A22-B6-C38; A22-B6-C39; A22-B6-C40;
A22-B6-C41; A22-B6-C42; A22-B6-C43; A22-B6-C44; A22-B6-C45; A22-B6-C46;
A23-B6-C1; A23-B6-C2; A23-B6-C3; A23-B6-C4; A23-B6-C5; A23-B6-C6;
A23-B6-C7; A23-B6-C8; A23-B6-C9; A23-B6-C10; A23-B6-C11; A23-B6-C12;
A23-B6-C13; A23-B6-C14; A23-B6-C15; A23-B6-C16; A23-B6-C17; A23-B6-C18;
A23-B6-C19; A23-B6-C20; A23-B6-C21; A23-B6-C22; A23-B6-C23; A23-B6-C24;
A23-B6-C25; A23-B6-C26; A23-B6-C27; A23-B6-C28; A23-B6-C29; A23-B6-C30;
A23-B6-C31; A23-B6-C32; A23-B6-C33; A23-B6-C34; A23-B6-C35; A23-B6-C36;
A23-B6-C37; A23-B6-C38; A23-B6-C39; A23-B6-C40; A23-B6-C41; A23-B6-C42;
A23-B6-C43; A23-B6-C44; A23-B6-C45; A23-B6-C46; A24-B6-C1; A24-B6-C2;
A24-B6-C3; A24-B6-C4; A24-B6-C5; A24-B6-C6; A24-B6-C7; A24-B6-C8;
A24-B6-C9; A24-B6-C10; A24-B6-C11; A24-B6-C12; A24-B6-C13; A24-B6-C14;
A24-B6-C15; A24-B6-C16; A24-B6-C17; A24-B6-C18; A24-B6-C19; A24-B6-C20;
A24-B6-C21; A24-B6-C22; A24-B6-C23; A24-B6-C24; A24-B6-C25; A24-B6-C26;
A24-B6-C27; A24-B6-C28; A24-B6-C29; A24-B6-C30; A24-B6-C31; A24-B6-C32;
A24-B6-C33; A24-B6-C34; A24-B6-C35; A24-B6-C36; A24-B6-C37; A24-B6-C38;
A24-B6-C39; A24-B6-C40; A24-B6-C41; A24-B6-C42; A24-B6-C43; A24-B6-C44;
A24-B6-C45; A24-B6-C46; A25-B6-C1; A25-B6-C2; A25-B6-C3; A25-B6-C4;
A25-B6-C5; A25-B6-C6; A25-B6-C7; A25-B6-C8; A25-B6-C9; A25-B6-C10;
A25-B6-C11; A25-B6-C12; A25-B6-C13; A25-B6-C14; A25-B6-C15; A25-B6-C16;
A25-B6-C17; A25-B6-C18; A25-B6-C19; A25-B6-C20; A25-B6-C21; A25-B6-C22;
A25-B6-C23; A25-B6-C24; A25-B6-C25; A25-B6-C26; A25-B6-C27; A25-B6-C28;
A25-B6-C29; A25-B6-C30; A25-B6-C31; A25-B6-C32; A25-B6-C33; A25-B6-C34;
A25-B6-C35; A25-B6-C36; A25-B6-C37; A25-B6-C38; A25-B6-C39; A25-B6-C40;
A25-B6-C41; A25-B6-C42; A25-B6-C43; A25-B6-C44; A25-B6-C45; A25-B6-C46;
A26-B6-C1; A26-B6-C2; A26-B6-C3; A26-B6-C4; A26-B6-C5; A26-B6-C6;
A26-B6-C7; A26-B6-C8; A26-B6-C9; A26-B6-C10; A26-B6-C11; A26-B6-C12;
A26-B6-C13; A26-B6-C14; A26-B6-C15; A26-B6-C16; A26-B6-C17; A26-B6-C18;
A26-B6-C19; A26-B6-C20; A26-B6-C21; A26-B6-C22; A26-B6-C23; A26-B6-C24;
A26-B6-C25; A26-B6-C26; A26-B6-C27; A26-B6-C28; A26-B6-C29; A26-B6-C30;
A26-B6-C31; A26-B6-C32; A26-B6-C33; A26-B6-C34; A26-B6-C35; A26-B6-C36;
A26-B6-C37; A26-B6-C38; A26-B6-C39; A26-B6-C40; A26-B6-C41; A26-B6-C42;
A26-B6-C43; A26-B6-C44; A26-B6-C45; A26-B6-C46; A27-B6-C1; A27-B6-C2;
A27-B6-C3; A27-B6-C4; A27-B6-C5; A27-B6-C6; A27-B6-C7; A27-B6-C8;
A27-B6-C9; A27-B6-C10; A27-B6-C11; A27-B6-C12; A27-B6-C13; A27-B6-C14;
A27-B6-C15; A27-B6-C16; A27-B6-C17; A27-B6-C18; A27-B6-C19; A27-B6-C20;
A27-B6-C21; A27-B6-C22; A27-B6-C23; A27-B6-C24; A27-B6-C25; A27-B6-C26;
A27-B6-C27; A27-B6-C28; A27-B6-C29; A27-B6-C30; A27-B6-C31; A27-B6-C32;
A27-B6-C33; A27-B6-C34; A27-B6-C35; A27-B6-C36; A27-B6-C37; A27-B6-C38;
A27-B6-C39; A27-B6-C40; A27-B6-C41; A27-B6-C42; A27-B6-C43; A27-B6-C44;
A27-B6-C45; A27-B6-C46; A28-B6-C1; A28-B6-C2; A28-B6-C3; A28-B6-C4;
A28-B6-C5; A28-B6-C6; A28-B6-C7; A28-B6-C8; A28-B6-C9; A28-B6-C10;
A28-B6-C11; A28-B6-C12; A28-B6-C13; A28-B6-C14; A28-B6-C15; A28-B6-C16;
A28-B6-C17; A28-B6-C18; A28-B6-C19; A28-B6-C20; A28-B6-C21; A28-B6-C22;
A28-B6-C23; A28-B6-C24; A28-B6-C25; A28-B6-C26; A28-B6-C27; A28-B6-C28;
A28-B6-C29; A28-B6-C30; A28-B6-C31; A28-B6-C32; A28-B6-C33; A28-B6-C34;
A28-B6-C35; A28-B6-C36; A28-B6-C37; A28-B6-C38; A28-B6-C39; A28-B6-C40;
A28-B6-C41; A28-B6-C42; A28-B6-C43; A28-B6-C44; A28-B6-C45; A28-B6-C46;
A1-B7-C1; A1-B7-C2; A1-B7-C3; A1-B7-C4; A1-B7-C5; A1-B7-C6;
A1-B7-C7; A1-B7-C8; A1-B7-C9; A1-B7-C10; A1-B7-C11; A1-B7-C12;
A1-B7-C13; A1-B7-C14; A1-B7-C15; A1-B7-C16; A1-B7-C17; A1-B7-C18;
A1-B7-C19; A1-B7-C20; A1-B7-C21; A1-B7-C22; A1-B7-C23; A1-B7-C24;
A1-B7-C25; A1-B7-C26; A1-B7-C27; A1-B7-C28; A1-B7-C29; A1-B7-C30;
A1-B7-C31; A1-B7-C32; A1-B7-C33; A1-B7-C34; A1-B7-C35; A1-B7-C36;
A1-B7-C37; A1-B7-C38; A1-B7-C39; A1-B7-C40; A1-B7-C41; A1-B7-C42;
A1-B7-C43; A1-B7-C44; A1-B7-C45; A1-B7-C46; A2-B7-C1; A2-B7-C2;
A2-B7-C3; A2-B7-C4; A2-B7-C5; A2-B7-C6; A2-B7-C7; A2-B7-C8;
A2-B7-C9; A2-B7-C10; A2-B7-C11; A2-B7-C12; A2-B7-C13; A2-B7-C14;
A2-B7-C15; A2-B7-C16; A2-B7-C17; A2-B7-C18; A2-B7-C19; A2-B7-C20;
A2-B7-C21; A2-B7-C22; A2-B7-C23; A2-B7-C24; A2-B7-C25; A2-B7-C26;
A2-B7-C27; A2-B7-C28; A2-B7-C29; A2-B7-C30; A2-B7-C31; A2-B7-C32;
A2-B7-C33; A2-B7-C34; A2-B7-C35; A2-B7-C36; A2-B7-C37; A2-B7-C38;
A2-B7-C39; A2-B7-C40; A2-B7-C41; A2-B7-C42; A2-B7-C43; A2-B7-C44;
A2-B7-C45; A2-B7-C46; A3-B7-C1; A3-B7-C2; A3-B7-C3; A3-B7-C4;

-continued

| | | | | | |
|---|---|---|---|---|---|
| A3-B7-C5; | A3-B7-C6; | A3-B7-C7; | A3-B7-C8; | A3-B7-C9; | A3-B7-C10; |
| A3-B7-C11; | A3-B7-C12; | A3-B7-C13; | A3-B7-C14; | A3-B7-C15; | A3-B7-C16; |
| A3-B7-C17; | A3-B7-C18; | A3-B7-C19; | A3-B7-C20; | A3-B7-C21; | A3-B7-C22; |
| A3-B7-C23; | A3-B7-C24; | A3-B7-C25; | A3-B7-C26; | A3-B7-C27; | A3-B7-C28; |
| A3-B7-C29; | A3-B7-C30; | A3-B7-C31; | A3-B7-C32; | A3-B7-C33; | A3-B7-C34; |
| A3-B7-C35; | A3-B7-C36; | A3-B7-C37; | A3-B7-C38; | A3-B7-C39; | A3-B7-C40; |
| A3-B7-C41; | A3-B7-C42; | A3-B7-C43; | A3-B7-C44; | A3-B7-C45; | A3-B7-C46; |
| A4-B7-C1; | A4-B7-C2; | A4-B7-C3; | A4-B7-C4; | A4-B7-C5; | A4-B7-C6; |
| A4-B7-C7; | A4-B7-C8; | A4-B7-C9; | A4-B7-C10; | A4-B7-C11; | A4-B7-C12; |
| A4-B7-C13; | A4-B7-C14; | A4-B7-C15; | A4-B7-C16; | A4-B7-C17; | A4-B7-C18; |
| A4-B7-C19; | A4-B7-C20; | A4-B7-C21; | A4-B7-C22; | A4-B7-C23; | A4-B7-C24; |
| A4-B7-C25; | A4-B7-C26; | A4-B7-C27; | A4-B7-C28; | A4-B7-C29; | A4-B7-C30; |
| A4-B7-C31; | A4-B7-C32; | A4-B7-C33; | A4-B7-C34; | A4-B7-C35; | A4-B7-C36; |
| A4-B7-C37; | A4-B7-C38; | A4-B7-C39; | A4-B7-C40; | A4-B7-C41; | A4-B7-C42; |
| A4-B7-C43; | A4-B7-C44; | A4-B7-C45; | A4-B7-C46; | A5-B7-C1; | A5-B7-C2; |
| A5-B7-C3; | A5-B7-C4; | A5-B7-C5; | A5-B7-C6; | A5-B7-C7; | A5-B7-C8; |
| A5-B7-C9; | A5-B7-C10; | A5-B7-C11; | A5-B7-C12; | A5-B7-C13; | A5-B7-C14; |
| A5-B7-C15; | A5-B7-C16; | A5-B7-C17; | A5-B7-C18; | A5-B7-C19; | A5-B7-C20; |
| A5-B7-C21; | A5-B7-C22; | A5-B7-C23; | A5-B7-C24; | A5-B7-C25; | A5-B7-C26; |
| A5-B7-C27; | A5-B7-C28; | A5-B7-C29; | A5-B7-C30; | A5-B7-C31; | A5-B7-C32; |
| A5-B7-C33; | A5-B7-C34; | A5-B7-C35; | A5-B7-C36; | A5-B7-C37; | A5-B7-C38; |
| A5-B7-C39; | A5-B7-C40; | A5-B7-C41; | A5-B7-C42; | A5-B7-C43; | A5-B7-C44; |
| A5-B7-C45; | A5-B7-C46; | A6-B7-C1; | A6-B7-C2; | A6-B7-C3; | A6-B7-C4; |
| A6-B7-C5; | A6-B7-C6; | A6-B7-C7; | A6-B7-C8; | A6-B7-C9; | A6-B7-C10; |
| A6-B7-C11; | A6-B7-C12; | A6-B7-C13; | A6-B7-C14; | A6-B7-C15; | A6-B7-C16; |
| A6-B7-C17; | A6-B7-C18; | A6-B7-C19; | A6-B7-C20; | A6-B7-C21; | A6-B7-C22; |
| A6-B7-C23; | A6-B7-C24; | A6-B7-C25; | A6-B7-C26; | A6-B7-C27; | A6-B7-C28; |
| A6-B7-C29; | A6-B7-C30; | A6-B7-C31; | A6-B7-C32; | A6-B7-C33; | A6-B7-C34; |
| A6-B7-C35; | A6-B7-C36; | A6-B7-C37; | A6-B7-C38; | A6-B7-C39; | A6-B7-C40; |
| A6-B7-C41; | A6-B7-C42; | A6-B7-C43; | A6-B7-C44; | A6-B7-C45; | A6-B7-C46; |
| A7-B7-C1; | A7-B7-C2; | A7-B7-C3; | A7-B7-C4; | A7-B7-C5; | A7-B7-C6; |
| A7-B7-C7; | A7-B7-C8; | A7-B7-C9; | A7-B7-C10; | A7-B7-C11; | A7-B7-C12; |
| A7-B7-C13; | A7-B7-C14; | A7-B7-C15; | A7-B7-C16; | A7-B7-C17; | A7-B7-C18; |
| A7-B7-C19; | A7-B7-C20; | A7-B7-C21; | A7-B7-C22; | A7-B7-C23; | A7-B7-C24; |
| A7-B7-C25; | A7-B7-C26; | A7-B7-C27; | A7-B7-C28; | A7-B7-C29; | A7-B7-C30; |
| A7-B7-C31; | A7-B7-C32; | A7-B7-C33; | A7-B7-C34; | A7-B7-C35; | A7-B7-C36; |
| A7-B7-C37; | A7-B7-C38; | A7-B7-C39; | A7-B7-C40; | A7-B7-C41; | A7-B7-C42; |
| A7-B7-C43; | A7-B7-C44; | A7-B7-C45; | A7-B7-C46; | A8-B7-C1; | A8-B7-C2; |
| A8-B7-C3; | A8-B7-C4; | A8-B7-C5; | A8-B7-C6; | A8-B7-C7; | A8-B7-C8; |
| A8-B7-C9; | A8-B7-C10; | A8-B7-C11; | A8-B7-C12; | A8-B7-C13; | A8-B7-C14; |
| A8-B7-C15; | A8-B7-C16; | A8-B7-C17; | A8-B7-C18; | A8-B7-C19; | A8-B7-C20; |
| A8-B7-C21; | A8-B7-C22; | A8-B7-C23; | A8-B7-C24; | A8-B7-C25; | A8-B7-C26; |
| A8-B7-C27; | A8-B7-C28; | A8-B7-C29; | A8-B7-C30; | A8-B7-C31; | A8-B7-C32; |
| A8-B7-C33; | A8-B7-C34; | A8-B7-C35; | A8-B7-C36; | A8-B7-C37; | A8-B7-C38; |
| A8-B7-C39; | A8-B7-C40; | A8-B7-C41; | A8-B7-C42; | A8-B7-C43; | A8-B7-C44; |
| A8-B7-C45; | A8-B7-C46; | A9-B7-C1; | A9-B7-C2; | A9-B7-C3; | A9-B7-C4; |
| A9-B7-C5; | A9-B7-C6; | A9-B7-C7; | A9-B7-C8; | A9-B7-C9; | A9-B7-C10; |
| A9-B7-C11; | A9-B7-C12; | A9-B7-C13; | A9-B7-C14; | A9-B7-C15; | A9-B7-C16; |
| A9-B7-C17; | A9-B7-C18; | A9-B7-C19; | A9-B7-C20; | A9-B7-C21; | A9-B7-C22; |
| A9-B7-C23; | A9-B7-C24; | A9-B7-C25; | A9-B7-C26; | A9-B7-C27; | A9-B7-C28; |
| A9-B7-C29; | A9-B7-C30; | A9-B7-C31; | A9-B7-C32; | A9-B7-C33; | A9-B7-C34; |
| A9-B7-C35; | A9-B7-C36; | A9-B7-C37; | A9-B7-C38; | A9-B7-C39; | A9-B7-C40; |
| A9-B7-C41; | A9-B7-C42; | A9-B7-C43; | A9-B7-C44; | A9-B7-C45; | A9-B7-C46; |
| A10-B7-C1; | A10-B7-C2; | A10-B7-C3; | A10-B7-C4; | A10-B7-C5; | A10-B7-C6; |
| A10-B7-C7; | A10-B7-C8; | A10-B7-C9; | A10-B7-C10; | A10-B7-C11; | A10-B7-C12; |
| A10-B7-C13; | A10-B7-C14; | A10-B7-C15; | A10-B7-C16; | A10-B7-C17; | A10-B7-C18; |
| A10-B7-C19; | A10-B7-C20; | A10-B7-C21; | A10-B7-C22; | A10-B7-C23; | A10-B7-C24; |
| A10-B7-C25; | A10-B7-C26; | A10-B7-C27; | A10-B7-C28; | A10-B7-C29; | A10-B7-C30; |
| A10-B7-C31; | A10-B7-C32; | A10-B7-C33; | A10-B7-C34; | A10-B7-C35; | A10-B7-C36; |
| A10-B7-C37; | A10-B7-C38; | A10-B7-C39; | A10-B7-C40; | A10-B7-C41; | A10-B7-C42; |
| A10-B7-C43; | A10-B7-C44; | A10-B7-C45; | A10-B7-C46; | A11-B7-C1; | A11-B7-C2; |
| A11-B7-C3; | A11-B7-C4; | A11-B7-C5; | A11-B7-C6; | A11-B7-C7; | A11-B7-C8; |
| A11-B7-C9; | A11-B7-C10; | A11-B7-C11; | A11-B7-C12; | A11-B7-C13; | A11-B7-C14; |
| A11-B7-C15; | A11-B7-C16; | A11-B7-C17; | A11-B7-C18; | A11-B7-C19; | A11-B7-C20; |
| A11-B7-C21; | A11-B7-C22; | A11-B7-C23; | A11-B7-C24; | A11-B7-C25; | A11-B7-C26; |
| A11-B7-C27; | A11-B7-C28; | A11-B7-C29; | A11-B7-C30; | A11-B7-C31; | A11-B7-C32; |
| A11-B7-C33; | A11-B7-C34; | A11-B7-C35; | A11-B7-C36; | A11-B7-C37; | A11-B7-C38; |
| A11-B7-C39; | A11-B7-C40; | A11-B7-C41; | A11-B7-C42; | A11-B7-C43; | A11-B7-C44; |
| A11-B7-C45; | A11-B7-C46; | A12-B7-C1; | A12-B7-C2; | A12-B7-C3; | A12-B7-C4; |
| A12-B7-C5; | A12-B7-C6; | A12-B7-C7; | A12-B7-C8; | A12-B7-C9; | A12-B7-C10; |
| A12-B7-C11; | A12-B7-C12; | A12-B7-C13; | A12-B7-C14; | A12-B7-C15; | A12-B7-C16; |
| A12-B7-C17; | A12-B7-C18; | A12-B7-C19; | A12-B7-C20; | A12-B7-C21; | A12-B7-C22; |
| A12-B7-C23; | A12-B7-C24; | A12-B7-C25; | A12-B7-C26; | A12-B7-C27; | A12-B7-C28; |
| A12-B7-C29; | A12-B7-C30; | A12-B7-C31; | A12-B7-C32; | A12-B7-C33; | A12-B7-C34; |
| A12-B7-C35; | A12-B7-C36; | A12-B7-C37; | A12-B7-C38; | A12-B7-C39; | A12-B7-C40; |
| A12-B7-C41; | A12-B7-C42; | A12-B7-C43; | A12-B7-C44; | A12-B7-C45; | A12-B7-C46; |
| A13-B7-C1; | A13-B7-C2; | A13-B7-C3; | A13-B7-C4; | A13-B7-C5; | A13-B7-C6; |
| A13-B7-C7; | A13-B7-C8; | A13-B7-C9; | A13-B7-C10; | A13-B7-C11; | A13-B7-C12; |
| A13-B7-C13; | A13-B7-C14; | A13-B7-C15; | A13-B7-C16; | A13-B7-C17; | A13-B7-C18; |

-continued

| | | | | | |
|---|---|---|---|---|---|
| A13-B7-C19; | A13-B7-C20; | A13-B7-C21; | A13-B7-C22; | A13-B7-C23; | A13-B7-C24; |
| A13-B7-C25; | A13-B7-C26; | A13-B7-C27; | A13-B7-C28; | A13-B7-C29; | A13-B7-C30; |
| A13-B7-C31; | A13-B7-C32; | A13-B7-C33; | A13-B7-C34; | A13-B7-C35; | A13-B7-C36; |
| A13-B7-C37; | A13-B7-C38; | A13-B7-C39; | A13-B7-C40; | A13-B7-C41; | A13-B7-C42; |
| A13-B7-C43; | A13-B7-C44; | A13-B7-C45; | A13-B7-C46; | A14-B7-C1; | A14-B7-C2; |
| A14-B7-C3; | A14-B7-C4; | A14-B7-C5; | A14-B7-C6; | A14-B7-C7; | A14-B7-C8; |
| A14-B7-C9; | A14-B7-C10; | A14-B7-C11; | A14-B7-C12; | A14-B7-C13; | A14-B7-C14; |
| A14-B7-C15; | A14-B7-C16; | A14-B7-C17; | A14-B7-C18; | A14-B7-C19; | A14-B7-C20; |
| A14-B7-C21; | A14-B7-C22; | A14-B7-C23; | A14-B7-C24; | A14-B7-C25; | A14-B7-C26; |
| A14-B7-C27; | A14-B7-C28; | A14-B7-C29; | A14-B7-C30; | A14-B7-C31; | A14-B7-C32; |
| A14-B7-C33; | A14-B7-C34; | A14-B7-C35; | A14-B7-C36; | A14-B7-C37; | A14-B7-C38; |
| A14-B7-C39; | A14-B7-C40; | A14-B7-C41; | A14-B7-C42; | A14-B7-C43; | A14-B7-C44; |
| A14-B7-C45; | A14-B7-C46; | A15-B7-C1; | A15-B7-C2; | A15-B7-C3; | A15-B7-C4; |
| A15-B7-C5; | A15-B7-C6; | A15-B7-C7; | A15-B7-C8; | A15-B7-C9; | A15-B7-C10; |
| A15-B7-C11; | A15-B7-C12; | A15-B7-C13; | A15-B7-C14; | A15-B7-C15; | A15-B7-C16; |
| A15-B7-C17; | A15-B7-C18; | A15-B7-C19; | A15-B7-C20; | A15-B7-C21; | A15-B7-C22; |
| A15-B7-C23; | A15-B7-C24; | A15-B7-C25; | A15-B7-C26; | A15-B7-C27; | A15-B7-C28; |
| A15-B7-C29; | A15-B7-C30; | A15-B7-C31; | A15-B7-C32; | A15-B7-C33; | A15-B7-C34; |
| A15-B7-C35; | A15-B7-C36; | A15-B7-C37; | A15-B7-C38; | A15-B7-C39; | A15-B7-C40; |
| A15-B7-C41; | A15-B7-C42; | A15-B7-C43; | A15-B7-C44; | A15-B7-C45; | A15-B7-C46; |
| A16-B7-C1; | A16-B7-C2; | A16-B7-C3; | A16-B7-C4; | A16-B7-C5; | A16-B7-C6; |
| A16-B7-C7; | A16-B7-C8; | A16-B7-C9; | A16-B7-C10; | A16-B7-C11; | A16-B7-C12; |
| A16-B7-C13; | A16-B7-C14; | A16-B7-C15; | A16-B7-C16; | A16-B7-C17; | A16-B7-C18; |
| A16-B7-C19; | A16-B7-C20; | A16-B7-C21; | A16-B7-C22; | A16-B7-C23; | A16-B7-C24; |
| A16-B7-C25; | A16-B7-C26; | A16-B7-C27; | A16-B7-C28; | A16-B7-C29; | A16-B7-C30; |
| A16-B7-C31; | A16-B7-C32; | A16-B7-C33; | A16-B7-C34; | A16-B7-C35; | A16-B7-C36; |
| A16-B7-C37; | A16-B7-C38; | A16-B7-C39; | A16-B7-C40; | A16-B7-C41; | A16-B7-C42; |
| A16-B7-C43; | A16-B7-C44; | A16-B7-C45; | A16-B7-C46; | A17-B7-C1; | A17-B7-C2; |
| A17-B7-C3; | A17-B7-C4; | A17-B7-C5; | A17-B7-C6; | A17-B7-C7; | A17-B7-C8; |
| A17-B7-C9; | A17-B7-C10; | A17-B7-C11; | A17-B7-C12; | A17-B7-C13; | A17-B7-C14; |
| A17-B7-C15; | A17-B7-C16; | A17-B7-C17; | A17-B7-C18; | A17-B7-C19; | A17-B7-C20; |
| A17-B7-C21; | A17-B7-C22; | A17-B7-C23; | A17-B7-C24; | A17-B7-C25; | A17-B7-C26; |
| A17-B7-C27; | A17-B7-C28; | A17-B7-C29; | A17-B7-C30; | A17-B7-C31; | A17-B7-C32; |
| A17-B7-C33; | A17-B7-C34; | A17-B7-C35; | A17-B7-C36; | A17-B7-C37; | A17-B7-C38; |
| A17-B7-C39; | A17-B7-C40; | A17-B7-C41; | A17-B7-C42; | A17-B7-C43; | A17-B7-C44; |
| A17-B7-C45; | A17-B7-C46; | A18-B7-C1; | A18-B7-C2; | A18-B7-C3; | A18-B7-C4; |
| A18-B7-C5; | A18-B7-C6; | A18-B7-C7; | A18-B7-C8; | A18-B7-C9; | A18-B7-C10; |
| A18-B7-C11; | A18-B7-C12; | A18-B7-C13; | A18-B7-C14; | A18-B7-C15; | A18-B7-C16; |
| A18-B7-C17; | A18-B7-C18; | A18-B7-C19; | A18-B7-C20; | A18-B7-C21; | A18-B7-C22; |
| A18-B7-C23; | A18-B7-C24; | A18-B7-C25; | A18-B7-C26; | A18-B7-C27; | A18-B7-C28; |
| A18-B7-C29; | A18-B7-C30; | A18-B7-C31; | A18-B7-C32; | A18-B7-C33; | A18-B7-C34; |
| A18-B7-C35; | A18-B7-C36; | A18-B7-C37; | A18-B7-C38; | A18-B7-C39; | A18-B7-C40; |
| A18-B7-C41; | A18-B7-C42; | A18-B7-C43; | A18-B7-C44; | A18-B7-C45; | A18-B7-C46; |
| A19-B7-C1; | A19-B7-C2; | A19-B7-C3; | A19-B7-C4; | A19-B7-C5; | A19-B7-C6; |
| A19-B7-C7; | A19-B7-C8; | A19-B7-C9; | A19-B7-C10; | A19-B7-C11; | A19-B7-C12; |
| A19-B7-C13; | A19-B7-C14; | A19-B7-C15; | A19-B7-C16; | A19-B7-C17; | A19-B7-C18; |
| A19-B7-C19; | A19-B7-C20; | A19-B7-C21; | A19-B7-C22; | A19-B7-C23; | A19-B7-C24; |
| A19-B7-C25; | A19-B7-C26; | A19-B7-C27; | A19-B7-C28; | A19-B7-C29; | A19-B7-C30; |
| A19-B7-C31; | A19-B7-C32; | A19-B7-C33; | A19-B7-C34; | A19-B7-C35; | A19-B7-C36; |
| A19-B7-C37; | A19-B7-C38; | A19-B7-C39; | A19-B7-C40; | A19-B7-C41; | A19-B7-C42; |
| A19-B7-C43; | A19-B7-C44; | A19-B7-C45; | A19-B7-C46; | A20-B7-C1; | A20-B7-C2; |
| A20-B7-C3; | A20-B7-C4; | A20-B7-C5; | A20-B7-C6; | A20-B7-C7; | A20-B7-C8; |
| A20-B7-C9; | A20-B7-C10; | A20-B7-C11; | A20-B7-C12; | A20-B7-C13; | A20-B7-C14; |
| A20-B7-C15; | A20-B7-C16; | A20-B7-C17; | A20-B7-C18; | A20-B7-C19; | A20-B7-C20; |
| A20-B7-C21; | A20-B7-C22; | A20-B7-C23; | A20-B7-C24; | A20-B7-C25; | A20-B7-C26; |
| A20-B7-C27; | A20-B7-C28; | A20-B7-C29; | A20-B7-C30; | A20-B7-C31; | A20-B7-C32; |
| A20-B7-C33; | A20-B7-C34; | A20-B7-C35; | A20-B7-C36; | A20-B7-C37; | A20-B7-C38; |
| A20-B7-C39; | A20-B7-C40; | A20-B7-C41; | A20-B7-C42; | A20-B7-C43; | A20-B7-C44; |
| A20-B7-C45; | A20-B7-C46; | A21-B7-C1; | A21-B7-C2; | A21-B7-C3; | A21-B7-C4; |
| A21-B7-C5; | A21-B7-C6; | A21-B7-C7; | A21-B7-C8; | A21-B7-C9; | A21-B7-C10; |
| A21-B7-C11; | A21-B7-C12; | A21-B7-C13; | A21-B7-C14; | A21-B7-C15; | A21-B7-C16; |
| A21-B7-C17; | A21-B7-C18; | A21-B7-C19; | A21-B7-C20; | A21-B7-C21; | A21-B7-C22; |
| A21-B7-C23; | A21-B7-C24; | A21-B7-C25; | A21-B7-C26; | A21-B7-C27; | A21-B7-C28; |
| A21-B7-C29; | A21-B7-C30; | A21-B7-C31; | A21-B7-C32; | A21-B7-C33; | A21-B7-C34; |
| A21-B7-C35; | A21-B7-C36; | A21-B7-C37; | A21-B7-C38; | A21-B7-C39; | A21-B7-C40; |
| A21-B7-C41; | A21-B7-C42; | A21-B7-C43; | A21-B7-C44; | A21-B7-C45; | A21-B7-C46; |
| A22-B7-C1; | A22-B7-C2; | A22-B7-C3; | A22-B7-C4; | A22-B7-C5; | A22-B7-C6; |
| A22-B7-C7; | A22-B7-C8; | A22-B7-C9; | A22-B7-C10; | A22-B7-C11; | A22-B7-C12; |
| A22-B7-C13; | A22-B7-C14; | A22-B7-C15; | A22-B7-C16; | A22-B7-C17; | A22-B7-C18; |
| A22-B7-C19; | A22-B7-C20; | A22-B7-C21; | A22-B7-C22; | A22-B7-C23; | A22-B7-C24; |
| A22-B7-C25; | A22-B7-C26; | A22-B7-C27; | A22-B7-C28; | A22-B7-C29; | A22-B7-C30; |
| A22-B7-C31; | A22-B7-C32; | A22-B7-C33; | A22-B7-C34; | A22-B7-C35; | A22-B7-C36; |
| A22-B7-C37; | A22-B7-C38; | A22-B7-C39; | A22-B7-C40; | A22-B7-C41; | A22-B7-C42; |
| A22-B7-C43; | A22-B7-C44; | A22-B7-C45; | A22-B7-C46; | A23-B7-C1; | A23-B7-C2; |
| A23-B7-C3; | A23-B7-C4; | A23-B7-C5; | A23-B7-C6; | A23-B7-C7; | A23-B7-C8; |
| A23-B7-C9; | A23-B7-C10; | A23-B7-C11; | A23-B7-C12; | A23-B7-C13; | A23-B7-C14; |
| A23-B7-C15; | A23-B7-C16; | A23-B7-C17; | A23-B7-C18; | A23-B7-C19; | A23-B7-C20; |
| A23-B7-C21; | A23-B7-C22; | A23-B7-C23; | A23-B7-C24; | A23-B7-C25; | A23-B7-C26; |
| A23-B7-C27; | A23-B7-C28; | A23-B7-C29; | A23-B7-C30; | A23-B7-C31; | A23-B7-C32; |

-continued

| | | | | | |
|---|---|---|---|---|---|
| A23-B7-C33; | A23-B7-C34; | A23-B7-C35; | A23-B7-C36; | A23-B7-C37; | A23-B7-C38; |
| A23-B7-C39; | A23-B7-C40; | A23-B7-C41; | A23-B7-C42; | A23-B7-C43; | A23-B7-C44; |
| A23-B7-C45; | A23-B7-C46; | A24-B7-C1; | A24-B7-C2; | A24-B7-C3; | A24-B7-C4; |
| A24-B7-C5; | A24-B7-C6; | A24-B7-C7; | A24-B7-C8; | A24-B7-C9; | A24-B7-C10; |
| A24-B7-C11; | A24-B7-C12; | A24-B7-C13; | A24-B7-C14; | A24-B7-C15; | A24-B7-C16; |
| A24-B7-C17; | A24-B7-C18; | A24-B7-C19; | A24-B7-C20; | A24-B7-C21; | A24-B7-C22; |
| A24-B7-C23; | A24-B7-C24; | A24-B7-C25; | A24-B7-C26; | A24-B7-C27; | A24-B7-C28; |
| A24-B7-C29; | A24-B7-C30; | A24-B7-C31; | A24-B7-C32; | A24-B7-C33; | A24-B7-C34; |
| A24-B7-C35; | A24-B7-C36; | A24-B7-C37; | A24-B7-C38; | A24-B7-C39; | A24-B7-C40; |
| A24-B7-C41; | A24-B7-C42; | A24-B7-C43; | A24-B7-C44; | A24-B7-C45; | A24-B7-C46; |
| A25-B7-C1; | A25-B7-C2; | A25-B7-C3; | A25-B7-C4; | A25-B7-C5; | A25-B7-C6; |
| A25-B7-C7; | A25-B7-C8; | A25-B7-C9; | A25-B7-C10; | A25-B7-C11; | A25-B7-C12; |
| A25-B7-C13; | A25-B7-C14; | A25-B7-C15; | A25-B7-C16; | A25-B7-C17; | A25-B7-C18; |
| A25-B7-C19; | A25-B7-C20; | A25-B7-C21; | A25-B7-C22; | A25-B7-C23; | A25-B7-C24; |
| A25-B7-C25; | A25-B7-C26; | A25-B7-C27; | A25-B7-C28; | A25-B7-C29; | A25-B7-C30; |
| A25-B7-C31; | A25-B7-C32; | A25-B7-C33; | A25-B7-C34; | A25-B7-C35; | A25-B7-C36; |
| A25-B7-C37; | A25-B7-C38; | A25-B7-C39; | A25-B7-C40; | A25-B7-C41; | A25-B7-C42; |
| A25-B7-C43; | A25-B7-C44; | A25-B7-C45; | A25-B7-C46; | A26-B7-C1; | A26-B7-C2; |
| A26-B7-C3; | A26-B7-C4; | A26-B7-C5; | A26-B7-C6; | A26-B7-C7; | A26-B7-C8; |
| A26-B7-C9; | A26-B7-C10; | A26-B7-C11; | A26-B7-C12; | A26-B7-C13; | A26-B7-C14; |
| A26-B7-C15; | A26-B7-C16; | A26-B7-C17; | A26-B7-C18; | A26-B7-C19; | A26-B7-C20; |
| A26-B7-C21; | A26-B7-C22; | A26-B7-C23; | A26-B7-C24; | A26-B7-C25; | A26-B7-C26; |
| A26-B7-C27; | A26-B7-C28; | A26-B7-C29; | A26-B7-C30; | A26-B7-C31; | A26-B7-C32; |
| A26-B7-C33; | A26-B7-C34; | A26-B7-C35; | A26-B7-C36; | A26-B7-C37; | A26-B7-C38; |
| A26-B7-C39; | A26-B7-C40; | A26-B7-C41; | A26-B7-C42; | A26-B7-C43; | A26-B7-C44; |
| A26-B7-C45; | A26-B7-C46; | A27-B7-C1; | A27-B7-C2; | A27-B7-C3; | A27-B7-C4; |
| A27-B7-C5; | A27-B7-C6; | A27-B7-C7; | A27-B7-C8; | A27-B7-C9; | A27-B7-C10; |
| A27-B7-C11; | A27-B7-C12; | A27-B7-C13; | A27-B7-C14; | A27-B7-C15; | A27-B7-C16; |
| A27-B7-C17; | A27-B7-C18; | A27-B7-C19; | A27-B7-C20; | A27-B7-C21; | A27-B7-C22; |
| A27-B7-C23; | A27-B7-C24; | A27-B7-C25; | A27-B7-C26; | A27-B7-C27; | A27-B7-C28; |
| A27-B7-C29; | A27-B7-C30; | A27-B7-C31; | A27-B7-C32; | A27-B7-C33; | A27-B7-C34; |
| A27-B7-C35; | A27-B7-C36; | A27-B7-C37; | A27-B7-C38; | A27-B7-C39; | A27-B7-C40; |
| A27-B7-C41; | A27-B7-C42; | A27-B7-C43; | A27-B7-C44; | A27-B7-C45; | A27-B7-C46; |
| A28-B7-C1; | A28-B7-C2; | A28-B7-C3; | A28-B7-C4; | A28-B7-C5; | A28-B7-C6; |
| A28-B7-C7; | A28-B7-C8; | A28-B7-C9; | A28-B7-C10; | A28-B7-C11; | A28-B7-C12; |
| A28-B7-C13; | A28-B7-C14; | A28-B7-C15; | A28-B7-C16; | A28-B7-C17; | A28-B7-C18; |
| A28-B7-C19; | A28-B7-C20; | A28-B7-C21; | A28-B7-C22; | A28-B7-C23; | A28-B7-C24; |
| A28-B7-C25; | A28-B7-C26; | A28-B7-C27; | A28-B7-C28; | A28-B7-C29; | A28-B7-C30; |
| A28-B7-C31; | A28-B7-C32; | A28-B7-C33; | A28-B7-C34; | A28-B7-C35; | A28-B7-C36; |
| A28-B7-C37; | A28-B7-C38; | A28-B7-C39; | A28-B7-C40; | A28-B7-C41; | A28-B7-C42; |
| A28-B7-C43; | A28-B7-C44; | A28-B7-C45; | A28-B7-C46; | A1-B8-C1; | A1-B8-C2; |
| A1-B8-C3; | A1-B8-C4; | A1-B8-C5; | A1-B8-C6; | A1-B8-C7; | A1-B8-C8; |
| A1-B8-C9; | A1-B8-C10; | A1-B8-C11; | A1-B8-C12; | A1-B8-C13; | A1-B8-C14; |
| A1-B8-C15; | A1-B8-C16; | A1-B8-C17; | A1-B8-C18; | A1-B8-C19; | A1-B8-C20; |
| A1-B8-C21; | A1-B8-C22; | A1-B8-C23; | A1-B8-C24; | A1-B8-C25; | A1-B8-C26; |
| A1-B8-C27; | A1-B8-C28; | A1-B8-C29; | A1-B8-C30; | A1-B8-C31; | A1-B8-C32; |
| A1-B8-C33; | A1-B8-C34; | A1-B8-C35; | A1-B8-C36; | A1-B8-C37; | A1-B8-C38; |
| A1-B8-C39; | A1-B8-C40; | A1-B8-C41; | A1-B8-C42; | A1-B8-C43; | A1-B8-C44; |
| A1-B8-C45; | A1-B8-C46; | A2-B8-C1; | A2-B8-C2; | A2-B8-C3; | A2-B8-C4; |
| A2-B8-C5; | A2-B8-C6; | A2-B8-C7; | A2-B8-C8; | A2-B8-C9; | A2-B8-C10; |
| A2-B8-C11; | A2-B8-C12; | A2-B8-C13; | A2-B8-C14; | A2-B8-C15; | A2-B8-C16; |
| A2-B8-C17; | A2-B8-C18; | A2-B8-C19; | A2-B8-C20; | A2-B8-C21; | A2-B8-C22; |
| A2-B8-C23; | A2-B8-C24; | A2-B8-C25; | A2-B8-C26; | A2-B8-C27; | A2-B8-C28; |
| A2-B8-C29; | A2-B8-C30; | A2-B8-C31; | A2-B8-C32; | A2-B8-C33; | A2-B8-C34; |
| A2-B8-C35; | A2-B8-C36; | A2-B8-C37; | A2-B8-C38; | A2-B8-C39; | A2-B8-C40; |
| A2-B8-C41; | A2-B8-C42; | A2-B8-C43; | A2-B8-C44; | A2-B8-C45; | A2-B8-C46; |
| A3-B8-C1; | A3-B8-C2; | A3-B8-C3; | A3-B8-C4; | A3-B8-C5; | A3-B8-C6; |
| A3-B8-C7; | A3-B8-C8; | A3-B8-C9; | A3-B8-C10; | A3-B8-C11; | A3-B8-C12; |
| A3-B8-C13; | A3-B8-C14; | A3-B8-C15; | A3-B8-C16; | A3-B8-C17; | A3-B8-C18; |
| A3-B8-C19; | A3-B8-C20; | A3-B8-C21; | A3-B8-C22; | A3-B8-C23; | A3-B8-C24; |
| A3-B8-C25; | A3-B8-C26; | A3-B8-C27; | A3-B8-C28; | A3-B8-C29; | A3-B8-C30; |
| A3-B8-C31; | A3-B8-C32; | A3-B8-C33; | A3-B8-C34; | A3-B8-C35; | A3-B8-C36; |
| A3-B8-C37; | A3-B8-C38; | A3-B8-C39; | A3-B8-C40; | A3-B8-C41; | A3-B8-C42; |
| A3-B8-C43; | A3-B8-C44; | A3-B8-C45; | A3-B8-C46; | A4-B8-C1; | A4-B8-C2; |
| A4-B8-C3; | A4-B8-C4; | A4-B8-C5; | A4-B8-C6; | A4-B8-C7; | A4-B8-C8; |
| A4-B8-C9; | A4-B8-C10; | A4-B8-C11; | A4-B8-C12; | A4-B8-C13; | A4-B8-C14; |
| A4-B8-C15; | A4-B8-C16; | A4-B8-C17; | A4-B8-C18; | A4-B8-C19; | A4-B8-C20; |
| A4-B8-C21; | A4-B8-C22; | A4-B8-C23; | A4-B8-C24; | A4-B8-C25; | A4-B8-C26; |
| A4-B8-C27; | A4-B8-C28; | A4-B8-C29; | A4-B8-C30; | A4-B8-C31; | A4-B8-C32; |
| A4-B8-C33; | A4-B8-C34; | A4-B8-C35; | A4-B8-C36; | A4-B8-C37; | A4-B8-C38; |
| A4-B8-C39; | A4-B8-C40; | A4-B8-C41; | A4-B8-C42; | A4-B8-C43; | A4-B8-C44; |
| A4-B8-C45; | A4-B8-C46; | A5-B8-C1; | A5-B8-C2; | A5-B8-C3; | A5-B8-C4; |
| A5-B8-C5; | A5-B8-C6; | A5-B8-C7; | A5-B8-C8; | A5-B8-C9; | A5-B8-C10; |
| A5-B8-C11; | A5-B8-C12; | A5-B8-C13; | A5-B8-C14; | A5-B8-C15; | A5-B8-C16; |
| A5-B8-C17; | A5-B8-C18; | A5-B8-C19; | A5-B8-C20; | A5-B8-C21; | A5-B8-C22; |
| A5-B8-C23; | A5-B8-C24; | A5-B8-C25; | A5-B8-C26; | A5-B8-C27; | A5-B8-C28; |
| A5-B8-C29; | A5-B8-C30; | A5-B8-C31; | A5-B8-C32; | A5-B8-C33; | A5-B8-C34; |
| A5-B8-C35; | A5-B8-C36; | A5-B8-C37; | A5-B8-C38; | A5-B8-C39; | A5-B8-C40; |
| A5-B8-C41; | A5-B8-C42; | A5-B8-C43; | A5-B8-C44; | A5-B8-C45; | A5-B8-C46; |

-continued

| | | | | | |
|---|---|---|---|---|---|
| A6-B8-C1; | A6-B8-C2; | A6-B8-C3; | A6-B8-C4; | A6-B8-C5; | A6-B8-C6; |
| A6-B8-C7; | A6-B8-C8; | A6-B8-C9; | A6-B8-C10; | A6-B8-C11; | A6-B8-C12; |
| A6-B8-C13; | A6-B8-C14; | A6-B8-C15; | A6-B8-C16; | A6-B8-C17; | A6-B8-C18; |
| A6-B8-C19; | A6-B8-C20; | A6-B8-C21; | A6-B8-C22; | A6-B8-C23; | A6-B8-C24; |
| A6-B8-C25; | A6-B8-C26; | A6-B8-C27; | A6-B8-C28; | A6-B8-C29; | A6-B8-C30; |
| A6-B8-C31; | A6-B8-C32; | A6-B8-C33; | A6-B8-C34; | A6-B8-C35; | A6-B8-C36; |
| A6-B8-C37; | A6-B8-C38; | A6-B8-C39; | A6-B8-C40; | A6-B8-C41; | A6-B8-C42; |
| A6-B8-C43; | A6-B8-C44; | A6-B8-C45; | A6-B8-C46; | A7-B8-C1; | A7-B8-C2; |
| A7-B8-C3; | A7-B8-C4; | A7-B8-C5; | A7-B8-C6; | A7-B8-C7; | A7-B8-C8; |
| A7-B8-C9; | A7-B8-C10; | A7-B8-C11; | A7-B8-C12; | A7-B8-C13; | A7-B8-C14; |
| A7-B8-C15; | A7-B8-C16; | A7-B8-C17; | A7-B8-C18; | A7-B8-C19; | A7-B8-C20; |
| A7-B8-C21; | A7-B8-C22; | A7-B8-C23; | A7-B8-C24; | A7-B8-C25; | A7-B8-C26; |
| A7-B8-C27; | A7-B8-C28; | A7-B8-C29; | A7-B8-C30; | A7-B8-C31; | A7-B8-C32; |
| A7-B8-C33; | A7-B8-C34; | A7-B8-C35; | A7-B8-C36; | A7-B8-C37; | A7-B8-C38; |
| A7-B8-C39; | A7-B8-C40; | A7-B8-C41; | A7-B8-C42; | A7-B8-C43; | A7-B8-C44; |
| A7-B8-C45; | A7-B8-C46; | A8-B8-C1; | A8-B8-C2; | A8-B8-C3; | A8-B8-C4; |
| A8-B8-C5; | A8-B8-C6; | A8-B8-C7; | A8-B8-C8; | A8-B8-C9; | A8-B8-C10; |
| A8-B8-C11; | A8-B8-C12; | A8-B8-C13; | A8-B8-C14; | A8-B8-C15; | A8-B8-C16; |
| A8-B8-C17; | A8-B8-C18; | A8-B8-C19; | A8-B8-C20; | A8-B8-C21; | A8-B8-C22; |
| A8-B8-C23; | A8-B8-C24; | A8-B8-C25; | A8-B8-C26; | A8-B8-C27; | A8-B8-C28; |
| A8-B8-C29; | A8-B8-C30; | A8-B8-C31; | A8-B8-C32; | A8-B8-C33; | A8-B8-C34; |
| A8-B8-C35; | A8-B8-C36; | A8-B8-C37; | A8-B8-C38; | A8-B8-C39; | A8-B8-C40; |
| A8-B8-C41; | A8-B8-C42; | A8-B8-C43; | A8-B8-C44; | A8-B8-C45; | A8-B8-C46; |
| A9-B8-C1; | A9-B8-C2; | A9-B8-C3; | A9-B8-C4; | A9-B8-C5; | A9-B8-C6; |
| A9-B8-C7; | A9-B8-C8; | A9-B8-C9; | A9-B8-C10; | A9-B8-C11; | A9-B8-C12; |
| A9-B8-C13; | A9-B8-C14; | A9-B8-C15; | A9-B8-C16; | A9-B8-C17; | A9-B8-C18; |
| A9-B8-C19; | A9-B8-C20; | A9-B8-C21; | A9-B8-C22; | A9-B8-C23; | A9-B8-C24; |
| A9-B8-C25; | A9-B8-C26; | A9-B8-C27; | A9-B8-C28; | A9-B8-C29; | A9-B8-C30; |
| A9-B8-C31; | A9-B8-C32; | A9-B8-C33; | A9-B8-C34; | A9-B8-C35; | A9-B8-C36; |
| A9-B8-C37; | A9-B8-C38; | A9-B8-C39; | A9-B8-C40; | A9-B8-C41; | A9-B8-C42; |
| A9-B8-C43; | A9-B8-C44; | A9-B8-C45; | A9-B8-C46; | A10-B8-C1; | A10-B8-C2; |
| A10-B8-C3; | A10-B8-C4; | A10-B8-C5; | A10-B8-C6; | A10-B8-C7; | A10-B8-C8; |
| A10-B8-C9; | A10-B8-C10; | A10-B8-C11; | A10-B8-C12; | A10-B8-C13; | A10-B8-C14; |
| A10-B8-C15; | A10-B8-C16; | A10-B8-C17; | A10-B8-C18; | A10-B8-C19; | A10-B8-C20; |
| A10-B8-C21; | A10-B8-C22; | A10-B8-C23; | A10-B8-C24; | A10-B8-C25; | A10-B8-C26; |
| A10-B8-C27; | A10-B8-C28; | A10-B8-C29; | A10-B8-C30; | A10-B8-C31; | A10-B8-C32; |
| A10-B8-C33; | A10-B8-C34; | A10-B8-C35; | A10-B8-C36; | A10-B8-C37; | A10-B8-C38; |
| A10-B8-C39; | A10-B8-C40; | A10-B8-C41; | A10-B8-C42; | A10-B8-C43; | A10-B8-C44; |
| A10-B8-C45; | A10-B8-C46; | A11-B8-C1; | A11-B8-C2; | A11-B8-C3; | A11-B8-C4; |
| A11-B8-C5; | A11-B8-C6; | A11-B8-C7; | A11-B8-C8; | A11-B8-C9; | A11-B8-C10; |
| A11-B8-C11; | A11-B8-C12; | A11-B8-C13; | A11-B8-C14; | A11-B8-C15; | A11-B8-C16; |
| A11-B8-C17; | A11-B8-C18; | A11-B8-C19; | A11-B8-C20; | A11-B8-C21; | A11-B8-C22; |
| A11-B8-C23; | A11-B8-C24; | A11-B8-C25; | A11-B8-C26; | A11-B8-C27; | A11-B8-C28; |
| A11-B8-C29; | A11-B8-C30; | A11-B8-C31; | A11-B8-C32; | A11-B8-C33; | A11-B8-C34; |
| A11-B8-C35; | A11-B8-C36; | A11-B8-C37; | A11-B8-C38; | A11-B8-C39; | A11-B8-C40; |
| A11-B8-C41; | A11-B8-C42; | A11-B8-C43; | A11-B8-C44; | A11-B8-C45; | A11-B8-C46; |
| A12-B8-C1; | A12-B8-C2; | A12-B8-C3; | A12-B8-C4; | A12-B8-C5; | A12-B8-C6; |
| A12-B8-C7; | A12-B8-C8; | A12-B8-C9; | A12-B8-C10; | A12-B8-C11; | A12-B8-C12; |
| A12-B8-C13; | A12-B8-C14; | A12-B8-C15; | A12-B8-C16; | A12-B8-C17; | A12-B8-C18; |
| A12-B8-C19; | A12-B8-C20; | A12-B8-C21; | A12-B8-C22; | A12-B8-C23; | A12-B8-C24; |
| A12-B8-C25; | A12-B8-C26; | A12-B8-C27; | A12-B8-C28; | A12-B8-C29; | A12-B8-C30; |
| A12-B8-C31; | A12-B8-C32; | A12-B8-C33; | A12-B8-C34; | A12-B8-C35; | A12-B8-C36; |
| A12-B8-C37; | A12-B8-C38; | A12-B8-C39; | A12-B8-C40; | A12-B8-C41; | A12-B8-C42; |
| A12-B8-C43; | A12-B8-C44; | A12-B8-C45; | A12-B8-C46; | A13-B8-C1; | A13-B8-C2; |
| A13-B8-C3; | A13-B8-C4; | A13-B8-C5; | A13-B8-C6; | A13-B8-C7; | A13-B8-C8; |
| A13-B8-C9; | A13-B8-C10; | A13-B8-C11; | A13-B8-C12; | A13-B8-C13; | A13-B8-C14; |
| A13-B8-C15; | A13-B8-C16; | A13-B8-C17; | A13-B8-C18; | A13-B8-C19; | A13-B8-C20; |
| A13-B8-C21; | A13-B8-C22; | A13-B8-C23; | A13-B8-C24; | A13-B8-C25; | A13-B8-C26; |
| A13-B8-C27; | A13-B8-C28; | A13-B8-C29; | A13-B8-C30; | A13-B8-C31; | A13-B8-C32; |
| A13-B8-C33; | A13-B8-C34; | A13-B8-C35; | A13-B8-C36; | A13-B8-C37; | A13-B8-C38; |
| A13-B8-C39; | A13-B8-C40; | A13-B8-C41; | A13-B8-C42; | A13-B8-C43; | A13-B8-C44; |
| A13-B8-C45; | A13-B8-C46; | A14-B8-C1; | A14-B8-C2; | A14-B8-C3; | A14-B8-C4; |
| A14-B8-C5; | A14-B8-C6; | A14-B8-C7; | A14-B8-C8; | A14-B8-C9; | A14-B8-C10; |
| A14-B8-C11; | A14-B8-C12; | A14-B8-C13; | A14-B8-C14; | A14-B8-C15; | A14-B8-C16; |
| A14-B8-C17; | A14-B8-C18; | A14-B8-C19; | A14-B8-C20; | A14-B8-C21; | A14-B8-C22; |
| A14-B8-C23; | A14-B8-C24; | A14-B8-C25; | A14-B8-C26; | A14-B8-C27; | A14-B8-C28; |
| A14-B8-C29; | A14-B8-C30; | A14-B8-C31; | A14-B8-C32; | A14-B8-C33; | A14-B8-C34; |
| A14-B8-C35; | A14-B8-C36; | A14-B8-C37; | A14-B8-C38; | A14-B8-C39; | A14-B8-C40; |
| A14-B8-C41; | A14-B8-C42; | A14-B8-C43; | A14-B8-C44; | A14-B8-C45; | A14-B8-C46; |
| A15-B8-C1; | A15-B8-C2; | A15-B8-C3; | A15-B8-C4; | A15-B8-C5; | A15-B8-C6; |
| A15-B8-C7; | A15-B8-C8; | A15-B8-C9; | A15-B8-C10; | A15-B8-C11; | A15-B8-C12; |
| A15-B8-C13; | A15-B8-C14; | A15-B8-C15; | A15-B8-C16; | A15-B8-C17; | A15-B8-C18; |
| A15-B8-C19; | A15-B8-C20; | A15-B8-C21; | A15-B8-C22; | A15-B8-C23; | A15-B8-C24; |
| A15-B8-C25; | A15-B8-C26; | A15-B8-C27; | A15-B8-C28; | A15-B8-C29; | A15-B8-C30; |
| A15-B8-C31; | A15-B8-C32; | A15-B8-C33; | A15-B8-C34; | A15-B8-C35; | A15-B8-C36; |
| A15-B8-C37; | A15-B8-C38; | A15-B8-C39; | A15-B8-C40; | A15-B8-C41; | A15-B8-C42; |
| A15-B8-C43; | A15-B8-C44; | A15-B8-C45; | A15-B8-C46; | A16-B8-C1; | A16-B8-C2; |
| A16-B8-C3; | A16-B8-C4; | A16-B8-C5; | A16-B8-C6; | A16-B8-C7; | A16-B8-C8; |
| A16-B8-C9; | A16-B8-C10; | A16-B8-C11; | A16-B8-C12; | A16-B8-C13; | A16-B8-C14; |

| | | | | | |
|---|---|---|---|---|---|
| A16-B8-C15; | A16-B8-C16; | A16-B8-C17; | A16-B8-C18; | A16-B8-C19; | A16-B8-C20; |
| A16-B8-C21; | A16-B8-C22; | A16-B8-C23; | A16-B8-C24; | A16-B8-C25; | A16-B8-C26; |
| A16-B8-C27; | A16-B8-C28; | A16-B8-C29; | A16-B8-C30; | A16-B8-C31; | A16-B8-C32; |
| A16-B8-C33; | A16-B8-C34; | A16-B8-C35; | A16-B8-C36; | A16-B8-C37; | A16-B8-C38; |
| A16-B8-C39; | A16-B8-C40; | A16-B8-C41; | A16-B8-C42; | A16-B8-C43; | A16-B8-C44; |
| A16-B8-C45; | A16-B8-C46; | A17-B8-C1; | A17-B8-C2; | A17-B8-C3; | A17-B8-C4; |
| A17-B8-C5; | A17-B8-C6; | A17-B8-C7; | A17-B8-C8; | A17-B8-C9; | A17-B8-C10; |
| A17-B8-C11; | A17-B8-C12; | A17-B8-C13; | A17-B8-C14; | A17-B8-C15; | A17-B8-C16; |
| A17-B8-C17; | A17-B8-C18; | A17-B8-C19; | A17-B8-C20; | A17-B8-C21; | A17-B8-C22; |
| A17-B8-C23; | A17-B8-C24; | A17-B8-C25; | A17-B8-C26; | A17-B8-C27; | A17-B8-C28; |
| A17-B8-C29; | A17-B8-C30; | A17-B8-C31; | A17-B8-C32; | A17-B8-C33; | A17-B8-C34; |
| A17-B8-C35; | A17-B8-C36; | A17-B8-C37; | A17-B8-C38; | A17-B8-C39; | A17-B8-C40; |
| A17-B8-C41; | A17-B8-C42; | A17-B8-C43; | A17-B8-C44; | A17-B8-C45; | A17-B8-C46; |
| A18-B8-C1; | A18-B8-C2; | A18-B8-C3; | A18-B8-C4; | A18-B8-C5; | A18-B8-C6; |
| A18-B8-C7; | A18-B8-C8; | A18-B8-C9; | A18-B8-C10; | A18-B8-C11; | A18-B8-C12; |
| A18-B8-C13; | A18-B8-C14; | A18-B8-C15; | A18-B8-C16; | A18-B8-C17; | A18-B8-C18; |
| A18-B8-C19; | A18-B8-C20; | A18-B8-C21; | A18-B8-C22; | A18-B8-C23; | A18-B8-C24; |
| A18-B8-C25; | A18-B8-C26; | A18-B8-C27; | A18-B8-C28; | A18-B8-C29; | A18-B8-C30; |
| A18-B8-C31; | A18-B8-C32; | A18-B8-C33; | A18-B8-C34; | A18-B8-C35; | A18-B8-C36; |
| A18-B8-C37; | A18-B8-C38; | A18-B8-C39; | A18-B8-C40; | A18-B8-C41; | A18-B8-C42; |
| A18-B8-C43; | A18-B8-C44; | A18-B8-C45; | A18-B8-C46; | A19-B8-C1; | A19-B8-C2; |
| A19-B8-C3; | A19-B8-C4; | A19-B8-C5; | A19-B8-C6; | A19-B8-C7; | A19-B8-C8; |
| A19-B8-C9; | A19-B8-C10; | A19-B8-C11; | A19-B8-C12; | A19-B8-C13; | A19-B8-C14; |
| A19-B8-C15; | A19-B8-C16; | A19-B8-C17; | A19-B8-C18; | A19-B8-C19; | A19-B8-C20; |
| A19-B8-C21; | A19-B8-C22; | A19-B8-C23; | A19-B8-C24; | A19-B8-C25; | A19-B8-C26; |
| A19-B8-C27; | A19-B8-C28; | A19-B8-C29; | A19-B8-C30; | A19-B8-C31; | A19-B8-C32; |
| A19-B8-C33; | A19-B8-C34; | A19-B8-C35; | A19-B8-C36; | A19-B8-C37; | A19-B8-C38; |
| A19-B8-C39; | A19-B8-C40; | A19-B8-C41; | A19-B8-C42; | A19-B8-C43; | A19-B8-C44; |
| A19-B8-C45; | A19-B8-C46; | A20-B8-C1; | A20-B8-C2; | A20-B8-C3; | A20-B8-C4; |
| A20-B8-C5; | A20-B8-C6; | A20-B8-C7; | A20-B8-C8; | A20-B8-C9; | A20-B8-C10; |
| A20-B8-C11; | A20-B8-C12; | A20-B8-C13; | A20-B8-C14; | A20-B8-C15; | A20-B8-C16; |
| A20-B8-C17; | A20-B8-C18; | A20-B8-C19; | A20-B8-C20; | A20-B8-C21; | A20-B8-C22; |
| A20-B8-C23; | A20-B8-C24; | A20-B8-C25; | A20-B8-C26; | A20-B8-C27; | A20-B8-C28; |
| A20-B8-C29; | A20-B8-C30; | A20-B8-C31; | A20-B8-C32; | A20-B8-C33; | A20-B8-C34; |
| A20-B8-C35; | A20-B8-C36; | A20-B8-C37; | A20-B8-C38; | A20-B8-C39; | A20-B8-C40; |
| A20-B8-C41; | A20-B8-C42; | A20-B8-C43; | A20-B8-C44; | A20-B8-C45; | A20-B8-C46; |
| A21-B8-C1; | A21-B8-C2; | A21-B8-C3; | A21-B8-C4; | A21-B8-C5; | A21-B8-C6; |
| A21-B8-C7; | A21-B8-C8; | A21-B8-C9; | A21-B8-C10; | A21-B8-C11; | A21-B8-C12; |
| A21-B8-C13; | A21-B8-C14; | A21-B8-C15; | A21-B8-C16; | A21-B8-C17; | A21-B8-C18; |
| A21-B8-C19; | A21-B8-C20; | A21-B8-C21; | A21-B8-C22; | A21-B8-C23; | A21-B8-C24; |
| A21-B8-C25; | A21-B8-C26; | A21-B8-C27; | A21-B8-C28; | A21-B8-C29; | A21-B8-C30; |
| A21-B8-C31; | A21-B8-C32; | A21-B8-C33; | A21-B8-C34; | A21-B8-C35; | A21-B8-C36; |
| A21-B8-C37; | A21-B8-C38; | A21-B8-C39; | A21-B8-C40; | A21-B8-C41; | A21-B8-C42; |
| A21-B8-C43; | A21-B8-C44; | A21-B8-C45; | A21-B8-C46; | A22-B8-C1; | A22-B8-C2; |
| A22-B8-C3; | A22-B8-C4; | A22-B8-C5; | A22-B8-C6; | A22-B8-C7; | A22-B8-C8; |
| A22-B8-C9; | A22-B8-C10; | A22-B8-C11; | A22-B8-C12; | A22-B8-C13; | A22-B8-C14; |
| A22-B8-C15; | A22-B8-C16; | A22-B8-C17; | A22-B8-C18; | A22-B8-C19; | A22-B8-C20; |
| A22-B8-C21; | A22-B8-C22; | A22-B8-C23; | A22-B8-C24; | A22-B8-C25; | A22-B8-C26; |
| A22-B8-C27; | A22-B8-C28; | A22-B8-C29; | A22-B8-C30; | A22-B8-C31; | A22-B8-C32; |
| A22-B8-C33; | A22-B8-C34; | A22-B8-C35; | A22-B8-C36; | A22-B8-C37; | A22-B8-C38; |
| A22-B8-C39; | A22-B8-C40; | A22-B8-C41; | A22-B8-C42; | A22-B8-C43; | A22-B8-C44; |
| A22-B8-C45; | A22-B8-C46; | A23-B8-C1; | A23-B8-C2; | A23-B8-C3; | A23-B8-C4; |
| A23-B8-C5; | A23-B8-C6; | A23-B8-C7; | A23-B8-C8; | A23-B8-C9; | A23-B8-C10; |
| A23-B8-C11; | A23-B8-C12; | A23-B8-C13; | A23-B8-C14; | A23-B8-C15; | A23-B8-C16; |
| A23-B8-C17; | A23-B8-C18; | A23-B8-C19; | A23-B8-C20; | A23-B8-C21; | A23-B8-C22; |
| A23-B8-C23; | A23-B8-C24; | A23-B8-C25; | A23-B8-C26; | A23-B8-C27; | A23-B8-C28; |
| A23-B8-C29; | A23-B8-C30; | A23-B8-C31; | A23-B8-C32; | A23-B8-C33; | A23-B8-C34; |
| A23-B8-C35; | A23-B8-C36; | A23-B8-C37; | A23-B8-C38; | A23-B8-C39; | A23-B8-C40; |
| A23-B8-C41; | A23-B8-C42; | A23-B8-C43; | A23-B8-C44; | A23-B8-C45; | A23-B8-C46; |
| A24-B8-C1; | A24-B8-C2; | A24-B8-C3; | A24-B8-C4; | A24-B8-C5; | A24-B8-C6; |
| A24-B8-C7; | A24-B8-C8; | A24-B8-C9; | A24-B8-C10; | A24-B8-C11; | A24-B8-C12; |
| A24-B8-C13; | A24-B8-C14; | A24-B8-C15; | A24-B8-C16; | A24-B8-C17; | A24-B8-C18; |
| A24-B8-C19; | A24-B8-C20; | A24-B8-C21; | A24-B8-C22; | A24-B8-C23; | A24-B8-C24; |
| A24-B8-C25; | A24-B8-C26; | A24-B8-C27; | A24-B8-C28; | A24-B8-C29; | A24-B8-C30; |
| A24-B8-C31; | A24-B8-C32; | A24-B8-C33; | A24-B8-C34; | A24-B8-C35; | A24-B8-C36; |
| A24-B8-C37; | A24-B8-C38; | A24-B8-C39; | A24-B8-C40; | A24-B8-C41; | A24-B8-C42; |
| A24-B8-C43; | A24-B8-C44; | A24-B8-C45; | A24-B8-C46; | A25-B8-C1; | A25-B8-C2; |
| A25-B8-C3; | A25-B8-C4; | A25-B8-C5; | A25-B8-C6; | A25-B8-C7; | A25-B8-C8; |
| A25-B8-C9; | A25-B8-C10; | A25-B8-C11; | A25-B8-C12; | A25-B8-C13; | A25-B8-C14; |
| A25-B8-C15; | A25-B8-C16; | A25-B8-C17; | A25-B8-C18; | A25-B8-C19; | A25-B8-C20; |
| A25-B8-C21; | A25-B8-C22; | A25-B8-C23; | A25-B8-C24; | A25-B8-C25; | A25-B8-C26; |
| A25-B8-C27; | A25-B8-C28; | A25-B8-C29; | A25-B8-C30; | A25-B8-C31; | A25-B8-C32; |
| A25-B8-C33; | A25-B8-C34; | A25-B8-C35; | A25-B8-C36; | A25-B8-C37; | A25-B8-C38; |
| A25-B8-C39; | A25-B8-C40; | A25-B8-C41; | A25-B8-C42; | A25-B8-C43; | A25-B8-C44; |
| A25-B8-C45; | A25-B8-C46; | A26-B8-C1; | A26-B8-C2; | A26-B8-C3; | A26-B8-C4; |
| A26-B8-C5; | A26-B8-C6; | A26-B8-C7; | A26-B8-C8; | A26-B8-C9; | A26-B8-C10; |
| A26-B8-C11; | A26-B8-C12; | A26-B8-C13; | A26-B8-C14; | A26-B8-C15; | A26-B8-C16; |
| A26-B8-C17; | A26-B8-C18; | A26-B8-C19; | A26-B8-C20; | A26-B8-C21; | A26-B8-C22; |
| A26-B8-C23; | A26-B8-C24; | A26-B8-C25; | A26-B8-C26; | A26-B8-C27; | A26-B8-C28; |

-continued

| | | | | | |
|---|---|---|---|---|---|
| A26-B8-C29; | A26-B8-C30; | A26-B8-C31; | A26-B8-C32; | A26-B8-C33; | A26-B8-C34; |
| A26-B8-C35; | A26-B8-C36; | A26-B8-C37; | A26-B8-C38; | A26-B8-C39; | A26-B8-C40; |
| A26-B8-C41; | A26-B8-C42; | A26-B8-C43; | A26-B8-C44; | A26-B8-C45; | A26-B8-C46; |
| A27-B8-C1; | A27-B8-C2; | A27-B8-C3; | A27-B8-C4; | A27-B8-C5; | A27-B8-C6; |
| A27-B8-C7; | A27-B8-C8; | A27-B8-C9; | A27-B8-C10; | A27-B8-C11; | A27-B8-C12; |
| A27-B8-C13; | A27-B8-C14; | A27-B8-C15; | A27-B8-C16; | A27-B8-C17; | A27-B8-C18; |
| A27-B8-C19; | A27-B8-C20; | A27-B8-C21; | A27-B8-C22; | A27-B8-C23; | A27-B8-C24; |
| A27-B8-C25; | A27-B8-C26; | A27-B8-C27; | A27-B8-C28; | A27-B8-C29; | A27-B8-C30; |
| A27-B8-C31; | A27-B8-C32; | A27-B8-C33; | A27-B8-C34; | A27-B8-C35; | A27-B8-C36; |
| A27-B8-C37; | A27-B8-C38; | A27-B8-C39; | A27-B8-C40; | A27-B8-C41; | A27-B8-C42; |
| A27-B8-C43; | A27-B8-C44; | A27-B8-C45; | A27-B8-C46; | A28-B8-C1; | A28-B8-C2; |
| A28-B8-C3; | A28-B8-C4; | A28-B8-C5; | A28-B8-C6; | A28-B8-C7; | A28-B8-C8; |
| A28-B8-C9; | A28-B8-C10; | A28-B8-C11; | A28-B8-C12; | A28-B8-C13; | A28-B8-C14; |
| A28-B8-C15; | A28-B8-C16; | A28-B8-C17; | A28-B8-C18; | A28-B8-C19; | A28-B8-C20; |
| A28-B8-C21; | A28-B8-C22; | A28-B8-C23; | A28-B8-C24; | A28-B8-C25; | A28-B8-C26; |
| A28-B8-C27; | A28-B8-C28; | A28-B8-C29; | A28-B8-C30; | A28-B8-C31; | A28-B8-C32; |
| A28-B8-C33; | A28-B8-C34; | A28-B8-C35; | A28-B8-C36; | A28-B8-C37; | A28-B8-C38; |
| A28-B8-C39; | A28-B8-C40; | A28-B8-C41; | A28-B8-C42; | A28-B8-C43; | A28-B8-C44; |
| A28-B8-C45; | A28-B8-C46; | A1-B9-C1; | A1-B9-C2; | A1-B9-C3; | A1-B9-C4; |
| A1-B9-C5; | A1-B9-C6; | A1-B9-C7; | A1-B9-C8; | A1-B9-C9; | A1-B9-C10; |
| A1-B9-C11; | A1-B9-C12; | A1-B9-C13; | A1-B9-C14; | A1-B9-C15; | A1-B9-C16; |
| A1-B9-C17; | A1-B9-C18; | A1-B9-C19; | A1-B9-C20; | A1-B9-C21; | A1-B9-C22; |
| A1-B9-C23; | A1-B9-C24; | A1-B9-C25; | A1-B9-C26; | A1-B9-C27; | A1-B9-C28; |
| A1-B9-C29; | A1-B9-C30; | A1-B9-C31; | A1-B9-C32; | A1-B9-C33; | A1-B9-C34; |
| A1-B9-C35; | A1-B9-C36; | A1-B9-C37; | A1-B9-C38; | A1-B9-C39; | A1-B9-C40; |
| A1-B9-C41; | A1-B9-C42; | A1-B9-C43; | A1-B9-C44; | A1-B9-C45; | A1-B9-C46; |
| A2-B9-C1; | A2-B9-C2; | A2-B9-C3; | A2-B9-C4; | A2-B9-C5; | A2-B9-C6; |
| A2-B9-C7; | A2-B9-C8; | A2-B9-C9; | A2-B9-C10; | A2-B9-C11; | A2-B9-C12; |
| A2-B9-C13; | A2-B9-C14; | A2-B9-C15; | A2-B9-C16; | A2-B9-C17; | A2-B9-C18; |
| A2-B9-C19; | A2-B9-C20; | A2-B9-C21; | A2-B9-C22; | A2-B9-C23; | A2-B9-C24; |
| A2-B9-C25; | A2-B9-C26; | A2-B9-C27; | A2-B9-C28; | A2-B9-C29; | A2-B9-C30; |
| A2-B9-C31; | A2-B9-C32; | A2-B9-C33; | A2-B9-C34; | A2-B9-C35; | A2-B9-C36; |
| A2-B9-C37; | A2-B9-C38; | A2-B9-C39; | A2-B9-C40; | A2-B9-C41; | A2-B9-C42; |
| A2-B9-C43; | A2-B9-C44; | A2-B9-C45; | A2-B9-C46; | A3-B9-C1; | A3-B9-C2; |
| A3-B9-C3; | A3-B9-C4; | A3-B9-C5; | A3-B9-C6; | A3-B9-C7; | A3-B9-C8; |
| A3-B9-C9; | A3-B9-C10; | A3-B9-C11; | A3-B9-C12; | A3-B9-C13; | A3-B9-C14; |
| A3-B9-C15; | A3-B9-C16; | A3-B9-C17; | A3-B9-C18; | A3-B9-C19; | A3-B9-C20; |
| A3-B9-C21; | A3-B9-C22; | A3-B9-C23; | A3-B9-C24; | A3-B9-C25; | A3-B9-C26; |
| A3-B9-C27; | A3-B9-C28; | A3-B9-C29; | A3-B9-C30; | A3-B9-C31; | A3-B9-C32; |
| A3-B9-C33; | A3-B9-C34; | A3-B9-C35; | A3-B9-C36; | A3-B9-C37; | A3-B9-C38; |
| A3-B9-C39; | A3-B9-C40; | A3-B9-C41; | A3-B9-C42; | A3-B9-C43; | A3-B9-C44; |
| A3-B9-C45; | A3-B9-C46; | A4-B9-C1; | A4-B9-C2; | A4-B9-C3; | A4-B9-C4; |
| A4-B9-C5; | A4-B9-C6; | A4-B9-C7; | A4-B9-C8; | A4-B9-C9; | A4-B9-C10; |
| A4-B9-C11; | A4-B9-C12; | A4-B9-C13; | A4-B9-C14; | A4-B9-C15; | A4-B9-C16; |
| A4-B9-C17; | A4-B9-C18; | A4-B9-C19; | A4-B9-C20; | A4-B9-C21; | A4-B9-C22; |
| A4-B9-C23; | A4-B9-C24; | A4-B9-C25; | A4-B9-C26; | A4-B9-C27; | A4-B9-C28; |
| A4-B9-C29; | A4-B9-C30; | A4-B9-C31; | A4-B9-C32; | A4-B9-C33; | A4-B9-C34; |
| A4-B9-C35; | A4-B9-C36; | A4-B9-C37; | A4-B9-C38; | A4-B9-C39; | A4-B9-C40; |
| A4-B9-C41; | A4-B9-C42; | A4-B9-C43; | A4-B9-C44; | A4-B9-C45; | A4-B9-C46; |
| A5-B9-C1; | A5-B9-C2; | A5-B9-C3; | A5-B9-C4; | A5-B9-C5; | A5-B9-C6; |
| A5-B9-C7; | A5-B9-C8; | A5-B9-C9; | A5-B9-C10; | A5-B9-C11; | A5-B9-C12; |
| A5-B9-C13; | A5-B9-C14; | A5-B9-C15; | A5-B9-C16; | A5-B9-C17; | A5-B9-C18; |
| A5-B9-C19; | A5-B9-C20; | A5-B9-C21; | A5-B9-C22; | A5-B9-C23; | A5-B9-C24; |
| A5-B9-C25; | A5-B9-C26; | A5-B9-C27; | A5-B9-C28; | A5-B9-C29; | A5-B9-C30; |
| A5-B9-C31; | A5-B9-C32; | A5-B9-C33; | A5-B9-C34; | A5-B9-C35; | A5-B9-C36; |
| A5-B9-C37; | A5-B9-C38; | A5-B9-C39; | A5-B9-C40; | A5-B9-C41; | A5-B9-C42; |
| A5-B9-C43; | A5-B9-C44; | A5-B9-C45; | A5-B9-C46; | A6-B9-C1; | A6-B9-C2; |
| A6-B9-C3; | A6-B9-C4; | A6-B9-C5; | A6-B9-C6; | A6-B9-C7; | A6-B9-C8; |
| A6-B9-C9; | A6-B9-C10; | A6-B9-C11; | A6-B9-C12; | A6-B9-C13; | A6-B9-C14; |
| A6-B9-C15; | A6-B9-C16; | A6-B9-C17; | A6-B9-C18; | A6-B9-C19; | A6-B9-C20; |
| A6-B9-C21; | A6-B9-C22; | A6-B9-C23; | A6-B9-C24; | A6-B9-C25; | A6-B9-C26; |
| A6-B9-C27; | A6-B9-C28; | A6-B9-C29; | A6-B9-C30; | A6-B9-C31; | A6-B9-C32; |
| A6-B9-C33; | A6-B9-C34; | A6-B9-C35; | A6-B9-C36; | A6-B9-C37; | A6-B9-C38; |
| A6-B9-C39; | A6-B9-C40; | A6-B9-C41; | A6-B9-C42; | A6-B9-C43; | A6-B9-C44; |
| A6-B9-C45; | A6-B9-C46; | A7-B9-C1; | A7-B9-C2; | A7-B9-C3; | A7-B9-C4; |
| A7-B9-C5; | A7-B9-C6; | A7-B9-C7; | A7-B9-C8; | A7-B9-C9; | A7-B9-C10; |
| A7-B9-C11; | A7-B9-C12; | A7-B9-C13; | A7-B9-C14; | A7-B9-C15; | A7-B9-C16; |
| A7-B9-C17; | A7-B9-C18; | A7-B9-C19; | A7-B9-C20; | A7-B9-C21; | A7-B9-C22; |
| A7-B9-C23; | A7-B9-C24; | A7-B9-C25; | A7-B9-C26; | A7-B9-C27; | A7-B9-C28; |
| A7-B9-C29; | A7-B9-C30; | A7-B9-C31; | A7-B9-C32; | A7-B9-C33; | A7-B9-C34; |
| A7-B9-C35; | A7-B9-C36; | A7-B9-C37; | A7-B9-C38; | A7-B9-C39; | A7-B9-C40; |
| A7-B9-C41; | A7-B9-C42; | A7-B9-C43; | A7-B9-C44; | A7-B9-C45; | A7-B9-C46; |
| A8-B9-C1; | A8-B9-C2; | A8-B9-C3; | A8-B9-C4; | A8-B9-C5; | A8-B9-C6; |
| A8-B9-C7; | A8-B9-C8; | A8-B9-C9; | A8-B9-C10; | A8-B9-C11; | A8-B9-C12; |
| A8-B9-C13; | A8-B9-C14; | A8-B9-C15; | A8-B9-C16; | A8-B9-C17; | A8-B9-C18; |
| A8-B9-C19; | A8-B9-C20; | A8-B9-C21; | A8-B9-C22; | A8-B9-C23; | A8-B9-C24; |
| A8-B9-C25; | A8-B9-C26; | A8-B9-C27; | A8-B9-C28; | A8-B9-C29; | A8-B9-C30; |
| A8-B9-C31; | A8-B9-C32; | A8-B9-C33; | A8-B9-C34; | A8-B9-C35; | A8-B9-C36; |
| A8-B9-C37; | A8-B9-C38; | A8-B9-C39; | A8-B9-C40; | A8-B9-C41; | A8-B9-C42; |

-continued

| | | | | | |
|---|---|---|---|---|---|
| A8-B9-C43; | A8-B9-C44; | A8-B9-C45; | A8-B9-C46; | A9-B9-C1; | A9-B9-C2; |
| A9-B9-C3; | A9-B9-C4; | A9-B9-C5; | A9-B9-C6; | A9-B9-C7; | A9-B9-C8; |
| A9-B9-C9; | A9-B9-C10; | A9-B9-C11; | A9-B9-C12; | A9-B9-C13; | A9-B9-C14; |
| A9-B9-C15; | A9-B9-C16; | A9-B9-C17; | A9-B9-C18; | A9-B9-C19; | A9-B9-C20; |
| A9-B9-C21; | A9-B9-C22; | A9-B9-C23; | A9-B9-C24; | A9-B9-C25; | A9-B9-C26; |
| A9-B9-C27; | A9-B9-C28; | A9-B9-C29; | A9-B9-C30; | A9-B9-C31; | A9-B9-C32; |
| A9-B9-C33; | A9-B9-C34; | A9-B9-C35; | A9-B9-C36; | A9-B9-C37; | A9-B9-C38; |
| A9-B9-C39; | A9-B9-C40; | A9-B9-C41; | A9-B9-C42; | A9-B9-C43; | A9-B9-C44; |
| A9-B9-C45; | A9-B9-C46; | A10-B9-C1; | A10-B9-C2; | A10-B9-C3; | A10-B9-C4; |
| A10-B9-C5; | A10-B9-C6; | A10-B9-C7; | A10-B9-C8; | A10-B9-C9; | A10-B9-C10; |
| A10-B9-C11; | A10-B9-C12; | A10-B9-C13; | A10-B9-C14; | A10-B9-C15; | A10-B9-C16; |
| A10-B9-C17; | A10-B9-C18; | A10-B9-C19; | A10-B9-C20; | A10-B9-C21; | A10-B9-C22; |
| A10-B9-C23; | A10-B9-C24; | A10-B9-C25; | A10-B9-C26; | A10-B9-C27; | A10-B9-C28; |
| A10-B9-C29; | A10-B9-C30; | A10-B9-C31; | A10-B9-C32; | A10-B9-C33; | A10-B9-C34; |
| A10-B9-C35; | A10-B9-C36; | A10-B9-C37; | A10-B9-C38; | A10-B9-C39; | A10-B9-C40; |
| A10-B9-C41; | A10-B9-C42; | A10-B9-C43; | A10-B9-C44; | A10-B9-C45; | A10-B9-C46; |
| A11-B9-C1; | A11-B9-C2; | A11-B9-C3; | A11-B9-C4; | A11-B9-C5; | A11-B9-C6; |
| A11-B9-C7; | A11-B9-C8; | A11-B9-C9; | A11-B9-C10; | A11-B9-C11; | A11-B9-C12; |
| A11-B9-C13; | A11-B9-C14; | A11-B9-C15; | A11-B9-C16; | A11-B9-C17; | A11-B9-C18; |
| A11-B9-C19; | A11-B9-C20; | A11-B9-C21; | A11-B9-C22; | A11-B9-C23; | A11-B9-C24; |
| A11-B9-C25; | A11-B9-C26; | A11-B9-C27; | A11-B9-C28; | A11-B9-C29; | A11-B9-C30; |
| A11-B9-C31; | A11-B9-C32; | A11-B9-C33; | A11-B9-C34; | A11-B9-C35; | A11-B9-C36; |
| A11-B9-C37; | A11-B9-C38; | A11-B9-C39; | A11-B9-C40; | A11-B9-C41; | A11-B9-C42; |
| A11-B9-C43; | A11-B9-C44; | A11-B9-C45; | A11-B9-C46; | A12-B9-C1; | A12-B9-C2; |
| A12-B9-C3; | A12-B9-C4; | A12-B9-C5; | A12-B9-C6; | A12-B9-C7; | A12-B9-C8; |
| A12-B9-C9; | A12-B9-C10; | A12-B9-C11; | A12-B9-C12; | A12-B9-C13; | A12-B9-C14; |
| A12-B9-C15; | A12-B9-C16; | A12-B9-C17; | A12-B9-C18; | A12-B9-C19; | A12-B9-C20; |
| A12-B9-C21; | A12-B9-C22; | A12-B9-C23; | A12-B9-C24; | A12-B9-C25; | A12-B9-C26; |
| A12-B9-C27; | A12-B9-C28; | A12-B9-C29; | A12-B9-C30; | A12-B9-C31; | A12-B9-C32; |
| A12-B9-C33; | A12-B9-C34; | A12-B9-C35; | A12-B9-C36; | A12-B9-C37; | A12-B9-C38; |
| A12-B9-C39; | A12-B9-C40; | A12-B9-C41; | A12-B9-C42; | A12-B9-C43; | A12-B9-C44; |
| A12-B9-C45; | A12-B9-C46; | A13-B9-C1; | A13-B9-C2; | A13-B9-C3; | A13-B9-C4; |
| A13-B9-C5; | A13-B9-C6; | A13-B9-C7; | A13-B9-C8; | A13-B9-C9; | A13-B9-C10; |
| A13-B9-C11; | A13-B9-C12; | A13-B9-C13; | A13-B9-C14; | A13-B9-C15; | A13-B9-C16; |
| A13-B9-C17; | A13-B9-C18; | A13-B9-C19; | A13-B9-C20; | A13-B9-C21; | A13-B9-C22; |
| A13-B9-C23; | A13-B9-C24; | A13-B9-C25; | A13-B9-C26; | A13-B9-C27; | A13-B9-C28; |
| A13-B9-C29; | A13-B9-C30; | A13-B9-C31; | A13-B9-C32; | A13-B9-C33; | A13-B9-C34; |
| A13-B9-C35; | A13-B9-C36; | A13-B9-C37; | A13-B9-C38; | A13-B9-C39; | A13-B9-C40; |
| A13-B9-C41; | A13-B9-C42; | A13-B9-C43; | A13-B9-C44; | A13-B9-C45; | A13-B9-C46; |
| A14-B9-C1; | A14-B9-C2; | A14-B9-C3; | A14-B9-C4; | A14-B9-C5; | A14-B9-C6; |
| A14-B9-C7; | A14-B9-C8; | A14-B9-C9; | A14-B9-C10; | A14-B9-C11; | A14-B9-C12; |
| A14-B9-C13; | A14-B9-C14; | A14-B9-C15; | A14-B9-C16; | A14-B9-C17; | A14-B9-C18; |
| A14-B9-C19; | A14-B9-C20; | A14-B9-C21; | A14-B9-C22; | A14-B9-C23; | A14-B9-C24; |
| A14-B9-C25; | A14-B9-C26; | A14-B9-C27; | A14-B9-C28; | A14-B9-C29; | A14-B9-C30; |
| A14-B9-C31; | A14-B9-C32; | A14-B9-C33; | A14-B9-C34; | A14-B9-C35; | A14-B9-C36; |
| A14-B9-C37; | A14-B9-C38; | A14-B9-C39; | A14-B9-C40; | A14-B9-C41; | A14-B9-C42; |
| A14-B9-C43; | A14-B9-C44; | A14-B9-C45; | A14-B9-C46; | A15-B9-C1; | A15-B9-C2; |
| A15-B9-C3; | A15-B9-C4; | A15-B9-C5; | A15-B9-C6; | A15-B9-C7; | A15-B9-C8; |
| A15-B9-C9; | A15-B9-C10; | A15-B9-C11; | A15-B9-C12; | A15-B9-C13; | A15-B9-C14; |
| A15-B9-C15; | A15-B9-C16; | A15-B9-C17; | A15-B9-C18; | A15-B9-C19; | A15-B9-C20; |
| A15-B9-C21; | A15-B9-C22; | A15-B9-C23; | A15-B9-C24; | A15-B9-C25; | A15-B9-C26; |
| A15-B9-C27; | A15-B9-C28; | A15-B9-C29; | A15-B9-C30; | A15-B9-C31; | A15-B9-C32; |
| A15-B9-C33; | A15-B9-C34; | A15-B9-C35; | A15-B9-C36; | A15-B9-C37; | A15-B9-C38; |
| A15-B9-C39; | A15-B9-C40; | A15-B9-C41; | A15-B9-C42; | A15-B9-C43; | A15-B9-C44; |
| A15-B9-C45; | A15-B9-C46; | A16-B9-C1; | A16-B9-C2; | A16-B9-C3; | A16-B9-C4; |
| A16-B9-C5; | A16-B9-C6; | A16-B9-C7; | A16-B9-C8; | A16-B9-C9; | A16-B9-C10; |
| A16-B9-C11; | A16-B9-C12; | A16-B9-C13; | A16-B9-C14; | A16-B9-C15; | A16-B9-C16; |
| A16-B9-C17; | A16-B9-C18; | A16-B9-C19; | A16-B9-C20; | A16-B9-C21; | A16-B9-C22; |
| A16-B9-C23; | A16-B9-C24; | A16-B9-C25; | A16-B9-C26; | A16-B9-C27; | A16-B9-C28; |
| A16-B9-C29; | A16-B9-C30; | A16-B9-C31; | A16-B9-C32; | A16-B9-C33; | A16-B9-C34; |
| A16-B9-C35; | A16-B9-C36; | A16-B9-C37; | A16-B9-C38; | A16-B9-C39; | A16-B9-C40; |
| A16-B9-C41; | A16-B9-C42; | A16-B9-C43; | A16-B9-C44; | A16-B9-C45; | A16-B9-C46; |
| A17-B9-C1; | A17-B9-C2; | A17-B9-C3; | A17-B9-C4; | A17-B9-C5; | A17-B9-C6; |
| A17-B9-C7; | A17-B9-C8; | A17-B9-C9; | A17-B9-C10; | A17-B9-C11; | A17-B9-C12; |
| A17-B9-C13; | A17-B9-C14; | A17-B9-C15; | A17-B9-C16; | A17-B9-C17; | A17-B9-C18; |
| A17-B9-C19; | A17-B9-C20; | A17-B9-C21; | A17-B9-C22; | A17-B9-C23; | A17-B9-C24; |
| A17-B9-C25; | A17-B9-C26; | A17-B9-C27; | A17-B9-C28; | A17-B9-C29; | A17-B9-C30; |
| A17-B9-C31; | A17-B9-C32; | A17-B9-C33; | A17-B9-C34; | A17-B9-C35; | A17-B9-C36; |
| A17-B9-C37; | A17-B9-C38; | A17-B9-C39; | A17-B9-C40; | A17-B9-C41; | A17-B9-C42; |
| A17-B9-C43; | A17-B9-C44; | A17-B9-C45; | A17-B9-C46; | A18-B9-C1; | A18-B9-C2; |
| A18-B9-C3; | A18-B9-C4; | A18-B9-C5; | A18-B9-C6; | A18-B9-C7; | A18-B9-C8; |
| A18-B9-C9; | A18-B9-C10; | A18-B9-C11; | A18-B9-C12; | A18-B9-C13; | A18-B9-C14; |
| A18-B9-C15; | A18-B9-C16; | A18-B9-C17; | A18-B9-C18; | A18-B9-C19; | A18-B9-C20; |
| A18-B9-C21; | A18-B9-C22; | A18-B9-C23; | A18-B9-C24; | A18-B9-C25; | A18-B9-C26; |
| A18-B9-C27; | A18-B9-C28; | A18-B9-C29; | A18-B9-C30; | A18-B9-C31; | A18-B9-C32; |
| A18-B9-C33; | A18-B9-C34; | A18-B9-C35; | A18-B9-C36; | A18-B9-C37; | A18-B9-C38; |
| A18-B9-C39; | A18-B9-C40; | A18-B9-C41; | A18-B9-C42; | A18-B9-C43; | A18-B9-C44; |
| A18-B9-C45; | A18-B9-C46; | A19-B9-C1; | A19-B9-C2; | A19-B9-C3; | A19-B9-C4; |
| A19-B9-C5; | A19-B9-C6; | A19-B9-C7; | A19-B9-C8; | A19-B9-C9; | A19-B9-C10; |

| | | | | | |
|---|---|---|---|---|---|
| A19-B9-C11; | A19-B9-C12; | A19-B9-C13; | A19-B9-C14; | A19-B9-C15; | A19-B9-C16; |
| A19-B9-C17; | A19-B9-C18; | A19-B9-C19; | A19-B9-C20; | A19-B9-C21; | A19-B9-C22; |
| A19-B9-C23; | A19-B9-C24; | A19-B9-C25; | A19-B9-C26; | A19-B9-C27; | A19-B9-C28; |
| A19-B9-C29; | A19-B9-C30; | A19-B9-C31; | A19-B9-C32; | A19-B9-C33; | A19-B9-C34; |
| A19-B9-C35; | A19-B9-C36; | A19-B9-C37; | A19-B9-C38; | A19-B9-C39; | A19-B9-C40; |
| A19-B9-C41; | A19-B9-C42; | A19-B9-C43; | A19-B9-C44; | A19-B9-C45; | A19-B9-C46; |
| A20-B9-C1; | A20-B9-C2; | A20-B9-C3; | A20-B9-C4; | A20-B9-C5; | A20-B9-C6; |
| A20-B9-C7; | A20-B9-C8; | A20-B9-C9; | A20-B9-C10; | A20-B9-C11; | A20-B9-C12; |
| A20-B9-C13; | A20-B9-C14; | A20-B9-C15; | A20-B9-C16; | A20-B9-C17; | A20-B9-C18; |
| A20-B9-C19; | A20-B9-C20; | A20-B9-C21; | A20-B9-C22; | A20-B9-C23; | A20-B9-C24; |
| A20-B9-C25; | A20-B9-C26; | A20-B9-C27; | A20-B9-C28; | A20-B9-C29; | A20-B9-C30; |
| A20-B9-C31; | A20-B9-C32; | A20-B9-C33; | A20-B9-C34; | A20-B9-C35; | A20-B9-C36; |
| A20-B9-C37; | A20-B9-C38; | A20-B9-C39; | A20-B9-C40; | A20-B9-C41; | A20-B9-C42; |
| A20-B9-C43; | A20-B9-C44; | A20-B9-C45; | A20-B9-C46; | A21-B9-C1; | A21-B9-C2; |
| A21-B9-C3; | A21-B9-C4; | A21-B9-C5; | A21-B9-C6; | A21-B9-C7; | A21-B9-C8; |
| A21-B9-C9; | A21-B9-C10; | A21-B9-C11; | A21-B9-C12; | A21-B9-C13; | A21-B9-C14; |
| A21-B9-C15; | A21-B9-C16; | A21-B9-C17; | A21-B9-C18; | A21-B9-C19; | A21-B9-C20; |
| A21-B9-C21; | A21-B9-C22; | A21-B9-C23; | A21-B9-C24; | A21-B9-C25; | A21-B9-C26; |
| A21-B9-C27; | A21-B9-C28; | A21-B9-C29; | A21-B9-C30; | A21-B9-C31; | A21-B9-C32; |
| A21-B9-C33; | A21-B9-C34; | A21-B9-C35; | A21-B9-C36; | A21-B9-C37; | A21-B9-C38; |
| A21-B9-C39; | A21-B9-C40; | A21-B9-C41; | A21-B9-C42; | A21-B9-C43; | A21-B9-C44; |
| A21-B9-C45; | A21-B9-C46; | A22-B9-C1; | A22-B9-C2; | A22-B9-C3; | A22-B9-C4; |
| A22-B9-C5; | A22-B9-C6; | A22-B9-C7; | A22-B9-C8; | A22-B9-C9; | A22-B9-C10; |
| A22-B9-C11; | A22-B9-C12; | A22-B9-C13; | A22-B9-C14; | A22-B9-C15; | A22-B9-C16; |
| A22-B9-C17; | A22-B9-C18; | A22-B9-C19; | A22-B9-C20; | A22-B9-C21; | A22-B9-C22; |
| A22-B9-C23; | A22-B9-C24; | A22-B9-C25; | A22-B9-C26; | A22-B9-C27; | A22-B9-C28; |
| A22-B9-C29; | A22-B9-C30; | A22-B9-C31; | A22-B9-C32; | A22-B9-C33; | A22-B9-C34; |
| A22-B9-C35; | A22-B9-C36; | A22-B9-C37; | A22-B9-C38; | A22-B9-C39; | A22-B9-C40; |
| A22-B9-C41; | A22-B9-C42; | A22-B9-C43; | A22-B9-C44; | A22-B9-C45; | A22-B9-C46; |
| A23-B9-C1; | A23-B9-C2; | A23-B9-C3; | A23-B9-C4; | A23-B9-C5; | A23-B9-C6; |
| A23-B9-C7; | A23-B9-C8; | A23-B9-C9; | A23-B9-C10; | A23-B9-C11; | A23-B9-C12; |
| A23-B9-C13; | A23-B9-C14; | A23-B9-C15; | A23-B9-C16; | A23-B9-C17; | A23-B9-C18; |
| A23-B9-C19; | A23-B9-C20; | A23-B9-C21; | A23-B9-C22; | A23-B9-C23; | A23-B9-C24; |
| A23-B9-C25; | A23-B9-C26; | A23-B9-C27; | A23-B9-C28; | A23-B9-C29; | A23-B9-C30; |
| A23-B9-C31; | A23-B9-C32; | A23-B9-C33; | A23-B9-C34; | A23-B9-C35; | A23-B9-C36; |
| A23-B9-C37; | A23-B9-C38; | A23-B9-C39; | A23-B9-C40; | A23-B9-C41; | A23-B9-C42; |
| A23-B9-C43; | A23-B9-C44; | A23-B9-C45; | A23-B9-C46; | A24-B9-C1; | A24-B9-C2; |
| A24-B9-C3; | A24-B9-C4; | A24-B9-C5; | A24-B9-C6; | A24-B9-C7; | A24-B9-C8; |
| A24-B9-C9; | A24-B9-C10; | A24-B9-C11; | A24-B9-C12; | A24-B9-C13; | A24-B9-C14; |
| A24-B9-C15; | A24-B9-C16; | A24-B9-C17; | A24-B9-C18; | A24-B9-C19; | A24-B9-C20; |
| A24-B9-C21; | A24-B9-C22; | A24-B9-C23; | A24-B9-C24; | A24-B9-C25; | A24-B9-C26; |
| A24-B9-C27; | A24-B9-C28; | A24-B9-C29; | A24-B9-C30; | A24-B9-C31; | A24-B9-C32; |
| A24-B9-C33; | A24-B9-C34; | A24-B9-C35; | A24-B9-C36; | A24-B9-C37; | A24-B9-C38; |
| A24-B9-C39; | A24-B9-C40; | A24-B9-C41; | A24-B9-C42; | A24-B9-C43; | A24-B9-C44; |
| A24-B9-C45; | A24-B9-C46; | A25-B9-C1; | A25-B9-C2; | A25-B9-C3; | A25-B9-C4; |
| A25-B9-C5; | A25-B9-C6; | A25-B9-C7; | A25-B9-C8; | A25-B9-C9; | A25-B9-C10; |
| A25-B9-C11; | A25-B9-C12; | A25-B9-C13; | A25-B9-C14; | A25-B9-C15; | A25-B9-C16; |
| A25-B9-C17; | A25-B9-C18; | A25-B9-C19; | A25-B9-C20; | A25-B9-C21; | A25-B9-C22; |
| A25-B9-C23; | A25-B9-C24; | A25-B9-C25; | A25-B9-C26; | A25-B9-C27; | A25-B9-C28; |
| A25-B9-C29; | A25-B9-C30; | A25-B9-C31; | A25-B9-C32; | A25-B9-C33; | A25-B9-C34; |
| A25-B9-C35; | A25-B9-C36; | A25-B9-C37; | A25-B9-C38; | A25-B9-C39; | A25-B9-C40; |
| A25-B9-C41; | A25-B9-C42; | A25-B9-C43; | A25-B9-C44; | A25-B9-C45; | A25-B9-C46; |
| A26-B9-C1; | A26-B9-C2; | A26-B9-C3; | A26-B9-C4; | A26-B9-C5; | A26-B9-C6; |
| A26-B9-C7; | A26-B9-C8; | A26-B9-C9; | A26-B9-C10; | A26-B9-C11; | A26-B9-C12; |
| A26-B9-C13; | A26-B9-C14; | A26-B9-C15; | A26-B9-C16; | A26-B9-C17; | A26-B9-C18; |
| A26-B9-C19; | A26-B9-C20; | A26-B9-C21; | A26-B9-C22; | A26-B9-C23; | A26-B9-C24; |
| A26-B9-C25; | A26-B9-C26; | A26-B9-C27; | A26-B9-C28; | A26-B9-C29; | A26-B9-C30; |
| A26-B9-C31; | A26-B9-C32; | A26-B9-C33; | A26-B9-C34; | A26-B9-C35; | A26-B9-C36; |
| A26-B9-C37; | A26-B9-C38; | A26-B9-C39; | A26-B9-C40; | A26-B9-C41; | A26-B9-C42; |
| A26-B9-C43; | A26-B9-C44; | A26-B9-C45; | A26-B9-C46; | A27-B9-C1; | A27-B9-C2; |
| A27-B9-C3; | A27-B9-C4; | A27-B9-C5; | A27-B9-C6; | A27-B9-C7; | A27-B9-C8; |
| A27-B9-C9; | A27-B9-C10; | A27-B9-C11; | A27-B9-C12; | A27-B9-C13; | A27-B9-C14; |
| A27-B9-C15; | A27-B9-C16; | A27-B9-C17; | A27-B9-C18; | A27-B9-C19; | A27-B9-C20; |
| A27-B9-C21; | A27-B9-C22; | A27-B9-C23; | A27-B9-C24; | A27-B9-C25; | A27-B9-C26; |
| A27-B9-C27; | A27-B9-C28; | A27-B9-C29; | A27-B9-C30; | A27-B9-C31; | A27-B9-C32; |
| A27-B9-C33; | A27-B9-C34; | A27-B9-C35; | A27-B9-C36; | A27-B9-C37; | A27-B9-C38; |
| A27-B9-C39; | A27-B9-C40; | A27-B9-C41; | A27-B9-C42; | A27-B9-C43; | A27-B9-C44; |
| A27-B9-C45; | A27-B9-C46; | A28-B9-C1; | A28-B9-C2; | A28-B9-C3; | A28-B9-C4; |
| A28-B9-C5; | A28-B9-C6; | A28-B9-C7; | A28-B9-C8; | A28-B9-C9; | A28-B9-C10; |
| A28-B9-C11; | A28-B9-C12; | A28-B9-C13; | A28-B9-C14; | A28-B9-C15; | A28-B9-C16; |
| A28-B9-C17; | A28-B9-C18; | A28-B9-C19; | A28-B9-C20; | A28-B9-C21; | A28-B9-C22; |
| A28-B9-C23; | A28-B9-C24; | A28-B9-C25; | A28-B9-C26; | A28-B9-C27; | A28-B9-C28; |
| A28-B9-C29; | A28-B9-C30; | A28-B9-C31; | A28-B9-C32; | A28-B9-C33; | A28-B9-C34; |
| A28-B9-C35; | A28-B9-C36; | A28-B9-C37; | A28-B9-C38; | A28-B9-C39; | A28-B9-C40; |
| A28-B9-C41; | A28-B9-C42; | A28-B9-C43; | A28-B9-C44; | A28-B9-C45; | A28-B9-C46; |
| A1-B10-C1; | A1-B10-C2; | A1-B10-C3; | A1-B10-C4; | A1-B10-C5; | A1-B10-C6; |
| A1-B10-C7; | A1-B10-C8; | A1-B10-C9; | A1-B10-C10; | A1-B10-C11; | A1-B10-C12; |
| A1-B10-C13; | A1-B10-C14; | A1-B10-C15; | A1-B10-C16; | A1-B10-C17; | A1-B10-C18; |
| A1-B10-C19; | A1-B10-C20; | A1-B10-C21; | A1-B10-C22; | A1-B10-C23; | A1-B10-C24; |

| | | | | | |
|---|---|---|---|---|---|
| A1-B10-C25; | A1-B10-C26; | A1-B10-C27; | A1-B10-C28; | A1-B10-C29; | A1-B10-C30; |
| A1-B10-C31; | A1-B10-C32; | A1-B10-C33; | A1-B10-C34; | A1-B10-C35; | A1-B10-C36; |
| A1-B10-C37; | A1-B10-C38; | A1-B10-C39; | A1-B10-C40; | A1-B10-C41; | A1-B10-C42; |
| A1-B10-C43; | A1-B10-C44; | A1-B10-C45; | A1-B10-C46; | A2-B10-C1; | A2-B10-C2; |
| A2-B10-C3; | A2-B10-C4; | A2-B10-C5; | A2-B10-C6; | A2-B10-C7; | A2-B10-C8; |
| A2-B10-C9; | A2-B10-C10; | A2-B10-C11; | A2-B10-C12; | A2-B10-C13; | A2-B10-C14; |
| A2-B10-C15; | A2-B10-C16; | A2-B10-C17; | A2-B10-C18; | A2-B10-C19; | A2-B10-C20; |
| A2-B10-C21; | A2-B10-C22; | A2-B10-C23; | A2-B10-C24; | A2-B10-C25; | A2-B10-C26; |
| A2-B10-C27; | A2-B10-C28; | A2-B10-C29; | A2-B10-C30; | A2-B10-C31; | A2-B10-C32; |
| A2-B10-C33; | A2-B10-C34; | A2-B10-C35; | A2-B10-C36; | A2-B10-C37; | A2-B10-C38; |
| A2-B10-C39; | A2-B10-C40; | A2-B10-C41; | A2-B10-C42; | A2-B10-C43; | A2-B10-C44; |
| A2-B10-C45; | A2-B10-C46; | A3-B10-C1; | A3-B10-C2; | A3-B10-C3; | A3-B10-C4; |
| A3-B10-C5; | A3-B10-C6; | A3-B10-C7; | A3-B10-C8; | A3-B10-C9; | A3-B10-C10; |
| A3-B10-C11; | A3-B10-C12; | A3-B10-C13; | A3-B10-C14; | A3-B10-C15; | A3-B10-C16; |
| A3-B10-C17; | A3-B10-C18; | A3-B10-C19; | A3-B10-C20; | A3-B10-C21; | A3-B10-C22; |
| A3-B10-C23; | A3-B10-C24; | A3-B10-C25; | A3-B10-C26; | A3-B10-C27; | A3-B10-C28; |
| A3-B10-C29; | A3-B10-C30; | A3-B10-C31; | A3-B10-C32; | A3-B10-C33; | A3-B10-C34; |
| A3-B10-C35; | A3-B10-C36; | A3-B10-C37; | A3-B10-C38; | A3-B10-C39; | A3-B10-C40; |
| A3-B10-C41; | A3-B10-C42; | A3-B10-C43; | A3-B10-C44; | A3-B10-C45; | A3-B10-C46; |
| A4-B10-C1; | A4-B10-C2; | A4-B10-C3; | A4-B10-C4; | A4-B10-C5; | A4-B10-C6; |
| A4-B10-C7; | A4-B10-C8; | A4-B10-C9; | A4-B10-C10; | A4-B10-C11; | A4-B10-C12; |
| A4-B10-C13; | A4-B10-C14; | A4-B10-C15; | A4-B10-C16; | A4-B10-C17; | A4-B10-C18; |
| A4-B10-C19; | A4-B10-C20; | A4-B10-C21; | A4-B10-C22; | A4-B10-C23; | A4-B10-C24; |
| A4-B10-C25; | A4-B10-C26; | A4-B10-C27; | A4-B10-C28; | A4-B10-C29; | A4-B10-C30; |
| A4-B10-C31; | A4-B10-C32; | A4-B10-C33; | A4-B10-C34; | A4-B10-C35; | A4-B10-C36; |
| A4-B10-C37; | A4-B10-C38; | A4-B10-C39; | A4-B10-C40; | A4-B10-C41; | A4-B10-C42; |
| A4-B10-C43; | A4-B10-C44; | A4-B10-C45; | A4-B10-C46; | A5-B10-C1; | A5-B10-C2; |
| A5-B10-C3; | A5-B10-C4; | A5-B10-C5; | A5-B10-C6; | A5-B10-C7; | A5-B10-C8; |
| A5-B10-C9; | A5-B10-C10; | A5-B10-C11; | A5-B10-C12; | A5-B10-C13; | A5-B10-C14; |
| A5-B10-C15; | A5-B10-C16; | A5-B10-C17; | A5-B10-C18; | A5-B10-C19; | A5-B10-C20; |
| A5-B10-C21; | A5-B10-C22; | A5-B10-C23; | A5-B10-C24; | A5-B10-C25; | A5-B10-C26; |
| A5-B10-C27; | A5-B10-C28; | A5-B10-C29; | A5-B10-C30; | A5-B10-C31; | A5-B10-C32; |
| A5-B10-C33; | A5-B10-C34; | A5-B10-C35; | A5-B10-C36; | A5-B10-C37; | A5-B10-C38; |
| A5-B10-C39; | A5-B10-C40; | A5-B10-C41; | A5-B10-C42; | A5-B10-C43; | A5-B10-C44; |
| A5-B10-C45; | A5-B10-C46; | A6-B10-C1; | A6-B10-C2; | A6-B10-C3; | A6-B10-C4; |
| A6-B10-C5; | A6-B10-C6; | A6-B10-C7; | A6-B10-C8; | A6-B10-C9; | A6-B10-C10; |
| A6-B10-C11; | A6-B10-C12; | A6-B10-C13; | A6-B10-C14; | A6-B10-C15; | A6-B10-C16; |
| A6-B10-C17; | A6-B10-C18; | A6-B10-C19; | A6-B10-C20; | A6-B10-C21; | A6-B10-C22; |
| A6-B10-C23; | A6-B10-C24; | A6-B10-C25; | A6-B10-C26; | A6-B10-C27; | A6-B10-C28; |
| A6-B10-C29; | A6-B10-C30; | A6-B10-C31; | A6-B10-C32; | A6-B10-C33; | A6-B10-C34; |
| A6-B10-C35; | A6-B10-C36; | A6-B10-C37; | A6-B10-C38; | A6-B10-C39; | A6-B10-C40; |
| A6-B10-C41; | A6-B10-C42; | A6-B10-C43; | A6-B10-C44; | A6-B10-C45; | A6-B10-C46; |
| A7-B10-C1; | A7-B10-C2; | A7-B10-C3; | A7-B10-C4; | A7-B10-C5; | A7-B10-C6; |
| A7-B10-C7; | A7-B10-C8; | A7-B10-C9; | A7-B10-C10; | A7-B10-C11; | A7-B10-C12; |
| A7-B10-C13; | A7-B10-C14; | A7-B10-C15; | A7-B10-C16; | A7-B10-C17; | A7-B10-C18; |
| A7-B10-C19; | A7-B10-C20; | A7-B10-C21; | A7-B10-C22; | A7-B10-C23; | A7-B10-C24; |
| A7-B10-C25; | A7-B10-C26; | A7-B10-C27; | A7-B10-C28; | A7-B10-C29; | A7-B10-C30; |
| A7-B10-C31; | A7-B10-C32; | A7-B10-C33; | A7-B10-C34; | A7-B10-C35; | A7-B10-C36; |
| A7-B10-C37; | A7-B10-C38; | A7-B10-C39; | A7-B10-C40; | A7-B10-C41; | A7-B10-C42; |
| A7-B10-C43; | A7-B10-C44; | A7-B10-C45; | A7-B10-C46; | A8-B10-C1; | A8-B10-C2; |
| A8-B10-C3; | A8-B10-C4; | A8-B10-C5; | A8-B10-C6; | A8-B10-C7; | A8-B10-C8; |
| A8-B10-C9; | A8-B10-C10; | A8-B10-C11; | A8-B10-C12; | A8-B10-C13; | A8-B10-C14; |
| A8-B10-C15; | A8-B10-C16; | A8-B10-C17; | A8-B10-C18; | A8-B10-C19; | A8-B10-C20; |
| A8-B10-C21; | A8-B10-C22; | A8-B10-C23; | A8-B10-C24; | A8-B10-C25; | A8-B10-C26; |
| A8-B10-C27; | A8-B10-C28; | A8-B10-C29; | A8-B10-C30; | A8-B10-C31; | A8-B10-C32; |
| A8-B10-C33; | A8-B10-C34; | A8-B10-C35; | A8-B10-C36; | A8-B10-C37; | A8-B10-C38; |
| A8-B10-C39; | A8-B10-C40; | A8-B10-C41; | A8-B10-C42; | A8-B10-C43; | A8-B10-C44; |
| A8-B10-C45; | A8-B10-C46; | A9-B10-C1; | A9-B10-C2; | A9-B10-C3; | A9-B10-C4; |
| A9-B10-C5; | A9-B10-C6; | A9-B10-C7; | A9-B10-C8; | A9-B10-C9; | A9-B10-C10; |
| A9-B10-C11; | A9-B10-C12; | A9-B10-C13; | A9-B10-C14; | A9-B10-C15; | A9-B10-C16; |
| A9-B10-C17; | A9-B10-C18; | A9-B10-C19; | A9-B10-C20; | A9-B10-C21; | A9-B10-C22; |
| A9-B10-C23; | A9-B10-C24; | A9-B10-C25; | A9-B10-C26; | A9-B10-C27; | A9-B10-C28; |
| A9-B10-C29; | A9-B10-C30; | A9-B10-C31; | A9-B10-C32; | A9-B10-C33; | A9-B10-C34; |
| A9-B10-C35; | A9-B10-C36; | A9-B10-C37; | A9-B10-C38; | A9-B10-C39; | A9-B10-C40; |
| A9-B10-C41; | A9-B10-C42; | A9-B10-C43; | A9-B10-C44; | A9-B10-C45; | A9-B10-C46; |
| A10-B10-C1; | A10-B10-C2; | A10-B10-C3; | A10-B10-C4; | A10-B10-C5; | A10-B10-C6; |
| A10-B10-C7; | A10-B10-C8; | A10-B10-C9; | A10-B10-C10; | A10-B10-C11; | A10-B10-C12; |
| A10-B10-C13; | A10-B10-C14; | A10-B10-C15; | A10-B10-C16; | A10-B10-C17; | A10-B10-C18; |
| A10-B10-C19; | A10-B10-C20; | A10-B10-C21; | A10-B10-C22; | A10-B10-C23; | A10-B10-C24; |
| A10-B10-C25; | A10-B10-C26; | A10-B10-C27; | A10-B10-C28; | A10-B10-C29; | A10-B10-C30; |
| A10-B10-C31; | A10-B10-C32; | A10-B10-C33; | A10-B10-C34; | A10-B10-C35; | A10-B10-C36; |
| A10-B10-C37; | A10-B10-C38; | A10-B10-C39; | A10-B10-C40; | A10-B10-C41; | A10-B10-C42; |
| A10-B10-C43; | A10-B10-C44; | A10-B10-C45; | A10-B10-C46; | A11-B10-C1; | A11-B10-C2; |
| A11-B10-C3; | A11-B10-C4; | A11-B10-C5; | A11-B10-C6; | A11-B10-C7; | A11-B10-C8; |
| A11-B10-C9; | A11-B10-C10; | A11-B10-C11; | A11-B10-C12; | A11-B10-C13; | A11-B10-C14; |
| A11-B10-C15; | A11-B10-C16; | A11-B10-C17; | A11-B10-C18; | A11-B10-C19; | A11-B10-C20; |
| A11-B10-C21; | A11-B10-C22; | A11-B10-C23; | A11-B10-C24; | A11-B10-C25; | A11-B10-C26; |
| A11-B10-C27; | A11-B10-C28; | A11-B10-C29; | A11-B10-C30; | A11-B10-C31; | A11-B10-C32; |
| A11-B10-C33; | A11-B10-C34; | A11-B10-C35; | A11-B10-C36; | A11-B10-C37; | A11-B10-C38; |

-continued

| | | | | | |
|---|---|---|---|---|---|
| A11-B10-C39; | A11-B10-C40; | A11-B10-C41; | A11-B10-C42; | A11-B10-C43; | A11-B10-C44; |
| A11-B10-C45; | A11-B10-C46; | A12-B10-C1; | A12-B10-C2; | A12-B10-C3; | A12-B10-C4; |
| A12-B10-C5; | A12-B10-C6; | A12-B10-C7; | A12-B10-C8; | A12-B10-C9; | A12-B10-C10; |
| A12-B10-C11; | A12-B10-C12; | A12-B10-C13; | A12-B10-C14; | A12-B10-C15; | A12-B10-C16; |
| A12-B10-C17; | A12-B10-C18; | A12-B10-C19; | A12-B10-C20; | A12-B10-C21; | A12-B10-C22; |
| A12-B10-C23; | A12-B10-C24; | A12-B10-C25; | A12-B10-C26; | A12-B10-C27; | A12-B10-C28; |
| A12-B10-C29; | A12-B10-C30; | A12-B10-C31; | A12-B10-C32; | A12-B10-C33; | A12-B10-C34; |
| A12-B10-C35; | A12-B10-C36; | A12-B10-C37; | A12-B10-C38; | A12-B10-C39; | A12-B10-C40; |
| A12-B10-C41; | A12-B10-C42; | A12-B10-C43; | A12-B10-C44; | A12-B10-C45; | A12-B10-C46; |
| A13-B10-C1; | A13-B10-C2; | A13-B10-C3; | A13-B10-C4; | A13-B10-C5; | A13-B10-C6; |
| A13-B10-C7; | A13-B10-C8; | A13-B10-C9; | A13-B10-C10; | A13-B10-C11; | A13-B10-C12; |
| A13-B10-C13; | A13-B10-C14; | A13-B10-C15; | A13-B10-C16; | A13-B10-C17; | A13-B10-C18; |
| A13-B10-C19; | A13-B10-C20; | A13-B10-C21; | A13-B10-C22; | A13-B10-C23; | A13-B10-C24; |
| A13-B10-C25; | A13-B10-C26; | A13-B10-C27; | A13-B10-C28; | A13-B10-C29; | A13-B10-C30; |
| A13-B10-C31; | A13-B10-C32; | A13-B10-C33; | A13-B10-C34; | A13-B10-C35; | A13-B10-C36; |
| A13-B10-C37; | A13-B10-C38; | A13-B10-C39; | A13-B10-C40; | A13-B10-C41; | A13-B10-C42; |
| A13-B10-C43; | A13-B10-C44; | A13-B10-C45; | A13-B10-C46; | A14-B10-C1; | A14-B10-C2; |
| A14-B10-C3; | A14-B10-C4; | A14-B10-C5; | A14-B10-C6; | A14-B10-C7; | A14-B10-C8; |
| A14-B10-C9; | A14-B10-C10; | A14-B10-C11; | A14-B10-C12; | A14-B10-C13; | A14-B10-C14; |
| A14-B10-C15; | A14-B10-C16; | A14-B10-C17; | A14-B10-C18; | A14-B10-C19; | A14-B10-C20; |
| A14-B10-C21; | A14-B10-C22; | A14-B10-C23; | A14-B10-C24; | A14-B10-C25; | A14-B10-C26; |
| A14-B10-C27; | A14-B10-C28; | A14-B10-C29; | A14-B10-C30; | A14-B10-C31; | A14-B10-C32; |
| A14-B10-C33; | A14-B10-C34; | A14-B10-C35; | A14-B10-C36; | A14-B10-C37; | A14-B10-C38; |
| A14-B10-C39; | A14-B10-C40; | A14-B10-C41; | A14-B10-C42; | A14-B10-C43; | A14-B10-C44; |
| A14-B10-C45; | A14-B10-C46; | A15-B10-C1; | A15-B10-C2; | A15-B10-C3; | A15-B10-C4; |
| A15-B10-C5; | A15-B10-C6; | A15-B10-C7; | A15-B10-C8; | A15-B10-C9; | A15-B10-C10; |
| A15-B10-C11; | A15-B10-C12; | A15-B10-C13; | A15-B10-C14; | A15-B10-C15; | A15-B10-C16; |
| A15-B10-C17; | A15-B10-C18; | A15-B10-C19; | A15-B10-C20; | A15-B10-C21; | A15-B10-C22; |
| A15-B10-C23; | A15-B10-C24; | A15-B10-C25; | A15-B10-C26; | A15-B10-C27; | A15-B10-C28; |
| A15-B10-C29; | A15-B10-C30; | A15-B10-C31; | A15-B10-C32; | A15-B10-C33; | A15-B10-C34; |
| A15-B10-C35; | A15-B10-C36; | A15-B10-C37; | A15-B10-C38; | A15-B10-C39; | A15-B10-C40; |
| A15-B10-C41; | A15-B10-C42; | A15-B10-C43; | A15-B10-C44; | A15-B10-C45; | A15-B10-C46; |
| A16-B10-C1; | A16-B10-C2; | A16-B10-C3; | A16-B10-C4; | A16-B10-C5; | A16-B10-C6; |
| A16-B10-C7; | A16-B10-C8; | A16-B10-C9; | A16-B10-C10; | A16-B10-C11; | A16-B10-C12; |
| A16-B10-C13; | A16-B10-C14; | A16-B10-C15; | A16-B10-C16; | A16-B10-C17; | A16-B10-C18; |
| A16-B10-C19; | A16-B10-C20; | A16-B10-C21; | A16-B10-C22; | A16-B10-C23; | A16-B10-C24; |
| A16-B10-C25; | A16-B10-C26; | A16-B10-C27; | A16-B10-C28; | A16-B10-C29; | A16-B10-C30; |
| A16-B10-C31; | A16-B10-C32; | A16-B10-C33; | A16-B10-C34; | A16-B10-C35; | A16-B10-C36; |
| A16-B10-C37; | A16-B10-C38; | A16-B10-C39; | A16-B10-C40; | A16-B10-C41; | A16-B10-C42; |
| A16-B10-C43; | A16-B10-C44; | A16-B10-C45; | A16-B10-C46; | A17-B10-C1; | A17-B10-C2; |
| A17-B10-C3; | A17-B10-C4; | A17-B10-C5; | A17-B10-C6; | A17-B10-C7; | A17-B10-C8; |
| A17-B10-C9; | A17-B10-C10; | A17-B10-C11; | A17-B10-C12; | A17-B10-C13; | A17-B10-C14; |
| A17-B10-C15; | A17-B10-C16; | A17-B10-C17; | A17-B10-C18; | A17-B10-C19; | A17-B10-C20; |
| A17-B10-C21; | A17-B10-C22; | A17-B10-C23; | A17-B10-C24; | A17-B10-C25; | A17-B10-C26; |
| A17-B10-C27; | A17-B10-C28; | A17-B10-C29; | A17-B10-C30; | A17-B10-C31; | A17-B10-C32; |
| A17-B10-C33; | A17-B10-C34; | A17-B10-C35; | A17-B10-C36; | A17-B10-C37; | A17-B10-C38; |
| A17-B10-C39; | A17-B10-C40; | A17-B10-C41; | A17-B10-C42; | A17-B10-C43; | A17-B10-C44; |
| A17-B10-C45; | A17-B10-C46; | A18-B10-C1; | A18-B10-C2; | A18-B10-C3; | A18-B10-C4; |
| A18-B10-C5; | A18-B10-C6; | A18-B10-C7; | A18-B10-C8; | A18-B10-C9; | A18-B10-C10; |
| A18-B10-C11; | A18-B10-C12; | A18-B10-C13; | A18-B10-C14; | A18-B10-C15; | A18-B10-C16; |
| A18-B10-C17; | A18-B10-C18; | A18-B10-C19; | A18-B10-C20; | A18-B10-C21; | A18-B10-C22; |
| A18-B10-C23; | A18-B10-C24; | A18-B10-C25; | A18-B10-C26; | A18-B10-C27; | A18-B10-C28; |
| A18-B10-C29; | A18-B10-C30; | A18-B10-C31; | A18-B10-C32; | A18-B10-C33; | A18-B10-C34; |
| A18-B10-C35; | A18-B10-C36; | A18-B10-C37; | A18-B10-C38; | A18-B10-C39; | A18-B10-C40; |
| A18-B10-C41; | A18-B10-C42; | A18-B10-C43; | A18-B10-C44; | A18-B10-C45; | A18-B10-C46; |
| A19-B10-C1; | A19-B10-C2; | A19-B10-C3; | A19-B10-C4; | A19-B10-C5; | A19-B10-C6; |
| A19-B10-C7; | A19-B10-C8; | A19-B10-C9; | A19-B10-C10; | A19-B10-C11; | A19-B10-C12; |
| A19-B10-C13; | A19-B10-C14; | A19-B10-C15; | A19-B10-C16; | A19-B10-C17; | A19-B10-C18; |
| A19-B10-C19; | A19-B10-C20; | A19-B10-C21; | A19-B10-C22; | A19-B10-C23; | A19-B10-C24; |
| A19-B10-C25; | A19-B10-C26; | A19-B10-C27; | A19-B10-C28; | A19-B10-C29; | A19-B10-C30; |
| A19-B10-C31; | A19-B10-C32; | A19-B10-C33; | A19-B10-C34; | A19-B10-C35; | A19-B10-C36; |
| A19-B10-C37; | A19-B10-C38; | A19-B10-C39; | A19-B10-C40; | A19-B10-C41; | A19-B10-C42; |
| A19-B10-C43; | A19-B10-C44; | A19-B10-C45; | A19-B10-C46; | A20-B10-C1; | A20-B10-C2; |
| A20-B10-C3; | A20-B10-C4; | A20-B10-C5; | A20-B10-C6; | A20-B10-C7; | A20-B10-C8; |
| A20-B10-C9; | A20-B10-C10; | A20-B10-C11; | A20-B10-C12; | A20-B10-C13; | A20-B10-C14; |
| A20-B10-C15; | A20-B10-C16; | A20-B10-C17; | A20-B10-C18; | A20-B10-C19; | A20-B10-C20; |
| A20-B10-C21; | A20-B10-C22; | A20-B10-C23; | A20-B10-C24; | A20-B10-C25; | A20-B10-C26; |
| A20-B10-C27; | A20-B10-C28; | A20-B10-C29; | A20-B10-C30; | A20-B10-C31; | A20-B10-C32; |
| A20-B10-C33; | A20-B10-C34; | A20-B10-C35; | A20-B10-C36; | A20-B10-C37; | A20-B10-C38; |
| A20-B10-C39; | A20-B10-C40; | A20-B10-C41; | A20-B10-C42; | A20-B10-C43; | A20-B10-C44; |
| A20-B10-C45; | A20-B10-C46; | A21-B10-C1; | A21-B10-C2; | A21-B10-C3; | A21-B10-C4; |
| A21-B10-C5; | A21-B10-C6; | A21-B10-C7; | A21-B10-C8; | A21-B10-C9; | A21-B10-C10; |
| A21-B10-C11; | A21-B10-C12; | A21-B10-C13; | A21-B10-C14; | A21-B10-C15; | A21-B10-C16; |
| A21-B10-C17; | A21-B10-C18; | A21-B10-C19; | A21-B10-C20; | A21-B10-C21; | A21-B10-C22; |
| A21-B10-C23; | A21-B10-C24; | A21-B10-C25; | A21-B10-C26; | A21-B10-C27; | A21-B10-C28; |
| A21-B10-C29; | A21-B10-C30; | A21-B10-C31; | A21-B10-C32; | A21-B10-C33; | A21-B10-C34; |
| A21-B10-C35; | A21-B10-C36; | A21-B10-C37; | A21-B10-C38; | A21-B10-C39; | A21-B10-C40; |
| A21-B10-C41; | A21-B10-C42; | A21-B10-C43; | A21-B10-C44; | A21-B10-C45; | A21-B10-C46; |
| A22-B10-C1; | A22-B10-C2; | A22-B10-C3; | A22-B10-C4; | A22-B10-C5; | A22-B10-C6; |

-continued

| | | | | | |
|---|---|---|---|---|---|
| A22-B10-C7; | A22-B10-C8; | A22-B10-C9; | A22-B10-C10; | A22-B10-C11; | A22-B10-C12; |
| A22-B10-C13; | A22-B10-C14; | A22-B10-C15; | A22-B10-C16; | A22-B10-C17; | A22-B10-C18; |
| A22-B10-C19; | A22-B10-C20; | A22-B10-C21; | A22-B10-C22; | A22-B10-C23; | A22-B10-C24; |
| A22-B10-C25; | A22-B10-C26; | A22-B10-C27; | A22-B10-C28; | A22-B10-C29; | A22-B10-C30; |
| A22-B10-C31; | A22-B10-C32; | A22-B10-C33; | A22-B10-C34; | A22-B10-C35; | A22-B10-C36; |
| A22-B10-C37; | A22-B10-C38; | A22-B10-C39; | A22-B10-C40; | A22-B10-C41; | A22-B10-C42; |
| A22-B10-C43; | A22-B10-C44; | A22-B10-C45; | A22-B10-C46; | A23-B10-C1; | A23-B10-C2; |
| A23-B10-C3; | A23-B10-C4; | A23-B10-C5; | A23-B10-C6; | A23-B10-C7; | A23-B10-C8; |
| A23-B10-C9; | A23-B10-C10; | A23-B10-C11; | A23-B10-C12; | A23-B10-C13; | A23-B10-C14; |
| A23-B10-C15; | A23-B10-C16; | A23-B10-C17; | A23-B10-C18; | A23-B10-C19; | A23-B10-C20; |
| A23-B10-C21; | A23-B10-C22; | A23-B10-C23; | A23-B10-C24; | A23-B10-C25; | A23-B10-C26; |
| A23-B10-C27; | A23-B10-C28; | A23-B10-C29; | A23-B10-C30; | A23-B10-C31; | A23-B10-C32; |
| A23-B10-C33; | A23-B10-C34; | A23-B10-C35; | A23-B10-C36; | A23-B10-C37; | A23-B10-C38; |
| A23-B10-C39; | A23-B10-C40; | A23-B10-C41; | A23-B10-C42; | A23-B10-C43; | A23-B10-C44; |
| A23-B10-C45; | A23-B10-C46; | A24-B10-C1; | A24-B10-C2; | A24-B10-C3; | A24-B10-C4; |
| A24-B10-C5; | A24-B10-C6; | A24-B10-C7; | A24-B10-C8; | A24-B10-C9; | A24-B10-C10; |
| A24-B10-C11; | A24-B10-C12; | A24-B10-C13; | A24-B10-C14; | A24-B10-C15; | A24-B10-C16; |
| A24-B10-C17; | A24-B10-C18; | A24-B10-C19; | A24-B10-C20; | A24-B10-C21; | A24-B10-C22; |
| A24-B10-C23; | A24-B10-C24; | A24-B10-C25; | A24-B10-C26; | A24-B10-C27; | A24-B10-C28; |
| A24-B10-C29; | A24-B10-C30; | A24-B10-C31; | A24-B10-C32; | A24-B10-C33; | A24-B10-C34; |
| A24-B10-C35; | A24-B10-C36; | A24-B10-C37; | A24-B10-C38; | A24-B10-C39; | A24-B10-C40; |
| A24-B10-C41; | A24-B10-C42; | A24-B10-C43; | A24-B10-C44; | A24-B10-C45; | A24-B10-C46; |
| A25-B10-C1; | A25-B10-C2; | A25-B10-C3; | A25-B10-C4; | A25-B10-C5; | A25-B10-C6; |
| A25-B10-C7; | A25-B10-C8; | A25-B10-C9; | A25-B10-C10; | A25-B10-C11; | A25-B10-C12; |
| A25-B10-C13; | A25-B10-C14; | A25-B10-C15; | A25-B10-C16; | A25-B10-C17; | A25-B10-C18; |
| A25-B10-C19; | A25-B10-C20; | A25-B10-C21; | A25-B10-C22; | A25-B10-C23; | A25-B10-C24; |
| A25-B10-C25; | A25-B10-C26; | A25-B10-C27; | A25-B10-C28; | A25-B10-C29; | A25-B10-C30; |
| A25-B10-C31; | A25-B10-C32; | A25-B10-C33; | A25-B10-C34; | A25-B10-C35; | A25-B10-C36; |
| A25-B10-C37; | A25-B10-C38; | A25-B10-C39; | A25-B10-C40; | A25-B10-C41; | A25-B10-C42; |
| A25-B10-C43; | A25-B10-C44; | A25-B10-C45; | A25-B10-C46; | A26-B10-C1; | A26-B10-C2; |
| A26-B10-C3; | A26-B10-C4; | A26-B10-C5; | A26-B10-C6; | A26-B10-C7; | A26-B10-C8; |
| A26-B10-C9; | A26-B10-C10; | A26-B10-C11; | A26-B10-C12; | A26-B10-C13; | A26-B10-C14; |
| A26-B10-C15; | A26-B10-C16; | A26-B10-C17; | A26-B10-C18; | A26-B10-C19; | A26-B10-C20; |
| A26-B10-C21; | A26-B10-C22; | A26-B10-C23; | A26-B10-C24; | A26-B10-C25; | A26-B10-C26; |
| A26-B10-C27; | A26-B10-C28; | A26-B10-C29; | A26-B10-C30; | A26-B10-C31; | A26-B10-C32; |
| A26-B10-C33; | A26-B10-C34; | A26-B10-C35; | A26-B10-C36; | A26-B10-C37; | A26-B10-C38; |
| A26-B10-C39; | A26-B10-C40; | A26-B10-C41; | A26-B10-C42; | A26-B10-C43; | A26-B10-C44; |
| A26-B10-C45; | A26-B10-C46; | A27-B10-C1; | A27-B10-C2; | A27-B10-C3; | A27-B10-C4; |
| A27-B10-C5; | A27-B10-C6; | A27-B10-C7; | A27-B10-C8; | A27-B10-C9; | A27-B10-C10; |
| A27-B10-C11; | A27-B10-C12; | A27-B10-C13; | A27-B10-C14; | A27-B10-C15; | A27-B10-C16; |
| A27-B10-C17; | A27-B10-C18; | A27-B10-C19; | A27-B10-C20; | A27-B10-C21; | A27-B10-C22; |
| A27-B10-C23; | A27-B10-C24; | A27-B10-C25; | A27-B10-C26; | A27-B10-C27; | A27-B10-C28; |
| A27-B10-C29; | A27-B10-C30; | A27-B10-C31; | A27-B10-C32; | A27-B10-C33; | A27-B10-C34; |
| A27-B10-C35; | A27-B10-C36; | A27-B10-C37; | A27-B10-C38; | A27-B10-C39; | A27-B10-C40; |
| A27-B10-C41; | A27-B10-C42; | A27-B10-C43; | A27-B10-C44; | A27-B10-C45; | A27-B10-C46; |
| A28-B10-C1; | A28-B10-C2; | A28-B10-C3; | A28-B10-C4; | A28-B10-C5; | A28-B10-C6; |
| A28-B10-C7; | A28-B10-C8; | A28-B10-C9; | A28-B10-C10; | A28-B10-C11; | A28-B10-C12; |
| A28-B10-C13; | A28-B10-C14; | A28-B10-C15; | A28-B10-C16; | A28-B10-C17; | A28-B10-C18; |
| A28-B10-C19; | A28-B10-C20; | A28-B10-C21; | A28-B10-C22; | A28-B10-C23; | A28-B10-C24; |
| A28-B10-C25; | A28-B10-C26; | A28-B10-C27; | A28-B10-C28; | A28-B10-C29; | A28-B10-C30; |
| A28-B10-C31; | A28-B10-C32; | A28-B10-C33; | A28-B10-C34; | A28-B10-C35; | A28-B10-C36; |
| A28-B10-C37; | A28-B10-C38; | A28-B10-C39; | A28-B10-C40; | A28-B10-C41; | A28-B10-C42; |
| A28-B10-C43; | A28-B10-C44; | A28-B10-C45; | A28-B10-C46; | A1-B11-C1; | A1-B11-C2; |
| A1-B11-C3; | A1-B11-C4; | A1-B11-C5; | A1-B11-C6; | A1-B11-C7; | A1-B11-C8; |
| A1-B11-C9; | A1-B11-C10; | A1-B11-C11; | A1-B11-C12; | A1-B11-C13; | A1-B11-C14; |
| A1-B11-C15; | A1-B11-C16; | A1-B11-C17; | A1-B11-C18; | A1-B11-C19; | A1-B11-C20; |
| A1-B11-C21; | A1-B11-C22; | A1-B11-C23; | A1-B11-C24; | A1-B11-C25; | A1-B11-C26; |
| A1-B11-C27; | A1-B11-C28; | A1-B11-C29; | A1-B11-C30; | A1-B11-C31; | A1-B11-C32; |
| A1-B11-C33; | A1-B11-C34; | A1-B11-C35; | A1-B11-C36; | A1-B11-C37; | A1-B11-C38; |
| A1-B11-C39; | A1-B11-C40; | A1-B11-C41; | A1-B11-C42; | A1-B11-C43; | A1-B11-C44; |
| A1-B11-C45; | A1-B11-C46; | A2-B11-C1; | A2-B11-C2; | A2-B11-C3; | A2-B11-C4; |
| A2-B11-C5; | A2-B11-C6; | A2-B11-C7; | A2-B11-C8; | A2-B11-C9; | A2-B11-C10; |
| A2-B11-C11; | A2-B11-C12; | A2-B11-C13; | A2-B11-C14; | A2-B11-C15; | A2-B11-C16; |
| A2-B11-C17; | A2-B11-C18; | A2-B11-C19; | A2-B11-C20; | A2-B11-C21; | A2-B11-C22; |
| A2-B11-C23; | A2-B11-C24; | A2-B11-C25; | A2-B11-C26; | A2-B11-C27; | A2-B11-C28; |
| A2-B11-C29; | A2-B11-C30; | A2-B11-C31; | A2-B11-C32; | A2-B11-C33; | A2-B11-C34; |
| A2-B11-C35; | A2-B11-C36; | A2-B11-C37; | A2-B11-C38; | A2-B11-C39; | A2-B11-C40; |
| A2-B11-C41; | A2-B11-C42; | A2-B11-C43; | A2-B11-C44; | A2-B11-C45; | A2-B11-C46; |
| A3-B11-C1; | A3-B11-C2; | A3-B11-C3; | A3-B11-C4; | A3-B11-C5; | A3-B11-C6; |
| A3-B11-C7; | A3-B11-C8; | A3-B11-C9; | A3-B11-C10; | A3-B11-C11; | A3-B11-C12; |
| A3-B11-C13; | A3-B11-C14; | A3-B11-C15; | A3-B11-C16; | A3-B11-C17; | A3-B11-C18; |
| A3-B11-C19; | A3-B11-C20; | A3-B11-C21; | A3-B11-C22; | A3-B11-C23; | A3-B11-C24; |
| A3-B11-C25; | A3-B11-C26; | A3-B11-C27; | A3-B11-C28; | A3-B11-C29; | A3-B11-C30; |
| A3-B11-C31; | A3-B11-C32; | A3-B11-C33; | A3-B11-C34; | A3-B11-C35; | A3-B11-C36; |
| A3-B11-C37; | A3-B11-C38; | A3-B11-C39; | A3-B11-C40; | A3-B11-C41; | A3-B11-C42; |
| A3-B11-C43; | A3-B11-C44; | A3-B11-C45; | A3-B11-C46; | A4-B11-C1; | A4-B11-C2; |
| A4-B11-C3; | A4-B11-C4; | A4-B11-C5; | A4-B11-C6; | A4-B11-C7; | A4-B11-C8; |
| A4-B11-C9; | A4-B11-C10; | A4-B11-C11; | A4-B11-C12; | A4-B11-C13; | A4-B11-C14; |
| A4-B11-C15; | A4-B11-C16; | A4-B11-C17; | A4-B11-C18; | A4-B11-C19; | A4-B11-C20; |

-continued

| | | | | | |
|---|---|---|---|---|---|
| A4-B11-C21; | A4-B11-C22; | A4-B11-C23; | A4-B11-C24; | A4-B11-C25; | A4-B11-C26; |
| A4-B11-C27; | A4-B11-C28; | A4-B11-C29; | A4-B11-C30; | A4-B11-C31; | A4-B11-C32; |
| A4-B11-C33; | A4-B11-C34; | A4-B11-C35; | A4-B11-C36; | A4-B11-C37; | A4-B11-C38; |
| A4-B11-C39; | A4-B11-C40; | A4-B11-C41; | A4-B11-C42; | A4-B11-C43; | A4-B11-C44; |
| A4-B11-C45; | A4-B11-C46; | A5-B11-C1; | A5-B11-C2; | A5-B11-C3; | A5-B11-C4; |
| A5-B11-C5; | A5-B11-C6; | A5-B11-C7; | A5-B11-C8; | A5-B11-C9; | A5-B11-C10; |
| A5-B11-C11; | A5-B11-C12; | A5-B11-C13; | A5-B11-C14; | A5-B11-C15; | A5-B11-C16; |
| A5-B11-C17; | A5-B11-C18; | A5-B11-C19; | A5-B11-C20; | A5-B11-C21; | A5-B11-C22; |
| A5-B11-C23; | A5-B11-C24; | A5-B11-C25; | A5-B11-C26; | A5-B11-C27; | A5-B11-C28; |
| A5-B11-C29; | A5-B11-C30; | A5-B11-C31; | A5-B11-C32; | A5-B11-C33; | A5-B11-C34; |
| A5-B11-C35; | A5-B11-C36; | A5-B11-C37; | A5-B11-C38; | A5-B11-C39; | A5-B11-C40; |
| A5-B11-C41; | A5-B11-C42; | A5-B11-C43; | A5-B11-C44; | A5-B11-C45; | A5-B11-C46; |
| A6-B11-C1; | A6-B11-C2; | A6-B11-C3; | A6-B11-C4; | A6-B11-C5; | A6-B11-C6; |
| A6-B11-C7; | A6-B11-C8; | A6-B11-C9; | A6-B11-C10; | A6-B11-C11; | A6-B11-C12; |
| A6-B11-C13; | A6-B11-C14; | A6-B11-C15; | A6-B11-C16; | A6-B11-C17; | A6-B11-C18; |
| A6-B11-C19; | A6-B11-C20; | A6-B11-C21; | A6-B11-C22; | A6-B11-C23; | A6-B11-C24; |
| A6-B11-C25; | A6-B11-C26; | A6-B11-C27; | A6-B11-C28; | A6-B11-C29; | A6-B11-C30; |
| A6-B11-C31; | A6-B11-C32; | A6-B11-C33; | A6-B11-C34; | A6-B11-C35; | A6-B11-C36; |
| A6-B11-C37; | A6-B11-C38; | A6-B11-C39; | A6-B11-C40; | A6-B11-C41; | A6-B11-C42; |
| A6-B11-C43; | A6-B11-C44; | A6-B11-C45; | A6-B11-C46; | A7-B11-C1; | A7-B11-C2; |
| A7-B11-C3; | A7-B11-C4; | A7-B11-C5; | A7-B11-C6; | A7-B11-C7; | A7-B11-C8; |
| A7-B11-C9; | A7-B11-C10; | A7-B11-C11; | A7-B11-C12; | A7-B11-C13; | A7-B11-C14; |
| A7-B11-C15; | A7-B11-C16; | A7-B11-C17; | A7-B11-C18; | A7-B11-C19; | A7-B11-C20; |
| A7-B11-C21; | A7-B11-C22; | A7-B11-C23; | A7-B11-C24; | A7-B11-C25; | A7-B11-C26; |
| A7-B11-C27; | A7-B11-C28; | A7-B11-C29; | A7-B11-C30; | A7-B11-C31; | A7-B11-C32; |
| A7-B11-C33; | A7-B11-C34; | A7-B11-C35; | A7-B11-C36; | A7-B11-C37; | A7-B11-C38; |
| A7-B11-C39; | A7-B11-C40; | A7-B11-C41; | A7-B11-C42; | A7-B11-C43; | A7-B11-C44; |
| A7-B11-C45; | A7-B11-C46; | A8-B11-C1; | A8-B11-C2; | A8-B11-C3; | A8-B11-C4; |
| A8-B11-C5; | A8-B11-C6; | A8-B11-C7; | A8-B11-C8; | A8-B11-C9; | A8-B11-C10; |
| A8-B11-C11; | A8-B11-C12; | A8-B11-C13; | A8-B11-C14; | A8-B11-C15; | A8-B11-C16; |
| A8-B11-C17; | A8-B11-C18; | A8-B11-C19; | A8-B11-C20; | A8-B11-C21; | A8-B11-C22; |
| A8-B11-C23; | A8-B11-C24; | A8-B11-C25; | A8-B11-C26; | A8-B11-C27; | A8-B11-C28; |
| A8-B11-C29; | A8-B11-C30; | A8-B11-C31; | A8-B11-C32; | A8-B11-C33; | A8-B11-C34; |
| A8-B11-C35; | A8-B11-C36; | A8-B11-C37; | A8-B11-C38; | A8-B11-C39; | A8-B11-C40; |
| A8-B11-C41; | A8-B11-C42; | A8-B11-C43; | A8-B11-C44; | A8-B11-C45; | A8-B11-C46; |
| A9-B11-C1; | A9-B11-C2; | A9-B11-C3; | A9-B11-C4; | A9-B11-C5; | A9-B11-C6; |
| A9-B11-C7; | A9-B11-C8; | A9-B11-C9; | A9-B11-C10; | A9-B11-C11; | A9-B11-C12; |
| A9-B11-C13; | A9-B11-C14; | A9-B11-C15; | A9-B11-C16; | A9-B11-C17; | A9-B11-C18; |
| A9-B11-C19; | A9-B11-C20; | A9-B11-C21; | A9-B11-C22; | A9-B11-C23; | A9-B11-C24; |
| A9-B11-C25; | A9-B11-C26; | A9-B11-C27; | A9-B11-C28; | A9-B11-C29; | A9-B11-C30; |
| A9-B11-C31; | A9-B11-C32; | A9-B11-C33; | A9-B11-C34; | A9-B11-C35; | A9-B11-C36; |
| A9-B11-C37; | A9-B11-C38; | A9-B11-C39; | A9-B11-C40; | A9-B11-C41; | A9-B11-C42; |
| A9-B11-C43; | A9-B11-C44; | A9-B11-C45; | A9-B11-C46; | A10-B11-C1; | A10-B11-C2; |
| A10-B11-C3; | A10-B11-C4; | A10-B11-C5; | A10-B11-C6; | A10-B11-C7; | A10-B11-C8; |
| A10-B11-C9; | A10-B11-C10; | A10-B11-C11; | A10-B11-C12; | A10-B11-C13; | A10-B11-C14; |
| A10-B11-C15; | A10-B11-C16; | A10-B11-C17; | A10-B11-C18; | A10-B11-C19; | A10-B11-C20; |
| A10-B11-C21; | A10-B11-C22; | A10-B11-C23; | A10-B11-C24; | A10-B11-C25; | A10-B11-C26; |
| A10-B11-C27; | A10-B11-C28; | A10-B11-C29; | A10-B11-C30; | A10-B11-C31; | A10-B11-C32; |
| A10-B11-C33; | A10-B11-C34; | A10-B11-C35; | A10-B11-C36; | A10-B11-C37; | A10-B11-C38; |
| A10-B11-C39; | A10-B11-C40; | A10-B11-C41; | A10-B11-C42; | A10-B11-C43; | A10-B11-C44; |
| A10-B11-C45; | A10-B11-C46; | A11-B11-C1; | A11-B11-C2; | A11-B11-C3; | A11-B11-C4; |
| A11-B11-C5; | A11-B11-C6; | A11-B11-C7; | A11-B11-C8; | A11-B11-C9; | A11-B11-C10; |
| A11-B11-C11; | A11-B11-C12; | A11-B11-C13; | A11-B11-C14; | A11-B11-C15; | A11-B11-C16; |
| A11-B11-C17; | A11-B11-C18; | A11-B11-C19; | A11-B11-C20; | A11-B11-C21; | A11-B11-C22; |
| A11-B11-C23; | A11-B11-C24; | A11-B11-C25; | A11-B11-C26; | A11-B11-C27; | A11-B11-C28; |
| A11-B11-C29; | A11-B11-C30; | A11-B11-C31; | A11-B11-C32; | A11-B11-C33; | A11-B11-C34; |
| A11-B11-C35; | A11-B11-C36; | A11-B11-C37; | A11-B11-C38; | A11-B11-C39; | A11-B11-C40; |
| A11-B11-C41; | A11-B11-C42; | A11-B11-C43; | A11-B11-C44; | A11-B11-C45; | A11-B11-C46; |
| A12-B11-C1; | A12-B11-C2; | A12-B11-C3; | A12-B11-C4; | A12-B11-C5; | A12-B11-C6; |
| A12-B11-C7; | A12-B11-C8; | A12-B11-C9; | A12-B11-C10; | A12-B11-C11; | A12-B11-C12; |
| A12-B11-C13; | A12-B11-C14; | A12-B11-C15; | A12-B11-C16; | A12-B11-C17; | A12-B11-C18; |
| A12-B11-C19; | A12-B11-C20; | A12-B11-C21; | A12-B11-C22; | A12-B11-C23; | A12-B11-C24; |
| A12-B11-C25; | A12-B11-C26; | A12-B11-C27; | A12-B11-C28; | A12-B11-C29; | A12-B11-C30; |
| A12-B11-C31; | A12-B11-C32; | A12-B11-C33; | A12-B11-C34; | A12-B11-C35; | A12-B11-C36; |
| A12-B11-C37; | A12-B11-C38; | A12-B11-C39; | A12-B11-C40; | A12-B11-C41; | A12-B11-C42; |
| A12-B11-C43; | A12-B11-C44; | A12-B11-C45; | A12-B11-C46; | A13-B11-C1; | A13-B11-C2; |
| A13-B11-C3; | A13-B11-C4; | A13-B11-C5; | A13-B11-C6; | A13-B11-C7; | A13-B11-C8; |
| A13-B11-C9; | A13-B11-C10; | A13-B11-C11; | A13-B11-C12; | A13-B11-C13; | A13-B11-C14; |
| A13-B11-C15; | A13-B11-C16; | A13-B11-C17; | A13-B11-C18; | A13-B11-C19; | A13-B11-C20; |
| A13-B11-C21; | A13-B11-C22; | A13-B11-C23; | A13-B11-C24; | A13-B11-C25; | A13-B11-C26; |
| A13-B11-C27; | A13-B11-C28; | A13-B11-C29; | A13-B11-C30; | A13-B11-C31; | A13-B11-C32; |
| A13-B11-C33; | A13-B11-C34; | A13-B11-C35; | A13-B11-C36; | A13-B11-C37; | A13-B11-C38; |
| A13-B11-C39; | A13-B11-C40; | A13-B11-C41; | A13-B11-C42; | A13-B11-C43; | A13-B11-C44; |
| A13-B11-C45; | A13-B11-C46; | A14-B11-C1; | A14-B11-C2; | A14-B11-C3; | A14-B11-C4; |
| A14-B11-C5; | A14-B11-C6; | A14-B11-C7; | A14-B11-C8; | A14-B11-C9; | A14-B11-C10; |
| A14-B11-C11; | A14-B11-C12; | A14-B11-C13; | A14-B11-C14; | A14-B11-C15; | A14-B11-C16; |
| A14-B11-C17; | A14-B11-C18; | A14-B11-C19; | A14-B11-C20; | A14-B11-C21; | A14-B11-C22; |
| A14-B11-C23; | A14-B11-C24; | A14-B11-C25; | A14-B11-C26; | A14-B11-C27; | A14-B11-C28; |
| A14-B11-C29; | A14-B11-C30; | A14-B11-C31; | A14-B11-C32; | A14-B11-C33; | A14-B11-C34; |

-continued

A14-B11-C35; A14-B11-C36; A14-B11-C37; A14-B11-C38; A14-B11-C39; A14-B11-C40;
A14-B11-C41; A14-B11-C42; A14-B11-C43; A14-B11-C44; A14-B11-C45; A14-B11-C46;
A15-B11-C1; A15-B11-C2; A15-B11-C3; A15-B11-C4; A15-B11-C5; A15-B11-C6;
A15-B11-C7; A15-B11-C8; A15-B11-C9; A15-B11-C10; A15-B11-C11; A15-B11-C12;
A15-B11-C13; A15-B11-C14; A15-B11-C15; A15-B11-C16; A15-B11-C17; A15-B11-C18;
A15-B11-C19; A15-B11-C20; A15-B11-C21; A15-B11-C22; A15-B11-C23; A15-B11-C24;
A15-B11-C25; A15-B11-C26; A15-B11-C27; A15-B11-C28; A15-B11-C29; A15-B11-C30;
A15-B11-C31; A15-B11-C32; A15-B11-C33; A15-B11-C34; A15-B11-C35; A15-B11-C36;
A15-B11-C37; A15-B11-C38; A15-B11-C39; A15-B11-C40; A15-B11-C41; A15-B11-C42;
A15-B11-C43; A15-B11-C44; A15-B11-C45; A15-B11-C46; A16-B11-C1; A16-B11-C2;
A16-B11-C3; A16-B11-C4; A16-B11-C5; A16-B11-C6; A16-B11-C7; A16-B11-C8;
A16-B11-C9; A16-B11-C10; A16-B11-C11; A16-B11-C12; A16-B11-C13; A16-B11-C14;
A16-B11-C15; A16-B11-C16; A16-B11-C17; A16-B11-C18; A16-B11-C19; A16-B11-C20;
A16-B11-C21; A16-B11-C22; A16-B11-C23; A16-B11-C24; A16-B11-C25; A16-B11-C26;
A16-B11-C27; A16-B11-C28; A16-B11-C29; A16-B11-C30; A16-B11-C31; A16-B11-C32;
A16-B11-C33; A16-B11-C34; A16-B11-C35; A16-B11-C36; A16-B11-C37; A16-B11-C38;
A16-B11-C39; A16-B11-C40; A16-B11-C41; A16-B11-C42; A16-B11-C43; A16-B11-C44;
A16-B11-C45; A16-B11-C46; A17-B11-C1; A17-B11-C2; A17-B11-C3; A17-B11-C4;
A17-B11-C5; A17-B11-C6; A17-B11-C7; A17-B11-C8; A17-B11-C9; A17-B11-C10;
A17-B11-C11; A17-B11-C12; A17-B11-C13; A17-B11-C14; A17-B11-C15; A17-B11-C16;
A17-B11-C17; A17-B11-C18; A17-B11-C19; A17-B11-C20; A17-B11-C21; A17-B11-C22;
A17-B11-C23; A17-B11-C24; A17-B11-C25; A17-B11-C26; A17-B11-C27; A17-B11-C28;
A17-B11-C29; A17-B11-C30; A17-B11-C31; A17-B11-C32; A17-B11-C33; A17-B11-C34;
A17-B11-C35; A17-B11-C36; A17-B11-C37; A17-B11-C38; A17-B11-C39; A17-B11-C40;
A17-B11-C41; A17-B11-C42; A17-B11-C43; A17-B11-C44; A17-B11-C45; A17-B11-C46;
A18-B11-C1; A18-B11-C2; A18-B11-C3; A18-B11-C4; A18-B11-C5; A18-B11-C6;
A18-B11-C7; A18-B11-C8; A18-B11-C9; A18-B11-C10; A18-B11-C11; A18-B11-C12;
A18-B11-C13; A18-B11-C14; A18-B11-C15; A18-B11-C16; A18-B11-C17; A18-B11-C18;
A18-B11-C19; A18-B11-C20; A18-B11-C21; A18-B11-C22; A18-B11-C23; A18-B11-C24;
A18-B11-C25; A18-B11-C26; A18-B11-C27; A18-B11-C28; A18-B11-C29; A18-B11-C30;
A18-B11-C31; A18-B11-C32; A18-B11-C33; A18-B11-C34; A18-B11-C35; A18-B11-C36;
A18-B11-C37; A18-B11-C38; A18-B11-C39; A18-B11-C40; A18-B11-C41; A18-B11-C42;
A18-B11-C43; A18-B11-C44; A18-B11-C45; A18-B11-C46; A19-B11-C1; A19-B11-C2;
A19-B11-C3; A19-B11-C4; A19-B11-C5; A19-B11-C6; A19-B11-C7; A19-B11-C8;
A19-B11-C9; A19-B11-C10; A19-B11-C11; A19-B11-C12; A19-B11-C13; A19-B11-C14;
A19-B11-C15; A19-B11-C16; A19-B11-C17; A19-B11-C18; A19-B11-C19; A19-B11-C20;
A19-B11-C21; A19-B11-C22; A19-B11-C23; A19-B11-C24; A19-B11-C25; A19-B11-C26;
A19-B11-C27; A19-B11-C28; A19-B11-C29; A19-B11-C30; A19-B11-C31; A19-B11-C32;
A19-B11-C33; A19-B11-C34; A19-B11-C35; A19-B11-C36; A19-B11-C37; A19-B11-C38;
A19-B11-C39; A19-B11-C40; A19-B11-C41; A19-B11-C42; A19-B11-C43; A19-B11-C44;
A19-B11-C45; A19-B11-C46; A20-B11-C1; A20-B11-C2; A20-B11-C3; A20-B11-C4;
A20-B11-C5; A20-B11-C6; A20-B11-C7; A20-B11-C8; A20-B11-C9; A20-B11-C10;
A20-B11-C11; A20-B11-C12; A20-B11-C13; A20-B11-C14; A20-B11-C15; A20-B11-C16;
A20-B11-C17; A20-B11-C18; A20-B11-C19; A20-B11-C20; A20-B11-C21; A20-B11-C22;
A20-B11-C23; A20-B11-C24; A20-B11-C25; A20-B11-C26; A20-B11-C27; A20-B11-C28;
A20-B11-C29; A20-B11-C30; A20-B11-C31; A20-B11-C32; A20-B11-C33; A20-B11-C34;
A20-B11-C35; A20-B11-C36; A20-B11-C37; A20-B11-C38; A20-B11-C39; A20-B11-C40;
A20-B11-C41; A20-B11-C42; A20-B11-C43; A20-B11-C44; A20-B11-C45; A20-B11-C46;
A21-B11-C1; A21-B11-C2; A21-B11-C3; A21-B11-C4; A21-B11-C5; A21-B11-C6;
A21-B11-C7; A21-B11-C8; A21-B11-C9; A21-B11-C10; A21-B11-C11; A21-B11-C12;
A21-B11-C13; A21-B11-C14; A21-B11-C15; A21-B11-C16; A21-B11-C17; A21-B11-C18;
A21-B11-C19; A21-B11-C20; A21-B11-C21; A21-B11-C22; A21-B11-C23; A21-B11-C24;
A21-B11-C25; A21-B11-C26; A21-B11-C27; A21-B11-C28; A21-B11-C29; A21-B11-C30;
A21-B11-C31; A21-B11-C32; A21-B11-C33; A21-B11-C34; A21-B11-C35; A21-B11-C36;
A21-B11-C37; A21-B11-C38; A21-B11-C39; A21-B11-C40; A21-B11-C41; A21-B11-C42;
A21-B11-C43; A21-B11-C44; A21-B11-C45; A21-B11-C46; A22-B11-C1; A22-B11-C2;
A22-B11-C3; A22-B11-C4; A22-B11-C5; A22-B11-C6; A22-B11-C7; A22-B11-C8;
A22-B11-C9; A22-B11-C10; A22-B11-C11; A22-B11-C12; A22-B11-C13; A22-B11-C14;
A22-B11-C15; A22-B11-C16; A22-B11-C17; A22-B11-C18; A22-B11-C19; A22-B11-C20;
A22-B11-C21; A22-B11-C22; A22-B11-C23; A22-B11-C24; A22-B11-C25; A22-B11-C26;
A22-B11-C27; A22-B11-C28; A22-B11-C29; A22-B11-C30; A22-B11-C31; A22-B11-C32;
A22-B11-C33; A22-B11-C34; A22-B11-C35; A22-B11-C36; A22-B11-C37; A22-B11-C38;
A22-B11-C39; A22-B11-C40; A22-B11-C41; A22-B11-C42; A22-B11-C43; A22-B11-C44;
A22-B11-C45; A22-B11-C46; A23-B11-C1; A23-B11-C2; A23-B11-C3; A23-B11-C4;
A23-B11-C5; A23-B11-C6; A23-B11-C7; A23-B11-C8; A23-B11-C9; A23-B11-C10;
A23-B11-C11; A23-B11-C12; A23-B11-C13; A23-B11-C14; A23-B11-C15; A23-B11-C16;
A23-B11-C17; A23-B11-C18; A23-B11-C19; A23-B11-C20; A23-B11-C21; A23-B11-C22;
A23-B11-C23; A23-B11-C24; A23-B11-C25; A23-B11-C26; A23-B11-C27; A23-B11-C28;
A23-B11-C29; A23-B11-C30; A23-B11-C31; A23-B11-C32; A23-B11-C33; A23-B11-C34;
A23-B11-C35; A23-B11-C36; A23-B11-C37; A23-B11-C38; A23-B11-C39; A23-B11-C40;
A23-B11-C41; A23-B11-C42; A23-B11-C43; A23-B11-C44; A23-B11-C45; A23-B11-C46;
A24-B11-C1; A24-B11-C2; A24-B11-C3; A24-B11-C4; A24-B11-C5; A24-B11-C6;
A24-B11-C7; A24-B11-C8; A24-B11-C9; A24-B11-C10; A24-B11-C11; A24-B11-C12;
A24-B11-C13; A24-B11-C14; A24-B11-C15; A24-B11-C16; A24-B11-C17; A24-B11-C18;
A24-B11-C19; A24-B11-C20; A24-B11-C21; A24-B11-C22; A24-B11-C23; A24-B11-C24;
A24-B11-C25; A24-B11-C26; A24-B11-C27; A24-B11-C28; A24-B11-C29; A24-B11-C30;
A24-B11-C31; A24-B11-C32; A24-B11-C33; A24-B11-C34; A24-B11-C35; A24-B11-C36;
A24-B11-C37; A24-B11-C38; A24-B11-C39; A24-B11-C40; A24-B11-C41; A24-B11-C42;
A24-B11-C43; A24-B11-C44; A24-B11-C45; A24-B11-C46; A25-B11-C1; A25-B11-C2;

-continued

A25-B11-C3; A25-B11-C4; A25-B11-C5; A25-B11-C6; A25-B11-C7; A25-B11-C8;
A25-B11-C9; A25-B11-C10; A25-B11-C11; A25-B11-C12; A25-B11-C13; A25-B11-C14;
A25-B11-C15; A25-B11-C16; A25-B11-C17; A25-B11-C18; A25-B11-C19; A25-B11-C20;
A25-B11-C21; A25-B11-C22; A25-B11-C23; A25-B11-C24; A25-B11-C25; A25-B11-C26;
A25-B11-C27; A25-B11-C28; A25-B11-C29; A25-B11-C30; A25-B11-C31; A25-B11-C32;
A25-B11-C33; A25-B11-C34; A25-B11-C35; A25-B11-C36; A25-B11-C37; A25-B11-C38;
A25-B11-C39; A25-B11-C40; A25-B11-C41; A25-B11-C42; A25-B11-C43; A25-B11-C44;
A25-B11-C45; A25-B11-C46; A26-B11-C1; A26-B11-C2; A26-B11-C3; A26-B11-C4;
A26-B11-C5; A26-B11-C6; A26-B11-C7; A26-B11-C8; A26-B11-C9; A26-B11-C10;
A26-B11-C11; A26-B11-C12; A26-B11-C13; A26-B11-C14; A26-B11-C15; A26-B11-C16;
A26-B11-C17; A26-B11-C18; A26-B11-C19; A26-B11-C20; A26-B11-C21; A26-B11-C22;
A26-B11-C23; A26-B11-C24; A26-B11-C25; A26-B11-C26; A26-B11-C27; A26-B11-C28;
A26-B11-C29; A26-B11-C30; A26-B11-C31; A26-B11-C32; A26-B11-C33; A26-B11-C34;
A26-B11-C35; A26-B11-C36; A26-B11-C37; A26-B11-C38; A26-B11-C39; A26-B11-C40;
A26-B11-C41; A26-B11-C42; A26-B11-C43; A26-B11-C44; A26-B11-C45; A26-B11-C46;
A27-B11-C1; A27-B11-C2; A27-B11-C3; A27-B11-C4; A27-B11-C5; A27-B11-C6;
A27-B11-C7; A27-B11-C8; A27-B11-C9; A27-B11-C10; A27-B11-C11; A27-B11-C12;
A27-B11-C13; A27-B11-C14; A27-B11-C15; A27-B11-C16; A27-B11-C17; A27-B11-C18;
A27-B11-C19; A27-B11-C20; A27-B11-C21; A27-B11-C22; A27-B11-C23; A27-B11-C24;
A27-B11-C25; A27-B11-C26; A27-B11-C27; A27-B11-C28; A27-B11-C29; A27-B11-C30;
A27-B11-C31; A27-B11-C32; A27-B11-C33; A27-B11-C34; A27-B11-C35; A27-B11-C36;
A27-B11-C37; A27-B11-C38; A27-B11-C39; A27-B11-C40; A27-B11-C41; A27-B11-C42;
A27-B11-C43; A27-B11-C44; A27-B11-C45; A27-B11-C46; A28-B11-C1; A28-B11-C2;
A28-B11-C3; A28-B11-C4; A28-B11-C5; A28-B11-C6; A28-B11-C7; A28-B11-C8;
A28-B11-C9; A28-B11-C10; A28-B11-C11; A28-B11-C12; A28-B11-C13; A28-B11-C14;
A28-B11-C15; A28-B11-C16; A28-B11-C17; A28-B11-C18; A28-B11-C19; A28-B11-C20;
A28-B11-C21; A28-B11-C22; A28-B11-C23; A28-B11-C24; A28-B11-C25; A28-B11-C26;
A28-B11-C27; A28-B11-C28; A28-B11-C29; A28-B11-C30; A28-B11-C31; A28-B11-C32;
A28-B11-C33; A28-B11-C34; A28-B11-C35; A28-B11-C36; A28-B11-C37; A28-B11-C38;
A28-B11-C39; A28-B11-C40; A28-B11-C41; A28-B11-C42; A28-B11-C43; A28-B11-C44;
A28-B11-C45; A28-B11-C46; A1-B12-C1; A1-B12-C2; A1-B12-C3; A1-B12-C4;
A1-B12-C5; A1-B12-C6; A1-B12-C7; A1-B12-C8; A1-B12-C9; A1-B12-C10;
A1-B12-C11; A1-B12-C12; A1-B12-C13; A1-B12-C14; A1-B12-C15; A1-B12-C16;
A1-B12-C17; A1-B12-C18; A1-B12-C19; A1-B12-C20; A1-B12-C21; A1-B12-C22;
A1-B12-C23; A1-B12-C24; A1-B12-C25; A1-B12-C26; A1-B12-C27; A1-B12-C28;
A1-B12-C29; A1-B12-C30; A1-B12-C31; A1-B12-C32; A1-B12-C33; A1-B12-C34;
A1-B12-C35; A1-B12-C36; A1-B12-C37; A1-B12-C38; A1-B12-C39; A1-B12-C40;
A1-B12-C41; A1-B12-C42; A1-B12-C43; A1-B12-C44; A1-B12-C45; A1-B12-C46;
A2-B12-C1; A2-B12-C2; A2-B12-C3; A2-B12-C4; A2-B12-C5; A2-B12-C6;
A2-B12-C7; A2-B12-C8; A2-B12-C9; A2-B12-C10; A2-B12-C11; A2-B12-C12;
A2-B12-C13; A2-B12-C14; A2-B12-C15; A2-B12-C16; A2-B12-C17; A2-B12-C18;
A2-B12-C19; A2-B12-C20; A2-B12-C21; A2-B12-C22; A2-B12-C23; A2-B12-C24;
A2-B12-C25; A2-B12-C26; A2-B12-C27; A2-B12-C28; A2-B12-C29; A2-B12-C30;
A2-B12-C31; A2-B12-C32; A2-B12-C33; A2-B12-C34; A2-B12-C35; A2-B12-C36;
A2-B12-C37; A2-B12-C38; A2-B12-C39; A2-B12-C40; A2-B12-C41; A2-B12-C42;
A2-B12-C43; A2-B12-C44; A2-B12-C45; A2-B12-C46; A3-B12-C1; A3-B12-C2;
A3-B12-C3; A3-B12-C4; A3-B12-C5; A3-B12-C6; A3-B12-C7; A3-B12-C8;
A3-B12-C9; A3-B12-C10; A3-B12-C11; A3-B12-C12; A3-B12-C13; A3-B12-C14;
A3-B12-C15; A3-B12-C16; A3-B12-C17; A3-B12-C18; A3-B12-C19; A3-B12-C20;
A3-B12-C21; A3-B12-C22; A3-B12-C23; A3-B12-C24; A3-B12-C25; A3-B12-C26;
A3-B12-C27; A3-B12-C28; A3-B12-C29; A3-B12-C30; A3-B12-C31; A3-B12-C32;
A3-B12-C33; A3-B12-C34; A3-B12-C35; A3-B12-C36; A3-B12-C37; A3-B12-C38;
A3-B12-C39; A3-B12-C40; A3-B12-C41; A3-B12-C42; A3-B12-C43; A3-B12-C44;
A3-B12-C45; A3-B12-C46; A4-B12-C1; A4-B12-C2; A4-B12-C3; A4-B12-C4;
A4-B12-C5; A4-B12-C6; A4-B12-C7; A4-B12-C8; A4-B12-C9; A4-B12-C10;
A4-B12-C11; A4-B12-C12; A4-B12-C13; A4-B12-C14; A4-B12-C15; A4-B12-C16;
A4-B12-C17; A4-B12-C18; A4-B12-C19; A4-B12-C20; A4-B12-C21; A4-B12-C22;
A4-B12-C23; A4-B12-C24; A4-B12-C25; A4-B12-C26; A4-B12-C27; A4-B12-C28;
A4-B12-C29; A4-B12-C30; A4-B12-C31; A4-B12-C32; A4-B12-C33; A4-B12-C34;
A4-B12-C35; A4-B12-C36; A4-B12-C37; A4-B12-C38; A4-B12-C39; A4-B12-C40;
A4-B12-C41; A4-B12-C42; A4-B12-C43; A4-B12-C44; A4-B12-C45; A4-B12-C46;
A5-B12-C1; A5-B12-C2; A5-B12-C3; A5-B12-C4; A5-B12-C5; A5-B12-C6;
A5-B12-C7; A5-B12-C8; A5-B12-C9; A5-B12-C10; A5-B12-C11; A5-B12-C12;
A5-B12-C13; A5-B12-C14; A5-B12-C15; A5-B12-C16; A5-B12-C17; A5-B12-C18;
A5-B12-C19; A5-B12-C20; A5-B12-C21; A5-B12-C22; A5-B12-C23; A5-B12-C24;
A5-B12-C25; A5-B12-C26; A5-B12-C27; A5-B12-C28; A5-B12-C29; A5-B12-C30;
A5-B12-C31; A5-B12-C32; A5-B12-C33; A5-B12-C34; A5-B12-C35; A5-B12-C36;
A5-B12-C37; A5-B12-C38; A5-B12-C39; A5-B12-C40; A5-B12-C41; A5-B12-C42;
A5-B12-C43; A5-B12-C44; A5-B12-C45; A5-B12-C46; A6-B12-C1; A6-B12-C2;
A6-B12-C3; A6-B12-C4; A6-B12-C5; A6-B12-C6; A6-B12-C7; A6-B12-C8;
A6-B12-C9; A6-B12-C10; A6-B12-C11; A6-B12-C12; A6-B12-C13; A6-B12-C14;
A6-B12-C15; A6-B12-C16; A6-B12-C17; A6-B12-C18; A6-B12-C19; A6-B12-C20;
A6-B12-C21; A6-B12-C22; A6-B12-C23; A6-B12-C24; A6-B12-C25; A6-B12-C26;
A6-B12-C27; A6-B12-C28; A6-B12-C29; A6-B12-C30; A6-B12-C31; A6-B12-C32;
A6-B12-C33; A6-B12-C34; A6-B12-C35; A6-B12-C36; A6-B12-C37; A6-B12-C38;
A6-B12-C39; A6-B12-C40; A6-B12-C41; A6-B12-C42; A6-B12-C43; A6-B12-C44;
A6-B12-C45; A6-B12-C46; A7-B12-C1; A7-B12-C2; A7-B12-C3; A7-B12-C4;
A7-B12-C5; A7-B12-C6; A7-B12-C7; A7-B12-C8; A7-B12-C9; A7-B12-C10;
A7-B12-C11; A7-B12-C12; A7-B12-C13; A7-B12-C14; A7-B12-C15; A7-B12-C16;

-continued

| | | | | | |
|---|---|---|---|---|---|
| A7-B12-C17; | A7-B12-C18; | A7-B12-C19; | A7-B12-C20; | A7-B12-C21; | A7-B12-C22; |
| A7-B12-C23; | A7-B12-C24; | A7-B12-C25; | A7-B12-C26; | A7-B12-C27; | A7-B12-C28; |
| A7-B12-C29; | A7-B12-C30; | A7-B12-C31; | A7-B12-C32; | A7-B12-C33; | A7-B12-C34; |
| A7-B12-C35; | A7-B12-C36; | A7-B12-C37; | A7-B12-C38; | A7-B12-C39; | A7-B12-C40; |
| A7-B12-C41; | A7-B12-C42; | A7-B12-C43; | A7-B12-C44; | A7-B12-C45; | A7-B12-C46; |
| A8-B12-C1; | A8-B12-C2; | A8-B12-C3; | A8-B12-C4; | A8-B12-C5; | A8-B12-C6; |
| A8-B12-C7; | A8-B12-C8; | A8-B12-C9; | A8-B12-C10; | A8-B12-C11; | A8-B12-C12; |
| A8-B12-C13; | A8-B12-C14; | A8-B12-C15; | A8-B12-C16; | A8-B12-C17; | A8-B12-C18; |
| A8-B12-C19; | A8-B12-C20; | A8-B12-C21; | A8-B12-C22; | A8-B12-C23; | A8-B12-C24; |
| A8-B12-C25; | A8-B12-C26; | A8-B12-C27; | A8-B12-C28; | A8-B12-C29; | A8-B12-C30; |
| A8-B12-C31; | A8-B12-C32; | A8-B12-C33; | A8-B12-C34; | A8-B12-C35; | A8-B12-C36; |
| A8-B12-C37; | A8-B12-C38; | A8-B12-C39; | A8-B12-C40; | A8-B12-C41; | A8-B12-C42; |
| A8-B12-C43; | A8-B12-C44; | A8-B12-C45; | A8-B12-C46; | A9-B12-C1; | A9-B12-C2; |
| A9-B12-C3; | A9-B12-C4; | A9-B12-C5; | A9-B12-C6; | A9-B12-C7; | A9-B12-C8; |
| A9-B12-C9; | A9-B12-C10; | A9-B12-C11; | A9-B12-C12; | A9-B12-C13; | A9-B12-C14; |
| A9-B12-C15; | A9-B12-C16; | A9-B12-C17; | A9-B12-C18; | A9-B12-C19; | A9-B12-C20; |
| A9-B12-C21; | A9-B12-C22; | A9-B12-C23; | A9-B12-C24; | A9-B12-C25; | A9-B12-C26; |
| A9-B12-C27; | A9-B12-C28; | A9-B12-C29; | A9-B12-C30; | A9-B12-C31; | A9-B12-C32; |
| A9-B12-C33; | A9-B12-C34; | A9-B12-C35; | A9-B12-C36; | A9-B12-C37; | A9-B12-C38; |
| A9-B12-C39; | A9-B12-C40; | A9-B12-C41; | A9-B12-C42; | A9-B12-C43; | A9-B12-C44; |
| A9-B12-C45; | A9-B12-C46; | A10-B12-C1; | A10-B12-C2; | A10-B12-C3; | A10-B12-C4; |
| A10-B12-C5; | A10-B12-C6; | A10-B12-C7; | A10-B12-C8; | A10-B12-C9; | A10-B12-C10; |
| A10-B12-C11; | A10-B12-C12; | A10-B12-C13; | A10-B12-C14; | A10-B12-C15; | A10-B12-C16; |
| A10-B12-C17; | A10-B12-C18; | A10-B12-C19; | A10-B12-C20; | A10-B12-C21; | A10-B12-C22; |
| A10-B12-C23; | A10-B12-C24; | A10-B12-C25; | A10-B12-C26; | A10-B12-C27; | A10-B12-C28; |
| A10-B12-C29; | A10-B12-C30; | A10-B12-C31; | A10-B12-C32; | A10-B12-C33; | A10-B12-C34; |
| A10-B12-C35; | A10-B12-C36; | A10-B12-C37; | A10-B12-C38; | A10-B12-C39; | A10-B12-C40; |
| A10-B12-C41; | A10-B12-C42; | A10-B12-C43; | A10-B12-C44; | A10-B12-C45; | A10-B12-C46; |
| A11-B12-C1; | A11-B12-C2; | A11-B12-C3; | A11-B12-C4; | A11-B12-C5; | A11-B12-C6; |
| A11-B12-C7; | A11-B12-C8; | A11-B12-C9; | A11-B12-C10; | A11-B12-C11; | A11-B12-C12; |
| A11-B12-C13; | A11-B12-C14; | A11-B12-C15; | A11-B12-C16; | A11-B12-C17; | A11-B12-C18; |
| A11-B12-C19; | A11-B12-C20; | A11-B12-C21; | A11-B12-C22; | A11-B12-C23; | A11-B12-C24; |
| A11-B12-C25; | A11-B12-C26; | A11-B12-C27; | A11-B12-C28; | A11-B12-C29; | A11-B12-C30; |
| A11-B12-C31; | A11-B12-C32; | A11-B12-C33; | A11-B12-C34; | A11-B12-C35; | A11-B12-C36; |
| A11-B12-C37; | A11-B12-C38; | A11-B12-C39; | A11-B12-C40; | A11-B12-C41; | A11-B12-C42; |
| A11-B12-C43; | A11-B12-C44; | A11-B12-C45; | A11-B12-C46; | A12-B12-C1; | A12-B12-C2; |
| A12-B12-C3; | A12-B12-C4; | A12-B12-C5; | A12-B12-C6; | A12-B12-C7; | A12-B12-C8; |
| A12-B12-C9; | A12-B12-C10; | A12-B12-C11; | A12-B12-C12; | A12-B12-C13; | A12-B12-C14; |
| A12-B12-C15; | A12-B12-C16; | A12-B12-C17; | A12-B12-C18; | A12-B12-C19; | A12-B12-C20; |
| A12-B12-C21; | A12-B12-C22; | A12-B12-C23; | A12-B12-C24; | A12-B12-C25; | A12-B12-C26; |
| A12-B12-C27; | A12-B12-C28; | A12-B12-C29; | A12-B12-C30; | A12-B12-C31; | A12-B12-C32; |
| A12-B12-C33; | A12-B12-C34; | A12-B12-C35; | A12-B12-C36; | A12-B12-C37; | A12-B12-C38; |
| A12-B12-C39; | A12-B12-C40; | A12-B12-C41; | A12-B12-C42; | A12-B12-C43; | A12-B12-C44; |
| A12-B12-C45; | A12-B12-C46; | A13-B12-C1; | A13-B12-C2; | A13-B12-C3; | A13-B12-C4; |
| A13-B12-C5; | A13-B12-C6; | A13-B12-C7; | A13-B12-C8; | A13-B12-C9; | A13-B12-C10; |
| A13-B12-C11; | A13-B12-C12; | A13-B12-C13; | A13-B12-C14; | A13-B12-C15; | A13-B12-C16; |
| A13-B12-C17; | A13-B12-C18; | A13-B12-C19; | A13-B12-C20; | A13-B12-C21; | A13-B12-C22; |
| A13-B12-C23; | A13-B12-C24; | A13-B12-C25; | A13-B12-C26; | A13-B12-C27; | A13-B12-C28; |
| A13-B12-C29; | A13-B12-C30; | A13-B12-C31; | A13-B12-C32; | A13-B12-C33; | A13-B12-C34; |
| A13-B12-C35; | A13-B12-C36; | A13-B12-C37; | A13-B12-C38; | A13-B12-C39; | A13-B12-C40; |
| A13-B12-C41; | A13-B12-C42; | A13-B12-C43; | A13-B12-C44; | A13-B12-C45; | A13-B12-C46; |
| A14-B12-C1; | A14-B12-C2; | A14-B12-C3; | A14-B12-C4; | A14-B12-C5; | A14-B12-C6; |
| A14-B12-C7; | A14-B12-C8; | A14-B12-C9; | A14-B12-C10; | A14-B12-C11; | A14-B12-C12; |
| A14-B12-C13; | A14-B12-C14; | A14-B12-C15; | A14-B12-C16; | A14-B12-C17; | A14-B12-C18; |
| A14-B12-C19; | A14-B12-C20; | A14-B12-C21; | A14-B12-C22; | A14-B12-C23; | A14-B12-C24; |
| A14-B12-C25; | A14-B12-C26; | A14-B12-C27; | A14-B12-C28; | A14-B12-C29; | A14-B12-C30; |
| A14-B12-C31; | A14-B12-C32; | A14-B12-C33; | A14-B12-C34; | A14-B12-C35; | A14-B12-C36; |
| A14-B12-C37; | A14-B12-C38; | A14-B12-C39; | A14-B12-C40; | A14-B12-C41; | A14-B12-C42; |
| A14-B12-C43; | A14-B12-C44; | A14-B12-C45; | A14-B12-C46; | A15-B12-C1; | A15-B12-C2; |
| A15-B12-C3; | A15-B12-C4; | A15-B12-C5; | A15-B12-C6; | A15-B12-C7; | A15-B12-C8; |
| A15-B12-C9; | A15-B12-C10; | A15-B12-C11; | A15-B12-C12; | A15-B12-C13; | A15-B12-C14; |
| A15-B12-C15; | A15-B12-C16; | A15-B12-C17; | A15-B12-C18; | A15-B12-C19; | A15-B12-C20; |
| A15-B12-C21; | A15-B12-C22; | A15-B12-C23; | A15-B12-C24; | A15-B12-C25; | A15-B12-C26; |
| A15-B12-C27; | A15-B12-C28; | A15-B12-C29; | A15-B12-C30; | A15-B12-C31; | A15-B12-C32; |
| A15-B12-C33; | A15-B12-C34; | A15-B12-C35; | A15-B12-C36; | A15-B12-C37; | A15-B12-C38; |
| A15-B12-C39; | A15-B12-C40; | A15-B12-C41; | A15-B12-C42; | A15-B12-C43; | A15-B12-C44; |
| A15-B12-C45; | A15-B12-C46; | A16-B12-C1; | A16-B12-C2; | A16-B12-C3; | A16-B12-C4; |
| A16-B12-C5; | A16-B12-C6; | A16-B12-C7; | A16-B12-C8; | A16-B12-C9; | A16-B12-C10; |
| A16-B12-C11; | A16-B12-C12; | A16-B12-C13; | A16-B12-C14; | A16-B12-C15; | A16-B12-C16; |
| A16-B12-C17; | A16-B12-C18; | A16-B12-C19; | A16-B12-C20; | A16-B12-C21; | A16-B12-C22; |
| A16-B12-C23; | A16-B12-C24; | A16-B12-C25; | A16-B12-C26; | A16-B12-C27; | A16-B12-C28; |
| A16-B12-C29; | A16-B12-C30; | A16-B12-C31; | A16-B12-C32; | A16-B12-C33; | A16-B12-C34; |
| A16-B12-C35; | A16-B12-C36; | A16-B12-C37; | A16-B12-C38; | A16-B12-C39; | A16-B12-C40; |
| A16-B12-C41; | A16-B12-C42; | A16-B12-C43; | A16-B12-C44; | A16-B12-C45; | A16-B12-C46; |
| A17-B12-C1; | A17-B12-C2; | A17-B12-C3; | A17-B12-C4; | A17-B12-C5; | A17-B12-C6; |
| A17-B12-C7; | A17-B12-C8; | A17-B12-C9; | A17-B12-C10; | A17-B12-C11; | A17-B12-C12; |
| A17-B12-C13; | A17-B12-C14; | A17-B12-C15; | A17-B12-C16; | A17-B12-C17; | A17-B12-C18; |
| A17-B12-C19; | A17-B12-C20; | A17-B12-C21; | A17-B12-C22; | A17-B12-C23; | A17-B12-C24; |
| A17-B12-C25; | A17-B12-C26; | A17-B12-C27; | A17-B12-C28; | A17-B12-C29; | A17-B12-C30; |

-continued

A17-B12-C31; A17-B12-C32; A17-B12-C33; A17-B12-C34; A17-B12-C35; A17-B12-C36;
A17-B12-C37; A17-B12-C38; A17-B12-C39; A17-B12-C40; A17-B12-C41; A17-B12-C42;
A17-B12-C43; A17-B12-C44; A17-B12-C45; A17-B12-C46; A18-B12-C1; A18-B12-C2;
A18-B12-C3; A18-B12-C4; A18-B12-C5; A18-B12-C6; A18-B12-C7; A18-B12-C8;
A18-B12-C9; A18-B12-C10; A18-B12-C11; A18-B12-C12; A18-B12-C13; A18-B12-C14;
A18-B12-C15; A18-B12-C16; A18-B12-C17; A18-B12-C18; A18-B12-C19; A18-B12-C20;
A18-B12-C21; A18-B12-C22; A18-B12-C23; A18-B12-C24; A18-B12-C25; A18-B12-C26;
A18-B12-C27; A18-B12-C28; A18-B12-C29; A18-B12-C30; A18-B12-C31; A18-B12-C32;
A18-B12-C33; A18-B12-C34; A18-B12-C35; A18-B12-C36; A18-B12-C37; A18-B12-C38;
A18-B12-C39; A18-B12-C40; A18-B12-C41; A18-B12-C42; A18-B12-C43; A18-B12-C44;
A18-B12-C45; A18-B12-C46; A19-B12-C1; A19-B12-C2; A19-B12-C3; A19-B12-C4;
A19-B12-C5; A19-B12-C6; A19-B12-C7; A19-B12-C8; A19-B12-C9; A19-B12-C10;
A19-B12-C11; A19-B12-C12; A19-B12-C13; A19-B12-C14; A19-B12-C15; A19-B12-C16;
A19-B12-C17; A19-B12-C18; A19-B12-C19; A19-B12-C20; A19-B12-C21; A19-B12-C22;
A19-B12-C23; A19-B12-C24; A19-B12-C25; A19-B12-C26; A19-B12-C27; A19-B12-C28;
A19-B12-C29; A19-B12-C30; A19-B12-C31; A19-B12-C32; A19-B12-C33; A19-B12-C34;
A19-B12-C35; A19-B12-C36; A19-B12-C37; A19-B12-C38; A19-B12-C39; A19-B12-C40;
A19-B12-C41; A19-B12-C42; A19-B12-C43; A19-B12-C44; A19-B12-C45; A19-B12-C46;
A20-B12-C1; A20-B12-C2; A20-B12-C3; A20-B12-C4; A20-B12-C5; A20-B12-C6;
A20-B12-C7; A20-B12-C8; A20-B12-C9; A20-B12-C10; A20-B12-C11; A20-B12-C12;
A20-B12-C13; A20-B12-C14; A20-B12-C15; A20-B12-C16; A20-B12-C17; A20-B12-C18;
A20-B12-C19; A20-B12-C20; A20-B12-C21; A20-B12-C22; A20-B12-C23; A20-B12-C24;
A20-B12-C25; A20-B12-C26; A20-B12-C27; A20-B12-C28; A20-B12-C29; A20-B12-C30;
A20-B12-C31; A20-B12-C32; A20-B12-C33; A20-B12-C34; A20-B12-C35; A20-B12-C36;
A20-B12-C37; A20-B12-C38; A20-B12-C39; A20-B12-C40; A20-B12-C41; A20-B12-C42;
A20-B12-C43; A20-B12-C44; A20-B12-C45; A20-B12-C46; A21-B12-C1; A21-B12-C2;
A21-B12-C3; A21-B12-C4; A21-B12-C5; A21-B12-C6; A21-B12-C7; A21-B12-C8;
A21-B12-C9; A21-B12-C10; A21-B12-C11; A21-B12-C12; A21-B12-C13; A21-B12-C14;
A21-B12-C15; A21-B12-C16; A21-B12-C17; A21-B12-C18; A21-B12-C19; A21-B12-C20;
A21-B12-C21; A21-B12-C22; A21-B12-C23; A21-B12-C24; A21-B12-C25; A21-B12-C26;
A21-B12-C27; A21-B12-C28; A21-B12-C29; A21-B12-C30; A21-B12-C31; A21-B12-C32;
A21-B12-C33; A21-B12-C34; A21-B12-C35; A21-B12-C36; A21-B12-C37; A21-B12-C38;
A21-B12-C39; A21-B12-C40; A21-B12-C41; A21-B12-C42; A21-B12-C43; A21-B12-C44;
A21-B12-C45; A21-B12-C46; A22-B12-C1; A22-B12-C2; A22-B12-C3; A22-B12-C4;
A22-B12-C5; A22-B12-C6; A22-B12-C7; A22-B12-C8; A22-B12-C9; A22-B12-C10;
A22-B12-C11; A22-B12-C12; A22-B12-C13; A22-B12-C14; A22-B12-C15; A22-B12-C16;
A22-B12-C17; A22-B12-C18; A22-B12-C19; A22-B12-C20; A22-B12-C21; A22-B12-C22;
A22-B12-C23; A22-B12-C24; A22-B12-C25; A22-B12-C26; A22-B12-C27; A22-B12-C28;
A22-B12-C29; A22-B12-C30; A22-B12-C31; A22-B12-C32; A22-B12-C33; A22-B12-C34;
A22-B12-C35; A22-B12-C36; A22-B12-C37; A22-B12-C38; A22-B12-C39; A22-B12-C40;
A22-B12-C41; A22-B12-C42; A22-B12-C43; A22-B12-C44; A22-B12-C45; A22-B12-C46;
A23-B12-C1; A23-B12-C2; A23-B12-C3; A23-B12-C4; A23-B12-C5; A23-B12-C6;
A23-B12-C7; A23-B12-C8; A23-B12-C9; A23-B12-C10; A23-B12-C11; A23-B12-C12;
A23-B12-C13; A23-B12-C14; A23-B12-C15; A23-B12-C16; A23-B12-C17; A23-B12-C18;
A23-B12-C19; A23-B12-C20; A23-B12-C21; A23-B12-C22; A23-B12-C23; A23-B12-C24;
A23-B12-C25; A23-B12-C26; A23-B12-C27; A23-B12-C28; A23-B12-C29; A23-B12-C30;
A23-B12-C31; A23-B12-C32; A23-B12-C33; A23-B12-C34; A23-B12-C35; A23-B12-C36;
A23-B12-C37; A23-B12-C38; A23-B12-C39; A23-B12-C40; A23-B12-C41; A23-B12-C42;
A23-B12-C43; A23-B12-C44; A23-B12-C45; A23-B12-C46; A24-B12-C1; A24-B12-C2;
A24-B12-C3; A24-B12-C4; A24-B12-C5; A24-B12-C6; A24-B12-C7; A24-B12-C8;
A24-B12-C9; A24-B12-C10; A24-B12-C11; A24-B12-C12; A24-B12-C13; A24-B12-C14;
A24-B12-C15; A24-B12-C16; A24-B12-C17; A24-B12-C18; A24-B12-C19; A24-B12-C20;
A24-B12-C21; A24-B12-C22; A24-B12-C23; A24-B12-C24; A24-B12-C25; A24-B12-C26;
A24-B12-C27; A24-B12-C28; A24-B12-C29; A24-B12-C30; A24-B12-C31; A24-B12-C32;
A24-B12-C33; A24-B12-C34; A24-B12-C35; A24-B12-C36; A24-B12-C37; A24-B12-C38;
A24-B12-C39; A24-B12-C40; A24-B12-C41; A24-B12-C42; A24-B12-C43; A24-B12-C44;
A24-B12-C45; A24-B12-C46; A25-B12-C1; A25-B12-C2; A25-B12-C3; A25-B12-C4;
A25-B12-C5; A25-B12-C6; A25-B12-C7; A25-B12-C8; A25-B12-C9; A25-B12-C10;
A25-B12-C11; A25-B12-C12; A25-B12-C13; A25-B12-C14; A25-B12-C15; A25-B12-C16;
A25-B12-C17; A25-B12-C18; A25-B12-C19; A25-B12-C20; A25-B12-C21; A25-B12-C22;
A25-B12-C23; A25-B12-C24; A25-B12-C25; A25-B12-C26; A25-B12-C27; A25-B12-C28;
A25-B12-C29; A25-B12-C30; A25-B12-C31; A25-B12-C32; A25-B12-C33; A25-B12-C34;
A25-B12-C35; A25-B12-C36; A25-B12-C37; A25-B12-C38; A25-B12-C39; A25-B12-C40;
A25-B12-C41; A25-B12-C42; A25-B12-C43; A25-B12-C44; A25-B12-C45; A25-B12-C46;
A26-B12-C1; A26-B12-C2; A26-B12-C3; A26-B12-C4; A26-B12-C5; A26-B12-C6;
A26-B12-C7; A26-B12-C8; A26-B12-C9; A26-B12-C10; A26-B12-C11; A26-B12-C12;
A26-B12-C13; A26-B12-C14; A26-B12-C15; A26-B12-C16; A26-B12-C17; A26-B12-C18;
A26-B12-C19; A26-B12-C20; A26-B12-C21; A26-B12-C22; A26-B12-C23; A26-B12-C24;
A26-B12-C25; A26-B12-C26; A26-B12-C27; A26-B12-C28; A26-B12-C29; A26-B12-C30;
A26-B12-C31; A26-B12-C32; A26-B12-C33; A26-B12-C34; A26-B12-C35; A26-B12-C36;
A26-B12-C37; A26-B12-C38; A26-B12-C39; A26-B12-C40; A26-B12-C41; A26-B12-C42;
A26-B12-C43; A26-B12-C44; A26-B12-C45; A26-B12-C46; A27-B12-C1; A27-B12-C2;
A27-B12-C3; A27-B12-C4; A27-B12-C5; A27-B12-C6; A27-B12-C7; A27-B12-C8;
A27-B12-C9; A27-B12-C10; A27-B12-C11; A27-B12-C12; A27-B12-C13; A27-B12-C14;
A27-B12-C15; A27-B12-C16; A27-B12-C17; A27-B12-C18; A27-B12-C19; A27-B12-C20;
A27-B12-C21; A27-B12-C22; A27-B12-C23; A27-B12-C24; A27-B12-C25; A27-B12-C26;
A27-B12-C27; A27-B12-C28; A27-B12-C29; A27-B12-C30; A27-B12-C31; A27-B12-C32;
A27-B12-C33; A27-B12-C34; A27-B12-C35; A27-B12-C36; A27-B12-C37; A27-B12-C38;
A27-B12-C39; A27-B12-C40; A27-B12-C41; A27-B12-C42; A27-B12-C43; A27-B12-C44;

-continued

A27-B12-C45; A27-B12-C46; A28-B12-C1; A28-B12-C2; A28-B12-C3; A28-B12-C4;
A28-B12-C5; A28-B12-C6; A28-B12-C7; A28-B12-C8; A28-B12-C9; A28-B12-C10;
A28-B12-C11; A28-B12-C12; A28-B12-C13; A28-B12-C14; A28-B12-C15; A28-B12-C16;
A28-B12-C17; A28-B12-C18; A28-B12-C19; A28-B12-C20; A28-B12-C21; A28-B12-C22;
A28-B12-C23; A28-B12-C24; A28-B12-C25; A28-B12-C26; A28-B12-C27; A28-B12-C28;
A28-B12-C29; A28-B12-C30; A28-B12-C31; A28-B12-C32; A28-B12-C33; A28-B12-C34;
A28-B12-C35; A28-B12-C36; A28-B12-C37; A28-B12-C38; A28-B12-C39; A28-B12-C40;
A28-B12-C41; A28-B12-C42; A28-B12-C43; A28-B12-C44; A28-B12-C45; A28-B12-C46;
A1-B13-C1; A1-B13-C2; A1-B13-C3; A1-B13-C4; A1-B13-C5; A1-B13-C6;
A1-B13-C7; A1-B13-C8; A1-B13-C9; A1-B13-C10; A1-B13-C11; A1-B13-C12;
A1-B13-C13; A1-B13-C14; A1-B13-C15; A1-B13-C16; A1-B13-C17; A1-B13-C18;
A1-B13-C19; A1-B13-C20; A1-B13-C21; A1-B13-C22; A1-B13-C23; A1-B13-C24;
A1-B13-C25; A1-B13-C26; A1-B13-C27; A1-B13-C28; A1-B13-C29; A1-B13-C30;
A1-B13-C31; A1-B13-C32; A1-B13-C33; A1-B13-C34; A1-B13-C35; A1-B13-C36;
A1-B13-C37; A1-B13-C38; A1-B13-C39; A1-B13-C40; A1-B13-C41; A1-B13-C42;
A1-B13-C43; A1-B13-C44; A1-B13-C45; A1-B13-C46; A2-B13-C1; A2-B13-C2;
A2-B13-C3; A2-B13-C4; A2-B13-C5; A2-B13-C6; A2-B13-C7; A2-B13-C8;
A2-B13-C9; A2-B13-C10; A2-B13-C11; A2-B13-C12; A2-B13-C13; A2-B13-C14;
A2-B13-C15; A2-B13-C16; A2-B13-C17; A2-B13-C18; A2-B13-C19; A2-B13-C20;
A2-B13-C21; A2-B13-C22; A2-B13-C23; A2-B13-C24; A2-B13-C25; A2-B13-C26;
A2-B13-C27; A2-B13-C28; A2-B13-C29; A2-B13-C30; A2-B13-C31; A2-B13-C32;
A2-B13-C33; A2-B13-C34; A2-B13-C35; A2-B13-C36; A2-B13-C37; A2-B13-C38;
A2-B13-C39; A2-B13-C40; A2-B13-C41; A2-B13-C42; A2-B13-C43; A2-B13-C44;
A2-B13-C45; A2-B13-C46; A3-B13-C1; A3-B13-C2; A3-B13-C3; A3-B13-C4;
A3-B13-C5; A3-B13-C6; A3-B13-C7; A3-B13-C8; A3-B13-C9; A3-B13-C10;
A3-B13-C11; A3-B13-C12; A3-B13-C13; A3-B13-C14; A3-B13-C15; A3-B13-C16;
A3-B13-C17; A3-B13-C18; A3-B13-C19; A3-B13-C20; A3-B13-C21; A3-B13-C22;
A3-B13-C23; A3-B13-C24; A3-B13-C25; A3-B13-C26; A3-B13-C27; A3-B13-C28;
A3-B13-C29; A3-B13-C30; A3-B13-C31; A3-B13-C32; A3-B13-C33; A3-B13-C34;
A3-B13-C35; A3-B13-C36; A3-B13-C37; A3-B13-C38; A3-B13-C39; A3-B13-C40;
A3-B13-C41; A3-B13-C42; A3-B13-C43; A3-B13-C44; A3-B13-C45; A3-B13-C46;
A4-B13-C1; A4-B13-C2; A4-B13-C3; A4-B13-C4; A4-B13-C5; A4-B13-C6;
A4-B13-C7; A4-B13-C8; A4-B13-C9; A4-B13-C10; A4-B13-C11; A4-B13-C12;
A4-B13-C13; A4-B13-C14; A4-B13-C15; A4-B13-C16; A4-B13-C17; A4-B13-C18;
A4-B13-C19; A4-B13-C20; A4-B13-C21; A4-B13-C22; A4-B13-C23; A4-B13-C24;
A4-B13-C25; A4-B13-C26; A4-B13-C27; A4-B13-C28; A4-B13-C29; A4-B13-C30;
A4-B13-C31; A4-B13-C32; A4-B13-C33; A4-B13-C34; A4-B13-C35; A4-B13-C36;
A4-B13-C37; A4-B13-C38; A4-B13-C39; A4-B13-C40; A4-B13-C41; A4-B13-C42;
A4-B13-C43; A4-B13-C44; A4-B13-C45; A4-B13-C46; A5-B13-C1; A5-B13-C2;
A5-B13-C3; A5-B13-C4; A5-B13-C5; A5-B13-C6; A5-B13-C7; A5-B13-C8;
A5-B13-C9; A5-B13-C10; A5-B13-C11; A5-B13-C12; A5-B13-C13; A5-B13-C14;
A5-B13-C15; A5-B13-C16; A5-B13-C17; A5-B13-C18; A5-B13-C19; A5-B13-C20;
A5-B13-C21; A5-B13-C22; A5-B13-C23; A5-B13-C24; A5-B13-C25; A5-B13-C26;
A5-B13-C27; A5-B13-C28; A5-B13-C29; A5-B13-C30; A5-B13-C31; A5-B13-C32;
A5-B13-C33; A5-B13-C34; A5-B13-C35; A5-B13-C36; A5-B13-C37; A5-B13-C38;
A5-B13-C39; A5-B13-C40; A5-B13-C41; A5-B13-C42; A5-B13-C43; A5-B13-C44;
A5-B13-C45; A5-B13-C46; A6-B13-C1; A6-B13-C2; A6-B13-C3; A6-B13-C4;
A6-B13-C5; A6-B13-C6; A6-B13-C7; A6-B13-C8; A6-B13-C9; A6-B13-C10;
A6-B13-C11; A6-B13-C12; A6-B13-C13; A6-B13-C14; A6-B13-C15; A6-B13-C16;
A6-B13-C17; A6-B13-C18; A6-B13-C19; A6-B13-C20; A6-B13-C21; A6-B13-C22;
A6-B13-C23; A6-B13-C24; A6-B13-C25; A6-B13-C26; A6-B13-C27; A6-B13-C28;
A6-B13-C29; A6-B13-C30; A6-B13-C31; A6-B13-C32; A6-B13-C33; A6-B13-C34;
A6-B13-C35; A6-B13-C36; A6-B13-C37; A6-B13-C38; A6-B13-C39; A6-B13-C40;
A6-B13-C41; A6-B13-C42; A6-B13-C43; A6-B13-C44; A6-B13-C45; A6-B13-C46;
A7-B13-C1; A7-B13-C2; A7-B13-C3; A7-B13-C4; A7-B13-C5; A7-B13-C6;
A7-B13-C7; A7-B13-C8; A7-B13-C9; A7-B13-C10; A7-B13-C11; A7-B13-C12;
A7-B13-C13; A7-B13-C14; A7-B13-C15; A7-B13-C16; A7-B13-C17; A7-B13-C18;
A7-B13-C19; A7-B13-C20; A7-B13-C21; A7-B13-C22; A7-B13-C23; A7-B13-C24;
A7-B13-C25; A7-B13-C26; A7-B13-C27; A7-B13-C28; A7-B13-C29; A7-B13-C30;
A7-B13-C31; A7-B13-C32; A7-B13-C33; A7-B13-C34; A7-B13-C35; A7-B13-C36;
A7-B13-C37; A7-B13-C38; A7-B13-C39; A7-B13-C40; A7-B13-C41; A7-B13-C42;
A7-B13-C43; A7-B13-C44; A7-B13-C45; A7-B13-C46; A8-B13-C1; A8-B13-C2;
A8-B13-C3; A8-B13-C4; A8-B13-C5; A8-B13-C6; A8-B13-C7; A8-B13-C8;
A8-B13-C9; A8-B13-C10; A8-B13-C11; A8-B13-C12; A8-B13-C13; A8-B13-C14;
A8-B13-C15; A8-B13-C16; A8-B13-C17; A8-B13-C18; A8-B13-C19; A8-B13-C20;
A8-B13-C21; A8-B13-C22; A8-B13-C23; A8-B13-C24; A8-B13-C25; A8-B13-C26;
A8-B13-C27; A8-B13-C28; A8-B13-C29; A8-B13-C30; A8-B13-C31; A8-B13-C32;
A8-B13-C33; A8-B13-C34; A8-B13-C35; A8-B13-C36; A8-B13-C37; A8-B13-C38;
A8-B13-C39; A8-B13-C40; A8-B13-C41; A8-B13-C42; A8-B13-C43; A8-B13-C44;
A8-B13-C45; A8-B13-C46; A9-B13-C1; A9-B13-C2; A9-B13-C3; A9-B13-C4;
A9-B13-C5; A9-B13-C6; A9-B13-C7; A9-B13-C8; A9-B13-C9; A9-B13-C10;
A9-B13-C11; A9-B13-C12; A9-B13-C13; A9-B13-C14; A9-B13-C15; A9-B13-C16;
A9-B13-C17; A9-B13-C18; A9-B13-C19; A9-B13-C20; A9-B13-C21; A9-B13-C22;
A9-B13-C23; A9-B13-C24; A9-B13-C25; A9-B13-C26; A9-B13-C27; A9-B13-C28;
A9-B13-C29; A9-B13-C30; A9-B13-C31; A9-B13-C32; A9-B13-C33; A9-B13-C34;
A9-B13-C35; A9-B13-C36; A9-B13-C37; A9-B13-C38; A9-B13-C39; A9-B13-C40;
A9-B13-C41; A9-B13-C42; A9-B13-C43; A9-B13-C44; A9-B13-C45; A9-B13-C46;
A10-B13-C1; A10-B13-C2; A10-B13-C3; A10-B13-C4; A10-B13-C5; A10-B13-C6;
A10-B13-C7; A10-B13-C8; A10-B13-C9; A10-B13-C10; A10-B13-C11; A10-B13-C12;

-continued

| | | | | | |
|---|---|---|---|---|---|
| A10-B13-C13; | A10-B13-C14; | A10-B13-C15; | A10-B13-C16; | A10-B13-C17; | A10-B13-C18; |
| A10-B13-C19; | A10-B13-C20; | A10-B13-C21; | A10-B13-C22; | A10-B13-C23; | A10-B13-C24; |
| A10-B13-C25; | A10-B13-C26; | A10-B13-C27; | A10-B13-C28; | A10-B13-C29; | A10-B13-C30; |
| A10-B13-C31; | A10-B13-C32; | A10-B13-C33; | A10-B13-C34; | A10-B13-C35; | A10-B13-C36; |
| A10-B13-C37; | A10-B13-C38; | A10-B13-C39; | A10-B13-C40; | A10-B13-C41; | A10-B13-C42; |
| A10-B13-C43; | A10-B13-C44; | A10-B13-C45; | A10-B13-C46; | A11-B13-C1; | A11-B13-C2; |
| A11-B13-C3; | A11-B13-C4; | A11-B13-C5; | A11-B13-C6; | A11-B13-C7; | A11-B13-C8; |
| A11-B13-C9; | A11-B13-C10; | A11-B13-C11; | A11-B13-C12; | A11-B13-C13; | A11-B13-C14; |
| A11-B13-C15; | A11-B13-C16; | A11-B13-C17; | A11-B13-C18; | A11-B13-C19; | A11-B13-C20; |
| A11-B13-C21; | A11-B13-C22; | A11-B13-C23; | A11-B13-C24; | A11-B13-C25; | A11-B13-C26; |
| A11-B13-C27; | A11-B13-C28; | A11-B13-C29; | A11-B13-C30; | A11-B13-C31; | A11-B13-C32; |
| A11-B13-C33; | A11-B13-C34; | A11-B13-C35; | A11-B13-C36; | A11-B13-C37; | A11-B13-C38; |
| A11-B13-C39; | A11-B13-C40; | A11-B13-C41; | A11-B13-C42; | A11-B13-C43; | A11-B13-C44; |
| A11-B13-C45; | A11-B13-C46; | A12-B13-C1; | A12-B13-C2; | A12-B13-C3; | A12-B13-C4; |
| A12-B13-C5; | A12-B13-C6; | A12-B13-C7; | A12-B13-C8; | A12-B13-C9; | A12-B13-C10; |
| A12-B13-C11; | A12-B13-C12; | A12-B13-C13; | A12-B13-C14; | A12-B13-C15; | A12-B13-C16; |
| A12-B13-C17; | A12-B13-C18; | A12-B13-C19; | A12-B13-C20; | A12-B13-C21; | A12-B13-C22; |
| A12-B13-C23; | A12-B13-C24; | A12-B13-C25; | A12-B13-C26; | A12-B13-C27; | A12-B13-C28; |
| A12-B13-C29; | A12-B13-C30; | A12-B13-C31; | A12-B13-C32; | A12-B13-C33; | A12-B13-C34; |
| A12-B13-C35; | A12-B13-C36; | A12-B13-C37; | A12-B13-C38; | A12-B13-C39; | A12-B13-C40; |
| A12-B13-C41; | A12-B13-C42; | A12-B13-C43; | A12-B13-C44; | A12-B13-C45; | A12-B13-C46; |
| A13-B13-C1; | A13-B13-C2; | A13-B13-C3; | A13-B13-C4; | A13-B13-C5; | A13-B13-C6; |
| A13-B13-C7; | A13-B13-C8; | A13-B13-C9; | A13-B13-C10; | A13-B13-C11; | A13-B13-C12; |
| A13-B13-C13; | A13-B13-C14; | A13-B13-C15; | A13-B13-C16; | A13-B13-C17; | A13-B13-C18; |
| A13-B13-C19; | A13-B13-C20; | A13-B13-C21; | A13-B13-C22; | A13-B13-C23; | A13-B13-C24; |
| A13-B13-C25; | A13-B13-C26; | A13-B13-C27; | A13-B13-C28; | A13-B13-C29; | A13-B13-C30; |
| A13-B13-C31; | A13-B13-C32; | A13-B13-C33; | A13-B13-C34; | A13-B13-C35; | A13-B13-C36; |
| A13-B13-C37; | A13-B13-C38; | A13-B13-C39; | A13-B13-C40; | A13-B13-C41; | A13-B13-C42; |
| A13-B13-C43; | A13-B13-C44; | A13-B13-C45; | A13-B13-C46; | A14-B13-C1; | A14-B13-C2; |
| A14-B13-C3; | A14-B13-C4; | A14-B13-C5; | A14-B13-C6; | A14-B13-C7; | A14-B13-C8; |
| A14-B13-C9; | A14-B13-C10; | A14-B13-C11; | A14-B13-C12; | A14-B13-C13; | A14-B13-C14; |
| A14-B13-C15; | A14-B13-C16; | A14-B13-C17; | A14-B13-C18; | A14-B13-C19; | A14-B13-C20; |
| A14-B13-C21; | A14-B13-C22; | A14-B13-C23; | A14-B13-C24; | A14-B13-C25; | A14-B13-C26; |
| A14-B13-C27; | A14-B13-C28; | A14-B13-C29; | A14-B13-C30; | A14-B13-C31; | A14-B13-C32; |
| A14-B13-C33; | A14-B13-C34; | A14-B13-C35; | A14-B13-C36; | A14-B13-C37; | A14-B13-C38; |
| A14-B13-C39; | A14-B13-C40; | A14-B13-C41; | A14-B13-C42; | A14-B13-C43; | A14-B13-C44; |
| A14-B13-C45; | A14-B13-C46; | A15-B13-C1; | A15-B13-C2; | A15-B13-C3; | A15-B13-C4; |
| A15-B13-C5; | A15-B13-C6; | A15-B13-C7; | A15-B13-C8; | A15-B13-C9; | A15-B13-C10; |
| A15-B13-C11; | A15-B13-C12; | A15-B13-C13; | A15-B13-C14; | A15-B13-C15; | A15-B13-C16; |
| A15-B13-C17; | A15-B13-C18; | A15-B13-C19; | A15-B13-C20; | A15-B13-C21; | A15-B13-C22; |
| A15-B13-C23; | A15-B13-C24; | A15-B13-C25; | A15-B13-C26; | A15-B13-C27; | A15-B13-C28; |
| A15-B13-C29; | A15-B13-C30; | A15-B13-C31; | A15-B13-C32; | A15-B13-C33; | A15-B13-C34; |
| A15-B13-C35; | A15-B13-C36; | A15-B13-C37; | A15-B13-C38; | A15-B13-C39; | A15-B13-C40; |
| A15-B13-C41; | A15-B13-C42; | A15-B13-C43; | A15-B13-C44; | A15-B13-C45; | A15-B13-C46; |
| A16-B13-C1; | A16-B13-C2; | A16-B13-C3; | A16-B13-C4; | A16-B13-C5; | A16-B13-C6; |
| A16-B13-C7; | A16-B13-C8; | A16-B13-C9; | A16-B13-C10; | A16-B13-C11; | A16-B13-C12; |
| A16-B13-C13; | A16-B13-C14; | A16-B13-C15; | A16-B13-C16; | A16-B13-C17; | A16-B13-C18; |
| A16-B13-C19; | A16-B13-C20; | A16-B13-C21; | A16-B13-C22; | A16-B13-C23; | A16-B13-C24; |
| A16-B13-C25; | A16-B13-C26; | A16-B13-C27; | A16-B13-C28; | A16-B13-C29; | A16-B13-C30; |
| A16-B13-C31; | A16-B13-C32; | A16-B13-C33; | A16-B13-C34; | A16-B13-C35; | A16-B13-C36; |
| A16-B13-C37; | A16-B13-C38; | A16-B13-C39; | A16-B13-C40; | A16-B13-C41; | A16-B13-C42; |
| A16-B13-C43; | A16-B13-C44; | A16-B13-C45; | A16-B13-C46; | A17-B13-C1; | A17-B13-C2; |
| A17-B13-C3; | A17-B13-C4; | A17-B13-C5; | A17-B13-C6; | A17-B13-C7; | A17-B13-C8; |
| A17-B13-C9; | A17-B13-C10; | A17-B13-C11; | A17-B13-C12; | A17-B13-C13; | A17-B13-C14; |
| A17-B13-C15; | A17-B13-C16; | A17-B13-C17; | A17-B13-C18; | A17-B13-C19; | A17-B13-C20; |
| A17-B13-C21; | A17-B13-C22; | A17-B13-C23; | A17-B13-C24; | A17-B13-C25; | A17-B13-C26; |
| A17-B13-C27; | A17-B13-C28; | A17-B13-C29; | A17-B13-C30; | A17-B13-C31; | A17-B13-C32; |
| A17-B13-C33; | A17-B13-C34; | A17-B13-C35; | A17-B13-C36; | A17-B13-C37; | A17-B13-C38; |
| A17-B13-C39; | A17-B13-C40; | A17-B13-C41; | A17-B13-C42; | A17-B13-C43; | A17-B13-C44; |
| A17-B13-C45; | A17-B13-C46; | A18-B13-C1; | A18-B13-C2; | A18-B13-C3; | A18-B13-C4; |
| A18-B13-C5; | A18-B13-C6; | A18-B13-C7; | A18-B13-C8; | A18-B13-C9; | A18-B13-C10; |
| A18-B13-C11; | A18-B13-C12; | A18-B13-C13; | A18-B13-C14; | A18-B13-C15; | A18-B13-C16; |
| A18-B13-C17; | A18-B13-C18; | A18-B13-C19; | A18-B13-C20; | A18-B13-C21; | A18-B13-C22; |
| A18-B13-C23; | A18-B13-C24; | A18-B13-C25; | A18-B13-C26; | A18-B13-C27; | A18-B13-C28; |
| A18-B13-C29; | A18-B13-C30; | A18-B13-C31; | A18-B13-C32; | A18-B13-C33; | A18-B13-C34; |
| A18-B13-C35; | A18-B13-C36; | A18-B13-C37; | A18-B13-C38; | A18-B13-C39; | A18-B13-C40; |
| A18-B13-C41; | A18-B13-C42; | A18-B13-C43; | A18-B13-C44; | A18-B13-C45; | A18-B13-C46; |
| A19-B13-C1; | A19-B13-C2; | A19-B13-C3; | A19-B13-C4; | A19-B13-C5; | A19-B13-C6; |
| A19-B13-C7; | A19-B13-C8; | A19-B13-C9; | A19-B13-C10; | A19-B13-C11; | A19-B13-C12; |
| A19-B13-C13; | A19-B13-C14; | A19-B13-C15; | A19-B13-C16; | A19-B13-C17; | A19-B13-C18; |
| A19-B13-C19; | A19-B13-C20; | A19-B13-C21; | A19-B13-C22; | A19-B13-C23; | A19-B13-C24; |
| A19-B13-C25; | A19-B13-C26; | A19-B13-C27; | A19-B13-C28; | A19-B13-C29; | A19-B13-C30; |
| A19-B13-C31; | A19-B13-C32; | A19-B13-C33; | A19-B13-C34; | A19-B13-C35; | A19-B13-C36; |
| A19-B13-C37; | A19-B13-C38; | A19-B13-C39; | A19-B13-C40; | A19-B13-C41; | A19-B13-C42; |
| A19-B13-C43; | A19-B13-C44; | A19-B13-C45; | A19-B13-C46; | A20-B13-C1; | A20-B13-C2; |
| A20-B13-C3; | A20-B13-C4; | A20-B13-C5; | A20-B13-C6; | A20-B13-C7; | A20-B13-C8; |
| A20-B13-C9; | A20-B13-C10; | A20-B13-C11; | A20-B13-C12; | A20-B13-C13; | A20-B13-C14; |
| A20-B13-C15; | A20-B13-C16; | A20-B13-C17; | A20-B13-C18; | A20-B13-C19; | A20-B13-C20; |
| A20-B13-C21; | A20-B13-C22; | A20-B13-C23; | A20-B13-C24; | A20-B13-C25; | A20-B13-C26; |

| | | | | | |
|---|---|---|---|---|---|
| A20-B13-C27; | A20-B13-C28; | A20-B13-C29; | A20-B13-C30; | A20-B13-C31; | A20-B13-C32; |
| A20-B13-C33; | A20-B13-C34; | A20-B13-C35; | A20-B13-C36; | A20-B13-C37; | A20-B13-C38; |
| A20-B13-C39; | A20-B13-C40; | A20-B13-C41; | A20-B13-C42; | A20-B13-C43; | A20-B13-C44; |
| A20-B13-C45; | A20-B13-C46; | A21-B13-C1; | A21-B13-C2; | A21-B13-C3; | A21-B13-C4; |
| A21-B13-C5; | A21-B13-C6; | A21-B13-C7; | A21-B13-C8; | A21-B13-C9; | A21-B13-C10; |
| A21-B13-C11; | A21-B13-C12; | A21-B13-C13; | A21-B13-C14; | A21-B13-C15; | A21-B13-C16; |
| A21-B13-C17; | A21-B13-C18; | A21-B13-C19; | A21-B13-C20; | A21-B13-C21; | A21-B13-C22; |
| A21-B13-C23; | A21-B13-C24; | A21-B13-C25; | A21-B13-C26; | A21-B13-C27; | A21-B13-C28; |
| A21-B13-C29; | A21-B13-C30; | A21-B13-C31; | A21-B13-C32; | A21-B13-C33; | A21-B13-C34; |
| A21-B13-C35; | A21-B13-C36; | A21-B13-C37; | A21-B13-C38; | A21-B13-C39; | A21-B13-C40; |
| A21-B13-C41; | A21-B13-C42; | A21-B13-C43; | A21-B13-C44; | A21-B13-C45; | A21-B13-C46; |
| A22-B13-C1; | A22-B13-C2; | A22-B13-C3; | A22-B13-C4; | A22-B13-C5; | A22-B13-C6; |
| A22-B13-C7; | A22-B13-C8; | A22-B13-C9; | A22-B13-C10; | A22-B13-C11; | A22-B13-C12; |
| A22-B13-C13; | A22-B13-C14; | A22-B13-C15; | A22-B13-C16; | A22-B13-C17; | A22-B13-C18; |
| A22-B13-C19; | A22-B13-C20; | A22-B13-C21; | A22-B13-C22; | A22-B13-C23; | A22-B13-C24; |
| A22-B13-C25; | A22-B13-C26; | A22-B13-C27; | A22-B13-C28; | A22-B13-C29; | A22-B13-C30; |
| A22-B13-C31; | A22-B13-C32; | A22-B13-C33; | A22-B13-C34; | A22-B13-C35; | A22-B13-C36; |
| A22-B13-C37; | A22-B13-C38; | A22-B13-C39; | A22-B13-C40; | A22-B13-C41; | A22-B13-C42; |
| A22-B13-C43; | A22-B13-C44; | A22-B13-C45; | A22-B13-C46; | A23-B13-C1; | A23-B13-C2; |
| A23-B13-C3; | A23-B13-C4; | A23-B13-C5; | A23-B13-C6; | A23-B13-C7; | A23-B13-C8; |
| A23-B13-C9; | A23-B13-C10; | A23-B13-C11; | A23-B13-C12; | A23-B13-C13; | A23-B13-C14; |
| A23-B13-C15; | A23-B13-C16; | A23-B13-C17; | A23-B13-C18; | A23-B13-C19; | A23-B13-C20; |
| A23-B13-C21; | A23-B13-C22; | A23-B13-C23; | A23-B13-C24; | A23-B13-C25; | A23-B13-C26; |
| A23-B13-C27; | A23-B13-C28; | A23-B13-C29; | A23-B13-C30; | A23-B13-C31; | A23-B13-C32; |
| A23-B13-C33; | A23-B13-C34; | A23-B13-C35; | A23-B13-C36; | A23-B13-C37; | A23-B13-C38; |
| A23-B13-C39; | A23-B13-C40; | A23-B13-C41; | A23-B13-C42; | A23-B13-C43; | A23-B13-C44; |
| A23-B13-C45; | A23-B13-C46; | A24-B13-C1; | A24-B13-C2; | A24-B13-C3; | A24-B13-C4; |
| A24-B13-C5; | A24-B13-C6; | A24-B13-C7; | A24-B13-C8; | A24-B13-C9; | A24-B13-C10; |
| A24-B13-C11; | A24-B13-C12; | A24-B13-C13; | A24-B13-C14; | A24-B13-C15; | A24-B13-C16; |
| A24-B13-C17; | A24-B13-C18; | A24-B13-C19; | A24-B13-C20; | A24-B13-C21; | A24-B13-C22; |
| A24-B13-C23; | A24-B13-C24; | A24-B13-C25; | A24-B13-C26; | A24-B13-C27; | A24-B13-C28; |
| A24-B13-C29; | A24-B13-C30; | A24-B13-C31; | A24-B13-C32; | A24-B13-C33; | A24-B13-C34; |
| A24-B13-C35; | A24-B13-C36; | A24-B13-C37; | A24-B13-C38; | A24-B13-C39; | A24-B13-C40; |
| A24-B13-C41; | A24-B13-C42; | A24-B13-C43; | A24-B13-C44; | A24-B13-C45; | A24-B13-C46; |
| A25-B13-C1; | A25-B13-C2; | A25-B13-C3; | A25-B13-C4; | A25-B13-C5; | A25-B13-C6; |
| A25-B13-C7; | A25-B13-C8; | A25-B13-C9; | A25-B13-C10; | A25-B13-C11; | A25-B13-C12; |
| A25-B13-C13; | A25-B13-C14; | A25-B13-C15; | A25-B13-C16; | A25-B13-C17; | A25-B13-C18; |
| A25-B13-C19; | A25-B13-C20; | A25-B13-C21; | A25-B13-C22; | A25-B13-C23; | A25-B13-C24; |
| A25-B13-C25; | A25-B13-C26; | A25-B13-C27; | A25-B13-C28; | A25-B13-C29; | A25-B13-C30; |
| A25-B13-C31; | A25-B13-C32; | A25-B13-C33; | A25-B13-C34; | A25-B13-C35; | A25-B13-C36; |
| A25-B13-C37; | A25-B13-C38; | A25-B13-C39; | A25-B13-C40; | A25-B13-C41; | A25-B13-C42; |
| A25-B13-C43; | A25-B13-C44; | A25-B13-C45; | A25-B13-C46; | A26-B13-C1; | A26-B13-C2; |
| A26-B13-C3; | A26-B13-C4; | A26-B13-C5; | A26-B13-C6; | A26-B13-C7; | A26-B13-C8; |
| A26-B13-C9; | A26-B13-C10; | A26-B13-C11; | A26-B13-C12; | A26-B13-C13; | A26-B13-C14; |
| A26-B13-C15; | A26-B13-C16; | A26-B13-C17; | A26-B13-C18; | A26-B13-C19; | A26-B13-C20; |
| A26-B13-C21; | A26-B13-C22; | A26-B13-C23; | A26-B13-C24; | A26-B13-C25; | A26-B13-C26; |
| A26-B13-C27; | A26-B13-C28; | A26-B13-C29; | A26-B13-C30; | A26-B13-C31; | A26-B13-C32; |
| A26-B13-C33; | A26-B13-C34; | A26-B13-C35; | A26-B13-C36; | A26-B13-C37; | A26-B13-C38; |
| A26-B13-C39; | A26-B13-C40; | A26-B13-C41; | A26-B13-C42; | A26-B13-C43; | A26-B13-C44; |
| A26-B13-C45; | A26-B13-C46; | A27-B13-C1; | A27-B13-C2; | A27-B13-C3; | A27-B13-C4; |
| A27-B13-C5; | A27-B13-C6; | A27-B13-C7; | A27-B13-C8; | A27-B13-C9; | A27-B13-C10; |
| A27-B13-C11; | A27-B13-C12; | A27-B13-C13; | A27-B13-C14; | A27-B13-C15; | A27-B13-C16; |
| A27-B13-C17; | A27-B13-C18; | A27-B13-C19; | A27-B13-C20; | A27-B13-C21; | A27-B13-C22; |
| A27-B13-C23; | A27-B13-C24; | A27-B13-C25; | A27-B13-C26; | A27-B13-C27; | A27-B13-C28; |
| A27-B13-C29; | A27-B13-C30; | A27-B13-C31; | A27-B13-C32; | A27-B13-C33; | A27-B13-C34; |
| A27-B13-C35; | A27-B13-C36; | A27-B13-C37; | A27-B13-C38; | A27-B13-C39; | A27-B13-C40; |
| A27-B13-C41; | A27-B13-C42; | A27-B13-C43; | A27-B13-C44; | A27-B13-C45; | A27-B13-C46; |
| A28-B13-C1; | A28-B13-C2; | A28-B13-C3; | A28-B13-C4; | A28-B13-C5; | A28-B13-C6; |
| A28-B13-C7; | A28-B13-C8; | A28-B13-C9; | A28-B13-C10; | A28-B13-C11; | A28-B13-C12; |
| A28-B13-C13; | A28-B13-C14; | A28-B13-C15; | A28-B13-C16; | A28-B13-C17; | A28-B13-C18; |
| A28-B13-C19; | A28-B13-C20; | A28-B13-C21; | A28-B13-C22; | A28-B13-C23; | A28-B13-C24; |
| A28-B13-C25; | A28-B13-C26; | A28-B13-C27; | A28-B13-C28; | A28-B13-C29; | A28-B13-C30; |
| A28-B13-C31; | A28-B13-C32; | A28-B13-C33; | A28-B13-C34; | A28-B13-C35; | A28-B13-C36; |
| A28-B13-C37; | A28-B13-C38; | A28-B13-C39; | A28-B13-C40; | A28-B13-C41; | A28-B13-C42; |
| A28-B13-C43; | A28-B13-C44; | A28-B13-C45; | A28-B13-C46; | A1-B14-C1; | A1-B14-C2; |
| A1-B14-C3; | A1-B14-C4; | A1-B14-C5; | A1-B14-C6; | A1-B14-C7; | A1-B14-C8; |
| A1-B14-C9; | A1-B14-C10; | A1-B14-C11; | A1-B14-C12; | A1-B14-C13; | A1-B14-C14; |
| A1-B14-C15; | A1-B14-C16; | A1-B14-C17; | A1-B14-C18; | A1-B14-C19; | A1-B14-C20; |
| A1-B14-C21; | A1-B14-C22; | A1-B14-C23; | A1-B14-C24; | A1-B14-C25; | A1-B14-C26; |
| A1-B14-C27; | A1-B14-C28; | A1-B14-C29; | A1-B14-C30; | A1-B14-C31; | A1-B14-C32; |
| A1-B14-C33; | A1-B14-C34; | A1-B14-C35; | A1-B14-C36; | A1-B14-C37; | A1-B14-C38; |
| A1-B14-C39; | A1-B14-C40; | A1-B14-C41; | A1-B14-C42; | A1-B14-C43; | A1-B14-C44; |
| A1-B14-C45; | A1-B14-C46; | A2-B14-C1; | A2-B14-C2; | A2-B14-C3; | A2-B14-C4; |
| A2-B14-C5; | A2-B14-C6; | A2-B14-C7; | A2-B14-C8; | A2-B14-C9; | A2-B14-C10; |
| A2-B14-C11; | A2-B14-C12; | A2-B14-C13; | A2-B14-C14; | A2-B14-C15; | A2-B14-C16; |
| A2-B14-C17; | A2-B14-C18; | A2-B14-C19; | A2-B14-C20; | A2-B14-C21; | A2-B14-C22; |
| A2-B14-C23; | A2-B14-C24; | A2-B14-C25; | A2-B14-C26; | A2-B14-C27; | A2-B14-C28; |
| A2-B14-C29; | A2-B14-C30; | A2-B14-C31; | A2-B14-C32; | A2-B14-C33; | A2-B14-C34; |
| A2-B14-C35; | A2-B14-C36; | A2-B14-C37; | A2-B14-C38; | A2-B14-C39; | A2-B14-C40; |

-continued

| | | | | | |
|---|---|---|---|---|---|
| A2-B14-C41; | A2-B14-C42; | A2-B14-C43; | A2-B14-C44; | A2-B14-C45; | A2-B14-C46; |
| A3-B14-C1; | A3-B14-C2; | A3-B14-C3; | A3-B14-C4; | A3-B14-C5; | A3-B14-C6; |
| A3-B14-C7; | A3-B14-C8; | A3-B14-C9; | A3-B14-C10; | A3-B14-C11; | A3-B14-C12; |
| A3-B14-C13; | A3-B14-C14; | A3-B14-C15; | A3-B14-C16; | A3-B14-C17; | A3-B14-C18; |
| A3-B14-C19; | A3-B14-C20; | A3-B14-C21; | A3-B14-C22; | A3-B14-C23; | A3-B14-C24; |
| A3-B14-C25; | A3-B14-C26; | A3-B14-C27; | A3-B14-C28; | A3-B14-C29; | A3-B14-C30; |
| A3-B14-C31; | A3-B14-C32; | A3-B14-C33; | A3-B14-C34; | A3-B14-C35; | A3-B14-C36; |
| A3-B14-C37; | A3-B14-C38; | A3-B14-C39; | A3-B14-C40; | A3-B14-C41; | A3-B14-C42; |
| A3-B14-C43; | A3-B14-C44; | A3-B14-C45; | A3-B14-C46; | A4-B14-C1; | A4-B14-C2; |
| A4-B14-C3; | A4-B14-C4; | A4-B14-C5; | A4-B14-C6; | A4-B14-C7; | A4-B14-C8; |
| A4-B14-C9; | A4-B14-C10; | A4-B14-C11; | A4-B14-C12; | A4-B14-C13; | A4-B14-C14; |
| A4-B14-C15; | A4-B14-C16; | A4-B14-C17; | A4-B14-C18; | A4-B14-C19; | A4-B14-C20; |
| A4-B14-C21; | A4-B14-C22; | A4-B14-C23; | A4-B14-C24; | A4-B14-C25; | A4-B14-C26; |
| A4-B14-C27; | A4-B14-C28; | A4-B14-C29; | A4-B14-C30; | A4-B14-C31; | A4-B14-C32; |
| A4-B14-C33; | A4-B14-C34; | A4-B14-C35; | A4-B14-C36; | A4-B14-C37; | A4-B14-C38; |
| A4-B14-C39; | A4-B14-C40; | A4-B14-C41; | A4-B14-C42; | A4-B14-C43; | A4-B14-C44; |
| A4-B14-C45; | A4-B14-C46; | A5-B14-C1; | A5-B14-C2; | A5-B14-C3; | A5-B14-C4; |
| A5-B14-C5; | A5-B14-C6; | A5-B14-C7; | A5-B14-C8; | A5-B14-C9; | A5-B14-C10; |
| A5-B14-C11; | A5-B14-C12; | A5-B14-C13; | A5-B14-C14; | A5-B14-C15; | A5-B14-C16; |
| A5-B14-C17; | A5-B14-C18; | A5-B14-C19; | A5-B14-C20; | A5-B14-C21; | A5-B14-C22; |
| A5-B14-C23; | A5-B14-C24; | A5-B14-C25; | A5-B14-C26; | A5-B14-C27; | A5-B14-C28; |
| A5-B14-C29; | A5-B14-C30; | A5-B14-C31; | A5-B14-C32; | A5-B14-C33; | A5-B14-C34; |
| A5-B14-C35; | A5-B14-C36; | A5-B14-C37; | A5-B14-C38; | A5-B14-C39; | A5-B14-C40; |
| A5-B14-C41; | A5-B14-C42; | A5-B14-C43; | A5-B14-C44; | A5-B14-C45; | A5-B14-C46; |
| A6-B14-C1; | A6-B14-C2; | A6-B14-C3; | A6-B14-C4; | A6-B14-C5; | A6-B14-C6; |
| A6-B14-C7; | A6-B14-C8; | A6-B14-C9; | A6-B14-C10; | A6-B14-C11; | A6-B14-C12; |
| A6-B14-C13; | A6-B14-C14; | A6-B14-C15; | A6-B14-C16; | A6-B14-C17; | A6-B14-C18; |
| A6-B14-C19; | A6-B14-C20; | A6-B14-C21; | A6-B14-C22; | A6-B14-C23; | A6-B14-C24; |
| A6-B14-C25; | A6-B14-C26; | A6-B14-C27; | A6-B14-C28; | A6-B14-C29; | A6-B14-C30; |
| A6-B14-C31; | A6-B14-C32; | A6-B14-C33; | A6-B14-C34; | A6-B14-C35; | A6-B14-C36; |
| A6-B14-C37; | A6-B14-C38; | A6-B14-C39; | A6-B14-C40; | A6-B14-C41; | A6-B14-C42; |
| A6-B14-C43; | A6-B14-C44; | A6-B14-C45; | A6-B14-C46; | A7-B14-C1; | A7-B14-C2; |
| A7-B14-C3; | A7-B14-C4; | A7-B14-C5; | A7-B14-C6; | A7-B14-C7; | A7-B14-C8; |
| A7-B14-C9; | A7-B14-C10; | A7-B14-C11; | A7-B14-C12; | A7-B14-C13; | A7-B14-C14; |
| A7-B14-C15; | A7-B14-C16; | A7-B14-C17; | A7-B14-C18; | A7-B14-C19; | A7-B14-C20; |
| A7-B14-C21; | A7-B14-C22; | A7-B14-C23; | A7-B14-C24; | A7-B14-C25; | A7-B14-C26; |
| A7-B14-C27; | A7-B14-C28; | A7-B14-C29; | A7-B14-C30; | A7-B14-C31; | A7-B14-C32; |
| A7-B14-C33; | A7-B14-C34; | A7-B14-C35; | A7-B14-C36; | A7-B14-C37; | A7-B14-C38; |
| A7-B14-C39; | A7-B14-C40; | A7-B14-C41; | A7-B14-C42; | A7-B14-C43; | A7-B14-C44; |
| A7-B14-C45; | A7-B14-C46; | A8-B14-C1; | A8-B14-C2; | A8-B14-C3; | A8-B14-C4; |
| A8-B14-C5; | A8-B14-C6; | A8-B14-C7; | A8-B14-C8; | A8-B14-C9; | A8-B14-C10; |
| A8-B14-C11; | A8-B14-C12; | A8-B14-C13; | A8-B14-C14; | A8-B14-C15; | A8-B14-C16; |
| A8-B14-C17; | A8-B14-C18; | A8-B14-C19; | A8-B14-C20; | A8-B14-C21; | A8-B14-C22; |
| A8-B14-C23; | A8-B14-C24; | A8-B14-C25; | A8-B14-C26; | A8-B14-C27; | A8-B14-C28; |
| A8-B14-C29; | A8-B14-C30; | A8-B14-C31; | A8-B14-C32; | A8-B14-C33; | A8-B14-C34; |
| A8-B14-C35; | A8-B14-C36; | A8-B14-C37; | A8-B14-C38; | A8-B14-C39; | A8-B14-C40; |
| A8-B14-C41; | A8-B14-C42; | A8-B14-C43; | A8-B14-C44; | A8-B14-C45; | A8-B14-C46; |
| A9-B14-C1; | A9-B14-C2; | A9-B14-C3; | A9-B14-C4; | A9-B14-C5; | A9-B14-C6; |
| A9-B14-C7; | A9-B14-C8; | A9-B14-C9; | A9-B14-C10; | A9-B14-C11; | A9-B14-C12; |
| A9-B14-C13; | A9-B14-C14; | A9-B14-C15; | A9-B14-C16; | A9-B14-C17; | A9-B14-C18; |
| A9-B14-C19; | A9-B14-C20; | A9-B14-C21; | A9-B14-C22; | A9-B14-C23; | A9-B14-C24; |
| A9-B14-C25; | A9-B14-C26; | A9-B14-C27; | A9-B14-C28; | A9-B14-C29; | A9-B14-C30; |
| A9-B14-C31; | A9-B14-C32; | A9-B14-C33; | A9-B14-C34; | A9-B14-C35; | A9-B14-C36; |
| A9-B14-C37; | A9-B14-C38; | A9-B14-C39; | A9-B14-C40; | A9-B14-C41; | A9-B14-C42; |
| A9-B14-C43; | A9-B14-C44; | A9-B14-C45; | A9-B14-C46; | A10-B14-C1; | A10-B14-C2; |
| A10-B14-C3; | A10-B14-C4; | A10-B14-C5; | A10-B14-C6; | A10-B14-C7; | A10-B14-C8; |
| A10-B14-C9; | A10-B14-C10; | A10-B14-C11; | A10-B14-C12; | A10-B14-C13; | A10-B14-C14; |
| A10-B14-C15; | A10-B14-C16; | A10-B14-C17; | A10-B14-C18; | A10-B14-C19; | A10-B14-C20; |
| A10-B14-C21; | A10-B14-C22; | A10-B14-C23; | A10-B14-C24; | A10-B14-C25; | A10-B14-C26; |
| A10-B14-C27; | A10-B14-C28; | A10-B14-C29; | A10-B14-C30; | A10-B14-C31; | A10-B14-C32; |
| A10-B14-C33; | A10-B14-C34; | A10-B14-C35; | A10-B14-C36; | A10-B14-C37; | A10-B14-C38; |
| A10-B14-C39; | A10-B14-C40; | A10-B14-C41; | A10-B14-C42; | A10-B14-C43; | A10-B14-C44; |
| A10-B14-C45; | A10-B14-C46; | A11-B14-C1; | A11-B14-C2; | A11-B14-C3; | A11-B14-C4; |
| A11-B14-C5; | A11-B14-C6; | A11-B14-C7; | A11-B14-C8; | A11-B14-C9; | A11-B14-C10; |
| A11-B14-C11; | A11-B14-C12; | A11-B14-C13; | A11-B14-C14; | A11-B14-C15; | A11-B14-C16; |
| A11-B14-C17; | A11-B14-C18; | A11-B14-C19; | A11-B14-C20; | A11-B14-C21; | A11-B14-C22; |
| A11-B14-C23; | A11-B14-C24; | A11-B14-C25; | A11-B14-C26; | A11-B14-C27; | A11-B14-C28; |
| A11-B14-C29; | A11-B14-C30; | A11-B14-C31; | A11-B14-C32; | A11-B14-C33; | A11-B14-C34; |
| A11-B14-C35; | A11-B14-C36; | A11-B14-C37; | A11-B14-C38; | A11-B14-C39; | A11-B14-C40; |
| A11-B14-C41; | A11-B14-C42; | A11-B14-C43; | A11-B14-C44; | A11-B14-C45; | A11-B14-C46; |
| A12-B14-C1; | A12-B14-C2; | A12-B14-C3; | A12-B14-C4; | A12-B14-C5; | A12-B14-C6; |
| A12-B14-C7; | A12-B14-C8; | A12-B14-C9; | A12-B14-C10; | A12-B14-C11; | A12-B14-C12; |
| A12-B14-C13; | A12-B14-C14; | A12-B14-C15; | A12-B14-C16; | A12-B14-C17; | A12-B14-C18; |
| A12-B14-C19; | A12-B14-C20; | A12-B14-C21; | A12-B14-C22; | A12-B14-C23; | A12-B14-C24; |
| A12-B14-C25; | A12-B14-C26; | A12-B14-C27; | A12-B14-C28; | A12-B14-C29; | A12-B14-C30; |
| A12-B14-C31; | A12-B14-C32; | A12-B14-C33; | A12-B14-C34; | A12-B14-C35; | A12-B14-C36; |
| A12-B14-C37; | A12-B14-C38; | A12-B14-C39; | A12-B14-C40; | A12-B14-C41; | A12-B14-C42; |
| A12-B14-C43; | A12-B14-C44; | A12-B14-C45; | A12-B14-C46; | A13-B14-C1; | A13-B14-C2; |
| A13-B14-C3; | A13-B14-C4; | A13-B14-C5; | A13-B14-C6; | A13-B14-C7; | A13-B14-C8; |

-continued

| | | | | | |
|---|---|---|---|---|---|
| A13-B14-C9; | A13-B14-C10; | A13-B14-C11; | A13-B14-C12; | A13-B14-C13; | A13-B14-C14; |
| A13-B14-C15; | A13-B14-C16; | A13-B14-C17; | A13-B14-C18; | A13-B14-C19; | A13-B14-C20; |
| A13-B14-C21; | A13-B14-C22; | A13-B14-C23; | A13-B14-C24; | A13-B14-C25; | A13-B14-C26; |
| A13-B14-C27; | A13-B14-C28; | A13-B14-C29; | A13-B14-C30; | A13-B14-C31; | A13-B14-C32; |
| A13-B14-C33; | A13-B14-C34; | A13-B14-C35; | A13-B14-C36; | A13-B14-C37; | A13-B14-C38; |
| A13-B14-C39; | A13-B14-C40; | A13-B14-C41; | A13-B14-C42; | A13-B14-C43; | A13-B14-C44; |
| A13-B14-C45; | A13-B14-C46; | A14-B14-C1; | A14-B14-C2; | A14-B14-C3; | A14-B14-C4; |
| A14-B14-C5; | A14-B14-C6; | A14-B14-C7; | A14-B14-C8; | A14-B14-C9; | A14-B14-C10; |
| A14-B14-C11; | A14-B14-C12; | A14-B14-C13; | A14-B14-C14; | A14-B14-C15; | A14-B14-C16; |
| A14-B14-C17; | A14-B14-C18; | A14-B14-C19; | A14-B14-C20; | A14-B14-C21; | A14-B14-C22; |
| A14-B14-C23; | A14-B14-C24; | A14-B14-C25; | A14-B14-C26; | A14-B14-C27; | A14-B14-C28; |
| A14-B14-C29; | A14-B14-C30; | A14-B14-C31; | A14-B14-C32; | A14-B14-C33; | A14-B14-C34; |
| A14-B14-C35; | A14-B14-C36; | A14-B14-C37; | A14-B14-C38; | A14-B14-C39; | A14-B14-C40; |
| A14-B14-C41; | A14-B14-C42; | A14-B14-C43; | A14-B14-C44; | A14-B14-C45; | A14-B14-C46; |
| A15-B14-C1; | A15-B14-C2; | A15-B14-C3; | A15-B14-C4; | A15-B14-C5; | A15-B14-C6; |
| A15-B14-C7; | A15-B14-C8; | A15-B14-C9; | A15-B14-C10; | A15-B14-C11; | A15-B14-C12; |
| A15-B14-C13; | A15-B14-C14; | A15-B14-C15; | A15-B14-C16; | A15-B14-C17; | A15-B14-C18; |
| A15-B14-C19; | A15-B14-C20; | A15-B14-C21; | A15-B14-C22; | A15-B14-C23; | A15-B14-C24; |
| A15-B14-C25; | A15-B14-C26; | A15-B14-C27; | A15-B14-C28; | A15-B14-C29; | A15-B14-C30; |
| A15-B14-C31; | A15-B14-C32; | A15-B14-C33; | A15-B14-C34; | A15-B14-C35; | A15-B14-C36; |
| A15-B14-C37; | A15-B14-C38; | A15-B14-C39; | A15-B14-C40; | A15-B14-C41; | A15-B14-C42; |
| A15-B14-C43; | A15-B14-C44; | A15-B14-C45; | A15-B14-C46; | A16-B14-C1; | A16-B14-C2; |
| A16-B14-C3; | A16-B14-C4; | A16-B14-C5; | A16-B14-C6; | A16-B14-C7; | A16-B14-C8; |
| A16-B14-C9; | A16-B14-C10; | A16-B14-C11; | A16-B14-C12; | A16-B14-C13; | A16-B14-C14; |
| A16-B14-C15; | A16-B14-C16; | A16-B14-C17; | A16-B14-C18; | A16-B14-C19; | A16-B14-C20; |
| A16-B14-C21; | A16-B14-C22; | A16-B14-C23; | A16-B14-C24; | A16-B14-C25; | A16-B14-C26; |
| A16-B14-C27; | A16-B14-C28; | A16-B14-C29; | A16-B14-C30; | A16-B14-C31; | A16-B14-C32; |
| A16-B14-C33; | A16-B14-C34; | A16-B14-C35; | A16-B14-C36; | A16-B14-C37; | A16-B14-C38; |
| A16-B14-C39; | A16-B14-C40; | A16-B14-C41; | A16-B14-C42; | A16-B14-C43; | A16-B14-C44; |
| A16-B14-C45; | A16-B14-C46; | A17-B14-C1; | A17-B14-C2; | A17-B14-C3; | A17-B14-C4; |
| A17-B14-C5; | A17-B14-C6; | A17-B14-C7; | A17-B14-C8; | A17-B14-C9; | A17-B14-C10; |
| A17-B14-C11; | A17-B14-C12; | A17-B14-C13; | A17-B14-C14; | A17-B14-C15; | A17-B14-C16; |
| A17-B14-C17; | A17-B14-C18; | A17-B14-C19; | A17-B14-C20; | A17-B14-C21; | A17-B14-C22; |
| A17-B14-C23; | A17-B14-C24; | A17-B14-C25; | A17-B14-C26; | A17-B14-C27; | A17-B14-C28; |
| A17-B14-C29; | A17-B14-C30; | A17-B14-C31; | A17-B14-C32; | A17-B14-C33; | A17-B14-C34; |
| A17-B14-C35; | A17-B14-C36; | A17-B14-C37; | A17-B14-C38; | A17-B14-C39; | A17-B14-C40; |
| A17-B14-C41; | A17-B14-C42; | A17-B14-C43; | A17-B14-C44; | A17-B14-C45; | A17-B14-C46; |
| A18-B14-C1; | A18-B14-C2; | A18-B14-C3; | A18-B14-C4; | A18-B14-C5; | A18-B14-C6; |
| A18-B14-C7; | A18-B14-C8; | A18-B14-C9; | A18-B14-C10; | A18-B14-C11; | A18-B14-C12; |
| A18-B14-C13; | A18-B14-C14; | A18-B14-C15; | A18-B14-C16; | A18-B14-C17; | A18-B14-C18; |
| A18-B14-C19; | A18-B14-C20; | A18-B14-C21; | A18-B14-C22; | A18-B14-C23; | A18-B14-C24; |
| A18-B14-C25; | A18-B14-C26; | A18-B14-C27; | A18-B14-C28; | A18-B14-C29; | A18-B14-C30; |
| A18-B14-C31; | A18-B14-C32; | A18-B14-C33; | A18-B14-C34; | A18-B14-C35; | A18-B14-C36; |
| A18-B14-C37; | A18-B14-C38; | A18-B14-C39; | A18-B14-C40; | A18-B14-C41; | A18-B14-C42; |
| A18-B14-C43; | A18-B14-C44; | A18-B14-C45; | A18-B14-C46; | A19-B14-C1; | A19-B14-C2; |
| A19-B14-C3; | A19-B14-C4; | A19-B14-C5; | A19-B14-C6; | A19-B14-C7; | A19-B14-C8; |
| A19-B14-C9; | A19-B14-C10; | A19-B14-C11; | A19-B14-C12; | A19-B14-C13; | A19-B14-C14; |
| A19-B14-C15; | A19-B14-C16; | A19-B14-C17; | A19-B14-C18; | A19-B14-C19; | A19-B14-C20; |
| A19-B14-C21; | A19-B14-C22; | A19-B14-C23; | A19-B14-C24; | A19-B14-C25; | A19-B14-C26; |
| A19-B14-C27; | A19-B14-C28; | A19-B14-C29; | A19-B14-C30; | A19-B14-C31; | A19-B14-C32; |
| A19-B14-C33; | A19-B14-C34; | A19-B14-C35; | A19-B14-C36; | A19-B14-C37; | A19-B14-C38; |
| A19-B14-C39; | A19-B14-C40; | A19-B14-C41; | A19-B14-C42; | A19-B14-C43; | A19-B14-C44; |
| A19-B14-C45; | A19-B14-C46; | A20-B14-C1; | A20-B14-C2; | A20-B14-C3; | A20-B14-C4; |
| A20-B14-C5; | A20-B14-C6; | A20-B14-C7; | A20-B14-C8; | A20-B14-C9; | A20-B14-C10; |
| A20-B14-C11; | A20-B14-C12; | A20-B14-C13; | A20-B14-C14; | A20-B14-C15; | A20-B14-C16; |
| A20-B14-C17; | A20-B14-C18; | A20-B14-C19; | A20-B14-C20; | A20-B14-C21; | A20-B14-C22; |
| A20-B14-C23; | A20-B14-C24; | A20-B14-C25; | A20-B14-C26; | A20-B14-C27; | A20-B14-C28; |
| A20-B14-C29; | A20-B14-C30; | A20-B14-C31; | A20-B14-C32; | A20-B14-C33; | A20-B14-C34; |
| A20-B14-C35; | A20-B14-C36; | A20-B14-C37; | A20-B14-C38; | A20-B14-C39; | A20-B14-C40; |
| A20-B14-C41; | A20-B14-C42; | A20-B14-C43; | A20-B14-C44; | A20-B14-C45; | A20-B14-C46; |
| A21-B14-C1; | A21-B14-C2; | A21-B14-C3; | A21-B14-C4; | A21-B14-C5; | A21-B14-C6; |
| A21-B14-C7; | A21-B14-C8; | A21-B14-C9; | A21-B14-C10; | A21-B14-C11; | A21-B14-C12; |
| A21-B14-C13; | A21-B14-C14; | A21-B14-C15; | A21-B14-C16; | A21-B14-C17; | A21-B14-C18; |
| A21-B14-C19; | A21-B14-C20; | A21-B14-C21; | A21-B14-C22; | A21-B14-C23; | A21-B14-C24; |
| A21-B14-C25; | A21-B14-C26; | A21-B14-C27; | A21-B14-C28; | A21-B14-C29; | A21-B14-C30; |
| A21-B14-C31; | A21-B14-C32; | A21-B14-C33; | A21-B14-C34; | A21-B14-C35; | A21-B14-C36; |
| A21-B14-C37; | A21-B14-C38; | A21-B14-C39; | A21-B14-C40; | A21-B14-C41; | A21-B14-C42; |
| A21-B14-C43; | A21-B14-C44; | A21-B14-C45; | A21-B14-C46; | A22-B14-C1; | A22-B14-C2; |
| A22-B14-C3; | A22-B14-C4; | A22-B14-C5; | A22-B14-C6; | A22-B14-C7; | A22-B14-C8; |
| A22-B14-C9; | A22-B14-C10; | A22-B14-C11; | A22-B14-C12; | A22-B14-C13; | A22-B14-C14; |
| A22-B14-C15; | A22-B14-C16; | A22-B14-C17; | A22-B14-C18; | A22-B14-C19; | A22-B14-C20; |
| A22-B14-C21; | A22-B14-C22; | A22-B14-C23; | A22-B14-C24; | A22-B14-C25; | A22-B14-C26; |
| A22-B14-C27; | A22-B14-C28; | A22-B14-C29; | A22-B14-C30; | A22-B14-C31; | A22-B14-C32; |
| A22-B14-C33; | A22-B14-C34; | A22-B14-C35; | A22-B14-C36; | A22-B14-C37; | A22-B14-C38; |
| A22-B14-C39; | A22-B14-C40; | A22-B14-C41; | A22-B14-C42; | A22-B14-C43; | A22-B14-C44; |
| A22-B14-C45; | A22-B14-C46; | A23-B14-C1; | A23-B14-C2; | A23-B14-C3; | A23-B14-C4; |
| A23-B14-C5; | A23-B14-C6; | A23-B14-C7; | A23-B14-C8; | A23-B14-C9; | A23-B14-C10; |
| A23-B14-C11; | A23-B14-C12; | A23-B14-C13; | A23-B14-C14; | A23-B14-C15; | A23-B14-C16; |
| A23-B14-C17; | A23-B14-C18; | A23-B14-C19; | A23-B14-C20; | A23-B14-C21; | A23-B14-C22; |

-continued

A23-B14-C23; A23-B14-C24; A23-B14-C25; A23-B14-C26; A23-B14-C27; A23-B14-C28;
A23-B14-C29; A23-B14-C30; A23-B14-C31; A23-B14-C32; A23-B14-C33; A23-B14-C34;
A23-B14-C35; A23-B14-C36; A23-B14-C37; A23-B14-C38; A23-B14-C39; A23-B14-C40;
A23-B14-C41; A23-B14-C42; A23-B14-C43; A23-B14-C44; A23-B14-C45; A23-B14-C46;
A24-B14-C1; A24-B14-C2; A24-B14-C3; A24-B14-C4; A24-B14-C5; A24-B14-C6;
A24-B14-C7; A24-B14-C8; A24-B14-C9; A24-B14-C10; A24-B14-C11; A24-B14-C12;
A24-B14-C13; A24-B14-C14; A24-B14-C15; A24-B14-C16; A24-B14-C17; A24-B14-C18;
A24-B14-C19; A24-B14-C20; A24-B14-C21; A24-B14-C22; A24-B14-C23; A24-B14-C24;
A24-B14-C25; A24-B14-C26; A24-B14-C27; A24-B14-C28; A24-B14-C29; A24-B14-C30;
A24-B14-C31; A24-B14-C32; A24-B14-C33; A24-B14-C34; A24-B14-C35; A24-B14-C36;
A24-B14-C37; A24-B14-C38; A24-B14-C39; A24-B14-C40; A24-B14-C41; A24-B14-C42;
A24-B14-C43; A24-B14-C44; A24-B14-C45; A24-B14-C46; A25-B14-C1; A25-B14-C2;
A25-B14-C3; A25-B14-C4; A25-B14-C5; A25-B14-C6; A25-B14-C7; A25-B14-C8;
A25-B14-C9; A25-B14-C10; A25-B14-C11; A25-B14-C12; A25-B14-C13; A25-B14-C14;
A25-B14-C15; A25-B14-C16; A25-B14-C17; A25-B14-C18; A25-B14-C19; A25-B14-C20;
A25-B14-C21; A25-B14-C22; A25-B14-C23; A25-B14-C24; A25-B14-C25; A25-B14-C26;
A25-B14-C27; A25-B14-C28; A25-B14-C29; A25-B14-C30; A25-B14-C31; A25-B14-C32;
A25-B14-C33; A25-B14-C34; A25-B14-C35; A25-B14-C36; A25-B14-C37; A25-B14-C38;
A25-B14-C39; A25-B14-C40; A25-B14-C41; A25-B14-C42; A25-B14-C43; A25-B14-C44;
A25-B14-C45; A25-B14-C46; A26-B14-C1; A26-B14-C2; A26-B14-C3; A26-B14-C4;
A26-B14-C5; A26-B14-C6; A26-B14-C7; A26-B14-C8; A26-B14-C9; A26-B14-C10;
A26-B14-C11; A26-B14-C12; A26-B14-C13; A26-B14-C14; A26-B14-C15; A26-B14-C16;
A26-B14-C17; A26-B14-C18; A26-B14-C19; A26-B14-C20; A26-B14-C21; A26-B14-C22;
A26-B14-C23; A26-B14-C24; A26-B14-C25; A26-B14-C26; A26-B14-C27; A26-B14-C28;
A26-B14-C29; A26-B14-C30; A26-B14-C31; A26-B14-C32; A26-B14-C33; A26-B14-C34;
A26-B14-C35; A26-B14-C36; A26-B14-C37; A26-B14-C38; A26-B14-C39; A26-B14-C40;
A26-B14-C41; A26-B14-C42; A26-B14-C43; A26-B14-C44; A26-B14-C45; A26-B14-C46;
A27-B14-C1; A27-B14-C2; A27-B14-C3; A27-B14-C4; A27-B14-C5; A27-B14-C6;
A27-B14-C7; A27-B14-C8; A27-B14-C9; A27-B14-C10; A27-B14-C11; A27-B14-C12;
A27-B14-C13; A27-B14-C14; A27-B14-C15; A27-B14-C16; A27-B14-C17; A27-B14-C18;
A27-B14-C19; A27-B14-C20; A27-B14-C21; A27-B14-C22; A27-B14-C23; A27-B14-C24;
A27-B14-C25; A27-B14-C26; A27-B14-C27; A27-B14-C28; A27-B14-C29; A27-B14-C30;
A27-B14-C31; A27-B14-C32; A27-B14-C33; A27-B14-C34; A27-B14-C35; A27-B14-C36;
A27-B14-C37; A27-B14-C38; A27-B14-C39; A27-B14-C40; A27-B14-C41; A27-B14-C42;
A27-B14-C43; A27-B14-C44; A27-B14-C45; A27-B14-C46; A28-B14-C1; A28-B14-C2;
A28-B14-C3; A28-B14-C4; A28-B14-C5; A28-B14-C6; A28-B14-C7; A28-B14-C8;
A28-B14-C9; A28-B14-C10; A28-B14-C11; A28-B14-C12; A28-B14-C13; A28-B14-C14;
A28-B14-C15; A28-B14-C16; A28-B14-C17; A28-B14-C18; A28-B14-C19; A28-B14-C20;
A28-B14-C21; A28-B14-C22; A28-B14-C23; A28-B14-C24; A28-B14-C25; A28-B14-C26;
A28-B14-C27; A28-B14-C28; A28-B14-C29; A28-B14-C30; A28-B14-C31; A28-B14-C32;
A28-B14-C33; A28-B14-C34; A28-B14-C35; A28-B14-C36; A28-B14-C37; A28-B14-C38;
A28-B14-C39; A28-B14-C40; A28-B14-C41; A28-B14-C42; A28-B14-C43; A28-B14-C44;
A28-B14-C45; A28-B14-C46; A1-B15-C1; A1-B15-C2; A1-B15-C3; A1-B15-C4;
A1-B15-C5; A1-B15-C6; A1-B15-C7; A1-B15-C8; A1-B15-C9; A1-B15-C10;
A1-B15-C11; A1-B15-C12; A1-B15-C13; A1-B15-C14; A1-B15-C15; A1-B15-C16;
A1-B15-C17; A1-B15-C18; A1-B15-C19; A1-B15-C20; A1-B15-C21; A1-B15-C22;
A1-B15-C23; A1-B15-C24; A1-B15-C25; A1-B15-C26; A1-B15-C27; A1-B15-C28;
A1-B15-C29; A1-B15-C30; A1-B15-C31; A1-B15-C32; A1-B15-C33; A1-B15-C34;
A1-B15-C35; A1-B15-C36; A1-B15-C37; A1-B15-C38; A1-B15-C39; A1-B15-C40;
A1-B15-C41; A1-B15-C42; A1-B15-C43; A1-B15-C44; A1-B15-C45; A1-B15-C46;
A2-B15-C1; A2-B15-C2; A2-B15-C3; A2-B15-C4; A2-B15-C5; A2-B15-C6;
A2-B15-C7; A2-B15-C8; A2-B15-C9; A2-B15-C10; A2-B15-C11; A2-B15-C12;
A2-B15-C13; A2-B15-C14; A2-B15-C15; A2-B15-C16; A2-B15-C17; A2-B15-C18;
A2-B15-C19; A2-B15-C20; A2-B15-C21; A2-B15-C22; A2-B15-C23; A2-B15-C24;
A2-B15-C25; A2-B15-C26; A2-B15-C27; A2-B15-C28; A2-B15-C29; A2-B15-C30;
A2-B15-C31; A2-B15-C32; A2-B15-C33; A2-B15-C34; A2-B15-C35; A2-B15-C36;
A2-B15-C37; A2-B15-C38; A2-B15-C39; A2-B15-C40; A2-B15-C41; A2-B15-C42;
A2-B15-C43; A2-B15-C44; A2-B15-C45; A2-B15-C46; A3-B15-C1; A3-B15-C2;
A3-B15-C3; A3-B15-C4; A3-B15-C5; A3-B15-C6; A3-B15-C7; A3-B15-C8;
A3-B15-C9; A3-B15-C10; A3-B15-C11; A3-B15-C12; A3-B15-C13; A3-B15-C14;
A3-B15-C15; A3-B15-C16; A3-B15-C17; A3-B15-C18; A3-B15-C19; A3-B15-C20;
A3-B15-C21; A3-B15-C22; A3-B15-C23; A3-B15-C24; A3-B15-C25; A3-B15-C26;
A3-B15-C27; A3-B15-C28; A3-B15-C29; A3-B15-C30; A3-B15-C31; A3-B15-C32;
A3-B15-C33; A3-B15-C34; A3-B15-C35; A3-B15-C36; A3-B15-C37; A3-B15-C38;
A3-B15-C39; A3-B15-C40; A3-B15-C41; A3-B15-C42; A3-B15-C43; A3-B15-C44;
A3-B15-C45; A3-B15-C46; A4-B15-C1; A4-B15-C2; A4-B15-C3; A4-B15-C4;
A4-B15-C5; A4-B15-C6; A4-B15-C7; A4-B15-C8; A4-B15-C9; A4-B15-C10;
A4-B15-C11; A4-B15-C12; A4-B15-C13; A4-B15-C14; A4-B15-C15; A4-B15-C16;
A4-B15-C17; A4-B15-C18; A4-B15-C19; A4-B15-C20; A4-B15-C21; A4-B15-C22;
A4-B15-C23; A4-B15-C24; A4-B15-C25; A4-B15-C26; A4-B15-C27; A4-B15-C28;
A4-B15-C29; A4-B15-C30; A4-B15-C31; A4-B15-C32; A4-B15-C33; A4-B15-C34;
A4-B15-C35; A4-B15-C36; A4-B15-C37; A4-B15-C38; A4-B15-C39; A4-B15-C40;
A4-B15-C41; A4-B15-C42; A4-B15-C43; A4-B15-C44; A4-B15-C45; A4-B15-C46;
A5-B15-C1; A5-B15-C2; A5-B15-C3; A5-B15-C4; A5-B15-C5; A5-B15-C6;
A5-B15-C7; A5-B15-C8; A5-B15-C9; A5-B15-C10; A5-B15-C11; A5-B15-C12;
A5-B15-C13; A5-B15-C14; A5-B15-C15; A5-B15-C16; A5-B15-C17; A5-B15-C18;
A5-B15-C19; A5-B15-C20; A5-B15-C21; A5-B15-C22; A5-B15-C23; A5-B15-C24;
A5-B15-C25; A5-B15-C26; A5-B15-C27; A5-B15-C28; A5-B15-C29; A5-B15-C30;
A5-B15-C31; A5-B15-C32; A5-B15-C33; A5-B15-C34; A5-B15-C35; A5-B15-C36;

-continued

A5-B15-C37; A5-B15-C38; A5-B15-C39; A5-B15-C40; A5-B15-C41; A5-B15-C42;
A5-B15-C43; A5-B15-C44; A5-B15-C45; A5-B15-C46; A6-B15-C1; A6-B15-C2;
A6-B15-C3; A6-B15-C4; A6-B15-C5; A6-B15-C6; A6-B15-C7; A6-B15-C8;
A6-B15-C9; A6-B15-C10; A6-B15-C11; A6-B15-C12; A6-B15-C13; A6-B15-C14;
A6-B15-C15; A6-B15-C16; A6-B15-C17; A6-B15-C18; A6-B15-C19; A6-B15-C20;
A6-B15-C21; A6-B15-C22; A6-B15-C23; A6-B15-C24; A6-B15-C25; A6-B15-C26;
A6-B15-C27; A6-B15-C28; A6-B15-C29; A6-B15-C30; A6-B15-C31; A6-B15-C32;
A6-B15-C33; A6-B15-C34; A6-B15-C35; A6-B15-C36; A6-B15-C37; A6-B15-C38;
A6-B15-C39; A6-B15-C40; A6-B15-C41; A6-B15-C42; A6-B15-C43; A6-B15-C44;
A6-B15-C45; A6-B15-C46; A7-B15-C1; A7-B15-C2; A7-B15-C3; A7-B15-C4;
A7-B15-C5; A7-B15-C6; A7-B15-C7; A7-B15-C8; A7-B15-C9; A7-B15-C10;
A7-B15-C11; A7-B15-C12; A7-B15-C13; A7-B15-C14; A7-B15-C15; A7-B15-C16;
A7-B15-C17; A7-B15-C18; A7-B15-C19; A7-B15-C20; A7-B15-C21; A7-B15-C22;
A7-B15-C23; A7-B15-C24; A7-B15-C25; A7-B15-C26; A7-B15-C27; A7-B15-C28;
A7-B15-C29; A7-B15-C30; A7-B15-C31; A7-B15-C32; A7-B15-C33; A7-B15-C34;
A7-B15-C35; A7-B15-C36; A7-B15-C37; A7-B15-C38; A7-B15-C39; A7-B15-C40;
A7-B15-C41; A7-B15-C42; A7-B15-C43; A7-B15-C44; A7-B15-C45; A7-B15-C46;
A8-B15-C1; A8-B15-C2; A8-B15-C3; A8-B15-C4; A8-B15-C5; A8-B15-C6;
A8-B15-C7; A8-B15-C8; A8-B15-C9; A8-B15-C10; A8-B15-C11; A8-B15-C12;
A8-B15-C13; A8-B15-C14; A8-B15-C15; A8-B15-C16; A8-B15-C17; A8-B15-C18;
A8-B15-C19; A8-B15-C20; A8-B15-C21; A8-B15-C22; A8-B15-C23; A8-B15-C24;
A8-B15-C25; A8-B15-C26; A8-B15-C27; A8-B15-C28; A8-B15-C29; A8-B15-C30;
A8-B15-C31; A8-B15-C32; A8-B15-C33; A8-B15-C34; A8-B15-C35; A8-B15-C36;
A8-B15-C37; A8-B15-C38; A8-B15-C39; A8-B15-C40; A8-B15-C41; A8-B15-C42;
A8-B15-C43; A8-B15-C44; A8-B15-C45; A8-B15-C46; A9-B15-C1; A9-B15-C2;
A9-B15-C3; A9-B15-C4; A9-B15-C5; A9-B15-C6; A9-B15-C7; A9-B15-C8;
A9-B15-C9; A9-B15-C10; A9-B15-C11; A9-B15-C12; A9-B15-C13; A9-B15-C14;
A9-B15-C15; A9-B15-C16; A9-B15-C17; A9-B15-C18; A9-B15-C19; A9-B15-C20;
A9-B15-C21; A9-B15-C22; A9-B15-C23; A9-B15-C24; A9-B15-C25; A9-B15-C26;
A9-B15-C27; A9-B15-C28; A9-B15-C29; A9-B15-C30; A9-B15-C31; A9-B15-C32;
A9-B15-C33; A9-B15-C34; A9-B15-C35; A9-B15-C36; A9-B15-C37; A9-B15-C38;
A9-B15-C39; A9-B15-C40; A9-B15-C41; A9-B15-C42; A9-B15-C43; A9-B15-C44;
A9-B15-C45; A9-B15-C46; A10-B15-C1; A10-B15-C2; A10-B15-C3; A10-B15-C4;
A10-B15-C5; A10-B15-C6; A10-B15-C7; A10-B15-C8; A10-B15-C9; A10-B15-C10;
A10-B15-C11; A10-B15-C12; A10-B15-C13; A10-B15-C14; A10-B15-C15; A10-B15-C16;
A10-B15-C17; A10-B15-C18; A10-B15-C19; A10-B15-C20; A10-B15-C21; A10-B15-C22;
A10-B15-C23; A10-B15-C24; A10-B15-C25; A10-B15-C26; A10-B15-C27; A10-B15-C28;
A10-B15-C29; A10-B15-C30; A10-B15-C31; A10-B15-C32; A10-B15-C33; A10-B15-C34;
A10-B15-C35; A10-B15-C36; A10-B15-C37; A10-B15-C38; A10-B15-C39; A10-B15-C40;
A10-B15-C41; A10-B15-C42; A10-B15-C43; A10-B15-C44; A10-B15-C45; A10-B15-C46;
A11-B15-C1; A11-B15-C2; A11-B15-C3; A11-B15-C4; A11-B15-C5; A11-B15-C6;
A11-B15-C7; A11-B15-C8; A11-B15-C9; A11-B15-C10; A11-B15-C11; A11-B15-C12;
A11-B15-C13; A11-B15-C14; A11-B15-C15; A11-B15-C16; A11-B15-C17; A11-B15-C18;
A11-B15-C19; A11-B15-C20; A11-B15-C21; A11-B15-C22; A11-B15-C23; A11-B15-C24;
A11-B15-C25; A11-B15-C26; A11-B15-C27; A11-B15-C28; A11-B15-C29; A11-B15-C30;
A11-B15-C31; A11-B15-C32; A11-B15-C33; A11-B15-C34; A11-B15-C35; A11-B15-C36;
A11-B15-C37; A11-B15-C38; A11-B15-C39; A11-B15-C40; A11-B15-C41; A11-B15-C42;
A11-B15-C43; A11-B15-C44; A11-B15-C45; A11-B15-C46; A12-B15-C1; A12-B15-C2;
A12-B15-C3; A12-B15-C4; A12-B15-C5; A12-B15-C6; A12-B15-C7; A12-B15-C8;
A12-B15-C9; A12-B15-C10; A12-B15-C11; A12-B15-C12; A12-B15-C13; A12-B15-C14;
A12-B15-C15; A12-B15-C16; A12-B15-C17; A12-B15-C18; A12-B15-C19; A12-B15-C20;
A12-B15-C21; A12-B15-C22; A12-B15-C23; A12-B15-C24; A12-B15-C25; A12-B15-C26;
A12-B15-C27; A12-B15-C28; A12-B15-C29; A12-B15-C30; A12-B15-C31; A12-B15-C32;
A12-B15-C33; A12-B15-C34; A12-B15-C35; A12-B15-C36; A12-B15-C37; A12-B15-C38;
A12-B15-C39; A12-B15-C40; A12-B15-C41; A12-B15-C42; A12-B15-C43; A12-B15-C44;
A12-B15-C45; A12-B15-C46; A13-B15-C1; A13-B15-C2; A13-B15-C3; A13-B15-C4;
A13-B15-C5; A13-B15-C6; A13-B15-C7; A13-B15-C8; A13-B15-C9; A13-B15-C10;
A13-B15-C11; A13-B15-C12; A13-B15-C13; A13-B15-C14; A13-B15-C15; A13-B15-C16;
A13-B15-C17; A13-B15-C18; A13-B15-C19; A13-B15-C20; A13-B15-C21; A13-B15-C22;
A13-B15-C23; A13-B15-C24; A13-B15-C25; A13-B15-C26; A13-B15-C27; A13-B15-C28;
A13-B15-C29; A13-B15-C30; A13-B15-C31; A13-B15-C32; A13-B15-C33; A13-B15-C34;
A13-B15-C35; A13-B15-C36; A13-B15-C37; A13-B15-C38; A13-B15-C39; A13-B15-C40;
A13-B15-C41; A13-B15-C42; A13-B15-C43; A13-B15-C44; A13-B15-C45; A13-B15-C46;
A14-B15-C1; A14-B15-C2; A14-B15-C3; A14-B15-C4; A14-B15-C5; A14-B15-C6;
A14-B15-C7; A14-B15-C8; A14-B15-C9; A14-B15-C10; A14-B15-C11; A14-B15-C12;
A14-B15-C13; A14-B15-C14; A14-B15-C15; A14-B15-C16; A14-B15-C17; A14-B15-C18;
A14-B15-C19; A14-B15-C20; A14-B15-C21; A14-B15-C22; A14-B15-C23; A14-B15-C24;
A14-B15-C25; A14-B15-C26; A14-B15-C27; A14-B15-C28; A14-B15-C29; A14-B15-C30;
A14-B15-C31; A14-B15-C32; A14-B15-C33; A14-B15-C34; A14-B15-C35; A14-B15-C36;
A14-B15-C37; A14-B15-C38; A14-B15-C39; A14-B15-C40; A14-B15-C41; A14-B15-C42;
A14-B15-C43; A14-B15-C44; A14-B15-C45; A14-B15-C46; A15-B15-C1; A15-B15-C2;
A15-B15-C3; A15-B15-C4; A15-B15-C5; A15-B15-C6; A15-B15-C7; A15-B15-C8;
A15-B15-C9; A15-B15-C10; A15-B15-C11; A15-B15-C12; A15-B15-C13; A15-B15-C14;
A15-B15-C15; A15-B15-C16; A15-B15-C17; A15-B15-C18; A15-B15-C19; A15-B15-C20;
A15-B15-C21; A15-B15-C22; A15-B15-C23; A15-B15-C24; A15-B15-C25; A15-B15-C26;
A15-B15-C27; A15-B15-C28; A15-B15-C29; A15-B15-C30; A15-B15-C31; A15-B15-C32;
A15-B15-C33; A15-B15-C34; A15-B15-C35; A15-B15-C36; A15-B15-C37; A15-B15-C38;
A15-B15-C39; A15-B15-C40; A15-B15-C41; A15-B15-C42; A15-B15-C43; A15-B15-C44;
A15-B15-C45; A15-B15-C46; A16-B15-C1; A16-B15-C2; A16-B15-C3; A16-B15-C4;

-continued

| | | | | | |
|---|---|---|---|---|---|
| A16-B15-C5; | A16-B15-C6; | A16-B15-C7; | A16-B15-C8; | A16-B15-C9; | A16-B15-C10; |
| A16-B15-C11; | A16-B15-C12; | A16-B15-C13; | A16-B15-C14; | A16-B15-C15; | A16-B15-C16; |
| A16-B15-C17; | A16-B15-C18; | A16-B15-C19; | A16-B15-C20; | A16-B15-C21; | A16-B15-C22; |
| A16-B15-C23; | A16-B15-C24; | A16-B15-C25; | A16-B15-C26; | A16-B15-C27; | A16-B15-C28; |
| A16-B15-C29; | A16-B15-C30; | A16-B15-C31; | A16-B15-C32; | A16-B15-C33; | A16-B15-C34; |
| A16-B15-C35; | A16-B15-C36; | A16-B15-C37; | A16-B15-C38; | A16-B15-C39; | A16-B15-C40; |
| A16-B15-C41; | A16-B15-C42; | A16-B15-C43; | A16-B15-C44; | A16-B15-C45; | A16-B15-C46; |
| A17-B15-C1; | A17-B15-C2; | A17-B15-C3; | A17-B15-C4; | A17-B15-C5; | A17-B15-C6; |
| A17-B15-C7; | A17-B15-C8; | A17-B15-C9; | A17-B15-C10; | A17-B15-C11; | A17-B15-C12; |
| A17-B15-C13; | A17-B15-C14; | A17-B15-C15; | A17-B15-C16; | A17-B15-C17; | A17-B15-C18; |
| A17-B15-C19; | A17-B15-C20; | A17-B15-C21; | A17-B15-C22; | A17-B15-C23; | A17-B15-C24; |
| A17-B15-C25; | A17-B15-C26; | A17-B15-C27; | A17-B15-C28; | A17-B15-C29; | A17-B15-C30; |
| A17-B15-C31; | A17-B15-C32; | A17-B15-C33; | A17-B15-C34; | A17-B15-C35; | A17-B15-C36; |
| A17-B15-C37; | A17-B15-C38; | A17-B15-C39; | A17-B15-C40; | A17-B15-C41; | A17-B15-C42; |
| A17-B15-C43; | A17-B15-C44; | A17-B15-C45; | A17-B15-C46; | A18-B15-C1; | A18-B15-C2; |
| A18-B15-C3; | A18-B15-C4; | A18-B15-C5; | A18-B15-C6; | A18-B15-C7; | A18-B15-C8; |
| A18-B15-C9; | A18-B15-C10; | A18-B15-C11; | A18-B15-C12; | A18-B15-C13; | A18-B15-C14; |
| A18-B15-C15; | A18-B15-C16; | A18-B15-C17; | A18-B15-C18; | A18-B15-C19; | A18-B15-C20; |
| A18-B15-C21; | A18-B15-C22; | A18-B15-C23; | A18-B15-C24; | A18-B15-C25; | A18-B15-C26; |
| A18-B15-C27; | A18-B15-C28; | A18-B15-C29; | A18-B15-C30; | A18-B15-C31; | A18-B15-C32; |
| A18-B15-C33; | A18-B15-C34; | A18-B15-C35; | A18-B15-C36; | A18-B15-C37; | A18-B15-C38; |
| A18-B15-C39; | A18-B15-C40; | A18-B15-C41; | A18-B15-C42; | A18-B15-C43; | A18-B15-C44; |
| A18-B15-C45; | A18-B15-C46; | A19-B15-C1; | A19-B15-C2; | A19-B15-C3; | A19-B15-C4; |
| A19-B15-C5; | A19-B15-C6; | A19-B15-C7; | A19-B15-C8; | A19-B15-C9; | A19-B15-C10; |
| A19-B15-C11; | A19-B15-C12; | A19-B15-C13; | A19-B15-C14; | A19-B15-C15; | A19-B15-C16; |
| A19-B15-C17; | A19-B15-C18; | A19-B15-C19; | A19-B15-C20; | A19-B15-C21; | A19-B15-C22; |
| A19-B15-C23; | A19-B15-C24; | A19-B15-C25; | A19-B15-C26; | A19-B15-C27; | A19-B15-C28; |
| A19-B15-C29; | A19-B15-C30; | A19-B15-C31; | A19-B15-C32; | A19-B15-C33; | A19-B15-C34; |
| A19-B15-C35; | A19-B15-C36; | A19-B15-C37; | A19-B15-C38; | A19-B15-C39; | A19-B15-C40; |
| A19-B15-C41; | A19-B15-C42; | A19-B15-C43; | A19-B15-C44; | A19-B15-C45; | A19-B15-C46; |
| A20-B15-C1; | A20-B15-C2; | A20-B15-C3; | A20-B15-C4; | A20-B15-C5; | A20-B15-C6; |
| A20-B15-C7; | A20-B15-C8; | A20-B15-C9; | A20-B15-C10; | A20-B15-C11; | A20-B15-C12; |
| A20-B15-C13; | A20-B15-C14; | A20-B15-C15; | A20-B15-C16; | A20-B15-C17; | A20-B15-C18; |
| A20-B15-C19; | A20-B15-C20; | A20-B15-C21; | A20-B15-C22; | A20-B15-C23; | A20-B15-C24; |
| A20-B15-C25; | A20-B15-C26; | A20-B15-C27; | A20-B15-C28; | A20-B15-C29; | A20-B15-C30; |
| A20-B15-C31; | A20-B15-C32; | A20-B15-C33; | A20-B15-C34; | A20-B15-C35; | A20-B15-C36; |
| A20-B15-C37; | A20-B15-C38; | A20-B15-C39; | A20-B15-C40; | A20-B15-C41; | A20-B15-C42; |
| A20-B15-C43; | A20-B15-C44; | A20-B15-C45; | A20-B15-C46; | A21-B15-C1; | A21-B15-C2; |
| A21-B15-C3; | A21-B15-C4; | A21-B15-C5; | A21-B15-C6; | A21-B15-C7; | A21-B15-C8; |
| A21-B15-C9; | A21-B15-C10; | A21-B15-C11; | A21-B15-C12; | A21-B15-C13; | A21-B15-C14; |
| A21-B15-C15; | A21-B15-C16; | A21-B15-C17; | A21-B15-C18; | A21-B15-C19; | A21-B15-C20; |
| A21-B15-C21; | A21-B15-C22; | A21-B15-C23; | A21-B15-C24; | A21-B15-C25; | A21-B15-C26; |
| A21-B15-C27; | A21-B15-C28; | A21-B15-C29; | A21-B15-C30; | A21-B15-C31; | A21-B15-C32; |
| A21-B15-C33; | A21-B15-C34; | A21-B15-C35; | A21-B15-C36; | A21-B15-C37; | A21-B15-C38; |
| A21-B15-C39; | A21-B15-C40; | A21-B15-C41; | A21-B15-C42; | A21-B15-C43; | A21-B15-C44; |
| A21-B15-C45; | A21-B15-C46; | A22-B15-C1; | A22-B15-C2; | A22-B15-C3; | A22-B15-C4; |
| A22-B15-C5; | A22-B15-C6; | A22-B15-C7; | A22-B15-C8; | A22-B15-C9; | A22-B15-C10; |
| A22-B15-C11; | A22-B15-C12; | A22-B15-C13; | A22-B15-C14; | A22-B15-C15; | A22-B15-C16; |
| A22-B15-C17; | A22-B15-C18; | A22-B15-C19; | A22-B15-C20; | A22-B15-C21; | A22-B15-C22; |
| A22-B15-C23; | A22-B15-C24; | A22-B15-C25; | A22-B15-C26; | A22-B15-C27; | A22-B15-C28; |
| A22-B15-C29; | A22-B15-C30; | A22-B15-C31; | A22-B15-C32; | A22-B15-C33; | A22-B15-C34; |
| A22-B15-C35; | A22-B15-C36; | A22-B15-C37; | A22-B15-C38; | A22-B15-C39; | A22-B15-C40; |
| A22-B15-C41; | A22-B15-C42; | A22-B15-C43; | A22-B15-C44; | A22-B15-C45; | A22-B15-C46; |
| A23-B15-C1; | A23-B15-C2; | A23-B15-C3; | A23-B15-C4; | A23-B15-C5; | A23-B15-C6; |
| A23-B15-C7; | A23-B15-C8; | A23-B15-C9; | A23-B15-C10; | A23-B15-C11; | A23-B15-C12; |
| A23-B15-C13; | A23-B15-C14; | A23-B15-C15; | A23-B15-C16; | A23-B15-C17; | A23-B15-C18; |
| A23-B15-C19; | A23-B15-C20; | A23-B15-C21; | A23-B15-C22; | A23-B15-C23; | A23-B15-C24; |
| A23-B15-C25; | A23-B15-C26; | A23-B15-C27; | A23-B15-C28; | A23-B15-C29; | A23-B15-C30; |
| A23-B15-C31; | A23-B15-C32; | A23-B15-C33; | A23-B15-C34; | A23-B15-C35; | A23-B15-C36; |
| A23-B15-C37; | A23-B15-C38; | A23-B15-C39; | A23-B15-C40; | A23-B15-C41; | A23-B15-C42; |
| A23-B15-C43; | A23-B15-C44; | A23-B15-C45; | A23-B15-C46; | A24-B15-C1; | A24-B15-C2; |
| A24-B15-C3; | A24-B15-C4; | A24-B15-C5; | A24-B15-C6; | A24-B15-C7; | A24-B15-C8; |
| A24-B15-C9; | A24-B15-C10; | A24-B15-C11; | A24-B15-C12; | A24-B15-C13; | A24-B15-C14; |
| A24-B15-C15; | A24-B15-C16; | A24-B15-C17; | A24-B15-C18; | A24-B15-C19; | A24-B15-C20; |
| A24-B15-C21; | A24-B15-C22; | A24-B15-C23; | A24-B15-C24; | A24-B15-C25; | A24-B15-C26; |
| A24-B15-C27; | A24-B15-C28; | A24-B15-C29; | A24-B15-C30; | A24-B15-C31; | A24-B15-C32; |
| A24-B15-C33; | A24-B15-C34; | A24-B15-C35; | A24-B15-C36; | A24-B15-C37; | A24-B15-C38; |
| A24-B15-C39; | A24-B15-C40; | A24-B15-C41; | A24-B15-C42; | A24-B15-C43; | A24-B15-C44; |
| A24-B15-C45; | A24-B15-C46; | A25-B15-C1; | A25-B15-C2; | A25-B15-C3; | A25-B15-C4; |
| A25-B15-C5; | A25-B15-C6; | A25-B15-C7; | A25-B15-C8; | A25-B15-C9; | A25-B15-C10; |
| A25-B15-C11; | A25-B15-C12; | A25-B15-C13; | A25-B15-C14; | A25-B15-C15; | A25-B15-C16; |
| A25-B15-C17; | A25-B15-C18; | A25-B15-C19; | A25-B15-C20; | A25-B15-C21; | A25-B15-C22; |
| A25-B15-C23; | A25-B15-C24; | A25-B15-C25; | A25-B15-C26; | A25-B15-C27; | A25-B15-C28; |
| A25-B15-C29; | A25-B15-C30; | A25-B15-C31; | A25-B15-C32; | A25-B15-C33; | A25-B15-C34; |
| A25-B15-C35; | A25-B15-C36; | A25-B15-C37; | A25-B15-C38; | A25-B15-C39; | A25-B15-C40; |
| A25-B15-C41; | A25-B15-C42; | A25-B15-C43; | A25-B15-C44; | A25-B15-C45; | A25-B15-C46; |
| A26-B15-C1; | A26-B15-C2; | A26-B15-C3; | A26-B15-C4; | A26-B15-C5; | A26-B15-C6; |
| A26-B15-C7; | A26-B15-C8; | A26-B15-C9; | A26-B15-C10; | A26-B15-C11; | A26-B15-C12; |
| A26-B15-C13; | A26-B15-C14; | A26-B15-C15; | A26-B15-C16; | A26-B15-C17; | A26-B15-C18; |

-continued

A26-B15-C19; A26-B15-C20; A26-B15-C21; A26-B15-C22; A26-B15-C23; A26-B15-C24;
A26-B15-C25; A26-B15-C26; A26-B15-C27; A26-B15-C28; A26-B15-C29; A26-B15-C30;
A26-B15-C31; A26-B15-C32; A26-B15-C33; A26-B15-C34; A26-B15-C35; A26-B15-C36;
A26-B15-C37; A26-B15-C38; A26-B15-C39; A26-B15-C40; A26-B15-C41; A26-B15-C42;
A26-B15-C43; A26-B15-C44; A26-B15-C45; A26-B15-C46; A27-B15-C1; A27-B15-C2;
A27-B15-C3; A27-B15-C4; A27-B15-C5; A27-B15-C6; A27-B15-C7; A27-B15-C8;
A27-B15-C9; A27-B15-C10; A27-B15-C11; A27-B15-C12; A27-B15-C13; A27-B15-C14;
A27-B15-C15; A27-B15-C16; A27-B15-C17; A27-B15-C18; A27-B15-C19; A27-B15-C20;
A27-B15-C21; A27-B15-C22; A27-B15-C23; A27-B15-C24; A27-B15-C25; A27-B15-C26;
A27-B15-C27; A27-B15-C28; A27-B15-C29; A27-B15-C30; A27-B15-C31; A27-B15-C32;
A27-B15-C33; A27-B15-C34; A27-B15-C35; A27-B15-C36; A27-B15-C37; A27-B15-C38;
A27-B15-C39; A27-B15-C40; A27-B15-C41; A27-B15-C42; A27-B15-C43; A27-B15-C44;
A27-B15-C45; A27-B15-C46; A28-B15-C1; A28-B15-C2; A28-B15-C3; A28-B15-C4;
A28-B15-C5; A28-B15-C6; A28-B15-C7; A28-B15-C8; A28-B15-C9; A28-B15-C10;
A28-B15-C11; A28-B15-C12; A28-B15-C13; A28-B15-C14; A28-B15-C15; A28-B15-C16;
A28-B15-C17; A28-B15-C18; A28-B15-C19; A28-B15-C20; A28-B15-C21; A28-B15-C22;
A28-B15-C23; A28-B15-C24; A28-B15-C25; A28-B15-C26; A28-B15-C27; A28-B15-C28;
A28-B15-C29; A28-B15-C30; A28-B15-C31; A28-B15-C32; A28-B15-C33; A28-B15-C34;
A28-B15-C35; A28-B15-C36; A28-B15-C37; A28-B15-C38; A28-B15-C39; A28-B15-C40;
A28-B15-C41; A28-B15-C42; A28-B15-C43; A28-B15-C44; A28-B15-C45; A28-B15-C46;
A1-B16-C1; A1-B16-C2; A1-B16-C3; A1-B16-C4; A1-B16-C5; A1-B16-C6;
A1-B16-C7; A1-B16-C8; A1-B16-C9; A1-B16-C10; A1-B16-C11; A1-B16-C12;
A1-B16-C13; A1-B16-C14; A1-B16-C15; A1-B16-C16; A1-B16-C17; A1-B16-C18;
A1-B16-C19; A1-B16-C20; A1-B16-C21; A1-B16-C22; A1-B16-C23; A1-B16-C24;
A1-B16-C25; A1-B16-C26; A1-B16-C27; A1-B16-C28; A1-B16-C29; A1-B16-C30;
A1-B16-C31; A1-B16-C32; A1-B16-C33; A1-B16-C34; A1-B16-C35; A1-B16-C36;
A1-B16-C37; A1-B16-C38; A1-B16-C39; A1-B16-C40; A1-B16-C41; A1-B16-C42;
A1-B16-C43; A1-B16-C44; A1-B16-C45; A1-B16-C46; A2-B16-C1; A2-B16-C2;
A2-B16-C3; A2-B16-C4; A2-B16-C5; A2-B16-C6; A2-B16-C7; A2-B16-C8;
A2-B16-C9; A2-B16-C10; A2-B16-C11; A2-B16-C12; A2-B16-C13; A2-B16-C14;
A2-B16-C15; A2-B16-C16; A2-B16-C17; A2-B16-C18; A2-B16-C19; A2-B16-C20;
A2-B16-C21; A2-B16-C22; A2-B16-C23; A2-B16-C24; A2-B16-C25; A2-B16-C26;
A2-B16-C27; A2-B16-C28; A2-B16-C29; A2-B16-C30; A2-B16-C31; A2-B16-C32;
A2-B16-C33; A2-B16-C34; A2-B16-C35; A2-B16-C36; A2-B16-C37; A2-B16-C38;
A2-B16-C39; A2-B16-C40; A2-B16-C41; A2-B16-C42; A2-B16-C43; A2-B16-C44;
A2-B16-C45; A2-B16-C46; A3-B16-C1; A3-B16-C2; A3-B16-C3; A3-B16-C4;
A3-B16-C5; A3-B16-C6; A3-B16-C7; A3-B16-C8; A3-B16-C9; A3-B16-C10;
A3-B16-C11; A3-B16-C12; A3-B16-C13; A3-B16-C14; A3-B16-C15; A3-B16-C16;
A3-B16-C17; A3-B16-C18; A3-B16-C19; A3-B16-C20; A3-B16-C21; A3-B16-C22;
A3-B16-C23; A3-B16-C24; A3-B16-C25; A3-B16-C26; A3-B16-C27; A3-B16-C28;
A3-B16-C29; A3-B16-C30; A3-B16-C31; A3-B16-C32; A3-B16-C33; A3-B16-C34;
A3-B16-C35; A3-B16-C36; A3-B16-C37; A3-B16-C38; A3-B16-C39; A3-B16-C40;
A3-B16-C41; A3-B16-C42; A3-B16-C43; A3-B16-C44; A3-B16-C45; A3-B16-C46;
A4-B16-C1; A4-B16-C2; A4-B16-C3; A4-B16-C4; A4-B16-C5; A4-B16-C6;
A4-B16-C7; A4-B16-C8; A4-B16-C9; A4-B16-C10; A4-B16-C11; A4-B16-C12;
A4-B16-C13; A4-B16-C14; A4-B16-C15; A4-B16-C16; A4-B16-C17; A4-B16-C18;
A4-B16-C19; A4-B16-C20; A4-B16-C21; A4-B16-C22; A4-B16-C23; A4-B16-C24;
A4-B16-C25; A4-B16-C26; A4-B16-C27; A4-B16-C28; A4-B16-C29; A4-B16-C30;
A4-B16-C31; A4-B16-C32; A4-B16-C33; A4-B16-C34; A4-B16-C35; A4-B16-C36;
A4-B16-C37; A4-B16-C38; A4-B16-C39; A4-B16-C40; A4-B16-C41; A4-B16-C42;
A4-B16-C43; A4-B16-C44; A4-B16-C45; A4-B16-C46; A5-B16-C1; A5-B16-C2;
A5-B16-C3; A5-B16-C4; A5-B16-C5; A5-B16-C6; A5-B16-C7; A5-B16-C8;
A5-B16-C9; A5-B16-C10; A5-B16-C11; A5-B16-C12; A5-B16-C13; A5-B16-C14;
A5-B16-C15; A5-B16-C16; A5-B16-C17; A5-B16-C18; A5-B16-C19; A5-B16-C20;
A5-B16-C21; A5-B16-C22; A5-B16-C23; A5-B16-C24; A5-B16-C25; A5-B16-C26;
A5-B16-C27; A5-B16-C28; A5-B16-C29; A5-B16-C30; A5-B16-C31; A5-B16-C32;
A5-B16-C33; A5-B16-C34; A5-B16-C35; A5-B16-C36; A5-B16-C37; A5-B16-C38;
A5-B16-C39; A5-B16-C40; A5-B16-C41; A5-B16-C42; A5-B16-C43; A5-B16-C44;
A5-B16-C45; A5-B16-C46; A6-B16-C1; A6-B16-C2; A6-B16-C3; A6-B16-C4;
A6-B16-C5; A6-B16-C6; A6-B16-C7; A6-B16-C8; A6-B16-C9; A6-B16-C10;
A6-B16-C11; A6-B16-C12; A6-B16-C13; A6-B16-C14; A6-B16-C15; A6-B16-C16;
A6-B16-C17; A6-B16-C18; A6-B16-C19; A6-B16-C20; A6-B16-C21; A6-B16-C22;
A6-B16-C23; A6-B16-C24; A6-B16-C25; A6-B16-C26; A6-B16-C27; A6-B16-C28;
A6-B16-C29; A6-B16-C30; A6-B16-C31; A6-B16-C32; A6-B16-C33; A6-B16-C34;
A6-B16-C35; A6-B16-C36; A6-B16-C37; A6-B16-C38; A6-B16-C39; A6-B16-C40;
A6-B16-C41; A6-B16-C42; A6-B16-C43; A6-B16-C44; A6-B16-C45; A6-B16-C46;
A7-B16-C1; A7-B16-C2; A7-B16-C3; A7-B16-C4; A7-B16-C5; A7-B16-C6;
A7-B16-C7; A7-B16-C8; A7-B16-C9; A7-B16-C10; A7-B16-C11; A7-B16-C12;
A7-B16-C13; A7-B16-C14; A7-B16-C15; A7-B16-C16; A7-B16-C17; A7-B16-C18;
A7-B16-C19; A7-B16-C20; A7-B16-C21; A7-B16-C22; A7-B16-C23; A7-B16-C24;
A7-B16-C25; A7-B16-C26; A7-B16-C27; A7-B16-C28; A7-B16-C29; A7-B16-C30;
A7-B16-C31; A7-B16-C32; A7-B16-C33; A7-B16-C34; A7-B16-C35; A7-B16-C36;
A7-B16-C37; A7-B16-C38; A7-B16-C39; A7-B16-C40; A7-B16-C41; A7-B16-C42;
A7-B16-C43; A7-B16-C44; A7-B16-C45; A7-B16-C46; A8-B16-C1; A8-B16-C2;
A8-B16-C3; A8-B16-C4; A8-B16-C5; A8-B16-C6; A8-B16-C7; A8-B16-C8;
A8-B16-C9; A8-B16-C10; A8-B16-C11; A8-B16-C12; A8-B16-C13; A8-B16-C14;
A8-B16-C15; A8-B16-C16; A8-B16-C17; A8-B16-C18; A8-B16-C19; A8-B16-C20;
A8-B16-C21; A8-B16-C22; A8-B16-C23; A8-B16-C24; A8-B16-C25; A8-B16-C26;
A8-B16-C27; A8-B16-C28; A8-B16-C29; A8-B16-C30; A8-B16-C31; A8-B16-C32;

-continued

| | | | | | |
|---|---|---|---|---|---|
| A8-B16-C33; | A8-B16-C34; | A8-B16-C35; | A8-B16-C36; | A8-B16-C37; | A8-B16-C38; |
| A8-B16-C39; | A8-B16-C40; | A8-B16-C41; | A8-B16-C42; | A8-B16-C43; | A8-B16-C44; |
| A8-B16-C45; | A8-B16-C46; | A9-B16-C1; | A9-B16-C2; | A9-B16-C3; | A9-B16-C4; |
| A9-B16-C5; | A9-B16-C6; | A9-B16-C7; | A9-B16-C8; | A9-B16-C9; | A9-B16-C10; |
| A9-B16-C11; | A9-B16-C12; | A9-B16-C13; | A9-B16-C14; | A9-B16-C15; | A9-B16-C16; |
| A9-B16-C17; | A9-B16-C18; | A9-B16-C19; | A9-B16-C20; | A9-B16-C21; | A9-B16-C22; |
| A9-B16-C23; | A9-B16-C24; | A9-B16-C25; | A9-B16-C26; | A9-B16-C27; | A9-B16-C28; |
| A9-B16-C29; | A9-B16-C30; | A9-B16-C31; | A9-B16-C32; | A9-B16-C33; | A9-B16-C34; |
| A9-B16-C35; | A9-B16-C36; | A9-B16-C37; | A9-B16-C38; | A9-B16-C39; | A9-B16-C40; |
| A9-B16-C41; | A9-B16-C42; | A9-B16-C43; | A9-B16-C44; | A9-B16-C45; | A9-B16-C46; |
| A10-B16-C1; | A10-B16-C2; | A10-B16-C3; | A10-B16-C4; | A10-B16-C5; | A10-B16-C6; |
| A10-B16-C7; | A10-B16-C8; | A10-B16-C9; | A10-B16-C10; | A10-B16-C11; | A10-B16-C12; |
| A10-B16-C13; | A10-B16-C14; | A10-B16-C15; | A10-B16-C16; | A10-B16-C17; | A10-B16-C18; |
| A10-B16-C19; | A10-B16-C20; | A10-B16-C21; | A10-B16-C22; | A10-B16-C23; | A10-B16-C24; |
| A10-B16-C25; | A10-B16-C26; | A10-B16-C27; | A10-B16-C28; | A10-B16-C29; | A10-B16-C30; |
| A10-B16-C31; | A10-B16-C32; | A10-B16-C33; | A10-B16-C34; | A10-B16-C35; | A10-B16-C36; |
| A10-B16-C37; | A10-B16-C38; | A10-B16-C39; | A10-B16-C40; | A10-B16-C41; | A10-B16-C42; |
| A10-B16-C43; | A10-B16-C44; | A10-B16-C45; | A10-B16-C46; | A11-B16-C1; | A11-B16-C2; |
| A11-B16-C3; | A11-B16-C4; | A11-B16-C5; | A11-B16-C6; | A11-B16-C7; | A11-B16-C8; |
| A11-B16-C9; | A11-B16-C10; | A11-B16-C11; | A11-B16-C12; | A11-B16-C13; | A11-B16-C14; |
| A11-B16-C15; | A11-B16-C16; | A11-B16-C17; | A11-B16-C18; | A11-B16-C19; | A11-B16-C20; |
| A11-B16-C21; | A11-B16-C22; | A11-B16-C23; | A11-B16-C24; | A11-B16-C25; | A11-B16-C26; |
| A11-B16-C27; | A11-B16-C28; | A11-B16-C29; | A11-B16-C30; | A11-B16-C31; | A11-B16-C32; |
| A11-B16-C33; | A11-B16-C34; | A11-B16-C35; | A11-B16-C36; | A11-B16-C37; | A11-B16-C38; |
| A11-B16-C39; | A11-B16-C40; | A11-B16-C41; | A11-B16-C42; | A11-B16-C43; | A11-B16-C44; |
| A11-B16-C45; | A11-B16-C46; | A12-B16-C1; | A12-B16-C2; | A12-B16-C3; | A12-B16-C4; |
| A12-B16-C5; | A12-B16-C6; | A12-B16-C7; | A12-B16-C8; | A12-B16-C9; | A12-B16-C10; |
| A12-B16-C11; | A12-B16-C12; | A12-B16-C13; | A12-B16-C14; | A12-B16-C15; | A12-B16-C16; |
| A12-B16-C17; | A12-B16-C18; | A12-B16-C19; | A12-B16-C20; | A12-B16-C21; | A12-B16-C22; |
| A12-B16-C23; | A12-B16-C24; | A12-B16-C25; | A12-B16-C26; | A12-B16-C27; | A12-B16-C28; |
| A12-B16-C29; | A12-B16-C30; | A12-B16-C31; | A12-B16-C32; | A12-B16-C33; | A12-B16-C34; |
| A12-B16-C35; | A12-B16-C36; | A12-B16-C37; | A12-B16-C38; | A12-B16-C39; | A12-B16-C40; |
| A12-B16-C41; | A12-B16-C42; | A12-B16-C43; | A12-B16-C44; | A12-B16-C45; | A12-B16-C46; |
| A13-B16-C1; | A13-B16-C2; | A13-B16-C3; | A13-B16-C4; | A13-B16-C5; | A13-B16-C6; |
| A13-B16-C7; | A13-B16-C8; | A13-B16-C9; | A13-B16-C10; | A13-B16-C11; | A13-B16-C12; |
| A13-B16-C13; | A13-B16-C14; | A13-B16-C15; | A13-B16-C16; | A13-B16-C17; | A13-B16-C18; |
| A13-B16-C19; | A13-B16-C20; | A13-B16-C21; | A13-B16-C22; | A13-B16-C23; | A13-B16-C24; |
| A13-B16-C25; | A13-B16-C26; | A13-B16-C27; | A13-B16-C28; | A13-B16-C29; | A13-B16-C30; |
| A13-B16-C31; | A13-B16-C32; | A13-B16-C33; | A13-B16-C34; | A13-B16-C35; | A13-B16-C36; |
| A13-B16-C37; | A13-B16-C38; | A13-B16-C39; | A13-B16-C40; | A13-B16-C41; | A13-B16-C42; |
| A13-B16-C43; | A13-B16-C44; | A13-B16-C45; | A13-B16-C46; | A14-B16-C1; | A14-B16-C2; |
| A14-B16-C3; | A14-B16-C4; | A14-B16-C5; | A14-B16-C6; | A14-B16-C7; | A14-B16-C8; |
| A14-B16-C9; | A14-B16-C10; | A14-B16-C11; | A14-B16-C12; | A14-B16-C13; | A14-B16-C14; |
| A14-B16-C15; | A14-B16-C16; | A14-B16-C17; | A14-B16-C18; | A14-B16-C19; | A14-B16-C20; |
| A14-B16-C21; | A14-B16-C22; | A14-B16-C23; | A14-B16-C24; | A14-B16-C25; | A14-B16-C26; |
| A14-B16-C27; | A14-B16-C28; | A14-B16-C29; | A14-B16-C30; | A14-B16-C31; | A14-B16-C32; |
| A14-B16-C33; | A14-B16-C34; | A14-B16-C35; | A14-B16-C36; | A14-B16-C37; | A14-B16-C38; |
| A14-B16-C39; | A14-B16-C40; | A14-B16-C41; | A14-B16-C42; | A14-B16-C43; | A14-B16-C44; |
| A14-B16-C45; | A14-B16-C46; | A15-B16-C1; | A15-B16-C2; | A15-B16-C3; | A15-B16-C4; |
| A15-B16-C5; | A15-B16-C6; | A15-B16-C7; | A15-B16-C8; | A15-B16-C9; | A15-B16-C10; |
| A15-B16-C11; | A15-B16-C12; | A15-B16-C13; | A15-B16-C14; | A15-B16-C15; | A15-B16-C16; |
| A15-B16-C17; | A15-B16-C18; | A15-B16-C19; | A15-B16-C20; | A15-B16-C21; | A15-B16-C22; |
| A15-B16-C23; | A15-B16-C24; | A15-B16-C25; | A15-B16-C26; | A15-B16-C27; | A15-B16-C28; |
| A15-B16-C29; | A15-B16-C30; | A15-B16-C31; | A15-B16-C32; | A15-B16-C33; | A15-B16-C34; |
| A15-B16-C35; | A15-B16-C36; | A15-B16-C37; | A15-B16-C38; | A15-B16-C39; | A15-B16-C40; |
| A15-B16-C41; | A15-B16-C42; | A15-B16-C43; | A15-B16-C44; | A15-B16-C45; | A15-B16-C46; |
| A16-B16-C1; | A16-B16-C2; | A16-B16-C3; | A16-B16-C4; | A16-B16-C5; | A16-B16-C6; |
| A16-B16-C7; | A16-B16-C8; | A16-B16-C9; | A16-B16-C10; | A16-B16-C11; | A16-B16-C12; |
| A16-B16-C13; | A16-B16-C14; | A16-B16-C15; | A16-B16-C16; | A16-B16-C17; | A16-B16-C18; |
| A16-B16-C19; | A16-B16-C20; | A16-B16-C21; | A16-B16-C22; | A16-B16-C23; | A16-B16-C24; |
| A16-B16-C25; | A16-B16-C26; | A16-B16-C27; | A16-B16-C28; | A16-B16-C29; | A16-B16-C30; |
| A16-B16-C31; | A16-B16-C32; | A16-B16-C33; | A16-B16-C34; | A16-B16-C35; | A16-B16-C36; |
| A16-B16-C37; | A16-B16-C38; | A16-B16-C39; | A16-B16-C40; | A16-B16-C41; | A16-B16-C42; |
| A16-B16-C43; | A16-B16-C44; | A16-B16-C45; | A16-B16-C46; | A17-B16-C1; | A17-B16-C2; |
| A17-B16-C3; | A17-B16-C4; | A17-B16-C5; | A17-B16-C6; | A17-B16-C7; | A17-B16-C8; |
| A17-B16-C9; | A17-B16-C10; | A17-B16-C11; | A17-B16-C12; | A17-B16-C13; | A17-B16-C14; |
| A17-B16-C15; | A17-B16-C16; | A17-B16-C17; | A17-B16-C18; | A17-B16-C19; | A17-B16-C20; |
| A17-B16-C21; | A17-B16-C22; | A17-B16-C23; | A17-B16-C24; | A17-B16-C25; | A17-B16-C26; |
| A17-B16-C27; | A17-B16-C28; | A17-B16-C29; | A17-B16-C30; | A17-B16-C31; | A17-B16-C32; |
| A17-B16-C33; | A17-B16-C34; | A17-B16-C35; | A17-B16-C36; | A17-B16-C37; | A17-B16-C38; |
| A17-B16-C39; | A17-B16-C40; | A17-B16-C41; | A17-B16-C42; | A17-B16-C43; | A17-B16-C44; |
| A17-B16-C45; | A17-B16-C46; | A18-B16-C1; | A18-B16-C2; | A18-B16-C3; | A18-B16-C4; |
| A18-B16-C5; | A18-B16-C6; | A18-B16-C7; | A18-B16-C8; | A18-B16-C9; | A18-B16-C10; |
| A18-B16-C11; | A18-B16-C12; | A18-B16-C13; | A18-B16-C14; | A18-B16-C15; | A18-B16-C16; |
| A18-B16-C17; | A18-B16-C18; | A18-B16-C19; | A18-B16-C20; | A18-B16-C21; | A18-B16-C22; |
| A18-B16-C23; | A18-B16-C24; | A18-B16-C25; | A18-B16-C26; | A18-B16-C27; | A18-B16-C28; |
| A18-B16-C29; | A18-B16-C30; | A18-B16-C31; | A18-B16-C32; | A18-B16-C33; | A18-B16-C34; |
| A18-B16-C35; | A18-B16-C36; | A18-B16-C37; | A18-B16-C38; | A18-B16-C39; | A18-B16-C40; |
| A18-B16-C41; | A18-B16-C42; | A18-B16-C43; | A18-B16-C44; | A18-B16-C45; | A18-B16-C46; |

-continued

A19-B16-C1; A19-B16-C2; A19-B16-C3; A19-B16-C4; A19-B16-C5; A19-B16-C6;
A19-B16-C7; A19-B16-C8; A19-B16-C9; A19-B16-C10; A19-B16-C11; A19-B16-C12;
A19-B16-C13; A19-B16-C14; A19-B16-C15; A19-B16-C16; A19-B16-C17; A19-B16-C18;
A19-B16-C19; A19-B16-C20; A19-B16-C21; A19-B16-C22; A19-B16-C23; A19-B16-C24;
A19-B16-C25; A19-B16-C26; A19-B16-C27; A19-B16-C28; A19-B16-C29; A19-B16-C30;
A19-B16-C31; A19-B16-C32; A19-B16-C33; A19-B16-C34; A19-B16-C35; A19-B16-C36;
A19-B16-C37; A19-B16-C38; A19-B16-C39; A19-B16-C40; A19-B16-C41; A19-B16-C42;
A19-B16-C43; A19-B16-C44; A19-B16-C45; A19-B16-C46; A20-B16-C1; A20-B16-C2;
A20-B16-C3; A20-B16-C4; A20-B16-C5; A20-B16-C6; A20-B16-C7; A20-B16-C8;
A20-B16-C9; A20-B16-C10; A20-B16-C11; A20-B16-C12; A20-B16-C13; A20-B16-C14;
A20-B16-C15; A20-B16-C16; A20-B16-C17; A20-B16-C18; A20-B16-C19; A20-B16-C20;
A20-B16-C21; A20-B16-C22; A20-B16-C23; A20-B16-C24; A20-B16-C25; A20-B16-C26;
A20-B16-C27; A20-B16-C28; A20-B16-C29; A20-B16-C30; A20-B16-C31; A20-B16-C32;
A20-B16-C33; A20-B16-C34; A20-B16-C35; A20-B16-C36; A20-B16-C37; A20-B16-C38;
A20-B16-C39; A20-B16-C40; A20-B16-C41; A20-B16-C42; A20-B16-C43; A20-B16-C44;
A20-B16-C45; A20-B16-C46; A21-B16-C1; A21-B16-C2; A21-B16-C3; A21-B16-C4;
A21-B16-C5; A21-B16-C6; A21-B16-C7; A21-B16-C8; A21-B16-C9; A21-B16-C10;
A21-B16-C11; A21-B16-C12; A21-B16-C13; A21-B16-C14; A21-B16-C15; A21-B16-C16;
A21-B16-C17; A21-B16-C18; A21-B16-C19; A21-B16-C20; A21-B16-C21; A21-B16-C22;
A21-B16-C23; A21-B16-C24; A21-B16-C25; A21-B16-C26; A21-B16-C27; A21-B16-C28;
A21-B16-C29; A21-B16-C30; A21-B16-C31; A21-B16-C32; A21-B16-C33; A21-B16-C34;
A21-B16-C35; A21-B16-C36; A21-B16-C37; A21-B16-C38; A21-B16-C39; A21-B16-C40;
A21-B16-C41; A21-B16-C42; A21-B16-C43; A21-B16-C44; A21-B16-C45; A21-B16-C46;
A22-B16-C1; A22-B16-C2; A22-B16-C3; A22-B16-C4; A22-B16-C5; A22-B16-C6;
A22-B16-C7; A22-B16-C8; A22-B16-C9; A22-B16-C10; A22-B16-C11; A22-B16-C12;
A22-B16-C13; A22-B16-C14; A22-B16-C15; A22-B16-C16; A22-B16-C17; A22-B16-C18;
A22-B16-C19; A22-B16-C20; A22-B16-C21; A22-B16-C22; A22-B16-C23; A22-B16-C24;
A22-B16-C25; A22-B16-C26; A22-B16-C27; A22-B16-C28; A22-B16-C29; A22-B16-C30;
A22-B16-C31; A22-B16-C32; A22-B16-C33; A22-B16-C34; A22-B16-C35; A22-B16-C36;
A22-B16-C37; A22-B16-C38; A22-B16-C39; A22-B16-C40; A22-B16-C41; A22-B16-C42;
A22-B16-C43; A22-B16-C44; A22-B16-C45; A22-B16-C46; A23-B16-C1; A23-B16-C2;
A23-B16-C3; A23-B16-C4; A23-B16-C5; A23-B16-C6; A23-B16-C7; A23-B16-C8;
A23-B16-C9; A23-B16-C10; A23-B16-C11; A23-B16-C12; A23-B16-C13; A23-B16-C14;
A23-B16-C15; A23-B16-C16; A23-B16-C17; A23-B16-C18; A23-B16-C19; A23-B16-C20;
A23-B16-C21; A23-B16-C22; A23-B16-C23; A23-B16-C24; A23-B16-C25; A23-B16-C26;
A23-B16-C27; A23-B16-C28; A23-B16-C29; A23-B16-C30; A23-B16-C31; A23-B16-C32;
A23-B16-C33; A23-B16-C34; A23-B16-C35; A23-B16-C36; A23-B16-C37; A23-B16-C38;
A23-B16-C39; A23-B16-C40; A23-B16-C41; A23-B16-C42; A23-B16-C43; A23-B16-C44;
A23-B16-C45; A23-B16-C46; A24-B16-C1; A24-B16-C2; A24-B16-C3; A24-B16-C4;
A24-B16-C5; A24-B16-C6; A24-B16-C7; A24-B16-C8; A24-B16-C9; A24-B16-C10;
A24-B16-C11; A24-B16-C12; A24-B16-C13; A24-B16-C14; A24-B16-C15; A24-B16-C16;
A24-B16-C17; A24-B16-C18; A24-B16-C19; A24-B16-C20; A24-B16-C21; A24-B16-C22;
A24-B16-C23; A24-B16-C24; A24-B16-C25; A24-B16-C26; A24-B16-C27; A24-B16-C28;
A24-B16-C29; A24-B16-C30; A24-B16-C31; A24-B16-C32; A24-B16-C33; A24-B16-C34;
A24-B16-C35; A24-B16-C36; A24-B16-C37; A24-B16-C38; A24-B16-C39; A24-B16-C40;
A24-B16-C41; A24-B16-C42; A24-B16-C43; A24-B16-C44; A24-B16-C45; A24-B16-C46;
A25-B16-C1; A25-B16-C2; A25-B16-C3; A25-B16-C4; A25-B16-C5; A25-B16-C6;
A25-B16-C7; A25-B16-C8; A25-B16-C9; A25-B16-C10; A25-B16-C11; A25-B16-C12;
A25-B16-C13; A25-B16-C14; A25-B16-C15; A25-B16-C16; A25-B16-C17; A25-B16-C18;
A25-B16-C19; A25-B16-C20; A25-B16-C21; A25-B16-C22; A25-B16-C23; A25-B16-C24;
A25-B16-C25; A25-B16-C26; A25-B16-C27; A25-B16-C28; A25-B16-C29; A25-B16-C30;
A25-B16-C31; A25-B16-C32; A25-B16-C33; A25-B16-C34; A25-B16-C35; A25-B16-C36;
A25-B16-C37; A25-B16-C38; A25-B16-C39; A25-B16-C40; A25-B16-C41; A25-B16-C42;
A25-B16-C43; A25-B16-C44; A25-B16-C45; A25-B16-C46; A26-B16-C1; A26-B16-C2;
A26-B16-C3; A26-B16-C4; A26-B16-C5; A26-B16-C6; A26-B16-C7; A26-B16-C8;
A26-B16-C9; A26-B16-C10; A26-B16-C11; A26-B16-C12; A26-B16-C13; A26-B16-C14;
A26-B16-C15; A26-B16-C16; A26-B16-C17; A26-B16-C18; A26-B16-C19; A26-B16-C20;
A26-B16-C21; A26-B16-C22; A26-B16-C23; A26-B16-C24; A26-B16-C25; A26-B16-C26;
A26-B16-C27; A26-B16-C28; A26-B16-C29; A26-B16-C30; A26-B16-C31; A26-B16-C32;
A26-B16-C33; A26-B16-C34; A26-B16-C35; A26-B16-C36; A26-B16-C37; A26-B16-C38;
A26-B16-C39; A26-B16-C40; A26-B16-C41; A26-B16-C42; A26-B16-C43; A26-B16-C44;
A26-B16-C45; A26-B16-C46; A27-B16-C1; A27-B16-C2; A27-B16-C3; A27-B16-C4;
A27-B16-C5; A27-B16-C6; A27-B16-C7; A27-B16-C8; A27-B16-C9; A27-B16-C10;
A27-B16-C11; A27-B16-C12; A27-B16-C13; A27-B16-C14; A27-B16-C15; A27-B16-C16;
A27-B16-C17; A27-B16-C18; A27-B16-C19; A27-B16-C20; A27-B16-C21; A27-B16-C22;
A27-B16-C23; A27-B16-C24; A27-B16-C25; A27-B16-C26; A27-B16-C27; A27-B16-C28;
A27-B16-C29; A27-B16-C30; A27-B16-C31; A27-B16-C32; A27-B16-C33; A27-B16-C34;
A27-B16-C35; A27-B16-C36; A27-B16-C37; A27-B16-C38; A27-B16-C39; A27-B16-C40;
A27-B16-C41; A27-B16-C42; A27-B16-C43; A27-B16-C44; A27-B16-C45; A27-B16-C46;
A28-B16-C1; A28-B16-C2; A28-B16-C3; A28-B16-C4; A28-B16-C5; A28-B16-C6;
A28-B16-C7; A28-B16-C8; A28-B16-C9; A28-B16-C10; A28-B16-C11; A28-B16-C12;
A28-B16-C13; A28-B16-C14; A28-B16-C15; A28-B16-C16; A28-B16-C17; A28-B16-C18;
A28-B16-C19; A28-B16-C20; A28-B16-C21; A28-B16-C22; A28-B16-C23; A28-B16-C24;
A28-B16-C25; A28-B16-C26; A28-B16-C27; A28-B16-C28; A28-B16-C29; A28-B16-C30;
A28-B16-C31; A28-B16-C32; A28-B16-C33; A28-B16-C34; A28-B16-C35; A28-B16-C36;
A28-B16-C37; A28-B16-C38; A28-B16-C39; A28-B16-C40; A28-B16-C41; A28-B16-C42;
A28-B16-C43; A28-B16-C44; A28-B16-C45; A28-B16-C46; A1-B17-C1; A1-B17-C2;
A1-B17-C3; A1-B17-C4; A1-B17-C5; A1-B17-C6; A1-B17-C7; A1-B17-C8;
A1-B17-C9; A1-B17-C10; A1-B17-C11; A1-B17-C12; A1-B17-C13; A1-B17-C14;

-continued

A1-B17-C15; A1-B17-C16; A1-B17-C17; A1-B17-C18; A1-B17-C19; A1-B17-C20;
A1-B17-C21; A1-B17-C22; A1-B17-C23; A1-B17-C24; A1-B17-C25; A1-B17-C26;
A1-B17-C27; A1-B17-C28; A1-B17-C29; A1-B17-C30; A1-B17-C31; A1-B17-C32;
A1-B17-C33; A1-B17-C34; A1-B17-C35; A1-B17-C36; A1-B17-C37; A1-B17-C38;
A1-B17-C39; A1-B17-C40; A1-B17-C41; A1-B17-C42; A1-B17-C43; A1-B17-C44;
A1-B17-C45; A1-B17-C46; A2-B17-C1; A2-B17-C2; A2-B17-C3; A2-B17-C4;
A2-B17-C5; A2-B17-C6; A2-B17-C7; A2-B17-C8; A2-B17-C9; A2-B17-C10;
A2-B17-C11; A2-B17-C12; A2-B17-C13; A2-B17-C14; A2-B17-C15; A2-B17-C16;
A2-B17-C17; A2-B17-C18; A2-B17-C19; A2-B17-C20; A2-B17-C21; A2-B17-C22;
A2-B17-C23; A2-B17-C24; A2-B17-C25; A2-B17-C26; A2-B17-C27; A2-B17-C28;
A2-B17-C29; A2-B17-C30; A2-B17-C31; A2-B17-C32; A2-B17-C33; A2-B17-C34;
A2-B17-C35; A2-B17-C36; A2-B17-C37; A2-B17-C38; A2-B17-C39; A2-B17-C40;
A2-B17-C41; A2-B17-C42; A2-B17-C43; A2-B17-C44; A2-B17-C45; A2-B17-C46;
A3-B17-C1; A3-B17-C2; A3-B17-C3; A3-B17-C4; A3-B17-C5; A3-B17-C6;
A3-B17-C7; A3-B17-C8; A3-B17-C9; A3-B17-C10; A3-B17-C11; A3-B17-C12;
A3-B17-C13; A3-B17-C14; A3-B17-C15; A3-B17-C16; A3-B17-C17; A3-B17-C18;
A3-B17-C19; A3-B17-C20; A3-B17-C21; A3-B17-C22; A3-B17-C23; A3-B17-C24;
A3-B17-C25; A3-B17-C26; A3-B17-C27; A3-B17-C28; A3-B17-C29; A3-B17-C30;
A3-B17-C31; A3-B17-C32; A3-B17-C33; A3-B17-C34; A3-B17-C35; A3-B17-C36;
A3-B17-C37; A3-B17-C38; A3-B17-C39; A3-B17-C40; A3-B17-C41; A3-B17-C42;
A3-B17-C43; A3-B17-C44; A3-B17-C45; A3-B17-C46; A4-B17-C1; A4-B17-C2;
A4-B17-C3; A4-B17-C4; A4-B17-C5; A4-B17-C6; A4-B17-C7; A4-B17-C8;
A4-B17-C9; A4-B17-C10; A4-B17-C11; A4-B17-C12; A4-B17-C13; A4-B17-C14;
A4-B17-C15; A4-B17-C16; A4-B17-C17; A4-B17-C18; A4-B17-C19; A4-B17-C20;
A4-B17-C21; A4-B17-C22; A4-B17-C23; A4-B17-C24; A4-B17-C25; A4-B17-C26;
A4-B17-C27; A4-B17-C28; A4-B17-C29; A4-B17-C30; A4-B17-C31; A4-B17-C32;
A4-B17-C33; A4-B17-C34; A4-B17-C35; A4-B17-C36; A4-B17-C37; A4-B17-C38;
A4-B17-C39; A4-B17-C40; A4-B17-C41; A4-B17-C42; A4-B17-C43; A4-B17-C44;
A4-B17-C45; A4-B17-C46; A5-B17-C1; A5-B17-C2; A5-B17-C3; A5-B17-C4;
A5-B17-C5; A5-B17-C6; A5-B17-C7; A5-B17-C8; A5-B17-C9; A5-B17-C10;
A5-B17-C11; A5-B17-C12; A5-B17-C13; A5-B17-C14; A5-B17-C15; A5-B17-C16;
A5-B17-C17; A5-B17-C18; A5-B17-C19; A5-B17-C20; A5-B17-C21; A5-B17-C22;
A5-B17-C23; A5-B17-C24; A5-B17-C25; A5-B17-C26; A5-B17-C27; A5-B17-C28;
A5-B17-C29; A5-B17-C30; A5-B17-C31; A5-B17-C32; A5-B17-C33; A5-B17-C34;
A5-B17-C35; A5-B17-C36; A5-B17-C37; A5-B17-C38; A5-B17-C39; A5-B17-C40;
A5-B17-C41; A5-B17-C42; A5-B17-C43; A5-B17-C44; A5-B17-C45; A5-B17-C46;
A6-B17-C1; A6-B17-C2; A6-B17-C3; A6-B17-C4; A6-B17-C5; A6-B17-C6;
A6-B17-C7; A6-B17-C8; A6-B17-C9; A6-B17-C10; A6-B17-C11; A6-B17-C12;
A6-B17-C13; A6-B17-C14; A6-B17-C15; A6-B17-C16; A6-B17-C17; A6-B17-C18;
A6-B17-C19; A6-B17-C20; A6-B17-C21; A6-B17-C22; A6-B17-C23; A6-B17-C24;
A6-B17-C25; A6-B17-C26; A6-B17-C27; A6-B17-C28; A6-B17-C29; A6-B17-C30;
A6-B17-C31; A6-B17-C32; A6-B17-C33; A6-B17-C34; A6-B17-C35; A6-B17-C36;
A6-B17-C37; A6-B17-C38; A6-B17-C39; A6-B17-C40; A6-B17-C41; A6-B17-C42;
A6-B17-C43; A6-B17-C44; A6-B17-C45; A6-B17-C46; A7-B17-C1; A7-B17-C2;
A7-B17-C3; A7-B17-C4; A7-B17-C5; A7-B17-C6; A7-B17-C7; A7-B17-C8;
A7-B17-C9; A7-B17-C10; A7-B17-C11; A7-B17-C12; A7-B17-C13; A7-B17-C14;
A7-B17-C15; A7-B17-C16; A7-B17-C17; A7-B17-C18; A7-B17-C19; A7-B17-C20;
A7-B17-C21; A7-B17-C22; A7-B17-C23; A7-B17-C24; A7-B17-C25; A7-B17-C26;
A7-B17-C27; A7-B17-C28; A7-B17-C29; A7-B17-C30; A7-B17-C31; A7-B17-C32;
A7-B17-C33; A7-B17-C34; A7-B17-C35; A7-B17-C36; A7-B17-C37; A7-B17-C38;
A7-B17-C39; A7-B17-C40; A7-B17-C41; A7-B17-C42; A7-B17-C43; A7-B17-C44;
A7-B17-C45; A7-B17-C46; A8-B17-C1; A8-B17-C2; A8-B17-C3; A8-B17-C4;
A8-B17-C5; A8-B17-C6; A8-B17-C7; A8-B17-C8; A8-B17-C9; A8-B17-C10;
A8-B17-C11; A8-B17-C12; A8-B17-C13; A8-B17-C14; A8-B17-C15; A8-B17-C16;
A8-B17-C17; A8-B17-C18; A8-B17-C19; A8-B17-C20; A8-B17-C21; A8-B17-C22;
A8-B17-C23; A8-B17-C24; A8-B17-C25; A8-B17-C26; A8-B17-C27; A8-B17-C28;
A8-B17-C29; A8-B17-C30; A8-B17-C31; A8-B17-C32; A8-B17-C33; A8-B17-C34;
A8-B17-C35; A8-B17-C36; A8-B17-C37; A8-B17-C38; A8-B17-C39; A8-B17-C40;
A8-B17-C41; A8-B17-C42; A8-B17-C43; A8-B17-C44; A8-B17-C45; A8-B17-C46;
A9-B17-C1; A9-B17-C2; A9-B17-C3; A9-B17-C4; A9-B17-C5; A9-B17-C6;
A9-B17-C7; A9-B17-C8; A9-B17-C9; A9-B17-C10; A9-B17-C11; A9-B17-C12;
A9-B17-C13; A9-B17-C14; A9-B17-C15; A9-B17-C16; A9-B17-C17; A9-B17-C18;
A9-B17-C19; A9-B17-C20; A9-B17-C21; A9-B17-C22; A9-B17-C23; A9-B17-C24;
A9-B17-C25; A9-B17-C26; A9-B17-C27; A9-B17-C28; A9-B17-C29; A9-B17-C30;
A9-B17-C31; A9-B17-C32; A9-B17-C33; A9-B17-C34; A9-B17-C35; A9-B17-C36;
A9-B17-C37; A9-B17-C38; A9-B17-C39; A9-B17-C40; A9-B17-C41; A9-B17-C42;
A9-B17-C43; A9-B17-C44; A9-B17-C45; A9-B17-C46; A10-B17-C1; A10-B17-C2;
A10-B17-C3; A10-B17-C4; A10-B17-C5; A10-B17-C6; A10-B17-C7; A10-B17-C8;
A10-B17-C9; A10-B17-C10; A10-B17-C11; A10-B17-C12; A10-B17-C13; A10-B17-C14;
A10-B17-C15; A10-B17-C16; A10-B17-C17; A10-B17-C18; A10-B17-C19; A10-B17-C20;
A10-B17-C21; A10-B17-C22; A10-B17-C23; A10-B17-C24; A10-B17-C25; A10-B17-C26;
A10-B17-C27; A10-B17-C28; A10-B17-C29; A10-B17-C30; A10-B17-C31; A10-B17-C32;
A10-B17-C33; A10-B17-C34; A10-B17-C35; A10-B17-C36; A10-B17-C37; A10-B17-C38;
A10-B17-C39; A10-B17-C40; A10-B17-C41; A10-B17-C42; A10-B17-C43; A10-B17-C44;
A10-B17-C45; A10-B17-C46; A11-B17-C1; A11-B17-C2; A11-B17-C3; A11-B17-C4;
A11-B17-C5; A11-B17-C6; A11-B17-C7; A11-B17-C8; A11-B17-C9; A11-B17-C10;
A11-B17-C11; A11-B17-C12; A11-B17-C13; A11-B17-C14; A11-B17-C15; A11-B17-C16;
A11-B17-C17; A11-B17-C18; A11-B17-C19; A11-B17-C20; A11-B17-C21; A11-B17-C22;
A11-B17-C23; A11-B17-C24; A11-B17-C25; A11-B17-C26; A11-B17-C27; A11-B17-C28;

-continued

| | | | | | |
|---|---|---|---|---|---|
| A11-B17-C29; | A11-B17-C30; | A11-B17-C31; | A11-B17-C32; | A11-B17-C33; | A11-B17-C34; |
| A11-B17-C35; | A11-B17-C36; | A11-B17-C37; | A11-B17-C38; | A11-B17-C39; | A11-B17-C40; |
| A11-B17-C41; | A11-B17-C42; | A11-B17-C43; | A11-B17-C44; | A11-B17-C45; | A11-B17-C46; |
| A12-B17-C1; | A12-B17-C2; | A12-B17-C3; | A12-B17-C4; | A12-B17-C5; | A12-B17-C6; |
| A12-B17-C7; | A12-B17-C8; | A12-B17-C9; | A12-B17-C10; | A12-B17-C11; | A12-B17-C12; |
| A12-B17-C13; | A12-B17-C14; | A12-B17-C15; | A12-B17-C16; | A12-B17-C17; | A12-B17-C18; |
| A12-B17-C19; | A12-B17-C20; | A12-B17-C21; | A12-B17-C22; | A12-B17-C23; | A12-B17-C24; |
| A12-B17-C25; | A12-B17-C26; | A12-B17-C27; | A12-B17-C28; | A12-B17-C29; | A12-B17-C30; |
| A12-B17-C31; | A12-B17-C32; | A12-B17-C33; | A12-B17-C34; | A12-B17-C35; | A12-B17-C36; |
| A12-B17-C37; | A12-B17-C38; | A12-B17-C39; | A12-B17-C40; | A12-B17-C41; | A12-B17-C42; |
| A12-B17-C43; | A12-B17-C44; | A12-B17-C45; | A12-B17-C46; | A13-B17-C1; | A13-B17-C2; |
| A13-B17-C3; | A13-B17-C4; | A13-B17-C5; | A13-B17-C6; | A13-B17-C7; | A13-B17-C8; |
| A13-B17-C9; | A13-B17-C10; | A13-B17-C11; | A13-B17-C12; | A13-B17-C13; | A13-B17-C14; |
| A13-B17-C15; | A13-B17-C16; | A13-B17-C17; | A13-B17-C18; | A13-B17-C19; | A13-B17-C20; |
| A13-B17-C21; | A13-B17-C22; | A13-B17-C23; | A13-B17-C24; | A13-B17-C25; | A13-B17-C26; |
| A13-B17-C27; | A13-B17-C28; | A13-B17-C29; | A13-B17-C30; | A13-B17-C31; | A13-B17-C32; |
| A13-B17-C33; | A13-B17-C34; | A13-B17-C35; | A13-B17-C36; | A13-B17-C37; | A13-B17-C38; |
| A13-B17-C39; | A13-B17-C40; | A13-B17-C41; | A13-B17-C42; | A13-B17-C43; | A13-B17-C44; |
| A13-B17-C45; | A13-B17-C46; | A14-B17-C1; | A14-B17-C2; | A14-B17-C3; | A14-B17-C4; |
| A14-B17-C5; | A14-B17-C6; | A14-B17-C7; | A14-B17-C8; | A14-B17-C9; | A14-B17-C10; |
| A14-B17-C11; | A14-B17-C12; | A14-B17-C13; | A14-B17-C14; | A14-B17-C15; | A14-B17-C16; |
| A14-B17-C17; | A14-B17-C18; | A14-B17-C19; | A14-B17-C20; | A14-B17-C21; | A14-B17-C22; |
| A14-B17-C23; | A14-B17-C24; | A14-B17-C25; | A14-B17-C26; | A14-B17-C27; | A14-B17-C28; |
| A14-B17-C29; | A14-B17-C30; | A14-B17-C31; | A14-B17-C32; | A14-B17-C33; | A14-B17-C34; |
| A14-B17-C35; | A14-B17-C36; | A14-B17-C37; | A14-B17-C38; | A14-B17-C39; | A14-B17-C40; |
| A14-B17-C41; | A14-B17-C42; | A14-B17-C43; | A14-B17-C44; | A14-B17-C45; | A14-B17-C46; |
| A15-B17-C1; | A15-B17-C2; | A15-B17-C3; | A15-B17-C4; | A15-B17-C5; | A15-B17-C6; |
| A15-B17-C7; | A15-B17-C8; | A15-B17-C9; | A15-B17-C10; | A15-B17-C11; | A15-B17-C12; |
| A15-B17-C13; | A15-B17-C14; | A15-B17-C15; | A15-B17-C16; | A15-B17-C17; | A15-B17-C18; |
| A15-B17-C19; | A15-B17-C20; | A15-B17-C21; | A15-B17-C22; | A15-B17-C23; | A15-B17-C24; |
| A15-B17-C25; | A15-B17-C26; | A15-B17-C27; | A15-B17-C28; | A15-B17-C29; | A15-B17-C30; |
| A15-B17-C31; | A15-B17-C32; | A15-B17-C33; | A15-B17-C34; | A15-B17-C35; | A15-B17-C36; |
| A15-B17-C37; | A15-B17-C38; | A15-B17-C39; | A15-B17-C40; | A15-B17-C41; | A15-B17-C42; |
| A15-B17-C43; | A15-B17-C44; | A15-B17-C45; | A15-B17-C46; | A16-B17-C1; | A16-B17-C2; |
| A16-B17-C3; | A16-B17-C4; | A16-B17-C5; | A16-B17-C6; | A16-B17-C7; | A16-B17-C8; |
| A16-B17-C9; | A16-B17-C10; | A16-B17-C11; | A16-B17-C12; | A16-B17-C13; | A16-B17-C14; |
| A16-B17-C15; | A16-B17-C16; | A16-B17-C17; | A16-B17-C18; | A16-B17-C19; | A16-B17-C20; |
| A16-B17-C21; | A16-B17-C22; | A16-B17-C23; | A16-B17-C24; | A16-B17-C25; | A16-B17-C26; |
| A16-B17-C27; | A16-B17-C28; | A16-B17-C29; | A16-B17-C30; | A16-B17-C31; | A16-B17-C32; |
| A16-B17-C33; | A16-B17-C34; | A16-B17-C35; | A16-B17-C36; | A16-B17-C37; | A16-B17-C38; |
| A16-B17-C39; | A16-B17-C40; | A16-B17-C41; | A16-B17-C42; | A16-B17-C43; | A16-B17-C44; |
| A16-B17-C45; | A16-B17-C46; | A17-B17-C1; | A17-B17-C2; | A17-B17-C3; | A17-B17-C4; |
| A17-B17-C5; | A17-B17-C6; | A17-B17-C7; | A17-B17-C8; | A17-B17-C9; | A17-B17-C10; |
| A17-B17-C11; | A17-B17-C12; | A17-B17-C13; | A17-B17-C14; | A17-B17-C15; | A17-B17-C16; |
| A17-B17-C17; | A17-B17-C18; | A17-B17-C19; | A17-B17-C20; | A17-B17-C21; | A17-B17-C22; |
| A17-B17-C23; | A17-B17-C24; | A17-B17-C25; | A17-B17-C26; | A17-B17-C27; | A17-B17-C28; |
| A17-B17-C29; | A17-B17-C30; | A17-B17-C31; | A17-B17-C32; | A17-B17-C33; | A17-B17-C34; |
| A17-B17-C35; | A17-B17-C36; | A17-B17-C37; | A17-B17-C38; | A17-B17-C39; | A17-B17-C40; |
| A17-B17-C41; | A17-B17-C42; | A17-B17-C43; | A17-B17-C44; | A17-B17-C45; | A17-B17-C46; |
| A18-B17-C1; | A18-B17-C2; | A18-B17-C3; | A18-B17-C4; | A18-B17-C5; | A18-B17-C6; |
| A18-B17-C7; | A18-B17-C8; | A18-B17-C9; | A18-B17-C10; | A18-B17-C11; | A18-B17-C12; |
| A18-B17-C13; | A18-B17-C14; | A18-B17-C15; | A18-B17-C16; | A18-B17-C17; | A18-B17-C18; |
| A18-B17-C19; | A18-B17-C20; | A18-B17-C21; | A18-B17-C22; | A18-B17-C23; | A18-B17-C24; |
| A18-B17-C25; | A18-B17-C26; | A18-B17-C27; | A18-B17-C28; | A18-B17-C29; | A18-B17-C30; |
| A18-B17-C31; | A18-B17-C32; | A18-B17-C33; | A18-B17-C34; | A18-B17-C35; | A18-B17-C36; |
| A18-B17-C37; | A18-B17-C38; | A18-B17-C39; | A18-B17-C40; | A18-B17-C41; | A18-B17-C42; |
| A18-B17-C43; | A18-B17-C44; | A18-B17-C45; | A18-B17-C46; | A19-B17-C1; | A19-B17-C2; |
| A19-B17-C3; | A19-B17-C4; | A19-B17-C5; | A19-B17-C6; | A19-B17-C7; | A19-B17-C8; |
| A19-B17-C9; | A19-B17-C10; | A19-B17-C11; | A19-B17-C12; | A19-B17-C13; | A19-B17-C14; |
| A19-B17-C15; | A19-B17-C16; | A19-B17-C17; | A19-B17-C18; | A19-B17-C19; | A19-B17-C20; |
| A19-B17-C21; | A19-B17-C22; | A19-B17-C23; | A19-B17-C24; | A19-B17-C25; | A19-B17-C26; |
| A19-B17-C27; | A19-B17-C28; | A19-B17-C29; | A19-B17-C30; | A19-B17-C31; | A19-B17-C32; |
| A19-B17-C33; | A19-B17-C34; | A19-B17-C35; | A19-B17-C36; | A19-B17-C37; | A19-B17-C38; |
| A19-B17-C39; | A19-B17-C40; | A19-B17-C41; | A19-B17-C42; | A19-B17-C43; | A19-B17-C44; |
| A19-B17-C45; | A19-B17-C46; | A20-B17-C1; | A20-B17-C2; | A20-B17-C3; | A20-B17-C4; |
| A20-B17-C5; | A20-B17-C6; | A20-B17-C7; | A20-B17-C8; | A20-B17-C9; | A20-B17-C10; |
| A20-B17-C11; | A20-B17-C12; | A20-B17-C13; | A20-B17-C14; | A20-B17-C15; | A20-B17-C16; |
| A20-B17-C17; | A20-B17-C18; | A20-B17-C19; | A20-B17-C20; | A20-B17-C21; | A20-B17-C22; |
| A20-B17-C23; | A20-B17-C24; | A20-B17-C25; | A20-B17-C26; | A20-B17-C27; | A20-B17-C28; |
| A20-B17-C29; | A20-B17-C30; | A20-B17-C31; | A20-B17-C32; | A20-B17-C33; | A20-B17-C34; |
| A20-B17-C35; | A20-B17-C36; | A20-B17-C37; | A20-B17-C38; | A20-B17-C39; | A20-B17-C40; |
| A20-B17-C41; | A20-B17-C42; | A20-B17-C43; | A20-B17-C44; | A20-B17-C45; | A20-B17-C46; |
| A21-B17-C1; | A21-B17-C2; | A21-B17-C3; | A21-B17-C4; | A21-B17-C5; | A21-B17-C6; |
| A21-B17-C7; | A21-B17-C8; | A21-B17-C9; | A21-B17-C10; | A21-B17-C11; | A21-B17-C12; |
| A21-B17-C13; | A21-B17-C14; | A21-B17-C15; | A21-B17-C16; | A21-B17-C17; | A21-B17-C18; |
| A21-B17-C19; | A21-B17-C20; | A21-B17-C21; | A21-B17-C22; | A21-B17-C23; | A21-B17-C24; |
| A21-B17-C25; | A21-B17-C26; | A21-B17-C27; | A21-B17-C28; | A21-B17-C29; | A21-B17-C30; |
| A21-B17-C31; | A21-B17-C32; | A21-B17-C33; | A21-B17-C34; | A21-B17-C35; | A21-B17-C36; |
| A21-B17-C37; | A21-B17-C38; | A21-B17-C39; | A21-B17-C40; | A21-B17-C41; | A21-B17-C42; |

| | | | | | |
|---|---|---|---|---|---|
| A21-B17-C43; | A21-B17-C44; | A21-B17-C45; | A21-B17-C46; | A22-B17-C1; | A22-B17-C2; |
| A22-B17-C3; | A22-B17-C4; | A22-B17-C5; | A22-B17-C6; | A22-B17-C7; | A22-B17-C8; |
| A22-B17-C9; | A22-B17-C10; | A22-B17-C11; | A22-B17-C12; | A22-B17-C13; | A22-B17-C14; |
| A22-B17-C15; | A22-B17-C16; | A22-B17-C17; | A22-B17-C18; | A22-B17-C19; | A22-B17-C20; |
| A22-B17-C21; | A22-B17-C22; | A22-B17-C23; | A22-B17-C24; | A22-B17-C25; | A22-B17-C26; |
| A22-B17-C27; | A22-B17-C28; | A22-B17-C29; | A22-B17-C30; | A22-B17-C31; | A22-B17-C32; |
| A22-B17-C33; | A22-B17-C34; | A22-B17-C35; | A22-B17-C36; | A22-B17-C37; | A22-B17-C38; |
| A22-B17-C39; | A22-B17-C40; | A22-B17-C41; | A22-B17-C42; | A22-B17-C43; | A22-B17-C44; |
| A22-B17-C45; | A22-B17-C46; | A23-B17-C1; | A23-B17-C2; | A23-B17-C3; | A23-B17-C4; |
| A23-B17-C5; | A23-B17-C6; | A23-B17-C7; | A23-B17-C8; | A23-B17-C9; | A23-B17-C10; |
| A23-B17-C11; | A23-B17-C12; | A23-B17-C13; | A23-B17-C14; | A23-B17-C15; | A23-B17-C16; |
| A23-B17-C17; | A23-B17-C18; | A23-B17-C19; | A23-B17-C20; | A23-B17-C21; | A23-B17-C22; |
| A23-B17-C23; | A23-B17-C24; | A23-B17-C25; | A23-B17-C26; | A23-B17-C27; | A23-B17-C28; |
| A23-B17-C29; | A23-B17-C30; | A23-B17-C31; | A23-B17-C32; | A23-B17-C33; | A23-B17-C34; |
| A23-B17-C35; | A23-B17-C36; | A23-B17-C37; | A23-B17-C38; | A23-B17-C39; | A23-B17-C40; |
| A23-B17-C41; | A23-B17-C42; | A23-B17-C43; | A23-B17-C44; | A23-B17-C45; | A23-B17-C46; |
| A24-B17-C1; | A24-B17-C2; | A24-B17-C3; | A24-B17-C4; | A24-B17-C5; | A24-B17-C6; |
| A24-B17-C7; | A24-B17-C8; | A24-B17-C9; | A24-B17-C10; | A24-B17-C11; | A24-B17-C12; |
| A24-B17-C13; | A24-B17-C14; | A24-B17-C15; | A24-B17-C16; | A24-B17-C17; | A24-B17-C18; |
| A24-B17-C19; | A24-B17-C20; | A24-B17-C21; | A24-B17-C22; | A24-B17-C23; | A24-B17-C24; |
| A24-B17-C25; | A24-B17-C26; | A24-B17-C27; | A24-B17-C28; | A24-B17-C29; | A24-B17-C30; |
| A24-B17-C31; | A24-B17-C32; | A24-B17-C33; | A24-B17-C34; | A24-B17-C35; | A24-B17-C36; |
| A24-B17-C37; | A24-B17-C38; | A24-B17-C39; | A24-B17-C40; | A24-B17-C41; | A24-B17-C42; |
| A24-B17-C43; | A24-B17-C44; | A24-B17-C45; | A24-B17-C46; | A25-B17-C1; | A25-B17-C2; |
| A25-B17-C3; | A25-B17-C4; | A25-B17-C5; | A25-B17-C6; | A25-B17-C7; | A25-B17-C8; |
| A25-B17-C9; | A25-B17-C10; | A25-B17-C11; | A25-B17-C12; | A25-B17-C13; | A25-B17-C14; |
| A25-B17-C15; | A25-B17-C16; | A25-B17-C17; | A25-B17-C18; | A25-B17-C19; | A25-B17-C20; |
| A25-B17-C21; | A25-B17-C22; | A25-B17-C23; | A25-B17-C24; | A25-B17-C25; | A25-B17-C26; |
| A25-B17-C27; | A25-B17-C28; | A25-B17-C29; | A25-B17-C30; | A25-B17-C31; | A25-B17-C32; |
| A25-B17-C33; | A25-B17-C34; | A25-B17-C35; | A25-B17-C36; | A25-B17-C37; | A25-B17-C38; |
| A25-B17-C39; | A25-B17-C40; | A25-B17-C41; | A25-B17-C42; | A25-B17-C43; | A25-B17-C44; |
| A25-B17-C45; | A25-B17-C46; | A26-B17-C1; | A26-B17-C2; | A26-B17-C3; | A26-B17-C4; |
| A26-B17-C5; | A26-B17-C6; | A26-B17-C7; | A26-B17-C8; | A26-B17-C9; | A26-B17-C10; |
| A26-B17-C11; | A26-B17-C12; | A26-B17-C13; | A26-B17-C14; | A26-B17-C15; | A26-B17-C16; |
| A26-B17-C17; | A26-B17-C18; | A26-B17-C19; | A26-B17-C20; | A26-B17-C21; | A26-B17-C22; |
| A26-B17-C23; | A26-B17-C24; | A26-B17-C25; | A26-B17-C26; | A26-B17-C27; | A26-B17-C28; |
| A26-B17-C29; | A26-B17-C30; | A26-B17-C31; | A26-B17-C32; | A26-B17-C33; | A26-B17-C34; |
| A26-B17-C35; | A26-B17-C36; | A26-B17-C37; | A26-B17-C38; | A26-B17-C39; | A26-B17-C40; |
| A26-B17-C41; | A26-B17-C42; | A26-B17-C43; | A26-B17-C44; | A26-B17-C45; | A26-B17-C46; |
| A27-B17-C1; | A27-B17-C2; | A27-B17-C3; | A27-B17-C4; | A27-B17-C5; | A27-B17-C6; |
| A27-B17-C7; | A27-B17-C8; | A27-B17-C9; | A27-B17-C10; | A27-B17-C11; | A27-B17-C12; |
| A27-B17-C13; | A27-B17-C14; | A27-B17-C15; | A27-B17-C16; | A27-B17-C17; | A27-B17-C18; |
| A27-B17-C19; | A27-B17-C20; | A27-B17-C21; | A27-B17-C22; | A27-B17-C23; | A27-B17-C24; |
| A27-B17-C25; | A27-B17-C26; | A27-B17-C27; | A27-B17-C28; | A27-B17-C29; | A27-B17-C30; |
| A27-B17-C31; | A27-B17-C32; | A27-B17-C33; | A27-B17-C34; | A27-B17-C35; | A27-B17-C36; |
| A27-B17-C37; | A27-B17-C38; | A27-B17-C39; | A27-B17-C40; | A27-B17-C41; | A27-B17-C42; |
| A27-B17-C43; | A27-B17-C44; | A27-B17-C45; | A27-B17-C46; | A28-B17-C1; | A28-B17-C2; |
| A28-B17-C3; | A28-B17-C4; | A28-B17-C5; | A28-B17-C6; | A28-B17-C7; | A28-B17-C8; |
| A28-B17-C9; | A28-B17-C10; | A28-B17-C11; | A28-B17-C12; | A28-B17-C13; | A28-B17-C14; |
| A28-B17-C15; | A28-B17-C16; | A28-B17-C17; | A28-B17-C18; | A28-B17-C19; | A28-B17-C20; |
| A28-B17-C21; | A28-B17-C22; | A28-B17-C23; | A28-B17-C24; | A28-B17-C25; | A28-B17-C26; |
| A28-B17-C27; | A28-B17-C28; | A28-B17-C29; | A28-B17-C30; | A28-B17-C31; | A28-B17-C32; |
| A28-B17-C33; | A28-B17-C34; | A28-B17-C35; | A28-B17-C36; | A28-B17-C37; | A28-B17-C38; |
| A28-B17-C39; | A28-B17-C40; | A28-B17-C41; | A28-B17-C42; | A28-B17-C43; | A28-B17-C44; |
| A28-B17-C45; | A28-B17-C46; | A1-B18-C1; | A1-B18-C2; | A1-B18-C3; | A1-B18-C4; |
| A1-B18-C5; | A1-B18-C6; | A1-B18-C7; | A1-B18-C8; | A1-B18-C9; | A1-B18-C10; |
| A1-B18-C11; | A1-B18-C12; | A1-B18-C13; | A1-B18-C14; | A1-B18-C15; | A1-B18-C16; |
| A1-B18-C17; | A1-B18-C18; | A1-B18-C19; | A1-B18-C20; | A1-B18-C21; | A1-B18-C22; |
| A1-B18-C23; | A1-B18-C24; | A1-B18-C25; | A1-B18-C26; | A1-B18-C27; | A1-B18-C28; |
| A1-B18-C29; | A1-B18-C30; | A1-B18-C31; | A1-B18-C32; | A1-B18-C33; | A1-B18-C34; |
| A1-B18-C35; | A1-B18-C36; | A1-B18-C37; | A1-B18-C38; | A1-B18-C39; | A1-B18-C40; |
| A1-B18-C41; | A1-B18-C42; | A1-B18-C43; | A1-B18-C44; | A1-B18-C45; | A1-B18-C46; |
| A2-B18-C1; | A2-B18-C2; | A2-B18-C3; | A2-B18-C4; | A2-B18-C5; | A2-B18-C6; |
| A2-B18-C7; | A2-B18-C8; | A2-B18-C9; | A2-B18-C10; | A2-B18-C11; | A2-B18-C12; |
| A2-B18-C13; | A2-B18-C14; | A2-B18-C15; | A2-B18-C16; | A2-B18-C17; | A2-B18-C18; |
| A2-B18-C19; | A2-B18-C20; | A2-B18-C21; | A2-B18-C22; | A2-B18-C23; | A2-B18-C24; |
| A2-B18-C25; | A2-B18-C26; | A2-B18-C27; | A2-B18-C28; | A2-B18-C29; | A2-B18-C30; |
| A2-B18-C31; | A2-B18-C32; | A2-B18-C33; | A2-B18-C34; | A2-B18-C35; | A2-B18-C36; |
| A2-B18-C37; | A2-B18-C38; | A2-B18-C39; | A2-B18-C40; | A2-B18-C41; | A2-B18-C42; |
| A2-B18-C43; | A2-B18-C44; | A2-B18-C45; | A2-B18-C46; | A3-B18-C1; | A3-B18-C2; |
| A3-B18-C3; | A3-B18-C4; | A3-B18-C5; | A3-B18-C6; | A3-B18-C7; | A3-B18-C8; |
| A3-B18-C9; | A3-B18-C10; | A3-B18-C11; | A3-B18-C12; | A3-B18-C13; | A3-B18-C14; |
| A3-B18-C15; | A3-B18-C16; | A3-B18-C17; | A3-B18-C18; | A3-B18-C19; | A3-B18-C20; |
| A3-B18-C21; | A3-B18-C22; | A3-B18-C23; | A3-B18-C24; | A3-B18-C25; | A3-B18-C26; |
| A3-B18-C27; | A3-B18-C28; | A3-B18-C29; | A3-B18-C30; | A3-B18-C31; | A3-B18-C32; |
| A3-B18-C33; | A3-B18-C34; | A3-B18-C35; | A3-B18-C36; | A3-B18-C37; | A3-B18-C38; |
| A3-B18-C39; | A3-B18-C40; | A3-B18-C41; | A3-B18-C42; | A3-B18-C43; | A3-B18-C44; |
| A3-B18-C45; | A3-B18-C46; | A4-B18-C1; | A4-B18-C2; | A4-B18-C3; | A4-B18-C4; |
| A4-B18-C5; | A4-B18-C6; | A4-B18-C7; | A4-B18-C8; | A4-B18-C9; | A4-B18-C10; |

| | | | | | |
|---|---|---|---|---|---|
| A4-B18-C11; | A4-B18-C12; | A4-B18-C13; | A4-B18-C14; | A4-B18-C15; | A4-B18-C16; |
| A4-B18-C17; | A4-B18-C18; | A4-B18-C19; | A4-B18-C20; | A4-B18-C21; | A4-B18-C22; |
| A4-B18-C23; | A4-B18-C24; | A4-B18-C25; | A4-B18-C26; | A4-B18-C27; | A4-B18-C28; |
| A4-B18-C29; | A4-B18-C30; | A4-B18-C31; | A4-B18-C32; | A4-B18-C33; | A4-B18-C34; |
| A4-B18-C35; | A4-B18-C36; | A4-B18-C37; | A4-B18-C38; | A4-B18-C39; | A4-B18-C40; |
| A4-B18-C41; | A4-B18-C42; | A4-B18-C43; | A4-B18-C44; | A4-B18-C45; | A4-B18-C46; |
| A5-B18-C1; | A5-B18-C2; | A5-B18-C3; | A5-B18-C4; | A5-B18-C5; | A5-B18-C6; |
| A5-B18-C7; | A5-B18-C8; | A5-B18-C9; | A5-B18-C10; | A5-B18-C11; | A5-B18-C12; |
| A5-B18-C13; | A5-B18-C14; | A5-B18-C15; | A5-B18-C16; | A5-B18-C17; | A5-B18-C18; |
| A5-B18-C19; | A5-B18-C20; | A5-B18-C21; | A5-B18-C22; | A5-B18-C23; | A5-B18-C24; |
| A5-B18-C25; | A5-B18-C26; | A5-B18-C27; | A5-B18-C28; | A5-B18-C29; | A5-B18-C30; |
| A5-B18-C31; | A5-B18-C32; | A5-B18-C33; | A5-B18-C34; | A5-B18-C35; | A5-B18-C36; |
| A5-B18-C37; | A5-B18-C38; | A5-B18-C39; | A5-B18-C40; | A5-B18-C41; | A5-B18-C42; |
| A5-B18-C43; | A5-B18-C44; | A5-B18-C45; | A5-B18-C46; | A6-B18-C1; | A6-B18-C2; |
| A6-B18-C3; | A6-B18-C4; | A6-B18-C5; | A6-B18-C6; | A6-B18-C7; | A6-B18-C8; |
| A6-B18-C9; | A6-B18-C10; | A6-B18-C11; | A6-B18-C12; | A6-B18-C13; | A6-B18-C14; |
| A6-B18-C15; | A6-B18-C16; | A6-B18-C17; | A6-B18-C18; | A6-B18-C19; | A6-B18-C20; |
| A6-B18-C21; | A6-B18-C22; | A6-B18-C23; | A6-B18-C24; | A6-B18-C25; | A6-B18-C26; |
| A6-B18-C27; | A6-B18-C28; | A6-B18-C29; | A6-B18-C30; | A6-B18-C31; | A6-B18-C32; |
| A6-B18-C33; | A6-B18-C34; | A6-B18-C35; | A6-B18-C36; | A6-B18-C37; | A6-B18-C38; |
| A6-B18-C39; | A6-B18-C40; | A6-B18-C41; | A6-B18-C42; | A6-B18-C43; | A6-B18-C44; |
| A6-B18-C45; | A6-B18-C46; | A7-B18-C1; | A7-B18-C2; | A7-B18-C3; | A7-B18-C4; |
| A7-B18-C5; | A7-B18-C6; | A7-B18-C7; | A7-B18-C8; | A7-B18-C9; | A7-B18-C10; |
| A7-B18-C11; | A7-B18-C12; | A7-B18-C13; | A7-B18-C14; | A7-B18-C15; | A7-B18-C16; |
| A7-B18-C17; | A7-B18-C18; | A7-B18-C19; | A7-B18-C20; | A7-B18-C21; | A7-B18-C22; |
| A7-B18-C23; | A7-B18-C24; | A7-B18-C25; | A7-B18-C26; | A7-B18-C27; | A7-B18-C28; |
| A7-B18-C29; | A7-B18-C30; | A7-B18-C31; | A7-B18-C32; | A7-B18-C33; | A7-B18-C34; |
| A7-B18-C35; | A7-B18-C36; | A7-B18-C37; | A7-B18-C38; | A7-B18-C39; | A7-B18-C40; |
| A7-B18-C41; | A7-B18-C42; | A7-B18-C43; | A7-B18-C44; | A7-B18-C45; | A7-B18-C46; |
| A8-B18-C1; | A8-B18-C2; | A8-B18-C3; | A8-B18-C4; | A8-B18-C5; | A8-B18-C6; |
| A8-B18-C7; | A8-B18-C8; | A8-B18-C9; | A8-B18-C10; | A8-B18-C11; | A8-B18-C12; |
| A8-B18-C13; | A8-B18-C14; | A8-B18-C15; | A8-B18-C16; | A8-B18-C17; | A8-B18-C18; |
| A8-B18-C19; | A8-B18-C20; | A8-B18-C21; | A8-B18-C22; | A8-B18-C23; | A8-B18-C24; |
| A8-B18-C25; | A8-B18-C26; | A8-B18-C27; | A8-B18-C28; | A8-B18-C29; | A8-B18-C30; |
| A8-B18-C31; | A8-B18-C32; | A8-B18-C33; | A8-B18-C34; | A8-B18-C35; | A8-B18-C36; |
| A8-B18-C37; | A8-B18-C38; | A8-B18-C39; | A8-B18-C40; | A8-B18-C41; | A8-B18-C42; |
| A8-B18-C43; | A8-B18-C44; | A8-B18-C45; | A8-B18-C46; | A9-B18-C1; | A9-B18-C2; |
| A9-B18-C3; | A9-B18-C4; | A9-B18-C5; | A9-B18-C6; | A9-B18-C7; | A9-B18-C8; |
| A9-B18-C9; | A9-B18-C10; | A9-B18-C11; | A9-B18-C12; | A9-B18-C13; | A9-B18-C14; |
| A9-B18-C15; | A9-B18-C16; | A9-B18-C17; | A9-B18-C18; | A9-B18-C19; | A9-B18-C20; |
| A9-B18-C21; | A9-B18-C22; | A9-B18-C23; | A9-B18-C24; | A9-B18-C25; | A9-B18-C26; |
| A9-B18-C27; | A9-B18-C28; | A9-B18-C29; | A9-B18-C30; | A9-B18-C31; | A9-B18-C32; |
| A9-B18-C33; | A9-B18-C34; | A9-B18-C35; | A9-B18-C36; | A9-B18-C37; | A9-B18-C38; |
| A9-B18-C39; | A9-B18-C40; | A9-B18-C41; | A9-B18-C42; | A9-B18-C43; | A9-B18-C44; |
| A9-B18-C45; | A9-B18-C46; | A10-B18-C1; | A10-B18-C2; | A10-B18-C3; | A10-B18-C4; |
| A10-B18-C5; | A10-B18-C6; | A10-B18-C7; | A10-B18-C8; | A10-B18-C9; | A10-B18-C10; |
| A10-B18-C11; | A10-B18-C12; | A10-B18-C13; | A10-B18-C14; | A10-B18-C15; | A10-B18-C16; |
| A10-B18-C17; | A10-B18-C18; | A10-B18-C19; | A10-B18-C20; | A10-B18-C21; | A10-B18-C22; |
| A10-B18-C23; | A10-B18-C24; | A10-B18-C25; | A10-B18-C26; | A10-B18-C27; | A10-B18-C28; |
| A10-B18-C29; | A10-B18-C30; | A10-B18-C31; | A10-B18-C32; | A10-B18-C33; | A10-B18-C34; |
| A10-B18-C35; | A10-B18-C36; | A10-B18-C37; | A10-B18-C38; | A10-B18-C39; | A10-B18-C40; |
| A10-B18-C41; | A10-B18-C42; | A10-B18-C43; | A10-B18-C44; | A10-B18-C45; | A10-B18-C46; |
| A11-B18-C1; | A11-B18-C2; | A11-B18-C3; | A11-B18-C4; | A11-B18-C5; | A11-B18-C6; |
| A11-B18-C7; | A11-B18-C8; | A11-B18-C9; | A11-B18-C10; | A11-B18-C11; | A11-B18-C12; |
| A11-B18-C13; | A11-B18-C14; | A11-B18-C15; | A11-B18-C16; | A11-B18-C17; | A11-B18-C18; |
| A11-B18-C19; | A11-B18-C20; | A11-B18-C21; | A11-B18-C22; | A11-B18-C23; | A11-B18-C24; |
| A11-B18-C25; | A11-B18-C26; | A11-B18-C27; | A11-B18-C28; | A11-B18-C29; | A11-B18-C30; |
| A11-B18-C31; | A11-B18-C32; | A11-B18-C33; | A11-B18-C34; | A11-B18-C35; | A11-B18-C36; |
| A11-B18-C37; | A11-B18-C38; | A11-B18-C39; | A11-B18-C40; | A11-B18-C41; | A11-B18-C42; |
| A11-B18-C43; | A11-B18-C44; | A11-B18-C45; | A11-B18-C46; | A12-B18-C1; | A12-B18-C2; |
| A12-B18-C3; | A12-B18-C4; | A12-B18-C5; | A12-B18-C6; | A12-B18-C7; | A12-B18-C8; |
| A12-B18-C9; | A12-B18-C10; | A12-B18-C11; | A12-B18-C12; | A12-B18-C13; | A12-B18-C14; |
| A12-B18-C15; | A12-B18-C16; | A12-B18-C17; | A12-B18-C18; | A12-B18-C19; | A12-B18-C20; |
| A12-B18-C21; | A12-B18-C22; | A12-B18-C23; | A12-B18-C24; | A12-B18-C25; | A12-B18-C26; |
| A12-B18-C27; | A12-B18-C28; | A12-B18-C29; | A12-B18-C30; | A12-B18-C31; | A12-B18-C32; |
| A12-B18-C33; | A12-B18-C34; | A12-B18-C35; | A12-B18-C36; | A12-B18-C37; | A12-B18-C38; |
| A12-B18-C39; | A12-B18-C40; | A12-B18-C41; | A12-B18-C42; | A12-B18-C43; | A12-B18-C44; |
| A12-B18-C45; | A12-B18-C46; | A13-B18-C1; | A13-B18-C2; | A13-B18-C3; | A13-B18-C4; |
| A13-B18-C5; | A13-B18-C6; | A13-B18-C7; | A13-B18-C8; | A13-B18-C9; | A13-B18-C10; |
| A13-B18-C11; | A13-B18-C12; | A13-B18-C13; | A13-B18-C14; | A13-B18-C15; | A13-B18-C16; |
| A13-B18-C17; | A13-B18-C18; | A13-B18-C19; | A13-B18-C20; | A13-B18-C21; | A13-B18-C22; |
| A13-B18-C23; | A13-B18-C24; | A13-B18-C25; | A13-B18-C26; | A13-B18-C27; | A13-B18-C28; |
| A13-B18-C29; | A13-B18-C30; | A13-B18-C31; | A13-B18-C32; | A13-B18-C33; | A13-B18-C34; |
| A13-B18-C35; | A13-B18-C36; | A13-B18-C37; | A13-B18-C38; | A13-B18-C39; | A13-B18-C40; |
| A13-B18-C41; | A13-B18-C42; | A13-B18-C43; | A13-B18-C44; | A13-B18-C45; | A13-B18-C46; |
| A14-B18-C1; | A14-B18-C2; | A14-B18-C3; | A14-B18-C4; | A14-B18-C5; | A14-B18-C6; |
| A14-B18-C7; | A14-B18-C8; | A14-B18-C9; | A14-B18-C10; | A14-B18-C11; | A14-B18-C12; |
| A14-B18-C13; | A14-B18-C14; | A14-B18-C15; | A14-B18-C16; | A14-B18-C17; | A14-B18-C18; |
| A14-B18-C19; | A14-B18-C20; | A14-B18-C21; | A14-B18-C22; | A14-B18-C23; | A14-B18-C24; |

-continued

A14-B18-C25; A14-B18-C26; A14-B18-C27; A14-B18-C28; A14-B18-C29; A14-B18-C30;
A14-B18-C31; A14-B18-C32; A14-B18-C33; A14-B18-C34; A14-B18-C35; A14-B18-C36;
A14-B18-C37; A14-B18-C38; A14-B18-C39; A14-B18-C40; A14-B18-C41; A14-B18-C42;
A14-B18-C43; A14-B18-C44; A14-B18-C45; A14-B18-C46; A15-B18-C1; A15-B18-C2;
A15-B18-C3; A15-B18-C4; A15-B18-C5; A15-B18-C6; A15-B18-C7; A15-B18-C8;
A15-B18-C9; A15-B18-C10; A15-B18-C11; A15-B18-C12; A15-B18-C13; A15-B18-C14;
A15-B18-C15; A15-B18-C16; A15-B18-C17; A15-B18-C18; A15-B18-C19; A15-B18-C20;
A15-B18-C21; A15-B18-C22; A15-B18-C23; A15-B18-C24; A15-B18-C25; A15-B18-C26;
A15-B18-C27; A15-B18-C28; A15-B18-C29; A15-B18-C30; A15-B18-C31; A15-B18-C32;
A15-B18-C33; A15-B18-C34; A15-B18-C35; A15-B18-C36; A15-B18-C37; A15-B18-C38;
A15-B18-C39; A15-B18-C40; A15-B18-C41; A15-B18-C42; A15-B18-C43; A15-B18-C44;
A15-B18-C45; A15-B18-C46; A16-B18-C1; A16-B18-C2; A16-B18-C3; A16-B18-C4;
A16-B18-C5; A16-B18-C6; A16-B18-C7; A16-B18-C8; A16-B18-C9; A16-B18-C10;
A16-B18-C11; A16-B18-C12; A16-B18-C13; A16-B18-C14; A16-B18-C15; A16-B18-C16;
A16-B18-C17; A16-B18-C18; A16-B18-C19; A16-B18-C20; A16-B18-C21; A16-B18-C22;
A16-B18-C23; A16-B18-C24; A16-B18-C25; A16-B18-C26; A16-B18-C27; A16-B18-C28;
A16-B18-C29; A16-B18-C30; A16-B18-C31; A16-B18-C32; A16-B18-C33; A16-B18-C34;
A16-B18-C35; A16-B18-C36; A16-B18-C37; A16-B18-C38; A16-B18-C39; A16-B18-C40;
A16-B18-C41; A16-B18-C42; A16-B18-C43; A16-B18-C44; A16-B18-C45; A16-B18-C46;
A17-B18-C1; A17-B18-C2; A17-B18-C3; A17-B18-C4; A17-B18-C5; A17-B18-C6;
A17-B18-C7; A17-B18-C8; A17-B18-C9; A17-B18-C10; A17-B18-C11; A17-B18-C12;
A17-B18-C13; A17-B18-C14; A17-B18-C15; A17-B18-C16; A17-B18-C17; A17-B18-C18;
A17-B18-C19; A17-B18-C20; A17-B18-C21; A17-B18-C22; A17-B18-C23; A17-B18-C24;
A17-B18-C25; A17-B18-C26; A17-B18-C27; A17-B18-C28; A17-B18-C29; A17-B18-C30;
A17-B18-C31; A17-B18-C32; A17-B18-C33; A17-B18-C34; A17-B18-C35; A17-B18-C36;
A17-B18-C37; A17-B18-C38; A17-B18-C39; A17-B18-C40; A17-B18-C41; A17-B18-C42;
A17-B18-C43; A17-B18-C44; A17-B18-C45; A17-B18-C46; A18-B18-C1; A18-B18-C2;
A18-B18-C3; A18-B18-C4; A18-B18-C5; A18-B18-C6; A18-B18-C7; A18-B18-C8;
A18-B18-C9; A18-B18-C10; A18-B18-C11; A18-B18-C12; A18-B18-C13; A18-B18-C14;
A18-B18-C15; A18-B18-C16; A18-B18-C17; A18-B18-C18; A18-B18-C19; A18-B18-C20;
A18-B18-C21; A18-B18-C22; A18-B18-C23; A18-B18-C24; A18-B18-C25; A18-B18-C26;
A18-B18-C27; A18-B18-C28; A18-B18-C29; A18-B18-C30; A18-B18-C31; A18-B18-C32;
A18-B18-C33; A18-B18-C34; A18-B18-C35; A18-B18-C36; A18-B18-C37; A18-B18-C38;
A18-B18-C39; A18-B18-C40; A18-B18-C41; A18-B18-C42; A18-B18-C43; A18-B18-C44;
A18-B18-C45; A18-B18-C46; A19-B18-C1; A19-B18-C2; A19-B18-C3; A19-B18-C4;
A19-B18-C5; A19-B18-C6; A19-B18-C7; A19-B18-C8; A19-B18-C9; A19-B18-C10;
A19-B18-C11; A19-B18-C12; A19-B18-C13; A19-B18-C14; A19-B18-C15; A19-B18-C16;
A19-B18-C17; A19-B18-C18; A19-B18-C19; A19-B18-C20; A19-B18-C21; A19-B18-C22;
A19-B18-C23; A19-B18-C24; A19-B18-C25; A19-B18-C26; A19-B18-C27; A19-B18-C28;
A19-B18-C29; A19-B18-C30; A19-B18-C31; A19-B18-C32; A19-B18-C33; A19-B18-C34;
A19-B18-C35; A19-B18-C36; A19-B18-C37; A19-B18-C38; A19-B18-C39; A19-B18-C40;
A19-B18-C41; A19-B18-C42; A19-B18-C43; A19-B18-C44; A19-B18-C45; A19-B18-C46;
A20-B18-C1; A20-B18-C2; A20-B18-C3; A20-B18-C4; A20-B18-C5; A20-B18-C6;
A20-B18-C7; A20-B18-C8; A20-B18-C9; A20-B18-C10; A20-B18-C11; A20-B18-C12;
A20-B18-C13; A20-B18-C14; A20-B18-C15; A20-B18-C16; A20-B18-C17; A20-B18-C18;
A20-B18-C19; A20-B18-C20; A20-B18-C21; A20-B18-C22; A20-B18-C23; A20-B18-C24;
A20-B18-C25; A20-B18-C26; A20-B18-C27; A20-B18-C28; A20-B18-C29; A20-B18-C30;
A20-B18-C31; A20-B18-C32; A20-B18-C33; A20-B18-C34; A20-B18-C35; A20-B18-C36;
A20-B18-C37; A20-B18-C38; A20-B18-C39; A20-B18-C40; A20-B18-C41; A20-B18-C42;
A20-B18-C43; A20-B18-C44; A20-B18-C45; A20-B18-C46; A21-B18-C1; A21-B18-C2;
A21-B18-C3; A21-B18-C4; A21-B18-C5; A21-B18-C6; A21-B18-C7; A21-B18-C8;
A21-B18-C9; A21-B18-C10; A21-B18-C11; A21-B18-C12; A21-B18-C13; A21-B18-C14;
A21-B18-C15; A21-B18-C16; A21-B18-C17; A21-B18-C18; A21-B18-C19; A21-B18-C20;
A21-B18-C21; A21-B18-C22; A21-B18-C23; A21-B18-C24; A21-B18-C25; A21-B18-C26;
A21-B18-C27; A21-B18-C28; A21-B18-C29; A21-B18-C30; A21-B18-C31; A21-B18-C32;
A21-B18-C33; A21-B18-C34; A21-B18-C35; A21-B18-C36; A21-B18-C37; A21-B18-C38;
A21-B18-C39; A21-B18-C40; A21-B18-C41; A21-B18-C42; A21-B18-C43; A21-B18-C44;
A21-B18-C45; A21-B18-C46; A22-B18-C1; A22-B18-C2; A22-B18-C3; A22-B18-C4;
A22-B18-C5; A22-B18-C6; A22-B18-C7; A22-B18-C8; A22-B18-C9; A22-B18-C10;
A22-B18-C11; A22-B18-C12; A22-B18-C13; A22-B18-C14; A22-B18-C15; A22-B18-C16;
A22-B18-C17; A22-B18-C18; A22-B18-C19; A22-B18-C20; A22-B18-C21; A22-B18-C22;
A22-B18-C23; A22-B18-C24; A22-B18-C25; A22-B18-C26; A22-B18-C27; A22-B18-C28;
A22-B18-C29; A22-B18-C30; A22-B18-C31; A22-B18-C32; A22-B18-C33; A22-B18-C34;
A22-B18-C35; A22-B18-C36; A22-B18-C37; A22-B18-C38; A22-B18-C39; A22-B18-C40;
A22-B18-C41; A22-B18-C42; A22-B18-C43; A22-B18-C44; A22-B18-C45; A22-B18-C46;
A23-B18-C1; A23-B18-C2; A23-B18-C3; A23-B18-C4; A23-B18-C5; A23-B18-C6;
A23-B18-C7; A23-B18-C8; A23-B18-C9; A23-B18-C10; A23-B18-C11; A23-B18-C12;
A23-B18-C13; A23-B18-C14; A23-B18-C15; A23-B18-C16; A23-B18-C17; A23-B18-C18;
A23-B18-C19; A23-B18-C20; A23-B18-C21; A23-B18-C22; A23-B18-C23; A23-B18-C24;
A23-B18-C25; A23-B18-C26; A23-B18-C27; A23-B18-C28; A23-B18-C29; A23-B18-C30;
A23-B18-C31; A23-B18-C32; A23-B18-C33; A23-B18-C34; A23-B18-C35; A23-B18-C36;
A23-B18-C37; A23-B18-C38; A23-B18-C39; A23-B18-C40; A23-B18-C41; A23-B18-C42;
A23-B18-C43; A23-B18-C44; A23-B18-C45; A23-B18-C46; A24-B18-C1; A24-B18-C2;
A24-B18-C3; A24-B18-C4; A24-B18-C5; A24-B18-C6; A24-B18-C7; A24-B18-C8;
A24-B18-C9; A24-B18-C10; A24-B18-C11; A24-B18-C12; A24-B18-C13; A24-B18-C14;
A24-B18-C15; A24-B18-C16; A24-B18-C17; A24-B18-C18; A24-B18-C19; A24-B18-C20;
A24-B18-C21; A24-B18-C22; A24-B18-C23; A24-B18-C24; A24-B18-C25; A24-B18-C26;
A24-B18-C27; A24-B18-C28; A24-B18-C29; A24-B18-C30; A24-B18-C31; A24-B18-C32;
A24-B18-C33; A24-B18-C34; A24-B18-C35; A24-B18-C36; A24-B18-C37; A24-B18-C38;

-continued

A24-B18-C39; A24-B18-C40; A24-B18-C41; A24-B18-C42; A24-B18-C43; A24-B18-C44;
A24-B18-C45; A24-B18-C46; A25-B18-C1; A25-B18-C2; A25-B18-C3; A25-B18-C4;
A25-B18-C5; A25-B18-C6; A25-B18-C7; A25-B18-C8; A25-B18-C9; A25-B18-C10;
A25-B18-C11; A25-B18-C12; A25-B18-C13; A25-B18-C14; A25-B18-C15; A25-B18-C16;
A25-B18-C17; A25-B18-C18; A25-B18-C19; A25-B18-C20; A25-B18-C21; A25-B18-C22;
A25-B18-C23; A25-B18-C24; A25-B18-C25; A25-B18-C26; A25-B18-C27; A25-B18-C28;
A25-B18-C29; A25-B18-C30; A25-B18-C31; A25-B18-C32; A25-B18-C33; A25-B18-C34;
A25-B18-C35; A25-B18-C36; A25-B18-C37; A25-B18-C38; A25-B18-C39; A25-B18-C40;
A25-B18-C41; A25-B18-C42; A25-B18-C43; A25-B18-C44; A25-B18-C45; A25-B18-C46;
A26-B18-C1; A26-B18-C2; A26-B18-C3; A26-B18-C4; A26-B18-C5; A26-B18-C6;
A26-B18-C7; A26-B18-C8; A26-B18-C9; A26-B18-C10; A26-B18-C11; A26-B18-C12;
A26-B18-C13; A26-B18-C14; A26-B18-C15; A26-B18-C16; A26-B18-C17; A26-B18-C18;
A26-B18-C19; A26-B18-C20; A26-B18-C21; A26-B18-C22; A26-B18-C23; A26-B18-C24;
A26-B18-C25; A26-B18-C26; A26-B18-C27; A26-B18-C28; A26-B18-C29; A26-B18-C30;
A26-B18-C31; A26-B18-C32; A26-B18-C33; A26-B18-C34; A26-B18-C35; A26-B18-C36;
A26-B18-C37; A26-B18-C38; A26-B18-C39; A26-B18-C40; A26-B18-C41; A26-B18-C42;
A26-B18-C43; A26-B18-C44; A26-B18-C45; A26-B18-C46; A27-B18-C1; A27-B18-C2;
A27-B18-C3; A27-B18-C4; A27-B18-C5; A27-B18-C6; A27-B18-C7; A27-B18-C8;
A27-B18-C9; A27-B18-C10; A27-B18-C11; A27-B18-C12; A27-B18-C13; A27-B18-C14;
A27-B18-C15; A27-B18-C16; A27-B18-C17; A27-B18-C18; A27-B18-C19; A27-B18-C20;
A27-B18-C21; A27-B18-C22; A27-B18-C23; A27-B18-C24; A27-B18-C25; A27-B18-C26;
A27-B18-C27; A27-B18-C28; A27-B18-C29; A27-B18-C30; A27-B18-C31; A27-B18-C32;
A27-B18-C33; A27-B18-C34; A27-B18-C35; A27-B18-C36; A27-B18-C37; A27-B18-C38;
A27-B18-C39; A27-B18-C40; A27-B18-C41; A27-B18-C42; A27-B18-C43; A27-B18-C44;
A27-B18-C45; A27-B18-C46; A28-B18-C1; A28-B18-C2; A28-B18-C3; A28-B18-C4;
A28-B18-C5; A28-B18-C6; A28-B18-C7; A28-B18-C8; A28-B18-C9; A28-B18-C10;
A28-B18-C11; A28-B18-C12; A28-B18-C13; A28-B18-C14; A28-B18-C15; A28-B18-C16;
A28-B18-C17; A28-B18-C18; A28-B18-C19; A28-B18-C20; A28-B18-C21; A28-B18-C22;
A28-B18-C23; A28-B18-C24; A28-B18-C25; A28-B18-C26; A28-B18-C27; A28-B18-C28;
A28-B18-C29; A28-B18-C30; A28-B18-C31; A28-B18-C32; A28-B18-C33; A28-B18-C34;
A28-B18-C35; A28-B18-C36; A28-B18-C37; A28-B18-C38; A28-B18-C39; A28-B18-C40;
A28-B18-C41; A28-B18-C42; A28-B18-C43; A28-B18-C44; A28-B18-C45; A28-B18-C46;
A1-B19-C1; A1-B19-C2; A1-B19-C3; A1-B19-C4; A1-B19-C5; A1-B19-C6;
A1-B19-C7; A1-B19-C8; A1-B19-C9; A1-B19-C10; A1-B19-C11; A1-B19-C12;
A1-B19-C13; A1-B19-C14; A1-B19-C15; A1-B19-C16; A1-B19-C17; A1-B19-C18;
A1-B19-C19; A1-B19-C20; A1-B19-C21; A1-B19-C22; A1-B19-C23; A1-B19-C24;
A1-B19-C25; A1-B19-C26; A1-B19-C27; A1-B19-C28; A1-B19-C29; A1-B19-C30;
A1-B19-C31; A1-B19-C32; A1-B19-C33; A1-B19-C34; A1-B19-C35; A1-B19-C36;
A1-B19-C37; A1-B19-C38; A1-B19-C39; A1-B19-C40; A1-B19-C41; A1-B19-C42;
A1-B19-C43; A1-B19-C44; A1-B19-C45; A1-B19-C46; A2-B19-C1; A2-B19-C2;
A2-B19-C3; A2-B19-C4; A2-B19-C5; A2-B19-C6; A2-B19-C7; A2-B19-C8;
A2-B19-C9; A2-B19-C10; A2-B19-C11; A2-B19-C12; A2-B19-C13; A2-B19-C14;
A2-B19-C15; A2-B19-C16; A2-B19-C17; A2-B19-C18; A2-B19-C19; A2-B19-C20;
A2-B19-C21; A2-B19-C22; A2-B19-C23; A2-B19-C24; A2-B19-C25; A2-B19-C26;
A2-B19-C27; A2-B19-C28; A2-B19-C29; A2-B19-C30; A2-B19-C31; A2-B19-C32;
A2-B19-C33; A2-B19-C34; A2-B19-C35; A2-B19-C36; A2-B19-C37; A2-B19-C38;
A2-B19-C39; A2-B19-C40; A2-B19-C41; A2-B19-C42; A2-B19-C43; A2-B19-C44;
A2-B19-C45; A2-B19-C46; A3-B19-C1; A3-B19-C2; A3-B19-C3; A3-B19-C4;
A3-B19-C5; A3-B19-C6; A3-B19-C7; A3-B19-C8; A3-B19-C9; A3-B19-C10;
A3-B19-C11; A3-B19-C12; A3-B19-C13; A3-B19-C14; A3-B19-C15; A3-B19-C16;
A3-B19-C17; A3-B19-C18; A3-B19-C19; A3-B19-C20; A3-B19-C21; A3-B19-C22;
A3-B19-C23; A3-B19-C24; A3-B19-C25; A3-B19-C26; A3-B19-C27; A3-B19-C28;
A3-B19-C29; A3-B19-C30; A3-B19-C31; A3-B19-C32; A3-B19-C33; A3-B19-C34;
A3-B19-C35; A3-B19-C36; A3-B19-C37; A3-B19-C38; A3-B19-C39; A3-B19-C40;
A3-B19-C41; A3-B19-C42; A3-B19-C43; A3-B19-C44; A3-B19-C45; A3-B19-C46;
A4-B19-C1; A4-B19-C2; A4-B19-C3; A4-B19-C4; A4-B19-C5; A4-B19-C6;
A4-B19-C7; A4-B19-C8; A4-B19-C9; A4-B19-C10; A4-B19-C11; A4-B19-C12;
A4-B19-C13; A4-B19-C14; A4-B19-C15; A4-B19-C16; A4-B19-C17; A4-B19-C18;
A4-B19-C19; A4-B19-C20; A4-B19-C21; A4-B19-C22; A4-B19-C23; A4-B19-C24;
A4-B19-C25; A4-B19-C26; A4-B19-C27; A4-B19-C28; A4-B19-C29; A4-B19-C30;
A4-B19-C31; A4-B19-C32; A4-B19-C33; A4-B19-C34; A4-B19-C35; A4-B19-C36;
A4-B19-C37; A4-B19-C38; A4-B19-C39; A4-B19-C40; A4-B19-C41; A4-B19-C42;
A4-B19-C43; A4-B19-C44; A4-B19-C45; A4-B19-C46; A5-B19-C1; A5-B19-C2;
A5-B19-C3; A5-B19-C4; A5-B19-C5; A5-B19-C6; A5-B19-C7; A5-B19-C8;
A5-B19-C9; A5-B19-C10; A5-B19-C11; A5-B19-C12; A5-B19-C13; A5-B19-C14;
A5-B19-C15; A5-B19-C16; A5-B19-C17; A5-B19-C18; A5-B19-C19; A5-B19-C20;
A5-B19-C21; A5-B19-C22; A5-B19-C23; A5-B19-C24; A5-B19-C25; A5-B19-C26;
A5-B19-C27; A5-B19-C28; A5-B19-C29; A5-B19-C30; A5-B19-C31; A5-B19-C32;
A5-B19-C33; A5-B19-C34; A5-B19-C35; A5-B19-C36; A5-B19-C37; A5-B19-C38;
A5-B19-C39; A5-B19-C40; A5-B19-C41; A5-B19-C42; A5-B19-C43; A5-B19-C44;
A5-B19-C45; A5-B19-C46; A6-B19-C1; A6-B19-C2; A6-B19-C3; A6-B19-C4;
A6-B19-C5; A6-B19-C6; A6-B19-C7; A6-B19-C8; A6-B19-C9; A6-B19-C10;
A6-B19-C11; A6-B19-C12; A6-B19-C13; A6-B19-C14; A6-B19-C15; A6-B19-C16;
A6-B19-C17; A6-B19-C18; A6-B19-C19; A6-B19-C20; A6-B19-C21; A6-B19-C22;
A6-B19-C23; A6-B19-C24; A6-B19-C25; A6-B19-C26; A6-B19-C27; A6-B19-C28;
A6-B19-C29; A6-B19-C30; A6-B19-C31; A6-B19-C32; A6-B19-C33; A6-B19-C34;
A6-B19-C35; A6-B19-C36; A6-B19-C37; A6-B19-C38; A6-B19-C39; A6-B19-C40;
A6-B19-C41; A6-B19-C42; A6-B19-C43; A6-B19-C44; A6-B19-C45; A6-B19-C46;
A7-B19-C1; A7-B19-C2; A7-B19-C3; A7-B19-C4; A7-B19-C5; A7-B19-C6;

-continued

| | | | | | |
|---|---|---|---|---|---|
| A7-B19-C7; | A7-B19-C8; | A7-B19-C9; | A7-B19-C10; | A7-B19-C11; | A7-B19-C12; |
| A7-B19-C13; | A7-B19-C14; | A7-B19-C15; | A7-B19-C16; | A7-B19-C17; | A7-B19-C18; |
| A7-B19-C19; | A7-B19-C20; | A7-B19-C21; | A7-B19-C22; | A7-B19-C23; | A7-B19-C24; |
| A7-B19-C25; | A7-B19-C26; | A7-B19-C27; | A7-B19-C28; | A7-B19-C29; | A7-B19-C30; |
| A7-B19-C31; | A7-B19-C32; | A7-B19-C33; | A7-B19-C34; | A7-B19-C35; | A7-B19-C36; |
| A7-B19-C37; | A7-B19-C38; | A7-B19-C39; | A7-B19-C40; | A7-B19-C41; | A7-B19-C42; |
| A7-B19-C43; | A7-B19-C44; | A7-B19-C45; | A7-B19-C46; | A8-B19-C1; | A8-B19-C2; |
| A8-B19-C3; | A8-B19-C4; | A8-B19-C5; | A8-B19-C6; | A8-B19-C7; | A8-B19-C8; |
| A8-B19-C9; | A8-B19-C10; | A8-B19-C11; | A8-B19-C12; | A8-B19-C13; | A8-B19-C14; |
| A8-B19-C15; | A8-B19-C16; | A8-B19-C17; | A8-B19-C18; | A8-B19-C19; | A8-B19-C20; |
| A8-B19-C21; | A8-B19-C22; | A8-B19-C23; | A8-B19-C24; | A8-B19-C25; | A8-B19-C26; |
| A8-B19-C27; | A8-B19-C28; | A8-B19-C29; | A8-B19-C30; | A8-B19-C31; | A8-B19-C32; |
| A8-B19-C33; | A8-B19-C34; | A8-B19-C35; | A8-B19-C36; | A8-B19-C37; | A8-B19-C38; |
| A8-B19-C39; | A8-B19-C40; | A8-B19-C41; | A8-B19-C42; | A8-B19-C43; | A8-B19-C44; |
| A8-B19-C45; | A8-B19-C46; | A9-B19-C1; | A9-B19-C2; | A9-B19-C3; | A9-B19-C4; |
| A9-B19-C5; | A9-B19-C6; | A9-B19-C7; | A9-B19-C8; | A9-B19-C9; | A9-B19-C10; |
| A9-B19-C11; | A9-B19-C12; | A9-B19-C13; | A9-B19-C14; | A9-B19-C15; | A9-B19-C16; |
| A9-B19-C17; | A9-B19-C18; | A9-B19-C19; | A9-B19-C20; | A9-B19-C21; | A9-B19-C22; |
| A9-B19-C23; | A9-B19-C24; | A9-B19-C25; | A9-B19-C26; | A9-B19-C27; | A9-B19-C28; |
| A9-B19-C29; | A9-B19-C30; | A9-B19-C31; | A9-B19-C32; | A9-B19-C33; | A9-B19-C34; |
| A9-B19-C35; | A9-B19-C36; | A9-B19-C37; | A9-B19-C38; | A9-B19-C39; | A9-B19-C40; |
| A9-B19-C41; | A9-B19-C42; | A9-B19-C43; | A9-B19-C44; | A9-B19-C45; | A9-B19-C46; |
| A10-B19-C1; | A10-B19-C2; | A10-B19-C3; | A10-B19-C4; | A10-B19-C5; | A10-B19-C6; |
| A10-B19-C7; | A10-B19-C8; | A10-B19-C9; | A10-B19-C10; | A10-B19-C11; | A10-B19-C12; |
| A10-B19-C13; | A10-B19-C14; | A10-B19-C15; | A10-B19-C16; | A10-B19-C17; | A10-B19-C18; |
| A10-B19-C19; | A10-B19-C20; | A10-B19-C21; | A10-B19-C22; | A10-B19-C23; | A10-B19-C24; |
| A10-B19-C25; | A10-B19-C26; | A10-B19-C27; | A10-B19-C28; | A10-B19-C29; | A10-B19-C30; |
| A10-B19-C31; | A10-B19-C32; | A10-B19-C33; | A10-B19-C34; | A10-B19-C35; | A10-B19-C36; |
| A10-B19-C37; | A10-B19-C38; | A10-B19-C39; | A10-B19-C40; | A10-B19-C41; | A10-B19-C42; |
| A10-B19-C43; | A10-B19-C44; | A10-B19-C45; | A10-B19-C46; | A11-B19-C1; | A11-B19-C2; |
| A11-B19-C3; | A11-B19-C4; | A11-B19-C5; | A11-B19-C6; | A11-B19-C7; | A11-B19-C8; |
| A11-B19-C9; | A11-B19-C10; | A11-B19-C11; | A11-B19-C12; | A11-B19-C13; | A11-B19-C14; |
| A11-B19-C15; | A11-B19-C16; | A11-B19-C17; | A11-B19-C18; | A11-B19-C19; | A11-B19-C20; |
| A11-B19-C21; | A11-B19-C22; | A11-B19-C23; | A11-B19-C24; | A11-B19-C25; | A11-B19-C26; |
| A11-B19-C27; | A11-B19-C28; | A11-B19-C29; | A11-B19-C30; | A11-B19-C31; | A11-B19-C32; |
| A11-B19-C33; | A11-B19-C34; | A11-B19-C35; | A11-B19-C36; | A11-B19-C37; | A11-B19-C38; |
| A11-B19-C39; | A11-B19-C40; | A11-B19-C41; | A11-B19-C42; | A11-B19-C43; | A11-B19-C44; |
| A11-B19-C45; | A11-B19-C46; | A12-B19-C1; | A12-B19-C2; | A12-B19-C3; | A12-B19-C4; |
| A12-B19-C5; | A12-B19-C6; | A12-B19-C7; | A12-B19-C8; | A12-B19-C9; | A12-B19-C10; |
| A12-B19-C11; | A12-B19-C12; | A12-B19-C13; | A12-B19-C14; | A12-B19-C15; | A12-B19-C16; |
| A12-B19-C17; | A12-B19-C18; | A12-B19-C19; | A12-B19-C20; | A12-B19-C21; | A12-B19-C22; |
| A12-B19-C23; | A12-B19-C24; | A12-B19-C25; | A12-B19-C26; | A12-B19-C27; | A12-B19-C28; |
| A12-B19-C29; | A12-B19-C30; | A12-B19-C31; | A12-B19-C32; | A12-B19-C33; | A12-B19-C34; |
| A12-B19-C35; | A12-B19-C36; | A12-B19-C37; | A12-B19-C38; | A12-B19-C39; | A12-B19-C40; |
| A12-B19-C41; | A12-B19-C42; | A12-B19-C43; | A12-B19-C44; | A12-B19-C45; | A12-B19-C46; |
| A13-B19-C1; | A13-B19-C2; | A13-B19-C3; | A13-B19-C4; | A13-B19-C5; | A13-B19-C6; |
| A13-B19-C7; | A13-B19-C8; | A13-B19-C9; | A13-B19-C10; | A13-B19-C11; | A13-B19-C12; |
| A13-B19-C13; | A13-B19-C14; | A13-B19-C15; | A13-B19-C16; | A13-B19-C17; | A13-B19-C18; |
| A13-B19-C19; | A13-B19-C20; | A13-B19-C21; | A13-B19-C22; | A13-B19-C23; | A13-B19-C24; |
| A13-B19-C25; | A13-B19-C26; | A13-B19-C27; | A13-B19-C28; | A13-B19-C29; | A13-B19-C30; |
| A13-B19-C31; | A13-B19-C32; | A13-B19-C33; | A13-B19-C34; | A13-B19-C35; | A13-B19-C36; |
| A13-B19-C37; | A13-B19-C38; | A13-B19-C39; | A13-B19-C40; | A13-B19-C41; | A13-B19-C42; |
| A13-B19-C43; | A13-B19-C44; | A13-B19-C45; | A13-B19-C46; | A14-B19-C1; | A14-B19-C2; |
| A14-B19-C3; | A14-B19-C4; | A14-B19-C5; | A14-B19-C6; | A14-B19-C7; | A14-B19-C8; |
| A14-B19-C9; | A14-B19-C10; | A14-B19-C11; | A14-B19-C12; | A14-B19-C13; | A14-B19-C14; |
| A14-B19-C15; | A14-B19-C16; | A14-B19-C17; | A14-B19-C18; | A14-B19-C19; | A14-B19-C20; |
| A14-B19-C21; | A14-B19-C22; | A14-B19-C23; | A14-B19-C24; | A14-B19-C25; | A14-B19-C26; |
| A14-B19-C27; | A14-B19-C28; | A14-B19-C29; | A14-B19-C30; | A14-B19-C31; | A14-B19-C32; |
| A14-B19-C33; | A14-B19-C34; | A14-B19-C35; | A14-B19-C36; | A14-B19-C37; | A14-B19-C38; |
| A14-B19-C39; | A14-B19-C40; | A14-B19-C41; | A14-B19-C42; | A14-B19-C43; | A14-B19-C44; |
| A14-B19-C45; | A14-B19-C46; | A15-B19-C1; | A15-B19-C2; | A15-B19-C3; | A15-B19-C4; |
| A15-B19-C5; | A15-B19-C6; | A15-B19-C7; | A15-B19-C8; | A15-B19-C9; | A15-B19-C10; |
| A15-B19-C11; | A15-B19-C12; | A15-B19-C13; | A15-B19-C14; | A15-B19-C15; | A15-B19-C16; |
| A15-B19-C17; | A15-B19-C18; | A15-B19-C19; | A15-B19-C20; | A15-B19-C21; | A15-B19-C22; |
| A15-B19-C23; | A15-B19-C24; | A15-B19-C25; | A15-B19-C26; | A15-B19-C27; | A15-B19-C28; |
| A15-B19-C29; | A15-B19-C30; | A15-B19-C31; | A15-B19-C32; | A15-B19-C33; | A15-B19-C34; |
| A15-B19-C35; | A15-B19-C36; | A15-B19-C37; | A15-B19-C38; | A15-B19-C39; | A15-B19-C40; |
| A15-B19-C41; | A15-B19-C42; | A15-B19-C43; | A15-B19-C44; | A15-B19-C45; | A15-B19-C46; |
| A16-B19-C1; | A16-B19-C2; | A16-B19-C3; | A16-B19-C4; | A16-B19-C5; | A16-B19-C6; |
| A16-B19-C7; | A16-B19-C8; | A16-B19-C9; | A16-B19-C10; | A16-B19-C11; | A16-B19-C12; |
| A16-B19-C13; | A16-B19-C14; | A16-B19-C15; | A16-B19-C16; | A16-B19-C17; | A16-B19-C18; |
| A16-B19-C19; | A16-B19-C20; | A16-B19-C21; | A16-B19-C22; | A16-B19-C23; | A16-B19-C24; |
| A16-B19-C25; | A16-B19-C26; | A16-B19-C27; | A16-B19-C28; | A16-B19-C29; | A16-B19-C30; |
| A16-B19-C31; | A16-B19-C32; | A16-B19-C33; | A16-B19-C34; | A16-B19-C35; | A16-B19-C36; |
| A16-B19-C37; | A16-B19-C38; | A16-B19-C39; | A16-B19-C40; | A16-B19-C41; | A16-B19-C42; |
| A16-B19-C43; | A16-B19-C44; | A16-B19-C45; | A16-B19-C46; | A17-B19-C1; | A17-B19-C2; |
| A17-B19-C3; | A17-B19-C4; | A17-B19-C5; | A17-B19-C6; | A17-B19-C7; | A17-B19-C8; |
| A17-B19-C9; | A17-B19-C10; | A17-B19-C11; | A17-B19-C12; | A17-B19-C13; | A17-B19-C14; |
| A17-B19-C15; | A17-B19-C16; | A17-B19-C17; | A17-B19-C18; | A17-B19-C19; | A17-B19-C20; |

-continued

A17-B19-C21; A17-B19-C22; A17-B19-C23; A17-B19-C24; A17-B19-C25; A17-B19-C26;
A17-B19-C27; A17-B19-C28; A17-B19-C29; A17-B19-C30; A17-B19-C31; A17-B19-C32;
A17-B19-C33; A17-B19-C34; A17-B19-C35; A17-B19-C36; A17-B19-C37; A17-B19-C38;
A17-B19-C39; A17-B19-C40; A17-B19-C41; A17-B19-C42; A17-B19-C43; A17-B19-C44;
A17-B19-C45; A17-B19-C46; A18-B19-C1; A18-B19-C2; A18-B19-C3; A18-B19-C4;
A18-B19-C5; A18-B19-C6; A18-B19-C7; A18-B19-C8; A18-B19-C9; A18-B19-C10;
A18-B19-C11; A18-B19-C12; A18-B19-C13; A18-B19-C14; A18-B19-C15; A18-B19-C16;
A18-B19-C17; A18-B19-C18; A18-B19-C19; A18-B19-C20; A18-B19-C21; A18-B19-C22;
A18-B19-C23; A18-B19-C24; A18-B19-C25; A18-B19-C26; A18-B19-C27; A18-B19-C28;
A18-B19-C29; A18-B19-C30; A18-B19-C31; A18-B19-C32; A18-B19-C33; A18-B19-C34;
A18-B19-C35; A18-B19-C36; A18-B19-C37; A18-B19-C38; A18-B19-C39; A18-B19-C40;
A18-B19-C41; A18-B19-C42; A18-B19-C43; A18-B19-C44; A18-B19-C45; A18-B19-C46;
A19-B19-C1; A19-B19-C2; A19-B19-C3; A19-B19-C4; A19-B19-C5; A19-B19-C6;
A19-B19-C7; A19-B19-C8; A19-B19-C9; A19-B19-C10; A19-B19-C11; A19-B19-C12;
A19-B19-C13; A19-B19-C14; A19-B19-C15; A19-B19-C16; A19-B19-C17; A19-B19-C18;
A19-B19-C19; A19-B19-C20; A19-B19-C21; A19-B19-C22; A19-B19-C23; A19-B19-C24;
A19-B19-C25; A19-B19-C26; A19-B19-C27; A19-B19-C28; A19-B19-C29; A19-B19-C30;
A19-B19-C31; A19-B19-C32; A19-B19-C33; A19-B19-C34; A19-B19-C35; A19-B19-C36;
A19-B19-C37; A19-B19-C38; A19-B19-C39; A19-B19-C40; A19-B19-C41; A19-B19-C42;
A19-B19-C43; A19-B19-C44; A19-B19-C45; A19-B19-C46; A20-B19-C1; A20-B19-C2;
A20-B19-C3; A20-B19-C4; A20-B19-C5; A20-B19-C6; A20-B19-C7; A20-B19-C8;
A20-B19-C9; A20-B19-C10; A20-B19-C11; A20-B19-C12; A20-B19-C13; A20-B19-C14;
A20-B19-C15; A20-B19-C16; A20-B19-C17; A20-B19-C18; A20-B19-C19; A20-B19-C20;
A20-B19-C21; A20-B19-C22; A20-B19-C23; A20-B19-C24; A20-B19-C25; A20-B19-C26;
A20-B19-C27; A20-B19-C28; A20-B19-C29; A20-B19-C30; A20-B19-C31; A20-B19-C32;
A20-B19-C33; A20-B19-C34; A20-B19-C35; A20-B19-C36; A20-B19-C37; A20-B19-C38;
A20-B19-C39; A20-B19-C40; A20-B19-C41; A20-B19-C42; A20-B19-C43; A20-B19-C44;
A20-B19-C45; A20-B19-C46; A21-B19-C1; A21-B19-C2; A21-B19-C3; A21-B19-C4;
A21-B19-C5; A21-B19-C6; A21-B19-C7; A21-B19-C8; A21-B19-C9; A21-B19-C10;
A21-B19-C11; A21-B19-C12; A21-B19-C13; A21-B19-C14; A21-B19-C15; A21-B19-C16;
A21-B19-C17; A21-B19-C18; A21-B19-C19; A21-B19-C20; A21-B19-C21; A21-B19-C22;
A21-B19-C23; A21-B19-C24; A21-B19-C25; A21-B19-C26; A21-B19-C27; A21-B19-C28;
A21-B19-C29; A21-B19-C30; A21-B19-C31; A21-B19-C32; A21-B19-C33; A21-B19-C34;
A21-B19-C35; A21-B19-C36; A21-B19-C37; A21-B19-C38; A21-B19-C39; A21-B19-C40;
A21-B19-C41; A21-B19-C42; A21-B19-C43; A21-B19-C44; A21-B19-C45; A21-B19-C46;
A22-B19-C1; A22-B19-C2; A22-B19-C3; A22-B19-C4; A22-B19-C5; A22-B19-C6;
A22-B19-C7; A22-B19-C8; A22-B19-C9; A22-B19-C10; A22-B19-C11; A22-B19-C12;
A22-B19-C13; A22-B19-C14; A22-B19-C15; A22-B19-C16; A22-B19-C17; A22-B19-C18;
A22-B19-C19; A22-B19-C20; A22-B19-C21; A22-B19-C22; A22-B19-C23; A22-B19-C24;
A22-B19-C25; A22-B19-C26; A22-B19-C27; A22-B19-C28; A22-B19-C29; A22-B19-C30;
A22-B19-C31; A22-B19-C32; A22-B19-C33; A22-B19-C34; A22-B19-C35; A22-B19-C36;
A22-B19-C37; A22-B19-C38; A22-B19-C39; A22-B19-C40; A22-B19-C41; A22-B19-C42;
A22-B19-C43; A22-B19-C44; A22-B19-C45; A22-B19-C46; A23-B19-C1; A23-B19-C2;
A23-B19-C3; A23-B19-C4; A23-B19-C5; A23-B19-C6; A23-B19-C7; A23-B19-C8;
A23-B19-C9; A23-B19-C10; A23-B19-C11; A23-B19-C12; A23-B19-C13; A23-B19-C14;
A23-B19-C15; A23-B19-C16; A23-B19-C17; A23-B19-C18; A23-B19-C19; A23-B19-C20;
A23-B19-C21; A23-B19-C22; A23-B19-C23; A23-B19-C24; A23-B19-C25; A23-B19-C26;
A23-B19-C27; A23-B19-C28; A23-B19-C29; A23-B19-C30; A23-B19-C31; A23-B19-C32;
A23-B19-C33; A23-B19-C34; A23-B19-C35; A23-B19-C36; A23-B19-C37; A23-B19-C38;
A23-B19-C39; A23-B19-C40; A23-B19-C41; A23-B19-C42; A23-B19-C43; A23-B19-C44;
A23-B19-C45; A23-B19-C46; A24-B19-C1; A24-B19-C2; A24-B19-C3; A24-B19-C4;
A24-B19-C5; A24-B19-C6; A24-B19-C7; A24-B19-C8; A24-B19-C9; A24-B19-C10;
A24-B19-C11; A24-B19-C12; A24-B19-C13; A24-B19-C14; A24-B19-C15; A24-B19-C16;
A24-B19-C17; A24-B19-C18; A24-B19-C19; A24-B19-C20; A24-B19-C21; A24-B19-C22;
A24-B19-C23; A24-B19-C24; A24-B19-C25; A24-B19-C26; A24-B19-C27; A24-B19-C28;
A24-B19-C29; A24-B19-C30; A24-B19-C31; A24-B19-C32; A24-B19-C33; A24-B19-C34;
A24-B19-C35; A24-B19-C36; A24-B19-C37; A24-B19-C38; A24-B19-C39; A24-B19-C40;
A24-B19-C41; A24-B19-C42; A24-B19-C43; A24-B19-C44; A24-B19-C45; A24-B19-C46;
A25-B19-C1; A25-B19-C2; A25-B19-C3; A25-B19-C4; A25-B19-C5; A25-B19-C6;
A25-B19-C7; A25-B19-C8; A25-B19-C9; A25-B19-C10; A25-B19-C11; A25-B19-C12;
A25-B19-C13; A25-B19-C14; A25-B19-C15; A25-B19-C16; A25-B19-C17; A25-B19-C18;
A25-B19-C19; A25-B19-C20; A25-B19-C21; A25-B19-C22; A25-B19-C23; A25-B19-C24;
A25-B19-C25; A25-B19-C26; A25-B19-C27; A25-B19-C28; A25-B19-C29; A25-B19-C30;
A25-B19-C31; A25-B19-C32; A25-B19-C33; A25-B19-C34; A25-B19-C35; A25-B19-C36;
A25-B19-C37; A25-B19-C38; A25-B19-C39; A25-B19-C40; A25-B19-C41; A25-B19-C42;
A25-B19-C43; A25-B19-C44; A25-B19-C45; A25-B19-C46; A26-B19-C1; A26-B19-C2;
A26-B19-C3; A26-B19-C4; A26-B19-C5; A26-B19-C6; A26-B19-C7; A26-B19-C8;
A26-B19-C9; A26-B19-C10; A26-B19-C11; A26-B19-C12; A26-B19-C13; A26-B19-C14;
A26-B19-C15; A26-B19-C16; A26-B19-C17; A26-B19-C18; A26-B19-C19; A26-B19-C20;
A26-B19-C21; A26-B19-C22; A26-B19-C23; A26-B19-C24; A26-B19-C25; A26-B19-C26;
A26-B19-C27; A26-B19-C28; A26-B19-C29; A26-B19-C30; A26-B19-C31; A26-B19-C32;
A26-B19-C33; A26-B19-C34; A26-B19-C35; A26-B19-C36; A26-B19-C37; A26-B19-C38;
A26-B19-C39; A26-B19-C40; A26-B19-C41; A26-B19-C42; A26-B19-C43; A26-B19-C44;
A26-B19-C45; A26-B19-C46; A27-B19-C1; A27-B19-C2; A27-B19-C3; A27-B19-C4;
A27-B19-C5; A27-B19-C6; A27-B19-C7; A27-B19-C8; A27-B19-C9; A27-B19-C10;
A27-B19-C11; A27-B19-C12; A27-B19-C13; A27-B19-C14; A27-B19-C15; A27-B19-C16;
A27-B19-C17; A27-B19-C18; A27-B19-C19; A27-B19-C20; A27-B19-C21; A27-B19-C22;
A27-B19-C23; A27-B19-C24; A27-B19-C25; A27-B19-C26; A27-B19-C27; A27-B19-C28;
A27-B19-C29; A27-B19-C30; A27-B19-C31; A27-B19-C32; A27-B19-C33; A27-B19-C34;

-continued

A27-B19-C35; A27-B19-C36; A27-B19-C37; A27-B19-C38; A27-B19-C39; A27-B19-C40;
A27-B19-C41; A27-B19-C42; A27-B19-C43; A27-B19-C44; A27-B19-C45; A27-B19-C46;
A28-B19-C1; A28-B19-C2; A28-B19-C3; A28-B19-C4; A28-B19-C5; A28-B19-C6;
A28-B19-C7; A28-B19-C8; A28-B19-C9; A28-B19-C10; A28-B19-C11; A28-B19-C12;
A28-B19-C13; A28-B19-C14; A28-B19-C15; A28-B19-C16; A28-B19-C17; A28-B19-C18;
A28-B19-C19; A28-B19-C20; A28-B19-C21; A28-B19-C22; A28-B19-C23; A28-B19-C24;
A28-B19-C25; A28-B19-C26; A28-B19-C27; A28-B19-C28; A28-B19-C29; A28-B19-C30;
A28-B19-C31; A28-B19-C32; A28-B19-C33; A28-B19-C34; A28-B19-C35; A28-B19-C36;
A28-B19-C37; A28-B19-C38; A28-B19-C39; A28-B19-C40; A28-B19-C41; A28-B19-C42;
A28-B19-C43; A28-B19-C44; A28-B19-C45; A28-B19-C46; A1-B20-C1; A1-B20-C2;
A1-B20-C3; A1-B20-C4; A1-B20-C5; A1-B20-C6; A1-B20-C7; A1-B20-C8;
A1-B20-C9; A1-B20-C10; A1-B20-C11; A1-B20-C12; A1-B20-C13; A1-B20-C14;
A1-B20-C15; A1-B20-C16; A1-B20-C17; A1-B20-C18; A1-B20-C19; A1-B20-C20;
A1-B20-C21; A1-B20-C22; A1-B20-C23; A1-B20-C24; A1-B20-C25; A1-B20-C26;
A1-B20-C27; A1-B20-C28; A1-B20-C29; A1-B20-C30; A1-B20-C31; A1-B20-C32;
A1-B20-C33; A1-B20-C34; A1-B20-C35; A1-B20-C36; A1-B20-C37; A1-B20-C38;
A1-B20-C39; A1-B20-C40; A1-B20-C41; A1-B20-C42; A1-B20-C43; A1-B20-C44;
A1-B20-C45; A1-B20-C46; A2-B20-C1; A2-B20-C2; A2-B20-C3; A2-B20-C4;
A2-B20-C5; A2-B20-C6; A2-B20-C7; A2-B20-C8; A2-B20-C9; A2-B20-C10;
A2-B20-C11; A2-B20-C12; A2-B20-C13; A2-B20-C14; A2-B20-C15; A2-B20-C16;
A2-B20-C17; A2-B20-C18; A2-B20-C19; A2-B20-C20; A2-B20-C21; A2-B20-C22;
A2-B20-C23; A2-B20-C24; A2-B20-C25; A2-B20-C26; A2-B20-C27; A2-B20-C28;
A2-B20-C29; A2-B20-C30; A2-B20-C31; A2-B20-C32; A2-B20-C33; A2-B20-C34;
A2-B20-C35; A2-B20-C36; A2-B20-C37; A2-B20-C38; A2-B20-C39; A2-B20-C40;
A2-B20-C41; A2-B20-C42; A2-B20-C43; A2-B20-C44; A2-B20-C45; A2-B20-C46;
A3-B20-C1; A3-B20-C2; A3-B20-C3; A3-B20-C4; A3-B20-C5; A3-B20-C6;
A3-B20-C7; A3-B20-C8; A3-B20-C9; A3-B20-C10; A3-B20-C11; A3-B20-C12;
A3-B20-C13; A3-B20-C14; A3-B20-C15; A3-B20-C16; A3-B20-C17; A3-B20-C18;
A3-B20-C19; A3-B20-C20; A3-B20-C21; A3-B20-C22; A3-B20-C23; A3-B20-C24;
A3-B20-C25; A3-B20-C26; A3-B20-C27; A3-B20-C28; A3-B20-C29; A3-B20-C30;
A3-B20-C31; A3-B20-C32; A3-B20-C33; A3-B20-C34; A3-B20-C35; A3-B20-C36;
A3-B20-C37; A3-B20-C38; A3-B20-C39; A3-B20-C40; A3-B20-C41; A3-B20-C42;
A3-B20-C43; A3-B20-C44; A3-B20-C45; A3-B20-C46; A4-B20-C1; A4-B20-C2;
A4-B20-C3; A4-B20-C4; A4-B20-C5; A4-B20-C6; A4-B20-C7; A4-B20-C8;
A4-B20-C9; A4-B20-C10; A4-B20-C11; A4-B20-C12; A4-B20-C13; A4-B20-C14;
A4-B20-C15; A4-B20-C16; A4-B20-C17; A4-B20-C18; A4-B20-C19; A4-B20-C20;
A4-B20-C21; A4-B20-C22; A4-B20-C23; A4-B20-C24; A4-B20-C25; A4-B20-C26;
A4-B20-C27; A4-B20-C28; A4-B20-C29; A4-B20-C30; A4-B20-C31; A4-B20-C32;
A4-B20-C33; A4-B20-C34; A4-B20-C35; A4-B20-C36; A4-B20-C37; A4-B20-C38;
A4-B20-C39; A4-B20-C40; A4-B20-C41; A4-B20-C42; A4-B20-C43; A4-B20-C44;
A4-B20-C45; A4-B20-C46; A5-B20-C1; A5-B20-C2; A5-B20-C3; A5-B20-C4;
A5-B20-C5; A5-B20-C6; A5-B20-C7; A5-B20-C8; A5-B20-C9; A5-B20-C10;
A5-B20-C11; A5-B20-C12; A5-B20-C13; A5-B20-C14; A5-B20-C15; A5-B20-C16;
A5-B20-C17; A5-B20-C18; A5-B20-C19; A5-B20-C20; A5-B20-C21; A5-B20-C22;
A5-B20-C23; A5-B20-C24; A5-B20-C25; A5-B20-C26; A5-B20-C27; A5-B20-C28;
A5-B20-C29; A5-B20-C30; A5-B20-C31; A5-B20-C32; A5-B20-C33; A5-B20-C34;
A5-B20-C35; A5-B20-C36; A5-B20-C37; A5-B20-C38; A5-B20-C39; A5-B20-C40;
A5-B20-C41; A5-B20-C42; A5-B20-C43; A5-B20-C44; A5-B20-C45; A5-B20-C46;
A6-B20-C1; A6-B20-C2; A6-B20-C3; A6-B20-C4; A6-B20-C5; A6-B20-C6;
A6-B20-C7; A6-B20-C8; A6-B20-C9; A6-B20-C10; A6-B20-C11; A6-B20-C12;
A6-B20-C13; A6-B20-C14; A6-B20-C15; A6-B20-C16; A6-B20-C17; A6-B20-C18;
A6-B20-C19; A6-B20-C20; A6-B20-C21; A6-B20-C22; A6-B20-C23; A6-B20-C24;
A6-B20-C25; A6-B20-C26; A6-B20-C27; A6-B20-C28; A6-B20-C29; A6-B20-C30;
A6-B20-C31; A6-B20-C32; A6-B20-C33; A6-B20-C34; A6-B20-C35; A6-B20-C36;
A6-B20-C37; A6-B20-C38; A6-B20-C39; A6-B20-C40; A6-B20-C41; A6-B20-C42;
A6-B20-C43; A6-B20-C44; A6-B20-C45; A6-B20-C46; A7-B20-C1; A7-B20-C2;
A7-B20-C3; A7-B20-C4; A7-B20-C5; A7-B20-C6; A7-B20-C7; A7-B20-C8;
A7-B20-C9; A7-B20-C10; A7-B20-C11; A7-B20-C12; A7-B20-C13; A7-B20-C14;
A7-B20-C15; A7-B20-C16; A7-B20-C17; A7-B20-C18; A7-B20-C19; A7-B20-C20;
A7-B20-C21; A7-B20-C22; A7-B20-C23; A7-B20-C24; A7-B20-C25; A7-B20-C26;
A7-B20-C27; A7-B20-C28; A7-B20-C29; A7-B20-C30; A7-B20-C31; A7-B20-C32;
A7-B20-C33; A7-B20-C34; A7-B20-C35; A7-B20-C36; A7-B20-C37; A7-B20-C38;
A7-B20-C39; A7-B20-C40; A7-B20-C41; A7-B20-C42; A7-B20-C43; A7-B20-C44;
A7-B20-C45; A7-B20-C46; A8-B20-C1; A8-B20-C2; A8-B20-C3; A8-B20-C4;
A8-B20-C5; A8-B20-C6; A8-B20-C7; A8-B20-C8; A8-B20-C9; A8-B20-C10;
A8-B20-C11; A8-B20-C12; A8-B20-C13; A8-B20-C14; A8-B20-C15; A8-B20-C16;
A8-B20-C17; A8-B20-C18; A8-B20-C19; A8-B20-C20; A8-B20-C21; A8-B20-C22;
A8-B20-C23; A8-B20-C24; A8-B20-C25; A8-B20-C26; A8-B20-C27; A8-B20-C28;
A8-B20-C29; A8-B20-C30; A8-B20-C31; A8-B20-C32; A8-B20-C33; A8-B20-C34;
A8-B20-C35; A8-B20-C36; A8-B20-C37; A8-B20-C38; A8-B20-C39; A8-B20-C40;
A8-B20-C41; A8-B20-C42; A8-B20-C43; A8-B20-C44; A8-B20-C45; A8-B20-C46;
A9-B20-C1; A9-B20-C2; A9-B20-C3; A9-B20-C4; A9-B20-C5; A9-B20-C6;
A9-B20-C7; A9-B20-C8; A9-B20-C9; A9-B20-C10; A9-B20-C11; A9-B20-C12;
A9-B20-C13; A9-B20-C14; A9-B20-C15; A9-B20-C16; A9-B20-C17; A9-B20-C18;
A9-B20-C19; A9-B20-C20; A9-B20-C21; A9-B20-C22; A9-B20-C23; A9-B20-C24;
A9-B20-C25; A9-B20-C26; A9-B20-C27; A9-B20-C28; A9-B20-C29; A9-B20-C30;
A9-B20-C31; A9-B20-C32; A9-B20-C33; A9-B20-C34; A9-B20-C35; A9-B20-C36;
A9-B20-C37; A9-B20-C38; A9-B20-C39; A9-B20-C40; A9-B20-C41; A9-B20-C42;
A9-B20-C43; A9-B20-C44; A9-B20-C45; A9-B20-C46; A10-B20-C1; A10-B20-C2;

-continued

| | | | | | |
|---|---|---|---|---|---|
| A10-B20-C3; | A10-B20-C4; | A10-B20-C5; | A10-B20-C6; | A10-B20-C7; | A10-B20-C8; |
| A10-B20-C9; | A10-B20-C10; | A10-B20-C11; | A10-B20-C12; | A10-B20-C13; | A10-B20-C14; |
| A10-B20-C15; | A10-B20-C16; | A10-B20-C17; | A10-B20-C18; | A10-B20-C19; | A10-B20-C20; |
| A10-B20-C21; | A10-B20-C22; | A10-B20-C23; | A10-B20-C24; | A10-B20-C25; | A10-B20-C26; |
| A10-B20-C27; | A10-B20-C28; | A10-B20-C29; | A10-B20-C30; | A10-B20-C31; | A10-B20-C32; |
| A10-B20-C33; | A10-B20-C34; | A10-B20-C35; | A10-B20-C36; | A10-B20-C37; | A10-B20-C38; |
| A10-B20-C39; | A10-B20-C40; | A10-B20-C41; | A10-B20-C42; | A10-B20-C43; | A10-B20-C44; |
| A10-B20-C45; | A10-B20-C46; | A11-B20-C1; | A11-B20-C2; | A11-B20-C3; | A11-B20-C4; |
| A11-B20-C5; | A11-B20-C6; | A11-B20-C7; | A11-B20-C8; | A11-B20-C9; | A11-B20-C10; |
| A11-B20-C11; | A11-B20-C12; | A11-B20-C13; | A11-B20-C14; | A11-B20-C15; | A11-B20-C16; |
| A11-B20-C17; | A11-B20-C18; | A11-B20-C19; | A11-B20-C20; | A11-B20-C21; | A11-B20-C22; |
| A11-B20-C23; | A11-B20-C24; | A11-B20-C25; | A11-B20-C26; | A11-B20-C27; | A11-B20-C28; |
| A11-B20-C29; | A11-B20-C30; | A11-B20-C31; | A11-B20-C32; | A11-B20-C33; | A11-B20-C34; |
| A11-B20-C35; | A11-B20-C36; | A11-B20-C37; | A11-B20-C38; | A11-B20-C39; | A11-B20-C40; |
| A11-B20-C41; | A11-B20-C42; | A11-B20-C43; | A11-B20-C44; | A11-B20-C45; | A11-B20-C46; |
| A12-B20-C1; | A12-B20-C2; | A12-B20-C3; | A12-B20-C4; | A12-B20-C5; | A12-B20-C6; |
| A12-B20-C7; | A12-B20-C8; | A12-B20-C9; | A12-B20-C10; | A12-B20-C11; | A12-B20-C12; |
| A12-B20-C13; | A12-B20-C14; | A12-B20-C15; | A12-B20-C16; | A12-B20-C17; | A12-B20-C18; |
| A12-B20-C19; | A12-B20-C20; | A12-B20-C21; | A12-B20-C22; | A12-B20-C23; | A12-B20-C24; |
| A12-B20-C25; | A12-B20-C26; | A12-B20-C27; | A12-B20-C28; | A12-B20-C29; | A12-B20-C30; |
| A12-B20-C31; | A12-B20-C32; | A12-B20-C33; | A12-B20-C34; | A12-B20-C35; | A12-B20-C36; |
| A12-B20-C37; | A12-B20-C38; | A12-B20-C39; | A12-B20-C40; | A12-B20-C41; | A12-B20-C42; |
| A12-B20-C43; | A12-B20-C44; | A12-B20-C45; | A12-B20-C46; | A13-B20-C1; | A13-B20-C2; |
| A13-B20-C3; | A13-B20-C4; | A13-B20-C5; | A13-B20-C6; | A13-B20-C7; | A13-B20-C8; |
| A13-B20-C9; | A13-B20-C10; | A13-B20-C11; | A13-B20-C12; | A13-B20-C13; | A13-B20-C14; |
| A13-B20-C15; | A13-B20-C16; | A13-B20-C17; | A13-B20-C18; | A13-B20-C19; | A13-B20-C20; |
| A13-B20-C21; | A13-B20-C22; | A13-B20-C23; | A13-B20-C24; | A13-B20-C25; | A13-B20-C26; |
| A13-B20-C27; | A13-B20-C28; | A13-B20-C29; | A13-B20-C30; | A13-B20-C31; | A13-B20-C32; |
| A13-B20-C33; | A13-B20-C34; | A13-B20-C35; | A13-B20-C36; | A13-B20-C37; | A13-B20-C38; |
| A13-B20-C39; | A13-B20-C40; | A13-B20-C41; | A13-B20-C42; | A13-B20-C43; | A13-B20-C44; |
| A13-B20-C45; | A13-B20-C46; | A14-B20-C1; | A14-B20-C2; | A14-B20-C3; | A14-B20-C4; |
| A14-B20-C5; | A14-B20-C6; | A14-B20-C7; | A14-B20-C8; | A14-B20-C9; | A14-B20-C10; |
| A14-B20-C11; | A14-B20-C12; | A14-B20-C13; | A14-B20-C14; | A14-B20-C15; | A14-B20-C16; |
| A14-B20-C17; | A14-B20-C18; | A14-B20-C19; | A14-B20-C20; | A14-B20-C21; | A14-B20-C22; |
| A14-B20-C23; | A14-B20-C24; | A14-B20-C25; | A14-B20-C26; | A14-B20-C27; | A14-B20-C28; |
| A14-B20-C29; | A14-B20-C30; | A14-B20-C31; | A14-B20-C32; | A14-B20-C33; | A14-B20-C34; |
| A14-B20-C35; | A14-B20-C36; | A14-B20-C37; | A14-B20-C38; | A14-B20-C39; | A14-B20-C40; |
| A14-B20-C41; | A14-B20-C42; | A14-B20-C43; | A14-B20-C44; | A14-B20-C45; | A14-B20-C46; |
| A15-B20-C1; | A15-B20-C2; | A15-B20-C3; | A15-B20-C4; | A15-B20-C5; | A15-B20-C6; |
| A15-B20-C7; | A15-B20-C8; | A15-B20-C9; | A15-B20-C10; | A15-B20-C11; | A15-B20-C12; |
| A15-B20-C13; | A15-B20-C14; | A15-B20-C15; | A15-B20-C16; | A15-B20-C17; | A15-B20-C18; |
| A15-B20-C19; | A15-B20-C20; | A15-B20-C21; | A15-B20-C22; | A15-B20-C23; | A15-B20-C24; |
| A15-B20-C25; | A15-B20-C26; | A15-B20-C27; | A15-B20-C28; | A15-B20-C29; | A15-B20-C30; |
| A15-B20-C31; | A15-B20-C32; | A15-B20-C33; | A15-B20-C34; | A15-B20-C35; | A15-B20-C36; |
| A15-B20-C37; | A15-B20-C38; | A15-B20-C39; | A15-B20-C40; | A15-B20-C41; | A15-B20-C42; |
| A15-B20-C43; | A15-B20-C44; | A15-B20-C45; | A15-B20-C46; | A16-B20-C1; | A16-B20-C2; |
| A16-B20-C3; | A16-B20-C4; | A16-B20-C5; | A16-B20-C6; | A16-B20-C7; | A16-B20-C8; |
| A16-B20-C9; | A16-B20-C10; | A16-B20-C11; | A16-B20-C12; | A16-B20-C13; | A16-B20-C14; |
| A16-B20-C15; | A16-B20-C16; | A16-B20-C17; | A16-B20-C18; | A16-B20-C19; | A16-B20-C20; |
| A16-B20-C21; | A16-B20-C22; | A16-B20-C23; | A16-B20-C24; | A16-B20-C25; | A16-B20-C26; |
| A16-B20-C27; | A16-B20-C28; | A16-B20-C29; | A16-B20-C30; | A16-B20-C31; | A16-B20-C32; |
| A16-B20-C33; | A16-B20-C34; | A16-B20-C35; | A16-B20-C36; | A16-B20-C37; | A16-B20-C38; |
| A16-B20-C39; | A16-B20-C40; | A16-B20-C41; | A16-B20-C42; | A16-B20-C43; | A16-B20-C44; |
| A16-B20-C45; | A16-B20-C46; | A17-B20-C1; | A17-B20-C2; | A17-B20-C3; | A17-B20-C4; |
| A17-B20-C5; | A17-B20-C6; | A17-B20-C7; | A17-B20-C8; | A17-B20-C9; | A17-B20-C10; |
| A17-B20-C11; | A17-B20-C12; | A17-B20-C13; | A17-B20-C14; | A17-B20-C15; | A17-B20-C16; |
| A17-B20-C17; | A17-B20-C18; | A17-B20-C19; | A17-B20-C20; | A17-B20-C21; | A17-B20-C22; |
| A17-B20-C23; | A17-B20-C24; | A17-B20-C25; | A17-B20-C26; | A17-B20-C27; | A17-B20-C28; |
| A17-B20-C29; | A17-B20-C30; | A17-B20-C31; | A17-B20-C32; | A17-B20-C33; | A17-B20-C34; |
| A17-B20-C35; | A17-B20-C36; | A17-B20-C37; | A17-B20-C38; | A17-B20-C39; | A17-B20-C40; |
| A17-B20-C41; | A17-B20-C42; | A17-B20-C43; | A17-B20-C44; | A17-B20-C45; | A17-B20-C46; |
| A18-B20-C1; | A18-B20-C2; | A18-B20-C3; | A18-B20-C4; | A18-B20-C5; | A18-B20-C6; |
| A18-B20-C7; | A18-B20-C8; | A18-B20-C9; | A18-B20-C10; | A18-B20-C11; | A18-B20-C12; |
| A18-B20-C13; | A18-B20-C14; | A18-B20-C15; | A18-B20-C16; | A18-B20-C17; | A18-B20-C18; |
| A18-B20-C19; | A18-B20-C20; | A18-B20-C21; | A18-B20-C22; | A18-B20-C23; | A18-B20-C24; |
| A18-B20-C25; | A18-B20-C26; | A18-B20-C27; | A18-B20-C28; | A18-B20-C29; | A18-B20-C30; |
| A18-B20-C31; | A18-B20-C32; | A18-B20-C33; | A18-B20-C34; | A18-B20-C35; | A18-B20-C36; |
| A18-B20-C37; | A18-B20-C38; | A18-B20-C39; | A18-B20-C40; | A18-B20-C41; | A18-B20-C42; |
| A18-B20-C43; | A18-B20-C44; | A18-B20-C45; | A18-B20-C46; | A19-B20-C1; | A19-B20-C2; |
| A19-B20-C3; | A19-B20-C4; | A19-B20-C5; | A19-B20-C6; | A19-B20-C7; | A19-B20-C8; |
| A19-B20-C9; | A19-B20-C10; | A19-B20-C11; | A19-B20-C12; | A19-B20-C13; | A19-B20-C14; |
| A19-B20-C15; | A19-B20-C16; | A19-B20-C17; | A19-B20-C18; | A19-B20-C19; | A19-B20-C20; |
| A19-B20-C21; | A19-B20-C22; | A19-B20-C23; | A19-B20-C24; | A19-B20-C25; | A19-B20-C26; |
| A19-B20-C27; | A19-B20-C28; | A19-B20-C29; | A19-B20-C30; | A19-B20-C31; | A19-B20-C32; |
| A19-B20-C33; | A19-B20-C34; | A19-B20-C35; | A19-B20-C36; | A19-B20-C37; | A19-B20-C38; |
| A19-B20-C39; | A19-B20-C40; | A19-B20-C41; | A19-B20-C42; | A19-B20-C43; | A19-B20-C44; |
| A19-B20-C45; | A19-B20-C46; | A20-B20-C1; | A20-B20-C2; | A20-B20-C3; | A20-B20-C4; |
| A20-B20-C5; | A20-B20-C6; | A20-B20-C7; | A20-B20-C8; | A20-B20-C9; | A20-B20-C10; |
| A20-B20-C11; | A20-B20-C12; | A20-B20-C13; | A20-B20-C14; | A20-B20-C15; | A20-B20-C16; |

-continued

A20-B20-C17; A20-B20-C18; A20-B20-C19; A20-B20-C20; A20-B20-C21; A20-B20-C22;
A20-B20-C23; A20-B20-C24; A20-B20-C25; A20-B20-C26; A20-B20-C27; A20-B20-C28;
A20-B20-C29; A20-B20-C30; A20-B20-C31; A20-B20-C32; A20-B20-C33; A20-B20-C34;
A20-B20-C35; A20-B20-C36; A20-B20-C37; A20-B20-C38; A20-B20-C39; A20-B20-C40;
A20-B20-C41; A20-B20-C42; A20-B20-C43; A20-B20-C44; A20-B20-C45; A20-B20-C46;
A21-B20-C1; A21-B20-C2; A21-B20-C3; A21-B20-C4; A21-B20-C5; A21-B20-C6;
A21-B20-C7; A21-B20-C8; A21-B20-C9; A21-B20-C10; A21-B20-C11; A21-B20-C12;
A21-B20-C13; A21-B20-C14; A21-B20-C15; A21-B20-C16; A21-B20-C17; A21-B20-C18;
A21-B20-C19; A21-B20-C20; A21-B20-C21; A21-B20-C22; A21-B20-C23; A21-B20-C24;
A21-B20-C25; A21-B20-C26; A21-B20-C27; A21-B20-C28; A21-B20-C29; A21-B20-C30;
A21-B20-C31; A21-B20-C32; A21-B20-C33; A21-B20-C34; A21-B20-C35; A21-B20-C36;
A21-B20-C37; A21-B20-C38; A21-B20-C39; A21-B20-C40; A21-B20-C41; A21-B20-C42;
A21-B20-C43; A21-B20-C44; A21-B20-C45; A21-B20-C46; A22-B20-C1; A22-B20-C2;
A22-B20-C3; A22-B20-C4; A22-B20-C5; A22-B20-C6; A22-B20-C7; A22-B20-C8;
A22-B20-C9; A22-B20-C10; A22-B20-C11; A22-B20-C12; A22-B20-C13; A22-B20-C14;
A22-B20-C15; A22-B20-C16; A22-B20-C17; A22-B20-C18; A22-B20-C19; A22-B20-C20;
A22-B20-C21; A22-B20-C22; A22-B20-C23; A22-B20-C24; A22-B20-C25; A22-B20-C26;
A22-B20-C27; A22-B20-C28; A22-B20-C29; A22-B20-C30; A22-B20-C31; A22-B20-C32;
A22-B20-C33; A22-B20-C34; A22-B20-C35; A22-B20-C36; A22-B20-C37; A22-B20-C38;
A22-B20-C39; A22-B20-C40; A22-B20-C41; A22-B20-C42; A22-B20-C43; A22-B20-C44;
A22-B20-C45; A22-B20-C46; A23-B20-C1; A23-B20-C2; A23-B20-C3; A23-B20-C4;
A23-B20-C5; A23-B20-C6; A23-B20-C7; A23-B20-C8; A23-B20-C9; A23-B20-C10;
A23-B20-C11; A23-B20-C12; A23-B20-C13; A23-B20-C14; A23-B20-C15; A23-B20-C16;
A23-B20-C17; A23-B20-C18; A23-B20-C19; A23-B20-C20; A23-B20-C21; A23-B20-C22;
A23-B20-C23; A23-B20-C24; A23-B20-C25; A23-B20-C26; A23-B20-C27; A23-B20-C28;
A23-B20-C29; A23-B20-C30; A23-B20-C31; A23-B20-C32; A23-B20-C33; A23-B20-C34;
A23-B20-C35; A23-B20-C36; A23-B20-C37; A23-B20-C38; A23-B20-C39; A23-B20-C40;
A23-B20-C41; A23-B20-C42; A23-B20-C43; A23-B20-C44; A23-B20-C45; A23-B20-C46;
A24-B20-C1; A24-B20-C2; A24-B20-C3; A24-B20-C4; A24-B20-C5; A24-B20-C6;
A24-B20-C7; A24-B20-C8; A24-B20-C9; A24-B20-C10; A24-B20-C11; A24-B20-C12;
A24-B20-C13; A24-B20-C14; A24-B20-C15; A24-B20-C16; A24-B20-C17; A24-B20-C18;
A24-B20-C19; A24-B20-C20; A24-B20-C21; A24-B20-C22; A24-B20-C23; A24-B20-C24;
A24-B20-C25; A24-B20-C26; A24-B20-C27; A24-B20-C28; A24-B20-C29; A24-B20-C30;
A24-B20-C31; A24-B20-C32; A24-B20-C33; A24-B20-C34; A24-B20-C35; A24-B20-C36;
A24-B20-C37; A24-B20-C38; A24-B20-C39; A24-B20-C40; A24-B20-C41; A24-B20-C42;
A24-B20-C43; A24-B20-C44; A24-B20-C45; A24-B20-C46; A25-B20-C1; A25-B20-C2;
A25-B20-C3; A25-B20-C4; A25-B20-C5; A25-B20-C6; A25-B20-C7; A25-B20-C8;
A25-B20-C9; A25-B20-C10; A25-B20-C11; A25-B20-C12; A25-B20-C13; A25-B20-C14;
A25-B20-C15; A25-B20-C16; A25-B20-C17; A25-B20-C18; A25-B20-C19; A25-B20-C20;
A25-B20-C21; A25-B20-C22; A25-B20-C23; A25-B20-C24; A25-B20-C25; A25-B20-C26;
A25-B20-C27; A25-B20-C28; A25-B20-C29; A25-B20-C30; A25-B20-C31; A25-B20-C32;
A25-B20-C33; A25-B20-C34; A25-B20-C35; A25-B20-C36; A25-B20-C37; A25-B20-C38;
A25-B20-C39; A25-B20-C40; A25-B20-C41; A25-B20-C42; A25-B20-C43; A25-B20-C44;
A25-B20-C45; A25-B20-C46; A26-B20-C1; A26-B20-C2; A26-B20-C3; A26-B20-C4;
A26-B20-C5; A26-B20-C6; A26-B20-C7; A26-B20-C8; A26-B20-C9; A26-B20-C10;
A26-B20-C11; A26-B20-C12; A26-B20-C13; A26-B20-C14; A26-B20-C15; A26-B20-C16;
A26-B20-C17; A26-B20-C18; A26-B20-C19; A26-B20-C20; A26-B20-C21; A26-B20-C22;
A26-B20-C23; A26-B20-C24; A26-B20-C25; A26-B20-C26; A26-B20-C27; A26-B20-C28;
A26-B20-C29; A26-B20-C30; A26-B20-C31; A26-B20-C32; A26-B20-C33; A26-B20-C34;
A26-B20-C35; A26-B20-C36; A26-B20-C37; A26-B20-C38; A26-B20-C39; A26-B20-C40;
A26-B20-C41; A26-B20-C42; A26-B20-C43; A26-B20-C44; A26-B20-C45; A26-B20-C46;
A27-B20-C1; A27-B20-C2; A27-B20-C3; A27-B20-C4; A27-B20-C5; A27-B20-C6;
A27-B20-C7; A27-B20-C8; A27-B20-C9; A27-B20-C10; A27-B20-C11; A27-B20-C12;
A27-B20-C13; A27-B20-C14; A27-B20-C15; A27-B20-C16; A27-B20-C17; A27-B20-C18;
A27-B20-C19; A27-B20-C20; A27-B20-C21; A27-B20-C22; A27-B20-C23; A27-B20-C24;
A27-B20-C25; A27-B20-C26; A27-B20-C27; A27-B20-C28; A27-B20-C29; A27-B20-C30;
A27-B20-C31; A27-B20-C32; A27-B20-C33; A27-B20-C34; A27-B20-C35; A27-B20-C36;
A27-B20-C37; A27-B20-C38; A27-B20-C39; A27-B20-C40; A27-B20-C41; A27-B20-C42;
A27-B20-C43; A27-B20-C44; A27-B20-C45; A27-B20-C46; A28-B20-C1; A28-B20-C2;
A28-B20-C3; A28-B20-C4; A28-B20-C5; A28-B20-C6; A28-B20-C7; A28-B20-C8;
A28-B20-C9; A28-B20-C10; A28-B20-C11; A28-B20-C12; A28-B20-C13; A28-B20-C14;
A28-B20-C15; A28-B20-C16; A28-B20-C17; A28-B20-C18; A28-B20-C19; A28-B20-C20;
A28-B20-C21; A28-B20-C22; A28-B20-C23; A28-B20-C24; A28-B20-C25; A28-B20-C26;
A28-B20-C27; A28-B20-C28; A28-B20-C29; A28-B20-C30; A28-B20-C31; A28-B20-C32;
A28-B20-C33; A28-B20-C34; A28-B20-C35; A28-B20-C36; A28-B20-C37; A28-B20-C38;
A28-B20-C39; A28-B20-C40; A28-B20-C41; A28-B20-C42; A28-B20-C43; A28-B20-C44;
A28-B20-C45; A28-B20-C46; A1-B21-C1; A1-B21-C2; A1-B21-C3; A1-B21-C4;
A1-B21-C5; A1-B21-C6; A1-B21-C7; A1-B21-C8; A1-B21-C9; A1-B21-C10;
A1-B21-C11; A1-B21-C12; A1-B21-C13; A1-B21-C14; A1-B21-C15; A1-B21-C16;
A1-B21-C17; A1-B21-C18; A1-B21-C19; A1-B21-C20; A1-B21-C21; A1-B21-C22;
A1-B21-C23; A1-B21-C24; A1-B21-C25; A1-B21-C26; A1-B21-C27; A1-B21-C28;
A1-B21-C29; A1-B21-C30; A1-B21-C31; A1-B21-C32; A1-B21-C33; A1-B21-C34;
A1-B21-C35; A1-B21-C36; A1-B21-C37; A1-B21-C38; A1-B21-C39; A1-B21-C40;
A1-B21-C41; A1-B21-C42; A1-B21-C43; A1-B21-C44; A1-B21-C45; A1-B21-C46;
A2-B21-C1; A2-B21-C2; A2-B21-C3; A2-B21-C4; A2-B21-C5; A2-B21-C6;
A2-B21-C7; A2-B21-C8; A2-B21-C9; A2-B21-C10; A2-B21-C11; A2-B21-C12;
A2-B21-C13; A2-B21-C14; A2-B21-C15; A2-B21-C16; A2-B21-C17; A2-B21-C18;
A2-B21-C19; A2-B21-C20; A2-B21-C21; A2-B21-C22; A2-B21-C23; A2-B21-C24;
A2-B21-C25; A2-B21-C26; A2-B21-C27; A2-B21-C28; A2-B21-C29; A2-B21-C30;

-continued

| | | | | | |
|---|---|---|---|---|---|
| A2-B21-C31; | A2-B21-C32; | A2-B21-C33; | A2-B21-C34; | A2-B21-C35; | A2-B21-C36; |
| A2-B21-C37; | A2-B21-C38; | A2-B21-C39; | A2-B21-C40; | A2-B21-C41; | A2-B21-C42; |
| A2-B21-C43; | A2-B21-C44; | A2-B21-C45; | A2-B21-C46; | A3-B21-C1; | A3-B21-C2; |
| A3-B21-C3; | A3-B21-C4; | A3-B21-C5; | A3-B21-C6; | A3-B21-C7; | A3-B21-C8; |
| A3-B21-C9; | A3-B21-C10; | A3-B21-C11; | A3-B21-C12; | A3-B21-C13; | A3-B21-C14; |
| A3-B21-C15; | A3-B21-C16; | A3-B21-C17; | A3-B21-C18; | A3-B21-C19; | A3-B21-C20; |
| A3-B21-C21; | A3-B21-C22; | A3-B21-C23; | A3-B21-C24; | A3-B21-C25; | A3-B21-C26; |
| A3-B21-C27; | A3-B21-C28; | A3-B21-C29; | A3-B21-C30; | A3-B21-C31; | A3-B21-C32; |
| A3-B21-C33; | A3-B21-C34; | A3-B21-C35; | A3-B21-C36; | A3-B21-C37; | A3-B21-C38; |
| A3-B21-C39; | A3-B21-C40; | A3-B21-C41; | A3-B21-C42; | A3-B21-C43; | A3-B21-C44; |
| A3-B21-C45; | A3-B21-C46; | A4-B21-C1; | A4-B21-C2; | A4-B21-C3; | A4-B21-C4; |
| A4-B21-C5; | A4-B21-C6; | A4-B21-C7; | A4-B21-C8; | A4-B21-C9; | A4-B21-C10; |
| A4-B21-C11; | A4-B21-C12; | A4-B21-C13; | A4-B21-C14; | A4-B21-C15; | A4-B21-C16; |
| A4-B21-C17; | A4-B21-C18; | A4-B21-C19; | A4-B21-C20; | A4-B21-C21; | A4-B21-C22; |
| A4-B21-C23; | A4-B21-C24; | A4-B21-C25; | A4-B21-C26; | A4-B21-C27; | A4-B21-C28; |
| A4-B21-C29; | A4-B21-C30; | A4-B21-C31; | A4-B21-C32; | A4-B21-C33; | A4-B21-C34; |
| A4-B21-C35; | A4-B21-C36; | A4-B21-C37; | A4-B21-C38; | A4-B21-C39; | A4-B21-C40; |
| A4-B21-C41; | A4-B21-C42; | A4-B21-C43; | A4-B21-C44; | A4-B21-C45; | A4-B21-C46; |
| A5-B21-C1; | A5-B21-C2; | A5-B21-C3; | A5-B21-C4; | A5-B21-C5; | A5-B21-C6; |
| A5-B21-C7; | A5-B21-C8; | A5-B21-C9; | A5-B21-C10; | A5-B21-C11; | A5-B21-C12; |
| A5-B21-C13; | A5-B21-C14; | A5-B21-C15; | A5-B21-C16; | A5-B21-C17; | A5-B21-C18; |
| A5-B21-C19; | A5-B21-C20; | A5-B21-C21; | A5-B21-C22; | A5-B21-C23; | A5-B21-C24; |
| A5-B21-C25; | A5-B21-C26; | A5-B21-C27; | A5-B21-C28; | A5-B21-C29; | A5-B21-C30; |
| A5-B21-C31; | A5-B21-C32; | A5-B21-C33; | A5-B21-C34; | A5-B21-C35; | A5-B21-C36; |
| A5-B21-C37; | A5-B21-C38; | A5-B21-C39; | A5-B21-C40; | A5-B21-C41; | A5-B21-C42; |
| A5-B21-C43; | A5-B21-C44; | A5-B21-C45; | A5-B21-C46; | A6-B21-C1; | A6-B21-C2; |
| A6-B21-C3; | A6-B21-C4; | A6-B21-C5; | A6-B21-C6; | A6-B21-C7; | A6-B21-C8; |
| A6-B21-C9; | A6-B21-C10; | A6-B21-C11; | A6-B21-C12; | A6-B21-C13; | A6-B21-C14; |
| A6-B21-C15; | A6-B21-C16; | A6-B21-C17; | A6-B21-C18; | A6-B21-C19; | A6-B21-C20; |
| A6-B21-C21; | A6-B21-C22; | A6-B21-C23; | A6-B21-C24; | A6-B21-C25; | A6-B21-C26; |
| A6-B21-C27; | A6-B21-C28; | A6-B21-C29; | A6-B21-C30; | A6-B21-C31; | A6-B21-C32; |
| A6-B21-C33; | A6-B21-C34; | A6-B21-C35; | A6-B21-C36; | A6-B21-C37; | A6-B21-C38; |
| A6-B21-C39; | A6-B21-C40; | A6-B21-C41; | A6-B21-C42; | A6-B21-C43; | A6-B21-C44; |
| A6-B21-C45; | A6-B21-C46; | A7-B21-C1; | A7-B21-C2; | A7-B21-C3; | A7-B21-C4; |
| A7-B21-C5; | A7-B21-C6; | A7-B21-C7; | A7-B21-C8; | A7-B21-C9; | A7-B21-C10; |
| A7-B21-C11; | A7-B21-C12; | A7-B21-C13; | A7-B21-C14; | A7-B21-C15; | A7-B21-C16; |
| A7-B21-C17; | A7-B21-C18; | A7-B21-C19; | A7-B21-C20; | A7-B21-C21; | A7-B21-C22; |
| A7-B21-C23; | A7-B21-C24; | A7-B21-C25; | A7-B21-C26; | A7-B21-C27; | A7-B21-C28; |
| A7-B21-C29; | A7-B21-C30; | A7-B21-C31; | A7-B21-C32; | A7-B21-C33; | A7-B21-C34; |
| A7-B21-C35; | A7-B21-C36; | A7-B21-C37; | A7-B21-C38; | A7-B21-C39; | A7-B21-C40; |
| A7-B21-C41; | A7-B21-C42; | A7-B21-C43; | A7-B21-C44; | A7-B21-C45; | A7-B21-C46; |
| A8-B21-C1; | A8-B21-C2; | A8-B21-C3; | A8-B21-C4; | A8-B21-C5; | A8-B21-C6; |
| A8-B21-C7; | A8-B21-C8; | A8-B21-C9; | A8-B21-C10; | A8-B21-C11; | A8-B21-C12; |
| A8-B21-C13; | A8-B21-C14; | A8-B21-C15; | A8-B21-C16; | A8-B21-C17; | A8-B21-C18; |
| A8-B21-C19; | A8-B21-C20; | A8-B21-C21; | A8-B21-C22; | A8-B21-C23; | A8-B21-C24; |
| A8-B21-C25; | A8-B21-C26; | A8-B21-C27; | A8-B21-C28; | A8-B21-C29; | A8-B21-C30; |
| A8-B21-C31; | A8-B21-C32; | A8-B21-C33; | A8-B21-C34; | A8-B21-C35; | A8-B21-C36; |
| A8-B21-C37; | A8-B21-C38; | A8-B21-C39; | A8-B21-C40; | A8-B21-C41; | A8-B21-C42; |
| A8-B21-C43; | A8-B21-C44; | A8-B21-C45; | A8-B21-C46; | A9-B21-C1; | A9-B21-C2; |
| A9-B21-C3; | A9-B21-C4; | A9-B21-C5; | A9-B21-C6; | A9-B21-C7; | A9-B21-C8; |
| A9-B21-C9; | A9-B21-C10; | A9-B21-C11; | A9-B21-C12; | A9-B21-C13; | A9-B21-C14; |
| A9-B21-C15; | A9-B21-C16; | A9-B21-C17; | A9-B21-C18; | A9-B21-C19; | A9-B21-C20; |
| A9-B21-C21; | A9-B21-C22; | A9-B21-C23; | A9-B21-C24; | A9-B21-C25; | A9-B21-C26; |
| A9-B21-C27; | A9-B21-C28; | A9-B21-C29; | A9-B21-C30; | A9-B21-C31; | A9-B21-C32; |
| A9-B21-C33; | A9-B21-C34; | A9-B21-C35; | A9-B21-C36; | A9-B21-C37; | A9-B21-C38; |
| A9-B21-C39; | A9-B21-C40; | A9-B21-C41; | A9-B21-C42; | A9-B21-C43; | A9-B21-C44; |
| A9-B21-C45; | A9-B21-C46; | A10-B21-C1; | A10-B21-C2; | A10-B21-C3; | A10-B21-C4; |
| A10-B21-C5; | A10-B21-C6; | A10-B21-C7; | A10-B21-C8; | A10-B21-C9; | A10-B21-C10; |
| A10-B21-C11; | A10-B21-C12; | A10-B21-C13; | A10-B21-C14; | A10-B21-C15; | A10-B21-C16; |
| A10-B21-C17; | A10-B21-C18; | A10-B21-C19; | A10-B21-C20; | A10-B21-C21; | A10-B21-C22; |
| A10-B21-C23; | A10-B21-C24; | A10-B21-C25; | A10-B21-C26; | A10-B21-C27; | A10-B21-C28; |
| A10-B21-C29; | A10-B21-C30; | A10-B21-C31; | A10-B21-C32; | A10-B21-C33; | A10-B21-C34; |
| A10-B21-C35; | A10-B21-C36; | A10-B21-C37; | A10-B21-C38; | A10-B21-C39; | A10-B21-C40; |
| A10-B21-C41; | A10-B21-C42; | A10-B21-C43; | A10-B21-C44; | A10-B21-C45; | A10-B21-C46; |
| A11-B21-C1; | A11-B21-C2; | A11-B21-C3; | A11-B21-C4; | A11-B21-C5; | A11-B21-C6; |
| A11-B21-C7; | A11-B21-C8; | A11-B21-C9; | A11-B21-C10; | A11-B21-C11; | A11-B21-C12; |
| A11-B21-C13; | A11-B21-C14; | A11-B21-C15; | A11-B21-C16; | A11-B21-C17; | A11-B21-C18; |
| A11-B21-C19; | A11-B21-C20; | A11-B21-C21; | A11-B21-C22; | A11-B21-C23; | A11-B21-C24; |
| A11-B21-C25; | A11-B21-C26; | A11-B21-C27; | A11-B21-C28; | A11-B21-C29; | A11-B21-C30; |
| A11-B21-C31; | A11-B21-C32; | A11-B21-C33; | A11-B21-C34; | A11-B21-C35; | A11-B21-C36; |
| A11-B21-C37; | A11-B21-C38; | A11-B21-C39; | A11-B21-C40; | A11-B21-C41; | A11-B21-C42; |
| A11-B21-C43; | A11-B21-C44; | A11-B21-C45; | A11-B21-C46; | A12-B21-C1; | A12-B21-C2; |
| A12-B21-C3; | A12-B21-C4; | A12-B21-C5; | A12-B21-C6; | A12-B21-C7; | A12-B21-C8; |
| A12-B21-C9; | A12-B21-C10; | A12-B21-C11; | A12-B21-C12; | A12-B21-C13; | A12-B21-C14; |
| A12-B21-C15; | A12-B21-C16; | A12-B21-C17; | A12-B21-C18; | A12-B21-C19; | A12-B21-C20; |
| A12-B21-C21; | A12-B21-C22; | A12-B21-C23; | A12-B21-C24; | A12-B21-C25; | A12-B21-C26; |
| A12-B21-C27; | A12-B21-C28; | A12-B21-C29; | A12-B21-C30; | A12-B21-C31; | A12-B21-C32; |
| A12-B21-C33; | A12-B21-C34; | A12-B21-C35; | A12-B21-C36; | A12-B21-C37; | A12-B21-C38; |
| A12-B21-C39; | A12-B21-C40; | A12-B21-C41; | A12-B21-C42; | A12-B21-C43; | A12-B21-C44; |

-continued

| | | | | | |
|---|---|---|---|---|---|
| A12-B21-C45; | A12-B21-C46; | A13-B21-C1; | A13-B21-C2; | A13-B21-C3; | A13-B21-C4; |
| A13-B21-C5; | A13-B21-C6; | A13-B21-C7; | A13-B21-C8; | A13-B21-C9; | A13-B21-C10; |
| A13-B21-C11; | A13-B21-C12; | A13-B21-C13; | A13-B21-C14; | A13-B21-C15; | A13-B21-C16; |
| A13-B21-C17; | A13-B21-C18; | A13-B21-C19; | A13-B21-C20; | A13-B21-C21; | A13-B21-C22; |
| A13-B21-C23; | A13-B21-C24; | A13-B21-C25; | A13-B21-C26; | A13-B21-C27; | A13-B21-C28; |
| A13-B21-C29; | A13-B21-C30; | A13-B21-C31; | A13-B21-C32; | A13-B21-C33; | A13-B21-C34; |
| A13-B21-C35; | A13-B21-C36; | A13-B21-C37; | A13-B21-C38; | A13-B21-C39; | A13-B21-C40; |
| A13-B21-C41; | A13-B21-C42; | A13-B21-C43; | A13-B21-C44; | A13-B21-C45; | A13-B21-C46; |
| A14-B21-C1; | A14-B21-C2; | A14-B21-C3; | A14-B21-C4; | A14-B21-C5; | A14-B21-C6; |
| A14-B21-C7; | A14-B21-C8; | A14-B21-C9; | A14-B21-C10; | A14-B21-C11; | A14-B21-C12; |
| A14-B21-C13; | A14-B21-C14; | A14-B21-C15; | A14-B21-C16; | A14-B21-C17; | A14-B21-C18; |
| A14-B21-C19; | A14-B21-C20; | A14-B21-C21; | A14-B21-C22; | A14-B21-C23; | A14-B21-C24; |
| A14-B21-C25; | A14-B21-C26; | A14-B21-C27; | A14-B21-C28; | A14-B21-C29; | A14-B21-C30; |
| A14-B21-C31; | A14-B21-C32; | A14-B21-C33; | A14-B21-C34; | A14-B21-C35; | A14-B21-C36; |
| A14-B21-C37; | A14-B21-C38; | A14-B21-C39; | A14-B21-C40; | A14-B21-C41; | A14-B21-C42; |
| A14-B21-C43; | A14-B21-C44; | A14-B21-C45; | A14-B21-C46; | A15-B21-C1; | A15-B21-C2; |
| A15-B21-C3; | A15-B21-C4; | A15-B21-C5; | A15-B21-C6; | A15-B21-C7; | A15-B21-C8; |
| A15-B21-C9; | A15-B21-C10; | A15-B21-C11; | A15-B21-C12; | A15-B21-C13; | A15-B21-C14; |
| A15-B21-C15; | A15-B21-C16; | A15-B21-C17; | A15-B21-C18; | A15-B21-C19; | A15-B21-C20; |
| A15-B21-C21; | A15-B21-C22; | A15-B21-C23; | A15-B21-C24; | A15-B21-C25; | A15-B21-C26; |
| A15-B21-C27; | A15-B21-C28; | A15-B21-C29; | A15-B21-C30; | A15-B21-C31; | A15-B21-C32; |
| A15-B21-C33; | A15-B21-C34; | A15-B21-C35; | A15-B21-C36; | A15-B21-C37; | A15-B21-C38; |
| A15-B21-C39; | A15-B21-C40; | A15-B21-C41; | A15-B21-C42; | A15-B21-C43; | A15-B21-C44; |
| A15-B21-C45; | A15-B21-C46; | A16-B21-C1; | A16-B21-C2; | A16-B21-C3; | A16-B21-C4; |
| A16-B21-C5; | A16-B21-C6; | A16-B21-C7; | A16-B21-C8; | A16-B21-C9; | A16-B21-C10; |
| A16-B21-C11; | A16-B21-C12; | A16-B21-C13; | A16-B21-C14; | A16-B21-C15; | A16-B21-C16; |
| A16-B21-C17; | A16-B21-C18; | A16-B21-C19; | A16-B21-C20; | A16-B21-C21; | A16-B21-C22; |
| A16-B21-C23; | A16-B21-C24; | A16-B21-C25; | A16-B21-C26; | A16-B21-C27; | A16-B21-C28; |
| A16-B21-C29; | A16-B21-C30; | A16-B21-C31; | A16-B21-C32; | A16-B21-C33; | A16-B21-C34; |
| A16-B21-C35; | A16-B21-C36; | A16-B21-C37; | A16-B21-C38; | A16-B21-C39; | A16-B21-C40; |
| A16-B21-C41; | A16-B21-C42; | A16-B21-C43; | A16-B21-C44; | A16-B21-C45; | A16-B21-C46; |
| A17-B21-C1; | A17-B21-C2; | A17-B21-C3; | A17-B21-C4; | A17-B21-C5; | A17-B21-C6; |
| A17-B21-C7; | A17-B21-C8; | A17-B21-C9; | A17-B21-C10; | A17-B21-C11; | A17-B21-C12; |
| A17-B21-C13; | A17-B21-C14; | A17-B21-C15; | A17-B21-C16; | A17-B21-C17; | A17-B21-C18; |
| A17-B21-C19; | A17-B21-C20; | A17-B21-C21; | A17-B21-C22; | A17-B21-C23; | A17-B21-C24; |
| A17-B21-C25; | A17-B21-C26; | A17-B21-C27; | A17-B21-C28; | A17-B21-C29; | A17-B21-C30; |
| A17-B21-C31; | A17-B21-C32; | A17-B21-C33; | A17-B21-C34; | A17-B21-C35; | A17-B21-C36; |
| A17-B21-C37; | A17-B21-C38; | A17-B21-C39; | A17-B21-C40; | A17-B21-C41; | A17-B21-C42; |
| A17-B21-C43; | A17-B21-C44; | A17-B21-C45; | A17-B21-C46; | A18-B21-C1; | A18-B21-C2; |
| A18-B21-C3; | A18-B21-C4; | A18-B21-C5; | A18-B21-C6; | A18-B21-C7; | A18-B21-C8; |
| A18-B21-C9; | A18-B21-C10; | A18-B21-C11; | A18-B21-C12; | A18-B21-C13; | A18-B21-C14; |
| A18-B21-C15; | A18-B21-C16; | A18-B21-C17; | A18-B21-C18; | A18-B21-C19; | A18-B21-C20; |
| A18-B21-C21; | A18-B21-C22; | A18-B21-C23; | A18-B21-C24; | A18-B21-C25; | A18-B21-C26; |
| A18-B21-C27; | A18-B21-C28; | A18-B21-C29; | A18-B21-C30; | A18-B21-C31; | A18-B21-C32; |
| A18-B21-C33; | A18-B21-C34; | A18-B21-C35; | A18-B21-C36; | A18-B21-C37; | A18-B21-C38; |
| A18-B21-C39; | A18-B21-C40; | A18-B21-C41; | A18-B21-C42; | A18-B21-C43; | A18-B21-C44; |
| A18-B21-C45; | A18-B21-C46; | A19-B21-C1; | A19-B21-C2; | A19-B21-C3; | A19-B21-C4; |
| A19-B21-C5; | A19-B21-C6; | A19-B21-C7; | A19-B21-C8; | A19-B21-C9; | A19-B21-C10; |
| A19-B21-C11; | A19-B21-C12; | A19-B21-C13; | A19-B21-C14; | A19-B21-C15; | A19-B21-C16; |
| A19-B21-C17; | A19-B21-C18; | A19-B21-C19; | A19-B21-C20; | A19-B21-C21; | A19-B21-C22; |
| A19-B21-C23; | A19-B21-C24; | A19-B21-C25; | A19-B21-C26; | A19-B21-C27; | A19-B21-C28; |
| A19-B21-C29; | A19-B21-C30; | A19-B21-C31; | A19-B21-C32; | A19-B21-C33; | A19-B21-C34; |
| A19-B21-C35; | A19-B21-C36; | A19-B21-C37; | A19-B21-C38; | A19-B21-C39; | A19-B21-C40; |
| A19-B21-C41; | A19-B21-C42; | A19-B21-C43; | A19-B21-C44; | A19-B21-C45; | A19-B21-C46; |
| A20-B21-C1; | A20-B21-C2; | A20-B21-C3; | A20-B21-C4; | A20-B21-C5; | A20-B21-C6; |
| A20-B21-C7; | A20-B21-C8; | A20-B21-C9; | A20-B21-C10; | A20-B21-C11; | A20-B21-C12; |
| A20-B21-C13; | A20-B21-C14; | A20-B21-C15; | A20-B21-C16; | A20-B21-C17; | A20-B21-C18; |
| A20-B21-C19; | A20-B21-C20; | A20-B21-C21; | A20-B21-C22; | A20-B21-C23; | A20-B21-C24; |
| A20-B21-C25; | A20-B21-C26; | A20-B21-C27; | A20-B21-C28; | A20-B21-C29; | A20-B21-C30; |
| A20-B21-C31; | A20-B21-C32; | A20-B21-C33; | A20-B21-C34; | A20-B21-C35; | A20-B21-C36; |
| A20-B21-C37; | A20-B21-C38; | A20-B21-C39; | A20-B21-C40; | A20-B21-C41; | A20-B21-C42; |
| A20-B21-C43; | A20-B21-C44; | A20-B21-C45; | A20-B21-C46; | A21-B21-C1; | A21-B21-C2; |
| A21-B21-C3; | A21-B21-C4; | A21-B21-C5; | A21-B21-C6; | A21-B21-C7; | A21-B21-C8; |
| A21-B21-C9; | A21-B21-C10; | A21-B21-C11; | A21-B21-C12; | A21-B21-C13; | A21-B21-C14; |
| A21-B21-C15; | A21-B21-C16; | A21-B21-C17; | A21-B21-C18; | A21-B21-C19; | A21-B21-C20; |
| A21-B21-C21; | A21-B21-C22; | A21-B21-C23; | A21-B21-C24; | A21-B21-C25; | A21-B21-C26; |
| A21-B21-C27; | A21-B21-C28; | A21-B21-C29; | A21-B21-C30; | A21-B21-C31; | A21-B21-C32; |
| A21-B21-C33; | A21-B21-C34; | A21-B21-C35; | A21-B21-C36; | A21-B21-C37; | A21-B21-C38; |
| A21-B21-C39; | A21-B21-C40; | A21-B21-C41; | A21-B21-C42; | A21-B21-C43; | A21-B21-C44; |
| A21-B21-C45; | A21-B21-C46; | A22-B21-C1; | A22-B21-C2; | A22-B21-C3; | A22-B21-C4; |
| A22-B21-C5; | A22-B21-C6; | A22-B21-C7; | A22-B21-C8; | A22-B21-C9; | A22-B21-C10; |
| A22-B21-C11; | A22-B21-C12; | A22-B21-C13; | A22-B21-C14; | A22-B21-C15; | A22-B21-C16; |
| A22-B21-C17; | A22-B21-C18; | A22-B21-C19; | A22-B21-C20; | A22-B21-C21; | A22-B21-C22; |
| A22-B21-C23; | A22-B21-C24; | A22-B21-C25; | A22-B21-C26; | A22-B21-C27; | A22-B21-C28; |
| A22-B21-C29; | A22-B21-C30; | A22-B21-C31; | A22-B21-C32; | A22-B21-C33; | A22-B21-C34; |
| A22-B21-C35; | A22-B21-C36; | A22-B21-C37; | A22-B21-C38; | A22-B21-C39; | A22-B21-C40; |
| A22-B21-C41; | A22-B21-C42; | A22-B21-C43; | A22-B21-C44; | A22-B21-C45; | A22-B21-C46; |
| A23-B21-C1; | A23-B21-C2; | A23-B21-C3; | A23-B21-C4; | A23-B21-C5; | A23-B21-C6; |
| A23-B21-C7; | A23-B21-C8; | A23-B21-C9; | A23-B21-C10; | A23-B21-C11; | A23-B21-C12; |

-continued

A23-B21-C13; A23-B21-C14; A23-B21-C15; A23-B21-C16; A23-B21-C17; A23-B21-C18;
A23-B21-C19; A23-B21-C20; A23-B21-C21; A23-B21-C22; A23-B21-C23; A23-B21-C24;
A23-B21-C25; A23-B21-C26; A23-B21-C27; A23-B21-C28; A23-B21-C29; A23-B21-C30;
A23-B21-C31; A23-B21-C32; A23-B21-C33; A23-B21-C34; A23-B21-C35; A23-B21-C36;
A23-B21-C37; A23-B21-C38; A23-B21-C39; A23-B21-C40; A23-B21-C41; A23-B21-C42;
A23-B21-C43; A23-B21-C44; A23-B21-C45; A23-B21-C46; A24-B21-C1; A24-B21-C2;
A24-B21-C3; A24-B21-C4; A24-B21-C5; A24-B21-C6; A24-B21-C7; A24-B21-C8;
A24-B21-C9; A24-B21-C10; A24-B21-C11; A24-B21-C12; A24-B21-C13; A24-B21-C14;
A24-B21-C15; A24-B21-C16; A24-B21-C17; A24-B21-C18; A24-B21-C19; A24-B21-C20;
A24-B21-C21; A24-B21-C22; A24-B21-C23; A24-B21-C24; A24-B21-C25; A24-B21-C26;
A24-B21-C27; A24-B21-C28; A24-B21-C29; A24-B21-C30; A24-B21-C31; A24-B21-C32;
A24-B21-C33; A24-B21-C34; A24-B21-C35; A24-B21-C36; A24-B21-C37; A24-B21-C38;
A24-B21-C39; A24-B21-C40; A24-B21-C41; A24-B21-C42; A24-B21-C43; A24-B21-C44;
A24-B21-C45; A24-B21-C46; A25-B21-C1; A25-B21-C2; A25-B21-C3; A25-B21-C4;
A25-B21-C5; A25-B21-C6; A25-B21-C7; A25-B21-C8; A25-B21-C9; A25-B21-C10;
A25-B21-C11; A25-B21-C12; A25-B21-C13; A25-B21-C14; A25-B21-C15; A25-B21-C16;
A25-B21-C17; A25-B21-C18; A25-B21-C19; A25-B21-C20; A25-B21-C21; A25-B21-C22;
A25-B21-C23; A25-B21-C24; A25-B21-C25; A25-B21-C26; A25-B21-C27; A25-B21-C28;
A25-B21-C29; A25-B21-C30; A25-B21-C31; A25-B21-C32; A25-B21-C33; A25-B21-C34;
A25-B21-C35; A25-B21-C36; A25-B21-C37; A25-B21-C38; A25-B21-C39; A25-B21-C40;
A25-B21-C41; A25-B21-C42; A25-B21-C43; A25-B21-C44; A25-B21-C45; A25-B21-C46;
A26-B21-C1; A26-B21-C2; A26-B21-C3; A26-B21-C4; A26-B21-C5; A26-B21-C6;
A26-B21-C7; A26-B21-C8; A26-B21-C9; A26-B21-C10; A26-B21-C11; A26-B21-C12;
A26-B21-C13; A26-B21-C14; A26-B21-C15; A26-B21-C16; A26-B21-C17; A26-B21-C18;
A26-B21-C19; A26-B21-C20; A26-B21-C21; A26-B21-C22; A26-B21-C23; A26-B21-C24;
A26-B21-C25; A26-B21-C26; A26-B21-C27; A26-B21-C28; A26-B21-C29; A26-B21-C30;
A26-B21-C31; A26-B21-C32; A26-B21-C33; A26-B21-C34; A26-B21-C35; A26-B21-C36;
A26-B21-C37; A26-B21-C38; A26-B21-C39; A26-B21-C40; A26-B21-C41; A26-B21-C42;
A26-B21-C43; A26-B21-C44; A26-B21-C45; A26-B21-C46; A27-B21-C1; A27-B21-C2;
A27-B21-C3; A27-B21-C4; A27-B21-C5; A27-B21-C6; A27-B21-C7; A27-B21-C8;
A27-B21-C9; A27-B21-C10; A27-B21-C11; A27-B21-C12; A27-B21-C13; A27-B21-C14;
A27-B21-C15; A27-B21-C16; A27-B21-C17; A27-B21-C18; A27-B21-C19; A27-B21-C20;
A27-B21-C21; A27-B21-C22; A27-B21-C23; A27-B21-C24; A27-B21-C25; A27-B21-C26;
A27-B21-C27; A27-B21-C28; A27-B21-C29; A27-B21-C30; A27-B21-C31; A27-B21-C32;
A27-B21-C33; A27-B21-C34; A27-B21-C35; A27-B21-C36; A27-B21-C37; A27-B21-C38;
A27-B21-C39; A27-B21-C40; A27-B21-C41; A27-B21-C42; A27-B21-C43; A27-B21-C44;
A27-B21-C45; A27-B21-C46; A28-B21-C1; A28-B21-C2; A28-B21-C3; A28-B21-C4;
A28-B21-C5; A28-B21-C6; A28-B21-C7; A28-B21-C8; A28-B21-C9; A28-B21-C10;
A28-B21-C11; A28-B21-C12; A28-B21-C13; A28-B21-C14; A28-B21-C15; A28-B21-C16;
A28-B21-C17; A28-B21-C18; A28-B21-C19; A28-B21-C20; A28-B21-C21; A28-B21-C22;
A28-B21-C23; A28-B21-C24; A28-B21-C25; A28-B21-C26; A28-B21-C27; A28-B21-C28;
A28-B21-C29; A28-B21-C30; A28-B21-C31; A28-B21-C32; A28-B21-C33; A28-B21-C34;
A28-B21-C35; A28-B21-C36; A28-B21-C37; A28-B21-C38; A28-B21-C39; A28-B21-C40;
A28-B21-C41; A28-B21-C42; A28-B21-C43; A28-B21-C44; A28-B21-C45; A28-B21-C46;
A1-B22; A2-B22; A3-B22; A4-B22; A5-B22; A6-B22;
A7-B22; A8-B22; A9-B22; A10-B22; A11-B22; A12-B22;
A13-B22; A14-B22; A15-B22; A16-B22; A17-B22; A18-B22;
A19-B22; A20-B22; A21-B22; A22-B22; A23-B22; A24-B22;
A25-B22; A26-B22; A27-B22; A28-B22; A1-B23; A2-B23;
A3-B23; A4-B23; A5-B23; A6-B23; A7-B23; A8-B23;
A9-B23; A10-B23; A11-B23; A12-B23; A13-B23; A14-B23;
A15-B23; A16-B23; A17-B23; A18-B23; A19-B23; A20-B23;
A21-B23; A22-B23; A23-B23; A24-B23; A25-B23; A26-B23;
A27-B23; A28-B23; A1-B24; A2-B24; A3-B24; A4-B24;
A5-B24; A6-B24; A7-B24; A8-B24; A9-B24; A10-B24;
A11-B24; A12-B24; A13-B24; A14-B24; A15-B24; A16-B24;
A17-B24; A18-B24; A19-B24; A20-B24; A21-B24; A22-B24;
A23-B24; A24-B24; A25-B24; A26-B24; A27-B24; A28-B24;
A1-B25; A2-B25; A3-B25; A4-B25; A5-B25; A6-B25;
A7-B25; A8-B25; A9-B25; A10-B25; A11-B25; A12-B25;
A13-B25; A14-B25; A15-B25; A16-B25; A17-B25; A18-B25;
A19-B25; A20-B25; A21-B25; A22-B25; A23-B25; A24-B25;
A25-B25; A26-B25; A27-B25; A28-B25; A1-B26; A2-B26;
A3-B26; A4-B26; A5-B26; A6-B26; A7-B26; A8-B26;
A9-B26; A10-B26; A11-B26; A12-B26; A13-B26; A14-B26;
A15-B26; A16-B26; A17-B26; A18-B26; A19-B26; A20-B26;
A21-B26; A22-B26; A23-B26; A24-B26; A25-B26; A26-B26;
A27-B26; A28-B26; A1-B27; A2-B27; A3-B27; A4-B27;
A5-B27; A6-B27; A7-B27; A8-B27; A9-B27; A10-B27;
A11-B27; A12-B27; A13-B27; A14-B27; A15-B27; A16-B27;
A17-B27; A18-B27; A19-B27; A20-B27; A21-B27; A22-B27;
A23-B27; A24-B27; A25-B27; A26-B27; A27-B27; A28-B27;
A1-B28; A2-B28; A3-B28; A4-B28; A5-B28; A6-B28;
A7-B28; A8-B28; A9-B28; A10-B28; A11-B28; A12-B28;
A13-B28; A14-B28; A15-B28; A16-B28; A17-B28; A18-B28;
A19-B28; A20-B28; A21-B28; A22-B28; A23-B28; A24-B28;
A25-B28; A26-B28; A27-B28; A28-B28; A1-B29; A2-B29;
A3-B29; A4-B29; A5-B29; A6-B29; A7-B29; A8-B29;
A9-B29; A10-B29; A11-B29; A12-B29; A13-B29; A14-B29;

-continued

| | | | | | |
|---|---|---|---|---|---|
| A15-B29; | A16-B29; | A17-B29; | A18-B29; | A19-B29; | A20-B29; |
| A21-B29; | A22-B29; | A23-B29; | A24-B29; | A25-B29; | A26-B29; |
| A27-B29; | A28-B29; | A1-B30; | A2-B30; | A3-B30; | A4-B30; |
| A5-B30; | A6-B30; | A7-B30; | A8-B30; | A9-B30; | A10-B30; |
| A11-B30; | A12-B30; | A13-B30; | A14-B30; | A15-B30; | A16-B30; |
| A17-B30; | A18-B30; | A19-B30; | A20-B30; | A21-B30; | A22-B30; |
| A23-B30; | A24-B30; | A25-B30; | A26-B30; | A27-B30; | A28-B30; |
| A1-B31; | A2-B31; | A3-B31; | A4-B31; | A5-B31; | A6-B31; |
| A7-B31; | A8-B31; | A9-B31; | A10-B31; | A11-B31; | A12-B31; |
| A13-B31; | A14-B31; | A15-B31; | A16-B31; | A17-B31; | A18-B31; |
| A19-B31; | A20-B31; | A21-B31; | A22-B31; | A23-B31; | A24-B31; |
| A25-B31; | A26-B31; | A27-B31; | A28-B31; | A1-B32; | A2-B32; |
| A3-B32; | A4-B32; | A5-B32; | A6-B32; | A7-B32; | A8-B32; |
| A9-B32; | A10-B32; | A11-B32; | A12-B32; | A13-B32; | A14-B32; |
| A15-B32; | A16-B32; | A17-B32; | A18-B32; | A19-B32; | A20-B32; |
| A21-B32; | A22-B32; | A23-B32; | A24-B32; | A25-B32; | A26-B32; |
| A27-B32; | A28-B32; | A29-B33; | A30-B33; | A31-B33; | A32-B33; |
| A33-B33; | A34-B33; | A35-B33; | A36-B33; | A37-B33; | A38-B33; |
| A39-B33; | A40-B33; | A41-B33; | A29-B34; | A30-B34; | A31-B34; |
| A32-B34; | A33-B34; | A34-B34; | A35-B34; | A36-B34; | A37-B34; |
| A38-B34; | A39-B34; | A40-B34; | A41-B34; | A29-B35; | A30-B35; |
| A31-B35; | A32-B35; | A33-B35; | A34-B35; | A35-B35; | A36-B35; |
| A37-B35; | A38-B35; | A39-B35; | A40-B35; | A41-B35; | A29-B36; |
| A30-B36; | A31-B36; | A32-B36; | A33-B36; | A34-B36; | A35-B36; |
| A36-B36; | A37-B36; | A38-B36; | A39-B36; | A40-B36; | A41-B36; |
| A29-B37; | A30-B37; | A31-B37; | A32-B37; | A33-B37; | A34-B37; |
| A35-B37; | A36-B37; | A37-B37; | A38-B37; | A39-B37; | A40-B37; |
| A41-B37; | A29-B38; | A30-B38; | A31-B38; | A32-B38; | A33-B38; |
| A34-B38; | A35-B38; | A36-B38; | A37-B38; | A38-B38; | A39-B38; |
| A40-B38; | A41-B38; | A29-B39; | A30-B39; | A31-B39; | A32-B39; |
| A33-B39; | A34-B39; | A35-B39; | A36-B39; | A37-B39; | A38-B39; |
| A39-B39; | A40-B39; | A41-B39; | A29-B40; | A30-B40; | A31-B40; |
| A32-B40; | A33-B40; | A34-B40; | A35-B40; | A36-B40; | A37-B40; |
| A38-B40; | A39-B40; | A40-B40; | A41-B40; | A29-B41; | A30-B41; |
| A31-B41; | A32-B41; | A33-B41; | A34-B41; | A35-B41; | A36-B41; |
| A37-B41; | A38-B41; | A39-B41; | A40-B41; | A41-B41; | A29-B42; |
| A30-B42; | A31-B42; | A32-B42; | A33-B42; | A34-B42; | A35-B42; |
| A36-B42; | A37-B42; | A38-B42; | A39-B42; | A40-B42; | A41-B42; |
| A29-B43; | A30-B43; | A31-B43; | A32-B43; | A33-B43; | A34-B43; |
| A35-B43; | A36-B43; | A37-B43; | A38-B43; | A39-B43; | A40-B43; |
| A41-B43; | A29-B44; | A30-B44; | A31-B44; | A32-B44; | A33-B44; |
| A34-B44; | A35-B44; | A36-B44; | A37-B44; | A38-B44; | A39-B44; |
| A40-B44; | A41-B44; | | | | |

Thus, for example, in the above list the compound denoted as A1-B1-C1 is the product of the combination of group A1 in Table 1 and B1 in Table 2 and C1 in Table 3, namely

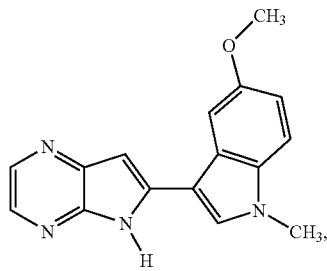

Example 1(a) hereinafter described.

Particular compounds of the invention are:
6-(5-methoxy-1-methyl-1H-indol-3-yl)-5H-pyrrolo[2,3-b]pyrazine;
6-(1-methyl-1H-indol-3-yl)-5H-pyrrolo[2,3-b]pyrazine;
6-(3-bromophenyl)-5H-pyrrolo[2,3-b]pyrazine;
7-iso-propyl-6-phenyl-5H-pyrrolo[2,3-b]pyrazine;
2-(4-bromophenyl)-1H-pyrrolo[2,3-b]pyrazine;
6-(4-[1,3]dioxan-2-yl-phenyl)-5H-pyrrolo[2,3-b]pyrazine;
6-(3-[1,3]dioxan-2-yl-phenyl)-5H-pyrrolo[2,3-b]pyrazine;
2-(5H-pyrrolo[2,3-b]pyrazin-6-yl)quinoline;
3-(5H-pyrrolo[2,3-b]pyrazin-6-yl)-isoquinoline;
6-[1-methyl-1H-indol-5-yl]-5H-pyrrolo[2,3-b]pyrazine;
6-(5-methoxy-1-methyl-1H-indol-3-yl)-2-methyl-5H-pyrrolo[2,3-b]pyrazine;
3-methyl-6-(1-methyl-1H-indol-3-yl)-5H-pyrrolo[2,3-b]pyrazine;
6-(1-benzyl-5-methoxy-1H-indol-3-yl)-5H-pyrrolo[2,3-b]pyrazine;
6-(1-methyl-1H-pyrrol-3-yl)-5H-pyrrolo[2,3-b]pyrazine;
6(1-methyl-1H-pyrrol-2-yl)-5H-pyrrolo[2,3-b]pyrazine;
6-indolizin-1-yl-5H-pyrrolo[2,3-b]pyrazine;
6-(3-methyl-indolizin-1-yl)-5H-pyrrolo[2,3-b]pyrazine;
6-(3-methyl-5-phenyl-1H-pyrrol-3-yl)-5H-pyrrolo[2,3-b]pyrazine;
6-(5,6,7,8-tetrahydro-indolizin-1yl)-5H-pyrrolo[2,3-b]pyrazine;
6-furan-3-yl-5H-pyrrolo[2,3-b]pyrazine;
dimethyl-[4-(5H-pyrrolo[2,3-b]pyrazin-6-yl)-phenyl]-amine;
6-(5-methoxy-1-methyl-1H-indol-3-yl)-7-methyl-5H-pyrrolo[2,3-b]pyrazine;
6-(4-tert-butylphenyl)-5H-pyrrolo[2,3-b]pyrazine;
6-(4-tert-butylphenyl)-7-methyl-5H-pyrrolo[2,3-b]pyrazine;
6-(3,4-dimethoxyphenyl)-5H-pyrrolo[2,3-b]pyrazine;

6-(4-aminophenyl)-7-methyl-5H-pyrrolo[2,3-b]pyrazine;
6-[4-(1-methyl)ethoxyphenyl]-5H-pyrrolo[2,3-b]pyrazine;
6-(1H-1-methyl-2-(methylthio)imidazol-5-yl)-5H-pyrrolo[2,3-b]pyrazine;
6-(1-methyl-1H-indazol-3-yl)-5H-pyrrolo[2,3-b]pyrazine;
6-(4-fluorophenyl)-5H-pyrrolo[2,3-b]pyrazine;
6-(4-methoxyphenyl)-5H-pyrrolo[2,3-b]pyrazine;
7prop-2-enyl)-6-[4tert-butyl)phenyl]-5H-pyrrolo[2,3-b]pyrazine;
6-(4-methylthiophenyl)-5H-pyrrolo[2,3-b]pyrazine;
6-(3-methoxylphenyl)-5H-pyrrolo[2,3-b]pyrazine;
6-(1-methyl-1H-pyrazol-4-yl)-5H-pyrrolo[2,3-b]pyrazine;
6-(1-methyl-5-phenyl-1H-pyrazol-3-yl)-5H-pyrrolo[2,3-b]pyrazine;
6-(pyridin-2-yl)-5H-pyrrolo[2,3-b]pyrazine;
6-(pyridin-4-yl)-5H-pyrrolo[2,3-b]pyrazine;
3-[3-(5H-pyrrolo[2,3-b]pyrazin-6-yl)-indol-1-yl]-propan-1-ol;
3-[5-methoxy-3-(5H-pyrrolo[2,3-b]pyrazin-6-yl)-indol-1-yl]-propan-1-ol;
2-[3-(5H-pyrrolo[2,3-b]pyrazinyl)-indol-1-yl]-ethanol;
2-[5-methoxy-3-(5H-pyrrolo[2,3-b]pyrazin-6-yl)-indol-1-yl]-ethanol;
3-[3-(5H-pyrrolo[2,3-b]pyrazin-6-yl)-indol-1-yl]-propylamine;
3-[5-methoxy-3-(5H-pyrrolo[2,3-b]pyrazin-6-yl)-indol-1-yl]-propylamine;
N-{3-[3-(5H-pyrrolo[2,3-b]pyrazin-6-yl)-indol-1-yl]-propyl}-acetamide;
6-[1-(3-morpholin-4-yl-propyl)-1H-indol-3-yl]-5H-pyrrolo[2,3-b]pyrazine;
6-[1-(3-piperidin-1-yl-propyl)-1H-indol-3-yl]-5H-pyrrolo[2,3-b]pyrazine;
6-{1-[3-(pyridin-3-yloxy)-propyl]-1H-indol-3-yl}-5H-pyrrolo[2,3-b]pyrazine;
1-methyl-3-(5H-pyrrolo[2,3-b]pyrazin-6-yl)-1H-indol-5-ol;
6-(2-chloro-5-methoxy-1-methyl-1H-indol-3-yl)-5H-pyrrolo[2,3-b]pyrazine;
3-(5H-pyrrolo[2,3-b]pyrazin-6-yl)-benzaldehyde;
4-(5H-pyrrolo[2,3-b]pyrazin-6-yl)-benzaldehyde;
[3-(5H-pyrrolo[2,3-b]pyrazin-6-yl)-phenyl]-methanol;
[4-(5H-pyrrolo[2,3-b]pyrazin-6-yl)-phenyl]-methanol;
6-(5-methoxy-1H-indol-3-yl)-5H-pyrrolo[2,3-b]pyrazine;
2-[5-methoxy-3-(5H-pyrrolo[2,3-b]pyrazin-6-yl)-indol-1-yl]-1-morpholin-4-yl-ethanone;
[5-methoxy-3-(1H-pyrrolo[2,3-b]pyridin-2-yl)-indol-1-yl]-acetic acid;
4-methoxy-2-(5-methoxy-1-methyl-1H-indol-3-yl)-1H-pyrrolo[2,3-b]pyridine;
4-methoxy-2-(5-methoxy-1H-indol-3-yl)-1 H-pyrrolo[2,3-b]pyridine;
4-chloro-2-(4-tertiary-butylphenyll)-1H-pyrrolo[2,3-b]pyridine;
5-phenyl-2-(5-methoxy-1-methyl-1H-indol-3-yl)-1H-pyrrolo[2,3-b]pyridine;
2-[5-methoxy-3-(1H-pyrrolo[2,3-b]pyridin-2-yl)-indol-1-yl]-1-morpholin-4-yl-ethanone;
1-[1-methyl-3-(1H-pyrrolo[2,3-b]pyridin-2-yl)-1H-indol-5-yloxy]-cyclobutanecarboxylic acid amide;
1-[1-methyl-3-(1H-pyrrolo[2,3-b]pyridin-2-yl)-1H-indol-5-yloxy]-cyclobutanecarboxylic acid methylamide;
1-methyl-3-(1H-pyrrolo[2,3-b]pyridin-2-yl)-1H-indole-5-carboxylic acid methylamide;
1-methyl-3-(1H-pyrrolo[2,3-b]pyridin-2-yl)-1H-indole-5-carboxylic acid (2-hydroxy-ethyl)-amide;
1-methyl-3-(1H-pyrrolo[2,3-b]pyridin-2-yl)-1H-indole-5-carboxylic acid (2-morpholin-4-yl-ethyl)-amide;
1-methyl-3-(1H-pyrrolo[2,3-b]pyridin-2-yl)-1H-indole-5-carboxylic acid (2-carbamoyl-ethyl)-amide;
1-methyl-3-(1H-pyrrolo[2,3-b]pyridin-2-yl)-1H-indole-5-carboxylic acid bis-(2-hydroxy-ethyl)-amide;
1-methyl-3-(1H-pyrrolo[2,3-b]pyridin-2-yl)-1H-indole-5-carboxylic acid amide;
1-methyl-3-(1H-pyrrolo[2,3-b]pyridin-2-yl)-1H-indole-5-carboxylic acid (2-hydroxy-1,1-bis-hydroxymethyl-ethyl)-amide;
1-methyl-3-(1H-pyrrolo[2,3-b]pyridin-2-yl)-1H-indole-5-carboxylic acid (2-hydroxy-1-hydroxymethyl-1-methyl-ethyl)-amide;
1-methyl-3-(1H-pyrrolo[2,3-b]pyridin-2-yl)-1H-indole-5-carboxylic acid (2,3-dihydroxy-propyl)-amide;
1-methyl-3-(1H-pyrrolo[2,3-b]pyridin-2-yl)-1H-indole-5-carboxylic acid (2-hydroxy-1,1-dimethyl-ethyl)-amide;
1-methyl-3-(1H-pyrrolo[2,3-b]pyridin-2-yl)-1H-indole-5-carboxylic acid (2-hydroxy-1-hydroxymethyl-ethyl)-amide;
1-methyl-3-(1H-pyrrolo[2,3-b]pyridin-2-yl)-1H-indole-6-carboxylic acid (2-carbamoyl-ethyl)-amide;
1-methyl-3-(1H-pyrrolo[2,3-b]pyridin-2-yl)-1H-indole-6-carboxylic acid (2-hydroxy-ethyl)-amide;
1-methyl-3-(1H-pyrrolo[2,3-b]pyridin-2-yl)-1H-indole-6-carboxylic acid (1H-[1,2,4]triazol-3-yl-amide;
1-methyl-3-(1H-pyrrolo[2,3-b]pyridin-2-yl)-1H-indole-6-carboxylic acid (2-hydroxy-1-hydroxymethyl-ethyl)-amide;
1-methyl-3-(5H-pyrrolo[2,3-b]pyrazin-6-yl)-1H-indole-5-carboxylic acid (2-hydroxy-1,1-dimethyl-ethyl)-amide;
3-[6-(4-tert-butylphenyl)-5H-pyrrolo[2,3-b]pyrazin-7-yl]-N-methylpropionamide;
3-[6-(4-tert-butylphenyl)-5H-pyrrolo[2,3-b]pyrazin-7-yl]-N,N-dimethylpropionamide;
1-methyl-3-(5H-pyrrolo[2,3-b]pyrazin-6-yl)-1H-indole-5-carboxylic acid 2-methoxyethylamide;
1-methyl-3-(5H-pyrrolo[2,3-b]pyrazin-6-yl)-1H-indole-5-carboxylic acid 2-thien-2-ylethylamide;
1-methyl-3-(5H-pyrrolo[2,3-b]pyrazin-6-yl)-1H-indole-5-carboxylic acid 2-fluoroethylamide;
1-methyl-3-(5H-pyrrolo[2,3-b]pyrazin-6-yl)-1H-indole-5-carboxylic acid 2-carboethoxyethylamide;
1-methyl-3-(5H-pyrrolo[2,3-b]pyrazin-6-yl)-1H-indole-5-carboxylic acid (hydroxymethyl)-carbomethoxy-methylamide;
1-methyl-3-(5H-pyrrolo[2,3-b]pyrazin-6-yl)-1H-indole-5-carboxylic acid 2-hydroxyethylamide;
1-methyl-3-(5H-pyrrolo[2,3-b]pyrazin-6-yl)-1H-indole-5-carboxylic acid methylamide;
1-methyl-3-(5H-pyrrolo[2,3-b]pyrazin-6-yl)-1H-indole-5-carboxylic acid dimethylamide;
[1-methyl-3-(5H-pyrrolo[2,3-b]pyrazin-6-yl)-1H-indol-5-yl]morpholin-4-yl ketone;
4-hydroxy-[1-[1-methyl-3-(5H-pyrrolo[2,3-b]pyrazin-6-yl)-1H-indol-5-yl]carbonylpiperidine
3-[1-methyl-3-(5H-pyrrolo[2,3-b]pyrazin-6-yl)-1H-indol-5-yl]carbonylaminopropionic acid methylamide;
1-methyl-3-(5H-pyrrolo[2,3-b]pyrazin-6-yl)-1H-indole-5-carboxylic acid 3-hydroxypropylamide;
3-{6-[4-(1-methyl)ethoxyphenyl]-5H-pyrrolo[2,3-b]pyrazin-7-yl}propionic acid methylamide;
3-[6-(4-methoxyphenyl)-5H-pyrrolo[2,3-b]pyrazin-7-yl]propionic acid methylamide;
3-{(6-[4-(1-methyl)ethoxyphenyl]-5H-pyrrolo[2,3-b]pyrazin-7-yl}propionamide;
3-{(6-(4-hydroxyphenyl)-5H-pyrrolo[2,3-b]pyrazin-7-yl}propionamide;

3-[6-(4-fluorophenyl)-5H-pyrrolo[2,3-b]pyrazin-7-yl]propionic acid methylamide;
[1-methyl-3-(1H-pyrrolo[2,3-b]pyridin-2-yl)-1H-indol-5-yloxy]-acetic acid;
2-[1-methyl-3-(1H-pyrrolo[2,3-b]pyridin-2-yl)-1H-indol-5-yloxy]-propionic acid;
1-[1-methyl-3-(1H-pyrrolo[2,3-b]pyridin-2-yl)-1H-indol-5-yloxy]-cyclobutanecarboxylic acid;
1-methyl-3-(1H-pyrrolo[2,3-b]pyridin-2-yl)-1H-indole-5-carboxylic acid;
1-methyl-3-(1H-pyrrolo[2,3-b]pyridin-2-yl)-1H-indol-5-ol;
1-{1-cyclobutanecarboxylic acid)-3-[1-(toluene-4-sulfonyl)-1H-pyrrolo[2,3-b]pyridin-2-yl]-1H-indol-5-yloxy}-cyclobutanecarboxylic acid;
1-methyl-3-(1H-pyrrolo[2,3-b]pyridin-2-yl)-1H-indole-6-carboxylic acid;
3-[1-methyl-3-(1H-pyrrolo[2,3-b]pyridin-2-yl)-1H-indol-5-yl]-propionic acid;
1-methyl-3-(5H-pyrrolo[2,3-b]pyrazin-6-yl)-1H-indole-5-carboxylic acid;
[2-methoxy-5-(5H-pyrrolo[2,3-b]pyrazin-6-yl)-phenoxy]acetic acid;
3-[2-dimethylamino-5-(5H-pyrrolo[2,3-b]pyrazin-6-yl)-phenyl]propionic acid;
2-[1-methyl-3-(1H-pyrrolo[2,3-b]pyridin-2-yl)-1H-indol-5-yloxy]-ethanol;
2-[1-methyl-3-(1H-pyrrolo[2,3-b]pyridin-2-yl)-1H-indol-5-yloxy]-propan-1-ol;
{1-[1-methyl-3-(1H-pyrrolo[2,3-b]pyridin-2-yl)-1H-indol-5-yloxy]-cyclobutyl}-methanol;
2-(6-phenyl-5H-pyrrolo[2,3-b]pyrazin-7-yl)-ethanol;
3-[1-methyl-3-(5H-pyrrolo[2,3-b]pyrazin-6-yl)-1H-indol-5-yl]carbonylaminopropionic acid;
2-[2-methoxy-5-(5H-pyrrolo[2,3-b]pyrazin-6-yl)-phenoxy]-ethanol;
3-[2-dimethylamino-5-(5H-pyrrolo[2,3-b]pyrazin-6-yl)-phenyl]-propan-1-ol;
3-{6-[4-(1-methyl)ethoxyphenyl]-5H-pyrrolo[2,3-b]pyrazin-7-yl}propanol;
2-(5-methoxy-1-methyl-1H-indol-3-yl)-1H-pyrrolo[2,3-b]pyridine;
3-[1-methyl-3-(1H-pyrrolo[2,3-b]pyridin-2-yl)-1H-indol-5-yloxy]-propane-1,2-diol;
3-[1-methyl-3-(1H-pyrrolo[2,3-b]pyridin-2-yl)-1H-indol-5-yloxy]-propan-1-ol;
3-[1-methyl-3-(1H-pyrrolo[2,3-b]pyridin-2-yl)-1H-indol-5-yloxy]-propan-2-ol;
2-[1-methyl-5-(2H-tetrazol-5-yl)-1H-indol-3-yl]-1H-pyrrolo[2,3-b]pyridine;
2-[1-methyl-5-(2-methyl-2H-tetrazol-5-yl)-1H-indol-3-yl]-1H-pyrrolo[2,3-b]pyridine;
2-[1-methyl-5-(1-methyl-1H-tetrazol-5-yl)-1H-indol-3-yl]-1H-pyrrolo[2,3-b]pyridine;
1-[1-methyl-3-(1H-pyrrolo[2,3-b]pyridin-2-yl)-1H-indol-5-yl]-ethanone;
2-(5,6-dimethoxy-1-methyl-1H-indol-3-yl)-1H-pyrrolo[2,3-b]pyridine;
2-[5-(2-methoxy-1-methyl-ethoxy)-1-methyl-1H-indol-3-yl]-1H-pyrrolo[2,3-b]pyridine;
2-[1-methyl-5-(5-methyl-[1,2,4]oxadiazol-3-yl)-1H-indol-3-yl]-1H-pyrrolo[2,3-b]pyridine;
3-[6-methoxy-1-methyl-3-(1H-pyrrolo[2,3-b]pyridin-2-yl)-1H-indol-5-yloxy]-propane-1,2-diol;
6-methoxy-1-methyl-3-(1H-pyrrolo[2,3-b]pyridin-2-yl)-1H-indol-5-ol;
2-(5-methoxy-1-methyl-1H-indol-3-yl)-4-phenyl-1H-pyrrolo[2,3-b]pyridine;
2-[5pyridin-4-yl)-1-methyl-1H-indol-3-yl]-1H-pyrrolo[2,3-b]pyridine;
2-(5-methoxy-1-methyl-1H-indol-3-yl)-1H-pyrrolo[2,3-b]pyridine-4-carbonitrile;
4-chloro-2-(5-methoxy-1-methyl-1H-indol-3-yl)-1H-pyrrolo[2,3-b]pyridine;
1-methyl-3-(1H-pyrrolo[2,3-b]pyridin-2-yl)-1H-indol-5-ylamine;
N-[1-methyl-3-(1H-pyrrolo[2,3-b]pyridin-2-yl)-1H-indol-5-yl]-methanesulfonamide;
N-[1-methyl-3-(1H-pyrrolo[2,3-b]pyridin-2-yl)-1H-indol-5-yl]-acetamide;
{1-[5-(1-hydroxymethyl-cyclobutoxy)-3-(1H-pyrrolo[2,3-b]pyridin-2-yl)-indol-1-yl]-cyclobutyl}-methanol;
{1-[1-methyl-3-(5H-pyrrolo[2,3-b]pyrazin-6-yl)-1H-indol-5-yloxy]-cyclobutyl}-methanol;
2-[6-(4-tert-butylphenyl)-5H-pyrrolo[2,3-b]pyrazin-7-yl]ethyl-2H-tetrazole;
3-[6-(4-tert-butylphenyl)-5H-pyrrolo[2,3-b]pyrazin-7-yl]-2H-propionitrile;
3-[6-(4-tert-butylphenyl-5H-pyrrolo[2,3-b]pyrazin-7-yl]-propionamide;
3-[6-(4-tert-butylphenyl)-5H-pyrrolo[2,3-b]pyrazin-7-yl]-propionic acid;
3-{(6-[4-(1-methyl)ethoxyphenyl]-5H-pyrrolo[2,3-b]pyrazin-7-yl}propionic acid;
3-[6-(4-fluorophenyl)-5H-pyrrolo[2,3-b]pyrazin-7-yl]propionic acid;
3-[6-(4-methoxyphenyl)-5H-pyrrolo[2,3-b]pyrazin-7-yl]propionic acid;
3-[6-(4-tert-butyl-phenyl)-5H-pyrrolo[2,3-b]pyrazin-7-yl]-propan-1-ol;
[2-methoxy-5-(5H-pyrrolo[2,3-b]pyrazin-6-yl)-phenoxy]acetic acid ethyl ester;
2-methoxy-5-(5H-pyrrolo[2,3-b]pyrazin-6-yl)phenol;
3-fluoro-2-(5-methoxy-1-methyl-1H-indol-3-yl)-1H-pyrrolo[2,3-b]pyridine;
3-{6-(4-hydroxyphenyl)-5H-pyrrolo[2,3-b]pyrazin-7-yl}propionic acid;
ethyl 3-{6-(4-hydroxyphenyl)-5H-pyrrolo[2,3-b]pyrazin-7-yl}propionate;
2-(5-methoxy-1H-indol-3-yl)-1H-pyrrolo[2,3-b]pyridine-4-carbonitrile;
6-(4-methylsulfinylphenyl)-5H-pyrrolo[2,3-b]pyrazine;
6-(4-methylsulfonylphenyl)-5H-pyrrolo[2,3-b]pyrazine;
3-(6-(4-tert-butylphenyl)-5H-pyrrolo[2,3-b]pyrazin-7-yl)propylamine;
N-{3-(6-(4-tert-butylphenyl)-5H-pyrrolo[2,3-b]pyrazin-7-yl)propyl}acetamide;
N-{3-(6-(4-tert-butylphenyl)-5H-pyrrolo[2,3-b]pyrazin-7-yl)propyl}cyclopropylcarboxylic acid amide;
N-{3-(6-(4-tert-butylphenyl)-5H-pyrrolo[2,3-b]pyrazin-7-yl)propyl}butyramide;
N-{3-(6-(4-tert-butylphenyl)-5H-pyrrolo[2,3-b]pyrazin-7-yl)propyl}methoxyacetamide;
N-{3-(6-(4-tert-butylphenyl)-5H-pyrrolo[2,3-b]pyrazin-7-yl)propyl}thien-2ylcarboxylic acid amide;
N-{3-(6-(4-tert-butylphenyl)-5H-pyrrolo[2,3-b]pyrazin-7-yl)propyl}-N'-propyl urea;
N-{3-(6-(4-tert-butylphenyl)-5H-pyrrolo[2,3-b]pyrazin-7-yl)propyl}-N'-carboethoxymethyl urea;
N-{3-(6-(4-tert-butylphenyl)-5H-pyrrolo[2,3-b]pyrazin-7-yl)propyl}-N',N'-diethyl urea;
N-{3-(6-(4-tert-butylphenyl)-5H-pyrrolo[2,3-b]pyrazin-7-yl)propyl}methanesulfonamide;
N-{3-(6-(4-tert-butylphenyl)-5H-pyrrolo[2,3-b]pyrazin-7-yl)propyl}thien-2-ylsulfonamide N-{3-(6-(4-tert-butylphenyl)-5H-pyrrolo[2,3-b]pyrazin-7-yl)propyl}dimethylisoxazol-4-ylsulfonamide;

N-{3-(6-(4-tert-butylphenyl)-5H-pyrrolo[2,3-b]pyrazin-7-yl)propyl}1-methylimidazol4-ylsulfonamide;

and the corresponding N-oxides, and their prodrugs; and pharmaceutically acceptable salts and solvates (e.g. hydrates) of such compounds and their N-oxides and prodrugs.

Preferred compounds of the invention are:

6-(5-methoxy-1-methyl-1H-indol-3-yl)-5H-pyrrolo[2,3-b]pyrazine (compound denoted as A1-B1-C1);

1-[1-methyl-3-(1H-pyrrolo[2,3-b]pyridin-2-yl)-1H-indol-5-yloxy]-cyclobutanecarboxylic acid amide(compound denoted as A2-B1-C31);

2-(5-methoxy-1-methyl-1H-indol-3-yl)-1H-pyrrolo[2,3-b]pyridine-4-carbonitrile(compound denoted as A3-B1-C28);

{1-[1-methyl-3-(5H-pyrrolo[2,3-b]pyrazin-6-yl)-1H-indol-5-yloxy]-cyclobutyl}-methanol(compound denoted as A1-B1-C28);

and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block kinase catalytic activity according to tests described in the literature and described in vitro procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of protein kinase inhibitors (e.g. Syk, FAK, KDR or Aurora2). For example, compounds of the present invention are useful in the treatment of inflammatory diseases, for example asthma: inflammatory dermatoses (e.g. psoriasis, dematitis herpetiformis, eczema, necrotizing and cutaneous vasculitis, bullous disease); allergic rhinitis and allergic conjunctivitis; joint inflammation, including arthritis, rheumatoid arthritis and other arthritic conditions such as rheumatoid spondylitis, gouty arthritis, traumatic arthritis, rubella arthritis, psoriatic arthritis and osteoarthritis. The compounds are also useful in the treatment of Chronic Obstructive Pulmonary Disease (COPD), acute synovitis, autoimmune diabetes, autoimmune encephalomyelitis, collitis, atherosclerosis, peripheral vascular disease, cardiovascular disease, multiple sclerosis, restenosis, myocarditis, B cell lymphomas, systemic lupus erythematosus, graft v host disease and other transplant associated rejection events, cancers and tumours (such as colorectal, prostate, breast, thyroid, colon and lung cancers) and inflammatory bowel disease. Additionally, the compounds are useful as tumor anti-angiogenic agents.

A special embodiment of the therapeutic methods of the present invention is the treating of asthma.

Another special embodiment of the therapeutic methods of the present invention is the treating of psoriasis Another special embodiment of the therapeutic methods of the present invention is the treating of joint inflammation.

Another special embodiment of the therapeutic methods of the present invention is the treating of inflammatory bowel disease.

A special embodiment of the therapeutic methods of the present invention is the treating of cancers and tumours.

According to a further feature of the invention there is provided a method for the treatment of a human or animal patient suffering from, or subject to, conditions which can be ameliorated by the administration of a protein kinase inhibitor (e.g. Syk, FAK, KDR or Aurora2) for example conditions as hereinbefore described, which comprises the administration to the patient of an effective amount of compound of the invention or a composition containing a compound of the invention. "Effective amount" is meant to describe an amount of compound of the present invention effective in inhibiting the catalytic activity a protein kinase, such as Syk, FAK, KDR or Aurora2, and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection.

The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I) wherein $R^1$, $R^2$ and $R^3$ are as hereinbefore defined, and $X^1$ is N or CH may be prepared by application or adaptation of the procedures described by Davis et al Tetrahedron, 1992, 48, page 939–952, for example:

(i) reaction of compounds of formula (III):

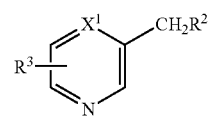

(III)

wherein $R^2$ and $R^3$ are as hereinbefore defined and $X^1$ is N or CH, with a suitable base, such as lithium diisopropylamide (or butyllithium), in an inert solvent, such as tetrahydrofuran, and at a temperature from about −26° C.;

(ii) treatment of the resulting anion with nitrites of formula (IV):

$$R^1\text{—CN} \qquad (IV)$$

wherein $R^1$ is as defined hereinbefore at a temperature at about −15° C. to about room temperature.

This procedure is particularly suitable for the preparation of compounds of formula (I) where $R^1$ is optionally substituted N-methylindol-3-yl, $R^2$ and $R^3$ are hydrogen and $X^1$ is N or CH.

Compounds of formula (I) wherein $R^1$, $R^2$, $R^3$ and $X^1$ are as hereinbefore defined may also be prepared by application or adaptation of the procedure described by Chang and Bag, J. Org. Chem., 1995, 21, pages 7030–7032, for example reaction of compounds of formula (V):

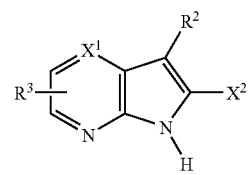

(V)

wherein $R^1$, $R^2$, $R^3$ and $X^1$ are as hereinbefore defined, and $X^2$ is a halogen, preferably iodine, atom or a triflate group, with a boronic acid of formula (VI):

$$R^1\text{—B(OH)}_2 \qquad (VI)$$

wherein $R^1$ is as defined hereinbefore. The coupling reaction may conveniently be carried out for example in the presence of a complex metal catalyst such as tetrakis(triphenylphosphine)palladium(0) and sodium bicarbonate, in aqueous dimethylformamide at a temperature up to reflux temperature.

Compounds of the invention may also be prepared by interconversion of other compounds of the invention.

Thus, for example, compounds of formula (I) containing a carboxy group may be prepared by hydrolysis of the corresponding esters. The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) containing a carboxy group may be prepared by acid catalysed removal of the tert-butyl group of the corresponding tert-butyl esters using standard reaction conditions, for example reaction with trifluoroacetic acid at a temperature at about room temperature.

As another example compounds of formula (I) containing a carboxy group may be prepared by hydrogenation of the corresponding benzyl esters. The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

As another example of the interconversion process, compounds of formula (I) containing a —C(=O)—NY$^1$Y$^2$ group may be prepared by coupling compounds of formula (I) containing a carboxy group with an amine of formula HNY$^1$Y$^2$ to give an amide bond using standard peptide coupling procedures, for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide) at room temperature. The coupling may also be brought about by reaction of compounds of formula (I) containing a carboxy group with N-{(dimethylamino)(1H-1,2,3-triazaolo[4,5-b]pyridin-1-yl)methylene}-N-methylmethanaminium hexafluorophosphate N-oxide in the presence of a suitable base, such as diisopropylethylamine, in an inert solvent, such as dimethylformamide, and at a temperature at about room temperature, followed by reaction with an amine of formula HNY$^1$Y$^2$ (ammonium chloride can be used for the preparation of compounds of formula (I) containing a —C(=O)—NH$_2$ group).

As another example of the interconversion process, compounds of formula (I) containing a —CH$_2$OH group may be prepared by the reduction of corresponding compounds of formula (I) containing a —CHO or —CO$_2$R$^7$ (in which R$^7$ is lower alkyl) group. For example, the reduction may conveniently be carried out by means of reaction with lithium aluminium hydride, in an inert solvent, such as tetrahydrofuran, and at a temperature from about room temperature to about reflux temperature.

As another example of the interconversion process, compounds of formula (I) in which R$^1$ is aryl or heteroaryl substituted by —CO$_2$Me may be prepared by:
  (i) treating compounds of formula (I) in which R$^1$ is aryl or heteroaryl substituted by hydroxy, with N-phenyltrifluoromethanesulfonimide in the presence of a suitable base, such as triethylamine, in an inert solvent, such as dichloromethane, and at a temperature at about −78° C.;
  (ii) reaction of the resulting triflate with carbon monoxide in the presence of a suitable catalyst (e.g. palladium acetate), 1,3-bis(diphenylphosphino)propane, triethylamine and methanol, in an inert solvent, such as dimethylformamide at a pressure of about 1 atmosphere, and at a temperature at about room temperature.

This procedure is particularly suitable for the preparation of compounds of formula (I) in which R$^1$ is 5-carboxymethyl-N-methylindol-3-yl.

As another example of the interconversion process, compounds of formula (D) in which R$^1$ is aryl or heteroaryl substituted by —SO$_2$NY$^1$Y$^2$ may be prepared by:
  (i) treating compounds of formula (I) in which R$^1$ is aryl or heteroaryl substituted by hydroxy, with N-phenyltrifluoromethanesulfonimide as described hereinabove;
  (ii) treating the resulting triflate with tertiary-butylmercaptan in the presence of sodium tertiary-butoxide, palladium acetate, lithium chloride and R(+)-2,2'-bis(diphenylphosphio)-1,1'-binaphthyl in an inert solvent, such as toluene, and at a temperature at about 110–120° C.;
  (iii) reaction of the resulting compounds of formula (I) in which R$^1$ is aryl or heteroaryl substituted by —S$^t$Bu, with trifluoroacetic acid and mercuric acetate, in an inert solvent, such as toluene, and at a temperature at about room temperature, followed by treatment with hydrogen sulfide;
  (iv) reaction of the resulting compounds of formula (I) in which R$^1$ is aryl or heteroaryl substituted by —SH, with chlorine in aqueous acetic acid at a temperature at about room temperature;
  (v) reaction of the resulting compounds of formula (I) in which R$^1$ is aryl or heteroaryl substituted by —SO$_2$Cl, with an amine of formula HNY$^1$Y$^2$.

As another example of the interconversion process, compounds of formula (I) in which R$^1$ is aryl or heteroaryl substituted by aryl (or heteroaryl) may be prepared by treating compounds of formula (I) in which R$^1$ is aryl or heteroaryl substituted by hydroxy with N-phenyltrifluoromethanesulfonimide as described hereinabove followed by reaction of the resulting triflate with an aryl (or heteroaryl) boronic acid ester in the presence of a suitable catalyst (e.g. palladium tetrakis(triphenylphosphine) and aqueous sodium bicarbonate, in an inert solvent, such as dimethylformamide, and at a temperature at about 120–150° C.

As another example of the interconversion process, compounds of formula (I) in which R$^1$ is aryl or heteroaryl substituted by hydroxy may be prepared by reaction of the corresponding compounds of formula (I) in which R$^1$ is aryl or heteroaryl substituted by methoxy with a Lewis acid, such as boron tribromide, in an inert solvent, such as dichloromethane and at a temperature from about 0° C. to about room temperature.

As another example of the interconversion process, compounds of formula (I) in which R$^1$ is aryl or heteroaryl substituted by —OR$^4$ may be prepared by alkylation the corresponding compounds of formula (I) in which R$^1$ is aryl or heteroaryl substituted by hydroxy, with compounds of formula (VII):

$$R^4\text{—}X^3 \qquad \text{(VII)}$$

wherein R$^4$ is as hereinbefore defined and X$^3$ is a halogen, preferably bromo, atom, or a tosyl group, using standard alkylation conditions. The alkylation may for example be carried out in the presence of a base, such as an alkali metal carbonate (e.g. potassium carbonate or cesium carbonate), an alkali metal alkoxide (e.g. potassium tertiary butoxide) or alkali metal hydride (e.g. sodium hydride), in dimethylformamide, or dimethyl sulfoxide, at a temperature from about 0° C. to about 100° C.

Alternatively compounds of formula (I) in which R$^1$ is aryl or heteroaryl substituted by —OR$^4$ may be prepared by reaction of the corresponding compounds of formula (I) in which $R^1$ is aryl or heteroaryl substituted by hydroxy with the appropriate alcohol of formula (VIII):

$$R^4\text{—OH} \qquad (VIII)$$

wherein $R^4$ is as hereinbefore defined in the presence of a triarylphosphine, such a triphenylphosphine, and a dialkyl acetylenedicarboxylate, such as diisopropylacetylenedicarboxylate or dimethylacetylenedicarboxylate, in an inert solvent, such as toluene, and at a temperature at about room temperature. This procedure is particularly suitable for the preparation of compounds of formula (I) in which $R^1$ is heteroaryl substituted by —$OR^4$.

As another example of the interconversion process, compounds of formula (I) in which $R^1$ is aryl or heteroaryl substituted by —$OR^4$, where $R^4$ is propyl substituted by hydroxy, may be prepared by reaction of the corresponding compounds of formula (I) in which $R^1$ is aryl or heteroaryl substituted by —$OR^4$, where $R^4$ is propenyl, with borane followed by reaction with hydrogen peroxide in the presence of sodium hydroxide. This procedure is particularly suitable for the preparation of compounds of formula (I) in which $R^1$ is indolyl substituted by —$OCH_2CH(CH_3)OH$ and —$OCH_2CH_2CH_2OH$.

As another example of the interconversion process, compounds of formula (I) in which $R^1$ is aryl or heteroaryl substituted by-$OR^4$, where $R^4$ is a 1,3-dihydroxyalkylene group, may be prepared by reaction of the corresponding compounds where $R^4$ is alkenyl with osmium tetroxide in the presence of 4-methyl-morpholine N-oxide. The reaction may conveniently be carried out in an inert solvent, such as acetone, and at a temperature at about room temperature.

As another example of the interconversion process, compounds of formula (Ia) in which $R^9$ is alkyl, alkenyl, cycloalkyl, heterocycloalkyl, or alkyl substituted by —$C(=O)NY^1Y^2$, —$OR^6$, —$C(=O)$—$OR^7$, —$NY^1Y^2$ may be prepared by alkylation of the corresponding compounds of formula (Ia) in which $R^9$ is hydrogen, with the appropriate halide of formula (IX):

$$R^9\text{—}X^4 \qquad (IX)$$

wherein $R^9$ is alkyl, alkenyl, cycloalkyl, heterocycloalkyl, or alkyl substituted by —$C(=O)NY^1Y^2$, —$OR^7$, —$C(=O)$—$OR^5$, —$NY^1Y^2$ and $X^4$ is a halogen, preferably bromine, atom, using standard alkylation conditions for example those described hereinbefore.

As another example of the interconversion process, compounds of formula (I) containing a —$N(R^6)$—$C(=O)$—$NY^3Y^4$ group in which $R^6$ and $Y^3$ are both hydrogen and $Y^4$ is as hereinbefore defined may be prepared by reaction of the corresponding compounds of formula (I) containing an amino group with an isocyanate of formula $O=C=NY^4$ in an inert solvent, such as tetrahydrofuran, and at a temperature at about room temperature.

As another example of the interconversion process, compounds of formula (I) containing sulfoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulfate in a medium such as aqueous methanol, buffered to about pH5, at temperatures between about 0° C. and room temperature. This latter method is preferred for compounds containing an acid-labile group.

As another example of the interconversion process, compounds of formula (I) containing sulfone linkages may be prepared by the oxidation of corresponding compounds containing —S— or sulfoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (I) containing a cyano group may be prepared by reaction of the corresponding compounds of formula (I) containing a —$C(=O)$—$NH_2$ group with phosphorus pentachloride in the presence of triethylamine. The reaction may conveniently be carried out in an inert solvent, such as tetrahydrofuran, and at a temperature at about reflux temperature.

As another example of the interconversion process, compounds of formula (I) containing a tetrazolyl group may be prepared by reaction of the corresponding compounds of formula (I) containing a cyano group with azidotributyltin. The reaction may conveniently be carried out in an inert solvent, such as toluene, and at a temperature at about reflux temperature.

As another example of the interconversion process, compounds of formula (I) in which $R^2$ is a fluoro may be prepared by reaction of the corresponding compounds of formula (I) in which $R^2$ is hydrogen with methyl magnesium bromide (in an inert solvent, such as tetrahydrofuran, and at a temperature at about 0° C.) followed by reaction with 1-chloromethyl-4-fluoro-1,4-diazoniabicyclo[2,2,2]octane bis(tetrafluoroborate) at a temperature from about 0° C. to about reflux temperature.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Compounds of formula (IV) wherein $R^1$ is as defined hereinbefore may be prepared by reaction of the corresponding compounds of formula (I):

$$R^1\text{—CHO} \tag{1}$$

wherein $R^1$ is as hereinbefore defined, with hydroxylamine hydrochloride in an inert solvent, such as dimethylformamide, and at a temperature at about 150° C.

Compounds of formula (IV) wherein $R^1$ is represented by the formula (IIa), in which $R^{10}$ and p are as hereinbefore defined and $R^9$ is alkyl, alkenyl, cycloalkyl or alkyl substituted by —C(=O)NY$^1$Y$^2$, —OR$^4$, —C(=O)—OR$^7$, —NY$^1$Y$^2$, may be prepared by alkylation of the corresponding 1H-indoles of formula (IV) wherein $R^1$ is represented by the formula (IIa), in which $R^{10}$ and p are as hereinbefore defined and $R^9$ is hydrogen, with the appropriate (optionally substituted)alkyl-, alkenyl- or cycloalkyl-halide using standard alkylation conditions. The alkylation may for example be carried out in the presence of a base, such as an alkali metal carbonate, e.g. potassium carbonate, or alkali metal hydride, e.g. sodium hydride, in an inert solvent, such as dimethylformamide or dimethyl sulfoxide, at a temperature from about room temperature to about 100° C.

Compounds of formula (IV) wherein $R^1$ is 5,6,7,8-tetrahydroindolizin-1-yl may be prepared by:
(i) reaction of piperidine-2-carboxylic acid with formic acid and acetic anhydride at a temperature at about room temperature;
(ii) treatment of the resulting sodium-1-formyl-piperidine-2-carboxylate with 4-toluenesulfonyl chloride in an inert solvent, such as dichloromethane, and at a temperature at about room temperature;
(iii) reaction with acrylonitrile in the presence of triethylamine at a temperature at about room temperature.

Compounds of formula (1) wherein $R^1$ is as defined hereinbefore may be prepared by formylation of compounds of formula (2):

$$R^1\text{—H} \tag{2}$$

wherein R is as defined hereinbefore using standard reaction conditions, for example using a Vilsmeier-Haack formylation reaction with phosphorus oxychloride in dimethylformamide. This procedure is particularly suitable for the preparation of compounds of formula (1) where $R^1$ is optionally substituted N-methylindol-3-yl.

Compounds of formula (V) wherein $R^2$, $R^3$ and $X^1$ are as hereinbefore defined and $X^2$ is an iodine atom, may be prepared by iodination of compounds of formula (3):

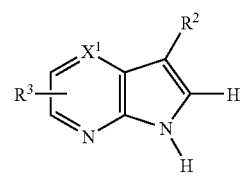

(3)

wherein $R^2$, $R^3$ and $X^1$ are as hereinbefore defined. The iodination reaction may conveniently be carried out by the application or adaptation of the procedure described by Saulnier and Gribble, J. Org. Chem., 1982, 47, 1982, for example by treatment of compounds of formula (3) with lithium diisopropylamide in an inert solvent, such as tetrahydrofuran, and at a temperature at about −78° C., followed by reaction of the resulting anion with iodine. This reaction is conveniently carried out with the indole NH protected with for example a tosyl group.

Compounds of formula (3) wherein $R^2$, $R^3$ and $X^1$ are as hereinbefore defined may be prepared by cyclisation of compounds of formula (4):

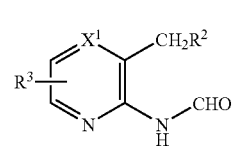

(4)

wherein $R^2$, $R^3$ and $X^1$ are as hereinbefore defined. The cyclisation reaction may conveniently be carried out in the presence of an alkali metal alkoxide, such as sodium ethoxide, in an inert solvent, such as ethanol, and at a temperature from about room temperature to about reflux temperature.

Compounds of formula (3) wherein $R^3$ and $X^1$ are as hereinbefore defined and $R^2$ is hydrogen may be prepared by cyclisation of compounds of formula (5):

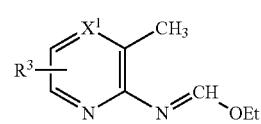

(5)

wherein $R^3$ and $X^1$ are as hereinbefore defined. The cyclisation reaction may conveniently be carried out in the presence of sodamide, in N-methylaniline and at a temperature from about 120° C. to about 200° C.

Compounds of formula (3) wherein $R^3$ and $X^1$ are as hereinbefore defined and $R^2$ is methyl (or $C_{1-4}$alkyl optionally substituted by -$Z^1R^8$, in which $Z^1$ and $R^8$ as hereinbefore defined) may be prepared by cyclisation of compounds of formula (6):

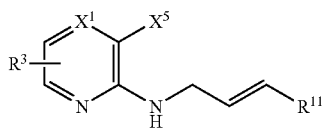

(6)

wherein $R^3$ and $X^1$ are as hereinbefore defined, $R^{11}$ is hydrogen (or $C_{1-3}$alkyl optionally substituted by $-Z^1R^8$, in which $Z^1$ and $R^8$ as hereinbefore defined) and $X^5$ represents a halogen, preferably a bromine, atom, or a triflate group. The cyclisation may conveniently be carried out in the presence of a complex metal catalyst such as tetrakis(triphenylphosphine)palladium(0), a tertiary amine, such as triethylamine, and a triarylphosphine, such as triphenylphosphine, in an inert solvent, such as dimethylformamide and at a temperature at about 60° C. to about 120° C. This procedure is particularly suitable for the preparation of compounds of formula (3) wherein $R^3$ and $X^1$ are as hereinbefore defined, $X^1$ is N and $R^2$ is C—CH$_3$.

Compounds of formula (3) wherein $R^3$, $R^2$ and $X^1$ are as hereinbefore defined may be prepared by:

(i) reaction of compounds of formula (7):

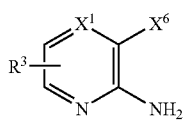

(7)

wherein $R^3$ and $X^1$ are as hereinbefore defined and $X^6$ is a halogen, preferably iodine, atom with acetylenes of formula (8):

R$^2$—C≡C—SiMe$_3$ (8)

wherein $R^2$ is as hereinbefore defined, in the presence of a complex metal catalyst such as [1,1'-bis(diphenylphosphino)-ferrocene]palladium (II) chloride, lithium chloride and sodium carbonate, in an inert solvent, such as dimethylformamide, and at a temperature up to about 100° C.

(ii) desilylation.

Compounds of formula (4) wherein $R^2$, $R^3$ and $X^1$ are as hereinbefore defined may be prepared by reaction of compounds of formula (9):

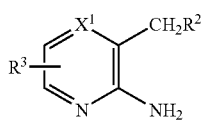

(9)

wherein $R^2$, $R^3$ and $X^1$ are as hereinbefore defined with a mixture of formic acid and acetic anhydride.

Compounds of formula (5) wherein $R^3$ and $X^1$ are as hereinbefore defined may be prepared by reaction of the corresponding compounds of formula (9) wherein $R^3$ and $X^1$ are as hereinbefore defined and $R^2$ is hydrogen with triethylorthoformate, in the presence of an acid catalyst, such as hydrogen chloride, in ethanol and at a temperature from about room temperature to about reflux temperature.

Compounds of formula (6) wherein $R^3$, $R^{11}$ and $X^1$ are as hereinbefore defined and $X^5$ is a halogen atom may be prepared by alkylation of compounds of formula (7) wherein $R^3$, $X^1$ and $X^6$ are as hereinbefore defined with the appropriate alkenyl halide of formula (10):

R$^{11}$CH=CH—CH$_2$—X$^7$ (10)

wherein $R^{11}$ is as hereinbefore defined and $X^7$ is a halogen, preferably bromine, atom. The alkylation may conveniently be carried out in the presence of an alkali metal hydride, such as sodium hydride, in an inert solvent, such as tetrahydrofuran, and at a temperature at about room temperature.

Compounds of formula (7) wherein $R^3$ and $X^1$ are as hereinbefore defined and $X^6$ is a bromine atom, may be prepared by bromination of compounds of formula (11):

(11)

wherein $R^3$ and $X^1$ are as hereinbefore defined, in dimethylsulfoxide.

Compounds of formula (7) wherein $R^3$ and $X^1$ are as hereinbefore defined and $X^5$ is an iodine atom, may be prepared by iodination of compounds of formula (11) wherein $R^3$ and $X^1$ are as hereinbefore defined. The iodination may be carried out by the application or adaptation of the method of W-W. Sy, Synth. Comm., 1992, 22, pages 3215–3219.

Compounds of formula (V) wherein $R^1$, $R^2$, $R^3$ and $X^1$ are as hereinbefore defined and $X^5$ is a triflate group may be prepared by reaction of compounds of formula (12):

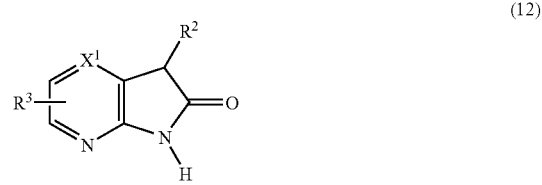

(12)

wherein $R^2$, $R^3$ and $X^1$ are as hereinbefore defined, with triflic anhydride in the presence of Hunigs base, in an inert solvent, such as dichloromethane, and at a temperature at about 0° C. This reaction is conveniently carried out with the indole NH protected with for example a tosyl group.

Compounds of formula (12) wherein $R^2$, $R^3$ and $X^1$ are as hereinbefore defined may be prepared by reaction of compounds of formula (13):

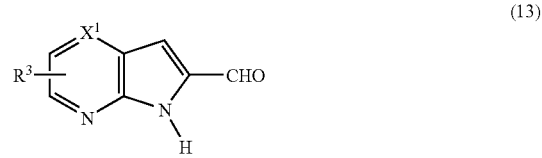

(13)

wherein $R^3$ and $X^1$ are as hereinbefore defined with meta-chloroperbenzoic acid, in an inert solvent, such as dichloromethane, and at a temperature at about 5° C. This reaction is conveniently carried out with the indole NH protected with for example a tosyl group.

Compounds of formula (13) wherein $R^3$ and $X^1$ are as hereinbefore defined may be prepared by reaction of compounds of formula (14):

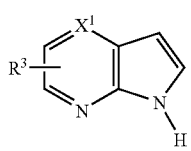

(14)

wherein $R^3$ and $X^1$ are as hereinbefore defined with lithium diisopropylamide, in an inert solvent, such as tetrahydrofuran, followed by reaction with dimethylformamide and at a temperature at about –78° C. This reaction is conveniently carried out with the indole NH protected with for example a tosyl group.

Compounds of formula (14) wherein $R^3$ and $X^1$ are as hereinbefore defined may be prepared by reaction of compounds of formula (7) wherein $R^3$ and $X^1$ are as hereinbefore defined and $X^6$ is iodo, with trimethylsilylacetylene in the presence of a complex metal catalyst such as [1,1'-bis(diphenylphosphino)-ferrocene]palladium (II) chloride, followed by desilylation.

Compounds of formula (VI) wherein $R^1$ is as defined hereinbefore may be prepared by: reaction of compounds of formula (15):

(15)

wherein R is as defined hereinbefore and $X^8$ is a halogen, preferably bromine, atom, in the presence of tributylborate, with a suitable base, such as butyllithium, in an inert solvent, such as tetrahydrofuran, and at a temperature at about –100° C.

Compounds of formula (VI) wherein $R^1$ is as defined hereinbefore may also be prepared by treatment of compounds of formula (15), wherein $R^1$ is as defined hereinbefore and $X^8$ is a —HgOAc group, with borane, in an inert solvent, such as tetrahydrofuran, and at a temperature at about room temperature.

Compounds of formula (15) wherein $R^1$ is optionally substituted indol-3-yl and $X^8$ is a bromine atom may be prepared by reaction of optionally substituted indoles with bromine in an inert solvent, such as dimethylformamide, and at a temperature at about room temperature.

Compounds of formula (13) wherein $R^1$ is optionally substituted indol-3-yl and $X^8$ is a —HgOAc group may be prepared by reaction of optionally substituted indolines with mercuric acetate in glacial acetic acid at a temperature at about room temperature.

The present invention is further Exemplified but not limited by the following illustrative Examples and Reference Examples.

400M Hz $^1$H nuclear magnetic resonance spectra (NMR) were recorded on a Varian Unity INOVA machine. In the nuclear magnetic resonance spectra (NMR) the chemical shifts (δ) are expressed in ppm relative to tetramethylsilane. Abbreviations have the following significances: s=singlet; d=doublet; t=triplet; m=multiplet; q=quartet; dd=doublet of doublets; ddd=doublet of double doublets.

The high pressure liquid chromatography retention times (HPLC: $R_T$ values) were determined by: (i) Method A, C18 Phenomenex (150×4.6 mm) column using gradient elution with a mixture of acetonitrile and water with 0.1% trifluoroacetic acid as the mobile phase (0–1 minute 5% acetonitrile; 1–12 minutes ramp up to 95% acetonitrile; 12–14.95 minutes 95% acetonitrile; 14.95–15 minutes 0% acetonitrile); or Method B, YMC ODS-AQ (2×50 mm) column using gradient elution with a mixtures of acetonitrile and water with 0.1% formic acid as the mobile phase [95/5/0.1% (A) to 5/95/0.1% (B)] and a flow rate of 0.4 mL/minute); or Method C, what column ?? column using gradient elution with a mixture of acetonitrile and water with 0.1% formic acid as the mobile phase (95/5/0.1%, water/acetonitrile/formic acid for 0.1 minute linear gradient to 5/95/0.1%, water/acetonitrile/formic acid at 2 minutes and hold until 3.5 minutes).

The thin layer chromatography (TLC) $R_F$ values were determined using Merck silica plates.

EXAMPLE 1

(a) 6-(5-Methoxy-1-methyl-1H-indol-3-yl)-5H-pyrrolo[2,3-b]pyrazine

A stirred solution of diisopropylamine (59.9 mL) in tetrahydrofuran (1400 mL), at –15° C. and under nitrogen, was treated with a solution of n-butyllithium in hexanes (131 mL, 1.6M) over 25 minutes, whilst maintaining the temperature below –10° C. After stirring for 30 minutes the mixture was treated with methylpyrazine (26.8 g) over 15 minutes, then stirred for 1 hour and then treated with a solution of 5-methoxy-1-methyl-1H-indole-3-carbonitrile [53g, Reference Example 1(a)] in tetrahydrofuran (600 mL) over 1 hour, keeping the temperature below –10° C. The reaction mixture was allowed to warm to room temperature over 2 hours, then stood overnight, then treated with water (100 mL). The tetrahydrofuran was removed in vacuo and the resultant mixture was partitioned between ethyl acetate (500 mL) and water (20 mL). The two layers were separated, and the aqueous layer was extracted with ethyl acetate (200 mL). The combined organics were washed with water (500 mL) then evaporated. The residue was subjected to flash chromatography on silica eluting with a mixture of dichloromethane and methanol (19:1, v/v) to give the title compound (19.4 g) as a grey solid, m.p. 270–272° C. MS: 279 (MH$^+$).

(b) By proceeding in a manner similar to Example 1(a) above but using 1-methyl-indole-3-carbonitrile [Reference Example 2(b)], there was prepared 6-(1-methyl-1H-indol-3-yl)-5H-pyrrolo[2,3-b]pyrazine as a yellow solid, m.p. 264–266° C. [Elemental analysis: C, 72.34; H, 4.68; N, 22.28%. Calculated for $C_{15}H_{12}N_4$: C, 72.56; H, 4.87; N, 22.57%].

(c) By proceeding in a manner similar to Example 1(a) above but using 3-bromobenzonitrile, there was prepared 6-(3-bromophenyl)-5H-pyrrolo[2,3-b]pyrazine as a colourless solid, m.p. 247–249° C. MS: 276 (MH$^+$).

(d) By proceeding in a manner similar to Example 1(a) above but using 2-isobutylpyrazine and benzonitrile, there was prepared 7-iso-propyl-6-phenyl-5H-pyrrolo[2,3-b]pyrazine as a colourless solid, m.p. 216–218° C. MS: 238 (MH$^+$).

(e) By proceeding in a manner similar to Example 1(a) above but using 4-bromobenzonitrile, there was prepared 6-(4-bromophenyl)-5H-pyrrolo[2,3-b]pyrazine as a colourless solid, m.p. 326–329° C. MS: 276 (MH$^+$).

(f) By proceeding in a manner similar to Example 1(a) above but using 2-(4-cyanophenyl)-1,3-dioxane (prepared as described in U.S. patent application Ser. No. 5,750,723 for example 3a), there was prepared 6-(4-[1,3]dioxan-2-yl-phenyl)-5H-pyrrolo[2,3-b]pyrazine as a yellow solid, m.p. 288–289° C. TLC: $R_F$=0.34 (ethyl acetate/pentane: 1/1).

(g) By proceeding in a manner similar to Example 1(a) above but using 243-cyanophenyl)-1,3-dioxane (prepared as described in U.S. patent application Ser. No. 5,750,723 for example 3a), there was prepared 6-(3-[1,3]dioxan-2-yl-phenyl)-5H-pyrrolo[2,3-b]pyrazine as a yellow solid, m.p. 205–206° C. [Elemental analysis: C, 68.28; H, 5.46; N,15.02%. Calculated for $C_{16}H_{15}N_3O_2$: C, 68.31; H, 5.37; N, 14.94%].

(h) By proceeding in a manner similar to Example 1(a) above but using 2quinolinecarbonitrile, there was prepared 2-(5H-pyrrolo[2,3-b]pyrazin-6-yl)quinoline as a pale yellow solid, m.p. 293–295° C. MS: 247 (MH$^+$). [Elemental analysis: C, 72.76; H, 3.82; N,22.56%. Calculated for $C_{16}H_{15}N_3O_2$;—C, 73.16; H, 4.09; N, 22.56%].

(i) By proceeding in a manner similar to Example 1(a) above but using 3-isoquinolinecarbonitrile, there was prepared 3-(5H-pyrrolo[2,3-b]pyrazin-6-yl)-isoquinoline as a green solid, m.p. 281–285° C. MS: 247 (MH$^+$).

(j) By proceeding in a manner similar to Example 1(a) above but using 1-methyl-1H-indole-5-carbonitrile [Reference Example 2(c)], there was prepared 6-[1-methyl-1H-indol-5-yl]-5H-pyrrolo[2,3-b]pyrazine as a yellow solid, m.p. 260–265° C. MS: 249 (MH$^+$).

(k) By proceeding in a manner similar to Example 1(a) above but using 2-6-dimethylpyrazine, there was prepared 6-(5-methoxy-1-methyl-1H-indol-3-yl)-2-methyl-5H-pyrrolo[2,3-b]pyrazine as a yellow solid, MS: 293 (MH$^+$). $^1$H NMR [(CD$_3$)$_2$SO: δ 12.2–12.3 (1H, broad s); 8.54, 8.56 (each 1H, s); 7.50 (1H, d, J=8.9 Hz); 7.47 (1H, d, J=2.4 Hz); 6.96 (1H, dd, J=8.9 and 2.4 Hz); 6.91 (1H, s); 3.91, 3.87 and 2.57(each 3H, s).

(l) By proceeding in a manner similar to Example 1(a) above but using 2,5-dimethylpyrazine and 1-methyl-1H-indole-3-carbonitrile [Reference Example 2(c)], there was prepared 3-methyl-6-(1-methyl-1H-indol-3-yl)-5H-pyrrolo[2,3-b]pyrazine as a yellow solid, m.p. 170–175° C. MS: 263 (MH$^+$).

(m) By proceeding in a manner similar to Example 1(a) above but using 1-benzyl-5-methoxy-1H-indole-3-carbonitrile [Reference Example 2(g)], there was prepared 6-(1-benzyl-5-methoxy-1H-indol-3-yl)-5H-pyrrolo[2,3-b]pyrazine as a yellow solid, m.p. 240–244° C. TLC: $R_F$=0.5 (dichloromethane/methanol: 19/1).

(n) By proceeding in a manner similar to Example 1(a) above but using 1-methyl-1H-pyrrole-3-carbonitrile [Reference Example 2(i)], there was prepared 6-(1-methyl-1H-pyrrol-3-yl)-5H-pyrrolo[2,3-b]pyrazine as a yellow solid, m.p. 211–213° C. MS: 199 (MH$^+$).

(o) By proceeding in a manner similar to Example 1(a) above but using 1-methyl-1H-pyrrole-2-carbonitrile [Reference Example 2(j)], there was prepared 6(1-methyl-1H-pyrrol-2-yl)-5H-pyrrolo[2,3-b]pyrazine as a yellow solid, m.p. 208–209° C. MS: 199 (MH$^+$).

(p) By proceeding in a manner similar to Example 1(a) above but using indolizine-1-carbonitrile [Reference Example 5], there was prepared 6-indolizin-1-yl-5H-pyrrolo[2,3-b]pyrazine as a yellow solid, m.p. 224–225° C. (with decomposition). MS: 235 (MH$^+$).

(q) By proceeding in a manner similar to Example 1(a) above but using 3-methyl-indolizine-1-carbonitrile [Reference Example 6], there was prepared 6-(3-methyl-indolizin-1-yl)-5H-pyrrolo[2,3-b]pyrazine as a yellow solid, m.p. 233–235° C. (with decomposition). MS: 249 (MH$^+$).

(r) By proceeding in a manner similar to Example 1(a) above but using 1-methyl-5-phenyl-1H-pyrrole-3-carbonitrile [Reference Example 2(k)], there was prepared 6(1-methyl-5-phenyl-1H-pyrrol-3-yl)-5H-pyrrolo[2,3-b]pyrazine as a yellow solid, m.p. 221–222° C. (with decomposition). MS: 275 (MH$^+$).

(s) By proceeding in a manner similar to Example 1(a) above but using 5,6,7,8-tetrahydro-indolizine-1-carbonitrile [Reference Example 8], there was prepared 6-(5,6,7,8-tetrahydro-indolizin-1yl)-5H-pyrrolo[2,3-b]pyrazine as a yellow solid, m.p. 236–238° C. (with decomposition). MS: 239 (MH$^+$).

(t) By proceeding in a manner similar to Example 1(a) above but using 3-furonitrile there was prepared 6-furan-3-yl-5H-pyrrolo[2,3-b]pyrazine as an orange solid. MS: 186.79 (MH$^+$). TLC: $R_F$=0.45 (dichloromethane/methanol: 19/1).

(u) By proceeding in a manner similar to Example 1(a) above but using 4-N,N-dimethylaminobenzonitrile, there was prepared dimethyl-[4-(5H-pyrrolo[2,3-b]pyrazin-6-yl)-phenyl]-amine as a yellow solid, m.p. 297–298° C. MS: 239 (MH$^+$).

(v) By proceeding in a similar manner to Example 1(a) but using ethylpyrazine there was prepared 6-(5-methoxy-1-methyl-1H-indol-3-yl)-7-methyl-5H-pyrrolo[2,3-b]pyrazine as a yellow solid, m.p. 243–244° C. HPLC (METHOD A): $R_T$=6.73 minutes.

(w) By proceeding in a manner similar to Example 1(a) above but using 4-tert-butylbenzonitrile, there was prepared 6-(4-tert-butylphenyl)-5H-pyrrolo[2,3-b]pyrazine as a yellow solid. LCMS: $R_T$=3.29 minutes; 252 (MH$^+$).

(x) By proceeding in a manner similar to Example 1(a) above but using 2-ethylpyrazine and 4-tert-butylbenzonitrile, there was prepared 6-(4-tert-butylphenyl)-7-methyl-5H-pyrrolo[2,3-b]pyrazine as a yellow solid, m.p. 213–214° C. MS: 266(MH$^+$).

(y) By proceeding in a manner similar to Example 1(a) above but using 3,4-dimethoxy-benzonitrile, there was prepared 6-(3,4-dimethoxyphenyl)-5H-pyrrolo[2,3-b]pyrazine as a yellow/orange solid, m.p. 212–214° C. MS: 256 (MH$^+$).

(z) By proceeding in a manner similar to Example 1(a) above but using 2-ethylpyrazine and 4-aminobenzonitrile, there was prepared 6-(4-aminophenyl)-7-methyl-5H-pyrrolo[2,3-b]pyrazine as a brown solid, m.p. 330–332° C. MS: 225 (MH$^+$).

(aa) By proceeding in a manner similar to Example 1(a) above but using 4-(1-methyl)-ethoxybenzonitrile [Reference Example 51], there was prepared 6-[4-(1-methyl)ethoxyphenyl]-5H-pyrrolo[2,3-b]pyrazine as a yellow solid. MS: 254 (MH$^+$). HPLC (METHOD B): $R_T$=1.64 minute.

(ab) By proceeding in a manner similar to Example 1(a) above but using 1H-5-cyano-1-methyl-2-methylthioimidazole [Reference Example 52], there was prepared 6-(1H-1-methyl-2-(methylthio)imidazol-5-yl)-5H-pyrrolo[2,3-b] pyrazine as a yellow solid, m.p. 230° C. MS: 246(MH$^+$).

(ac) By proceeding in a manner similar to Example 1(a) above but using 3-cyano-1-methyl-1H-indazole [Reference Example 56(a)], there was prepared 6-(1-methyl-1H-indazol-3-yl)-5H-pyrrolor2,3-b]pyrazine as a yellow solid. MS: 250(MH$^+$), 248 (MH$^-$). 1H NMR [(CD$_3$)$_2$SO]: δ 12.5–12.6 (1H, broad s); 8.38 (1H, d, J=2.4 Hz); 8.24 (d, 1H, J=7.9 Hz); 8.21 (s, 1H, J=2.4 Hz); 7.76 (d, 1H, J=8.1 Hz); 7.48 (t, 1H); 7.32 (t, 1H); 7.29 (s, 1H); 4.18 (s, 3H).

(ad) By proceeding in a manner similar to Example 1(a) above but using 3-cyano-1-methyl-4-phenyl-1H-pyrrole [Reference Example 56(b)], there was prepared 6-(1-methyl-4-phenyl-1H-pyrrol-3-yl)-5H-pyrrolo[2,3-b]pyrazine as a solid, m.p. 195° C. (with decomposition). MS: 275 (MH$^+$).

(ae) By proceeding in a manner similar to Example 1(a) above but using 4-fluorobenzonitrile, there was prepared 6-(4-fluorophenyl)-5H-pyrrolo[2,3-b]pyrazine as an off-white solid. $^1$H NMR [(CD$_3$)$_2$SO]: δ 12.3 (s, 1H) 8.4 (d, 1H), 8.2 (d, 1H), 8.05 (d, 2H), 7.4 (d, 2H), 7.2 (s, 1H). MS: 213(MH$^+$).

(af) By proceeding in a manner similar to Example 1(a) above but using 4-methoxy-benzonitrile, there was prepared 6-(4-methoxyphenyl)-5H-pyrrolo[2,3-b]pyrazine as an off-white solid, m.p. 244–246° C. MS: 225 (MH$^+$).

(ag) By proceeding in a manner similar to Example 1(a) above but using 4(-tertiary-butyl)benzonitrile and 4-(pyrazinyl)-1-butene [Reference Example 59] there was prepared 6-[4-tert-butyl)phenyl]-7-(propenyl)-5H-pyrrolo[2,3-b]pyrazine as a yellow solid, m.p. 207–208° C. MS: 292 (MH$^+$).

(ah) By proceeding in a manner similar to Example 1(a) above but using 4-(methylthio)benzonitrile there was prepared 6-(4-methylthiophenyl)-5H-pyrrolo[2,3-b]pyrazine as a yellow solid. MS: 242 (MH$^+$). $^1$H NMR [(CD$_3$)$_2$SO]: δ 12.48 (1H, s); 8.37 (1H, s); 8.18 (1H, s) 7.98 (2H, d, J=7.9 Hz); 7.19 (2H, d, J=7.9 Hz); 7.11 (1H, s); 2.52 (3H, s).

(ai) By proceeding in a manner similar to Example 1(a) above but using 3-methoxybenzonitrile there was prepared 6-(3-methoxyphenyl)-5H-pyrrolo[2,3-b]pyrazine as an orange solid, m.p. 194–196° C. MS:226(MH$^+$).

(aj) By proceeding in a manner similar to Example 1(a) above but using 1-methyl-4-cyanopyrazole (prepared according to the procedure described by Yoshida in J. Het. Chem., 1995, 32, page 701) there was prepared 6(1-methyl-1H-pyrazol-4-yl)-5H-pyrrolo[2,3-b]pyrazine as an orange solid, m.p. 232–234° C. MS: 200(MH$^+$).

(ak) By proceeding in a manner similar to Example 1(a) above but using 1-methyl-3-cyano-5-phenylpyrazole [Reference Example 1(k)] there was 6-(1-methyl-5-phenyl-1H-pyrazol-3-yl)-5H-pyrrolo[2,3-b]pyrazine as an orange solid, m.p. 222–223° C. HPLC R$_T$=7.36 minutes.

(al) By proceeding in a manner similar to Example 1(a) above but using 2-cyano-pyridine there was prepared 6-(pyridin-2-yl)-5H-pyrrolo[2,3-b]pyrazine as a yellow solid, m.p. 234–235° C. $^1$H NMR [(CD$_3$)$_2$SO]: δ 8.71 (1H, d, J=4.1 Hz); 8.38 (1H, s); 8.24 (1H, s); 8.17 (1H, d, J=8.2 Hz(; 7.93 (1H, t, J=8.2 Hz); 7.41 (1H, m); 7.36 (1H, s).

(am) By proceeding in a manner similar to Example 1(a) above but using 4-cyano-pyridine there was prepared 6-(pyridin-4-yl)-5H-pyrrolo[2,3-b]pyrazine as a yellow solid, m.p. 324–326° C. $^1$H NMR [(CD$_3$)$_2$SO]: δ 8.69 (2H, d, J=7.1 Hz); 8.45 (1H, s); 8.33 (1H, s); 8.00 (2H, d, J=7.1 Hz); 7.47 (1H, s).

EXAMPLE 2

(a) 3-[3-(5H-Pyrrolo[2,3-b]pyrazin-6-yl)-indol-1-yl]-propan-1-ol

A solution of 6-{1-[3-(tert-butyl-dimethyl-silanyloxy)-propyl]-1H-indol-3-yl}-5H-pyrrolo[2,3-b]pyrazine [29 g, Reference Example 3(a)] in tetrahydrofuran (500 mL) under nitrogen was treated with a solution of tetrabutylammonium fluoride in tetrahydrofuran (144 mL, 1.0M). After stirring at ambient temperature for 4 hours the reaction mixture was concentrated in vacuo. The residue was treated with water to give a solid which was filtered then washed with water and then dried to give the title compound (17.5 g) as a yellow-brown solid, m.p. 220–221° C. MS: 293 (MH$^+$).

(b) By proceeding in a manner similar to Example 2(a) above but using 6-{1-[3-tert-butyl-dimethyl-silanyloxy)-propyl]-5-methoxy-1H-indol-3-yl}-5H-pyrrolo[2,3-b]pyrazine [Reference Example 3(b)], there was prepared 3-[5-methoxy-3-(5H-pyrrolo[2,3-b]pyrazin-6-yl)-indol-1-yl]-propan-1-ol as a yellow solid, m.p. 225–228° C. MS: 323 (MH$^+$). TLC: R$_F$=0.16 (dichloromethane/methanol: 19/1).

(c) By proceeding in a manner similar to Example 2(a) above but using 6-{1-[2-(tert-butyl-dimethyl-silanyloxy)-ethyl]-1H-indol-3-yl}-5H-pyrrolo[2,3-b]pyrazine [Reference Example 3(c)], there was prepared 2-[3-(5H-pyrrolo[2,3-b]pyrazin-6-yl)-indol-1-yl]-ethanol as a yellow solid, m.p. 272–273° C. MS: 279 (MH$^+$).

(d) By proceeding in a manner similar to Example 2(a) above but using 6-{1-[2tert-butyl-dimethyl-silanyloxy)-ethyl]-5-methoxy-1H-indol-3-yl}-5H-pyrrolo[2,3-b]pyrazine [Reference Example 3(d)], there was prepared 2-[5-methoxy-3-(5H-pyrrolo[2,3-b]pyrazin-6-yl)-indol-1-yl-ethanol as a grey solid, m.p. 270–273° C. MS: 309.43 (MH$^+$).

EXAMPLE 3

(a) 3-[3-(5H-Pyrrolo[2,3-b]pyrazin-6-yl)-indol-1-yl]-propylamine

A solution of 3-[3-(5H-pyrrolo[2,3-b]pyrazin-6-yl)-indol-1-yl]-propan-1-ol [12 g, Example 2(a)] and carbon tetrabromide (19.1 g) in dichloromethane (300 mL) at ambient temperature was treated with a solution of triphenylphosphine (12.9 g) in dichloromethane (100 mL) over 5 minutes. After stirring at ambient temperature for 3 hour the reaction mixture was filtered and the solid was washed with sparing amounts of dichloromethane. The filtrate and washings were evaporated to yield a brown gum, which was mixed with liquid ammonia (ca 80 mL) in a sealed pressure vessel and allowed to stir at ambient temperature for 18 hours. The vessel was then cooled to −78° C. and then cautiously vented. The ammonia was allowed to evaporate and the residue was subjected to flash chromatography on silica eluting with a mixture of dichloromethane, methanol and concentrated ammonia (900:100:7, v/v/v) to give the title compound as a yellow solid (3 g), m.p. 170° C. $^1$H NMR [(CD$_3$)$_2$SO]: δ 8.28 (1H, d, J=2.7 Hz); 8.18 (1H, s); 8.10, 7.64 (each 1H, d, J=7.7 Hz); 8.09 (1H, d, J=2.7 Hz); 7.29, 7.23 (each 1H, td, J=7.1 and 1.0 Hz); 6.97 (1H, s); 4.32 (2H, t, J=7.0 Hz); 2.57 (2H, t, J=6.5 Hz); 1.89 (2H, quintet, J=6.4 Hz).

(b) By proceeding in a manner similar to Example 3(a) above but using 3-[5-methoxy-3-(5H-pyrrolo[2,3-b]pyrazin-6-yl)-indol-1-yl]-propan-1-ol [Example 2(b)], there was prepared 3-[5-methoxy-3-(5H-pyrrolo[2,3-b]pyrazin-6-yl)-indol-1-yl]-propylamine as a yellow solid, m.p. 95–100° C. and 150–160° C. MS: 322 (MH$^+$). TLC: R$_F$=0.2 (dichloromethane/methanol/concentrated ammonia: 900/100/7, v/v/v).

EXAMPLE 4

N-{3-[3-(5H-Pyrrolo[2,3-b]pyrazin-6-yl-indol-1-yl]-propyl}-acetamide

Acetyl chloride (31 μl) was added dropwise to a solution of 3-[3-(5H-pyrrolo[2,3-b]pyrazin-6-yl)-indol-1-yl]-propylamine [100 mg, Example 3(a)] and triethylamine (52.2 μl) and dichloromethane (30 mL) at ambient temperature under a nitrogen atmosphere. After stirring for 24 hours at ambient temperature the reaction mixture was evaporated. The residue was subjected to flash chromatography on silica eluting with a mixture of dichloromethane and methanol (9: 1, v/v) to give the title compound (82 mg) as a yellow solid, m.p. 260° C. MS: 334 (MH⁺).

EXAMPLE 5

(a) 6-[1-(3-Morpholin-4-yl-propyl)-1H-indol-3-yl]-5H-pyrrolo[2,3-b]pyrazine

A mixture of 3-[3-(5H-pyrrolo[2,3-b]pyrazin-6-yl)-indol-1-yl]-propylbromide [250 mg, Reference Example 4], morpholine (0.5 mL), potassium carbonate (100 mg) and potassium iodide (2 crystals) in ethyl methyl ketone was heated at reflux for 2 hours. The mixture was then allowed to cool to ambient temperature over 16 hours then evaporated. The residue was subjected to flash chromatography on silica eluting with a mixture of dichloromethane and methanol (9:1, v/v) to give a yellow glass which was triturated with ethyl acetate and pentane to give the title compound (40 mg) as a yellow solid, m.p. 180–185° C. MS: 362 (MH⁺).

(b) By proceeding in a manner similar to Example 5(a) above but using piperidine, there was prepared 6-[1-(3-piperidin-1-yl-propyl)-1H-indol-3-yl]-5H-pyrrolo[2,3-b]pyrazine as a yellow solid, m.p. 240° C. MS: 360 (MH⁺).

EXAMPLE 6

6-{1-[3-(Pyridin-3-yloxy)-propyl]-1H-indol-3-yl}-5H-pyrrolo[2,3-b]pyrazine

A solution of diisopropylazodicarboxylate (269 µM) in tetrahydrofuran (0.5 mL) was added dropwise, over 2 minutes, to a solution of triphenylphosphine (359 mg) in tetrahydrofuran (2.5 mL) at 0° C. under an atmosphere of nitrogen. After stirring at that temperature for 20 minutes the mixture was treated with a solution of 3-hydroxypyridine (65 mg) in tetrahydrofuran (1 mL) over 1 minute then with a suspension of 3-[3-(5H-pyrrolo[2,3-b]pyrazin-6-yl)-indol-1-yl]-propan-1-ol [200 mg, Example 2(a)] in tetrahydrofuran (2 mL). The mixture was allowed to warm to ambient temperature over 18 hours then evaporated. The residue was subjected to flash chromatography on silica eluting with a mixture of ethyl acetate and methanol (9:1, v/v) to give the title compound (110 mg) as a yellow solid, m.p. 208–209° C. MS: 370 (MH⁺).

EXAMPLE 7

1-Methyl-3-(5H-pyrrolo[2,3-b]pyrazin-6-yl)-1H-indol-5-ol

A mixture of 6-(5-methoxy-1-methyl-1H-indol-3-yl)-5H-pyrrolo[2,3-b]pyrazine [200 mg, Example 1(a)] hydrobromic acid (48%, 500 µl) and glacial acetic acid (3 mL) was heated under reflux for 14 hours. After cooling the mixture was neutralised by addition of saturated sodium bicarbonate solution. The resulting dark solid was filtered and then dried to give the title compound (180 mg) as a black solid, m.p. 289–290° C. MS: 264 (MH⁺).

EXAMPLE 8

6-(2-Chloro-5-methoxy-1-methyl-1H-indol-3-yl)-5H-pyrrolo[2,3-b]pyrazine

A solution of 6-(5-methoxy-1-methyl-1H-indol-3-yl)-5H-pyrrolo[2,3-b]pyrazine [100 mg, Example 1(a)] in dimethoxy ethanol (25 mL), cooled to −78° C., was treated with a solution of n-butyllithium in hexanes (172 µl, 2.5M). After stirring for 30 minutes the mixture was treated with 4-toluenesulfonyl chloride (82 mg) then allowed to warm slowly to ambient temperature and then evaporated. The residue was subjected to flash chromatography on silica eluting with a mixture of dichloromethane and methanol (19:1, v/v) to give the title compound (45 mg) as a black solid. MS: 313 (MH⁺). ¹H NMR [(CD₃)₂SO]: δ 12.20 (1H, s); 8.39 (1H, d, J=3 Hz); 8.21 (1H, d, J=3 Hz); 7.54 (1H, d, J=9 Hz); 7.30 (1H, d, J=2 Hz); 6.96 (1H, dd, J=9 and 2 Hz); 6.84 (1H, d, J=2 Hz); 3.82 (3H, s); 3.81 (3H, s).

EXAMPLE 9

(a) 3-(5H-Pyrrolo[2,3-b]pyrazin-6-yl)-benzaldehyde

A solution of 6-(3-[1,3]dioxan-2-yl-phenyl)-5H-pyrrolo[2,3-b]pyrazine [1.6 g, Example 1(g)] in dichloromethane (50 mL) was treated with trifluoroacetic acid (5 mL). The resultant mixture was heated at reflux for 6 hours, then allowed to cool overnight and then evaporated. The residue was triturated with diethyl ether to give a yellow solid which was recrystallised from ethyl acetate to give the title compound (0.6 g) as a yellow crystalline solid, m.p. 268–270° C. [Elemental analysis: C, 69.96; H, 3.92; N,18.69%. Calculated for C₁₃H₉N₃O: C, 69.95; H, 4.06; N, 18.82%]

(b) By proceeding in a manner similar to Example 9(a) above but using 6-(4-[1,3]dioxan-2-yl-phenyl)-5H-pyrrolo[2,3-b]pyrazine [Example 1(f)], there was prepared 4-(5H-pyrrolo[2,3-b]pyrazin-6-yl)-benzaldehyde hydrate as a yellow solid, m.p. >295° C. [Elemental analysis: C, 67.57; H, 4.33; N,18.04%. Calculated for C₁₃H₉N₃O.H₂O: C, 67.23; H, 4.34; N, 18.09%].

EXAMPLE 10

(a) [3-(5H-Pyrrolo[2,3-b]pyrazin-6-yl)-phenyl]-methanol

A suspension of 3-(5H-pyrrolo[2,3-b]pyrazin-6-yl)-benzaldehyde [0.4 g, Example 9(a)] in ethanol (50 mL) was treated with sodium borohydride (200 mg). The mixture was allowed to stir at ambient temperature for 1 hour then treated with water (10 mL) and then evaporated. The residual solid was triturated with water (50 mL) to give a pale yellow solid which was washed with water and then recrystallised from methanol to yield the title compound (0.35 g) as a yellow crystalline solid, m.p. 225–226° C. [Elemental analysis: C, 68.72; H, 4.73; N,18.44%. Calculated for C₁₃H₁₁N₃O: C, 69.32; H 4.92; N, 18.65%].

(b) By proceeding in a manner similar to Example 10(a) above but using 4-(5H-pyrrolo[2,3-b]pyrazin-6-yl)-benzaldehyde [Example 9(b)], there was prepared [4-(5H-pyrrolo[2,3-b]pyrazin-6-yl)-phenyl]-methanol as a yellow solid, m.p. 284–285° C. [Elemental analysis: C, 68.61; H, 4.65; N,18.28. Calculated for C₁₃H₁₁N₃O: C, 69.32; H, 4.92; N, 18.65%].

EXAMPLE 11

6-(5-Methoxy-1H-indol-3-yl)-5H-pyrrolo[2,3-b]pyrazine

A cooled (−78° C.) solution of 6-(1-benzyl-5-methoxy-1H-indol-3-yl)-5H-pyrrolo[2,3-b]pyrazine [50 mg, Example 1(m)] in tetrahydrofuran (20 mL) was treated with liquid ammonia (20 mL) then with sodium (100 mg). After stirring at −78° C. for 30 minutes the reaction mixture was allowed to warm slowly to ambient temperature, then treated with water (50 mL) and then extracted three times with ethyl acetate (50 mL). The combined extracts were dried over sodium sulfate and then evaporated. The residue was triturated with diethyl ether to give the title compound (14 mg) as a brown solid, m.p. 268–271° C. MS: 265.24 (MH⁺).

EXAMPLE 12

2-[5-Methoxy-3-(5H-pyrrolo[2,3-b]pyrazin-6-yl)-indol-1-yl]-1-morpholin-4-yl-ethanone A stirred solution of 6-(5-methoxy-1H-indol-3-yl)-5H-pyrrolo[2,3-b]pyrazine [70 mg, Example 11] in dry dimethylformamide (10 mL) was treated with sodium hydride (21.6 mg, 60% dispersion in mineral oil). After stirring for 30 minutes this mixture was treated with a solution of 4-(2-chloroacetyl)morpholine (44.1 mg) in dimethylformamide (1 mL) and stirring was continued for a further 3 hours. The reaction mixture was poured into water (20 mL) and then extracted three times with ethyl acetate (30 mL). The combined extracts were dried over sodium sulfate and then evaporated. The residue was triturated with diethyl ether to give the title compound (55 mg) as a yellow solid, m.p. 263–267° C. MS: 392.21 (MH$^+$).

EXAMPLE 13

(a) [5-Methoxy-3-(1H-pyrrolo[2,3-b]pyridin-2-yl)-indol-1-yl]-acetic acid

A mixture of {5-methoxy-3-[1-(toluene-4-sulfonyl)-1H-pyrrolo[2,3-b]pyridin-2-yl]-indol-1-yl}-acetic acid ethyl ester [4.67 g, Reference Example 13(a)], methanol (250 mL) and aqueous potassium hydroxide (S5M, 25 mL) were heated under reflux for 7 hours. The methanol was removed under reduced pressure and the residue was treated with water (20 mL) and the pH of this solution was adjusted to 7 by addition of concentrated hydrochloric acid. The resulting yellow solid was filtered and subjected to flash chromatography on silica eluting with a mixture of ethyl acetate and methanol (7:3, v/v) to give the title compound (1.69 g) as a white solid. MS: 320 (M–H$^+$). HPLC (METHOD A): R$_T$=6.67 minutes.

(b) By proceeding in a similar manner to Example 13(a) but using 4-methoxy-2-(5-methoxy-1-methyl-1H-indol-3-yl)-1-(toluene-4-sulfonyl)-1H-pyrrolo[2,3-b]pyridine [Reference Example 2(l)] there was prepared 4-methoxy-2-(5-methoxy-1-methyl-1H-indol-3-yl)-1H-pyrrolo[2,3-b] pyridine as a tan solid, m.p. 288–289° C. MS: 307(MH$^+$).

(c) By proceeding in a similar manner to Example 13(a) but using 4-methoxy-2-(5-methoxy-1H-indol-3-yl)-1-(toluene4-sulfonyl)-1H-pyrrolo[2,3-b]pyridine (Reference Example 39) there was prepared 4-methoxy-2-(5-methoxy-1H-indol-3-yl)-1H-pyrrolo[2,3-b]pyridine as a tan solid, m.p. 294–295° C. MS: 294(MH$^+$).

(d) By proceeding in a similar manner to Example 13(a) but using 4-chloro-2-(4-tertiary-butylphenyl)-1-(toluene-4-sulfonyl)-1H-pyrrolo[2,3-b]pyridine [Reference Example 12(j)] there was prepared 4-chloro-2-(4-tertiary-butylphenyl)-1H-pyrrolo[2,3-b]pyridine as a cream coloured solid. TLC:R$_F$=0.71 (ethylacetate/heptane 1:1). $^1$H NMR [(CD$_3$)$_2$SO]: δ 12.52(1H, s); 8.16 (1H, d, J=6.1 Hz); 7.93 (2H, d, J=8.1 Hz); 7.50 (2H, d, J=8.1 Hz); 7.21 (1H, d, J=6.1 Hz); 6.96 (1H, s); 1.30 (9H, s).

(e) By proceeding in a similar manner to Example 13(a) but using 2-(5-methoxy-1-methyl-1H-indol-3-yl)-5-phenyl-1toluene-4-sulfonyl)1H-pyrrolo[2,3-b]pyridine [Reference Example 13(j)] there was prepared 2-(5-methoxy-1-methyl-1H-indol-3-yl)-5-phenyl-1H-pyrrolo[2,3-b]pyridine as a cream coloured solid, m.p. 240–242° C. MS: 354 (MH$^+$).

EXAMPLE 14

(a) 2-{[5-Methoxy-3-(1H-pyrrolo[2,3-b]pyridin-2-yl)-indol-1-yl]-1-morpholin-4-yl}-ethanone A suspension of [5-methoxy-3-(1H-pyrrolo[2,3-b]pyridin-2-yl)-indol-1-yl]-acetic acid [60 mg, Example 13(a)] in dry dimethylformamide (7 mL) was treated with N-{(dimethylamino)(1H-1,2,3, -triazolo[4, 5,-b]pyridin-1-yl)methylene}-N-methylmethanaminium hexafluorophosphate N-oxide (71 mg) and diisopropylethylamine (45 µl). After stirring at room temperature for 30 minutes morpholine (18 µl) was added and the mixture stirred at ambient temperature for a further 12 hours. The solvent was removed in vacuo and the residue was suspended in saturated sodium bicarbonate solution. The precipitated solid was filtered then dried to give the title compound (10 mg) as a violet coloured solid, m.p. 243–247° C. MS: 391 (MH$^+$).

(b) By proceeding in a manner similar to Example 14(a) above but using 1-[1-methyl-3-(1H-pyrrolo[2,3-b]pyridin-2-yl)-1H-indol-5-yloxy]-cyclobutanecarboxylic acid [Example 15 (c)] and ammonium chloride, there was prepared 1-[1-methyl-3-(1H-pyrrolo[2,3-b]pyridin-2-yl)-1H-indol-5-yloxy]-cyclobutanecarboxylic acid amide as a pale lilac solid, m.p. 267–268° C. MS: 361 (MH$^+$).

(c) By proceeding in a manner similar to Example 14(a) above but using 1-[1-methyl-3-(1H-pyrrolo[2,3-b]pyridin-2-yl)-1H-indol-5-yloxy]-cyclobutanecarboxylic acid [Example 15(c )] and methylamine, there was prepared 1-[1-methyl-3-(1H-pyrrolo[2,3-b]pyridin-2-yl)-1H-indol-5-yloxy]-cyclobutanecarboxylic acid methylamide as a pale lilac solid, m.p. 249–250° C. MS: 375 (MH$^+$).

(d) By proceeding in a manner similar to Example 14(a) above but using 1-methyl-3-(1H-pyrrolo[2,3-b]pyridin-2-yl)-1H-indole-5-carboxylic acid [Example 15 (d)] and methylamine, there was prepared 1-methyl-3-(1H-pyrrolo[2,3-b]pyridin-2-yl)-1H-indole-5-carboxylic acid methylamide as a pale orange solid, m.p. 186° C. MS: 304 (MH$^+$).

(e) By proceeding in a manner similar to Example 14(a) above but using 1-methyl-3-(1H-pyrrolo[2,3-b]pyridin-2-yl)-1H-indole-5-carboxylic acid [Example 15 (d)] and ethanolamine, there was prepared 1-methyl-3-(1H-pyrrolo[2,3-b]pyridin-2-yl)-1H-indole-5-carboxylic acid (2-hydroxyethyl)-amide as a yellow solid, m.p. 256–257° C. MS: 335 (MH$^+$).

(f) By proceeding in a manner similar to Example 14(a) above but using 1-methyl-3-(1H-pyrrolo[2,3-b]pyridin-2-yl)-1H-indole-5-carboxylic acid [Example 15 (d)] and 2-aminoethyl morpholine, there was prepared 1-methyl-3-(1H-pyrrolo[2,3-b]pyridin-2-yl)-1H-indole-5-carboxylic acid (2-morpholin-4-yl-ethyl)-amide as a colourless solid, m.p. 268–270° C. MS: 404 (MH$^+$).

(g) By proceeding in a manner similar to Example 14(a) above but using 1-methyl-3-(1H-pyrrolo[2,3-b]pyridin-2-yl)-1H-indole-5-carboxylic acid [Example 15(d)] and β-alanine-amide, there was prepared 1-methyl-3-(1H-pyrrolo[2,3-b]pyridin-2-yl)-1H-indole-5-carboxylic acid (2-carbamoyl-ethyl)-amide as a colourless solid, m.p. 286–288° C. MS: 362 (MH$^+$).

(h) By proceeding in a manner similar to Example 14(a) above but using 1-methyl-3-(1H-pyrrolo[2,3-b]pyridin-2-yl)-1H-indole-5-carboxylic acid [Example 15 (d)] and diethanolamine, there was prepared 1-methyl-3-(1H-pyrrolo[2,3-b]pyridin-2-yl)-1H-indole-5-carboxylic acid bis-(2-hydroxy-ethyl)-amide as a yellow solid, m.p. 230–232° C. MS: 379 (MH$^+$).

(i) By proceeding in a manner similar to Example 14(a) above but using 1-methyl-3-(1H-pyrrolo[2,3-b]pyridin-2- yl)-1H-indole-5-carboxylic acid [Example 15 (d)] and ammonium chloride, there was prepared 1-methyl-3-(1H-pyrrolo[2,3-b]pyridin-2-yl)-1H-indole-5-carboxylic acid amide as a yellow solid, m.p. 330–332° C. MS: 291 (MH⁺).

(j) By proceeding in a manner similar to Example 14(a) above but using 1-methyl-3-(1H-pyrrolo[2,3-b]pyridin-2-yl)-1H-indole-5-carboxylic acid [Example 15 (d)] and tris (hydroxymethyl)aminomethane, there was prepared 1-methyl-3-(1H-pyrrolo[2,3-b]pyridin-2-yl)-1H-indole-5-carboxylic acid (2-hydroxy-1,1-bis-hydroxymethyl-ethyl)-amide as a yellow solid, m.p. 205–206° C. MS: 395 (MH⁺).

(k) By proceeding in a manner similar to Example 14(a) above but using 1-methyl-3-(1H-pyrrolo[2,3-b]pyridin-2-yl)-1H-indole-5-carboxylic acid [Example 15 (d)] and 2-amino-2-methyl-1,3-propanediol, there was prepared 1-methyl-3-(1H-pyrrolo[2,3-b]pyridin-2-yl)-1H-indole-5-carboxylic acid (2-hydroxy-1-hydroxymethyl-1-methyl-ethyl)-amide as a yellow solid, m.p. 180–182° C. MS: 379 (MH⁺).

(l) By proceeding in a manner similar to Example 14(a) above but using 1-methyl-3-(1H-pyrrolo[2,3-b]pyridin-2-yl)-1H-indole-5-carboxylic acid [Example 15 (d)] and 3-amino-1,2-propanediol, there was prepared 1-methyl-3-(1H-pyrrolo[2,3-b]pyridin-2-yl)-1H-indole-5-carboxylic acid (2,3-dihydroxy-propyl)-amide as a yellow solid, m.p. 171–172° C. MS: 365 (MH⁺).

(m) By proceeding in a manner similar to Example 14(a) above but using 1-methyl-3-(1H-pyrrolo[2,3-b]pyridin-2-yl)-1H-indole-5-carboxylic acid [Example 15 (d)] and 2-amino2-methyl-1-propanol, there was prepared 1-methyl-3-(1H-pyrrolo[2,3-b]pyridin-2-yl)-1H-indole-5-carboxylic acid (2-hydroxy-1-dimethyl-ethyl)-amide as a yellow solid, m.p. 161–162° C. MS: 365 (MH⁺).

(n) By proceeding in a manner similar to Example 14(a) above but using 1-methyl-3-(1H-pyrrolo[2,3-b]pyridin-2-yl)-1H-indole-5-carboxylic acid [Example 15 (d)] and serinol, there was prepared 1-methyl-3-(1H-pyrrolo[2,3-b]pyridin-2-yl)-1H-indole-5-carboxylic acid (2-hydroxy-1-hydroxymethyl-ethyl)-amide as a yellow solid, m.p. 178–179° C. MS: 365.41 (MH⁺).

(o) By proceeding in a manner similar to Example 14(a) above but using 1-methyl-3-(1H-pyrrolo[2,3-b]pyridin-2-yl)-1H-indole-6-carboxylic acid [Example 15(g)] and 3-amino-propionamide hydrochloride, there was prepared 1-methyl-3-(1H-pyrrolo[2,3-b]pyridin-2-yl)-1H-indole-6-carboxylic acid (2-carbamoyl-ethyl)-amide as a pale yellow solid, m.p. 277–280° C. MS: 362 (MH⁺).

(p) By proceeding in a manner similar to Example 14(a) above but using 1-methyl-3-(1H-pyrrolo[2,3-b]pyridin-2-yl)-1H-indole-6-carboxylic acid [Example 15(g)] and ethanolamine, there was prepared 1-methyl-3-(1H-pyrrolo[2,3-b]pyridin-2-yl)-1H-indole-6-carboxylic acid (2-hydroxy-ethyl)-amide as a brown solid, m.p. 264–267° C. MS: 335 (MH⁺).

(q) By proceeding in a manner similar to Example 14(a) above but using 1-methyl-3-(1H-pyrrolo[2,3-b]pyridin-2-yl)-1H-indole-6-carboxylic acid [Example 15(g)] and 1H-[1,2,4]triazol-3-ylamine, there was prepared 1-methyl-3-(1H-pyrrolo[2,3-b]pyridin-2-yl)-1H-indole-6-carboxylic acid (1H-[1,2,4]triazol-3-yl)-amide as a yellow solid, m.p. 343–345° C. MS: 358 (MH⁺).

(r) By proceeding in a manner similar to Example 14(a) above but using 1-methyl-3-(1H-pyrrolo[2,3-b]pyridin-2-yl)-1H-indole-6-carboxylic acid [Example 15(g)] and serinol, there was prepared 1-methyl-3-(1H-pyrrolo[2,3-b]pyridin-2-yl)-1H-indole-6-carboxylic acid (2-hydroxy-1-hydroxymethyl-ethyl)-amide as a light brown solid, m.p. 247–249° C. MS: 365 (MH⁺).

(s) By proceeding in a similar manner to Example 14(a) but using 1-methyl-3-(5H-pyrrolo[2,3-b]pyrazin-6-yl)-1H-indole-5-carboxylic acid [Example 15(i)] and 2-amino-2-methyl1-propanol there was prepared 1-methyl-3-(5H-pyrrolo[2,3-b]pyrazin-6-yl)-1H-indole-5-carboxylic acid (2-hydroxy-1,1-dimethyl-ethyl)-amide as a yellow solid, m.p. 210–214° C. MS: 364(MH⁺).

(t) By proceeding in a manner similar to Example 14(a) above but using 3-[6-(4-tert-butylphenyl-5H-pyrrolo[2,3-b]pyrazin-7-yl]-propionic acid [Example 25(a)] and methylamine, there was prepared 3-[6-(4-tert-butylphenyl-5H-pyrrolo[2,3-b]pyrazin-7-yl]-N-methylpropionamide as an off-white solid, m.p. 222–228° C. MS: 337 (MH⁺).

(u) By proceeding in a manner similar to Example 14(a) above but using 3-[6-(4-tert-butylphenyl-5H-pyrrolo[2,3-b]pyrazin-7-yl]-propionic acid [Example 25(a)] and dimethylamine, there was prepared 3-[6-(4-tert-butylphenyl-5H-pyrrolo[2,3-b]pyrazin-7-yl]-N,N-dimethylpropionamide as an off-white solid, m.p. 203–204° C. MS: 351 (MH⁺).

(v) By proceeding in a manner similar to Example 14 (a) above but using 1-methyl-3-(5H-pyrrolo[2,3-b]pyrazin-6-yl)-1H-indole-5-carboxylic acid [Example 15(i)] and 2-methoxyethylamine, there was prepared 1-methyl-3-(5H-pyrrolo[2,3-b]pyrazin-6-yl)-1H-indole-5-carboxylic acid 2-methoxyethylamide as an orange solid, MS: 350(MH⁺). HPLC (Method C): R$_T$=1.27 minutes.

(w) By proceeding in a manner similar to Example 14 (a) above but using ing 1-methyl-3-(5H-pyrrolo[2,3-b]pyrazin-6-yl)-1H-indole-5-carboxylic acid [Example 15(i)] and 2-thien-2-yl there was prepared 1-methyl-3-(5H-pyrrolo[2,3-b]pyrazin-6-yl)-1H-indole-5-carboxylic acid 2-thien-2-yl-ethylamide as a yellow solid. MS: 402(MH⁺). HPLC (MethodC): R$_T$=1.45 minutes.

(x) By proceeding in a manner similar to Example 14 (a) above but using 1-methyl-3-(5H-pyrrolo[2,3-b]pyrazin-6-yl)-1H-indole-5-carboxylic acid [15(i)] and 2-fluoroethylamine, there was prepared 1-methyl-3-(5H-pyrrolo[2,3-b]pyrazin-6-yl)-1H-indole-5-carboxylic acid 2-fluoroethylamide as an orange solid. MS: 338(MH⁺). HPLC (MethodC): R$_T$=1.30 minutes.

(y) By proceeding in a manner similar to Example 14 (a) above but using 1-methyl-3-(5H-pyrrolo[2,3-b]pyrazin-6-yl)-1H-indole-5-carboxylic acid [Example 15(i)] and alanine ethyl ester hydrochloride, there was prepared 1-methyl-3-(5H-pyrrolo[2,3-b]pyrazin-6-yl)-1H-indole-5-carboxylic acid 2-carboethoxyethylamide as an orange solid. MS: 392 (MH⁺). HPLC (Method C): R$_T$=1.38 minutes.

(z) By proceeding in a manner similar to Example 14 (a) above but using 1-methyl-3-(5H-pyrrolo[2,3-b]pyrazin-6-yl)-1H-indole-5-carboxylic acid [Example 15(i)] and serine methyl ester hydrochloride, there was prepared 1-methyl-3-(5H-pyrrolo[2,3-b]pyrazin-6-yl)-1H-indole-5-carboxylic acid (hydroxymethyl)-carbomethoxy-methylamide as an orange solid. MS: 394(MD⁺). HPLC (MethodC): R$_T$=1.24 minutes.

(aa) By proceeding in a manner similar to Example 14 (a) above but using 1-methyl-3-(5H-pyrrolo[2,3-b]pyrazin-6-yl)-1H-indole-5-carboxylic acid [Example 15(i)] and ethanolamine, there was prepared 1-methyl-3-(5H-pyrrolo[2,3-b]pyrazin-6-yl)-1H-indole-5-carboxylic acid 2-hydroxyethylamide as a yellow solid, m.p. 171–173° C. (with decomposition). MS: 336 (MH⁺).

(ab) By proceeding in a manner similar to Example 14 (a) above but using 1-methyl-3-(5H-pyrrolo[2,3-b]pyrazin-6-yl)-1H-indole-5-carboxylic acid [Example 15(i)] and methylamine, there was prepared 1-methyl-3-(5H-pyrrolo[2,3-b]pyrazin-6-yl)-1H-indole-5-carboxylic acid methylamide as a beige solid, MS: 304(MH$^+$). NMR $^1$H: ? solvent: δ 8.64 (1H, broad s); 8.59 (d, 1H, J=1.0 Hz); 8.27(d, 1H, J=2.4 Hz); 8.17 (s, 1H); 8.15 (d, 1H, J=2.4 Hz); 7.82(dd, 1H, J=1.0 Hz, 7.9 Hz); 7.62 (d, 1H, J=7.9 Hz); 7.21 (s, 1H); 3.96 (s, 3H); 2.82 (s, 3H).

(ac) By proceeding in a manner similar to Example 14 (a) above but 1-methyl-3-(5H-pyrrolo[2,3-b]pyrazin-6-yl)-1H-indole-5-carboxylic acid [Example 15(i)] and dimethylamine, there was prepared 1-methyl-3-(5H-pyrrolo[2,3-b]pyrazin-6-yl)-1H-indole-5-carboxylic acid dimethylamide as a yellow solid, MS: 320(MH). NMR $^1$H: ? solvent: δ 8.26 (d, 1H, J=2.1 Hz); 8.18 (s, 1H); 8.15 (d, 1H, J=2.1 Hz); 7.62(d, J=8.1 Hz); 7.372 (dd, 1H, J=1.0 Hz, 8.1 Hz); 6.98 (s, 1H); 3.94 (s, 3H); 3.05 (s, 6H).

(ad) By proceeding in a manner similar to Example 14 (a) above but using 1-methyl-3-(5H-pyrrolo[2,3-b]pyrazin-6-yl)-1H-indole-5-carboxylic acid [Example 15(i)] and morpholine, there was prepared [1-methyl-3-(5H-pyrrolo[2,3-b]pyrazin-6-yl)-1H-indol-5-yl]morpholin-4-yl ketone as a yellow solid, MS: 362(MH$^+$).

(ae) By proceeding in a manner similar to Example 14 (a) above but using 1-methyl-3-(5H-pyrrolo[2,3-b]pyrazin-6-yl)-1H-indole-5-carboxylic acid [Example 15(i)] and 4-hydroxypiperidine, there was prepared 4-hydroxy-[1-[1-methyl-3-(5H-pyrrolo[2,3-b]pyrazin-6-yl)-1H-indol-5-yl]carbonylpiperidine as a yellow solid, MS: 376(MH$^+$), 398 (MNa$^+$).

(af) By proceeding in a manner similar to Example 14 (a) above but using 3-[1-methyl-3-(5H-pyrrolo[2,3-b]pyrazin-6-yl)-1H-indol-5-yl]carbonylaminopropionic acid [Example 15(l)] and methylamine, there was prepared 3-[1-methyl-3-(5H-pyrrolo[2,3-b]pyrazin-6-yl)-1H-indol-5-yl]carbonylaminopropionic acid methylamide as a yellow solid. MS: 377 (MH$^+$). HPLC (MethodC): R$_T$=1.20 minutes.

(ag) By proceeding in a manner similar to Example 14 (a) above but using 1-methyl-3-(5H-pyrrolo[2,3-b]pyrazin-6-yl)-1H-indole-5-carboxylic acid [Example 15(i)] and 3-hydroxypropylamine, there was prepared 1-methyl-3-(5H-pyrrolo[2,3-b]pyrazin-6-yl)-1H-indole-5-carboxylic acid 3-hydroxypropylamide as a yellow solid. MS: 350 (MH$^+$). HPLC (MethodC): R$_T$=1.22 minutes.

(ah) By proceeding in a manner similar to Example 14(a) above but using 3-{6-[4-(1-methyl)ethoxyphenyl]-5H-pyrrolo[2,3-b]pyrazin-7-yl}propionic acid [Example 25(b)] and methylamine, there was prepared 3-{6-[4-(1-methyl)ethoxyphenyl]-5H-pyrrolo[2,3-b]pyrazin-7-yl}propionic acid methylamide as a yellow solid, MS: 339 (MH$^+$). HPLC (MethodC): R$_T$=1.49 minutes.

(ai) By proceeding in a manner similar to Example 14(a) above but using 3-[6-(4-methoxyphenyl)-5H-pyrrolo[2,3-b]pyrazin-7-yl]propionic acid [Example 25(d)] and methylamine, there was prepared 3-[6-(4-methoxyphenyl)-5H-pyrrolo[2,3-b]pyrazin-7-yl]propionic acid methylamide as an off-white solid.
$^1$H NMR [(CD$_3$)$_2$SO]: δ 12.0 (s, 1H) 8.3 (d, 1H), 8.2 (d, 1H), 7.7 (d, 2H), 7.1 (d, 2H), 3.8(s, 3H), 3.05 (t, 2H), 2.6 (t, 2H) 2.5 (s, 3 H). MS: 310 (MH$^+$).

(aj) By proceeding in a manner similar to Example 14(a) above but using 3-{6-[4-(1-methyl)ethoxyphenyl]-5H-pyrrolo[2,3-b]pyrazin-7-yl}propionic acid [Reference Example 25(b)] and ammonium chloride, there was prepared 3-{6-[4-(1-methyl)ethoxyphenyl]-5H-pyrrolo[2,3-b]pyrazin-7-yl}propionamide as a white solid. MS: 325 (MH$^+$). HPLC (MethodC): R$_T$=1.44 minutes.

(ak) By proceeding in a manner similar to Example 14(a) above but using 3-{6-(4-hydroxyphenyl)-5H-pyrrolo[2,3-b]pyrazin-7-yl}propionic acid [Example 30] and ammonium chloride, there was prepared 3-{6-(4-hydroxyphenyl)-5H-pyrrolo[2,3-b]pyrazin-7-yl}propionamide as a white solid. MS: 283 (MH$^+$). HPLC (Method C): R$_T$=2.18 minutes.

(al) By proceeding in a manner similar to Example 14(a) above but using 3-[6-(4-fluorophenyl)-5H-pyrrolo[2,3-b]pyrazin-7-yl]propionic acid [Example 25(c)] and methylamine, there was prepared 3-[6-(4-fluorophenyl)-5H-pyrrolo[2,3-b]pyrazin-7-yl]propionic acid methylamide as an off-white solid.
$^1$H NMR [(CD$_3$)$_2$SO]: δ 12.5 (s, 1H) 8.4 (d, 1H), 8.2 (d, 1H), 7.8 (d, 2H), 3.1 (t, 2H), 2.6 (t, 2H), 2.5 (s, 3H). MS: 298 (MH$^+$).

EXAMPLE 15

(a) [1-Methyl-3-(1H-pyrrolo[2,3-b]pyridin-2-yl)-1H-indol-5-yloxy]-acetic acid

A solution of {1-methyl-3-[1-(toluene-4-sulfonyl)-1H-pyrrolo[2,3-b]pyridin-2-yl]-1-indol-5-yloxy}-acetic acid ethyl ester [500 mg, Reference Example 15(b)] in methanol (25 mL) was treated with potassium hydroxide (5N, 3 mL) and then heated at reflux for 16 hours. The solvent was removed under reduced pressure and the residue was treated with water (10 mL). The pH of this mixture was adjusted to 7 by addition of acetic acid and the resulting colourless solid was collected by filtration then dried to give the title compound (170 mg) as a colourless solid, m.p. >300° C. MS: 322 (MH$^+$).

(b) By proceeding in a manner similar to Example 15(a) above but using 3-{1-methyl-3-[1-(toluene-4-sulfonyl)-1H-pyrrolo[2,3-b]pyridin-2-yl]-1H-indol-5-yloxy}-propionic acid ethyl est [Reference Example 15(c)], there was prepared 3-[1-methyl-3-(1H-pyrrolo[2,3-b]pyridin-2-yl)-1H-indol-5-yloxy]-propionic acid as a colourless solid, m.p. 177–178° C. MS: 336 (MH$^+$).

(c) By proceeding in a manner similar to Example 15(a) above but using 1-{1-methyl-3-[1-(toluene-4-sulfonyl)-1H-pyrrolo[2,3-b]pyridin-2-yl]-1H-indol-5-yloxy}-cyclobutanecarboxylic acid ethyl ester [Reference Example 15(d)], there was prepared 1-[1-methyl-3-(1H-pyrrolo[2,3-b]pyridin-2-yl)-1H-indol-5-yloxy]-cyclobutanecarboxylic acid as a colourless solid, m.p. 168–169° C. MS: 362 (MH$^+$).

(d) By proceeding in a manner similar to Example 15(a) above but using 1-methyl-3-[1-(toluene-4-sulfonyl)-1H-pyrrolo[2,3-b]pyridin-2-yl]-1H-indole-5-carboxylic acid methyl ester [Reference Example 19(a)], there was prepared 1-methyl-3-(1H-pyrrolo[2,3-b]pyridin-2-yl)-1H-indole-5-carboxylic acid as a yellow solid, m.p. >300° C. MS: 291 (MH$^+$).

(e) By proceeding in a manner similar to Example 15(a) above but using 1-methyl-3-[1-(toluene-4-sulfonyl)-1H-pyrrolo[2,3-b]pyridin-2-yl]-1H-indol-5-ol [Reference Example 14(a)], there was prepared 1-methyl-3-(1H-pyrrolo[2,3-b]pyridin-2-yl)-1H-indol-5-ol as a yellow solid, m.p. 199–200° C. MS: (MH$^+$).

(f) By proceeding in a manner similar to Example 15(a) above but using 1-{1-(cyclobutanecarboxylic acid ethyl ester)-3-[1-(toluene-4-sulfonyl)-1H-pyrrolo[2,3-b]pyridin-2-yl]-1H-indol-5-yloxy}-cyclobutanecarboxylic acid ethyl ester [Reference Example 23(d)], there was prepared 1-{1-(cyclobutanecarboxylic acid)-3-[1H-pyrrolo[2,3-b]pyridin-2-yl]-1H-indol-5-yloxy}-cyclobutanecarboxylic acid as a yellow solid, m.p. 240° C. (with decomposition). MS: 444 (MH$^-$).

(g) By proceeding in a manner similar to Example 15(a) above but using 1-methyl-3-[1-(toluene-4-sulfonyl)-1H-pyrrolo[2,3-b]pyridin-2-yl]-1H-indole-6-carboxylic acid methyl ester [Reference Example 13(g)], there was prepared 1-methyl-3-(1H-pyrrolo[2,3-b]pyridin-2-yl)-1H-indole-6-carboxylic acid as a yellow solid, m.p. 359–361° C. MS 292 (MH$^+$).

(h) By proceeding in a manner similar to Example 15(a) above but using 3-{1-methyl-3-[1-(toluene-4-sulfonyl)-1H-pyrrolo[2,3-b]pyridin-2-yl]-1H-indol-5-yl }-propionic acid ethyl ester [Reference Example 38(a)], there was prepared 3-[1-methyl-3-(1H-pyrrolo[2,3-b]pyridin-2-yl)-1H-indol-5-yl]-propionic acid as a yellow solid, m.p. 268–270° C. MS 320 (MH$^+$).

(i) By proceeding in a similar manner to Example 15(a) but using methyl 1-methyl-3-(5H-pyrrolo[2,3-b]pyrazin-6-yl)-1H-indole-5-carboxylate [Reference Example 19(b)] there was prepared 1-methyl-3-(5H-pyrrolo[2,3-b]pyrazin-6-yl)-1H-indole-5-carboxylic acid as a brown solid, m.p. 350° C. HPLC (METHOD A): $R_T$=5.85 minutes.

(j) By proceeding in a manner similar to Example 15 (a) above but using [2-methoxy-5-(5H-pyrrolo[2,3-b]pyrazin-6-yl)-phenoxy]-acetic acid ethyl ester [Example 27], there was prepared [2-methoxy-5-(5H-pyrrolo[2,3-b]pyrazin-6-yl)-phenoxy]acetic acid as a white solid, m.p. 330–332° C. MS: 300 (MH$^+$).

(k) By proceeding in a manner similar to Example 15 (a) above but using ethyl 3-[2-dimethylamino-5-(5H-pyrrolo[2,3-b]pyrazin-6-yl)phenyl]propionate [Reference Example 38(b)], there was prepared 3-[2-dimethylamino-5-(5H-pyrrolo[2,3-b]pyrazin-6-yl)-phenyl]propionic acid as an orange solid, m.p. 269–271° C. MS: 311 (MH$^+$).

(l) By proceeding in a manner similar to Example 15 (a) above but using 1-methyl-3-(5H-pyrrolo[2,3-b]pyrazin-6-yl)-1H-indole-5-carboxylic acid 2-carboethoxyethylamide [Example 14(y)] and sodium hydroxide, there was prepared 3-[1-methyl-3-(5H-pyrrolo[2,3-b]pyrazin-6-yl)-1H-indol-5-yl]carbonylaminopropionic acid as an orange solid (35 mg). MS: 364(MH$^+$). HPLC (Method C): $R_T$=1.24 minutes.

EXAMPLE 16

(a) 2-[1-Methyl-3-[1H-pyrrolo[2,3-b]pyridin-2-yl)-1H-indol-5-yloxy]-ethanol

A solution of {1-methyl-3-[1-(toluene-4-sulfonyl)-1H-pyrrolo[2,3-b]pyridin-2-yl]-1H-indol-5-yloxy}-acetic acid ethyl ester [120 mg, Reference Example 15(b)] in dry tetrahydrofuran (5 mL) was treated with lithium aluminium hydride (1.0M solution in tetrahydrofuran, 50 μl) at 0° C. under a nitrogen atmosphere. The mixture was allowed to warm to ambient temperature, then stirred for 3 hours and then carefully poured into water (75 mL). The mixture was extracted three times with ethyl acetate (25 mL). The combined organic extracts were washed with brine (75 mL), then dried over sodium sulfate and then evaporated to give the title compound (45 mg) as a colourless solid, m.p. 209–210° C. MS: 308 (MH$^+$).

(b) By proceeding in a manner similar to Example 16(a) above but using 3-{1-methyl-3-[1-(toluene-4-sulfonyl)-1H-pyrrolo[2,3-b]pyridin-2-yl]-1H-indol-5-yloxy}-propionic acid ethyl ester [Reference Example 15(c)], there was prepared 3-[1-methyl-3-(1H-pyrrolo[2,3-b]pyridin-2-yl)-1H-indol-5-yloxy]-propan-1-ol as a colourless solid, m.p. 164–165° C. MS: 320 (MH$^+$).

(c) By proceeding in a manner similar to Example 16(a) above but using 1-{1-methyl-3-[1-(toluene-4-sulfonyl)-1H-pyrrolo[2,3-b]pyridin-2-yl]-1H-indol-5-yloxy}-cyclobutanecarboxylic acid ethyl ester [Reference Example 15(d)], there was prepared {1-[1-methyl-3-(1H-pyrrolo[2,3-b]pyridin-2-yl)-1H-indol-5-yloxy]-cyclobutyl}-methanol as a colourless solid, m.p. 144–146° C. MS: 348 (MH$^+$). HPLC (METHOD A): $R_T$=6.37 minutes.

(d) By proceeding in a manner similar to Example 16(a) above but using (6-phenyl-5H-pyrrolo[2,3-b]pyrazin-7-yl)-acetic acid [Reference Example 35], there was prepared 2-(6-phenyl-5H-pyrrolo[2,3-b]pyrazin-7-yl)-ethanol as a colourless solid, m.p. 201–202° C. MS: 348 (MH$^+$). HPLC (METHOD A): $R_T$=6.37 minutes. [Elemental analysis: C, 70.68; H, 5.77; N,17.44%. Calculated for $C_{13}H_{11}N_3O$: C, 70.28; H, 5.48; N, 17.56%].

(e) By preceding in a manner similar to Example 16 (a) above but using [2-methoxy-5-(5H-pyrrolo[2,3-b]pyrazin-6-yl)-phenoxy]-acetic acid ethyl ester [Example 27], there was prepared 2-[2-methoxy-5-(5H-pyrrolo[2,3-b]pyrazin-6-yl)-phenoxy]-ethanol as a yellow solid, m.p. 203–205° C. MS: 286 (MH$^+$).

(f) By proceeding in a manner similar to Example 16 (a) above but using ethyl 3-[2-dimethylamino-5-(5H-pyrrolo[2,3-b]pyrazin-6-yl)phenyl]propionate [Reference Example 38(b)], there was prepared 3-[2-dimethylamino-5-(5H-pyrrolo[2,3-b]pyrazin-6-yl)-phenyl]-propan-1-ol as a yellow solid, m.p. 203–204° C. MS: 297(MH$^+$).

(g) By proceeding in a manner similar to Example 16 (a) above but using 3-{6-[4-(1-methyl)ethoxyphenyl]-5H-pyrrolo[2,3-b]pyrazin-7-yl}propionic acid [Example 25(b)] there was prepared 3-{6-[4-(1-methyl)ethoxyphenyl]-5H-pyrrolo[2,3-b]pyrazin-7-yl}propanol as a yellow solid (7 mg). MS: 312 (MH$^+$). HPLC (Method C): $R_T$=2.9 minutes.

EXAMPLE 17

(a) 2-(5-Methoxy-1-methyl-1H-indol-3-yl)-1H-pyrrolo[2,3-b]pyridine

A solution of 2-(5-methoxy-1-methyl-1H-indol-3-yl)-1-(toluene-4-sulfonyl)-1H-pyrrolo[2,3-b]pyridine [1.45 g, Reference Example 13(b)] in methanol (100 mL) was treated with potassium hydroxide (5N, 15 mL) then heated at reflux for 2 hours. The reaction mixture was cooled then evaporated. The residue was treated with water (150 mL) and the resulting solid was filtered then dried to give the title compound (0.75 g) as a tan solid, m.p. 226–227° C. MS: 278 (MH$^+$).

(b) By proceeding in a manner similar to Example 17(a) above but using 3-{1-methyl-3-[1-(toluene-4-sulfonyl)-1H-pyrrolo[2,3-b]pyridin-2-yl]-1H-indol-5-yloxy}-propane-1,2-diol [Reference Example 16], there was prepared 3-[1-methyl-3-(1H-pyrrolo[2,3-b]pyridin-2-yl)-1H-indol-5-propane-1,2-diol as a colourless solid, m.p. 202–203° C. MS: 338 (MH$^+$).

(c) By proceeding in a manner similar to Example 17(a) above but using 3-{1-methyl-3-[1-(toluene-4-sulfonyl)-1H-pyrrolo[2,3-b]pyridin-2-yl]-1H-indol-5-yloxy}-propan-1-ol [Reference Example 17], there was prepared 3-[1-methyl-3-(1H-pyrrolo[2,3-b]pyridin-2-yl)-1H-indol-5-yloxy]-propan-1-ol as a yellow solid, m.p. 192–193° C. MS: 322 (MH$^+$).

(d) By proceeding in a manner similar to Example 17(a) above but using 3-{1-methyl-3-[1-(toluene-4-sulfonyl)-1H-pyrrolo[2,3-b]pyridin-2-yl]-1H-indol-5-yloxy}-propan-2-ol [Reference Example 17], there was prepared 3-[1-methyl-3-(1H-pyrrolo[2,3-b]pyridin-2-yl)-1H-indol-5-yloxy]-propan-2-ol as a yellow solid, m.p. 201–202° C. MS: 322 (MH$^+$).

(e) By proceeding in a manner similar to Example 17(a) above but using 2-[1-methyl-5-(1-trimethylstannanyl-1H-tetrazol-5-yl)-1H-indol-3-yl]-1-(toluene-4-sulfonyl)-1H-pyrrolo[2,3-b]pyridine [Reference Example 20], there was prepared 2-[1-methyl-5-(2H-tetrazol-5-yl)-1H-indol-3-yl]-1H-pyrrolo[2,3-b]pyridine as a yellow solid, m.p. 303° C. MS: 316 (MH$^+$).

(f) By proceeding in a manner similar to Example 17(a) above but using 2-[1-methyl-5-(2-methyl-2H-tetrazol-5-yl)-1H-indol-3-yl]-1-(toluene-4-sulfonyl)-1H-pyrrolo[2,3-b]pyridine [Reference Example 21], there was prepared 2-[1-methyl-5-(2-methyl-2H-tetrazol-5-yl)-1H-indol-3-yl]-1H-pyrrolo[2,3-b]pyridine as a beige solid, m.p. 299–300° C. (with decomposition). MS: 330 (MH$^+$).

(g) By proceeding in a manner similar to Example 17(a) above but using 2-[1-methyl-5(1-methyl-1H-tetrazol-5-yl)-1H-indol-3-yl]-1-(toluene-4-sulfonyl)-1H-pyrrolo[2,3-b]pyridine [Reference Example 21), there was prepared 2-[1-methyl-5-(1-methyl-1H-tetrazol-5-yl)-1H-indol-3-yl]-1H-pyrrolo[2,3-b]pyridine as a beige solid, m.p. 286–289° C. (with decomposition). MS: 330 (MH$^+$).

(h) By proceeding in a manner similar to Example 17(a) above but using 1-[1-methyl-3-{(1-(toluene-4-sulfonyl)-1H-pyrrolo[2,3-b]pyridin-2-yl}-1H-indol-5-yl]-ethanone [Reference Example 22], there was prepared 1-[1-methyl-3(1H-pyrrolo[2,3-b]pyridin-2-yl)-1H-indol-5-yl]-ethanone as a beige solid, m.p. 210° C. (with decomposition). MS: 290 (MH$^+$).

(i) By proceeding in a manner similar to Example 17(a) above but using 2-(5,6-dimethoxy-1-methyl-1H-indol-3-yl)-1-(toluene-4-sulfonyl)-1H-pyrrolo[2,3-b]pyridine [Reference Example 13(d)], there was prepared 2-(5,6-dimethoxy-1-methyl-1H-indol-3-yl)-1H-pyrrolo[2,3-b]pyridine as a beige solid, m.p. 283–285° C. (with decomposition). MS: 308 (MH$^+$).

(j) By proceeding in a manner similar to Example 17(a) above but using (S)-3-{1-methyl-3-[1-(toluene-4-sulfonyl)-1H-pyrrolo[2,3-b]pyridin-2-yl]-1H-indol-5-yloxy}-propane-1,2-diol [Reference Example 24(a)], there was prepared (S)-3-[1-methyl-3-(1H-pyrrolo[2,3-b]pyridin-2-yl)-1H-indol-5-yloxy]-propane-1,2-diol as a colourless solid, m.p. 182–185° C. MS: 338 (MH$^+$).

(k) By proceeding in a manner similar to Example 17(a) above but using (R)-3-{1-methyl-3-[1-(toluene-4-sulfonyl)-1H-pyrrolo[2,3-b]pyridin-2-yl]-1H-indol-5-yloxy}-propane-1,2-diol [Reference Example 24(b)], there was prepared (R)-3-[1-methyl-3-(1H-pyrrolo[2,3-b]pyridin-2-yl)-1H-indol-5-yloxy]-propane-1,2-diol as a colourless solid, m.p. 153–156° C. MS: 338 (MH$^+$).

(l) By proceeding in a manner similar to Example 17(a) above but using 2-[5-2-methoxy-1-methyl-ethoxy)-1-methyl-1H-indol-3-yl]-1-(toluene-4-sulfonyl)-1H-pyrrolo[2,3-b]pyridine [Reference Example 25], there was prepared 2-[5-(2-methoxy-1-methyl-ethoxy)-1-methyl-1H-indol-3-yl]-1H-pyrrolo[2,3-b]pyridine as a yellow solid, m.p. 150–151° C. MS: 336 (MH$^+$).

(m) By proceeding in a manner similar to Example 17(a) above but using 2-[1-methyl-5-(5-methyl-[1,2,4]oxadiazol-3-yl)-1H-indol-3-yl]-1-(toluene-4-sulfonyl)-1H-pyrrolo[2,3-b]pyridine [Reference example 27], there was prepared 2-[1-methyl-5-(5-methyl-[1,2,4]oxadiazol-3-yl)-1H-indol-3-yl]-1H-pyrrolo[2,3-b]pyridine as a cream solid, m.p. 290–294° C. MS: 330 (MH$^+$).

(n) By proceeding in a manner similar to Example 17(a) above but using (S)-3-{6-methoxy-1-methyl-3-[1-(toluene-4-sulfonyl)-1H-pyrrolo[2,3-b]pyridin-2-yl]-1H-indol-5-yloxy}-propane-1,2-diol [Reference Example 24(c )], there was prepared (S)-3-[6-methoxy-1-methyl-3-(1H-pyrrolo[2,3-b]pyridin-2-yl)-1H-indol-5-yloxy]-propane-1,2-diol as a cream solid, MS: 368 (MH$^+$). HPLC (METHOD A): R$_T$ 5.81 minutes.

(o) By proceeding in a manner similar to Example 17(a) above but using 2-(5-hydroxy-6-methoxy-1-methyl-1H-indol-3-yl)-1-(toluene-4-sulfonyl)-1H-pyrrolo[2,3-b]pyridine [Reference Example 28], there was prepared 6-methoxy-1-methyl-3-(1H-pyrrolo[2,3-b]pyridin-2-yl)-1H-indol-5-ol as a brown solid, MS: 294 (MH$^+$). HPLC (METHOD A): R$_T$ 6.37 minutes.

(p) By proceeding in a similar manner to Example 17(a) but using 2-(5-methoxy-1-methyl-1H-indol-3-yl)-4-phenyl-1-(toluene-4-sulfonyl)-1H-pyrrolo[2,3-b]pyridine [Reference Example 2(m)] there was prepared 2-(5-methoxy-1-methyl-1H-indol-3-yl)-4-phenyl-1H-pyrrolo[2,3-b]pyridine as a yellow solid. $^1$H NMR [(CD$_3$)$_2$SO]; δ 11.98 (1H, s); 8.21 (1H, d, J=3.5 Hz); 7.94 (1H, s); 7.86 (2H, d, J=8.8 Hz); 7.59 (2H, t, J=8.8 Hz); 7.47 (2H, m); 7.39 (1H, d, J=1.9 Hz); 7.17(1H, d, J=3.5 Hz); 6.93 (1H, dd J=8.8, 1.9 Hz); 6.82 (1H, s); 3.84 (3H, s); 3.82 (3H, s).

(q) By proceeding in a similar manner to Example 17(a) but using 2-[5-(pyridin-4-yl)-1-methyl-1H-indol-3-yl]-1-(toluene-4-sulfonyl)-1H-pyrrolo[2,3-b]pyridine (Reference Example 60) there was prepared 2-[1-methyl-5-(pyridin-4-yl)-1H-indol-3-yl]-4-1H-pyrrolo[2,3-b]pyridine as a yellow solid, m.p. 325–330° C. $^1$H NMR [(CD$_3$)$_2$SO]; δ 8.65 (2H, d, J=7.2 Hz); 8.20 (1H, s); 8.15 (1H, m); 8.04 (1H, s); 7.88 (3H, m); 7.72 (2H, m); 7.03 (1H, t, J=7.2 Hz); 6.96 (1H, s); 3.93 (3H, s).

(r) By proceeding in a similar manner to Example 17(a) above but using 2-(5-methoxy-1-methyl-1H-indol-3-yl)-1-(toluene-4-sulfonyl)-1H-pyrrolo[2,3-b]pyridine-4-carbonitrile [Reference Example 13(h)] there was prepared 2-(5-methoxy-1-methyl-1H-indol-3-yl)-1H-pyrrolo[2,3-b]pyridine-4-carbonitrile as an orange solid, m.p. 304–305° C. $^1$H NMR [(CD$_3$)$_2$SO]: δ 12.60 (1H, s); 8.24 (1H, s); 8.07 (1H, s); 7.50 (3H, m); 6.96 (1H, d, J=8.6 Hz); 6.88 (1H, s); 3.91 (3H, s); 3.86 (3H, s).

(s) By proceeding in a similar manner to Example 17(a) above but using 4-chloro-2-(5-methoxy-1-methyl-1H-indol-3-yl)-1-(toluene-4-sulfonyl)-1H-pyrrolo[2,3-b]pyridine [Reference Example 13(i)] there was prepared 4-chloro-2-(5-methoxy-1-methyl-1H-indol-3-yl)-1H-pyrrolo[2,3-b]pyridine as a tan solid, m.p. 250–252° C. MS: 312 (MH$^+$).

EXAMPLE 18

1-Methyl-3-(1H-pyrrolo[2,3-b]pyridin-2-yl)-1H-indol-5-ylamine

A stirred solution of [1-methyl-3-(1H-pyrrolo[2,3-b]pyridin-2-yl)-1H-indol-5-yl]-carbamic acid tert-butyl ester [0.2 g, Reference Example 30] in dichloromethane was treated with trifluoroacetic acid (2 mL). After stirring at ambient temperature for 16 hours the reaction mixture was evaporated. The residue was suspended in saturated sodium bicarbonate solution (10 mL) and the resulting solid was filtered then dried to give the title compound as a yellow solid, m.p. 247–248° C. MS: 263 (MH$^+$).

EXAMPLE 19

(a) N-[1-Methyl-3-(1H-pyrrolo[2,3-b]pyridin-2-yl)-1H-indol-5-yl]-methanesulfonamide A solution of 1-methyl-3-(1H-pyrrolo[2,3-b]pyridin-2-yl)-1H-indol-5-ylamine [52.4 mg, Example 18] in dichloromethane (5 mL) was treated with triethylamine (30 μl)

followed by methane sulfonyl chloride (17 µl). After stirring at ambient temperature for 16 hours the reaction mixture was diluted with dichloromethane (10 mL), then washed with water (10 mL), then washed with brine (10 mL), then dried over magnesium sulfate and then evaporated. The residual solid was triturated with diethyl ether to give the title compound as a yellow solid, m.p. 223–224° C. MS: 341 (MH$^+$).

(b) By proceeding in a manner similar to Example 19(a) above but using acetyl chloride, there was prepared N-[1-methyl-3-(1H-pyrrolo[2,3-b]pyridin-2-yl)-1H-indol-5-yl]-acetamide as a yellow solid, m.p. 220–221° C. MS: 305 (MH$^+$).

EXAMPLE 20

(a) {1-[5-(1-Hydroxymethyl-cyclobutoxy)-3-(1H-pyrrolo[2,3-b]pyridin-2-yl)-indol-1-yl]-cyclobutyl}-methanol A stirred solution of 1-{1-(cyclobutanecarboxylic acid ethyl ester)-3-[1-(toluene-4-sulfonyl)-1H-pyrrolo[2,3-b]pyridin-2-yl]-1H-indol-5-yloxy}-cyclobutanecarboxylic acid ethyl ester [0.54 g, Reference Example 23(d)] in tetrahydrofuran (50 mL) at 0° C. under nitrogen was treated dropwise with a solution of lithium tetrahydridoaluminate in tetrahydrofuran (4.9 mL, 1.0M). After stirring for 2 hours at 0° C. the reaction mixture was stood at ambient temperature for a further 18 hours then treated dropwise with water (20 mL) and then filtered through Hyflo Super Cel®, diatomaceous earth. The filter pad was washed with ethyl acetate (20 mL), the two-phase filtrate was separated and the aqueous layer was extracted twice with ethyl acetate (25 mL). The combined organic phases were washed with brine (25 mL), then dried over magnesium sulfate and then evaporated. The residue was triturated with diethyl ether and the insoluble material was subjected to flash column chromatography on silica eluting with a mixture of dichloromethane and methanol (19: 1, v/v) to give the title compound (0.19 g) as a cream solid, m.p. 165–166° C. MS: 418 (MH$^+$).

(b) By proceeding in a similar manner to Example 20(a) above but using {1-[1-methyl-3-(5H-pyrrolo[2,3-b]pyrazin-6-yl)-1H-indol-5-yloxy]-cyclobutylcarboxylic acid ethyl ester (Reference Example 15(e) there was prepared {1-[1-methyl-3-(5H-pyrrolo[2,3-b]pyrazin-6-yl)-1H-indol-5-yloxy]-cyclobutyl}-methanol as a brown solid, m.p. 267–271° C. MS: 349(MH$^+$).

EXAMPLE 21

(a) 245-Methoxy-1-methyl-1H-indol-3-yl)-1H-pyrrolo[2,3-b]pyridine methanesulfonate Methane sulfonic acid (70 µl) was added to a solution of 2-(5-methoxy-1-methyl-1H-indol-3-yl)-1H-pyrrolo[2,3-b]pyridine [300 mg, Example 17(a)] in tetrahydrofuran (20 mL) at ambient temperature. The mixture was stirred for 45 minutes and the resultant precipitate isolated by filtration to give the title compound (390 mg), as a yellow solid, m.p. 256–257° C. [Elemental analysis: C, 57.60; H, 4.77; N, 10.90%. Calculated for $C_{13}H_{11}N_3O$: C, 57.90; H, 5.13; N, 11.25%].

(b) By proceeding in a manner similar to Example 21(a) above but using 6-(5-methoxy-1-methyl-1H-indol-3-yl)-5H-pyrrolo[2,3-b]pyrazine [Example 1(a)], there was prepared 6-(5-methoxy-1-methyl-1H-indol-3-yl)-5H-pyrrolo[2,3-b]pyrazine methanesulfonate as a yellow solid, m.p. 245–250° C. MS: 279(MH$^+$).

(c) By proceeding in a manner similar to Example 21(a) above but using 2-[5-methoxy-3-(1H-pyrrolo[2,3-b]pyridin-2-yl)-indol-1-yl]-1-morpholin-4-yl-ethanone [Example 14(a)], there was prepared 2-[5-methoxy-3-(1H-pyrrolo[2,3-b]pyridin-2-yl)-indol-1-yl]-1-morpholin-4-yl-ethanone methanesulfonate as a yellow solid, m.p. 214–215° C. MS: 391(MH$^+$).

(d) By proceeding in a manner similar to Example 21(a) above but using 1-methyl-3-(1H-pyrrolo[2,3-b]pyridin-2-yl)-1H-indole-5-carboxylic acid (2-hydroxy-1,1-dimethyl-ethyl)-amide [Example 14(m)], there was prepared 1-methyl-3-(1H-pyrrolo[2,3-b]pyridin-2-yl)-1H-indole-5-carboxylic acid (2-hydroxy-1,1-dimethyl-ethyl)-amide methanesulfonate as a yellow solid, m.p. 190–192° C. MS: 363(MH$^+$).

(e) By proceeding in a similar manner to Example 21(a) but using 1-methyl-3-(5H-pyrrolo[2,3-b]pyrazin-6-yl)-1H-indole-5-carboxylic acid (2-hydroxy-1,1-dimethyl-ethyl)-amide [Example 14(s)] there was prepared 2-[5-(2-hydroxy-1,1-dimethylethylcarbamoyl)-1-methyl-1 H-indol-3-yl]-1H-pyrrolo[2,3-b]pyrazine methanesulfonate as a brown solid, m.p. 240° C. (with decomposition). $^1$H NMR [(CD$_3$)$_2$SO]: δ 8.50 (1H, s); 8.37 (1H, d, J=3.0 Hz); 8.32 (1H, d, J=3.0 Hz); 8.29 (1H, s); 7.82 (1H, d, J=8.2 Hz); 7.77 (1H, s); 7.64 (1H, d, J=8.2 Hz); 7.20 (1H, s); 3.95 (3H, s); 3.59 (2H, s); 2.37 (3H, s); 1.38 (6H, s).

(f) By proceeding in a similar manner to Example 21(a) but using 2-[5-methoxy-3-(5H-pyrrolo[2,3-b]pyrazin-6-yl)-indol-1-yl]-1-morpholin-4-yl-ethanone (Example 12) there was prepared 2-[5-methoxy-3-(5H-pyrrolo[2,3-b]pyrazin-6-yl)-indol-1-yl]-1-morpholin-4-yl-ethanone methanesulfonate, m/p. 250° C. $^1$H NMR [(CD$_3$)$_2$SO]: δ 8.32 (1H, s); 8.22 (1H, s); 8.11 91H, s); 7.50 (1H, s); 7.44 (1H, d, J=8.8 Hz); 7.04 (1H, s); 6.93 91H, d, J=8.8 Hz); 5.36 (2H, s); 3.90 (3H, s); 3.61 (8H, m); 2.31 (3H, s).

EXAMPLE 22

5-[6-(4-tert-Butylphenyl-5H-pyrrolo[2,3-b]pyrazin-7-yl]ethyl-2H-tetrazole

To a stirred solution of 3-[6-(4-tert-butylphenyl-5H-pyrrolo[2,3-b]pyrazin-7-yl]-propionitrile [0.2 g, Example 23] in toluene (25 mL), at room temperature under nitrogen, was added azidotributyltin (0.61 mL). The reaction mixture was heated at 117° C. After 24 hours, an additional aliquot of azidotributyltin (0.21 mL) was added and the reaction mixture was heated for a further 24 hours. The reaction mixture was quenched with glacial acetic acid (44 mL) and stirred for 15 minutes before partitioning between water and ethyl acetate. The two layers were separated and the organic fraction was washed with water, dried over magnesium sulfate and then evaporated. The residue was subjected to flash column chromatography on silica eluting with ethyl acetate to give the title compound (0.06 g) as an off-white solid. MS: 348 (MH$^+$). HPLC (Method B): R$_T$=1.64 minutes.

EXAMPLE 23

3-[6-(4-tert-Butylphenyl-5H-pyrrolo[2,3-b]pyrazin-7-yl]-2H-propionitrile

To a solution of 3-[6-(4-tert-butylphenyl-5H-pyrrolo[2,3-b]pyrazin-7-yl]-propionamide [0.1 g, Example 24] in tetrahydrofuran (15 mL) at room temperature was added triethylamine (1 mL) and phosphorus oxychloride (1 mL). The reaction mixture was heated at reflux for 30 minutes then poured into a 10% solution of sodium hydrogen carbonate. The mixture was extracted with ethyl acetate and the combined organic extracts were washed with water, dried over magnesium sulfate and evaporated. The residue was subjected to flash column chromatography on silica eluting with first a mixture of ethyl acetate and pentane (1:1, v/v) then with ethyl acetate to give the title compound as a white solid. m.p. 215–216° C. MS: 305 (MH$^+$).

EXAMPLE 24

3-[6-(4-tert-Butylphenyl-5H-pyrrolo[2,3-b]pyrazin-7-yl]-propionamide

To a solution of 3-[6-(4-tert-butylphenyl-5H-pyrrolo[2,3-b]pyrazin-7-yl]-propionic acid [0.51 g, Example 25(a)] in dimethylformamide (15 mL) at room temperature under nitrogen was added O-benzotriazol-1-yl-N,N,N',N',-tetramethyluronium tetrafluoroborate (0.54 g) and triethylamine (0.22 mL). Ammonium gas was bubbled through the solution for 5 minutes and the stoppered reaction mixture was allowed to stand at room temperature overnight. The solution was then poured into water and extracted with ethyl acetate. The organic extracts were washed with water and dried over sodium sulfate to afford the title compound as a white solid without further purification. MS: 323 (MH$^+$). HPLC (Method B): $R_T$=4.49 minutes.

EXAMPLE 25

(a) 3-[6-(4-tert-Butylphenyl-5H-pyrrolo[2,3-b]pyrazin-7-yl]-propionic acid

To a solution of dimethyl 3-[6-(4-tert-butylphenyl-5H-pyrrolo[2,3-b]pyrazin-7-yl]-propionic-1,1-diacid 1,1-dicarboxylate [0.4 g, Reference Example 44(a)] in methanol (20 mL) was added 1N sodium hydroxide solution (4 mL). The reaction mixture was heated at 50° C. for 6 hours then allowed to stand at room temperature overnight. The solvent was removed by evaporation, 6N sulfuric acid solution (50 mL) was added and the reaction mixture refluxed for 2 hours. After cooling, the solution was basified to pH 4 with 1N sodium hydroxide solution and the resultant precipitate isolated by filtration and dried under vacuum to afford the title compound (0.26 g) as an off-white solid without further purification, m.p. 274–275° C. MS: 324 (MH$^+$).

(b) By proceeding in a manner similar to Example 25(a) but using dimethyl 3-[6-(4-(1-methyl)ethoxyphenyl)-5H-pyrrolo[2,3-b]pyrazin-7-yl]-propionic 1,1-diacid 1,1-dicarboxylate [Reference Example 44(b)], there was prepared 3-{6-[4-(1-methyl)ethoxyphenyl]-5H-pyrrolo[2,3-b]pyrazin-7-yl}propionic acid as a yellow solid. MS: 326 (MH$^+$). HPLC (MethodC): $R_T$=1.56 minutes.

(c) By proceeding in a manner similar to Example 25(a) but using dimethyl 3-[6-(4-fluorophenyl)-5H-pyrrolo[2,3-b]pyrazin-7-yl]-propionic 1,1-diacid 1,1-dicarboxylate [Reference Example 44(c)], there was prepared 3-[6-(4-fluorophenyl)-5H-pyrrolo[2,3-b]pyrazin-7-yl]propionic acid as an off-white solid. $^1$H NMR [(CD$_3$)$_2$SO]: δ 12.3 (s, 1H) 8.4 (d, 1H), 8.2 (d, 1H), 7.8 (d, 2H), 7.4 (d, 2H), 3.1 (t, 2H), 2.7 (t, 2H). MS: 285 (MH$^+$).

(d) By proceeding in a manner similar to Example 25(a) above but using dimethyl 3-[6-(4-methoxyphenyl)-5H-pyrrolo[2,3-b]pyrazin-7-yl]-propionic 1,1-diacid 1,1-dicarboxylate [Reference Example 44(d)], there was prepared 3-[6-(4-methoxyphenyl)-5H-pyrrolo[2,3-b]pyrazin-7-yl] propionic acid as an off-white solid. $^1$H NMR [(CD$_3$)$_2$SO]: δ 12.0 (s, 1H) 8.3 (d, 1H), 8.2 (d, 1H), 7.7 (d, 2H), 7.1 (d, 2H), 3.8(s, 3H), 3.05 (t, 2H), 2.6 (t, 2H). MS: 297 (MH$^+$).

EXAMPLE 26

3-[6-(4-tert-Butyl-phenyl)-5H-pyrrolo[2,3-b]pyrazin-7-yl]-propan-1-ol

To a mixture of 4N hydrochloric acid in dioxane and methanol (5 mL 1:1, v/v) was added 3-[6-(4-tert-butylphenyl-5H-pyrrolo[2,3-b]pyrazin-7-yl]-propionic acid [0.02 g, Example 25(a)] and the reaction mixture was allowed to stir at room temperature overnight. After evaporation, the residue was suspended between sodium hydrogen carbonate solution (10%) and ethyl acetate. The phases were separated and the organic fraction was washed with water and dried over sodium sulfate. After evaporation, the residue was suspended in diethyl ether (50 mL). Lithium aluminium hydride (0.12 mL of 1M solution in diethyl ether) was added and the suspension heated to reflux for 2 hour. An additional aliquot of lithium aluminium hydride (0.12 mL of 1M solution in diethyl ether) was added and the reaction mixture heat for a further 1 hour. The reaction was quenched with a cold aqueous (10%) solution of potassium hydrogen sulfate added dropwise until hydrogen evolution ceased, diluted with water and extracted with ether. The combined organic fractions were washed with water, dried over sodium sulfate and subjected to flash column chromatography on silica eluting with ethyl acetate to give the title compound (0.035 g) as an off-white solid, m.p. 187–189° C. MS: 310 (MH$^+$).

EXAMPLE 27

[2-Methoxy-5-(5H-pyrrolo[2,3-b]pyrazin-6-yl)-phenoxy] acetic acid ethyl ester

To a solution of 2-methoxy-5-(5H-pyrrolo[2,3-b]pyrazin-6-yl)-phenol [0.5 g, Example 28] in dimethylformamide (10 mL) and cesium carbonate (0.67g) was added ethyl chloroacetate (0.025 g). The reaction mixture was heated at 50° C. overnight. After cooling, the dimethylformamide was removed in vacuo and the residue partitioned between ethyl acetate and water. The organic fraction was dried over sodium sulfate, evaporated and subjected to flash column chromatography on silica eluting with 2.5% methanol in dichloromethane. This product was further triturated with a mixture of ethyl acetate and pentane to give the title compound as a white solid, m.p. 183–184° C. MS: 328 (MH$^+$).

EXAMPLE 28

2-Methoxy-5-(5H-pyrrolo[2,3-b]pyrazin-6-yl)phenol

To a solution of 6-(3-tert-butyldimethylsilyloxy-4-methoxy)phenyl-5H-pyrrolo[2,3-b]pyrazine [1.0 g, Reference example 49] in tetrahydrofuran (50 mL) was added tetrabutylammonium fluoride (5.63 mL of a 1M solution in tetrahydrofuran). The reaction mixture was stirred at room temperature for 3 hours. The tetrahydrofuran was removed under reduced pressure and the residue was suspended in water. The resultant solid was collected by filtration and dried under vacuum to afford the title compound as a white solid (0.56 g) which was used without further purification. MS: 242 (MH$^+$). HPLC (Method B): $R_T$=3.02 minutes.

EXAMPLE 29

3-Fluoro-2-(5-methoxy-1-methyl-1H-indol-3-yl)-1H-pyrrolo[2,3-b]pyridine

A solution of 2-(5-methoxy-1-methyl-1H-indol-3-yl)-]H-pyrrolo[2,3-b]pyridine [0.1 g, Example 17in dry tetrahydrofuran (4 mL), at 0° C., was treated with methyl magnesium bromide (0.042 mL) and after stirring for a further 20 minutes at 0° C. this mixture was treated with 1-chloromethyl-4-fluoro-1,4-diazoniabicyclo[2,2,2]octane bis(tetrafluoroborate) (0.13 g). The reaction mixture was stirred at room temperature for 4 hours, then stood at room temperature overnight, then heated at 40° C. for 4 hours, then heated at 80° C. for 2 hours, then cooled to room temperature and then partitioned between ethyl acetate and water. The aqueous layer was extracted three times with ethyl acetate (25 mL). The combined extracts and ethyl acetate layer from the partitioning were washed with brine, then dried over magnesium sulfate and then evaporated. The residue was triturated with ethyl acetate to give the title compound (0.057 g) as a white solid, m.p. 248–250° C. $^1$H NMR [(CD$_3$)$_2$SO]: δ 12.20 (1H, s); 8.24 (1H, m); 7.81 (1H, s); 7.79 (1H, d, J=9.6 Hz); 7.46 (1H, d, J=9.6 Hz); 7.27 (1H, s); 7.18 (1H, dd, J=13.1, 6.0 Hz); 6.90 (1H, d, J=9.6 Hz); 3.88 (3H, s); 3.80 (3H, s).

EXAMPLE 30

3-{6-(4-Hydroxyphenyl)-5H-pyrrolo[2,3-b]pyrazin-7-yl}propionic acid

To a solution of dimethyl 3-[6-(4-(1-methyl)ethoxyphenyl)-5H-pyrrolo[2,3-b]pyrazin-7-yl]-propionic 1,1-diacid 1,1-dicarboxylate [0.77 g, Reference Example 44(b)] in methanol (45 mL) was added 1N sodium hydroxide solution (7.7 mL). The reaction mixture was heated at 50° C. for 6 hours then allowed to stand at room temperature overnight. The solvent was removed by evaporation, 6N sulfuric acid solution (20 mL) was added and the reaction mixture refluxed for 12 hours. After cooling, the solution was basified to pH 4 with 4N sodium hydroxide solution and the resultant precipitate filtered and dried under vacuum to afford the title compound (0.42 g) as a yellow solid which was used without further purification. MS: 284 (MH$^+$). HPLC (Method C): R$_T$=2.3 minutes.

EXAMPLE 31

Ethyl 3-{6-(4-hydroxyphenyl)-5H-pyrrolo[2,3-b]pyrazin-7-yl}propionate

A solution of 3-{6-(4-hydroxyphenyl)-5H-pyrrolo[2,3-b]pyrazin-7-yl}propionic acid (0.02 g) [Example 30] in ethanol (2 mL) was treated with a catalytic amount of paratoluenesulfonic acid. The mixture was refluxed for 4 hours, the solvent removed by evaporation and the precipitate filtered. The solid was then taken in ethyl acetate, the organic layer washed with water, brine, dried over magnesium sulfate and evaporated to give a yellow solid which was subjected to flash chromatography on silica, eluting with ethyl acetate) to give the title compound. MS: 298 (MH$^+$). HPLC (MethodC): R$_T$=2.58 minutes.

EXAMPLE 32 AND REFERENCE EXAMPLE 100

2-(5-Methoxy-1H-indol-3-yl)-1H-pyrrolo[2,3-b]pyridine-4-carbonitrile

By proceeding in a similar manner to Reference Example 12(a) but using 2-iodo-1-(toluene-4-sulfonyl)-1H-pyrrolo[2,3-b]pyridine-4-carbonitrile [Reference Example 62(a)] there was prepared the title compound as a yellow solid, m.p. 303–304° C., TLC R$_F$=0.07 (ethyl acetate/heptane 1:1) and 2-(5-methoxy-1H-indol-3-y)-1-(toluene-4-sulfonyl)-1H-pyrrolo[2,3-b]pyridine-4-carbonitrile [Reference Example 100] as a brown oil. MS: 443 (MH$^+$). TLC: R$_F$=0.38 (ethyl acetate/heptane 1:1).

EXAMPLE 33

6-(4-Methylsulfinylphenyl)-5H-pyrrolo[2,3-b]pyrazine

A stirred suspension of 6-(4-methylthiophenyl)-5H-pyrrolo[2,3-b]pyrazine [0.2362 g, Example 1(ah)] in dichloromethane (20 mL) was treated with TBA oxone (2.545 g). After 2 hours the resulting orange solution was evaporated. The residue was subjected to flash chromatography eluting with a mixture of methanol and dichloromethane (1:1, v/v) to give the title compound as a white solid. MS: 258 (MH$^+$). $^1$H NMR [(CD$_3$)$_2$SO]: δ 12.66 (1H, s); 8.41 (1H, s); 8.24 (3H, m); 7.82 (2H, d, J=8.7 Hz); 7.33 (1H, s); 2.81 (3H, s).

EXAMPLE 34

6-(4-Methylsulfonylphenyl)-5H-pyrrolo[2,3-b]pyrazine

A stirred suspension of 6-(4-methylthiophenyl)-5H-pyrrolo[2,3-b]pyrazine [0.125 g, Example 1(ah)] in dichloromethane (15 mL) was treated with TBA oxone (1.35 g). After 4 hours the reaction mixture was evaporated. The residue was subjected to flash chromatography eluting with a mixture of methanol and dichloromethane (1:1, v/v) to give the title compound as a white solid. MS: 274 (MH$^+$). $^1$H NMR [(CD$_3$)$_2$SO]: δ 12.78 (1H, s); 8.44 (1H, s); 8.28 (3H, m); 8.04 (2H, d, J=8.8 Hz); 7.40 (1H, s); 3.27 (3H, s).

EXAMPLE 35

3-(6-(4-tert-Butylphenyl)-5H-pyrrolo[2,3-b]pyrazin-7-yl) propylamine

A solution of the 3-[6-(4-tert-butylphenyl-5H-pyrrolo[2,3-b]pyrazin-7-yl]-propionamide [0.2 g, Example 24] in dry tetrahydrofuran (20 mL) was treated with a solution of lithium aluminum hydride in diethyl ether (5 mL, 1M). The solution was stirred at room temperature for 24 hours then treated with water (20 mL). This mixture was filtered through celite and the celite was washed twice with ethyl acetate (20 mL). The combined filtrate and washings were washed with water, then with brine, then dried over magnesium sulfate and then evaporated to give the title compound as a yellow solid (0.12 g). MS: 309 (MH$^+$). HPLC (Method C): R$_T$=2.54 minutes.

EXAMPLE 36

(a) N-{3-(6-(4-tert-Butylphenyl)-5H-pyrrolo[2,3-b]pyrazin-7-yl)propyl}acetamide

A solution of 3-(6-(4-tert-butylphenyl)-5H-pyrrolo[2,3-b]pyrazin-7-yl)propylamine (0.0324 mmol) [Example 35] in tetrahydrofuran (1.5 mL) was treated with acetyl chloride (0.0324 mmol) and triethylamine (0.0788 mmol). The solution was stirred at room temperature for 12 hours and then treated with water and ethyl acetate. The organic phase was dried over magnesium sulfate and then evaporated. The residue was subjected to column chromatography on silica eluting with ethyl acetate followed by a mixture of ethyl acetate and methanol (9:1, v/v)) to give the title compound as a yellow solid. MS: 351 (MH$^+$). HPLC (Method C): R$_T$=3.05 minutes.

(b) By proceeding in a manner similar to Example 36(a) above but using cyclopropylcarbonyl chloride, there was prepared N-{3-(6-(4-tert-butylphenyl)-5H-pyrrolo[2,3-b]pyrazin-7-yl)propyl}cyclopropylcarboxylic acid amide as a yellow gummy solid. MS: 377 (MH$^+$). HPLC (Method C): R$_T$=3.25 minutes.

(c) By proceeding in a manner similar to Example 36(a) above but using n-butyroyl chloride, there was prepared N-{3-(6-(4-tert-butylphenyl)-5H-pyrrolo[2,3-b]pyrazin-7-yl)propyl}butyramide as a yellow gummy solid. MS: 379 (MH$^+$). HPLC (Method C): R$_T$=3.28 minutes.

(d) By proceeding in a manner similar to Example 36(a) above but using methoxyacetyl chloride, there was prepared N-{3-(6-(4-tert-butylphenyl)-5H-pyrrolo[2,3-b]pyrazin-7-yl)propyl}methoxyacetamide as a white solid. MS: 381 (MH$^+$). HPLC (Method C): R$_T$=3.15 minutes.

(e) By proceeding in a manner similar to Example 36(a) above but using thien-2-ylcarbonyl chloride, there was prepared N-{3-(6-(4-tert-butylphenyl)-5H-pyrrolo[2,3-b]pyrazin-7-yl)propyl}thien-2ylcarboxylic acid amide as a yellow solid. MS: 419 (MH$^+$). HPLC (Method C): R$_T$=3.28 minutes.

EXAMPLE 37

(a) N-{3-(6-(4-tert-Butylphenyl)-5H-pyrrolo[2,3-b]pyrazin-7-yl)propyl}-N'n-propyl urea A solution of 3-(6-(4-tert-butylphenyl)-5H-pyrrolo[2,3-b]pyrazin-7-yl)propylamine (0.0324 mmol). The [Example 24] in tetrahydrofuran (2 mL) was treated with n-propyl-isocyanate (0.0324 mmol). The solution was stirred at room temperature for 12 hours and then treated with water (3 mL). The resulting precipitate was filtered, then washed with water and then dried under vacuum at 50° C. to give the title compound as a beige solid. MS: 394 (MH$^+$). HPLC (Method C): R$_T$=3.25 minutes.

b) By proceeding in a manner similar to Example 37(a) above but using ethyl-isocyanatoacetate, there was prepared N-{3-(6-(4-tert-butylphenyl)-5H-pyrrolo2,3-b]pyrazin-7-yl)propyl}-N'-carboethoxymethyl urea as a yellow solid. MS: 437 (MH$^+$). HPLC (Method C): R$_T$=3.18 minutes.

EXAMPLE 38

N-{3-(6-(4-tert-Butylphenyl)-5H-pyrrolo[2,3-b]pyrazin-7-yl)propyl}-N',N'-diethyl urea A solution of 3-(6-(4-tert-butylphenyl)-5H-pyrrolo[2,3-b]pyrazin-7-yl)propylamine [0.0324 mmol, Example 24] in tetrahydrofuran (1.5 mL) was treated with diethylcarbamyl chloride (0.0324 mmol) and triethylamine (0.0788 mmol). The solution was stirred at room temperature for 12 hours and water and ethyl acetate were added. The layers were separated and the organic solution was dried over magnesium sulfate. The drying agent was filtered and the solvent was evaporated. The residue was purified by column chromatography (silica gel, ethyl acetate followed by 10% methanol in ethyl acetate) to give the title compound as a yellow solid. MS: 408 (MH$^+$). HPLC (Method C): R$_T$=3.43 minutes.

EXAMPLE 39

(a) N-{3-(6-(4-tert-Butylphenyl)-5H-pyrrolo[2,3-b]pyrazin-7-yl)propyl}methanesulfonamide A solution of 3-(6-(4-tert-butylphenyl)-5H-pyrrolo[2,3-b]pyrazin-7-yl)propylamine [0.0324 mmol, Example 24] in tetrahydrofuran (1.5 mL) was treated with methanesulfonyl chloride (0.0324 mmol) and triethylamine (0.0788 mmol). The solution was stirred at room temperature for 12 hours and water and ethyl acetate were added. The layers were separated and the organic solution was dried over magnesium sulfate. The drying agent was filtered and the solvent was evaporated. The residue was purified by column chromatography (silica gel, ethyl acetate followed by 10% methanol in ethyl acetate) to give the title compound as a yellow solid. MS: 387 (MH$^+$). HPLC (Method C): R$_T$=3.23 minutes.

(b) By proceeding in a manner similar to Example 39(a) above but using thien-2-ylsulfonyl chloride, there was prepared N-{3-(6-(4-tert-Butylphenyl)-5H-pyrrolo[2,3-b]pyrazin-7-yl)propyl}thien-2-ylsulfonamide as a yellow solid. MS: 455 (MH$^+$). HPLC (Method C): R$_T$=3.56 minutes.

(c) By proceeding in a manner similar to Example 39(a) above but using 3,5-dimethylisoxazol-4-ylsulfonyl chloride, there was prepared N-{3-(6-(4-tert-butylphenyl)-5H-pyrrolo[2,3-b]pyrazin-7-yl)propyl}dimethylisoxazol-4-ylsulfonamide as a gummy white solid. MS: 468 (MH$^+$). HPLC (Method C): R$_T$=3.55 minutes.

(c) By proceeding in a manner similar to Example 39(a) above but using 1-methylimidazol-4-ylsulfonyl chloride, there was prepared N-{3-(6-(4-tert-butylphenyl)-5H-pyrrolo[2,3-b]pyrazin-7-yl)propyl}1-methylimidazol-4-ylsulfonamide as a gummy white solid. MS: 453 (MH$^+$). HPLC (Method C): R$_T$=3.13 minutes.

REFERENCE EXAMPLE 1

(a) 5-Methoxy-1-methyl-1H-indole-3-carbonitrile

5-Methoxy-1-methyl-1H-indole-3-carbaldehyde [76 g, Reference Example 2(a)] and hydroxylamine hydrochloride (55.9 g) were stirred together in dimethylformamide (900 mL) under reflux for 1 hour. The mixture was allowed to cool, then poured into water and then extracted with ethyl acetate. The combined extracts were washed with water then evaporated to give the title compound (53 g) as a pale brown solid, m.p. 100–104° C. $^1$H NMR [(CD$_3$)$_2$SO]: δ 8.17 (1H, s); 7.54 (1H, d, J=9.0 Hz); 7.09 (1H, d, J=2.4 Hz); 6.97 (1H, dd, J=9.0 and 2.4 Hz); 3.82 and 3.84 (6H, s).

(b) By proceeding in a manner similar to Reference Example 1 (a) above but using 1-methyl-5-phenylpyrazole-3carbaldehyde [Reference Example 53(b)] there was prepared 1-methyl-3-cyano-5-phenylpyrazole.

REFERENCE EXAMPLE 2

(a) 5-Methoxy-1-methyl-1H-indole-3-carbaldehyde

A solution of 5-methoxyindole-3-carboxaldehyde (80 g) in dimethylformamide (1L) under nitrogen was treated portion-wise with sodium hydride (20.1 g, 60% dispersion in mineral oil) over 15 minutes. After stirring at ambient temperature for 30 minutes the mixture was treated dropwise with methyl iodide (31.3 mL) over 10 minutes and stirring was then continued for a further 2 hours. The reaction mixture was poured cautiously into water then extracted with ethyl acetate. The organic phase was washed with water, then dried over sodium sulfate and then evaporated. The residue was triturated with pentane to give the title compound (76 g) as a pale brown solid, m.p. 133–134° C. $^1$H NMR [(CD$_3$)$_2$SO]: δ 9.86 (1H, s); 8.20 (1H, s); 7.60 (1H, d, J=2.6 Hz); 7.50 (1H, d, J=8.9 Hz); 6.96 (1H, dd, J=8.9 and 2.6 Hz); 3.86 and 3.80 (6H, s).

(b) By proceeding in a manner similar to Reference Example 2(a) above but using indole-3-carbonitrile, there was prepared 1-methyl-1H-indole-3-carbonitrile, as a colourless crystalline solid, m.p. 61–63° C.

(c) By proceeding in a manner similar to Reference Example 2(a) above but using indole-5-carbonitrile, there was prepared 1-methyl-1H-indole-5-carbonitrile, as a colourless crystalline solid, m.p. 77–79° C.

(d) By proceeding in a manner similar to Reference Example 2(a) above but using indole-3-carbonitrile and (3-bromopropoxy)-tert-butyldimethylsilane, there was prepared 1-[3-(tert-butyl-dimethyl-silanyloxy)-propyl]-1H-indole-3-carbonitrile, as a clear colourless oil, TLC: $R_F$=0.6 (Dichloromethane). $^1$H NMR (CDCl$_3$): δ 7.70 (1H, d, J=8 Hz); 7.56 (1H, s); 7.39 (1H, d, J=8 Hz); 7.27 (1H, t, J=8 Hz); 7.22 (1H, t, J=8 Hz); 4.25 (2H, t, J=6 Hz); 3.49 (2H, t, J=6 Hz); 1.95 (2H, quintet, J=6 Hz); 0.87 (9H, s); 0.00 (6H, s).

(e) By proceeding in a manner similar to Reference Example 2(a) above but using 5-methoxy-1H-indole-3-carbonitrile [Reference Example 1(a)] and (3-bromopropoxy)-tert-butyldimethylsilane, there was prepared 1-[3-(tert-butyl-dimethyl-silanyloxy)-propyl]-5-methoxy-1H-indole-3-carbonitrile, as a clear colourless oil, $^1$H NMR [(CD$_3$)$_2$SO]: δ 8.18 (1H, s); 7.55 (1H, d, J=9 Hz); 7.09 (1H, d, J=2 Hz); 6.95 (1H, dd, J=9 and 2 Hz); 4.27 (2H, t, J=6 Hz); 3.82 (3H, s); 3.53 (2H, t, J=6 Hz); 1.95 (2H, quintet, J=6 Hz); 0.87 (9H, s); 0.00 (6H, s).

(f) By proceeding in a manner similar to Reference Example 2(a) above but using indole-3-carbonitrile and (2-bromoethoxy)-tert-butyldimethylsilane, there was prepared 1-[2-(tert-butyl-dimethyl-silanyloxy)-ethyl]-1H-indole-3-carbonitrile, as a clear colourless oil. TLC: $R_F$=0.65 (dichloromethane).

(g) By proceeding in a manner similar to Reference Example 2(a) above but using 5-methoxy-1H-indole-3-carbonitrile [Reference Example 1(a)] and benzyl bromide, there was prepared 1-benzyl-5-methoxy-1H-indole-3-carbonitrile, as a brown solid, MS: 263.22 (MH$^+$). TLC: $R_F$=0.8 (dichloromethane/methanol: 19/1).

(h) By proceeding in a manner similar to Reference Example 2(a) above but using 5-methoxy-1H-indole-3-carbonitrile [Reference Example 1(a)] and 2-bromoethoxy-dimethyl-tertiarybutylsilane, there was prepared 1-[2-(tertiarybutyl-dimethyl-silanyloxy)-ethyl]-5-methoxy-1H-indole-3-carbonitrile, as a pale yellow solid, MS: 331.23 (MH$^+$). TLC: $R_F$=0.6 (pentane/ethyl acetate: 8/2).

(i) By proceeding in a manner similar to Reference Example 2(a) above but using 1H-pyrrole-3-carbonitrile (prepared as described in Tetrahedron Letters, 1972, 52, 5337–5340), there was prepared 1-methyl-1H-pyrrole-3-carbonitrile, as a brown oil, MS: 107 (MH$^+$). $^1$H NMR [CDCl$_3$]: δ 7.09 (1H, m); 6.60 (1H, m); 6.40 (1H, m); 3.68 (3H, s).

(j) By proceeding in a manner similar to Reference Example 2(a) above but using 1H-pyrrole-2-carbonitrile, there was prepared 1-methyl-1H-pyrrole-2-carbonitrile as a colourless liquid. MS: 106 (MH$^+$). $^1$H NMR [CDCl$_3$]: δ 6.80 (1H, m); 6.67 (1H, m); 6.15 (1H, m); 3.79 (3H, s).

(k) By proceeding in a manner similar to Reference Example 2(a) above but using 2-phenyl-1H-pyrrole-4-carbonitrile (prepared as described in Synthetic Communications, 25, (1995) 6, 795–802), there was prepared 1-methyl-2-phenyl-1H-pyrrole-4-carbonitrile as a cream solid, m.p. 50–51° C. MS: 183 (MH$^+$).

(l) By proceeding in a similar manner to Reference Example 2(a) but using 4-methoxy-2-(5-methoxy-1H-indol-3-yl)-1-(toluene-4-sulfonyl)-1H-pyrrolo[2,3-b]pyridine (Reference Example 39) there was prepared 4-methoxy-2-(5-methoxy-1-methyl-1H-indol-3-yl)-1-(toluene-4-sulfonyl)-1H-pyrrolo[2,3-b]pyridine as a dark oil, HPLC (METHOD A): $R_T$ 9.49 minutes. TLC: $R_F$ 0.50 (pentane/ethyl acetate: 1/1).

(m) By proceeding in a similar manner to Reference Example 2(a) but using 2-(5-methoxy-1H-indol-3-yl)-4-phenyl-1-(toluene-4-sulfonyl)-1H-pyrrolo[2,3-b]pyridine (Reference Example 12(g)) there was prepared 2-(5-methoxy-1-methyl-1H-indol-3-yl)-4-phenyl-1-(toluene-4-sulfonyl)-1H-pyrrolo[2,3-b]pyridine as a tan solid. $^1$H NMR [(CD$_3$)$_2$SO]; δ]8.39 (1H, d, J=4.4 Hz); 7.71 (2H, d, J=7.2 Hz); 7.63 (3H, m); 7.52 (2H, t, J=8.5 Hz); 7.44 (3H, m); 7.29 (2H, d, J=7.2 Hz); 6.94 (1H, s); 6.86 (1H, d, J=8.5 Hz); 6.82 (1H, s); 3.86 (3H, s); 3.71 (3H, s); 2.29 (3H, s).

REFERENCE EXAMPLE 3

(a) 6-{1-[3-(tert-Butyl-dimethyl-silanyloxy)-propyl]-1H-indol-3-yl}-5H-pyrrolo[2,3-b]pyrazine By proceeding in a manner similar to Example 1(a) herein but using 1-[3-(tert-butyl-dimethyl-silanyloxy)-propyl]-1H-indole-3-carbonitrile [Reference Example 2(d)], there was prepared the title compound as a solid, $^1$H NMR [(CD$_3$)$_2$SO]: δ 12.1–12.2 (1H, broad s); 8.27 (1H, d, J=2.7 Hz); 8.14 (1H, s); 8.10, 7.59 (each 1H, d, J=7.8 Hz); 8.09 (1H, d, J=2.7 Hz); 7.29, 7.23 (each 1H, td, J=7.1 and 1.1 Hz); 6.96 (1H, s); 4.33 (2H, t, J=7.1 Hz); 3.62 (2H, t, J=6.0 Hz); 2.03 (2H, quintet, J=6.2 Hz); 0.89 (9H, s); 0.00 (6H, s). MS: 407 (MH$^+$).

(b) By proceeding in a manner similar to Example 1(a) herein but using 1-[3-(tert-butyl-dimethyl-silanyloxy)-propyl]-5-methoxy-1H-indole-3-carbonitrile [Reference Example 2(e)], there was prepared 6-{1-[3-(tert-butyl-dimethyl-silanyloxy)-propyl]-5-methoxy-1H-indol-3-yl}-5H-pyrrolo[2,3-b]pyrazine as a solid, TLC: $R_F$=0.4 (ethyl acetate/pentane: 1/1). δH (d$^6$ DMSO) 8.27 (1H, d, 4 Hz); 8.08 (2H, m); 7.50 (2H, m); 6.96 (1H, s); 6.91 (1H, dd, 6, 2 Hz); 4.29 (2H, t, 6 Hz); 3.89 (3H, s); 3.61 (2H, t, 6 Hz); 2.00 (2H, m); 0.89 (9H, s); 0.03 (6H, s).

(c) By proceeding in a manner similar to Example 1(a) herein but using 1-[2-(tert-butyl-dimethyl-silanyloxy)-ethyl]-1H-indole-3-carbonitrile [Reference Example 2(f)], there was prepared 6-{1-[3-(tert-butyl-dimethyl-silanyloxy)-ethyl]-1H-indol-3-yl}-5H-pyrrolo[2,3-b]pyrazine as a solid, TLC: $R_F$=0.3 (ethyl acetate/pentane: 1/1). MS: 393 (MH$^+$).

(d) By proceeding in a manner similar to Example 1(a) herein but using 1-[2-(tert-butyl-dimethyl-silanyloxy)-ethyl]-5-methoxy-1H-indole-3-carbonitrile [Reference Example 2(h)], there was prepared 6-{1-[2-(tert-butyl-dimethyl-silanyloxy)-ethyl]-5-methoxy-1H-indol-3-yl}-5H-pyrrolo[2,3-b]pyrazine as a brown solid, TLC: $R_F$=0.4 (dichloromethane/methanol: 19/1). MS: 423 (MH$^+$).

REFERENCE EXAMPLE 4

3-[3-(5H-Pyrrolo[2,3-b]pyrazin-6-yl)-indol-1-yl]-propyl-bromide

To a solution of 3-[3-(5H-pyrrolo[2,3-b]pyrazin-6-yl)-indol-1-yl]-propan-1-ol [1 g, Example 2(a)] and carbon tetrabromide (1.59 g) in dichloromethane (40 mL) at ambient temperature was added a solution of triphenylphosphine (1.1 g) in dichloromethane (10 mL) over 2 minutes. The reaction mixture was stirred at ambient temperature for 3 hour, then stood for 18 hours and then evaporated to give the title compound which was used without further purification.

REFERENCE EXAMPLE 5

Indolizine-1-carbonitrile

A mixture of 2-pyridylacetontrile (5 g), and chloroacetaldehyde (4.42 g of 50% wt. solution in water) was heated at reflux in 1,4-dioxane (25 mL) for 5.5 hours. The reaction mixture was allowed to cool to ambient temperature then evaporated. The residue was partitioned between ethyl acetate (100 mL) and hydrochloric acid (100 mL, 1M). The aqueous layer was extracted twice with ethyl acetate (100 mL). The combined organic phases were washed with brine (50 mL), then dried over magnesium sulfate and then evaporated. The residue was subjected to flash column chromatography on silica eluting with dichloromethane to give the title compound (1.83 g) as a colourless solid, m.p. 53–54° C. MS: 143 (MH$^+$).

REFERENCE EXAMPLE 6

3-Methyl-indolizine-1-carbonitrile

A solution of propionaldehyde (36 mL) in diethyl ether (200 mL) and 1,4-dioxane (1.7 mL) at 5° C. under nitrogen was treated dropwise with bromine (24.7 mL) over 2 hours whilst maintaining the temperature at 5° C. After the addition was complete, the reaction mixture was stirred for a further 30 minutes and then washed carefully with saturated sodium bicarbonate solution (100 mL). The organic phase was dried over sodium sulfate then concentrated in vacuo at 10° C. and then added immediately to a solution of 2-pyridylacetonitrile (8.36 mL) in acetone (50 mL). The resultant mixture was heated at reflux under nitrogen for 6 hours, then allowed to stand at ambient temperature overnight and then evaporated. The residue was partitioned between ethyl acetate (500 mL) and hydrochloric acid (100 mL, 1M). The organic layer was washed with brine (100 mL) and then evaporated. The residue was subjected to flash column chromatography on silica eluting with a mixture of ethyl acetate and pentane (1:4, v/v) and then triturated with diethyl ether to give the title compound (4.0 g) as a white solid, m.p. 98–100° C. MS: 157(MH$^+$).

REFERENCE EXAMPLE 7

Sodium-1-formyl-piperidine-2-carboxylate

To a solution of piperidine-2-carboxylic acid (30 g) in formic acid (230 mL) was added acetic anhydride (147 mL) dropwise. The resultant exotherm was controlled by cooling the reaction mixture in an ice/water bath. After stirring at ambient temperature for 24 hours the reaction mixture was diluted with water (20 mL) and then concentrated in vacuo. The resultant oil was dissolved in a mixture of methanol (50 mL) and acetonitrile (500 mL). Sodium hydroxide solution (10M, 23 mL) was added and the reaction mixture stirred for 8 hours. The resultant precipitate was filtered, washed with acetonitrile, and ethyl acetate and dried in a vacuum oven to afford the title compound as a white solid which was used immediately without further purification.

REFERENCE EXAMPLE 8

5,6,7,8-Tetrahydro-indolizine-1-carbonitrile

To a solution of sodium-1-formyl-piperidine-2-carboxylate (2.0 g) (Reference Example 7) in dichloromethane (50 mL) at ambient temperature under nitrogen was added para-toluenesulfonyl chloride (2.31 g). After stirring for 10 minutes the mixture was treated dropwise with acrylonitrile (0.88 mL) and triethylamine (1.5 mL) and stirring was continued for a further 1 hour when a second portion of triethylamine (1.0 mL) was added. The reaction mixture was stirred for 18 hours and the dichloromethane removed in vacuo. The residue was taken up in water (50 mL) and extracted with ethyl acetate (200 mL). The combined organic extracts were evaporated in vacuo and the residue was subjected to flash column chromatography on silica eluting with a mixture of ethyl acetate and pentane (1:4, v/v) to give the title compound (1.38 g) as an orange oil, MS: 147 (MH$^+$). $^1$H NMR(CDCl$_3$): δ 6.48 (1H, d, J=3.1 Hz); 6.36 (1H, d, J=3.1 Hz); 3.91 (2H, t, J=6.0 Hz); 2.89 (2H, t, J=6.0 Hz); 1.98 (2H, m); 1.88 (2H, m).

REFERENCE EXAMPLE 9

(a) 1-(Toluene-4-sulfonyl)-1H-pyrrolo[2,3-b]pyridine

To a solution of 7-azaindole (25 g), para-toluenesulfonyl chloride (44.5 g) and a catalytic amount of tetrabutylammoniun sulfate in dry toluene (300 mL) was added sodium hydroxide (160 g in 500 mL of water). The biphasic solution was stirred at ambient temperature for 3 hours then extracted twice with toluene (100 mL). The combined extracts were dried over magnesium sulfate then concentrated under vacuo. The resultant solid was triturated with diethyl ether then dried at 60° C. under vacuo to yield the title compound (39.74 g) as a pale yellow solid, m.p. 136–138° C.

(b) By proceeding in a similar manner to Reference Example 9(a) but using 4-nitro-1H-pyrrolo[2,3-b]pyridine (prepared according to the procedure described by A. Ippolito et al., J. Med. Chem. (1982), 25(10), 1258–61) there was prepared 4-nitro-1-(1-toluene-4-sulfonyl)-1H-pyrrolo[2,3-b]pyridine as an orange solid, m.p. 145–146° C. HPLC (METHOD A): R$_T$=10.80 minutes.

(c) By proceeding in a similar manner to Reference Example 9(a) but using 4-chloro-1H-pyrrolo[2,3-b]pyridine (Reference Example 64) there was prepared 4-chloro-1-(toluene-4-sulfonyl)-1H-pyrrolo[2,3-b]pyridine as a white solid. MS: 307 (MH$^+$). $^1$H NMR (CDCl$_3$): δ 8.3 (d, 1H), 8.05 (d, 2H), 7.8 (d, 1H), 7.3 (d, 2H), 7.2 (d, 1H), 6.7 (d, 1H), 2.4 (s, 3H).

(d) By proceeding in a similar manner to Reference Example 9(a) but using 5-bromo-1H-pyrrolo[2,3-b]pyridine there was prepared 5-bromo-1-(toluene-4-sulfonyl)-1H-pyrrolo[2,3-b]pyridine as a white solid, m.p. 138–140° C.

(e) By proceeding in a similar manner to Reference Example 9(a) but using 4-phenyl-1H-pyrrolo[2,3-b]pyrazine (Reference Example 42) there was prepared 4-phenyl-1-(toluene-4-sulfonyl)-1H-pyrrolo[2,3-b]pyrazine as a white solid. $^1$H NMR [(CD$_3$)$_2$SO]: δ 8.44 (1H, d, J=4.5 Hz); 8.04 (2H, d, J=8.2 Hz); 7.98 (1H, d, J=4.5 Hz); 7.69 (2H, d, J=6.8 Hz); 7.57 (tt, J=6.2, 1.8 Hz); 7.51 (1H, tt, J=6.8, 1.8 Hz); 7.44 (2H, d, J=8.2 Hz); 7.42 (1H, d, J=4.5 Hz); 6.92 (1H, d, J=4.5 Hz) which was without further purification

REFERENCE EXAMPLE 10

2-Iodo-1-(toluene-4-sulfonyl)-1H-pyrrolo[2,3-b]pyridine

A solution of 1-(toluene-4-sulfonyl)-1H-pyrrolo[2,3-b]pyridine [54.4 g, Reference Example 9(a)] in dry tetrahydrofuran (1200 mL) cooled to −78° C., was treated with a solution of butyllithium in hexanes (2.5M, 92 mL) over a 20 minute period. The solution was maintained at −78° C. for 30 minutes, then a solution of iodine (101 g) in tetrahydrofuran (600 mL) was added until the iodine colour persisted (ca.300 mL). The mixture was allowed to warm slowly to ambient temperature and the solvent removed under vacuo. The residue was partitioned between ethyl acetate (1000 mL) and water (500 mL) and the water re-extracted with ethyl acetate (2×500 mL). The organic extracts were combined, dried over sodium sulfate and removed under reduced pressure to give a yellow solid which was triturated with diethyl ether to give the title compound (79.6 g) as a pale yellow solid. m.p. 105–107° C.

MS: 399(MH$^+$).

REFERENCE EXAMPLE 11

(a) 3-Bromo-5-methoxy-indole-1-carboxylic acid tert-butyl ester

A solution of 5-methoxyindole (10 g) in dry dimethylformamide (150 mL) at ambient temperature was treated with bromine (4 mL) dropwise ensuring the temperature did not rise above 30° C. The mixture was treated immediately with triethylamine (28 mL) and 4-dimethylaminopyridine (0.5 g) followed by a solution of di-tert-butyldicarbonate (18 g) in dry dimethylformamide (80 mL) and stirring was continued for a further 4 hours. The reaction mixture was evaporated and the residue was partitioned between ethyl acetate (250 mL) and water (200 mL). The aqueous layer was extracted with ethyl acetate (100 mL). The combined organic phases were washed with water (100 mL), then with brine (100 mL), then dried over magnesium sulfate and then evaporated. The residue was subjected to flash column chromatography on silica eluting with a mixture of pentane and ethyl acetate (19/1, v/v) to give the title compound (23.4 g) as a colourless solid, m.p. 111–112° C.

(b) By proceeding in a manner similar to Reference Example 11(a) above but using 5-cyano-indole, there was prepared 3-bromo-5-cyano-indole-1-carboxylic acid tert-butyl ester as a grey solid, m.p. 172–174° C. MS: 322(MH$^+$).

(c) By proceeding in a manner similar to Reference Example 11(a) above but using 5,6-dimethoxy-indole, there was prepared 3-bromo-5,6-dimethoxy-indole-1-carboxylic acid tert-butyl ester as a lilac solid. TLC: R$_F$=0.6 (pentane/ethyl acetate: 19/1).

(d) By proceeding in a manner similar to Reference Example 11(a) above but using 5-benzyloxy-6-methoxy-indole [prepared according to the method described by Benigni, J. D. and Minnis, R. L., Heterocycles, 387, 2, 1965] there was prepared 5-benzloxy-3-bromo-6-methoxy-indole-1-carboxylic acid tert-butyl ester as a colourless solid. MS: 433(MH$^+$). HPLC (METHOD A): R$_T$=13.99 minutes.

(e) By proceeding in a manner similar to Reference Example 11(a) above but using 5-amino-indole and an excess of di-tert-butyldicarbonate there was prepared 3-bromo-5-tert-butoxycarbonylamino-indole-1-carboxylic acid tert-butyl ester as an orange oil. MS: 412(MH$^+$). TLC: R$_F$=0.8 (pentane/ethyl acetate: 9/1).

(f) By proceeding in a manner similar to Reference Example 11(a) above but using 1H-indole-6-carboxylic acid methyl ester [Reference Example 31] there was prepared 3-bromo-indole-1,6-dicarboxylic acid 1-tert-butyl ester 6-methyl ester as a pale violet solid, m.p. 117–119° C. MS: 355(MH$^+$).

REFERENCE EXAMPLE 12

(a) 2-(5-Methoxy-1H-indol-3-yl)-4-(toluene-4-sulfonyl)-1H-pyrrolo[2,3-b]pyridine A stirred solution of 3-bromo-5-methoxy-indole-1-carboxylic acid tert-butyl ester [50 g, Reference Example 11(a)] in tetrahydrofuran (800 mL), under nitrogen, was treated with tributylborate (49.5 mL) then cooled to −100° C. and then treated with a solution of n-butyllithium in hexanes (94 mL, 2.5M) whilst keeping the temperature below −90° C. Once the addition was complete the mixture was allowed to warm slowly to room temperature over 1 hour and quenched by the addition of ice (10 g). The organics were removed under reduced pressure and the residue was partitioned between ethyl acetate (500 mL) and water (400 mL). The organic layer was dried over magnesium sulfate and then evaporated. The resulting boronic acid, a cream coloured solid (28 g), was dissolved in dimethylformamide (600 mL) and the solution was treated with 2-iodo-1-(toluene-4-sulfonyl)-1H-pyrrolo[2,3-b]pyridine [38.3 g, Reference Example 10], then with saturated aqueous sodium bicarbonate (200 mL) and then with tetrakis(triphenylphosphine) palladium[0] (3 g). The mixture was heated at reflux for 4 hours then allowed to cool to ambient temperature then concentrated to remove the dimethylformamide. The residue was partitioned between water (400 mL) and ethyl acetate (500 mL) and the aqueous was extracted twice with ethyl acetate (300 mL). The combined organics were dried over sodium sulfate then evaporated. The residual brown gum was triturated with ethyl acetate to give the title compound (27 g) as a pale green solid. MS: 418.43(MH$^+$).

(b) By proceeding in a manner similar to Reference Example 12(a) above but using 3-bromo-5-cyano-indole-1-carboxylic acid tert-butyl ester [Reference Example 11(b)], there was prepared 3-[1-(toluene-4-sulfonyl)-1H-pyrrolo[2,3-b]pyridin-2-yl]-1H-indole-5-carbonitrile as a colourless solid, m.p. 209–214° C. MS: 413 (MH$^+$).

(c) By proceeding in a manner similar to Reference Example 12(a) above but using 3-bromo-5,6-dimethoxy-indole-1-carboxylic acid tert-butyl ester [Reference Example 11(c)], there was prepared 2-(5,6-dimethoxy-1H-indol-3-yl)-1-(toluene-4-sulfonyl)-1H-pyrrolo[2,3-b]pyridine as a brown solid, MS: 446 (M−H$^+$).

(d) By proceeding in a manner similar to Reference Example 12(a) above but using 5-benzyloxy-3-bromo-6-methoxy-indole-1-carboxylic acid tert-butyl ester [Reference Example 11(d)], there was prepared 2-(5-benzyloxy-6-methoxy-1H-indol-3-yl)-1-(toluene-4-sulfonyl)-1H-pyrrolo[2,3-b]pyridine as a colourless solid. MS: 524(MH$^+$). HPLC (METHOD A):R$_T$=10.09 minutes.

(e) By proceeding in a manner similar to Reference Example 12(a) above but using 3-bromo-5-tert-butoxycarbonylamino-indole-1-carboxylic acid tert-butyl ester [Reference Example 11(e)], there was prepared {3-[1-(toluene-4-sulfonyl)-1H-pyrrolo[2,3-b]pyridin-2-yl]-1H-indol-5-yl}-carbamic acid tert-butyl ester as a tan solid. MS: 503(MH$^+$). TLC: R$_F$=0.62 (pentane/ethyl acetate: 1/1).

(f) By proceeding in a manner similar to Reference Example 12(a) above but using 3-bromo-indole-1,6-dicarboxylic acid 1-tert-butyl ester 6-methyl ester [Reference Example 11(f)], there was prepared 3-[1-(toluene-4-sulfonyl)-1H-pyrrolo[2,3-b]pyridin-2-yl]-1H-indole-6-carboxylic acid methyl ester as a pale yellow solid, m.p. 214–216° C. MS: 446(MH$^+$).

(g) By proceeding in a similar manner to Reference Example 12(a) but using 2-iodo-4-phenyl-1-(toluene-4-sulfonyl)-1H-pyrrolo[2,3-b]pyridine [Reference Example 62(d)] there was prepared 2-(5-methoxy-1H-indol-3-yl)-4-phenyl-1-(toluene-4-sulfonyl)-1H-pyrrolo[2,3-b]pyridine as a white solid. HPLC (METHOD A): R$_T$=11.63 minutes. MS: 494(MH$^+$).

(h) By proceeding in a similar manner to Reference Example 12(a) but using 4-chloro-2-iodo-1-(toluene-4-sulfonyl)-1H-pyrrolo[2,3-b]pyridine [Reference Example 62(b)] there was prepared 4-chloro-2-(5-methoxy-1H-indol-3-yl)-1-(toluene-4-sulfonyl)-1H-pyrrolo[2,3-b]pyridine as a white sol MS: 452 (MH$^+$). $^1$H NMR (CDCl$_3$): δ 8.4 (d, 1H), 7.6 (d, 2H), 7.5 (s, 1H), 7.35 (d, 1H), 7.2 (d, 2H), 6.9 (m, 2H), 6.7 (s, 1H), 3.8 (s, 3H), 2.3 (s, 3H).

(i) By proceeding in a similar manner to Reference Example 12(a) but using 2-iodo-5-phenyl-1-(toluene-4-sulfonyl)-1H-pyrrolo[2,3-b]pyridine [Reference Example 62(c)] there was prepared 2-(5-methoxy-1H-indol-3-yl)-1-(toluene-4-sulfonyl)-5-phenyl-1H-pyrrolo[2,3-b]pyridine. MS: 494 (MH$^+$).

(j) By proceeding in a similar manner to Reference Example 12(a) but using 4-chloro-2-iodo-1-(para-toluenesulfonyl)-1H-pyrrolo[2,3-b]pyridine [Reference Example 62(b)]and 4-tertbutylphenyl bronic acid there was prepared 4-chloro-2-(4-tertiary-butylphenyll)-1-(para-toluenesulfonyl)-1H-pyrrolo[2,3-b]pyridine as a white solid. MS: 439 (MH$^+$). TLC R$_F$=0.78 (ethyl acetate/heptane, 1:1).

REFERENCE EXAMPLE 13

(a) {5-Methoxy-3-[1-(toluene-4-sulfonyl)-1H-pyrrolo[2,3-b]pyridin-2-yl]-indol-1-yl}-acetic acid ethyl ester A solution of 2-(5-methoxy-1H-indol-3-yl)-1-(toluene-4-sulfonyl)-1H-pyrrolo[2,3-b]pyridine [6.6 g, Reference Example 12(a)] in dimethylformamide (100 mL), under a nitrogen atmosphere, was treated with sodium hydride (700 mg, 60% dispersion in oil). After stirring at ambient temperature for 30 minutes the mixture was treated dropwise with ethyl chloroacetate (2.0 mL, 23.75 mmol) and stirring was continued for an additional 4 hours. The reaction mixture was evaporated and the residue was partitioned between ethyl acetate and water. The organic phase was washed with brine, then dried over sodium sulfate and then evaporated to give the title compound (5.77 g) as a yellow solid, MS: 504(MH$^+$). HPLC (METHOD A): R$_T$=11.88 minutes.

(b) By proceeding in a manner similar to Reference Example 13(a) above but using methyl iodide, there was prepared 2-(5-methoxy-1-methyl-1H-indol-3-yl)-1-(toluene-4-sulfonyl)-1H-pyrrolo[2,3-b]pyridine, as a yellow solid, m.p. 103–105° C. MS: 432(MH$^+$).

(c) By proceeding in a manner similar to Reference Example 13(a) above but using 3-[1-(toluene-4-sulfonyl)-1H-pyrrolo[2,3-b]pyridin-2-yl]-1H-indole-5-carbonitrile [Reference Example 12(b)] and methyl iodide, there was prepared 1-methyl-3-[1-(toluene-4-sulfonyl)-1H-pyrrolo[2,3-b]pyridin-2-yl]-1H-indole-5-carbonitrile, as a colourless solid, m.p. 189–191° C. MS: 427(MH$^+$).

(d) By proceeding in a manner similar to Reference Example 13(a) above but using 2-(5,6-dimethoxy-1H-indol-3-yl)-1-(toluene-4-sulfonyl)-1H-pyrrolo[2,3-b]pyridine [Reference Example 12(c)] and methyl iodide, there was prepared 2-(5,6-dimethoxy-1-methyl-1H-indol-3-yl)-1-(toluene-4-sulfonyl)-1H-pyrrolo[2,3-b]pyridine, as a brown solid, MS: 462(MH$^+$).

(e) By proceeding in a manner similar to Reference Example 13(a) above but using 2-(5-benzyloxy-6-methoxy-1H-indol-3-yl)-1-(toluene-4-sulfonyl)-1H-pyrrolo[2,3-b]pyridine [Reference Example 12(d)] and methyl iodide, there was prepared 2-(5-benzyloxy-6-methoxy-1-methyl-1H-indol-3-yl)-1-(toluene-4-sulfonyl)-1H-pyrrolo[2,3-b]pyridine as a colourless solid. MS: 538(MH$^+$). HPLC (METHOD A): R$_T$=11.57 minutes.

(f) By proceeding in a manner similar to Reference Example 13(a) above but using {3-[1toluene-4-sulfonyl)-1H-pyrrolo[2,3-b]pyridin-2-yl]-1H-indol-5-yl}-carbamic acid tert-butyl ester [Reference Example 12(e)] and methyl iodide, there was prepared {1-methyl-3-[1-(toluene-4-sulfonyl)-1H-pyrrolo[2,3-b]pyridin-2-yl]-1H-indol-5-yl}-carbamic acid tert-butyl ester as a tan solid. MS: 517(MH$^+$). TLC: R$_F$=0.7 (pentane/ethyl acetate: 1/1).

(g) By proceeding in a manner similar to Reference Example 13(a) above but using 3-[1-(toluene-4-sulfonyl)-1H-pyrrolo[2,3-b]pyridin-2-yl]-1H-indole-6-carboxylic acid methyl ester [Reference Example 12(f)] and methyl iodide, there was prepared 1-methyl-3-[1-(toluene-4-sulfonyl)-1H-pyrrolo[2,3-b]pyridin-2-yl]-1H-indole-6-carboxylic acid methyl ester as a tan solid. MS: 460(MH$^+$). TLC: R$_F$=0.6 (pentane/ethyl acetate: 1/1).

(h) By proceeding in a similar manner to Reference Example 13(a) above but using 2-(5-methoxy-1H-indol-3-yl)-1-(toluene-4-sulfonyl)-1H-pyrrolo[2,3-b]pyridine-4-carbonitrile (Reference Example 100) there was prepared 2-(5-methoxy-1-methyl-1H-indol-3-yl)-1-(toluene-4-sulfonyl)-1H-pyrrolo[2,3-b]pyridine-4-carbonitrile as a yellow oil. TLC: R$_F$=0.40 (ethyl acetate:heptane 1:1). MS: 457 (MH$^+$).

(i) By proceeding in a similar manner to Reference Example 13(a) above but using 4-chloro-2-(5-methoxy-1H-indol-3-yl)-1-(toluene-4-sulfonyl)-1H-pyrrolo[2,3-b]pyridine [Reference Example 12(h)] and methyl iodide, there was prepared 4-chloro-2-(5-methoxy-1-methyl-1H-indol-3-yl)-1-(toluene-4-sulfonyl)-1H-pyrrolo[2,3-b]pyridine as a off-white solid. MS: 466 (MH$^+$). $^1$H NMR (CDCl$_3$): δ 8.35 (d, 1H); 7.56 (d, 2H), 7.39 (s, 1H); 7.16–7.3 (m, 2H), 7.05 (d, 2H), 6.95–7.0 (m, 2H) 6.6 (s, 1H) 3.9 (s, 3H) 3.8 (s, 3H) 2.3 (s, 3H).

(j) By proceeding in a similar manner to Reference Example 13(a) above but using 2-(5-methoxy-1H-indol-3-yl)-5-phenyl-1-(toluene-4-sulfonyl)-1H-pyrrolo[2,3-b]pyridine [Reference Example 12(i)] and methyl iodide, there was prepared 2-(5-methoxy-1-methyl-1H-indol-3-yl)-5-phenyl-1-(toluene-4-sulfonyl)-1H-pyrrolo[2,3-b]pyridine as a yellow solid, m.p. 181–183° C. MS: 508 (MH$^+$).

REFERENCE EXAMPLE 14

(a) 1-Methyl-3-[1-(toluene-4-sulfonyl)-1H-pyrrolo[2,3-b]pyridin-2-yl]-1H-indol-5-ol To a solution of 2-(5-methoxy-1-methyl-1H-indol-3-yl)-1-(toluene-4-sulfonyl)-1H-pyrrolo[2,3-b]pyridine [24.5 g, Reference Example 13(b)] in dichloromethane (500 mL), at 0° C. under an atmosphere of nitrogen, was added a solution of boron tribromide in dichloromethane (60 mL, 1.0M) and the mixture was stirred at 0° C. for 1 hour. The reaction mixture was allowed to warm slowly to ambient temperature and stirring continued for 12 hours. A solution of sodium carbonate (1M, 250 mL) was added to the mixture and stirring was continued vigorously for 3 hours. The precipitated solid was collected by filtration, washed with dichloromethane (100 mL) and dried to give the title compound (18.75 g) as a colourless solid, m.p. 256–257° C. MS: 418(MH$^+$).

(b) By proceeding in a manner similar to Reference Example 14(a) above but using 2-(5-methoxy-1H-indol-3-yl)-1-(toluene-4-sulfonyl)-1H-pyrrolo[2,3-b]pyridine [Reference example 12(a)], there was prepared 3-[1-(toluene-4-sulfonyl)-1H-pyrrolo[2,3-b]pyridin-2-yl]-1H-indol-5-ol as a beige solid, m.p. 188–191° C. MS: 403(MH$^+$).

REFERENCE EXAMPLE 15

(a) 2-(5-Allyloxy-1-methyl-1H-indol-3-yl)-1-(toluene-4-sulfonyl)-1H-pyrrolo[2,3-b]pyridine A solution of 1-methyl-3-[1-(toluene-4-sulfonyl)-1H-pyrrolo[2,3-b]pyridin-2-yl]-1H-indol-5-ol [2.1 g, Reference Example 14(a)] in dry dimethylformamide (50 mL) was treated with potassium tert-butoxide (620 mg) at 0° C. under nitrogen. After stirring for 10 minutes the mixture was treated with allyl bromide (480 µl) and then allowed to warm slowly to ambient temperature. Stirring was continued for a further 6 hours after which time the mixture was poured carefully into water and the aqueous phase extracted exhaustively with ethyl acetate. The combined organic extracts were washed twice with brine (100 mL), then dried over sodium sulfate and then evaporated. The residue was subjected to flash column chromatography on silica eluting with a mixture of ethyl acetate and pentane (1:1, v/v) to give the title compound (1.2 g) as a yellow foam, m.p. 257–259° C. MS: 458($MH^+$).

(b) By proceeding in a manner similar to Reference Example 15(a) above but using ethyl-2-chloroacetate there was prepared {1-methyl-3-[1-(toluene-4-sulfonyl)-1H-pyrrolo[2,3-b]pyridin-2-yl]-1H-indol-5-yloxy}-acetic acid ethyl ester as a yellow solid. TLC: $R_F$=0.45 (ethyl acetate/pentane: 1/1). MS: 504($MH^+$).

(c) By proceeding in a manner similar to Reference Example 15(a) above but using ethyl 2-bromoproprionate there was prepared 3-{1-methyl-3-[1-(toluene-4-sulfonyl)-1H-pyrrolo[2,3-b]pyridin-2-yl]-1H-indol-5-yloxy}-propionic acid ethyl ester as a yellow solid. TLC: $R_F$=0.47 (ethyl acetate/pentane: 1/1). MS: 519($MH^+$).

(d) By proceeding in a manner similar to Reference Example 15(a) above but using ethyl-1-bromocyclobutanecarboxylate there was prepared 1-{1-methyl-3-[1-(toluene-4-sulfonyl)-1H-pyrrolo[2,3-b]pyridin-2-yl]-1H-indol-5-yloxy}-cyclobutanecarboxylic acid ethyl ester as a colourless solid, m.p. 189–190° C. MS: 544 ($MH^+$).

(e) By proceeding in a similar manner to Reference Example 15(a) above but using 1-methyl-3-(5H-pyrrolo[2,3-b]pyrazin-6-yl)-1H-indol-5-ol (Example 7) and ethyl 1-bromocyclobutane carboxylate there was prepared {1-[1-methyl-3-(5H-pyrrolo[2,3-b]pyrazin-6-yl)-1H-indol-5-yloxy]-cyclobutylcarboxylic acid ethyl ester as a tan solid. TLC: $R_F$=0.23 (dichloromethane/methanol, 19:1). HPLC (METHOD A): $R_T$=7.71 minutes.

REFERENCE EXAMPLE 16

3-{1-Methyl-3-[1-(toluene-4-sulfonyl)-1H-pyrrolo[2,3-b]pyridin-2-yl]-1H-indol-5-yloxy}-propane-1,2-diol A solution of 2-(5-allyloxy-1-methyl-1H-indol-3-yl)-1-(toluene-4-sulfonyl)-1H-pyrrolo[2,3-b]pyridine [45.7 mg, Reference Example 15 (a)] in acetone (10 mL) was treated with a solution of 4-methylmorpholine-N-oxide (6 mg) in water (1 mL). This mixture was then treated with osmium tetroxide (2.5%/wt in tert-butanol, 6 drops) and the mixture stirred at room temperature for 12 hours. The reaction mixture was diluted with water (75 mL), and extracted exhaustively with ethyl acetate. The combined organics were washed twice with brine (75 mL), then dried over magnesium sulfate and then evaporated. The residue was subjected to flash column chromatography on silica eluting with ethyl acetate to give the title compound (33 mg) as a colourless solid. TLC: $R_F$=0.25 (ethyl acetate). MS: 492($MH^+$).

REFERENCE EXAMPLE 17

3-{1-Methyl-3-[1-(toluene-4-sulfonyl)-1H-pyrrolo[2,3-b]pyridin-2-yl]-1H-indol-5-yloxy}-propan-1-ol and 3-{1-Methyl-3-[1-(toluene-4-sulfonyl)-1H-pyrrolo[2,3-b]pyridin-2-yl]-1H-indol-5-yloxy}-propan-2-ol A solution of 2-(5-allyloxy-1-methyl-1H-indol-3-yl)-1-(toluene-4-sulfonyl)-1H-pyrrolo[2,3-b]pyridine [91 mg, Reference Example 15(a)] in dry tetrahydrofuran (5 mL) was treated with a solution of borane-tetrahydrofuran complex in tetrahydrofuran(1200 μl, 1.0M). After stirring at ambient temperature for 7 hours the reaction mixture was treated with ethanol (9 drops), 5N potassium hydroxide (4 drops) and hydrogen peroxide (6 drops) and stirring was continued for 12 hours during which time a white solid was precipitated. The reaction mixture was diluted with water (50 mL) and the pH of this mixture was adjusted to 10 by addition of potassium hydroxide solution (1M) before exhaustively extracting with ethyl acetate. The combined organic extracts were dried over sodium sulfate then evaporated. The residue was subjected to flash column chromatography on silica eluting with a mixture of ethyl acetate and pentane (2:1, v/v) to give 3-{1-methyl-3-[1-(toluene-4-sulfonyl)-1H-pyrrolo[2,3-b]pyridin-2yl]-1H-indol-5-yloxy}-propan-1-ol (50 mg) as a colourless solid [TLC: $R_F$=0.15 (ethyl acetate). MS: 476($MH^+$)] and 3-{1-methyl-3-[1-(toluene-4-sulfonyl)-1H-pyrrolo[2,3-b]pyridin-2-yl]-1H-indol-5-yloxy}-propan-2-ol (8 mg) as a colourless solid. [TLC: $R_F$=0.3 (ethyl acetate); MS: 476($MH^+$)].

REFERENCE EXAMPLE 18

(a) Trifluoro-methanesulfonic acid 1-methyl-3-[1-(toluene-4-sulfonyl)-1H-pyrrolo[2,3-b]pyridin-2-yl]-1H-indol-5-yl ester A suspension of 1-methyl-3-[1-(toluene-4-sulfonyl)-1H-pyrrolo[2,3-b]pyridin-2-yl]-1H-indol-5-ol [398 mg, Reference Example 14(a)] in dichloromethane (10 mL), cooled to −78° C. under a nitrogen atmosphere, was treated with triethylamine (0.15 mL) followed by N-phenyltrifluormethanesulfonimide (1.7 g). The resultant mixture was allowed to warm slowly to ambient temperature, stirring was continued for a further 12 hours then saturated sodium bicarbonate (20 mL) was added. The organic phase was separated and the aqueous phase was extracted twice with dichloromethane (20 mL). The combined organics were dried over sodium sulfate then evaporated. The residue was subjected to flash column chromatography on silica eluting with a mixture of ethyl acetate and pentane (2:3, v/v) to give the title compound (380 mg) as a colourless solid. MS: 492($MH^+$). HPLC (METHOD A): $R_T$=2.02 minutes.

(b) By proceeding in a similar manner to Reference Example 18(a) but using 1-methyl-3-(5H-pyrrolo[2,3-b]pyrazin-6-yl)-1H-indol-5-ol (Example 7) there was prepared 2-(1-methyl-5-trifluoromethylsulfonyloxyindol-3-yl)-1H-pyrrolo[2,3-b]pyrazine as a purple solid. HPLC (METHOD A): $R_T$=8.12 minutes. $^1$H NMR [($CD_3$)$_2$SO]: δ 12.30 (1H, s); 8.32 (1H, s); 8.27 (1H, d, J=3.5 Hz); 8.23 (1H, s); 7.97 (1H, s); 7.76 (1H, d, J=8.6 Hz); 7.08 (1H, s); 3.96 (3H, s).

REFERENCE EXAMPLE 19

(a) 1-Methyl-3-[1-(toluene-4-sulfonyl)-1H-pyrrolo[2,3-b]pyridin-2-yl]-1H-indole-5-carboxylic acid methyl ester A solution of trifluoro-methanesulfonic acid 1-methyl-3-[1-(toluene-4-sulfonyl)-1H-pyrrolo[2,3-b]pyridin-2-yl]-1H-indol-5-yl ester [300 mg, Reference Example 18(a)] in a mixture of dry dimethylformamide (10 mL), methanol (6 mL) and triethylamine (2 mL) was treated with palladium acetate (24 mg) and 1,3 bis(diphenylphosphino)propane and the mixture stirred at ambient temperature for 30 minutes. Carbon monoxide was introduced via a septum to the reaction vessel at a steady rate and the mixture heated at 90° C. until no starting material was present as indicated by TLC (ethyl acetate/pentane: 2/3). The mixture was then concentrated in vacuo and the residue partitioned between dichloromethane and water. The organic phase was washed with a saturated solution of lithium chloride, then dried over sodium sulfate and then evaporated. The residue was subjected to flash column chromatography on silica eluting with a mixture of ethyl acetate and pentane (2:3, v/v) to give the title compound (200 mg) as a colourless solid. MS: 460 (MH+). HPLC (METHOD A): $R_T$=10.23 minutes.

(b) By proceeding in a similar manner to Reference Example 19(a) but using 2-(1-methyl-5-trifluoromethylsulfonyloxyindol-3-yl)-1H-pyrrolo[2,3-b]pyrazine (Reference Example 18(b)) there was prepared methyl 1-methyl-3-(5H-pyrrolo[2,3-b]pyrazin-6-yl)-1H-indole-5-carboxylate as a brown solid. MS 307 (MH$^+$). HPLC (METHOD A): $R_T$=6.64 minutes.

REFERENCE EXAMPLE 20

2-[1-Methyl-5-(1-trimethylstannanyl-1H-tetrazol-5-yl)-1H-indol-3-yl]-1-(toluene-4-sulfonyl)-1H-pyrrolo[2,3-b]pyridine A solution of 1-methyl-3-[1-(toluene-4-sulfonyl)-1H-pyrrolo[2,3-b]pyridin-2-yl]-1H-indole-5-carbonitrile [100 mg, Reference Example 13(c)] in toluene (10 mL) was treated with trimethyltin azide (56 mg, 0.28 mmol) then heated under reflux for 14 hours. The white precipitate was collected by filtration washed with toluene (10 mL) and then dried to give the title compound (125 mg) as a colourless solid, m.p. 240–243° C. (with decomposition). MS: 633 (MH$^+$).

REFERENCE EXAMPLE 21

2-[1-Methyl-5-(1-methyl-1H-tetrazol-5-yl)-1H-indol-3-yl]-1-(toluene-4-sulfonyl)-1H-pyrrolo[2,3-b]pyridine and 2-[1-Methyl-5-(2-methyl-2H-tetrazol-5-yl)-1H-indol-3-yl]-1-(toluene-4-sulfonyl)-1H-pyrrolo[2,3-b]pyridine Methyl iodide (2.5 mL) was added to a solution of 2-[1-methyl-5-(1-trimethylstannanyl-1H-tetrazol-5-yl)-1H-indol-3-yl]-1-(toluene-4-sulfonyl)-1H-pyrrolo[2,3-b]pyridine [620 mg, Reference Example 20] at ambient temperature. The mixture was then allowed to stir at ambient temperature for 4 hours then was poured into water and then extracted with ethyl acetate. The combined extract was washed with brine, then dried over magnesium sulfate and then evaporated. The residue was subjected to flash chromatography on silica eluting with a mixture of ethyl acetate and petroleum ether (1:1, v/v) to give 2-[1-methyl-5-(1-methyl-1H-tetrazol-5-yl)-1H-indol-3-yl]-1-(toluene-4-sulfonyl)-1H-pyrrolo[2,3-b]pyridine (191 mg) as a colourless solid, [MS: 506(MNa$^+$). $^1$H NMR [(CD$_3$)$_2$SO]: δ 8.39 (dd, 1H, J=4.8 and 1.6 Hz); 7.97 (m, 1H); 7.96 (d, 1H, J=4.0 Hz); 7.90 (s, 1H); 7.80 (dd, 1H, J=8.7 and 0.6 Hz); 7.70 (dd, 1H, J=8.7 and 1.8 Hz); 7.56 (m, 2H); 7.30 (dd, 1H, J=7.7 and 4.8 Hz); 7.22 (m, 2H); 6.82 (s, 1H); 4.19 (s, 3H); 4.0 (s, 3H); 2.23 (s, 3H)] and 2-[1-Methyl-5-(2-methyl-2H-tetrazol-5-yl)-1H-indol-3-yl]-1-(toluene-4-sulfonyl)-1H-pyrrolo[2,3-b]pyridine (77 mg) as a colourless solid, m.p. 215–218° C. [MS: 506 (MNa$^+$)].

REFERENCE EXAMPLE 22

1-{1-Methyl-3-[1-(toluene-4-sulfonyl)-1H-pyrrolo[2,3-b]pyridin-2-yl]-1H-indol-5-yl}ethanone To dry, degassed dimethylformamide (110 mL) under nitrogen at ambient temperature, was added trifluoro-methanesulfonic acid 1-methyl-3-[1-(toluene-4-sulfonyl)-1H-pyrrolo[2,3-b]pyridin-2-yl]-1H-indol-5-yl ester [2.2 g, Reference Example 18], triethylamine (1.15 mL), n-butylvinylether (2.87 mL), 1,3-bis(diphenylphosphinopropane) (413 mg) and palladium acetate (232 mg) sequentially. The mixture was heated at reflux for 2 hours then cooled to ambient temperature and then added to hydrochloric acid (90 mL, 1M). This mixture was extracted with dichloromethane (200 mL). The organic extract was washed with saturated aqueous sodium bicarbonate, then with brine, then dried over magnesium sulfate and then evaporated. The residue was subjected to flash chromatography on silica eluting with a mixture of ethyl acetate and pentane (2:3, v/v) to give the title compound (1.1 g) as a yellow solid, m.p. 177–178° C. MS: 444(MH$^+$).

REFERENCE EXAMPLE 23

(a) 2-[5-({S}-(+)-2,2-Dimethyl-[1,3]dioxolan-4-ylmethoxy)-1-methyl-1H-indol-3-yl]-1-(toluene-4-sulfonyl)-1H-pyrrolo[2,3-b]pyridine A solution of 1-methyl-3-[1-(toluene-4-sulfonyl)-1H-pyrrolo[2,3-b]pyridin-2-yl]-1H-indol-5-ol [1.17 g, Reference Example 14(a)] in dry dimethylformamide (50 mL) was treated with caesium carbonate (1.1 g) and tetrabutylammonium hydrogen sulfate (40 mg). After stirring at ambient temperature for 30 minutes the mixture was treated with (R)-(+)-2,2-dimethyl-1,3-dioxolane-4-ylmethyl-paratoluenesulfonate (0.96 g) then heated at 120° C. overnight. The reaction mixture was concentrated in vacuo and the residue partitioned twice between dichloromethane (100 mL) and water (50 mL) and the aqueous layers were extracted with dichloromethane (100 mL). The combined organic phases were washed twice with brine (150 mL), then dried over magnesium sulfate and then evaporated. The residue was subjected to flash chromatography on silica eluting with a mixture of dichloromethane and methanol (199:1, v/v) to give the title compound (1.04 g) as a yellow oil, MS: 532(MH$^+$). $^1$H NMR [(CD$_3$)$_2$SO]: δ 1.30 (3H, s); 1.37 (3H, s); 2.29 (3H, s); 3.76 (1H, dd, J=8.3 and 6.5 Hz); 3.90 (3H, s); 3.94–3.98 (2H, m); 4.10 (1H, dd, J=8.20 and 6.5 Hz); 4.41 (1H, m); 6.74 (1H, s); 6.91 and 2.3 Hz); 6.98 (1H, d, J=2.4 Hz); 7.25 (2H, d, J=7.9 Hz); 7.29 (1H, dd, J=7.8 and 4.9 Hz); 7.44 (1H, d, J=8.8 Hz); 7.56 (1H, d, J=8.3 Hz); 7.63 (1H, s); 7.81 (2H, d, J=8.0 Hz); 7.92 (1H, dd, J=7.7 and 1.6 Hz); 8.33. (1H, dd, J=4.9 and 1.7 Hz).

(b) By proceeding in a manner similar to Example 23(a) above but using (S)-(–)-2,2-dimethyl-1,3-dioxolane-4-ylmethyl-paratoluenesulfonate there was prepared 2-[5-({R})-(–)-2,2-dimethyl-[1,3]dioxolan-4-ylmethoxy)-1-methyl-1H-indol-3-yl]-1-(toluene-4-sulfonyl)-1H-pyrrolo[2,3-b]pyridine as a yellow oil, MS: 532 (MH$^+$). $^1$H NMR [(CD$_3$)$_2$SO]: δ 1.33 (3H, s); 1.37 (3H, s); 137 (3H, s); 2.29 (3H, s); 3.77 (1H, dd, J=8.3 and 6.5 Hz); 3.88 (3H, s); 3.97–3.99 (2H, m); 4.11 (1H, dd, J=8.3 and 6.6 Hz); 4.41 (1H, m); 6.74 (1H, s); 6.94 (1H, dd, J=8.8 and 2.3 Hz); 6.97 (1H, d, J=2.3 Hz); 7.25 (2H, d, J=8.1 Hz); 7.29 (1H, dd, J=7.8 and 4.9 Hz); 7.44 (1H. d. J=8.8 Hz); 7.57 (2H, d, J=8.4 Hz); 7.63 (1H, s); 7.95 (1H, dd, J=7.81 and 1.7 Hz); 8.33 (1H, dd, J=4.88 and 1.7 Hz).

(c) By proceeding in a manner similar to Example 23(a) above but using 2-(5-hydroxy-6-methoxy-1-methyl-1H-indol-3-yl)-1-(toluene-4-sulfonyl)-1H-pyrrolo[2,3-b]pyridine [Reference Example 28(a)], there was prepared 2-[5-({S}-(+)-2,2-dimethyl-[1,3dioxolan-4-ylmethoxy)-6-methoxy-1-methyl-1H-indol-3-yl]-1-(toluene-4-sulfonyl)-1H-pyrrolo[2,3-b]pyridine as a cream solid. MS: 548(MH$^+$). HPLC (METHOD A): $R_T$=11.60 minutes.

(d) By proceeding in a manner similar to Example 23(a) above but using 3-[1-(toluene-4-sulfonyl)-1H-pyrrolo[2,3-b]pyridin-2-yl]-1H-indol-5-ol [Reference Example 14(b)] and ethyl 1-bromocyclobutane carboxylate, there was prepared 1-{1-(cyclobutanecarboxylic acid ethyl ester)-3-[1-(toluene-4-sulfonyl)-1H-pyrrolo[2,3-b]pyridin-2-yl]-1H-indol-5-yloxy}-cyclobutanecarboxylic acid ethyl ester as a cream solid. MS: 657(MH$^+$). $^1$H NMR [(CD$_3$)$_2$SO]: δ 8.35 (1H, dd, J=4.8 and 1.6 Hz); 7.9 (2H, m); 7.48 (3H, m); 7.28 (1H, dd, J=7.7 and 4.8 Hz); 7.24 (2H, d, J=8.4 Hz); 6.71 (1H, dd, J=8.9 and 2.4 Hz); 6.68 (1H, s); 6.64 (1H, d, J=2.4 Hz); 5.12 (1H, dd, J=8.8 and 8.8 Hz); 4.13–4.03 (4H, m); 3.66 (1H, dd, J=9.4 and 9.4 Hz); 2.64–1.82 (13H, m); 1.15 (3H, t, J=7.1 Hz); 0.94 (3H, t, J=7.1 Hz).

REFERENCE EXAMPLE 24

(a) (S)-3-{1-Methyl-3-[1-(toluene-4-sulfonyl)-1H-pyrrolo[2,3-b]pyridin-2-yl]-1H-indol-5-yloxy}-propane-1,2-diol A solution of 2-[5-({R}-(−)-2,2-dimethyl-[1,3]dioxolan-4-ylmethoxy)-1-methyl-1H-indol-3-yl]-1-(toluene-4-sulfonyl)-1H-pyrrolo[2,3-b]pyridine [1.04 g, Reference Example 23(b)] in methanol (20 mL) was treated with hydrochloric acid (20 mL, 1M) then heated under reflux for 3 hours. The reaction mixture was concentrated in vacuo and the residue subjected to flash chromatography on silica eluting with a mixture of ethyl acetate and pentane (2:1, v/v) to give the title compound (380 mg) as a clear oil. TLC: R$_F$=0.2 (pentane/ethyl acetate: 1/2). MS: 492(MH$^+$).

(b) By proceeding in a manner similar to Example 24(a) but using 2-[5-({S}-(+)-2,2-dimethyl-[1,3]dioxolan-4-ylmethoxy)-1-methyl-1H-indol-3-yl]-1-(toluene-4-sulfonyl)-1H-pyrrolo[2,3-b]pyridine [Reference Example 23(a)] there was prepared (R)-3-{1-methyl-3-[1-(toluene-4-sulfonyl)-1H-pyrrolo[2,3-b]pyridin-2-yl]-1H-indol-5-yloxy}-propane-1,2-diol as a clear oil.

MS: 492(MH$^+$). $^1$H NMR [(CD$_3$)$_2$SO]: δ 8.33 (1H, dd, 4.9, J=1.7 Hz); 7.92 (1H, dd, J=7.8 and 1.7 Hz); 7.62 (1H, s); 7.56 (2H, d, J=8.8 Hz); 7.45 (1H, d, J=8.8 Hz); 7.29 (1H, dd, J=7.8 and 4.8 Hz); 7.25 (2H, d, J=8.1 Hz); 6.96 (1H, d, J=2.3 Hz); 6.92 (1H, dd, J=8.8 and 2.3 Hz); 6.75 (1H, s); 4.93 (1H, s); 4.66 (1H, s); 5.13 (1H, d, J=5.13 Hz); 3.88 (3H, s); 3.80 (2H, d, J=5.9 Hz); 3.46 (2H, s); 2.23 (3H, s).

(c) By proceeding in a manner similar to Example 24(a) above but using 2-[5-({S}-(+)-2,2-dimethyl-[1,3]dioxolan-4-ylmethoxy)-6-methoxy-1-methyl-1H-indol-3-yl]-1-(toluene-4-sulfonyl)-1H-pyrrolo[2,3-b]pyridine [Reference Example 23(c )] there was prepared (R)-3-{6-methoxy-1-methyl-3-[1-(toluene-4-sulfonyl)-1H-pyrrolo[2,3-b]pyridin-2-yl]-1H-indol-5-yloxy}-propane-1,2-diol as a cream solid. MS: 522(MH$^+$). HPLC (METHOD A): R$_T$=8.15 minutes.

REFERENCE EXAMPLE 25

2-[5-(2-Methoxy-1-methyl-ethoxy)-1-methyl-1H-indol-3-yl]-1-(toluene-4-sulfonyl)-1H-pyrrolo[2,3-b]pyridine A solution of triphenylphosphine (470 mg) and diisopropyldiazodicarboxylate (350 μl) in dry toluene (15 mL) was treated with 1-methyl-3-[1-(toluene-4-sulfonyl)-1H-pyrrolo[2,3-b]pyridin-2-yl]-1H-indol-5-ol [150 mg, Reference Example 14(a)] followed by 1-methoxy-2-propanol (150 μl). The resulting mixture was heated under reflux for 5 hours then cooled and then evaporated. The residue was subjected to flash chromatography on silica eluting with a mixture of ethyl acetate and pentane (1:1, v/v) to give the title compound (50 mg) as a clear oil. TLC: R$_F$=0.65 (pentane/ethyl acetate: 1/1). MS: 480(MH$^+$).

REFERENCE EXAMPLE 26

N-Hydroxy-1-methyl-3-[1-toluene-4-sulfonyl)-1H-pyrrolo[2,3-b]pyridin-2-yl]-1H-indole-5-carboxamidine A solution of 1-methyl-3-[1-(toluene-4-sulfonyl)-1H-pyrrolo[2,3-b]pyridin-2-yl]-1H-indole-5-carbonitrile [2.11 g, Reference Example 13(c)] in ethanol (150 mL) at ambient temperature was treated with hydroxylamine hydrochloride (1.72 g) and potassium carbonate (3.43 g). The reaction mixture was heated at reflux under nitrogen for 15 hours then filtered. The filtrate was evaporated to give the title compound (2.8 g) as a dark green solid. MS: 460(MH$^+$). HPLC (METHOD A): R$_T$=6.19 minutes.

REFERENCE EXAMPLE 27

2-[1-Methyl-5-(5-methyl-[1,2,4]oxadiazol-3-yl)-1H-indol-3-yl]-1-(toluene-4-sulfonyl)-1H-pyrrolo[2,3-b]pyridine To a suspension of N-hydroxy-1-methyl-3-[1-(toluene-4-sulfonyl)-1H-pyrrolo[2,3-b]pyridin-2-yl]-1H-indole-5-carboxamidine [0.7 g, Reference Example 26] in toluene (30 mL) at ambient temperature under nitrogen was added acetic anhydride (0.467 g). The reaction mixture was heated at reflux for 4.5 hours then filtered. The filtrate was evaporated to give the title compound (0.32 g) as a dark red oil which was used immediately without further purification.

REFERENCE EXAMPLE 28

2(5-Hydroxy-6-methoxy-1-methyl-1H-indol-3-yl)-1-(toluene-4-sulfonyl)-1H-pyrrolo[2,3-b]pyridine A solution of 2-(5-benzyloxy-6-methoxy-1-methyl-1H-indol-3-yl)-1-(toluene-4-sulfonyl)-1H-pyrrolo[2,3-b]pyridine [6.26 g, Reference Example 13(e)] in acetonitrile (500 mL) was treated with sodium iodide (4.38 g) followed by trimethylsilyl chloride (3.17 mL). The mixture stirred at 40° C. for 3 hours then treated with further portions of sodium iodide (4.38 g) and trimethylsilyl chloride (3.17 mL). After stirring at 40° C. for a further 12 hours the reaction mixture was evaporated. The residue was treated with water (200 mL) and the mixture was extracted three times with ethyl acetate (200 mL). The combined extracts were dried over magnesium sulfate then evaporated. The residual brown foam was triturated with ethyl acetate and diisopropyl ether to give the title compound (3.04 g) as a light brown solid, m.p. 211–214° C. HPLC (METHOD A): R$_T$=9.30 minutes.

REFERENCE EXAMPLE 29

1-{6-Methoxy-1-methyl-3-[1-toluene-4-sulfonyl)-1H-pyrrolo[2,3-b]pyridin-2-yl]-1H-indol-5-yloxy}-cyclobutanecarboxylic acid ethyl ester Sodium hydride (43 mg, 60% dispersion in mineral oil) was added to a stirred solution of 2-(5-hydroxy-6-methoxy-1-methyl-1H-indol-3-yl)-1-(toluene-4-sulfonyl)-1H-pyrrolo[2,3-b]pyridine [400 mg, Reference Example 28(a)] in dry dimethylformamide (20 mL) under a nitrogen atmosphere at ambient temperature. The mixture was allowed to stir for 1 hour then treated with ethyl-1-bromocyclobutanecarboxylate (216 μl) and stirring was continued overnight. Additional portions of sodium hydride (43 mg, 60% dispersion in mineral oil) and ethyl 1-bromocyclobutanecarboxylate (216 μl ) were then added, then the mixture was heated at 50° C. for 5 hours. The cooled reaction mixture was evaporated and the residue was partitioned between ethyl acetate and water. The organic phase was washed with water, then with brine, then dried over magnesium sulfate and then evaporated. The yellow residue was subjected to flash chromatography on silica eluting with a mixture of ethyl acetate and pentane (2:3, v/v) to give the title compound (266 mg) as a yellow oil. MS: 576(MH$^+$). HPLC (METHOD A): R$_T$=11.07 minutes.

REFERENCE EXAMPLE 30

[1-Methyl-3-(1H-pyrrolo[2,3-b]pyridin-2-yl)-1H-indol-5-yl]-carbamic acid tert-butyl ester A solution of {1-methyl-3-[1-(toluene-4-sulfonyl)-1H-pyrrolo[2,3-b]pyridin-2-yl]-1H-indol-5-yl}-carbamic acid tert-butyl ester [0.3 g, Reference Example 13(f)] in methanol (15 mL) was treated with potassium hydroxide solution (5N, 2 mL) then heated at reflux for 4 hours. The reaction mixture was evaporated and the residue triturated with water to give the title compound (0.2 g) as a tan solid. MS: 263(MH$^+$). TLC: R$_F$=0.3 (ethyl acetate).

REFERENCE EXAMPLE 31

1H-Indole-6-carboxylic acid methyl ester

A solution of 1H-indole-6-carboxylic acid (10 g) in methanol (300 mL) was treated with concentrated sulfuric acid (0.5 mL) then heated on a steam bath for 10 hours. The solvent was removed under reduced pressure and the residue partitioned between saturated sodium bicarbonate solution (150 mL) and dichloromethane (150 mL). The aqueous layer was further extracted twice with dichloromethane (150 mL). The combined organics were dried over sodium sulfate then evaporated. The residue was subjected to flash chromatography on silica eluting with a mixture of ethyl acetate and pentane (7:3, v/v) to give the title compound (7.4 g) as a white solid, m.p. 79–81° C. MS: 176(MH$^+$).

REFERENCE EXAMPLE 32

Dimethyl-(6-phenyl-5H-pyrrolo[2,3-b]pyrazin-7-ylmethyl)-amine

A solution of dimethylamine in tetrahydrofuran (0.5 mL, 2.0M) at 0° C. was treated with glacial acetic acid (15 µl) then with formaldehyde (75 µl, 40% solution). After stirring at 0° C. for 10 minutes this mixture was treated with 6-phenyl-5H-pyrrolo[2,3-b]pyrazine [0.195 g, Example 2(c)] and then with tetrahydrofuran (3 mL) to ensure complete dissolution. The reaction mixture was allowed to warm to ambient temperature, then stirred overnight, then diluted with ethyl acetate (5 mL) and then extracted three times with hydrochloric acid (5 mL, 1N). The combined acid extracts were adjusted to pH 6–7 by addition of potassium hydroxide solution (5N). The resulting pale yellow solid was filtered, then washed with water and then dried to give the title compound (0.16 g) as a pale yellow solid, m.p. 191–192° C.

REFERENCE EXAMPLE 33

Trimethyl-(6-phenyl-5H-pyrrolo[2,3-b]pyrazin-7-ylmethyl)-ammonium iodide

A solution of dimethyl-(6-phenyl-5H-pyrrolo[2,3-b]pyrazin-7-ylmethyl)-amine [5.1 g, Reference Example 32] in ethyl acetate (100 mL) at 0° C. was treated with a solution of iodomethane (40 mL) in ethanol (150 mL). The resulting mixture was stirred at 0° C. for 2 hours. The precipitated solid was filtered then washed with ethyl acetate (10 mL) and then with diethyl ether (20 mL) to give the title compound as a yellow solid (4.5 g), m.p. 224–225° C.

REFERENCE EXAMPLE 34

(6-Phenyl-5H-pyrrolo[2,3-b]pyrazin-7-yl)-acetonitrile

A solution of potassium cyanide (0.84 g) in water (20 mL) was added rapidly to a stirred solution of trimethyl(6-phenyl-5H-pyrrolo[2,3-b]pyrazin-7-ylmethyl)-ammonium iodide [1.1 g, Reference Example 33] in dimethylformamide (20 mL) and the mixture heated at 75° C. for 6 hours. The cooled solution was diluted with water (100 mL) and the precipitated solid filtered to give the title compound as a yellow solid, m.p. 247–248° C.

REFERENCE EXAMPLE 35

(6-Phenyl-5H-pyrrolo[2,3-b]pyrazin-7-yl)-acetic acid

A solution of (6-phenyl-5H-pyrrolo[2,3-b]pyrazin-7-yl)-acetonitrile [70 mg, Reference Example 34] in potassium hydroxide (10M, 5 mL) was heated at 100° C. for 1.5 hours. The reaction mixture was allowed to cooled, then diluted with water (25 mL) and then acidified to pH 1 by addition of concentrated hydrochloric acid. The resulting pale yellow solid was filtered, then washed with water and then dried to give the title compound (40 mg) as a yellow solid, m.p. 276–277° C.

REFERENCE EXAMPLE 36

1-Methyl-3-[1-(toluene-4-sulfonyl)-1H-pyrrolo[2,3-b]pyridin-2-yl]-1H-indole-5-carbaldehyde To a solution of 1-methyl-3-[1-(toluene-4-sulfonyl)-1H-pyrrolo[2,3-b]pyridin-2-yl]-1H-indole-5-carbonitrile [500 mg, Reference Example 13(c)] in tetrahydrofuran (20 mL) at 0° C. was added diisobutylaluminium hydride (12 mL, 1M in tetrahydrofuran) under an atmosphere of nitrogen. The resultant solution was then allowed to warm to ambient temperature and stirred at this temperature for 2 hours. The reaction mixture was then poured into a solution of cold 1N aqueous hydrochloric acid (20 mL). After 1 hour, the mixture was made alkaline with saturated aqueous sodium hydroxide and extracted with ethyl acetate (40 mL). The organic layer was separated and the aqueous further extracted with ethyl acetate (2×20 mL). The organic extracts were combined, dried over magnesium sulfate and concentrated in vacuo to give the title compound (221 mg) as a white solid, m.p. 188–189° C. MS: 430 (MH$^+$).

REFERENCE EXAMPLE 37

3-{1-Methyl-3-[1-(toluene-4-sulfonyl)-1H-pyrrolo[2,3-b]pyridin-2-yl]-1H-indol-5-yl}-acrylic acid ethyl ester Triethylphosphonoacetate (60 mL) was added at 0° C. to a suspension of sodium hydride (22.4 mg, 60% dispersion in mineral oil) in dimethoxyethane (3 mL). The resultant suspension was stirred at ambient temperature for 1 hour. 1-Methyl-3-[1-(toluene-4-sulfonyl)-1H-pyrrolo[2,3-b]pyridin-2-yl]-1H-indole-5-carbaldehyde [120 mg, Reference Example 36] in dimethoxyethane (2 mL) was added and stirring was continued for 3 hours. The reaction mixture was then poured into water and extracted with ethyl acetate (2×30 mL). The combined organics were then washed with brine before drying over magnesium sulfate and then concentrated in vacuo to give the title compound (126 mg) as a yellow solid, m.p. 159–162° C. MS: 500 (MH$^+$).

REFERENCE EXAMPLE 38

(a) 3-{1-Methyl-3-[1-(toluene-4-sulfonyl)-1H-pyrrolo[2,3-b]pyridin-2-yl]-1H-indol-5-yl}-propionic acid ethyl ester Palladium (15.7 mg, 10% on activated carbon) was added to a suspension of 3-{1-methyl-3-[1-(toluene-4-sulfonyl)-1H-pyrrolo[2,3-b]pyridin-2-yl]-1H-indol-5-yl}-acrylic acid ethyl ester [100 mg, Reference Example 37] in industrial methylated spirit (25 mL). The resultant suspension was then stirred under an atmosphere of hydrogen for 16 hours. The reaction mixture was then filtered through a pad of celite and the filtrate evaporated in vacuo. The resultant solid was triturated with water, filtered and dried to give the title compound (92 mg) as a white solid, m.p. 280–282° C. MS: 502 (MH$^+$).

(b) By proceeding in a manner similar to Example 38 (a) above but using ethyl 3-[2-dimethylamino-5-(5H-pyrrolo[2,3-b]pyrazin-6-yl)phenyl]prop-2-enonate (Reference Example 47), there was prepared ethyl 3-[2-dimethylamino-5-(5H-pyrrolo[2,3-b]pyrazin-6-yl)phenyl]propionate as an orange gum which was used directly in the next reaction. $^1$H NMR [(CD3)$_2$SO]; δ 8.33 (1H, s); 8.17 (1H, s); 7.94 (1H, s); 7.82 (1H, d, J=8.4 Hz); 7.20 (1H, d, J=8.4 Hz); 7.03 (1H, s); 4.07 (2H, q, J=7.6 Hz); 3.38 (2H, t, J=7.1 Hz); 3.00 (2H, t, J=7.1 Hz); 2.70 (6H, s); 1.19 (3H, t, J=7.1 Hz).

REFERENCE EXAMPLE 39

4-Methoxy-2-(5-methoxy-1H-indol-3-yl)-1-(toluene-4-sulfonyl)-1H-pyrrolo[2,3-b]pyridine By proceeding in a similar manner to Example 18 but using 2-(1-N-tertbutyloxycarbonyl-5-methoxy-1H-indol-3-yl)-4-methoxy-1-(toluene-4-sulfonyl)-1H-pyrrolo[2,3-b]pyridine (Reference Example 40) there was prepared the title compound as a tan solid. HPLC (METHOD A): R$_T$=8.49 minutes. MS: 448 (MH$^+$).

REFERENCE EXAMPLE 40

2-(1-tert-Butyloxycarbonyl-5-methoxy-1H-indol-3-yl)-4-methoxy-1-(toluene-4-sulfonyl)-1H-pyrrolo[2,3-b]pyridine A stirred solution of diisopropylamine (0.21 mL) in tetrahydrofuran (5 mL), at −70° C. and under nitrogen, was treated with a solution of n-butyllithium in hexanes (0.6 mL, 2.5M) over 5 minutes, whilst maintaining the temperature below −65° C. After stirring for 1 hour the mixture was added, at −30° C., to a solution of 4-methoxy-1-(1-toluene-4-sulfonyl)-1H-pyrrolo[2,3-b]pyridine (Reference Example 41, 280 mg) in tetrahydrofuran (10 mL), whilst maintaining the temperature below −25° C. After allowing to warm to −15° C. over 1 hour a solution of zinc chloride in tetrahydrofuran (2.8 mL, 0.5M) was added, maintaining the temperature below −10° C. After 30 minutes the reaction mixture was treated with tetrakis(triphenylphosphine)palladium [0] (54 mg) and 3-bromo-5-methoxy-indole-1-carboxylic acid tert-butyl ester (Reference Example 11(a), 152 mg) and stirred at 60° C. for 16 hours, then treated with water (30 mL). The mixture was extracted with ethyl acetate (3×25 mL). The combined organics were washed with brine (2×15 mL), dried over magnesium sulfate and then evaporated. The residue was subjected to flash chromatography on silica eluting with a mixture of ethyl acetate and pentane (1:1, v/v) to give the title compound (45 mg) as a white foam. TLC R$_F$=0.34 (ethyl acetate/pentane: 1/1). HPLC (METHOD A): R$_T$=9.72 minutes.

REFERENCE EXAMPLE 41

4-Methoxy-1-(1-toluene-4-sulfonyl)-1H-pyrrolo[2,3-b]pyridine

A mixture of 4-nitro-1-(1-toluene-4-sulfonyl)-1H-pyrrolo[2,3-b]pyridine [Reference Example 9(b), 0.77 g] and dry dimethylformamide (25 mL) was treated with sodium methoxide (0.17 g) and stirred at 50° C. for 16 hours. A further portion of sodium methoxide (0.085 g) was then added and stirring continued for 8 hours, then the dimethylformamide was removed in vacuo. The residue was dissolved in ethyl acetate (100 mL) and washed with a water/brine mixture (1/1, 60 mL). The organics were dried over magnesium sulfate and then evaporated. The residue was subjected to flash chromatography on silica eluting with ethyl acetate to give the title compound as a cream solid. HPLC: R$_T$=9.73 minutes. $^1$H NMR [(CD$_3$)$_2$SO]: δ 8.22 (1H, d, J=8.2 Hz); 7.96 (2H, d, J=9.4 Hz); 7.71 (1H, d, J=3.5 Hz); 7.39 (2H, d, J=9.4 Hz); 6.89 (1H, d, J=8.2 Hz); 6.72 (1H, d, J=3.5 Hz); 3.93 (3H, s); 2.30 (3H, s).

REFERENCE EXAMPLE 42

4-Phenyl-1H-pyrrolo[2,3-b]pyridine

A suspension of 1-(2,6-dimethyl-1,4-dihydropyridin-4-one)-1H-pyrrolo[2,3-b]pyridinium tetrafluoroborate (Reference Example 43, 1.0 g) in tetrahydrofuran (100 mL) was treated with a solution of phenylmagnesium bromide in tetrahydrofuran (9.6 mL, 1M) and stirred at room temperature for 72 hours before adding water ((100 mL) and the tetrahydrofuran removed in vacuo. The residue was extracted with chloroform (3×100 mL), and the combined organics dried over sodium sulphate and evaporated. The residue was subjected to flash chromatography on silica eluting with a mixture of dichloromethane and methanol (99:1 v/v) to give the title compound (83 mg) as a white solid. MS: 195 (MH$^+$). $^1$H NMR (CD$_3$)$_2$SO]: δ 8.27 (1H, d, J=4.1 Hz); 7.78 (2H, d, J=8.2 Hz); 7.57 (3H, m); 7.48 (1H, t, J=8.2 Hz); 7.19 (1H, d, J=3.5 Hz); 6.60 (1H, s).

REFERENCE EXAMPLE 43

1-(2,6-Dimethyl-1,4-dihydropyridin-4-one)-1H-pyrrolo[2,3-b]pyridinium tetrafluoroborate A mixture of ethyl O-2,4,6-trimethylsulfonylacetohydroxamate (28.5 g) in perchloric acid (160 mL, 70%) was stirred at room temperature for 2 hours, then dichloromethane (30 mL) was added. The mixture was poured onto ice/water (1 litre) and rapidly extracted three times with dichloromethane (100 mL). The combined organics were washed twice with brine (100 mL) and dried over sodium sulfate. The organics were then added slowly to a solution of 1H-pyrrolo[2,3-b]pyridine (11.8 g) in dichloromethane (100 mL). Filtration gave 1-amino-1H-pyrrolo[2,3-b]pyridinium 2,4,6-trimethylphenylsulfonate, which was used directly in the next step.

A mixture of 1-amino-1H-pyrrolo[2,3-b]pyridinium 2,4,6-trimethylphenylsulfonate (16.6 g) and 3-acetyl-6-methyl-2H-pyran-2,4(3H)-dione (8.8 g) in concentrated hydrochloric acid (40 mL) was stirred at reflux for 4 hours, then cooled and concentrated in vacuo. The residue was dissolved in ethanol (30 mL) and diluted with a solution of tetrafluoroboric acid in diethyl ether (54% v/v, 30 mL) and stirred for 1 hour at room temperature. Filtration gave the title compound (15.0 g) as a white solid, m.p. 247–248° C. $^1$H NMR [(CD$_3$)$_2$SO]: δ 9.24 (1H, d, J=7.5 Hz); 9.13 (1H, d, J=7.5 Hz); 8.08 (1H, d, J=4.2 Hz); 7.93 (1H, t, J=7.5 Hz); 7.22 (1H, d, J=4.2 Hz); 6.83 (2H, s); 1.96 (6H, s).

REFERENCE EXAMPLE 44

(a) Dimethyl 3-[6-(4-tert-butylphenyl-5H-pyrrolo[2,3-b]pyrazin-7-yl]-propionic1,1-diacid 1,1-dicarboxylate To a solution of dimethyl malonate (1.3 g) dissolved in N-methylpyrrolidinone (30 mL) at 0° C. under nitrogen was added sodium hydride (0.39 g). After 10 minutes, a solution of [6-4-tert-butylphenyl-5H-pyrrolo[2,3-b]pyrazin-7-yl]methyltrimethylammonium iodide [1.12 g, Reference Example 45(a)] was added and the reaction mixture was warmed to room temperature and allowed to stir for 3 hours. The reaction mixture was poured into water (200 mL) and extracted three times with ethyl acetate (100 mL). The combined organic fractions were dried over magnesium sulfate and then evaporated. The residue was subjected to flash column chromatography on silica eluting with a mixture of ethyl acetate and pentane (1:1, v/v) to give the title compound (0.5 g) as a white solid.

$^1$H NMR(CDCl$_3$): δ 9.48 (1H, s); 8.42 (1H, s); 8.16 (1H, s); 7.64 (2H, d, J=9.0 Hz); 7.58 (2H, d, J=9.0 Hz); 4.45 (1H, t, J=8.2 Hz); 3.63 (2H, d, J=8.2 Hz); 3.58 (6H, s); 1.40 (9H, s).

(b) By proceeding in a manner similar to Reference Example 44(a) above but using [6-(4-(1-methyl)ethoxy)phenyl-5H-pyrrolo[2,3-b]pyrazin-7-yl]methyltrimethyl ammonium iodide [Reference Example 45(b)], there was prepared dimethyl 3-[6-(4-(1methyl)ethoxyphenyl)-5H-pyrrolo[2,3-b]pyrazin-7-yl]-propionic 1,1-diacid 1,1-dicarboxylate as a beige solid. MS: 398 (MH$^+$). $^1$H NMR [CDCl$_3$]: δ 10.1(broad s, 1H); 8.41(d, 1H, J=2.3 Hz); 8.16(d, 1H, J=2.3 Hz); 7.62(d, 2H, J=8.21 Hz); 7.03(d, 2H, J=8.20 Hz); 4.64(m, 1H); 4.45(t, 1H); 3.78(d, 1H); 3.60(s, 6H); 1.41(d, 6H, J=4.41 Hz).

(c) By proceeding in a manner similar to Reference Example 44(a) above but using [6-(4-fluorophenyl)-5H-pyrrolo[2,3-b]pyrazin-7-yl]methyltrimethylammonium iodide [Reference Example 45 (c)], there was prepared dimethyl 3-[6-(4-fluorophenyl)-5H-pyrrolo[2,3-b]pyrazin-7-yl]-propionic 1,1-diacid 1,1-dicarboxylate as an off-white solid. NMR DMSO 12.2 (s, 1H), 8.4 (d, 1H), 8.2 (d, 1H), 7.8 (d, 2H), 7.4 (d, 2H), 4.4 (t, 1H) 3.7 (s, 6H), 3.6 (d, 2H). MS: 357 (MH$^+$).

(d) By proceeding in a manner similar to Reference Example 44(a) above but using [6-(4-methoxyphenyl)-5H-pyrrolo[2,3-b]pyrazin-7-yl]methyltrimethylammonium iodide [Reference Example 45 (d)], there was prepared dimethyl 3-[6-(4-methoxyphenyl)-5H-pyrrolo[2,3-b]pyrazin-7-yl]-propionic 1,1-diacid 1,1-dicarboxylate as an off-white solid. MS: 369 (MH$^+$).

REFERENCE EXAMPLE 45

(a) [6-(4-tert-Butylphenyl-5H-pyrrolo[2,3-b]pyrazin-7-yl]methyltrimethylammonium iodide To a solution of [6-(4-tert-butylphenyl-5H-pyrrolo[2,3-b]pyrazin-7-yl]methyldimethylamine [0.8 g. Reference Example 46(a)] in tetrahydrofuran (50 mL) under nitrogen at 40 C was added methyl iodide (4.5 mL). The reaction mixture was stirred for 4 hours and the solvent was evaporated. The residue was chased with toluene (30 mL) and dried under vacuum to afford the title compound as a yellow solid which was used immediately without further purification in the next reaction.

(b) By proceeding in a manner similar to Reference Example 45(a) above but using 6-4-1-methyl)ethoxy)phenyl-5H-pyrrolo[2,3-b]pyrazin-7-yl]methyldimethylamine [Reference Example 46(b)], there was prepared [6-(4-(1-methyl)ethoxy)phenyl-5H-pyrrolo[2,3-b]pyrazin-7-yl]methyltrimethylammonium iodide as a beige solid, which was used immediately without further purification.

(c) By proceeding in a manner similar to Reference Example 45 (a) above but using [6-4-fluorophenyl-5H-pyrrolo[2,3-b]pyrazin-7-yl]methyldimethylamine [Reference Example 46 (c)], there was prepared 6-(4-fluorophenyl)-5H-pyrrolo[2,3-b]pyrazin-7-yl]methyltrimethylammonium iodide as a yellow solid. $^1$H NMR [(CD$_3$)$_2$SO]: δ 13.0 (s, 1H), 8.5 (d, 1H), 8.4 (d, 1H), 7.7 (d, 2H), 7.6 (d, 2H), 3.1 (d, 2H), 2.9 (s, 9H). MS: 285 (MH$^+$).

(d) By proceeding in a manner similar to Reference Example 45 (a) above but using [6-(4-methoxyphenyl-5H-pyrrolo[2,3-b]pyrazin-7-yl]methyldimethylamine [Reference Example 46 (d)], there was prepared 6-(4-methoxyphenyl)-5H-pyrrolo[2,3-b]pyrazin-7-yl]methyltrimethylammonium iodide as an off-white solid. MS: 297 (MH$^+$).

REFERENCE EXAMPLE 46

(a) [6-(4-tert-Butylphenyl-5H-pyrrolo[2,3-b]pyrazin-7-yl]methyldimethylamine

To a solution of dimethylamine (15 mL of a 2M solution in tetrahydrofuran) and acetic acid (0.45 mL) at 0 C was added formaldehyde (2.25 mL of a 40% aqueous solution). The reaction mixture was stirred for 10 minutes. A solution of 6-(4-tert-butylphenyl)-5H-pyrrolo[2,3-b]pyrazine [6.9 g, Example 1(w)] in tetrahydrofuran (400 mL) was added and the reaction mixture allowed to stir at room temperature overnight. The reaction mixture was washed with 1N sodium hydroxide solution, brine, dried over magnesium sulfate and evaporated in vacuo. The residue was subjected to flash column chromatography on silica eluting with a mixture of tetrahydrofuran and methanol (1:1, v/v) to give the title compound (0.8 g) as a yellow solid. MS: 309 (MH$^+$). HPLC (Method A): R$_T$=1.93 minutes.

(b) By proceeding in a manner similar to Reference Example 46(a) above but using 6-[4-(1-methyl)ethoxyphenyl]-5H-pyrrolo[2,3-b]pyrazine [Example 1(aa)], there was prepared 6-(4-(1-methyl)ethoxy)phenyl-5H-pyrrolo[2,3-b]pyrazin-7-yl]methyl-dimethylamine as a beige solid.

(c) By proceeding in a manner similar to Reference Example 46 (a) above but using 6-[4-fluorophenyl)-5H-pyrrolo[2,3-b]pyrazine [Example 1 (ae)], there was prepared [6-(4-fluorophenyl-5H-pyrrolo[2,3-b]pyrazin-7-yl]methyldimethylamine as an off-white solid. $^1$H NMR [(CD$_3$)$_2$SO]: δ 12.0 (s, 1H), 8.5 (d, 1H), 8.2 (d, 1H), 7.7 (d, 2H), 7.6 (d, 2H), 3.9 (d, 2H), 2.9 (s, 6H). MS: 270 (MH$^+$).

(d) By proceeding in a manner similar to Reference Example 46 (a) above but using 6-(4-methoxyphenyl)-5H-pyrrolo[2,3-b]pyrazine [Example 1(af)], there was prepared [6-(4-methoxyphenyl-5H-pyrrolo[2,3-b]pyrazin-7-yl]methyldimethylamine as a off-white solid. MS: 282 (MH$^+$).

REFERENCE EXAMPLE 47

Ethyl 3-[2-dimethylamino-5-(5H-pyrrolo[2,3-b]pyrazin-6-yl)phenyl]prop-2-enonate

To a solution of 6-(4-amino-3-bromo)phenyl-5H-pyrrolo[2,3-b]pyrazine [0.1 g, Reference Example 48] in dry dimethylformamide (10 mL) in a schlenk tube was added ethyl acrylate (0.25 mL), palladium (II) acetate (0.05 g), tri-(2-methylphenyl)phosphine (0.07 g) and tributylamine (0.8 g). The tube was sealed and heated at 95° C. for 24 hours then allowed to stand at room temperature for a further 24 hours.

The reaction mixture was quenched with water (150 mL) and extracted into ethyl acetate (100 mL), washed with brine and dried over magnesium sulfate. After concentration in vacuo the resultant orange gum was triturated with toluene to afford the title compound as an orange solid (0.04 g). TLC: $R_F$=0.46 (ethyl acetate). $^1$H NMR [(CD$_3$)$_2$SO]: δ 12.40 (1H, s); 8.38 (1H, s); 8.34 (1H, s); 8.02 (1H, d, J=8.6 Hz); 7.89 (1H, d, J=16.5 Hz); 7.22 (1H, d, J=8.6 Hz); 7.19 (1H, s); 6.81 91H, d, J=16.5 Hz); 4.23 (2H, q, J=7.1 Hz); 2.78 (6H, s); 1.30 (3H, t, J=7.1 Hz).

REFERENCE EXAMPLE 48

6-(3-Bromo-4-dimethylamino)phenyl-5H-pyrrolo[2,3-b]pyrazine

To a stirred solution of 4-(dimethylamino)benzonitrile (2.19 g) in chloroform (15 mL) was added pyridine (1.2 mL) and a solution of bromine (0.75 mL) in chloroform (15 mL) dropwise over 45 minutes. Upon complete addition, the mixture was stirred for a further 30 minutes. The reaction mixture was diluted with dichloromethane and washed with water, brine and evaporated to afford a yellow oil of 3-bromo-4-dimethylaminobenzonitrile which was dissolved in tetrahydrofuran (25 mL). Meanwhile, a stirred solution of diisopropylamine (2.7 mL) in tetrahydrofuran (50 mL), at −15° C. and under nitrogen, was treated with a solution of n-butyllithium in hexanes (7.70 mL, 2.5M) over 30 minutes, whilst maintaining the temperature below −10° C. After stirring for 30 minutes the mixture was treated with methylpyrazine (1.21 g) over 15 minutes, then stirred for 1 hour. The solution of 3-bromo-4-(dimethylamino)benzonitrile was added over 1 hour, keeping the temperature below −10° C. The reaction mixture was allowed to warm to room temperature over 2 hours, then stood overnight, then treated with water (10 mL). The tetrahydrofuran was removed in vacuo and the resultant mixture was treated with a mixture of water and ethyl acetate (1:1 v/v) and the mixture stirred for 15 minutes. The resultant precipitate was collected by filtration and washed thoroughly with water/ethyl acetate (1:1 v/v) to afford the title compound as a yellow solid (1.0 g). TLC: $R_F$=0.41 (ethyl acetate).

REFERENCE EXAMPLE 49

6-(3-tert-Butyldimethylsilyloxy-4-methoxy)phenyl-5H-pyrrolo[2,3-b]pyrazine

A stirred solution of diisopropylamine (3.6 mL) in tetrahydrofuran (133 mL), at −15° C. and under nitrogen, was treated with a solution of n-butyllithium in hexanes (11.21 mL, 2.5M) over 30 minutes, whilst maintaining the temperature below −10° C. After stirring for 30 minutes the mixture was treated with methylpyrazine (2.04 g) over 15 minutes, then stirred for 1 hour and then treated with a solution of 3-tert-butyldimethylsilyloxy-4-methoxybenzonitrile (5.7 g, Reference Example 50) in tetrahydrofuran (20 mL) over 1 hour, keeping the temperature below −10° C. The reaction mixture was allowed to warm to room temperature over 2 hours, then stood overnight, then treated with water (10 mL). The tetrahydrofuran was removed in vacuo and the resultant mixture was partitioned between ethyl acetate and water. The two layers were separated, and the aqueous layer was extracted with ethyl acetate. The combined organics were dried over sodium sulfate and evaporated. The residue was subjected to flash chromatography on silica eluting with a mixture of dichloromethane and methanol (32:1, v/v) to give the title compound (1.62 g) as a tan solid, which was used directly in the next step. $^1$H NMR [(CD$_3$)$_2$SO]: δ 8.12 (1H, s); 7.96 (1H, s); 7.44 (1H, d, J=8.2 Hz); 7.33 (1H, s); 6.93 (1H, d, J=8.2 Hz); 6.84 (1H, s); 3.63 (3H, s); 0.82 (9H, s); 0.01 (6H, s).

REFERENCE EXAMPLE 50

3-tert-Butyldimethylsilyloxy-4-methoxy)benzonitrile

A solution of iso-vanillin (10.0 g) in dimethylformamide (100 mL) was treated with hydroxylamine hydrochloride (9.14 g) and heated under reflux for 1 hour. The dimethylformamide was removed under reduced pressure and the residue partitioned between ethyl acetate and water. The aqueous fraction was exhaustively extracted with ethyl acetate and the combined organic fractions were dried over sodium sulfate and concentrated in vacuo to afford a brown solid, which was dissolved in tetrahydrofuran (200 mL). After treatment with sodium hydride (2.8 g), the reaction mixture was stirred at room temperature for 1 hour. A solution of tert-butyldimethylsilyl chloride (10.9 g) in tetrahydrofuran (50 mL) was added and the mixture stirred under nitrogen overnight. The mixture was partitioned between water and diethyl ether. The organic extract was dried over sodium sulfate, concentrated in vacuo and subjected to flash column chromatography on silica eluting with a mixture of pentane and dichloromethane (1:3, v/v) to give the title compound (14.7 g) as a colourless oil which was used immediately in the next reaction. $^1$H NMR [(CD$_3$)$_2$SO]: δ 7.30 (1H, d, J=8.0 Hz); 7.11 (1H, s); 7.01 (1H, s); 3.70 (3H, s); 0.81 (9H, s); 0.01 (6H, s).

REFERENCE EXAMPLE 51

4-(1-Methyl)ethoxybenzonitrile

A solution of 4-cyanobenzene (1 g) in hexamethylenetetramine (10 mL) was stirred at ambient temperature until dissolution. 25% aqueous sodium hydroxide (2.7 mL) was then added and the resulting solution stirred at ambient temperature for 30 minutes. 1-Methylethyl iodide (5.71 g) was added dropwise and the resulting solution stirred at ambient temperature for 5 hours then poured into water (30 mL). The mixture was extracted three times with ethyl acetate (30 mL) and the combined organic extracts were washed with water, then with brine, then dried over magnesium sulfate and then evaporated. The residue was subjected to flash chromatography on silica eluting with a mixture of ethyl acetate and heptane (1:1, v/v) to give the title compound (1.2 g) as a white solid. MS: 162(MH$^+$). 1H NMR(CD$_3$)$_2$SO: δ: 7.58(d, 2H, J=8.12 Hz); 6.84(d, 2H, J=8.12 Hz); 4.62(m, 1H); 1.38(d, 6H, J=5.4 Hz).

REFERENCE EXAMPLE 52

1H-5-Cyano-1-methyl-2-(methylthio)imidazole

A solution of 1H-1-methyl-2-(methylthio)imidazole-5-carboxaldehyde (0.76 g) [Reference Example 53(a)] in dimethylformamide (15 mL) was treated with hydroxylamine hydrochloride (0.68 g). The mixture was refluxed for 4 hours, cooled to ambient temperature and poured into water. Ethyl acetate was added and the organic layer washed with water, brine, dried over magnesium sulfate and evaporated to give the title compound (0.47 g) as a beige solid which was used without further purification, m.p. 115° C. MS: 154 (MH$^+$).

REFERENCE EXAMPLE 53

(a) 1H-1-Methyl-2-methylthio) imidazole-5-carboxaldehyde

A stirred solution of 1H-1-methyl-2-(methylthio)imidazol-5ylmethanol (8.1 g) [Reference Example 54] and manganese dioxide (28.97 g) in dichloromethane (160 mL) was refluxed for 7 hours. The reaction mixture was cooled to ambient temperature and filtered through a pad of celite. The dichloromethane was evaporated to give the title compound (6.61 g) as a yellow solid, which was used immediately in the next reaction.

(b) By proceeding in a manner similar to Reference Example 53(a) above but using 1-methyl-5-phenylpyrazol-3-ylmethanol [Reference Example 66], there was prepared, 1-methyl-5-phenylpyrazole-3-carbaldehyde, m.p. 106–108° C.

REFERENCE EXAMPLE 54

1H-1-Methyl-2-(methylthio)imidazol-5ylmethanol

To a stirring suspension of 1H-1-methyl-2-(thio)imidazol-5ylmethanol (5 g) [Reference example 55] in methanol (500 mL) is added dropwise 1 N sodium hydroxide solution (36 mL) at room temperature. The suspension was stirred at ambient temperature for 10 minutes. Iodomethane was added dropwise and stirring was continued for 12 hours. After evaporation of the methanol, the residue was dissolved in dichloromethane and water was added. The organic layer was washed with water, brine, dried over magnesium sulfate and evaporated. The residue was crystallized from ether to give the title compound (4.3 g) as a white solid, m.p. 51° C.

REFERENCE EXAMPLE 55

1H-1-Methyl-2-(thio)imidazol-5ylmethanol

A mixture of 12.8 g of dihydroxyacetone dimer, 20.7 g of potassium thiocyanate and 12.4 g of methylamine was added to a solution of 16 mL of acetic acid and 100 mL of butanol. The resulting white mixture was stirred for 70 h after which it was suspended in 50 mL of water and filtered. The solid was washed with water (60 mL), then diethyl ether (60 mL) and dried in vacuo to give the title compound (16 g) as a white solid, m.p 204° C.

REFERENCE EXAMPLE 56

(a) 3-Cyano-1-methyl-1H-indazole

Sodium hydride (0.37 g, 60% dispersion in mineral oil) was added to a solution of 3-cyano-1H-indazole (1.20 g, Reference Example 57) in dry dimethylformamide (30 mL) under a nitrogen atmosphere at ambient temperature. The mixture was allowed to stir for 1 hour then treated with methyl iodide (0.85 mL) and stirring was continued for 1 hour. The reaction mixture was then poured into ice-water (15 mL). The precipitated solid was filtered then washed with water and then dried to give the title compound (0.80 g) as a beige solid, m.p. 73° C. $^1$H NMR [(CD$_3$)$_2$SO]: δ 7.91 (m, 2H); 7.60 (t, 1H); 7.42 (t, 1H); 4.21 (s, 3H).

(b) By proceeding in a manner similar to Reference Example 56(a) above but using 3-Cyano-4-phenyl-1H-pyrrole [Reference Example 58], there was prepared 3-cyano-1-methyl-4-phenyl-1H-pyrrole.

REFERENCE EXAMPLE 57

3-Cyano-1H-indazole

A solution of o-aminobenzyl cyanide (0.5 g) in aqueous hydrochloric acid 1N (9.6 mL), was treated with a solution of aqueous sodium nitrite 1N (3.85 mL). After stirring at room temperature for 15 minutes, the reaction mixture was filtered. The solid was recrystallised from ethanol to give the title compound (0.4 g) as a yellow solid, m.p. 138–140° C. $^1$H NMR [(CD$_3$)$_2$SO]: δ 7.89 (d, 1H, J=7.7 Hz); 7.76 (d, 1H, J=7.9 Hz); 7.48 (t, 1H); 7.41 (t, 1H).

REFERENCE EXAMPLE 58

3-Cyano-4-phenyl-1H-pyrrole

A solution of cinnamonitrile (16.53 g) and (para-toluenesulfonyl)methylisocyanide (25 g) in a mixture of ether and dimethyl sulphoxide (450 mL, 2:1) was added dropwise to a stirred suspension of sodium hydride (6.14 g, 60% dispersion in mineral oil) in ether (50 mL). An exothermic reaction took place. The reaction mixture was then stirred at room temperature for 2 hours, then diluted with water (500 mL) and this mixture was extracted three times with ether (250 mL). The combined extracts were washed with brine, then dried over magnesium sulfate and then evaporated. The residue was subjected to filter chromatography on a pad of silica eluting with a mixture of ethyl acetate and pentane (1L, 1:4, v/v) and then with a mixture of ethyl acetate and pentane (2L, 2:3, v/v). Fractions containing the required material were evaporated and the residue was suspended in pentane (500 mL) with stirring, then filtered to give the title compound as a solid, m.p. 120–122° C. MS: 167 (MH$^-$).

REFERENCE EXAMPLE 59

4-Pyrazinyl-1-butene

A solution of lithium diisopropylamine [prepared from a solution of butyl lithium in hexanes (100 mL, 2.5M) and diisopropylamine (25.3 g) at −35° C.] was treated with a solution of 2-methylpyrazine (23.5 g) in dry tetrahydrofuran (300 mL) at −20° C. The mixture was stirred at −20° C. for 1 hour then cooled to −78° C. and treated with a solution of allyl bromide (30.8 g) in dry tetrahydrofuran (300 mL). This mixture was warned to room temperature and stirred at this temperature for 2 hours then left overnight and then treated with saturated ammonium chloride solution (50 mL) followed by water (200 mL). The mixture was then extracted twice with ether (200 mL). The combined extracts were dried over magnesium sulfate then evaporated. The residue was distilled to give the title compound (22 g) as a colorless oil, b.p. 70° C./1 mm Hg.

REFERENCE EXAMPLE 60

2-[5-pyridin-4-yl)-1-methyl-1H-indol-3-yl]-1toluene-4-sulfonyl)-1H-pyrrolo[2,3-b]pyridine A mixture of 2-[5-(1-benzyloxycarbonyl-1,2,5,6-tetrahydropyridin-4-yl)-1-methyl-1H-indol-3-yl]-1-(toluene-4-sulfonyl)-1H-pyrrolo[2,3-b]pyridine (1.7 g, Reference Example 61) ethanol (53 mL) and palladium on carbon (0.35 g) was stirred in the presence of hydrogen for 4 hours, then left standing at room temperature overnight. After a further day a further quantity of palladium on carbon (0.18 g, 10%) was added and stirring was continued in the presence of hydrogen for a further 8 hours. After standing at room temperature for 4 days the reaction mixture was filtered through Hyflo and the filter pad was washed well with ethanol. The combined filtrate and washings was treated with palladium on carbon (0.35 g) and the mixture was stirred in the presence of hydrogen. The mixture was filtered through Hyflo and the filter pad was washed well with ethanol. The combined filtrate and washings was evaporated and the residue was subjected to flash chromatography on silica eluting with a mixture of ethyl acetate and pentane (4:1, v/v) to give the title compound as a light brown solid, m.p. 82–85° C.

REFERENCE EXAMPLE 61

2-[5-(1-benzyloxycarbonyl-1,2,5,6-tetrahydropyridin-4-yl)-1-methyl-1H-indol-3-yl-]-1-(toluene-4-sulfonyl)-1H-pyrrolo[2,3-b]pyridine A mixture of benzyl 1-[3,6-dihydro-4-(4,4,5,5-tetramethyl-1,3,2-dioxaborolan-2-yl](2H)pyridinecarboxylate (2 g, prepared according to the procedure described by P. Eastwood, Tetrahedron Letters, 2000, 41, pages 3705–3708), dichloro[1,1'-bis(diphenylphosphino)-ferrocene]palladium[II] (0.25 g,) and potassium carbonate (2.42 g), under nitrogen, was treated with a solution of trifluoro-methanesulfonic acid 1-methyl-3-[1-(toluene-4-sulfonyl)-1H-pyrrolo[2,3-b]pyridin-2-yl]-1H-indol-5-yl ester [1.6 g, Reference Example 18(a)] in dimethylformamide (76 mL). The mixture was heated at 80° C. for 4 hours (tlc indicated that starting material was still present), then treated with a further quantity of trifluoro-methanesulfonic acid 1-methyl-3-[1-(toluene-4-sulfonyl)-1H-pyrrolo[2,3-b]pyridin-2-yl]-1H-indol-5-yl ester (0.15 g), then heated at reflux temperature for 4 hours and then left at room temperature overnight. A further quantity of trifluoro-methanesulfonic acid 1-methyl-3-[1-(toluene-4-sulfonyl)-1H-pyrrolo[2,3-b]pyridin-2-yl]-1H-indol-5-yl ester [0.15 g, Reference Example 18(a)] was added and the mixture was heated at reflux temperature for a further 4 hours then evaporated. The residue was partitioned between ethyl acetate and water, and the aqueous layer was extracted three times with ethyl acetate (50 mL). The combined organic phases were washed with brine, then dried over magnesium sulfate and then evaporated. The residue was subjected to flash chromatography on silica eluting with a mixture of ethyl acetate and pentane (1:1, v/v) to give the title compound as a light brown viscous liquid which was used without further purification.

REFERENCE EXAMPLE 62

(a) 2-Iodo-1-(toluene-4-sulfonyl)-1H-pyrrolo[2,3-b]pyridine-4-carbonitrile

A stirred solution of diisopropylamine (0.38 mL) in tetrahydrofuran (7 mL), at −70° C. and under nitrogen, was treated with a solution of n-butyllithium in hexanes (1.06 mL, 2.5M) over 5 minutes, whilst maintaining the temperature below −65° C. After stirring for 20 minutes the mixture was added, at −70° C., to a solution of 1-(toluene-4-sulfonyl)-1H-pyrrolo[2,3-b]pyridine-4-carbonitrile (0.65 g, Reference Example 63) in tetrahydrofuran (15 mL) and stirred at −70° C. for 45 minutes. A solution of iodine (0.9 g) in tetrahydrofuran (10 mL) was then added at −70° C. The reaction mixture was allowed to warm up to room temperature over 1 hour, and stirred for 18 hours, then treated with water (10 mL). The reaction mixture was evaporated in vacuo and the residue partitioned between ethyl acetate (75 mL) and water (50 mL). The insoluble material was filtered, washed with ether and dried in vacuo to give the title compound (0.45 g) as a white solid. The filtrate was separated and the organics washed sequentially with saturated sodium thiosulphate solution (2×30 mL), water (30 mL) and brine (30 mL), dried over sodium sulphate and evaporated. The residue was triturated with diethyl ether to give the title compound (0.25 g) as a cream solid. TLC $R_F$=0.43 (ethyl acetate/heptane 1:1). MS: 424 (MH$^+$).

(b) By proceeding in a similar manner to Reference Example 62(a) but using 4-chloro-1-(toluene-4-sulfonyl)-1H-pyrrolo[2,3-b]pyridine [Reference Example 9(c)], there was prepared 4-chloro-2-iodo-1-(toluene-4-sulfonyl)-1H-pyrrolo[2,3-b]pyridine as an off white foam. MS: 432 (MH$^+$). $^1$H NMR (CDCl$_3$): δ 8.25 (d, 1H), 8.05 (d, 2H), 7.3 (d, 2H), 7.15 (d, 1H), 7.1 (s, 1H), 2.4 (s, 3H)

(c) By proceeding in a similar manner to Reference Example 62(a) but using 5-phenyl-1-(toluene-4-sulfonyl)-1H-pyrrolo[2,3-b]pyridine [Reference Example 67], there was prepared 2-iodo-5-phenyl-1-(toluene-4-sulfonyl)-1H-pyrrolo[2,3-b]pyridine as a light brown solid.

(d) By proceeding in a similar manner to Reference Example 62(a) but using 4-phenyl-1-(toluene-4-sulfonyl)-1H-pyrrolo[2,3-b]pyridine [Reference Example 9(e)], there was prepared the 2-iodo-4-phenyl-1-(toluene-4-sulfonyl)-1H-pyrrolo[2,3-b]pyridine as a white solid. $^1$H NMR [(CD$_3$)$_2$ SO]; δ 8.43 (1H, d, J=4.5 Hz); 8.04 (2H, d, J=8.2 Hz); 7.98 (1H, d, J=4.5 Hz); 7.69 (2H, dd, J=7.2, 1.9 Hz); 7.56 (2H, tt, J=7.2, 1.9 Hz); 7.44 (2H, d, J=8.2 Hz); 7.42 (1H, d, J=5.0 Hz), 6.92 (1H, d, J=4.0 Hz), which was used without further purification.

REFERENCE EXAMPLE 63

1-(Toluene-4-sulfonyl)-1H-pyrrolo[2,3-b]pyridine-4-carbonitrile

A mixture of 1-(2,6-dimethyl-1,4-dihydropyridin-4-one)-1H-pyrrolo[2,3-b] pyridinium tetrafluoroborate (Reference Example 43, 5.0 g) and water (80 mL) was treated with a saturated aqueous solution of potassium cyanide (25 mL) and stirred at room temperature for 48 hours. A solution of toluene-4-sulfonyl chloride (2.9 g) in toluene (100 mL), a solution of sodium hydroxide (4.0 g) in water (10 mL) and tetrabutylammonium hydrogen sulphate (0.05 g) were added and stirred at room temperature 72 hours. The mixture was filtered through Celite and partitioned. The aqueous was extracted three times with ethyl acetate (50 mL) and the combined organics were washed with water (50 mL), brine (50 mL), dried over magnesium sulphate and evaporated in vacuo. The residue was subjected to flash chromatography on silica eluting with a mixture of ethyl acetate and heptane (3/7, v/v) to give the title compound (1.1 g) as a white solid, TLC: $R_F$=0.60 (ethyl acetate/heptane, 3:7); $^1$H NMR [(CD$_3$)$_2$ SO]: δ 8.54 (1H, d, J=4.7 Hz); 8.08 (2H, d, J=8.2 Hz); 7.95 (1H, d, J=3.6 Hz); 7.44 (1H, d, J=4.3 Hz); 7.31 (2H, d, J=8.2 Hz); 6.82 (1H, d, J=3.3 Hz); 2.39 (3H, s); and 1H-pyrrolo[2,3-b]pyridine-4-carbonitrile (0.13 g) as a white solid, TLC $R_F$=0.24 (ethyl acetate/heptane 3:7); $^1$H NMR [(CD$_3$)$_2$SO]: δ 10.19 (1H, s); 8.44 (1H, d, J=4.6 Hz); 7.59 (1H, m); 7.40 (1H, d, J=4.6 Hz), 6.78 (1H, m).

REFERENCE EXAMPLE 64

4-Chloro-1H-pyrrolo[2,3-b]pyridine

1H-Pyrrolo[2,3-b]pyridine-N-oxide (Reference Example 65) (10.0 g) in phosphorous oxychloride (75 mL) was heated at reflux for 8 hours. The excess phosphorous oxychloride was evaporated and the residue was taken up in water and the solution was brought to a pH=8–9, the resultant precipitate was filtered and air-dried to give the title compound as an off-white solid (10.2 g). MS: 152 (MH$^+$). $^1$H NMR (CDCl$_3$): δ 8.2 (d, 1H), 7.5 (d, 1H), 7.2 (d, 2H), 6.6 (d, 2H).

REFERENCE EXAMPLE 65

1H-Pyrrolo[2,3-b]pyridine-7-oxide

A solution of 3-chloroperbenzoic acid (224.3 g) in dichloromethane (1500 mL) was cooled to 0° C. To this a solution of 1H-pyrrolo[2,3-b]pyridine (59.1 g) in dichloromethane (500 mL) was added dropwise over 30 minutes. The reaction mixture was stirred at room temperature for 1 hour. The solution was concentrated, diluted with methanol (1500 mL) and treated with 10% potassium carbonate in water (300 mL). The slurry was filtered and the filtrate was evaporated to dryness. The residue was chromatographed on neutral alumina with 20% methanol in dichloromethane to give the title compound as a tan solid (47.0 g). MS: 135 (MH$^+$). $^1$HNMR (CDCl$_3$): δ 13.1 (s, 1H), 8.2 (d, 1H), 7.65 (d, 1H), 7.4 (d, 1H), 7.0 (m, 1H), 6.55 (d, 1H).

REFERENCE EXAMPLE 66

1-Methyl-5-phenylpyrazol-3-ylmethanol

A stirred suspension of sodium borohydride (1.28 g) in dry tetrahydrofuran (80 mL) was treated with calcium chloride (1.88 g). The mixture was stirred for 1 hour then treated with a solution of ethyl 1-methyl-5-phenylpyrazol-3-ylcarboxylate (5.2 g, prepared according to the procedure described by Martins et al., J. Heterocycl. Chem. (1999), 36(1), 217–220) in dry tetrahydrofuran (40 mL). After stirring at room temperature for 3 days and at reflux temperature for 8 hours the mixture was treated with sodium hydroxide solution (50 mL, 1N). This mixture was stirred at room temperature for 1 hour, then evaporated to remove the organic solvents and then extracted three times with dichloromethane (140 mL). The combined extracts were washed with water, then dried over magnesium sulfate and then evaporated to give the title compound as a white solid, m.p. 95–99° C.

REFERENCE EXAMPLE 67

5-Phenyl-1-(toluene-4-sulfonyl)-1H-pyrrolo[2,3-b]pyridine

A mixture of phenyl boronic acid (1.74 g), 5-bromo-1-(toluene-4-sulfonyl)-1H-pyrrolo[2,3-b]pyridine [5 g, Reference Example 9(d)], (tetrakis)tripyhenylphosphine palladium[0] (0.49 g) and saturated aqueous sodium bicarbonate solution (133 mL) and dimethylformamide (266 mL), under nitrogen, was heated at reflux temperature overnight. The reaction mixture was filtered through Hyflo and then evaporated. The residue was partitioned between ethyl acetate (50 mL) and water (25 mL) and the aqueous layer was extracted with ethyl acetate (25 mL). The combined organic phases were washed with water (25 mL), then with brine (20 mL), then dried over magnesium sulfate and then evaporated. The residue subjected to chromatography on silica eluting with a mixture of pentane and ether (1;1, v/v) to give the title compound as a white solid, mp. 151–152° C. MS: 335 (MH$^+$).

In vitro Test Procedures

A. In Vitro Test Procedures for Syk

1. Inhibitory Effects of Compounds on Syk Kinase

Inhibitory effects of compounds on Syk kinase were determined using a time-resolved fluorescent assay.

The catalytic domain of Syk kinase (residues A340-N635) was expressed as a fusion protein in yeast cells and purified to homogeneity. Kinase activity was determined in 50 mM Tris-HCl buffer pH 7.0 containing 50 mM NaCl, 5 mM MgCl$_2$, 5 mM MnCl$_2$, 1 μM adenosine triphosphate and 10 μM synthetic peptide Biotin (β-Alanine)$_3$-DEEDYEIPP-NH$_2$. Enzyme reactions were terminated by the addition of buffer containing 0.4M KF, 133 mM EDTA, pH 7.0, containing a streptavidin-XL665 conjugate and a monoclonal phosphospecfic antibody conjugated to a europium cryptate (Eu—K). Features of the two fluorophores, XL-665 and Eu—K are given in G. Mathis et al., Anticancer Research, 1997, 17, pages 3011–3014. The specific long time signal of XL-665, produced only when the synthetic peptide is phosphorylated by Syk, was measured on a Packard Discovery Microplate analyzer. Inhibition of syk activity with compounds of the invention was expressed as percentage inhibition of control activity exhibited in the absence of test compounds. Particular compounds of the invention inhibit syk activity with IC$_{50}$s in the range 100 micromolar to 10 nanomolar. Preferred compounds of the invention inhibit syk activity with IC$_{50}$s in the range 100 nanomolar to 10 nanomolar.

2. Antigen-Induced Degranulation of Rat Bosophilic Leukemia (RBL) Cells as Measured by [$^3$H] 5-hydoxytryptamine (Serotonin) Release 2.1 Cell Culture, Labelling of RBL-2H3 Cells and Performance of Assay.

For each 24-well culture plate to be set up, 6×10$^6$ cells RBL-2H3 cells were washed and resuspended in 15 mL DMEM-10 containing 25 μl of 1 mCi/mL [$^3$H]-serotonin (0.5 μCi/mL final concentration) and 1 μg/mL (15 mL) of anti-DNP IgE. 0.5 mL of cell suspension was added into each well of a 24-well plate. Cells were incubated for 2 days at 37° C., until they have reached confluence. The medium was gently aspirated from each well and the cells were then washed with assay buffer. A final volume of 200 mL of assay buffer (+ or − the test compounds at the appropriate concentrations) was then added to each of three replicate wells. 100 ng/mL of DNP (antigen) was then added to all wells (excluding negative control wells i.e. to measure spontaneous [$^3$H]-serotonin release in the absence of receptor cross-linking). The cells were incubated for 30 minutes at 37° C. and the reaction was stopped by transferring 100 μl of the supernatant from each sample into a liquid scintillation microtitre plate kept on ice. 200 μl of scintillant-40 was then added to each well of the microtitre plate and the plate was read on a Topcount Liquid Scintillation Counter.

2.2 Calculation of Results (i) The mean±s.e.m. of each set of triplicate wells was calculated.

(ii) Maximum response was the positive control wells containing antigen (10 ng/mL) but no compound.

(iii) Minimum response was the control wells containing no antigen and no compound.

(iv) Using these values as the maximum (100%) and minimum (0%) values respectively, the data was normalised to give a percentage of the maximum response.

(v) A dose response curve was plotted and the IC$_{50}$ of the compound was calculated.

Compounds of the invention inhibit antigen-induced degranulation of Rat Bosophilic leukemia (RBL) cells with EC$_{50}$s in the range 100 micromolar to 0.01 micromolar.

B. In Vitro Test Procedures for KDR
  1. Inhibitory Effects of Compounds on KDR
  Inhibitory effects of compounds on KDR-substrate phosphorylation assay—were determined using a flashplate (96-multiwell plates, New England Nuclear) assay.

The cytroplasmic domain of human enzyme has been cloned as glutathione S-transferase (GST) fusion into the pFastBac-GST tagged (reading frame) B baculovirus expression vector. The protein has been expressed in SF21 cells and purified to about 60% homogeneity.

Kinase activity was determined in 20 mM 4-morpholinepropanesulfonic acid sodium salt, 10 mM $MgCl_2$, 10 mM $MnCl_2$, 1 mM Dithiothreitol, 2.5 mM ethyleneglycol-bis (beta-aminoethylether)-N,N'-tetraacetic acid, 10 mM β-glycerophosphate, pH 7.2 containing 10 mM $MgCl_2$, 100 µM $Na_3VO_4$, 1 mM NaF. 10 µl of compound were added to 70 µl of kinase buffer containing 100 ng of Kinase Domain Receptor (KDR) enzyme at 4° C. Reaction was started by addition of 20 µl of solution containing 2 µg of substrate (SH2-SH3 fragment of PLCγ expressed as GST fusion protein ), 2 µCi $\gamma^{33}$P[ATP] and 2 µM cold ATP. After 1 h incubation at 37° C., reaction was stopped by addition of 1 volume (100 µl) of 200 mM EDTA. The assay buffer was then discarded and the wells washed three fold with 300 µl of phosphate buffered saline. Radioactivity was measured in each well using a Packard Model Top Count NXT instrument.

Background signal was deduced from the measurement of radioactivity in quadruplate wells containing radioactive ATP and substrate alone in kinase buffer.

Control activity was deduced from the measurement of radioactivity of quadruplate wells containing the complete assay cocktail ($\gamma^{33}$P-[ATP], KDR and PLCg substrate) in the absence of test compound.

Inhibition of KDR activity with compound of the invention was expressed as percentage inhibition of control activity exhibited in the absence of test compound.

SU5614 1 µM (Calbiochem) was included in each plate in quadruplate as a control of inhibition. $IC_{50}$'s were calculated for compounds of the invention by plotting a dose-response curve. $IC_{50}$ corresponded to the concentration of compound of the invention that induced a 50% inhibition of kinase activity.

Particular compounds of the invention inhibit KDR activity with $IC_{50}$s in the range 100 micromolar to 0.3 micromolar.

2. Cellular Activity on Endothelial Cell
  2.1 Inhibition of Vascular Endothelial Growth Factor (VEGF)-Dependent Human Dermal Microvascular Endothelial Cells (HDMEC) Proliferation.

The anti-KDR activity of the molecules of the invention was evaluated by [$^{14}$C]-thymidine uptake on HDMEC (Human Dermal Microvascular Endothelial Cell) in response to VEGF.

HDMEC (Promocell, passage 5 to 7) were seeded in 100 µl at 5,000 cells per well in Cytostar 96-multiwell plates (Amersham) precoated with Attachment factor (AF, Cascad Biologics) at 37° C., 5% $CO_2$, at day 1. On day 2, complete cell medium (Basal medium supplemented with 5% of Fetal calf serum (FCS) and cocktail of growth factors) was replaced by minimum medium (basal medium supplemented with 5% of FCS) and cells were incubated for another 24 h. On day 3, medium was replaced by 200 µl of fresh minimum medium supplemented or not with 100 ng/ml VEGF (R&D System) and containing or not compounds of the invention and 0.1 µCi [$^{14}$C]-thymidine. Cells were incubated at 37° C., 5% $CO_2$ for 4 days. [$^{14}$C]-thymidine uptake was then quantified by counting the radioactivity. Assays were performed in three replicate wells. The final concentration of DMSO in the assay is 0.1%. The % inhibition is calculated as $[cpm_{(+VEGF)}-cpm_{(+VEGF+cpd)}/cpm_{(+VEGF)}-cpm_{(BM5\%FCS)}] \times 100$.

2.2 Effect of Molecules on VEGF-independent HDMEC Growth:
  HDMEC (5,000 cells per well) are seeded in complete medium (CM) in Cytostar 96-multiwell plates (Amersham) precoated with Attachment factor (AF, Cascad Biologics) at 37° C., 5% $CO_2$, at day 1. Complete medium is then removed and cells are incubated in 200 µl of complete medium containing molecules of the invention and [$^{14}$C]-thymidine (0.1 µCi). The uptake of [$^{14}$C]-thymidine is quantified using Wallac betaplate after 3 days of incubation. The % inhibition is calculated as $[cpm_{(CM)}-cpm_{(CM+cpd)}/cpm_{(CM)}] \times 100$.

C. In Vitro Test Procedures for Aurora2
  1. Inhibitory Effects of Compounds on Aurora2 Kinase
  Inhibitory effects of compounds on Aurora2 kinase were determined using a nichel-chelate flashplate radioactive assay.

N-terminally His-tagged full length recombinant aurora2 was expressed in *E. coli* and purified to near homogeneity.

N-terminally His-tagged NuMA (Nuclear protein that associates with the Mitotic Apparatus) C-terminal fragment (Q1687-H2101) was expressed in *E. coli*, purified by nichel chelate chromatography and used as substrate in Aurora2 kinase assay. For kinase activity determination NuMAsubstrate was freshly equilibrated in kinase buffer (50 mM Tris-HCl, pH7.5, 50 mM NaCl, 10 mM $MgCl_2$) supplemented with 10% (v/v) glycerol and 0.05% (w/v) NP40 by chromatography on a Pharmacia PD10 column.

The kinase activity of Aurora2 was measured in a nichel chelate flashplate (New England Nuclear, model SMP107). Each well contained 100 µl of the following solution: 0.02 µM Aurora2; 0.5 µM NuMAsubstrate; 1 µM ATP supplemented with 0.5 µCi[γ-$^{33}$P]-ATP. The solutions were incubated for 30 minutes at 37° C. The assay buffer was then discarded and the wells rinsed twice with 300 µl of kinase buffer. Radioactivity was measured in each well using a Packard Model Top Count NXT instrument.

Background signal was deduced from the measurement of radioactivity in duplicate wells containing radioactive ATP alone in kinase buffer treated in the same manner as other samples.

Control activity was deduced from the measurement of radioactivity of duplicate wells containing the complete assay cocktail (ATP, Aurora2 and NuMA substrate) in the absence of test compound.

Inhibition of Aurora2 activity with compound of the invention was expressed as percentage inhibition of control activity exhibited in the absence of test compound. Staurosporin was included in each plate as a control of inhibition.

$IC_{50}$'s were calculated for compounds of the invention by plotting a dose-response curve. $IC_{50}$ corresponded to the concentration of compound of the invention that induced a 50% inhibition of kinase activity.

Particular compounds of the invention inhibit Aurora2 activity with $IC_{50}$s in the range 100 micromolar to 0.3 micromolar.

C. In Vitro Test Procedures for FAK
  1. Inhibitory Effects of Compounds on FAK
  Inhibitory effects of compounds on FAK kinase—autophosphorylation assay—were determined using a time-resolved fluorescent assay.

The full length cDNA of human enzyme has been cloned into the pFastBac HTc baculovirus expression vector. The protein has been expressed and purified to about 70% homogeneity.

Kinase activity was determined in 50 mM Hepes pH 7.2 containing 10 mM $MgCl_2$, 100 µM $Na_3VO_4$, 15 µM adenosine triphosphate. Enzyme reactions were terminated by the addition of Hepes buffer pH 7.0, containing 0.4 M KF, 133 mM EDTA, BSA 0.1% containing an anti-6His antibody labelled with XL665 (FAK is His-tagged) and a monoclonal tyrosine phosphospecfic antibody conjugated to a europium cryptate (Eu—K). Features of the two fluorophores, XL-665 and Eu—K are given in G. Mathis et al., Anticancer Research, 1997, 17, pages 3011–3014. The specific long time signal of XL-665, produced only when the FAK enzyme is autophosphorylated, was measured on a Packard Discovery Microplate analyzer. Inhibition of FAK activity with compounds of the invention was expressed as percentage inhibition of control activity exhibited in the absence of test compounds.

2. Proliferation/Viability of Human Melanoma SK-Mel-28 Cells as Measured by [$^{14}$C] Thymidine Uptake 2.1 Cell Culture, Labelling of SK-Mel-28 Cells and Performance of Assay.

SK-Mel-28 were seeded at 5,000 cells per well in Cytostar 96-multiwell plates (Amersham) at 37° C., 5% $CO_2$, at day 1. On day 2, cell medium was replaced by fresh Eagle's minimum essential medium (MEM) culture medium supplemented with 10% FCS, 1% non essential amino acids, 1% sodium pyruvate and containing 0.1 µCi of [$^{14}$C]-Thymidine plus increasing concentrations of compounds in a 200 µl final volume. Cells were incubated at 37° C., 5% $CO_2$ for 48 hours. [$^{14}$C]-Thymidine uptake was quantified by counting the radioactivity 48 hours after initiation of treatment. Assays were performed in three replicate wells.

2.2 Calculation of Results (i) The mean ±s.e.m. of each set of triplicate wells was calculated.
(ii) Maximum response was the positive control wells containing cells but no compound.
(iii) Minimum response was the control wells containing no cell and no compound.
(iv) Using these values as the maximum (100%) and minimum (0%) values respectively, the data were normalized to give a percentage of the maximum response.
(v) A dose response curve was plotted and the $IC_{50}$ (the concentration of drug that induces a 50% decrease in [$^{14}$C]-thymidine uptake) of the compound was calculated.

3. Migration of Human Melanoma SK-Mel-28 Cells on Fibronectin Matrix 3.1 Cell Culture and Performance of Assay.

SK-Mel-28 (250,000 cells) were pretreated with increasing concentrations of compounds for 15 min at 37° C., 5% $CO_2$. They were then loaded in presence of the compound on the upper side of 12 µm 12-multiwell chemotaxis Boyden chambers (Becton Dickinson) and allowed to migrate to the lower chamber containing fibronectin (10 µg/ml) as chemoattractant in basal RPMI culture medium for 24 hours at 37° C., 5% $CO_2$. Cells were then fixed and stained in Diff-Quick (Diff-Quick Fix, I and II solutions, Dade Behring) and cells from the upper side of the chamber were removed. Stain was solubilized from lower side adherent cells and cell migration was quantified by optic density measurement. Assays were performed in two replicate wells.

3.2 Calculation of Results (i) The mean±s.e.m. of each set of duplicate wells was calculated.
(ii) Maximum response was positive control wells containing cells but no compound and allowed to migrate on fibronectin.
(iii) Minimum response was the control wells containing cells but no compound and allowed to migrate on basal culture medium w/o chemoattractant.
(iv) Using these values as the maximum (100%) and minimum (0%) values respectively, the data were normalized to give a percentage of the maximum response.
(v) A dose response curve was plotted and the $IC_{50}$ (the concentration of drug that induces a 50% decrease in cell migration) of the compound was calculated.

Particular compounds of the invention inhibit FAK activity with $IC_{50}$s in the range 100 micromolar to 0.3 micromolar.

In Vivo Test Procedures

1. Inhibition of Antipen Induced Airway Inflammation—Single-and Multiple-day Oral Dosing Studies.

Compounds of the invention were assessed in the allergic Brown Norway rat. The models used in these in vivo studies mimic relevant pathological features of allergic airway disease. These studies demonstrated that compounds of the invention inhibit the accumulation of inflammatory cells in the airways allergic twenty-four hours after antigen inhalation. The endpoints measured included the appearance of inflammatory leukocytes in the bronchoalveolar lavage fluid (BALF), lung digest fluid, and in the tissue as quantified by histopathological analysis.

Protocol for Sensitization and Challenge

Brown Norway rats were sensitized on days 0, 12 and 21 with ovalbumin (100 µg, i.p) administered with aluminum hydroxide (100 mg, i.p). On day 30, the rats were exposed to a 1% aerosol of ovalbumin for a period of 30 minutes. The animals were then returned to housing.

Protocol for Dosing

Test drug was administered orally 1 hour before the initiation of the allergen inhalation challenge. Four hours after the end of the antigen inhalation challenge, a second dose of drug was given orally. Doses of compound were administered at half log divisions between 3 and 100 mg/kg.

In separate studies drug was administered two times daily for 4 days before the inhalation of antigen. The final dose of compound in these studies was also given at 4 hours after the antigen challenge.

Protocol for Bronchoalveolar Lavage (BAL) Recovery

Twenty-four hours after the antigen inhalation challenge, cells were recovered from the airway lumen by bronchoalveolar lavage by euthanizing the animals, and washing the lungs with three 5-ml aliquots of RPMI/FCS. The washes were allowed to remain in the lungs for 30 seconds each before gentile removal. The three samples were pooled and total and differential white blood cell counts were measured on BAL samples. An ARGOS system was used to assess total cells and differential cell counts were made using light microscopy of Wright-Giemsa stained cytocentrifuge preparations.

Protocol for Histopathology of Lungs

Immediately after BAL, the lungs were insufflated with 10% neutral buffered formalin (NBF), at 30 cm water pressure. The lungs were removed and placed in jars of 10% NBF. After fixation in 10% NBF for a minimum of 24 hours the lungs were processed through graded alcohol and into wax locks. The lungs were blocked longitudinally and one 2

μm longitudinal section for each animal was cut at the level of the main bronchi. Sections were then stained with haematoxylin and eosin. Pathological assessment of sections was performed and a grading for the bronchiolar epithelium and sub-mucosa was assigned Protocol for Lung Digest In some studies the lug itself was digested, to recover the inflammatory cells localized within the tissue. In these studies the cells were obtained by perfusing the left lung with RPMI/FCS in order to remove the blood pool of cells immediately after BAL. In the se studies the he right hand side of the lung was insufflated and fixed with buffered formalin for histopathological analysis. The lung to undergo digestion was standardized across animals by taking a 300 mg the section of the lung tissue and exposing it to collagenase digestion. This freed the cells within the lung tissue and allowed their recovery. Total and differential cell counts were performed on these recovered cells.

Results (i) Following antigen inhalation there was a significant increase in the numbers of eosinophils and neutrophils in the nonrug treated groups. His was evidenced by the significant increase in BAL and tissue digest eosinophil and neutrophil numbers as well as the lung histopathology score.

(ii) No changes in BAL macrophage/monocyte cell numbers were observed with antigen challenge or with any drug treatment.

(iii) The compound as able to inhibit significantly the infiltration of neutrophils and eosinophils 24 hours after antigenic challenge compared to the non-drug treated controls as assessed in all three methods noted above. The dose range for efficacy was between 3 and 100 mg/kg po.

(iv) In the multiple-day drug administration studies, there was quantitatively similar inhibition of the cellular influx as seen in the single day studies.

These results indicate that compounds of the invention demonstrate anti-inflammatory activity when given prophylacticly in a rat model of antigen induced leukocyte infiltration 2. Inhibition of Antigen Induced Airway Inflammation—Single-Day ip Dosing Studies Protocol for Sensitization and Challenge Brown Norway rats were sensitized on days 0, 12 and 21 with ovalbumin (100 μg, i.p) administered with aluminum hydroxide (100 mg, i.p). On day 30, the rats were exposed to a 1% aerosol of ovalbumin for a period of 30 minutes. The animals were then returned to housing.

Protocol for Dosing

Test drug was administered four times intraperitoneally rather than po. The dosing regimen was 30 min pre-challenge and 2, 4 and 8 hours after allergen inhalation challenge.

Protocol for Bronchoalveolar Lavage (BAL) Recovery

Twenty-four hours after the antigen inhalation challenge, cells were recovered from the airway lumen by bronchoalveolar lavage by euthanizing the animals, and washing the lungs with three 5-ml aliquots of RPMI/FCS. The washes were allowed to remain in the lungs for 30 seconds each before gentile removal. The three samples were pooled and total and differential white blood cell counts were measured on BAL samples. An ARGOS system was used to assess total cells and differential cell counts were made using light microscopy of Wright-Giemsa stained cytocentrifuge preparations.

Protocol for Histopathology of Lungs

Immediately after BAL, the lungs were insufflated with 10% neutral buffered formalin (NBF), at 30 cm water pressure. The lungs were removed and placed in jars of 10% NBF. After fixation in 10% NBF for a minimum of 24 hours the lungs were processed through graded alcohol and into wax locks. The lungs were blocked longitudinally and one 2 μm longitudinal section for each animal was cut at the level of the main bronchi. Sections were then stained with haematoxylin and eosin. Pathological assessment of sections was performed and a grading for the bronchiolar epithelium and sub-mucosa was assigned Protocol for Lung Digest In some studies the lug itself was digested, to recover the inflammatory cells localized within the tissue. In these studies the cells were obtained by perfusing the left lung with RPMI/FCS in order to remove the blood pool of cells immediately after BAL. In the se studies the he right hand side of the lung was insufflated and fixed with buffered formalin for histopathological analysis. The lung to undergo digestion was standardized across animals by taking a 300 mg the section of the lung tissue and exposing it to collagenase digestion. This freed the cells within the lung tissue and allowed their recovery. Total and differential cell counts were performed on these recovered cells.

Results (i) Following antigen inhalation there was a significant increase in the numbers of eosinophils and neutrophils in the non-drug treated groups. This was evidenced by the significant increase in BAL and tissue digest eosinophil and neutrophil numbers as well as the lung histopathology score.

(ii) Compounds of the invention were able to inhibit significantly the infiltration of neutrophils and eosinophils 24 hours after antigenic challenge compared to the non-drug treated controls as assessed in all three methods noted above. The dose range for efficacy was between 3 and 100 mg/kg po.

These results indicate that compounds of the invention demonstrate anti-inflammatory activity when given prophylacticly in a rat model of antigen induced leukocyte infiltration either orally or intraperitoneally.

3. Inhibition of Acute Antigen Induced Bronchoconstriction in the Allergic Rat

Protocol for Sensitization and Challenge

Brown Norway rats were sensitized on days 0, 12 and 21 with ovalbumin (100 μg, i.p) administered with aluminum hydroxide (100 mg, i.p). On the day of study the rats were surgically prepared for the measurement of pulmonary mechanics and mechanically ventilated. After a five-minute equilibration period, the animals received a bolus of ovalbumin (1 mg per rat). The animals were then followed for 15 minutes and peak changes from base line resistance recorded as the response to antigen challenge.

Protocol for Dosing

Test drug was given either p.o. or i.p. 24 and 2 hours before the iv bolus injection of ovalbumin. The range of compound delivered in these studies was 10–100 mg/kg po.

Results

Following antigen challenge in the non-drug treated and budesonide control-treated animals there was a significant increase in the airway resistance over baseline. In contrast, compounds of the invention significantly inhibited the antigen-induced bronchoconstriction.

These results indicate that compounds of the invention inhibit antigen-induced bronchoconstriction.

4. Inhibition of Sephadex Induced Rat Lung Edema and Cytokine Gene Expression in the Allergic Rat Protocol for Sephadex Administration Male Sprague-Dawley rats (400 g), were dosed i.t. with vehicle (saline) or Sephadex (5 mg/kg) in a dose volume of 1 ml/kg under halothane anesthesia (4% in oxygen for 3 min).

Protocol for Dosing

Drug was administered p.o. 1 hour before and 5 hours after Sephadex i.t in a dose volume of 1 ml/kg.

Protocol for Assessing Edema as an Endpoint

Twenty-four hours after Sephadex administration the animals were sacrificed with Euthatal (1 ml/kg i.p.), the heart and lungs removed en bloc. An increase in wet weight was used as an index of edema. The wet weight determined and then corrected for 100 g initial body weight.

Protocol for RT-PCR (Measurement of Cytokine Gene Expression)

RNA was isolated from lung tissue by a guanidium thiocyanate-phenol-chloroform extraction technique. RNA was reverse transcribed to cDNA using AMV reverse transcriptase. cDNA for IL-5, IL-4, eotaxin and GAPDH (control gene) were amplified by PCR using oligonucleotide sequences synthesized (Gibco) from published sequences.

The PCR reagents were overlaid with mineral oil and amplification was carried out through 25–35 cycles of denaturation at 95° C. for 1 minute, annealing at 55–65° C. for 1 minute and extending at 72° C. for 7 minutes. The PCR products, stained with ethidium bromide, were electrophoresed in 2% agarose gels to visualize cDNA bands.

Bands of each target fragment were visualized by ultraviolet transillumination and photographed. Photographs were scanned on a densitometer and integrated optical densities (OD×mm) of each band were calculated by image analysis software (Imagemaster, Pharmacia). For each animal, the amount of each cytokine PCR product was normalized to the amount of GAPDH PCR product.

Results (i) Sephadex instillation alone evoked a significant edema of 32%

(ii) Compounds of the invention inhibited the edema in a dose dependant manner by at doses of 10, 30 and 100 mg/kg (iii) Sephadex caused an increased expression of the Th-2 cytokines IL-4 and IL-5 together with the CC chemokine eotaxin in the lung 24 hours after challenge. There was a trend toward an increase in the expression of IL-5 and eotaxin mRNA.

(iv) L-4 mRNA expression was dose dependently inhibited by compounds of the invention. Compounds of the invention inhibit Sephadex induced lung edema in the rat, which is associated with a reduction in Sephadex induction of IL-4.

5. Inhibition of Antigen-Induced Histamine Release in the Allergic Brown-Norway Rat Protocol for Sensitization and Challenge Brown Norway rats were sensitized on days 0, 12 and 21 with ovalbumin (100 µg, i.p) administered with aluminum hydroxide (100 mg, i.p). On the day of study, the rats were surgically prepared for the infusion of antigen. After a five-minute equilibration period, the animals received a bolus of ovalbumin (1 mg per rat). Blood samples were taken 2 minutes after ovalbumin challenge and plasma histamine levels were measured using a histamine ELISA.

Protocol for Dosing

Test drug was given i.p. 30 min before ovalbumin challenge. Only a single 30 mg/kg i.p. concentration was used in this study Results Following antigen challenge, the Syk Kinase inhibitors significantly inhibited the antigen-induced histamine release in comparison to the vehicle treated group.

These results indicate that compounds of the invention inhibit antigen-induced histamine release.

6. Inhibition of ED-1+Alveolar Macrophages in Rat Lung Tissue

Protocol for Sensitization and Challenge

Brown Norway rats were sensitized on days 0, 12 and 21 with ovalbumin (100 µg, i.p) administered with aluminum hydroxide (100 mg, i.p). On day 30, the rats were exposed to a 1% aerosol of ovalbumin for a period of 30 minutes. The animals were then returned to housing.

Protocol for Dosing

Test drug was given either p.o. or i.p. 24 and 2 hours before the iv bolus injection of ovalbumin. The range of compound delivered in these studies was 10–100 mg/kg po.

Protocol for ED1 Quantification

Alveolar macrophages were quantified following immunostaining with ED-1 antibody in paraffin-embedded lung tissue sections.

Results (i) Ovalbumin challenge resulted in a 10-fold increase in the number of ED1+macrophages in the alveolar bed.

(ii) Inhibition of Syk Kinase significantly reduced the ovalbumin-induced increase in ED1 alveolar macrophages in a dose-dependent manner.

Oral administration of compounds of the invention produced a dose-related reduction in ED-1+alveolar macrophages following ovalbumin challenge.

7. Inhibition of Antigen-induced Airway Neutrophilia in the Brown-Norway Rat Protocol for Sensitization and Challenge Brown Norway rats were sensitized on days 0, 12 and 21 with ovalbumin (100 µg, i.p) administered with aluminum hydroxide (100 mg, i.p). On day 30, the rats were exposed to a 1% aerosol of ovalbumin for a period of 30 minutes. The animals were then returned to housing.

Protocol for Drug Dosing

One hour before antigen challenge, rats were dosed orally. The range of compound delivered in these studies was 1–100 mg/kg po.

Protocol for Cell Analysis

Four hours after challenge, cells were recovered from the airway lumen by bronchoalveolar lavage (RPMI/FCS as previously described). Immediately after lavage, lungs were perfused with RPMI/FCS to remove the blood pool of cells. 300 mg of tissue was chopped and cells were recovered by enzymatic (collagenase) disaggregation. Differential cell counts were made by light microscopy of stained cytocentrifage preparations stained with Wright-Giemsa stain.

Results (i) Four hours after antigen challenge a significant increase in neutrophils was observed in both the BAL and lung tissue.

(ii) The ovalbumin-induced increase in neutrophils in the BAL, but not the lung tissue, was significantly suppressed by compounds of the invention.

We claim:

1. A compound of formula (Ia):

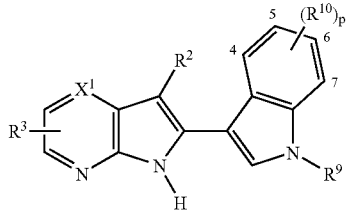

wherein:

$R^2$ represents hydrogen, acyl, cyano, halo, lower alkenyl or lower alkyl optionally substituted by a substituent selected from cyano, heteroaryl, heterocycloalkyl, $-Z^1R^8$, $-C(=O)-NY^3Y^4$, $-CO_2R^8$, $-NY^3Y^4$, $-N(R^6)-C(=O)-R^7$, $-N(R^6)-C(=O)-NY^3Y^4$, $-N(R^6)-C(=O)-OR^7$, $-N(R^6)-SO_2-R^7$, $-N(R^6)-SO_2-NY^3Y^4$ and one or more halogen atoms;

$R^3$ represents hydrogen, aryl, cyano, halo, heteroaryl, lower alkyl, $-C(=O)-OR^5$;

$R^4$ represents alkyl, cycloalkyl or cycloalkylalkyl each optionally substituted by a substituent selected from aryl, cycloalkyl, cyano, halo, heteroaryl, heterocycloalkyl, —CHO ( or a 5-, 6- or 7-membered cyclic acetal derivative thereof), $-C(=O)-NY^1Y^2$, $-C(=O)-OR^5$, $-NY^1Y^2$, $-N(R^6)-C(=O)-R^7$, $-N(R^6)-C(=O)-NY^3Y^4$, $-N(R^6)-SO_2-R^7$, $-N(R^6)-SO_2-NY^3Y^4$, $-OR^7$ and one or more groups selected from hydroxy and carboxy;

$R^5$ represents hydrogen, alkyl, alkenyl, aryl, arylalkyl, heteroaryl or heteroarylalkyl;

$R^6$ represents hydrogen or lower alkyl;

$R^7$ represents alkyl, aryl, arylalkyl, cycloalkyl, cycloalkylalkyl, heteroaryl, heteroarylalkyl, heterocycloalkyl or heterocycloalkylalkyl;

$R^8$ represents hydrogen or lower alkyl;

$X^1$ represents CH, C-halo, C-lower alkoxy, C-aryl, or C-CN $Y^1$ and $Y^2$ are independently hydrogen, alkenyl, aryl, cycloalkyl, heteroaryl or alkyl optionally substituted by one or more groups selected from aryl, halo, heteroaryl, hydroxy, $-C(=O)-NY^3Y^4$, $-C(=O)-OR^5$, $-NY^3Y^4$, $-N(R^6)-C(=O)-R^7$, $-N(R^6)-C(=O)-NY^3Y^4$, $-N(R^6)-SO_2-R^7$, $-N(R^6)-SO_2-NY^3Y^4$ and $-OR^7$; or the group $-NY^1Y^2$ may form a cyclic amine;

$Y^3$ and $Y^4$ are independently hydrogen, alkenyl, alkyl, aryl, arylalkyl, cycloalkyl, heteroaryl or heteroarylalkyl; or the group $-NY^3Y^4$ may form a cyclic amine;

$Z^1$ represents O or S;

$Z^2$ represents O or $S(O)_n$;

n is zero or an integer 1 or 2;

$R^9$ is hydrogen, $R^4$, alkenyl or heterocycloalkyl; $R^{10}$ is alkenyloxy, carboxy, cyano, halo, hydroxy, heteroaryl, $R^4$, $-C(=)-R^4$, $-C(=O)-NY^1Y^2$, $-OR^4$, $-N(R^6)-C(=O)-R^7$, $-N(R^6)-SO_2-R^7$ or $-NY^1Y^2$; and p is zero, an integer 1 or 2; acceptable salt of said compound.

2. A compound according to claim 1 in which $R^2$ is hydrogen.

3. A compound according to claim 1 in which $R^3$ is hydrogen, aryl or lower alkyl.

4. A compound of formula (Ib):

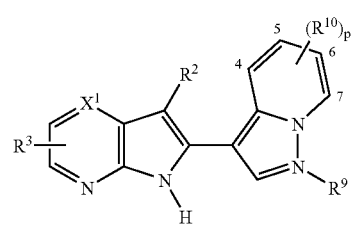

in which $R^2$, $R^3$, $R^9$, $R^{10}$, $X^1$ and p are as hereinbefore defined in claim 1, or a pharmaceutically acceptable salt of said compound.

5. A compound according to claim 4 in which $R^2$ is hydrogen.

6. A compound according to claim 4 in which $R^3$ is hydrogen, aryl or lower alkyl.

7. A compound of formula (Ic):

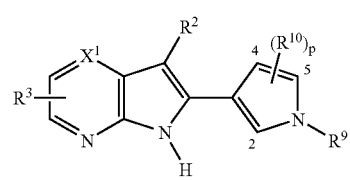

in which $R^2$, $R^3$, $R^9$, $R^{10}$, $X^1$ and p are as hereinbefore defined in claim 1, or a pharmaceutically acceptable salt of said compound.

8. A compound according to claim 7 in which $R^2$ is hydrogen.

9. A compound according to claim 7 in which $R^3$ is hydrogen, aryl or lower alkyl.

* * * * *